US008642752B2

(12) United States Patent  
Swayze et al.

(10) Patent No.: US 8,642,752 B2
(45) Date of Patent: Feb. 4, 2014

(54) MODULATION OF HEPATITIS B VIRUS (HBV) EXPRESSION

(75) Inventors: Eric E. Swayze, Encinitas, CA (US); Susan M. Freier, San Diego, CA (US); Michael L. McCaleb, La Jolla, CA (US); Hong Zhang, Fremont, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/452,703

(22) Filed: Apr. 20, 2012

(65) Prior Publication Data

US 2013/0035366 A1 Feb. 7, 2013

Related U.S. Application Data

(60) Provisional application No. 61/478,040, filed on Apr. 21, 2011, provisional application No. 61/478,038, filed on Apr. 21, 2011, provisional application No. 61/596,690, filed on Feb. 8, 2012, provisional application No. 61/596,692, filed on Feb. 8, 2012.

(51) Int. Cl.
*C07H 21/04* (2006.01)
*C12N 15/113* (2010.01)

(52) U.S. Cl.
USPC ........................................ 536/24.5; 514/44 A

(58) Field of Classification Search
None
See application file for complete search history.

(56) References Cited

U.S. PATENT DOCUMENTS

| 4,806,463 | A | 2/1989 | Goodchild et al. |
| 5,004,810 | A | 4/1991 | Draper |
| 5,166,195 | A | 11/1992 | Ecker |
| 5,194,428 | A | 3/1993 | Agrawal et al. |
| 5,264,423 | A | 11/1993 | Cohen et al. |
| 5,276,019 | A | 1/1994 | Cohen et al. |
| 5,610,050 | A | 3/1997 | Blum et al. |
| 5,646,262 | A | 7/1997 | Korba et al. |
| 5,728,518 | A | 3/1998 | Carmichael |
| 5,736,334 | A | 4/1998 | Spies |
| 5,780,219 | A | 7/1998 | McDonough et al. |
| 5,801,154 | A | 9/1998 | Baracchini et al. |
| 5,856,084 | A | 1/1999 | Karayiannis et al. |
| 5,985,662 | A | 11/1999 | Anderson et al. |
| 6,017,756 | A | 1/2000 | Draper |
| 6,410,009 | B1 | 6/2002 | Galun et al. |
| 6,503,533 | B1 | 1/2003 | Korba et al. |
| 6,518,417 | B1 | 2/2003 | Sczakiel et al. |
| 6,582,908 | B2 | 6/2003 | Fodor et al. |
| 6,828,105 | B2 | 12/2004 | Stein et al. |
| 6,984,729 | B1 | 1/2006 | Frank et al. |
| 7,015,317 | B2 | 3/2006 | Mullen et al. |
| 7,067,249 | B2 | 6/2006 | Kung et al. |
| 7,186,700 | B2 | 3/2007 | Standring et al. |
| 7,344,837 | B2 | 3/2008 | Lee et al. |
| 7,521,184 | B2 | 4/2009 | Radka et al. |
| 7,863,437 | B2 * | 1/2011 | Hedtjarn ...................... 536/24.5 |
| 7,923,547 | B2 | 4/2011 | McSwiggen et al. |
| 7,927,601 | B2 | 4/2011 | Sheldon et al. |
| 7,928,086 | B2 | 4/2011 | Standring et al. |
| 8,090,542 | B2 | 1/2012 | Khvorova et al. |
| 8,158,606 | B2 | 4/2012 | Standring et al. |
| 8,178,503 | B2 | 5/2012 | Rigousos et al. |
| 8,182,992 | B2 | 5/2012 | Sampath |
| 8,193,157 | B2 | 6/2012 | Balzaini et al. |
| 8,202,979 | B2 | 6/2012 | McSwiggen et al. |
| 8,232,257 | B2 | 7/2012 | McCaffrey et al. |
| 8,273,866 | B2 | 9/2012 | McSwiggen et al. |
| 2001/0053519 | A1 | 12/2001 | Fodor et al. |
| 2003/0068301 | A1 | 4/2003 | Draper et al. |
| 2003/0139363 | A1 | 7/2003 | Kay et al. |
| 2003/0143527 | A1 | 7/2003 | Venkatakrishna |
| 2003/0148985 | A1 | 8/2003 | Morrissey et al. |
| 2003/0206887 | A1 | 11/2003 | Morrissey et al. |
| 2003/0228597 | A1 | 12/2003 | Cowsert et al. |
| 2004/0053214 | A1 | 3/2004 | Schroder et al. |
| 2004/0054156 | A1 * | 3/2004 | Draper et al. ................ 536/23.1 |
| 2004/0127446 | A1 | 7/2004 | Blatt et al. |
| 2004/0185452 | A1 | 9/2004 | Chen et al. |
| 2004/0191776 | A1 | 9/2004 | Chen et al. |
| 2005/0175990 | A1 | 8/2005 | Stuybe et al. |
| 2005/0266422 | A1 | 12/2005 | Vagle et al. |
| 2006/0194217 | A1 | 8/2006 | Zoulim et al. |
| 2006/0258610 | A1 * | 11/2006 | Karras et al. ..................... 514/44 |
| 2006/0263764 | A1 | 11/2006 | Pachuk |
| 2007/0031844 | A1 | 2/2007 | Khvorova et al. |
| 2008/0070854 | A1 | 3/2008 | Pachuk et al. |

(Continued)

FOREIGN PATENT DOCUMENTS

CN 101603042 A1 * 12/2008
EP 0528903 9/1996

(Continued)

OTHER PUBLICATIONS

Machine translation of CN101603042 retrieved from Dialog using internet,[retrieved on Jan. 21, 2013] <URL: http://toolkit.dialog.com/intranet/cgi/present>.*
Blum et al., "Inhibition of hepatitis B virus by antisense oligodeoxynucleotides" Lance (1991) 337:1230.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.

(Continued)

Primary Examiner — Tracy Vivlemore
(74) Attorney, Agent, or Firm — Isis Pharmaceuticals, Inc. Patent Dept.

(57) ABSTRACT

Disclosed herein are antisense compounds and methods for decreasing HBV mRNA, DNA and protein expression. Such methods, compounds, and compositions are useful to treat, prevent, or ameliorate HBV-related diseases, disorders or conditions.

37 Claims, No Drawings

(56) References Cited

U.S. PATENT DOCUMENTS

| | | |
|---|---|---|
| 2008/0081328 A1 | 4/2008 | Linnen et al. |
| 2008/0096839 A1 | 4/2008 | Kim et al. |
| 2008/0145346 A1 | 6/2008 | Ng et al. |
| 2008/0161256 A1 | 7/2008 | Morrisey et al. |
| 2008/0207539 A1 | 8/2008 | Arbuthnot et al. |
| 2008/0280287 A1 | 11/2008 | Biron et al. |
| 2008/0317717 A1 | 12/2008 | Eagles et al. |
| 2009/0081675 A1 | 3/2009 | Colston et al. |
| 2009/0318536 A1 | 12/2009 | Freier et al. |
| 2009/0318676 A1 | 12/2009 | Manoharan et al. |
| 2010/0003668 A1 | 1/2010 | Huang et al. |
| 2010/0015218 A1 | 1/2010 | Jadhav et al. |
| 2010/0015708 A1 | 1/2010 | Quay et al. |
| 2010/0056607 A1 | 3/2010 | Dobie et al. |
| 2010/0063132 A1 | 3/2010 | Kim et al. |
| 2010/0099740 A1 | 4/2010 | Kay et al. |
| 2010/0137414 A1 | 6/2010 | Freier et al. |
| 2010/0184840 A1 | 7/2010 | Arbuthnot et al. |
| 2010/0197762 A1 | 8/2010 | Swayze |
| 2010/0211327 A1 | 8/2010 | Hahner et al. |
| 2010/0255482 A1 | 10/2010 | Shen et al. |
| 2011/0008787 A1 | 1/2011 | Satterfield et al. |
| 2011/0054005 A1 | 3/2011 | Naito et al. |
| 2011/0129824 A1 | 6/2011 | Dagland et al. |
| 2011/0160252 A1 | 6/2011 | Mizokami et al. |
| 2012/0035240 A1 | 2/2012 | Pachuk et al. |
| 2012/0045796 A1 | 2/2012 | Satterfield et al. |
| 2012/0052487 A9 | 3/2012 | Khvorova et al. |
| 2012/0207709 A1* | 8/2012 | Hamatake ............ 424/85.7 |
| 2012/0295961 A1 | 11/2012 | Swayze et al. |

FOREIGN PATENT DOCUMENTS

| | | |
|---|---|---|
| WO | WO 90/13667 | 11/1990 |
| WO | WO 91/14789 | 10/1991 |
| WO | WO 93/13120 | 7/1993 |
| WO | WO 94/24864 | 11/1994 |
| WO | WO 95/02690 | 1/1995 |
| WO | WO 9517414 A1 * | 6/1995 |
| WO | WO 95/19433 | 7/1995 |
| WO | WO 96/03152 | 2/1996 |
| WO | WO 97/03211 | 1/1997 |
| WO | WO 98/58055 | 12/1998 |
| WO | WO 01/16312 | 3/2001 |
| WO | WO 01/38498 | 5/2001 |
| WO | WO 01/40279 | 6/2001 |
| WO | WO 02/00613 | 1/2002 |
| WO | WO 02/081494 | 10/2002 |
| WO | WO 03/031934 | 4/2003 |
| WO | WO 03/087351 | 10/2003 |
| WO | WO 03/106714 | 12/2003 |
| WO | WO 2005/023297 | 8/2004 |
| WO | WO 2004/078181 | 9/2004 |
| WO | WO 2005/014806 | 2/2005 |
| WO | WO 2006/039739 | 4/2006 |
| WO | WO 2006/069064 | 6/2006 |
| WO | WO 2007/078029 | 7/2007 |
| WO | WO 2007/084567 | 7/2007 |
| WO | WO 2008/078102 | 7/2008 |
| WO | WO 2008/103276 | 8/2008 |
| WO | WO 2009/038266 | 3/2009 |
| WO | WO 2010/012244 | 4/2010 |
| WO | WO 2011/047312 | 4/2011 |
| WO | WO 2012/004790 | 1/2012 |
| WO | WO 2012/024170 | 2/2012 |
| WO | WO 2012/045894 | 4/2012 |
| WO | WO 2012/055362 | 5/2012 |
| WO | WO 2013/003520 | 1/2013 |

OTHER PUBLICATIONS

Goodarzi et al., "Antisense oligodeoxyribonucleotides inhibit the expression of the gene for hepatitis B virus surface antigen" J. Gen. Virol. (1990) 71:3021-3025.

Hamasaki et al., "Short interfering RNA-directed inhibition of hepatitis B virus replication" FEBS Letters (2003) 543:51-54.

Junker-Niepmann et al., "A short cis-acting sequence is required for hepatitis B virus pregenome encapsidation and sufficient for packaging of foreign RNA" EMBO J. (1990) 9(10):3389-3396.

Mccaffrey et al., "Inhibition of hepatitis B virus in mice by RNA interference" Nature Biotechnology (2003) 21(6):639-644.

Morrissey et al., "Potent and persistent in vivo anti-HBV activity of chemically modified siRNAs" Nature Biotechnology (2005) 23(8):1002-1007.

Morrissey et al., "Activity of Stabilized Short Interfering RNA in a Mouse Model of Hepatitis B Virus Replication" Hepatology (2005) 41(6):1349-1356.

New England Biolabs 1998/99 Catalog (cover page and pp. 121 and 284).

Offensperger et al., "In vivo inhibition of duck hepatitis B virus replication and gene expression by phosphorothioate modified antisense oligodeoxynucleotides" EMBO J. (1993) 12:1257-1262.

Offensperger et al., "Molecular therapeutic strategies in hepatitis B virus infection" Clinical Investigator (1994) 72:737-741.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Shlomai et al., "Inhibition of Hepatitis B Virus Expression and Replication by RNA Interference" Hepatology (2003) 37:764-770.

Wu et al., "Specific Inhibition of Hepatitis B Viral Gene Expression in Vitro by Targeted Antisense Oligonucleotides" J. Biol. Chem. (1992) 267:12436-12439.

Giladi et al., "Small Interfering RNA Inhibits Hepatitis B Virus Replication in Mice" Molecular Therapy (2003) 8(5):769-776.

Peng et al., "Inhibition of hepatitis B virus replication by various RNAi constructs and their pharmacodynamic properties" J. Gen. Virol. (2005) 86(12):3227-3234.

Qureshi et al., "Diabetes Mellitus is equally frequent in Chronic HCV and HBV Infection" JPMA (2002) 52(7):280-286.

International Search Report for application PCT/US12/34520 dated Aug. 16, 2012.

International Search Report for application PCT/US12/34550 dated Sep. 20, 2012.

Machine translation of abstract from Chinese patent publication CN1580070 taken from the website of the State Intellectual Property Office of P.R. China on Aug. 26, 2013.

Machine translation of abstract from Chinese patent publication CN1584053 taken from the website of the State Intellectual Property Office of P.R. China on Aug. 26, 2013.

Machine translation of abstract from Chinese patent publication CN102212619 taken from the website of the State Intellectual Property Office of P.R. China on Aug. 26, 2013.

Machine translation of Japanese application JP2006217864 taken from the WIPO website on Aug. 26, 2013.

* cited by examiner

SEQUENCE LISTING

```
<160> NUMBER OF SEQ ID NOS: 1381

<210> SEQ ID NO 1
<211> LENGTH: 3182
<212> TYPE: DNA
<213> ORGANISM: Hepatitis B virus

<400> SEQUENCE: 1
aattccacaa ccttttcacca aactctgcaa gatcccagag tgagaggcct gtatttccct      60
gctggtggct ccagttcagg agcagtaaac cctgttccga ctactgcctc tcccttatcg     120
tcaatcttct cgaggattgg ggaccctgcg ctgaacatgg agaacatcac atcaggattc     180
ctaggacccc ttctcgtgtt acaggcgggg ttttttcttgt tgacaagaat cctcacaata     240
ccgcagagtc tagactcgtg gtggacttct ctcaattttc taggggggaac taccgtgtgt     300 cttggccaaa attcgcagtc cccaacctcc aatcactcac caacctcctg tcctccaact     360
tgtcctggtt atcgctggat gtgtctgcgg cgttttatca tcttcctctt catcctgctg     420
ctatgcctca tcttcttgtt ggttcttctg gactatcaag gtatgttgcc cgtttgtcct     480
ctaattccag gatcctcaac caccagcacg ggaccatgcc gaacctgcat gactactgct     540
caaggaacct ctatgtatcc ctcctgttgc tgtaccaaac cttcggacgg aaattgcacc     600
tgtattccca tcccatcatc ctgggctttc ggaaaattcc tatgggagtg ggcctcagcc     660
cgtttctcct ggctcagttt actagtgcca tttgttcagt ggttcgtagg gctttccccc     720
actgtttggc tttcagttat atggatgatg tggtattggg ggccaagtct gtacagcatc     780
ttgagtccct ttttaccgct gttaccaatt ttcttttgtc tttgggtata catttaaacc     840
ctaacaaaac aaagagatgg ggttactctc tgaatttat gggttatgtc attggaagtt     900
atgggtcctt gccacaagaa cacatcatac aaaaaatcaa gaatgttttt agaaaacttc     960
ctattaacag gcctattgat tggaaagtat gtcaacgaat tgtgggtctt ttgggttttg    1020
ctgccccatt tacacaatgt ggttatcctg cgttaatgcc cttgtatgca tgtattcaat    1080
ctaagcaggc tttcactttc tcgccaactt acaaggcctt tctgtgtaaa caatacctga    1140
acctttaccc cgttgcccgg caacggccag gtctgtgcca agtgtttgct gacgcaaccc    1200
ccactggctg gggcttggtc atgggccatc agcgcgtgcg tggaaccttt tcggctcctc    1260
tgccgatcca tactgcggaa ctcctagccg cttgttttgc tcgcagcagg tctggagcaa    1320
acattatcgg gactgataac tctgttgtcc tctcccgcaa atatacatcg tatccatggc    1380
tgctaggctg tgctgccaac tggatcctgc gcgggacgtc ctttgtttac gtcccgtcgg    1440
cgctgaatcc tgcggacgac ccttctcggg gtcgcttggg actctctcgt ccccttctcc    1500
gtctgccgtt ccgaccgacc acggggcgca cctctcttta cgcggactcc ccgtctgtgc    1560
cttctcatct gccggaccgt gtgcacttcg cttcacctct gcacgtcgca tggagaccac    1620
```

```
cgtgaacgcc caccgaatgt tgcccaaggt cttacataag aggactcttg gactctctgc    1680
aatgtcaacg accgaccttg aggcatactt caaagactgt ttgtttaaag actgggagga    1740
gttgggggag gagattagat taaaggtctt tgtactagga ggctgtaggc ataaattggt    1800
ctgcgcacca gcaccatgca acttttcac ctctgcctaa tcatctcttg ttcatgtcct     1860
actgttcaag cctccaagct gtgccttggg tggctttggg gcatggacat cgacccttat    1920
aaagaatttg gagctactgt ggagttactc tcgttttgc cttctgactt ctttccttca     1980
gtacgagatc ttctagatac cgcctcagct ctgtatcggg aagcttaga gtctcctgag     2040
cattgttcac ctcaccatac tgcactcagg caagcaattc tttgctgggg ggaactaatg    2100
actctagcta cctgggtggg tgttaatttg gaagatccag catctagaga cctagtagtc    2160
agttatgtca acactaatat gggcctaaag ttcaggcaac tcttgtggtt tcacatttct    2220
tgtctcactt ttggaagaga aaccgttata gagtatttgg tgtctttcgg agtgtggatt    2280
cgcactcctc cagcttatag accaccaaat gccctatcc tatcaacact tccggaaact     2340
actgttgtta gacgacgagg caggtcccct agaagaagaa ctccctcgcc tcgcagacga    2400
aggtctcaat cgccgcgtcg cagaagatct caatctcggg aacctcaatg ttagtattcc    2460
ttggactcat aaggtgggga actttactgg tctttattct tctactgtac ctgtctttaa    2520
tcctcattgg aaaacaccat cttttcctaa tatacattta caccaagaca ttatcaaaaa    2580
atgtgaacag tttgtaggcc cacttacagt taatgagaaa agaagattgc aattgattat    2640
gcctgctagg ttttatccaa aggttaccaa atatttacca ttggataagg gtattaaacc    2700
ttattatcca gaacatctag ttaatcatta cttccaaact agacactatt tacacactct    2760
atggaaggcg ggtatattat ataagagaga acaacacat agcgcctcat tttgtgggtc     2820
accatattct tgggaacaag atctacagca tggggcagaa tctttccacc agcaatcctc    2880
tgggattctt tcccgaccac cagttggatc cagccttcag agcaaacaca gcaaatccag    2940
attgggactt caatcccaac aaggacacct ggccagacgc caacaaggta ggagctggag    3000
cattcgggct gggtttcacc ccaccgcacg gaggcctttt ggggtggagc cctcaggctc    3060
agggcatact acaaactttg ccagcaaatc cgcctcctgc ctccaccaat cgccagacag    3120
gaaggcagcc taccccgctg tctccacctt tgagaaacac tcatcctcag gccatgcagt    3180
gg                                                                   3182

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
cttggtcatg ggccatcag                                                   19

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cggctaggag ttccgcagta                                                  20

<210> SEQ ID NO 4
```

```
<211> LENGTH: 22
<212> TYPE: DNA
<213> ORGANISM: Artificial Sequence
<220> FEATURE:
<223> OTHER INFORMATION: Probe

<400> SEQUENCE: 4
tgcgtggaac cttttcggct cc                                              22

<210> SEQ ID NO 5
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 5
ccacgagtct agactct                                                    17

<210> SEQ ID NO 6
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 6
gtccaccacg agtctag                                                    17

<210> SEQ ID NO 7
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 7
agtccaccac gagtcta                                                    17

<210> SEQ ID NO 8
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 8
aagtccacca cgagtct                                                    17

<210> SEQ ID NO 9
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 9
gaagtccacc acgagtc                                                    17

<210> SEQ ID NO 10
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 10
```

-continued agaagtccac cacgagt					17

<210> SEQ ID NO 11
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 11
gagaagtcca ccacgag					17

<210> SEQ ID NO 12
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 12
agagaagtcc accacga					17

<210> SEQ ID NO 13
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 13
gagagaagtc caccacg					17

<210> SEQ ID NO 14
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 14
tgagagaagt ccaccac					17

<210> SEQ ID NO 15
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 15
tgataaaacg ccgcaga					17

<210> SEQ ID NO 16
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 16
atgataaaac gccgcag					17

<210> SEQ ID NO 17
<211> LENGTH: 17
<212> TYPE: DNA
<213> ORGANISM: Artificial Sequence
<220> FEATURE:

```
<223> OTHER INFORMATION: Synthetic oligonucleotide

<400> SEQUENCE: 17
ggcatagcag caggatg                                                    17

<210> SEQ ID NO 18
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 18
aggcatagca gcaggat                                                    17

<210> SEQ ID NO 19
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 19
gaggcatagc agcagga                                                    17

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
agatgaggca tagcagcagg                                                 20

<210> SEQ ID NO 21
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 21
tgaggcatag cagcagg                                                    17

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
aagatgaggc atagcagcag                                                 20

<210> SEQ ID NO 23
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 23
atgaggcata gcagcag                                                    17

<210> SEQ ID NO 24
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gaagatgagg catagcagca                                               20

<210> SEQ ID NO 25
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 25
gatgaggcat agcagca                                                  17

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
agaagatgag gcatagcagc                                               20

<210> SEQ ID NO 27
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 27
agatgaggca tagcagc                                                  17

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
aagaagatga ggcatagcag                                               20

<210> SEQ ID NO 29
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 29
aagatgaggc atagcag                                                  17

<210> SEQ ID NO 30
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 30
```
gaagatgagg catagca                                                    17

<210> SEQ ID NO 31
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 31
agaagatgag gcatagc                                                    17

<210> SEQ ID NO 32
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 32
aagaagatga ggcatag                                                    17

<210> SEQ ID NO 33
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 33
acgggcaaca taccttg                                                    17

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
ctgaggccca ctcccatagg                                                 20

<210> SEQ ID NO 35
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 35
aggcccactc ccatagg                                                    17

<210> SEQ ID NO 36
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 36
gaggcccact cccatag                                                    17

<210> SEQ ID NO 37
<211> LENGTH: 17
<212> TYPE: DNA
<213> ORGANISM: Artificial Sequence
<220> FEATURE:

```
<223> OTHER INFORMATION: Synthetic oligonucleotide

<400> SEQUENCE: 37
tgaggcccac tcccata                                                    17

<210> SEQ ID NO 38
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 38
ctgaggccca ctcccat                                                    17

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
cgaaccactg aacaaatggc                                                 20

<210> SEQ ID NO 40
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 40
accactgaac aaatggc                                                    17

<210> SEQ ID NO 41
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 41
aaccactgaa caaatgg                                                    17

<210> SEQ ID NO 42
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 42
gaaccactga acaaatg                                                    17

<210> SEQ ID NO 43
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 43
cgaaccactg aacaaat                                                    17

<210> SEQ ID NO 44
```

```
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 44
accacatcat ccatata                                                  17

<210> SEQ ID NO 45
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 45
tcagcaaaca cttggca                                                  17

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
aatttatgcc tacagcctcc                                               20

<210> SEQ ID NO 47
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 47
ttatgcctac agcctcc                                                  17

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
caatttatgc ctacagcctc                                               20

<210> SEQ ID NO 49
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 49
tttatgccta cagcctc                                                  17

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
```

```
ccaatttatg cctacagcct                                              20

<210> SEQ ID NO 51
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 51
atttatgcct acagcct                                                 17

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
accaatttat gcctacagcc                                              20

<210> SEQ ID NO 53
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 53
aatttatgcc tacagcc                                                 17

<210> SEQ ID NO 54
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 54
caatttatgc ctacagc                                                 17

<210> SEQ ID NO 55
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 55
ccaatttatg cctacag                                                 17

<210> SEQ ID NO 56
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 56
accaatttat gcctaca                                                 17

<210> SEQ ID NO 57
<211> LENGTH: 17
<212> TYPE: DNA
<213> ORGANISM: Artificial Sequence
<220> FEATURE:
```

```
<223> OTHER INFORMATION: Synthetic oligonucleotide

<400> SEQUENCE: 57
aggcagaggt gaaaaag                                                  17

<210> SEQ ID NO 58
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 58
taggcagagg tgaaaaa                                                  17

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
gcacagcttg gaggcttgaa                                               20

<210> SEQ ID NO 60
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 60
cagcttggag gcttgaa                                                  17

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
ggcacagctt ggaggcttga                                               20

<210> SEQ ID NO 62
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 62
acagcttgga ggcttga                                                  17

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
aggcacagct tggaggcttg                                               20

<210> SEQ ID NO 64
```

```
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 64
cacagcttgg aggcttg                                                    17

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
aaggcacagc ttggaggctt                                                 20

<210> SEQ ID NO 66
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 66
gcacagcttg gaggctt                                                    17

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
caaggcacag cttggaggct                                                 20

<210> SEQ ID NO 68
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 68
ggcacagctt ggaggct                                                    17

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
ccaaggcaca gcttggaggc                                                 20

<210> SEQ ID NO 70
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 70
```
aggcacagct tggaggc                                                17

<210> SEQ ID NO 71
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 71
aaggcacagc ttggagg                                                17

<210> SEQ ID NO 72
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 72
caaggcacag cttggag                                                17

<210> SEQ ID NO 73
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 73
ccaaggcaca gcttgga                                                17

<210> SEQ ID NO 74
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 74
gctccaaatt ctttata                                                17

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
tctgcgaggc gagggagttc                                             20

<210> SEQ ID NO 76
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 76
gcgaggcgag ggagttc                                                17

<210> SEQ ID NO 77
<211> LENGTH: 17
<212> TYPE: DNA
<213> ORGANISM: Artificial Sequence
<220> FEATURE:

<223> OTHER INFORMATION: Synthetic oligonucleotide

<400> SEQUENCE: 77
tgcgaggcga gggagtt                                                        17

<210> SEQ ID NO 78
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 78
ctgcgaggcg agggagt                                                        17

<210> SEQ ID NO 79
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 79
tctgcgaggc gagggag                                                        17

<210> SEQ ID NO 80
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 80
ttcccaagaa tatggtg                                                        17

<210> SEQ ID NO 81
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 81
gttcccaaga atatggt                                                        17

<210> SEQ ID NO 82
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 82
tgttcccaag aatatgg                                                        17

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
gaactggagc caccagcagg                                                     20

<210> SEQ ID NO 84

```
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 84
gagccaccag cagg                                                        14

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
cctgaactgg agccaccagc                                                  20

<210> SEQ ID NO 86
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 86
gaactggagc caccag                                                      16

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 87
aaaaaccccg cctgtaacac                                                  20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
aagaaaaacc ccgcctgtaa                                                  20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
gtcaacaaga aaaccccgc                                                   20

<210> SEQ ID NO 90
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 90
```
gtattgtgag gatt                                                    14

<210> SEQ ID NO 91
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 91
ggtattgtga ggat                                                    14

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 92
caccacgagt ctagactctg                                              20

<210> SEQ ID NO 93
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 93
cacgagtcta gactct                                                  16

<210> SEQ ID NO 94
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 94
cgagtctaga ctct                                                    14

<210> SEQ ID NO 95
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 95
ccacgagtct agactc                                                  16

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
gtccaccacg agtctagact                                              20

<210> SEQ ID NO 97
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 97
gaagtccacc acgagtctag        20

<210> SEQ ID NO 98
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 98
tccaccacga gtctag        16

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
agaagtccac cacgagtcta        20

<210> SEQ ID NO 100
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 100
gtccaccacg agtcta        16

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
gagaagtcca ccacgagtct        20

<210> SEQ ID NO 102
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 102
agtccaccac gagtct        16

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
agagaagtcc accacgagtc        20

<210> SEQ ID NO 104

```
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 104
aagtccacca cgagtc                                                         16

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
gagagaagtc caccacgagt                                                     20

<210> SEQ ID NO 106
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 106
gaagtccacc acgagt                                                         16

<210> SEQ ID NO 107
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 107
agtccaccac gagt                                                           14

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
tgagagaagt ccaccacgag                                                     20

<210> SEQ ID NO 109
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 109
agaagtccac cacgag                                                         16

<210> SEQ ID NO 110
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 110
```
aagtccacca cgag                                                    14

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 111
ttgagagaag tccaccacga                                              20

<210> SEQ ID NO 112
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 112
gagaagtcca ccacga                                                  16

<210> SEQ ID NO 113
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 113
gaagtccacc acga                                                    14

<210> SEQ ID NO 114
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 114
agaagtccac cacg                                                    14

<210> SEQ ID NO 115
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 115
gagagaagtc caccac                                                  16

<210> SEQ ID NO 116
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 116
gagaagtcca ccac                                                    14

<210> SEQ ID NO 117
<211> LENGTH: 16
<212> TYPE: DNA
<213> ORGANISM: Artificial Sequence
<220> FEATURE:

-continued

<223> OTHER INFORMATION: Synthetic oligonucleotide

<400> SEQUENCE: 117
tgagagaagt ccacca                                                    16

<210> SEQ ID NO 118
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 118
agagaagtcc acca                                                      14

<210> SEQ ID NO 119
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 119
gagagaagtc cacc                                                      14

<210> SEQ ID NO 120
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 120
tgagagaagt ccac                                                      14

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 121
agaaaattga gagaagtcca                                                20

<210> SEQ ID NO 122
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 122
cctagaaaat tgagagaagt                                                20

<210> SEQ ID NO 123
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 123
attttggcca agacacacgg                                                20

<210> SEQ ID NO 124

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 124
cgaattttgg ccaagacaca                                              20

<210> SEQ ID NO 125
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 125
ggactgcgaa ttttggccaa                                              20

<210> SEQ ID NO 126
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 126
tccagcgata accaggacaa                                              20

<210> SEQ ID NO 127
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 127
gacacatcca gcgataacca                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 128
gcagacacat ccagcgataa                                              20

<210> SEQ ID NO 129
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 129
gataaaacgc cgcaga                                                  16

<210> SEQ ID NO 130
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 130
```

-continued taaaacgccg caga                                                14

<210> SEQ ID NO 131
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 131
ataaaacgcc gcag                                                14

<210> SEQ ID NO 132
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 132
atgataaaac gccgca                                              16

<210> SEQ ID NO 133
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 133
gataaaacgc cgca                                                14

<210> SEQ ID NO 134
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 134
tgataaaacg ccgc                                                14

<210> SEQ ID NO 135
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 135
atgataaaac gccg                                                14

<210> SEQ ID NO 136
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 136
tgaggcatag cagcaggatg                                          20

<210> SEQ ID NO 137
<211> LENGTH: 16
<212> TYPE: DNA
<213> ORGANISM: Artificial Sequence
<220> FEATURE:

<223> OTHER INFORMATION: Synthetic oligonucleotide

<400> SEQUENCE: 137
gcatagcagc aggatg                                           16

<210> SEQ ID NO 138
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 138
atagcagcag gatg                                             14

<210> SEQ ID NO 139
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 139
atgaggcata gcagcaggat                                       20

<210> SEQ ID NO 140
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 140
ggcatagcag caggat                                           16

<210> SEQ ID NO 141
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 141
catagcagca ggat                                             14

<210> SEQ ID NO 142
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 142
gatgaggcat agcagcagga                                       20

<210> SEQ ID NO 143
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 143
aggcatagca gcagga                                           16

<210> SEQ ID NO 144

```
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 144
gcatagcagc agga                                                        14

<210> SEQ ID NO 145
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 145
gaggcatagc agcagg                                                      16

<210> SEQ ID NO 146
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 146
ggcatagcag cagg                                                        14

<210> SEQ ID NO 147
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 147
tgaggcatag cagcag                                                      16

<210> SEQ ID NO 148
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 148
aggcatagca gcag                                                        14

<210> SEQ ID NO 149
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 149
atgaggcata gcagca                                                      16

<210> SEQ ID NO 150
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 150
```
gaggcatagc agca                                                    14

<210> SEQ ID NO 151
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 151
gatgaggcat agcagc                                                  16

<210> SEQ ID NO 152
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 152
tgaggcatag cagc                                                    14

<210> SEQ ID NO 153
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 153
agatgaggca tagcag                                                  16

<210> SEQ ID NO 154
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 154
atgaggcata gcag                                                    14

<210> SEQ ID NO 155
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 155
aagatgaggc atagca                                                  16

<210> SEQ ID NO 156
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 156
gatgaggcat agca                                                    14

<210> SEQ ID NO 157
<211> LENGTH: 16
<212> TYPE: DNA
<213> ORGANISM: Artificial Sequence
<220> FEATURE:

<223> OTHER INFORMATION: Synthetic oligonucleotide

<400> SEQUENCE: 157
gaagatgagg catagc                                                        16

<210> SEQ ID NO 158
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 158
agatgaggca tagc                                                          14

<210> SEQ ID NO 159
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 159
agaagatgag gcatag                                                        16

<210> SEQ ID NO 160
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 160
aagatgaggc atag                                                          14

<210> SEQ ID NO 161
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 161
aagaagatga ggcata                                                        16

<210> SEQ ID NO 162
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 162
gaagatgagg cata                                                          14

<210> SEQ ID NO 163
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 163
agaagatgag gcat                                                          14

<210> SEQ ID NO 164

```
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 164
aagaagatga ggca                                                        14

<210> SEQ ID NO 165
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 165
acgggcaaca taccttgata                                                  20

<210> SEQ ID NO 166
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 166
caaacgggca acataccttg                                                  20

<210> SEQ ID NO 167
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 167
cgggcaacat accttg                                                      16

<210> SEQ ID NO 168
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 168
acgggcaaca tacct                                                       16

<210> SEQ ID NO 169
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 169
gggcaacata cctt                                                        14

<210> SEQ ID NO 170
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 170
```
cgggcaacat acct                                              14

<210> SEQ ID NO 171
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 171
acgggcaaca tacc                                              14

<210> SEQ ID NO 172
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 172
agaggacaaa cgggcaacat                                        20

<210> SEQ ID NO 173
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 173
attagaggac aaacgggcaa                                        20

<210> SEQ ID NO 174
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 174
cctggaatta gaggacaaac                                        20

<210> SEQ ID NO 175
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 175
gatcctggaa ttagaggaca                                        20

<210> SEQ ID NO 176
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 176
ggcccactcc catagg                                            16

<210> SEQ ID NO 177
<211> LENGTH: 16
<212> TYPE: DNA
<213> ORGANISM: Artificial Sequence
<220> FEATURE:

<223> OTHER INFORMATION: Synthetic oligonucleotide

<400> SEQUENCE: 177
gaggcccact cccata                                                    16

<210> SEQ ID NO 178
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 178
tgaggcccac tcccat                                                    16

<210> SEQ ID NO 179
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 179
ctgaggccca ctccca                                                    16

<210> SEQ ID NO 180
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 180
ggcactagta aactgagcca                                                20

<210> SEQ ID NO 181
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 181
ctagtaaact gagcca                                                    16

<210> SEQ ID NO 182
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 182
agtaaactga gcca                                                      14

<210> SEQ ID NO 183
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 183
tagtaaactg agcc                                                      14

<210> SEQ ID NO 184

```
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 184
ctagtaaact gagc                                                         14

<210> SEQ ID NO 185
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 185
aatggcacta gtaaactgag                                                   20

<210> SEQ ID NO 186
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 186
tgaacaaatg gcactagtaa                                                   20

<210> SEQ ID NO 187
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 187
cactgaacaa atggcactag                                                   20

<210> SEQ ID NO 188
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 188
ccactgaaca aatggc                                                       16

<210> SEQ ID NO 189
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 189
acgaaccact gaacaaatgg                                                   20

<210> SEQ ID NO 190
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 190
```

-continued accactgaac aaatgg                                                    16

<210> SEQ ID NO 191
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 191
aaccactgaa caaatg                                                    16

<210> SEQ ID NO 192
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 192
gaaccactga acaaat                                                    16

<210> SEQ ID NO 193
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 193
cctacgaacc actgaacaaa                                                20

<210> SEQ ID NO 194
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 194
cgaaccactg aacaaa                                                    16

<210> SEQ ID NO 195
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 195
aaccactgaa caaa                                                      14

<210> SEQ ID NO 196
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 196
gaaccactga acaa                                                      14

<210> SEQ ID NO 197
<211> LENGTH: 14
<212> TYPE: DNA
<213> ORGANISM: Artificial Sequence
<220> FEATURE:

```
<223> OTHER INFORMATION: Synthetic oligonucleotide

<400> SEQUENCE: 197
cgaaccactg aaca                                                     14

<210> SEQ ID NO 198
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 198
gaaagcccta cgaaccactg                                               20

<210> SEQ ID NO 199
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 199
ccacatcatc catata                                                   16

<210> SEQ ID NO 200
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 200
acatcatcca tata                                                     14

<210> SEQ ID NO 201
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 201
accacatcat ccatat                                                   16

<210> SEQ ID NO 202
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 202
cacatcatcc atat                                                     14

<210> SEQ ID NO 203
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 203
ccacatcatc cata                                                     14

<210> SEQ ID NO 204
```

```
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 204
accacatcat ccat                                                       14

<210> SEQ ID NO 205
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 205
tgtacagact tggcccccaa                                                 20

<210> SEQ ID NO 206
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 206
agggtttaaa tgtataccca                                                 20

<210> SEQ ID NO 207
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 207
gcaaacactt ggcacagacc                                                 20

<210> SEQ ID NO 208
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 208
cagcaaacac ttggca                                                     16

<210> SEQ ID NO 209
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 209
tcagcaaaca cttggc                                                     16

<210> SEQ ID NO 210
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 210
```

```
ccgcagtatg gatcggcaga                                              20

<210> SEQ ID NO 211
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 211
gcagtatgga tcggca                                                  16

<210> SEQ ID NO 212
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 212
gttccgcagt atggatcggc                                              20

<210> SEQ ID NO 213
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 213
ctaggagttc cgcagtatgg                                              20

<210> SEQ ID NO 214
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 214
cggctaggag ttccgcagta                                              20

<210> SEQ ID NO 215
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 215
aacaagcggc taggagttcc                                              20

<210> SEQ ID NO 216
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 216
caaaacaagc ggctaggagt                                              20

<210> SEQ ID NO 217
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 217
gagcaaaaca agcggctagg                                               20

<210> SEQ ID NO 218
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 218
tgcgagcaaa acaagcggct                                               20

<210> SEQ ID NO 219
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 219
acaaaggacg tccc                                                     14

<210> SEQ ID NO 220
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 220
gaggtgcgcc ccgtggtcgg                                               20

<210> SEQ ID NO 221
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 221
agagaggtgc gccccgtggt                                               20

<210> SEQ ID NO 222
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 222
taaagagagg tgcgccccgt                                               20

<210> SEQ ID NO 223
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 223
aaggcacaga cggg                                                     14

<210> SEQ ID NO 224

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 224
gtgaagcgaa gtgcacacgg                                          20

<210> SEQ ID NO 225
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 225
gaggtgaagc gaagtgcaca                                          20

<210> SEQ ID NO 226
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 226
gcagaggtga agcgaagtgc                                          20

<210> SEQ ID NO 227
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 227
cgtgcagagg tgaagcgaag                                          20

<210> SEQ ID NO 228
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 228
agtccaagag tcctcttatg                                          20

<210> SEQ ID NO 229
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 229
cagtctttga agta                                                14

<210> SEQ ID NO 230
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 230
```

```
tatgcctaca gcctcc                                                       16

<210> SEQ ID NO 231
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 231
ttatgcctac agcctc                                                       16

<210> SEQ ID NO 232
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 232
tttatgccta cagcct                                                       16

<210> SEQ ID NO 233
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 233
atttatgcct acagcc                                                       16

<210> SEQ ID NO 234
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 234
aatttatgcc tacagc                                                       16

<210> SEQ ID NO 235
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 235
caatttatgc ctacag                                                       16

<210> SEQ ID NO 236
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 236
ccaatttatg cctaca                                                       16

<210> SEQ ID NO 237
<211> LENGTH: 16
<212> TYPE: DNA
<213> ORGANISM: Artificial Sequence
<220> FEATURE:
```

-continued

<223> OTHER INFORMATION: Synthetic oligonucleotide

<400> SEQUENCE: 237
accaatttat gcctac                                                      16

<210> SEQ ID NO 238
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 238
aaagttgcat ggtgctggtg                                                  20

<210> SEQ ID NO 239
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 239
gaaaaagttg catggtgctg                                                  20

<210> SEQ ID NO 240
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 240
ggtgaaaaag ttgcatggtg                                                  20

<210> SEQ ID NO 241
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 241
agaggtgaaa aagttgcatg                                                  20

<210> SEQ ID NO 242
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 242
ggcagaggtg aaaagttgc                                                   20

<210> SEQ ID NO 243
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 243
ttaggcagag gtgaaaaagt                                                  20

<210> SEQ ID NO 244

```
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 244
ggcagaggtg aaaaag                                                     16

<210> SEQ ID NO 245
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 245
aggcagaggt gaaaaa                                                     16

<210> SEQ ID NO 246
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 246
tgattaggca gaggtgaaaa                                                 20

<210> SEQ ID NO 247
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 247
taggcagagg tgaaaa                                                     16

<210> SEQ ID NO 248
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 248
taggcagagg tgaa                                                       14

<210> SEQ ID NO 249
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 249
agatgattag gcagaggtga                                                 20

<210> SEQ ID NO 250
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 250
```

-continued agcttggagg cttgaacagt                                                          20

<210> SEQ ID NO 251
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 251
cacagcttgg aggcttgaac                                                          20

<210> SEQ ID NO 252
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 252
agcttggagg cttgaa                                                              16

<210> SEQ ID NO 253
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 253
cttggaggct tgaa                                                                14

<210> SEQ ID NO 254
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 254
cagcttggag gcttga                                                              16

<210> SEQ ID NO 255
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 255
gcttggaggc ttga                                                                14

<210> SEQ ID NO 256
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 256
acagcttgga ggcttg                                                              16

<210> SEQ ID NO 257
<211> LENGTH: 14
<212> TYPE: DNA
<213> ORGANISM: Artificial Sequence
<220> FEATURE:

<223> OTHER INFORMATION: Synthetic oligonucleotide

<400> SEQUENCE: 257
agcttggagg cttg                                                                  14

<210> SEQ ID NO 258
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 258
cacagcttgg aggctt                                                                16

<210> SEQ ID NO 259
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 259
cagcttggag gctt                                                                  14

<210> SEQ ID NO 260
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 260
gcacagcttg gaggct                                                                16

<210> SEQ ID NO 261
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 261
acagcttgga ggct                                                                  14

<210> SEQ ID NO 262
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 262
ggcacagctt ggaggc                                                                16

<210> SEQ ID NO 263
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 263
cacagcttgg aggc                                                                  14

<210> SEQ ID NO 264

```
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 264
aggcacagct tggagg                                                      16

<210> SEQ ID NO 265
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 265
gcacagcttg gagg                                                        14

<210> SEQ ID NO 266
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 266
aaggcacagc ttggag                                                      16

<210> SEQ ID NO 267
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 267
ggcacagctt ggag                                                        14

<210> SEQ ID NO 268
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 268
cacccaaggc acagcttgga                                                  20

<210> SEQ ID NO 269
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 269
caaggcacag cttgga                                                      16

<210> SEQ ID NO 270
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 270
```
aggcacagct tgga                                              14

<210> SEQ ID NO 271
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 271
ccaaggcaca gcttgg                                            16

<210> SEQ ID NO 272
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 272
agccacccaa ggcacagctt                                        20

<210> SEQ ID NO 273
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 273
caaagccacc caaggcacag                                        20

<210> SEQ ID NO 274
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 274
ccccaaagcc acccaaggca                                        20

<210> SEQ ID NO 275
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 275
atgccccaaa gccacccaag                                        20

<210> SEQ ID NO 276
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 276
tccatgcccc aaagccaccc                                        20

<210> SEQ ID NO 277
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 277
atgtccatgc cccaaagcca                                              20

<210> SEQ ID NO 278
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 278
ctccaaattc tttata                                                  16

<210> SEQ ID NO 279
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 279
ccaaattctt tata                                                    14

<210> SEQ ID NO 280
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 280
gctccaaatt ctttat                                                  16

<210> SEQ ID NO 281
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 281
tccaaattct ttat                                                    14

<210> SEQ ID NO 282
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 282
ctccaaattc ttta                                                    14

<210> SEQ ID NO 283
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 283
gctccaaatt cttt                                                    14

<210> SEQ ID NO 284

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 284
ggaaagaagt cagaaggcaa                                                    20

<210> SEQ ID NO 285
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 285
gtgcgaatcc acactc                                                        16

<210> SEQ ID NO 286
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 286
gcgaatccac actc                                                          14

<210> SEQ ID NO 287
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 287
tgcgaatcca cact                                                          14

<210> SEQ ID NO 288
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 288
gtgcgaatcc acac                                                          14

<210> SEQ ID NO 289
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 289
gagggagttc ttcttctagg                                                    20

<210> SEQ ID NO 290
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 290
```

```
cgaggcgagg gagttc                                              16

<210> SEQ ID NO 291
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 291
aggcgaggga gttc                                                14

<210> SEQ ID NO 292
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 292
gcgaggcgag ggagtt                                              16

<210> SEQ ID NO 293
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 293
gaggcgaggg agtt                                                14

<210> SEQ ID NO 294
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 294
tgcgaggcga gggagt                                              16

<210> SEQ ID NO 295
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 295
cgaggcgagg gagt                                                14

<210> SEQ ID NO 296
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 296
ctgcgaggcg agggag                                              16

<210> SEQ ID NO 297
<211> LENGTH: 14
<212> TYPE: DNA
<213> ORGANISM: Artificial Sequence
<220> FEATURE:
```

<223> OTHER INFORMATION: Synthetic oligonucleotide

<400> SEQUENCE: 297
gcgaggcgag ggag                                                           14

<210> SEQ ID NO 298
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 298
tctgcgaggc gaggga                                                         16

<210> SEQ ID NO 299
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 299
ccgagattga gatcttctgc                                                     20

<210> SEQ ID NO 300
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 300
cccaccttat gagtccaagg                                                     20

<210> SEQ ID NO 301
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 301
tgttcccaag aatatggtga                                                     20

<210> SEQ ID NO 302
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 302
tcccaagaat atggtg                                                         16

<210> SEQ ID NO 303
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 303
ttcccaagaa tatggt                                                         16

<210> SEQ ID NO 304

```
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 304
gttcccaaga atatgg                                                     16

<210> SEQ ID NO 305
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 305
tgttcccaag aatatg                                                     16

<210> SEQ ID NO 306
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 306
ttgttcccaa gaatat                                                     16

<210> SEQ ID NO 307
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 307
tgttcccaag aata                                                       14

<210> SEQ ID NO 308
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 308
gaaagaatcc cagaggattg                                                 20

<210> SEQ ID NO 309
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 309
actgcatggc ctgaggatga                                                 20

<210> SEQ ID NO 310
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 310
```

```
ccactgcatg gcctgaggat                                              20

<210> SEQ ID NO 311
<211> LENGTH: 19
<212> TYPE: DNA
<213> ORGANISM: Artificial Sequence
<220> FEATURE:
<223> OTHER INFORMATION: Primer

<400> SEQUENCE: 311
ccaaaccttc ggacggaaa                                               19

<210> SEQ ID NO 312
<211> LENGTH: 19
<212> TYPE: DNA
<213> ORGANISM: Artificial Sequence
<220> FEATURE:
<223> OTHER INFORMATION: Primer

<400> SEQUENCE: 312
tgaggcccac tcccatagg                                               19

<210> SEQ ID NO 313
<211> LENGTH: 26
<212> TYPE: DNA
<213> ORGANISM: Artificial Sequence
<220> FEATURE:
<223> OTHER INFORMATION: Probe

<400> SEQUENCE: 313
cccatcatcc tgggctttcg gaaaat                                       26

<210> SEQ ID NO 314
<211> LENGTH: 24
<212> TYPE: DNA
<213> ORGANISM: Artificial Sequence
<220> FEATURE:
<223> OTHER INFORMATION: Primer

<400> SEQUENCE: 314
atcctatcaa cacttccgga aact                                         24

<210> SEQ ID NO 315
<211> LENGTH: 16
<212> TYPE: DNA
<213> ORGANISM: Artificial Sequence
<220> FEATURE:
<223> OTHER INFORMATION: Primer

<400> SEQUENCE: 315
cgacgcggcg attgag                                                  16

<210> SEQ ID NO 316
<211> LENGTH: 24
<212> TYPE: DNA
<213> ORGANISM: Artificial Sequence
<220> FEATURE:
<223> OTHER INFORMATION: Probe

<400> SEQUENCE: 316
aagaactccc tcgcctcgca gacg                                         24

<210> SEQ ID NO 317
<211> LENGTH: 21
<212> TYPE: DNA
<213> ORGANISM: Artificial Sequence
<220> FEATURE:
```

```
<223> OTHER INFORMATION: Primer

<400> SEQUENCE: 317
ccgaccttga ggcatacttc a                                              21

<210> SEQ ID NO 318
<211> LENGTH: 27
<212> TYPE: DNA
<213> ORGANISM: Artificial Sequence
<220> FEATURE:
<223> OTHER INFORMATION: Primer

<400> SEQUENCE: 318
aatttatgcc tacagcctcc tagtaca                                        27

<210> SEQ ID NO 319
<211> LENGTH: 20
<212> TYPE: DNA
<213> ORGANISM: Artificial Sequence
<220> FEATURE:
<223> OTHER INFORMATION: Probe

<400> SEQUENCE: 319
ttaaagactg ggaggagttg                                                20

<210> SEQ ID NO 320
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 320
ccttccctga aggttcctcc                                                20

<210> SEQ ID NO 321
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 321
tggtgaaagg ttgtggaatt                                                20

<210> SEQ ID NO 322
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 322
gtttggtgaa aggttgtgga                                                20

<210> SEQ ID NO 323
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 323
agagtttggt gaaaggttgt                                                20

<210> SEQ ID NO 324
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 324
tgcagagttt ggtgaaaggt                                                   20

<210> SEQ ID NO 325
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 325
tcttgcagag tttggtgaaa                                                   20

<210> SEQ ID NO 326
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 326
ggatcttgca gagtttggtg                                                   20

<210> SEQ ID NO 327
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 327
ctgggatctt gcagagtttg                                                   20

<210> SEQ ID NO 328
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 328
actctgggat cttgcagagt                                                   20

<210> SEQ ID NO 329
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 329
ctcactctgg gatcttgcag                                                   20

<210> SEQ ID NO 330
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 330
```

```
cctctcactc tgggatcttg                                              20

<210> SEQ ID NO 331
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 331
aggcctctca ctctgggatc                                              20

<210> SEQ ID NO 332
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 332
tacaggcctc tcactctggg                                              20

<210> SEQ ID NO 333
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 333
aaatacaggc ctctcactct                                              20

<210> SEQ ID NO 334
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 334
gggaaataca ggcctctcac                                              20

<210> SEQ ID NO 335
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 335
gcagggaaat acaggcctct                                              20

<210> SEQ ID NO 336
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 336
ccagcaggga aatacaggcc                                              20

<210> SEQ ID NO 337
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 337
ccaccagcag ggaaatacag                                               20

<210> SEQ ID NO 338
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 338
gagccaccag cagggaaata                                               20

<210> SEQ ID NO 339
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 339
ctggagccac cagcagggaa                                               20

<210> SEQ ID NO 340
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 340
actggagcca ccagcaggga                                               20

<210> SEQ ID NO 341
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 341
aactggagcc accagcaggg                                               20

<210> SEQ ID NO 342
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 342
tgaactggag ccaccagcag                                               20

<210> SEQ ID NO 343
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 343
ctgaactgga gccaccagca                                               20

<210> SEQ ID NO 344

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 344
tcctgaactg gagccaccag                                              20

<210> SEQ ID NO 345
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 345
ctcctgaact ggagccacca                                              20

<210> SEQ ID NO 346
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 346
tgctcctgaa ctggagccac                                              20

<210> SEQ ID NO 347
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 347
tactgctcct gaactggagc                                              20

<210> SEQ ID NO 348
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 348
gtttactgct cctgaactgg                                              20

<210> SEQ ID NO 349
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 349
agggtttact gctcctgaac                                              20

<210> SEQ ID NO 350
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 350
```

-continued aacagggttt actgctcctg                                          20

<210> SEQ ID NO 351
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 351
cggaacaggg tttactgctc                                          20

<210> SEQ ID NO 352
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 352
agtcggaaca gggtttactg                                          20

<210> SEQ ID NO 353
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 353
agtagtcgga acagggttta                                          20

<210> SEQ ID NO 354
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 354
ggcagtagtc ggaacagggt                                          20

<210> SEQ ID NO 355
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 355
agaggcagta gtcggaacag                                          20

<210> SEQ ID NO 356
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 356
gggagaggca gtagtcggaa                                          20

<210> SEQ ID NO 357
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 357
taagggagag gcagtagtcg                                               20

<210> SEQ ID NO 358
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 358
cgataaggga gaggcagtag                                               20

<210> SEQ ID NO 359
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 359
tgacgataag ggagaggcag                                               20

<210> SEQ ID NO 360
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 360
gattgacgat aagggagagg                                               20

<210> SEQ ID NO 361
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 361
gaagattgac gataagggag                                               20

<210> SEQ ID NO 362
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 362
cgagaagatt gacgataagg                                               20

<210> SEQ ID NO 363
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 363
cctcgagaag attgacgata                                               20

<210> SEQ ID NO 364
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 364
aatcctcgag aagattgacg                                              20

<210> SEQ ID NO 365
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 365
cccaatcctc gagaagattg                                              20

<210> SEQ ID NO 366
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 366
gtccccaatc ctcgagaaga                                              20

<210> SEQ ID NO 367
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 367
agggtcccca atcctcgaga                                              20

<210> SEQ ID NO 368
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 368
cgcagggtcc ccaatcctcg                                              20

<210> SEQ ID NO 369
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 369
cagcgcaggg tccccaatcc                                              20

<210> SEQ ID NO 370
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 370
```

-continued gttcagcgca gggtccccaa                                          20

<210> SEQ ID NO 371
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 371
catgttcagc gcagggtccc                                          20

<210> SEQ ID NO 372
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 372
ctccatgttc agcgcagggt                                          20

<210> SEQ ID NO 373
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 373
gttctccatg ttcagcgcag                                          20

<210> SEQ ID NO 374
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 374
gatgttctcc atgttcagcg                                          20

<210> SEQ ID NO 375
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 375
tgtgatgttc tccatgttca                                          20

<210> SEQ ID NO 376
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 376
tcctgatgtg atgttctcca                                          20

<210> SEQ ID NO 377
<211> LENGTH: 20
<212> TYPE: DNA
<213> ORGANISM: Artificial Sequence
<220> FEATURE:

-continued

<223> OTHER INFORMATION: Synthetic oligonucleotide

<400> SEQUENCE: 377
gaatcctgat gtgatgttct					20

<210> SEQ ID NO 378
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 378
taggaatcct gatgtgatgt					20

<210> SEQ ID NO 379
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 379
tcctaggaat cctgatgtga					20

<210> SEQ ID NO 380
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 380
gggtcctagg aatcctgatg					20

<210> SEQ ID NO 381
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 381
cgcctgtaac acgagaaggg					20

<210> SEQ ID NO 382
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 382
ccccgcctgt aacacgagaa					20

<210> SEQ ID NO 383
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 383 aaacccccgcc tgtaacacga					20

<210> SEQ ID NO 384

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 384
aaaaccccgc ctgtaacacg                                           20

<210> SEQ ID NO 385
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 385
gaaaaacccc gcctgtaaca                                           20

<210> SEQ ID NO 386
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 386 agaaaaccc cgcctgtaac                                            20

<210> SEQ ID NO 387
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 387
caagaaaaac cccgcctgta                                           20

<210> SEQ ID NO 388
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 388
caacaagaaa aaccccgcct                                           20

<210> SEQ ID NO 389
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 389
tcaacaagaa aaaccccgcc                                           20

<210> SEQ ID NO 390
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 390
```

```
tgtcaacaag aaaaaccccg                                          20

<210> SEQ ID NO 391
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 391
ttgtcaacaa gaaaaacccc                                          20

<210> SEQ ID NO 392
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 392
tcttgtcaac aagaaaaacc                                          20

<210> SEQ ID NO 393
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 393
gattcttgtc aacaagaaaa                                          20

<210> SEQ ID NO 394
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 394
gaggattctt gtcaacaaga                                          20

<210> SEQ ID NO 395
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 395
tgtgaggatt cttgtcaaca                                          20

<210> SEQ ID NO 396
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 396
tattgtgagg attcttgtca                                          20

<210> SEQ ID NO 397
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 397
cggtattgtg aggattcttg                                                    20

<210> SEQ ID NO 398
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 398
ctgcggtatt gtgaggattc                                                    20

<210> SEQ ID NO 399
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 399
actctgcggt attgtgagga                                                    20

<210> SEQ ID NO 400
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 400
tagactctgc ggtattgtga                                                    20

<210> SEQ ID NO 401
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 401
gtctagactc tgcggtattg                                                    20

<210> SEQ ID NO 402
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 402
cgagtctaga ctctgcggta                                                    20

<210> SEQ ID NO 403
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 403
ccacgagtct agactctgcg                                                    20

<210> SEQ ID NO 404

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 404
accacgagtc tagactctgc                                               20

<210> SEQ ID NO 405
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 405
ccaccacgag tctagactct                                               20

<210> SEQ ID NO 406
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 406
tccaccacga gtctagactc                                               20

<210> SEQ ID NO 407
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 407
agtccaccac gagtctagac                                               20

<210> SEQ ID NO 408
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 408
aagtccacca cgagtctaga                                               20

<210> SEQ ID NO 409
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 409
attgagagaa gtccaccacg                                               20

<210> SEQ ID NO 410
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 410
```
aaaattgaga gaagtccacc                                              20

<210> SEQ ID NO 411
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 411
tagaaaattg agagaagtcc                                              20

<210> SEQ ID NO 412
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 412
ccctagaaaa ttgagagaag                                              20

<210> SEQ ID NO 413
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 413 tcccccctaga aaattgagag                                             20

<210> SEQ ID NO 414
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 414 agttcccct agaaaattga                                               20

<210> SEQ ID NO 415
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 415
ggtagttccc cctagaaaat                                              20

<210> SEQ ID NO 416
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 416
cacggtagtt cccctagaa                                               20

<210> SEQ ID NO 417
<211> LENGTH: 20
<212> TYPE: DNA
<213> ORGANISM: Artificial Sequence
<220> FEATURE:

-continued

<223> OTHER INFORMATION: Synthetic oligonucleotide

<400> SEQUENCE: 417
acacacggta gttccccta                                           20

<210> SEQ ID NO 418
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 418
aagacacacg gtagttcccc                                          20

<210> SEQ ID NO 419
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 419
gccaagacac acggtagttc                                          20

<210> SEQ ID NO 420
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 420
ttggccaaga cacacggtag                                          20

<210> SEQ ID NO 421
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 421
tttggccaag acacacggta                                          20

<210> SEQ ID NO 422
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 422
ttttggccaa gacacacggt                                          20

<210> SEQ ID NO 423
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 423
aattttggcc aagacacacg                                          20

<210> SEQ ID NO 424

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 424
gaattttggc caagacacac                                              20

<210> SEQ ID NO 425
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 425 tgcgaattttt ggccaagaca                                             20

<210> SEQ ID NO 426
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 426
actgcgaatt ttggccaaga                                              20

<210> SEQ ID NO 427
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 427
gactgcgaat tttggccaag                                              20

<210> SEQ ID NO 428
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 428
gggactgcga attttggcca                                              20

<210> SEQ ID NO 429
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 429
gtgagtgatt ggaggttggg                                              20

<210> SEQ ID NO 430
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 430
```
ttggtgagtg attggaggtt                                           20

<210> SEQ ID NO 431
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 431
aggttggtga gtgattggag                                           20

<210> SEQ ID NO 432
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 432
aggaggttgg tgagtgattg                                           20

<210> SEQ ID NO 433
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 433
gacaggaggt tggtgagtga                                           20

<210> SEQ ID NO 434
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 434
gaggacagga ggttggtgag                                           20

<210> SEQ ID NO 435
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 435
ttggaggaca ggaggttggt                                           20

<210> SEQ ID NO 436
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 436
aagttggagg acaggaggtt                                           20

<210> SEQ ID NO 437
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 437
gacaagttgg aggacaggag                                                20

<210> SEQ ID NO 438
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 438
caggacaagt tggaggacag                                                20

<210> SEQ ID NO 439
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 439
aaccaggaca agttggagga                                                20

<210> SEQ ID NO 440
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 440
gataaccagg acaagttgga                                                20

<210> SEQ ID NO 441
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 441
agcgataacc aggacaagtt                                                20

<210> SEQ ID NO 442
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 442
cagcgataac caggacaagt                                                20

<210> SEQ ID NO 443
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 443
ccagcgataa ccaggacaag                                                20

<210> SEQ ID NO 444
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 444
atccagcgat aaccaggaca                                              20

<210> SEQ ID NO 445
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 445
catccagcga taaccaggac                                              20

<210> SEQ ID NO 446
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 446
cacatccagc gataaccagg                                              20

<210> SEQ ID NO 447
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 447
acacatccag cgataaccag                                              20

<210> SEQ ID NO 448
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 448
agacacatcc agcgataacc                                              20

<210> SEQ ID NO 449
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 449
cagacacatc cagcgataac                                              20

<210> SEQ ID NO 450
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 450
```
cgcagacaca tccagcgata                                              20

<210> SEQ ID NO 451
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 451
cgccgcagac acatccagcg                                              20

<210> SEQ ID NO 452
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 452
agaggaagat gataaaacgc                                              20

<210> SEQ ID NO 453
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 453
tgaagaggaa gatgataaaa                                              20

<210> SEQ ID NO 454
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 454
ggatgaagag gaagatgata                                              20

<210> SEQ ID NO 455
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 455
gcaggatgaa gaggaagatg                                              20

<210> SEQ ID NO 456
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 456
gcagcaggat gaagaggaag                                              20

<210> SEQ ID NO 457
<211> LENGTH: 20
<212> TYPE: DNA
<213> ORGANISM: Artificial Sequence
<220> FEATURE:

-continued

<223> OTHER INFORMATION: Synthetic oligonucleotide

<400> SEQUENCE: 457
atagcagcag gatgaagagg					20

<210> SEQ ID NO 458
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 458
ggcatagcag caggatgaag					20

<210> SEQ ID NO 459
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 459
aggcatagca gcaggatgaa					20

<210> SEQ ID NO 460
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 460
gaggcatagc agcaggatga					20

<210> SEQ ID NO 461
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 461
caagaagatg aggcatagca					20

<210> SEQ ID NO 462
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 462
caacaagaag atgaggcata					20

<210> SEQ ID NO 463
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 463
aaccaacaag aagatgaggc					20

<210> SEQ ID NO 464

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 464
aagaaccaac aagaagatga                                              20

<210> SEQ ID NO 465
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 465
cagaagaacc aacaagaaga                                              20

<210> SEQ ID NO 466
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 466
gtccagaaga accaacaaga                                              20

<210> SEQ ID NO 467
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 467
atagtccaga agaaccaaca                                              20

<210> SEQ ID NO 468
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 468
ttgatagtcc agaagaacca                                              20

<210> SEQ ID NO 469
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 469
accttgatag tccagaagaa                                              20

<210> SEQ ID NO 470
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 470
```
cataccttga tagtccagaa                                              20

<210> SEQ ID NO 471
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 471
caacatacct tgatagtcca                                              20

<210> SEQ ID NO 472
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 472
gggcaacata ccttgatagt                                              20

<210> SEQ ID NO 473
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 473
aacgggcaac ataccttgat                                              20

<210> SEQ ID NO 474
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 474
aaacgggcaa cataccttga                                              20

<210> SEQ ID NO 475
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 475
acaaacgggc aacatacctt                                              20

<210> SEQ ID NO 476
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 476
gacaaacggg caacatacct                                              20

<210> SEQ ID NO 477
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 477
aggacaaacg ggcaacatac                                          20

<210> SEQ ID NO 478
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 478
tagaggacaa acgggcaaca                                          20

<210> SEQ ID NO 479
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 479
aattagagga caaacgggca                                          20

<210> SEQ ID NO 480
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 480
tggaattaga ggacaaacgg                                          20

<210> SEQ ID NO 481
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 481
ctggaattag aggacaaacg                                          20

<210> SEQ ID NO 482
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 482
tcctggaatt agaggacaaa                                          20

<210> SEQ ID NO 483
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 483
atcctggaat tagaggacaa                                          20

<210> SEQ ID NO 484
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 484
ggatcctgga attagaggac                                               20

<210> SEQ ID NO 485
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 485
tgaggatcct ggaattagag                                               20

<210> SEQ ID NO 486
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 486
ggttgaggat cctggaatta                                               20

<210> SEQ ID NO 487
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 487
ggtggttgag gatcctggaa                                               20

<210> SEQ ID NO 488
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 488
gctggtggtt gaggatcctg                                               20

<210> SEQ ID NO 489
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 489
cgtgctggtg gttgaggatc                                               20

<210> SEQ ID NO 490
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 490
```
tcccgtgctg gtggttgagg                                              20

<210> SEQ ID NO 491
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 491
tggtcccgtg ctggtggttg                                              20

<210> SEQ ID NO 492
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 492
gcatggtccc gtgctggtgg                                              20

<210> SEQ ID NO 493
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 493
tcggcatggt cccgtgctgg                                              20

<210> SEQ ID NO 494
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 494
ggttcggcat ggtcccgtgc                                              20

<210> SEQ ID NO 495
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 495
gcaggttcgg catggtcccg                                              20

<210> SEQ ID NO 496
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 496
catgcaggtt cggcatggtc                                              20

<210> SEQ ID NO 497
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 497
agtcatgcag gttcggcatg                                               20

<210> SEQ ID NO 498
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 498
agtagtcatg caggttcggc                                               20

<210> SEQ ID NO 499
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 499
agcagtagtc atgcaggttc                                               20

<210> SEQ ID NO 500
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 500
ttgagcagta gtcatgcagg                                               20

<210> SEQ ID NO 501
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 501
tccttgagca gtagtcatgc                                               20

<210> SEQ ID NO 502
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 502
ggttccttga gcagtagtca                                               20

<210> SEQ ID NO 503
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 503
agaggttcct tgagcagtag                                               20

<210> SEQ ID NO 504

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 504
catagaggtt ccttgagcag                                              20

<210> SEQ ID NO 505
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 505
atacatagag gttccttgag                                              20

<210> SEQ ID NO 506
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 506
gggatacata gaggttcctt                                              20

<210> SEQ ID NO 507
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 507
ggagggatac atagaggttc                                              20

<210> SEQ ID NO 508
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 508
acaggaggga tacatagagg                                              20

<210> SEQ ID NO 509
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 509
gcaacaggag ggatacatag                                              20

<210> SEQ ID NO 510
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 510
```
acagcaacag gagggataca                                                    20

<210> SEQ ID NO 511
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 511
ggtacagcaa caggagggat                                                    20

<210> SEQ ID NO 512
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 512
tttggtacag caacaggagg                                                    20

<210> SEQ ID NO 513
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 513
aggtttggta cagcaacagg                                                    20

<210> SEQ ID NO 514
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 514
cgaaggtttg gtacagcaac                                                    20

<210> SEQ ID NO 515
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 515
gtccgaaggt ttggtacagc                                                    20

<210> SEQ ID NO 516
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 516
tccgtccgaa ggtttggtac                                                    20

<210> SEQ ID NO 517
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 517
atttccgtcc gaaggtttgg                                                  20

<210> SEQ ID NO 518
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 518
gcaatttccg tccgaaggtt                                                  20

<210> SEQ ID NO 519
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 519
ggtgcaattt ccgtccgaag                                                  20

<210> SEQ ID NO 520
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 520
acaggtgcaa tttccgtccg                                                  20

<210> SEQ ID NO 521
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 521
aatacaggtg caatttccgt                                                  20

<210> SEQ ID NO 522
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 522
gggaatacag gtgcaatttc                                                  20

<210> SEQ ID NO 523
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 523
gatgggaata caggtgcaat                                                  20

<210> SEQ ID NO 524
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 524
agcccaggat gatgggatgg                                              20

<210> SEQ ID NO 525
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 525
gaaagcccag gatgatggga                                              20

<210> SEQ ID NO 526
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 526
tccgaaagcc caggatgatg                                              20

<210> SEQ ID NO 527
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 527
ttttccgaaa gcccaggatg                                              20

<210> SEQ ID NO 528
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 528
gaattttccg aaagcccagg                                              20

<210> SEQ ID NO 529
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 529
taggaatttt ccgaaagccc                                              20

<210> SEQ ID NO 530
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 530
```

```
cccataggaat tttccgaaag                                               20

<210> SEQ ID NO 531
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 531
ctcccatagg aattttccga                                                20

<210> SEQ ID NO 532
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 532
ccactcccat aggaattttc                                                20

<210> SEQ ID NO 533
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 533
ggcccactcc cataggaatt                                                20

<210> SEQ ID NO 534
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 534
tgaggcccac tcccatagga                                                20

<210> SEQ ID NO 535
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 535
ggctgaggcc cactcccata                                                20

<210> SEQ ID NO 536
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 536
acgggctgag gcccactccc                                                20

<210> SEQ ID NO 537
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 537
gaaacgggct gaggcccact                                          20

<210> SEQ ID NO 538
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 538
ggagaaacgg gctgaggccc                                          20

<210> SEQ ID NO 539
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 539
ccaggagaaa cgggctgagg                                          20

<210> SEQ ID NO 540
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 540
gagccaggag aaacgggctg                                          20

<210> SEQ ID NO 541
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 541
actgagccag gagaaacggg                                          20

<210> SEQ ID NO 542
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 542
taaactgagc caggagaaac                                          20

<210> SEQ ID NO 543
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 543
tagtaaactg agccaggaga                                          20

<210> SEQ ID NO 544

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 544
cactagtaaa ctgagccagg                                              20

<210> SEQ ID NO 545
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 545
gcactagtaa actgagccag                                              20

<210> SEQ ID NO 546
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 546
tggcactagt aaactgagcc                                              20

<210> SEQ ID NO 547
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 547
atggcactag taaactgagc                                              20

<210> SEQ ID NO 548
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 548
aaatggcact agtaaactga                                              20

<210> SEQ ID NO 549
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 549
aacaaatggc actagtaaac                                              20

<210> SEQ ID NO 550
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 550
```

-continued gaacaaatgg cactagtaaa                                               20

<210> SEQ ID NO 551
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 551
ctgaacaaat ggcactagta                                               20

<210> SEQ ID NO 552
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 552
actgaacaaa tggcactagt                                               20

<210> SEQ ID NO 553
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 553
ccactgaaca aatggcacta                                               20

<210> SEQ ID NO 554
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 554
accactgaac aaatggcact                                               20

<210> SEQ ID NO 555
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 555
gaaccactga acaaatggca                                               20

<210> SEQ ID NO 556
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 556
tacgaaccac tgaacaaatg                                               20

<210> SEQ ID NO 557
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 557
ctacgaacca ctgaacaaat                                                    20

<210> SEQ ID NO 558
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 558
ccctacgaac cactgaacaa                                                    20

<210> SEQ ID NO 559
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 559
gccctacgaa ccactgaaca                                                    20

<210> SEQ ID NO 560
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 560
aagccctacg aaccactgaa                                                    20

<210> SEQ ID NO 561
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 561
aaagccctac gaaccactga                                                    20

<210> SEQ ID NO 562
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 562
ggaaagccct acgaaccact                                                    20

<210> SEQ ID NO 563
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 563
gggaaagccc tacgaaccac                                                    20

<210> SEQ ID NO 564

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 564
actgaaagcc aaacagtggg                                               20

<210> SEQ ID NO 565
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 565
ataactgaaa gccaaacagt                                               20

<210> SEQ ID NO 566
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 566
catataactg aaagccaaac                                               20

<210> SEQ ID NO 567
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 567
atccatataa ctgaaagcca                                               20

<210> SEQ ID NO 568
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 568
atcatccata taactgaaag                                               20

<210> SEQ ID NO 569
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 569
cacatcatcc atataactga                                               20

<210> SEQ ID NO 570
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 570
```

-continued taccacatca tccatataac                                        20

<210> SEQ ID NO 571
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 571 cataccaca tcatccatat                                         20

<210> SEQ ID NO 572
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 572
ccccaatacc acatcatcca                                        20

<210> SEQ ID NO 573
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 573
ggcccccaat accacatcat                                        20

<210> SEQ ID NO 574
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 574
cttggccccc aataccacat                                        20

<210> SEQ ID NO 575
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 575
agacttggcc cccaatacca                                        20

<210> SEQ ID NO 576
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 576
tacagacttg gcccccaata                                        20

<210> SEQ ID NO 577
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 577
ctgtacagac ttggccccca                                                   20

<210> SEQ ID NO 578
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 578
atgctgtaca gacttggccc                                                   20

<210> SEQ ID NO 579
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 579
aagatgctgt acagacttgg                                                   20

<210> SEQ ID NO 580
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 580
ctcaagatgc tgtacagact                                                   20

<210> SEQ ID NO 581
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 581
ggactcaaga tgctgtacag                                                   20

<210> SEQ ID NO 582
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 582
aagggactca agatgctgta                                                   20

<210> SEQ ID NO 583
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 583
aaaaagggac tcaagatgct                                                   20

<210> SEQ ID NO 584

<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 584
ggtaaaaagg gactcaagat                                               20

<210> SEQ ID NO 585
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 585
agcggtaaaa agggactcaa                                               20

<210> SEQ ID NO 586
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 586
aacagcggta aaagggact                                                20

<210> SEQ ID NO 587
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 587
ggtaacagcg gtaaaaggg                                                20

<210> SEQ ID NO 588
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 588
attggtaaca gcggtaaaaa                                               20

<210> SEQ ID NO 589
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 589
aaaattggta acagcggtaa                                               20

<210> SEQ ID NO 590
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 590

-continued aagaaaattg gtaacagcgg                                              20

<210> SEQ ID NO 591
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 591 caaagaaaa ttggtaacag                                               20

<210> SEQ ID NO 592
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 592
agacaaaaga aaattggtaa                                              20

<210> SEQ ID NO 593
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 593
caaagacaaa agaaaattgg                                              20

<210> SEQ ID NO 594
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 594
acccaaagac aaagaaaat                                               20

<210> SEQ ID NO 595
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 595
tatacccaaa gacaaaagaa                                              20

<210> SEQ ID NO 596
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 596
atgtataccc aaagacaaaa                                              20

<210> SEQ ID NO 597
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 597
taaatgtata cccaaagaca                                               20

<210> SEQ ID NO 598
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 598
gtttaaatgt atcccaaag                                                20

<210> SEQ ID NO 599
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 599
ggtttaaatg tatcccaaa                                                20

<210> SEQ ID NO 600
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 600
gggtttaaat gtatcccaa                                                20

<210> SEQ ID NO 601
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 601
tagggtttaa atgtataccc                                               20

<210> SEQ ID NO 602
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 602
ttagggttta aatgtatacc                                               20

<210> SEQ ID NO 603
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 603
tgttagggtt taaatgtata                                               20

<210> SEQ ID NO 604
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 604
ttttgttagg gtttaaatgt                                               20

<210> SEQ ID NO 605
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 605
aaccccatct ctttgttttg                                               20

<210> SEQ ID NO 606
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 606
agtaacccca tctctttgtt                                               20

<210> SEQ ID NO 607
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 607
gagagtaacc ccatctcttt                                               20

<210> SEQ ID NO 608
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 608
tcagagagta accccatctc                                               20

<210> SEQ ID NO 609
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 609
aattcagaga gtaaccccat                                               20

<210> SEQ ID NO 610
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 610
```

```
taaaattcag agagtaaccc                                             20

<210> SEQ ID NO 611
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 611
ccataaaatt cagagagtaa                                             20

<210> SEQ ID NO 612
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 612
aacccataaa attcagagag                                             20

<210> SEQ ID NO 613
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 613
cataacccat aaaattcaga                                             20

<210> SEQ ID NO 614
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 614
tgacataacc cataaaattc                                             20

<210> SEQ ID NO 615
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 615
caatgacata acccataaaa                                             20

<210> SEQ ID NO 616
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 616
ttccaatgac ataacccata                                             20

<210> SEQ ID NO 617
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 617
aacttccaat gacataaccc                    20

<210> SEQ ID NO 618
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 618
cataacttcc aatgacataa                    20

<210> SEQ ID NO 619
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 619
acccataact tccaatgaca                    20

<210> SEQ ID NO 620
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 620
aggacccata acttccaatg                    20

<210> SEQ ID NO 621
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 621
gcaaggaccc ataacttcca                    20

<210> SEQ ID NO 622
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 622
gtggcaagga cccataactt                    20

<210> SEQ ID NO 623
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 623
cttgtggcaa ggacccataa                    20

<210> SEQ ID NO 624

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 624
gttcttgtgg caaggaccca                                               20

<210> SEQ ID NO 625
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 625
tgtgttcttg tggcaaggac                                               20

<210> SEQ ID NO 626
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 626
tgatgtgttc ttgtggcaag                                               20

<210> SEQ ID NO 627
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 627
gtatgatgtg ttcttgtggc                                               20

<210> SEQ ID NO 628
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 628
tttgtatgat gtgttcttgt                                               20

<210> SEQ ID NO 629
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 629
aaacattctt tgattttttg                                               20

<210> SEQ ID NO 630
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 630
```

| | |
|---|---|
| ctaaaacatt ctttgattt | 20 |

<210> SEQ ID NO 631
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 631

| | |
|---|---|
| tttctaaaac attctttgat | 20 |

<210> SEQ ID NO 632
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 632

| | |
|---|---|
| agttttctaa aacattcttt | 20 |

<210> SEQ ID NO 633
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 633

| | |
|---|---|
| ggaagttttc taaacattc | 20 |

<210> SEQ ID NO 634
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 634

| | |
|---|---|
| ataggaagtt ttctaaaaca | 20 |

<210> SEQ ID NO 635
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 635

| | |
|---|---|
| ttaataggaa gttttctaaa | 20 |

<210> SEQ ID NO 636
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 636

| | |
|---|---|
| ctgttaatag gaagttttct | 20 |

<210> SEQ ID NO 637
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 637
ggcctgttaa taggaagttt                                        20

<210> SEQ ID NO 638
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 638
ataggcctgt taataggaag                                        20

<210> SEQ ID NO 639
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 639
tcaataggcc tgttaatagg                                        20

<210> SEQ ID NO 640
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 640
caatcaatag gcctgttaat                                        20

<210> SEQ ID NO 641
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 641
ttccaatcaa taggcctgtt                                        20

<210> SEQ ID NO 642
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 642
actttccaat caataggcct                                        20

<210> SEQ ID NO 643
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 643
catactttcc aatcaatagg                                        20

<210> SEQ ID NO 644

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 644
tgacatactt tccaatcaat                                                    20

<210> SEQ ID NO 645
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 645
cgttgacata ctttccaatc                                                    20

<210> SEQ ID NO 646
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 646
cccaaaagac ccacaattcg                                                    20

<210> SEQ ID NO 647
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 647
aaacccaaaa gacccacaat                                                    20

<210> SEQ ID NO 648
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 648
gcaaaaccca aaagacccac                                                    20

<210> SEQ ID NO 649
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 649
gcagcaaaac ccaaaagacc                                                    20

<210> SEQ ID NO 650
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 650
```

```
aaccacattg tgtaaatggg                                        20

<210> SEQ ID NO 651
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 651
gataaccaca ttgtgtaaat                                        20

<210> SEQ ID NO 652
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 652
caggataacc acattgtgta                                        20

<210> SEQ ID NO 653
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 653
acgcaggata accacattgt                                        20

<210> SEQ ID NO 654
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 654
ttaacgcagg ataaccacat                                        20

<210> SEQ ID NO 655
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 655
gcattaacgc aggataacca                                        20

<210> SEQ ID NO 656
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 656
agggcattaa cgcaggataa                                        20

<210> SEQ ID NO 657
<211> LENGTH: 20
<212> TYPE: DNA
<213> ORGANISM: Artificial Sequence
<220> FEATURE:
```

-continued

<223> OTHER INFORMATION: Synthetic oligonucleotide

<400> SEQUENCE: 657
acaagggcat taacgcagga          20

<210> SEQ ID NO 658
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 658
catacaaggg cattaacgca          20

<210> SEQ ID NO 659
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 659
atgcatacaa gggcattaac          20

<210> SEQ ID NO 660
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 660
tacatgcata caagggcatt          20

<210> SEQ ID NO 661
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 661
gaatacatgc atacaagggc          20

<210> SEQ ID NO 662
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 662
attgaataca tgcatacaag          20

<210> SEQ ID NO 663
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 663
tagattgaat acatgcatac          20

<210> SEQ ID NO 664

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 664
gcttagattg aatacatgca                                               20

<210> SEQ ID NO 665
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 665
cctgcttaga ttgaatacat                                               20

<210> SEQ ID NO 666
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 666
aagcctgctt agattgaata                                               20

<210> SEQ ID NO 667
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 667
tgaaagcctg cttagattga                                               20

<210> SEQ ID NO 668
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 668
aagtgaaagc ctgcttagat                                               20

<210> SEQ ID NO 669
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 669
agaaagtgaa agcctgctta                                               20

<210> SEQ ID NO 670
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 670
```

-continued gcgagaaagt gaaagcctgc                                             20

<210> SEQ ID NO 671
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 671
ttggcgagaa agtgaaagcc                                             20

<210> SEQ ID NO 672
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 672
aagttggcga gaaagtgaaa                                             20

<210> SEQ ID NO 673
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 673
tgtaagttgg cgagaaagtg                                             20

<210> SEQ ID NO 674
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 674
ccttgtaagt tggcgagaaa                                             20

<210> SEQ ID NO 675
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 675
aggccttgta agttggcgag                                             20

<210> SEQ ID NO 676
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 676
gaaaggcctt gtaagttggc                                             20

<210> SEQ ID NO 677
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 677
acagaaaggc cttgtaagtt                                               20

<210> SEQ ID NO 678
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 678
tacacagaaa ggccttgtaa                                               20

<210> SEQ ID NO 679
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 679
gtttacacag aaaggccttg                                               20

<210> SEQ ID NO 680
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 680
attgtttaca cagaaaggcc                                               20

<210> SEQ ID NO 681
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 681
ggtattgttt acacagaaag                                               20

<210> SEQ ID NO 682
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 682
tcaggtattg tttacacaga                                               20

<210> SEQ ID NO 683
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 683
ggttcaggta ttgtttacac                                               20

<210> SEQ ID NO 684

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 684
aaaggttcag gtattgttta                                                     20

<210> SEQ ID NO 685
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 685
ggtaaaggtt caggtattgt                                                     20

<210> SEQ ID NO 686
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 686
tggccgttgc cgggcaacgg                                                     20

<210> SEQ ID NO 687
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 687
acctggccgt tgccgggcaa                                                     20

<210> SEQ ID NO 688
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 688
cagacctggc cgttgccggg                                                     20

<210> SEQ ID NO 689
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 689
gcacagacct ggccgttgcc                                                     20

<210> SEQ ID NO 690
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 690
```
ttggcacaga cctggccgtt                                              20

<210> SEQ ID NO 691
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 691
cacttggcac agacctggcc                                              20

<210> SEQ ID NO 692
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 692
aaacacttgg cacagacctg                                              20

<210> SEQ ID NO 693
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 693
caaacacttg gcacagacct                                              20

<210> SEQ ID NO 694
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 694
agcaaacact tggcacagac                                              20

<210> SEQ ID NO 695
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 695
cagcaaacac ttggcacaga                                              20

<210> SEQ ID NO 696
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 696
gtcagcaaac acttggcaca                                              20

<210> SEQ ID NO 697
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 697
accaagcccc agccagtggg                                               20

<210> SEQ ID NO 698
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 698
atgaccaagc cccagccagt                                               20

<210> SEQ ID NO 699
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 699
cccatgacca agccccagcc                                               20

<210> SEQ ID NO 700
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 700
tggcccatga ccaagcccca                                               20

<210> SEQ ID NO 701
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 701
tgatggccca tgaccaagcc                                               20

<210> SEQ ID NO 702
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 702
cgctgatggc ccatgaccaa                                               20

<210> SEQ ID NO 703
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 703
acgcgctgat ggcccatgac                                               20

<210> SEQ ID NO 704

-continued

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 704
cgcacgcgct gatggcccat                                               20

<210> SEQ ID NO 705
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 705
ccacgcacgc gctgatggcc                                               20

<210> SEQ ID NO 706
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 706
gttccacgca cgcgctgatg                                               20

<210> SEQ ID NO 707
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 707
aaggttccac gcacgcgctg                                               20

<210> SEQ ID NO 708
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 708
gaaaaggttc cacgcacgcg                                               20

<210> SEQ ID NO 709
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 709
gccgaaaagg ttccacgcac                                               20

<210> SEQ ID NO 710
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 710
```
ggagccgaaa aggttccacg                                            20

<210> SEQ ID NO 711
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 711
agaggagccg aaaaggttcc                                            20

<210> SEQ ID NO 712
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 712
ggcagaggag ccgaaaaggt                                            20

<210> SEQ ID NO 713
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 713
atcggcagag gagccgaaaa                                            20

<210> SEQ ID NO 714
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 714
tggatcggca gaggagccga                                            20

<210> SEQ ID NO 715
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 715
gtatggatcg gcagaggagc                                            20

<210> SEQ ID NO 716
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 716
gcagtatgga tcggcagagg                                            20

<210> SEQ ID NO 717
<211> LENGTH: 20
<212> TYPE: DNA
<213> ORGANISM: Artificial Sequence
<220> FEATURE:

-continued

<223> OTHER INFORMATION: Synthetic oligonucleotide

<400> SEQUENCE: 717
cgcagtatgg atcggcagag                                          20

<210> SEQ ID NO 718
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 718
tccgcagtat ggatcggcag                                          20

<210> SEQ ID NO 719
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 719
ttccgcagta tggatcggca                                          20

<210> SEQ ID NO 720
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 720
agttccgcag tatggatcgg                                          20

<210> SEQ ID NO 721
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 721
gagttccgca gtatggatcg                                          20

<210> SEQ ID NO 722
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 722
aggagttccg cagtatggat                                          20

<210> SEQ ID NO 723
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 723
gctaggagtt ccgcagtatg                                          20

<210> SEQ ID NO 724

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 724
gcggctagga gttccgcagt                                              20

<210> SEQ ID NO 725
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 725
caagcggcta ggagttccgc                                              20

<210> SEQ ID NO 726
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 726
aaacaagcgg ctaggagttc                                              20

<210> SEQ ID NO 727
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 727
gcaaaacaag cggctaggag                                              20

<210> SEQ ID NO 728
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 728
agcaaaacaa gcggctagga                                              20

<210> SEQ ID NO 729
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 729
cgagcaaaac aagcggctag                                              20

<210> SEQ ID NO 730
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 730
```
gcgagcaaaa caagcggcta 20

<210> SEQ ID NO 731
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 731
ctgcgagcaa acaagcggc 20

<210> SEQ ID NO 732
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 732
gctgcgagca aacaagcgg 20

<210> SEQ ID NO 733
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 733
ctgctgcgag caaacaagc 20

<210> SEQ ID NO 734
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 734
gacctgctgc gagcaaaaca 20

<210> SEQ ID NO 735
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 735
ccagacctgc tgcgagcaaa 20

<210> SEQ ID NO 736
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 736
gctccagacc tgctgcgagc 20

<210> SEQ ID NO 737
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 737
tttgctccag acctgctgcg                                               20

<210> SEQ ID NO 738
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 738
atgtttgctc cagacctgct                                               20

<210> SEQ ID NO 739
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 739
ataatgtttg ctccagacct                                               20

<210> SEQ ID NO 740
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 740
ccgataatgt ttgctccaga                                               20

<210> SEQ ID NO 741
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 741
gtcccgataa tgtttgctcc                                               20

<210> SEQ ID NO 742
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 742
tcagtcccga taatgtttgc                                               20

<210> SEQ ID NO 743
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 743
ttatcagtcc cgataatgtt                                               20

<210> SEQ ID NO 744

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 744
gagttatcag tcccgataat                                                     20

<210> SEQ ID NO 745
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 745
acagagttat cagtcccgat                                                     20

<210> SEQ ID NO 746
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 746
acaacagagt tatcagtccc                                                     20

<210> SEQ ID NO 747
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 747
aggacaacag agttatcagt                                                     20

<210> SEQ ID NO 748
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 748
gagaggacaa cagagttatc                                                     20

<210> SEQ ID NO 749
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 749
cgggagagga caacagagtt                                                     20

<210> SEQ ID NO 750
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 750
```

-continued ttgcgggaga ggacaacaga 20

<210> SEQ ID NO 751
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 751
tatttgcggg agaggacaac 20

<210> SEQ ID NO 752
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 752
gtatatttgc gggagaggac 20

<210> SEQ ID NO 753
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 753
gatgtatatt tgcgggagag 20

<210> SEQ ID NO 754
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 754
tacgatgtat atttgcggga 20

<210> SEQ ID NO 755
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 755
ggatacgatg tatatttgcg 20

<210> SEQ ID NO 756
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 756
catggatacg atgtatattt 20

<210> SEQ ID NO 757
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 757
agccatggat acgatgtata                                              20

<210> SEQ ID NO 758
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 758
agcagccatg gatacgatgt                                              20

<210> SEQ ID NO 759
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 759
cctagcagcc atggatacga                                              20

<210> SEQ ID NO 760
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 760
cagcctagca gccatggata                                              20

<210> SEQ ID NO 761
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 761
gcacagccta gcagccatgg                                              20

<210> SEQ ID NO 762
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 762
gcagcacagc ctagcagcca                                              20

<210> SEQ ID NO 763
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 763
ttggcagcac agcctagcag                                              20

<210> SEQ ID NO 764
```

<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 764
cagttggcag cacagcctag                                                    20

<210> SEQ ID NO 765
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 765
atccagttgg cagcacagcc                                                    20

<210> SEQ ID NO 766
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 766
aggatccagt tggcagcaca                                                    20

<210> SEQ ID NO 767
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 767
cgcaggatcc agttggcagc                                                    20

<210> SEQ ID NO 768
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 768
ccgcgcagga tccagttggc                                                    20

<210> SEQ ID NO 769
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 769
gtcccgcgca ggatccagtt                                                    20

<210> SEQ ID NO 770
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 770

-continued agcgaccccg agaagggtcg                    20

<210> SEQ ID NO 771
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 771
ccaagcgacc ccgagaaggg                    20

<210> SEQ ID NO 772
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 772
gtcccaagcg accccgagaa                    20

<210> SEQ ID NO 773
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 773
agagtcccaa gcgaccccga                    20

<210> SEQ ID NO 774
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 774
gagagagtcc caagcgaccc                    20

<210> SEQ ID NO 775
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 775
gacgagagag tcccaagcga                    20

<210> SEQ ID NO 776
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 776
gaacggcaga cggagaaggg                    20

<210> SEQ ID NO 777
<211> LENGTH: 20
<212> TYPE: DNA
<213> ORGANISM: Artificial Sequence
<220> FEATURE:

-continued

<223> OTHER INFORMATION: Synthetic oligonucleotide

<400> SEQUENCE: 777
cggtcggaac ggcagacgga                           20

<210> SEQ ID NO 778
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 778
ggtcggtcgg aacggcagac                           20

<210> SEQ ID NO 779
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 779
cgtggtcggt cggaacggca                           20

<210> SEQ ID NO 780
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 780
ccccgtggtc ggtcggaacg                           20

<210> SEQ ID NO 781
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 781
gcgccccgtg gtcggtcgga                           20

<210> SEQ ID NO 782
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 782
ggtgcgcccc gtggtcggtc                           20

<210> SEQ ID NO 783
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 783
aggtgcgccc cgtggtcggt                           20

<210> SEQ ID NO 784

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 784
agaggtgcgc cccgtggtcg                                                    20

<210> SEQ ID NO 785
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 785
gagaggtgcg ccccgtggtc                                                    20

<210> SEQ ID NO 786
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 786
aagagaggtg cgccccgtgg                                                    20

<210> SEQ ID NO 787
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 787
aaagagaggt gcgccccgtg                                                    20

<210> SEQ ID NO 788
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 788
gtaaagagag gtgcgccccg                                                    20

<210> SEQ ID NO 789
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 789
cgtaaagaga ggtgcgcccc                                                    20

<210> SEQ ID NO 790
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 790
```

| | |
|---|---|
| gatgagaagg cacagacggg | 20 |

<210> SEQ ID NO 791
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 791

| | |
|---|---|
| gcagatgaga aggcacagac | 20 |

<210> SEQ ID NO 792
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 792

| | |
|---|---|
| ccggcagatg agaaggcaca | 20 |

<210> SEQ ID NO 793
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 793

| | |
|---|---|
| ggtccggcag atgagaaggc | 20 |

<210> SEQ ID NO 794
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 794

| | |
|---|---|
| cacggtccgg cagatgagaa | 20 |

<210> SEQ ID NO 795
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 795

| | |
|---|---|
| gcacacggtc cggcagatga | 20 |

<210> SEQ ID NO 796
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 796

| | |
|---|---|
| agtgcacacg gtccggcaga | 20 |

<210> SEQ ID NO 797
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 797
cgaagtgcac acggtccggc                                               20

<210> SEQ ID NO 798
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 798
aagcgaagtg cacacggtcc                                               20

<210> SEQ ID NO 799
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 799
gaagcgaagt gcacacggtc                                               20

<210> SEQ ID NO 800
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 800
tgaagcgaag tgcacacggt                                               20

<210> SEQ ID NO 801
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 801
ggtgaagcga agtgcacacg                                               20

<210> SEQ ID NO 802
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 802
aggtgaagcg aagtgcacac                                               20

<210> SEQ ID NO 803

<400> SEQUENCE: 803

000

<210> SEQ ID NO 804
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 804
agaggtgaag cgaagtgcac                                               20

<210> SEQ ID NO 805
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 805
cagaggtgaa gcgaagtgca                                               20

<210> SEQ ID NO 806
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 806
tgcagaggtg aagcgaagtg                                               20

<210> SEQ ID NO 807
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 807
gtgcagaggt gaagcgaagt                                               20

<210> SEQ ID NO 808
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 808
acggtggtct ccatgcgacg                                               20

<210> SEQ ID NO 809
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 809
ttcacggtgg tctccatgcg                                               20

<210> SEQ ID NO 810
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 810
ccttgggcaa cattcggtgg                                               20

<210> SEQ ID NO 811
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 811
agaccttggg caacattcgg                                            20

<210> SEQ ID NO 812
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 812
gtaagacctt gggcaacatt                                            20

<210> SEQ ID NO 813
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 813
tatgtaagac cttgggcaac                                            20

<210> SEQ ID NO 814
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 814
tcttatgtaa gaccttgggc                                            20

<210> SEQ ID NO 815
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 815
tcctcttatg taagaccttg                                            20

<210> SEQ ID NO 816
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 816
gagtcctctt atgtaagacc                                            20

<210> SEQ ID NO 817
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 817
caagagtcct cttatgtaag                                            20
```

```
<210> SEQ ID NO 818
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 818
gtccaagagt cctcttatgt                                              20

<210> SEQ ID NO 819
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 819
agagtccaag agtcctctta                                              20

<210> SEQ ID NO 820
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 820
cagagagtcc aagagtcctc                                              20

<210> SEQ ID NO 821
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 821
ttgcagagag tccaagagtc                                              20

<210> SEQ ID NO 822
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 822
acattgcaga gagtccaaga                                              20

<210> SEQ ID NO 823
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 823
ttgacattgc agagagtcca                                              20

<210> SEQ ID NO 824
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 824
gtatgcctca aggtcggtcg                                              20

<210> SEQ ID NO 825
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 825
gaagtatgcc tcaaggtcgg                                              20

<210> SEQ ID NO 826
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 826
tttgaagtat gcctcaaggt                                              20

<210> SEQ ID NO 827
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 827
gtctttgaag tatgcctcaa                                              20

<210> SEQ ID NO 828
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 828
acagtctttg aagtatgcct                                              20

<210> SEQ ID NO 829
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 829
caaacagtct ttgaagtatg                                              20

<210> SEQ ID NO 830
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 830
aaacaaacag tctttgaagt                                              20

<210> SEQ ID NO 831
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 831
tttaaacaaa cagtctttga                                               20

<210> SEQ ID NO 832
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 832
gtctttaaac aaacagtctt                                               20

<210> SEQ ID NO 833
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 833
ccagtcttta aacaaacagt                                               20

<210> SEQ ID NO 834
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 834
ctcccagtct ttaaacaaac                                               20

<210> SEQ ID NO 835
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 835
ctcctcccag tctttaaaca                                               20

<210> SEQ ID NO 836
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 836
caactcctcc cagtctttaa                                               20

<210> SEQ ID NO 837
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 837
ccccaactcc tcccagtctt                                               20
```

<210> SEQ ID NO 838
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 838
ctcccccaac tcctcccagt					20

<210> SEQ ID NO 839
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 839
ctcctccccc aactcctccc					20

<210> SEQ ID NO 840
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 840
aatctcctcc cccaactcct					20

<210> SEQ ID NO 841
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 841
tctaatctcc tcccccaact					20

<210> SEQ ID NO 842
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 842
taatctaatc tcctccccca					20

<210> SEQ ID NO 843
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 843
ctttaatcta atctcctccc					20

<210> SEQ ID NO 844
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 844
gacctttaat ctaatctcct                                                      20

<210> SEQ ID NO 845
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 845
aaagaccttt aatctaatct                                                      20

<210> SEQ ID NO 846
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 846
tacaaagacc tttaatctaa                                                      20

<210> SEQ ID NO 847
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 847
tagtacaaag acctttaatc                                                      20

<210> SEQ ID NO 848
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 848
tcctagtaca aagaccttta                                                      20

<210> SEQ ID NO 849
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 849
gcctcctagt acaaagacct                                                      20

<210> SEQ ID NO 850
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 850
acagcctcct agtacaaaga                                                      20

<210> SEQ ID NO 851
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 851
cctacagcct cctagtacaa                                              20

<210> SEQ ID NO 852
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 852
atgcctacag cctcctagta                                              20

<210> SEQ ID NO 853
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 853
tttatgccta cagcctccta                                              20

<210> SEQ ID NO 854
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 854
atttatgcct acagcctcct                                              20

<210> SEQ ID NO 855
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 855
gaccaattta tgcctacagc                                              20

<210> SEQ ID NO 856
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 856
agaccaattt atgcctacag                                              20

<210> SEQ ID NO 857
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 857
gcagaccaat ttatgcctac                                              20
```

<210> SEQ ID NO 858
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 858
tgcgcagacc aatttatgcc                    20

<210> SEQ ID NO 859
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 859
tggtgcgcag accaatttat                    20

<210> SEQ ID NO 860
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 860
tgctggtgcg cagaccaatt                    20

<210> SEQ ID NO 861
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 861
tggtgctggt gcgcagacca                    20

<210> SEQ ID NO 862
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 862
gcatggtgct ggtgcgcaga                    20

<210> SEQ ID NO 863
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 863
gttgcatggt gctggtgcgc                    20

<210> SEQ ID NO 864
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 864
aaaagttgca tggtgctggt                                            20

<210> SEQ ID NO 865
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 865
tgaaaaagtt gcatggtgct                                            20

<210> SEQ ID NO 866
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 866
aggtgaaaaa gttgcatggt                                            20

<210> SEQ ID NO 867
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 867
cagaggtgaa aaagttgcat                                            20

<210> SEQ ID NO 868
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 868
aggcagaggt gaaaaagttg                                            20

<210> SEQ ID NO 869
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 869
attaggcaga ggtgaaaaag                                            20

<210> SEQ ID NO 870
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 870
gattaggcag aggtgaaaaa                                            20

<210> SEQ ID NO 871
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 871
atgattaggc agaggtgaaa                                                    20

<210> SEQ ID NO 872
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 872
gagatgatta ggcagaggtg                                                    20

<210> SEQ ID NO 873
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 873
caagagatga ttaggcagag                                                    20

<210> SEQ ID NO 874
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 874
gaacaagaga tgattaggca                                                    20

<210> SEQ ID NO 875
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 875
catgaacaag agatgattag                                                    20

<210> SEQ ID NO 876
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 876
ggacatgaac aagagatgat                                                    20

<210> SEQ ID NO 877
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 877
gtaggacatg aacaagagat                                                    20
```

<210> SEQ ID NO 878
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 878
acagtaggac atgaacaaga                                               20

<210> SEQ ID NO 879
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 879
tgaacagtag gacatgaaca                                               20

<210> SEQ ID NO 880
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 880
gcttgaacag taggacatga                                               20

<210> SEQ ID NO 881
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 881
gaggcttgaa cagtaggaca                                               20

<210> SEQ ID NO 882
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 882
ttggaggctt gaacagtagg                                               20

<210> SEQ ID NO 883
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 883
cagcttggag gcttgaacag                                               20

<210> SEQ ID NO 884
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 884
cccaaggcac agcttggagg                                               20

<210> SEQ ID NO 885
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 885
ccacccaagg cacagcttgg                                               20

<210> SEQ ID NO 886
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 886
aagccaccca aggcacagct                                               20

<210> SEQ ID NO 887
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 887
ccaaagccac ccaaggcaca                                               20

<210> SEQ ID NO 888
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 888
gccccaaagc cacccaaggc                                               20

<210> SEQ ID NO 889
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 889
catgccccaa agccacccaa                                               20

<210> SEQ ID NO 890
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 890
gtccatgccc caaagccacc                                               20

<210> SEQ ID NO 891
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 891
gatgtccatg ccccaaagcc                                            20

<210> SEQ ID NO 892
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 892
gtcgatgtcc atgccccaaa                                            20

<210> SEQ ID NO 893
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 893
agggtcgatg tccatgcccc                                            20

<210> SEQ ID NO 894
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 894
ataagggtcg atgtccatgc                                            20

<210> SEQ ID NO 895
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 895
tttataaggg tcgatgtcca                                            20

<210> SEQ ID NO 896
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 896
ttctttataa gggtcgatgt                                            20

<210> SEQ ID NO 897
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 897
aaattcttta tagggtcga                                             20
```

<210> SEQ ID NO 898
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 898
tccaaattct ttataagggt                                              20

<210> SEQ ID NO 899
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 899
agctccaaat tctttataag                                              20

<210> SEQ ID NO 900
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 900
agtagctcca aattctttat                                              20

<210> SEQ ID NO 901
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 901
cacagtagct ccaaattctt                                              20

<210> SEQ ID NO 902
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 902
ctccacagta gctccaaatt                                              20

<210> SEQ ID NO 903
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 903
taactccaca gtagctccaa                                              20

<210> SEQ ID NO 904
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 904
gagtaactcc acagtagctc                                               20

<210> SEQ ID NO 905
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 905
cgagagtaac tccacagtag                                               20

<210> SEQ ID NO 906
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 906
aaacgagagt aactccacag                                               20

<210> SEQ ID NO 907
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 907
caaaaacgag agtaactcca                                               20

<210> SEQ ID NO 908
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 908
aggcaaaaac gagagtaact                                               20

<210> SEQ ID NO 909
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 909
agaaggcaaa aacgagagta                                               20

<210> SEQ ID NO 910
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 910
gtcagaaggc aaaaacgaga                                               20

<210> SEQ ID NO 911
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 911
gaagtcagaa ggcaaaaacg                                              20

<210> SEQ ID NO 912
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 912
aaagaagtca gaaggcaaaa                                              20

<210> SEQ ID NO 913
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 913
aggaaagaag tcagaaggca                                              20

<210> SEQ ID NO 914
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 914
tgaaggaaag aagtcagaag                                              20

<210> SEQ ID NO 915
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 915
tactgaagga aagaagtcag                                              20

<210> SEQ ID NO 916
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 916
gcggtatcta gaagatctcg                                              20

<210> SEQ ID NO 917
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 917
gaggcggtat ctagaagatc                                              20
```

<210> SEQ ID NO 918
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 918
gctgaggcgg tatctagaag              20

<210> SEQ ID NO 919
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 919
agagctgagg cggtatctag              20

<210> SEQ ID NO 920
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 920
tacagagctg aggcggtatc              20

<210> SEQ ID NO 921
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 921
cgatacagag ctgaggcggt              20

<210> SEQ ID NO 922
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 922
tcccgataca gagctgaggc              20

<210> SEQ ID NO 923
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 923
gcttcccgat acagagctga              20

<210> SEQ ID NO 924
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 924
aaggcttccc gatacagagc                                                   20

<210> SEQ ID NO 925
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 925
tctaaggctt cccgatacag                                                   20

<210> SEQ ID NO 926
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 926
gactctaagg cttcccgata                                                   20

<210> SEQ ID NO 927
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 927
ggagactcta aggcttcccg                                                   20

<210> SEQ ID NO 928
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 928
tcaggagact ctaaggcttc                                                   20

<210> SEQ ID NO 929
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 929
tgctcaggag actctaaggc                                                   20

<210> SEQ ID NO 930
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 930
caatgctcag gagactctaa                                                   20

<210> SEQ ID NO 931
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 931
gaacaatgct caggagactc                                               20

<210> SEQ ID NO 932
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 932
ggtgaacaat gctcaggaga                                               20

<210> SEQ ID NO 933
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 933
tgaggtgaac aatgctcagg                                               20

<210> SEQ ID NO 934
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 934
tggtgaggtg aacaatgctc                                               20

<210> SEQ ID NO 935
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 935
gtatggtgag gtgaacaatg                                               20

<210> SEQ ID NO 936
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 936
gcagtatggt gaggtgaaca                                               20

<210> SEQ ID NO 937
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 937
agtgcagtat ggtgaggtga                                               20
```

<210> SEQ ID NO 938
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 938
ctgagtgcag tatggtgagg                                               20

<210> SEQ ID NO 939
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 939
tgcctgagtg cagtatggtg                                               20

<210> SEQ ID NO 940
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 940
gcttgcctga gtgcagtatg                                               20

<210> SEQ ID NO 941
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 941
attgcttgcc tgagtgcagt                                               20

<210> SEQ ID NO 942
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 942
agaattgctt gcctgagtgc                                               20

<210> SEQ ID NO 943
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 943
caaagaattg cttgcctgag                                               20

<210> SEQ ID NO 944
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 944
cagcaaagaa ttgcttgcct								20

<210> SEQ ID NO 945
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 945
ccccagcaaa gaattgcttg								20

<210> SEQ ID NO 946
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 946 tcccccagc aaagaattgc								20

<210> SEQ ID NO 947
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 947
agttcccccc agcaaagaat								20

<210> SEQ ID NO 948
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 948
attagttccc cccagcaaag								20

<210> SEQ ID NO 949
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 949
gtcattagtt cccccagca								20

<210> SEQ ID NO 950
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 950
agagtcatta gttcccccca								20

<210> SEQ ID NO 951
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 951
gctagagtca ttagttcccc                                              20

<210> SEQ ID NO 952
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 952
gtagctagag tcattagttc                                              20

<210> SEQ ID NO 953
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 953
caggtagcta gagtcattag                                              20

<210> SEQ ID NO 954
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 954
acccaggtag ctagagtcat                                              20

<210> SEQ ID NO 955
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 955
cccacccagg tagctagagt                                              20

<210> SEQ ID NO 956
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 956
acacccaccc aggtagctag                                              20

<210> SEQ ID NO 957
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 957
ttaacaccca cccaggtagc                                              20
```

<210> SEQ ID NO 958
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 958
aaattaacac ccacccaggt                                               20

<210> SEQ ID NO 959
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 959
tccaaattaa cacccaccca                                               20

<210> SEQ ID NO 960
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 960
tcttccaaat taacacccac                                               20

<210> SEQ ID NO 961
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 961
ggatcttcca aattaacacc                                               20

<210> SEQ ID NO 962
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 962
gctggatctt ccaaattaac                                               20

<210> SEQ ID NO 963
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 963
gatgctggat cttccaaatt                                               20

<210> SEQ ID NO 964
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 964
ctagatgctg gatcttccaa        20

<210> SEQ ID NO 965
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 965
tctctagatg ctggatcttc        20

<210> SEQ ID NO 966
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 966
aggtctctag atgctggatc        20

<210> SEQ ID NO 967
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 967
actaggtctc tagatgctgg        20

<210> SEQ ID NO 968
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 968
actactaggt ctctagatgc        20

<210> SEQ ID NO 969
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 969
ctgactacta ggtctctaga        20

<210> SEQ ID NO 970
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 970
taactgacta ctaggtctct        20

<210> SEQ ID NO 971
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 971
acataactga ctactaggtc                                              20

<210> SEQ ID NO 972
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 972
ttgacataac tgactactag                                              20

<210> SEQ ID NO 973
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 973
gtgttgacat aactgactac                                              20

<210> SEQ ID NO 974
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 974
ttagtgttga cataactgac                                              20

<210> SEQ ID NO 975
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 975
atattagtgt tgacataact                                              20

<210> SEQ ID NO 976
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 976
cccatattag tgttgacata                                              20

<210> SEQ ID NO 977
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 977
aggcccatat tagtgttgac                                              20
```

<210> SEQ ID NO 978
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 978
tttaggccca tattagtgtt                                              20

<210> SEQ ID NO 979
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 979
aactttaggc ccatattagt                                              20

<210> SEQ ID NO 980
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 980
ctgaacttta ggcccatatt                                              20

<210> SEQ ID NO 981
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 981
tgcctgaact ttaggcccat                                              20

<210> SEQ ID NO 982
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 982
agttgcctga actttaggcc                                              20

<210> SEQ ID NO 983
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 983
aagagttgcc tgaactttag                                              20

<210> SEQ ID NO 984
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 984
cacaagagtt gcctgaactt                                                    20

<210> SEQ ID NO 985
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 985
aaccacaaga gttgcctgaa                                                    20

<210> SEQ ID NO 986
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 986
tgaaaccaca agagttgcct                                                    20

<210> SEQ ID NO 987
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 987
atgtgaaacc acaagagttg                                                    20

<210> SEQ ID NO 988
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 988
gaaatgtgaa accacaagag                                                    20

<210> SEQ ID NO 989
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 989
caagaaatgt gaaaccacaa                                                    20

<210> SEQ ID NO 990
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 990
agacaagaaa tgtgaaacca                                                    20

<210> SEQ ID NO 991
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 991
gtgagacaag aaatgtgaaa                                          20

<210> SEQ ID NO 992
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 992
aaagtgagac aagaaatgtg                                          20

<210> SEQ ID NO 993
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 993
ccaaaagtga gacaagaaat                                          20

<210> SEQ ID NO 994
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 994
cttccaaaag tgagacaaga                                          20

<210> SEQ ID NO 995
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 995
tctcttccaa aagtgagaca                                          20

<210> SEQ ID NO 996
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 996
gtttctcttc caaaagtgag                                          20

<210> SEQ ID NO 997
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 997
acggtttctc ttccaaaagt                                          20
```

<210> SEQ ID NO 998
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 998
ataacggttt ctcttccaaa                                          20

<210> SEQ ID NO 999
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 999
tctataacgg tttctcttcc                                          20

<210> SEQ ID NO 1000
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1000
tactctataa cggtttctct                                          20

<210> SEQ ID NO 1001
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1001
aaatactcta taacggtttc                                          20

<210> SEQ ID NO 1002
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1002
accaaatact ctataacggt                                          20

<210> SEQ ID NO 1003
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1003
gacaccaaat actctataac                                          20

<210> SEQ ID NO 1004
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1004
aaagacacca aatactctat                                         20

<210> SEQ ID NO 1005
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1005
ccgaaagaca ccaaatactc                                         20

<210> SEQ ID NO 1006
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1006
actccgaaag acaccaaata                                         20

<210> SEQ ID NO 1007
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1007
cacactccga aagacaccaa                                         20

<210> SEQ ID NO 1008
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1008
atccacactc cgaaagacac                                         20

<210> SEQ ID NO 1009
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1009
cgaatccaca ctccgaaaga                                         20

<210> SEQ ID NO 1010
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1010
gtgcgaatcc acactccgaa                                         20

<210> SEQ ID NO 1011
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 1011
ggagtgcgaa tccacactcc                                               20

<210> SEQ ID NO 1012
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1012
ggaggagtgc gaatccacac                                               20

<210> SEQ ID NO 1013
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1013
gctggaggag tgcgaatcca                                               20

<210> SEQ ID NO 1014
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1014
taagctggag gagtgcgaat                                               20

<210> SEQ ID NO 1015
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1015
ctataagctg gaggagtgcg                                               20

<210> SEQ ID NO 1016
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1016
ggtctataag ctggaggagt                                               20

<210> SEQ ID NO 1017
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1017
ggtggtctat aagctggagg                                               20
```

```
<210> SEQ ID NO 1018
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1018
tttggtggtc tataagctgg                                                   20

<210> SEQ ID NO 1019
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1019
gcatttggtg gtctataagc                                                   20

<210> SEQ ID NO 1020
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1020
gaagtgttga taggataggg                                                   20

<210> SEQ ID NO 1021
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1021
ccggaagtgt tgataggata                                                   20

<210> SEQ ID NO 1022
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1022
tttccggaag tgttgatagg                                                   20

<210> SEQ ID NO 1023
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1023
tagtttccgg aagtgttgat                                                   20

<210> SEQ ID NO 1024
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 1024
cagtagtttc cggaagtgtt                                         20

<210> SEQ ID NO 1025
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1025
caacagtagt ttccggaagt                                         20

<210> SEQ ID NO 1026
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1026
taacaacagt agtttccgga                                         20

<210> SEQ ID NO 1027
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1027
gtctaacaac agtagtttcc                                         20

<210> SEQ ID NO 1028
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1028
cgagggagtt cttcttctag                                         20

<210> SEQ ID NO 1029
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1029
aggcgaggga gttcttcttc                                         20

<210> SEQ ID NO 1030
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1030
gcgaggcgag ggagttcttc                                         20

<210> SEQ ID NO 1031
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 1031
gtctgcgagg cgagggagtt                                          20

<210> SEQ ID NO 1032
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1032
cgcggcgatt gagaccttcg                                          20

<210> SEQ ID NO 1033
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1033
cgacgcggcg attgagacct                                          20

<210> SEQ ID NO 1034
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1034
ctgcgacgcg gcgattgaga                                          20

<210> SEQ ID NO 1035
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1035
cttctgcgac gcggcgattg                                          20

<210> SEQ ID NO 1036
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1036
gatcttctgc gacgcggcga                                          20

<210> SEQ ID NO 1037
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1037
tgagatcttc tgcgacgcgg                                          20
```

-continued

<210> SEQ ID NO 1038
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1038
gattgagatc ttctgcgacg                                           20

<210> SEQ ID NO 1039
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1039
cgagattgag atcttctgcg                                           20

<210> SEQ ID NO 1040
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1040
tcccgagatt gagatcttct                                           20

<210> SEQ ID NO 1041
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1041
ggttcccgag attgagatct                                           20

<210> SEQ ID NO 1042
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1042
tgaggttccc gagattgaga                                           20

<210> SEQ ID NO 1043
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1043
cattgaggtt cccgagattg                                           20

<210> SEQ ID NO 1044
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1044
taacattgag gttcccgaga						20

<210> SEQ ID NO 1045
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1045
tactaacatt gaggttcccg						20

<210> SEQ ID NO 1046
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1046
gaatactaac attgaggttc						20

<210> SEQ ID NO 1047
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1047
aaggaatact aacattgagg						20

<210> SEQ ID NO 1048
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1048
tccaaggaat actaacattg						20

<210> SEQ ID NO 1049
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1049
gagtccaagg aatactaaca						20

<210> SEQ ID NO 1050
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1050
tatgagtcca aggaatacta						20

<210> SEQ ID NO 1051
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 1051
ccttatgagt ccaaggaata                                               20

<210> SEQ ID NO 1052
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1052
ccaccttatg agtccaagga                                               20

<210> SEQ ID NO 1053
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1053
tccccacctt atgagtccaa                                               20

<210> SEQ ID NO 1054
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1054
agttccccac cttatgagtc                                               20

<210> SEQ ID NO 1055
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1055
taaagttccc caccttatga                                               20

<210> SEQ ID NO 1056
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1056
cagtaaagtt ccccacctta                                               20

<210> SEQ ID NO 1057
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1057
gaccagtaaa gttccccacc                                               20
```

<210> SEQ ID NO 1058
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1058
aaagaccagt aaagttcccc					20

<210> SEQ ID NO 1059
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1059
aataaagacc agtaaagttc					20

<210> SEQ ID NO 1060
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1060
aagaataaag accagtaaag					20

<210> SEQ ID NO 1061
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1061
tagaagaata aagaccagta					20

<210> SEQ ID NO 1062
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1062
cagtagaaga ataaagacca					20

<210> SEQ ID NO 1063
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1063
gtacagtaga agaataaaga					20

<210> SEQ ID NO 1064
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1064
caggtacagt agaagaataa                                              20

<210> SEQ ID NO 1065
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1065
agacaggtac agtagaagaa                                              20

<210> SEQ ID NO 1066
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1066
taaagacagg tacagtagaa                                              20

<210> SEQ ID NO 1067
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1067
gattaaagac aggtacagta                                              20

<210> SEQ ID NO 1068
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1068
gaggattaaa gacaggtaca                                              20

<210> SEQ ID NO 1069
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1069
aatgaggatt aaagacaggt                                              20

<210> SEQ ID NO 1070
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1070
tccaatgagg attaaagaca                                              20

<210> SEQ ID NO 1071
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 1071
ttttccaatg aggattaaag                                          20

<210> SEQ ID NO 1072
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1072
gtgttttcca atgaggatta                                          20

<210> SEQ ID NO 1073
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1073
atggtgtttt ccaatgagga                                          20

<210> SEQ ID NO 1074
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1074
aagatggtgt tttccaatga                                          20

<210> SEQ ID NO 1075
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1075
gaaaagatgg tgttttccaa                                          20

<210> SEQ ID NO 1076
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1076
taggaaaaga tggtgttttc                                          20

<210> SEQ ID NO 1077
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1077
tattaggaaa agatggtgtt                                          20
```

<210> SEQ ID NO 1078
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1078
gtatattagg aaaagatggt                                          20

<210> SEQ ID NO 1079
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1079
aatgtatatt aggaaaagat                                          20

<210> SEQ ID NO 1080
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1080
gtaaatgtat attaggaaaa                                          20

<210> SEQ ID NO 1081
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1081
ggtgtaaatg tatattagga                                          20

<210> SEQ ID NO 1082
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1082
cttggtgtaa atgtatatta                                          20

<210> SEQ ID NO 1083
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1083
tgtcttggtg taaatgtata                                          20

<210> SEQ ID NO 1084
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 1084
taatgtcttg gtgtaaatgt                                              20

<210> SEQ ID NO 1085
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1085
tgataatgtc ttggtgtaaa                                              20

<210> SEQ ID NO 1086
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1086
ttttgataat gtcttggtgt                                              20

<210> SEQ ID NO 1087
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1087
attttttgat aatgtcttgg                                              20

<210> SEQ ID NO 1088
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1088
cacatttttt gataatgtct                                              20

<210> SEQ ID NO 1089
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1089
gttcacattt tttgataatg                                              20

<210> SEQ ID NO 1090
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1090
actgttcaca ttttttgata                                              20

<210> SEQ ID NO 1091
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 1091
caaactgttc acattttttg                                                    20

<210> SEQ ID NO 1092
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1092
ctacaaactg ttcacatttt                                                    20

<210> SEQ ID NO 1093
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1093
ggcctacaaa ctgttcacat                                                    20

<210> SEQ ID NO 1094
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1094
gtgggcctac aaactgttca                                                    20

<210> SEQ ID NO 1095
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1095
taagtgggcc tacaaactgt                                                    20

<210> SEQ ID NO 1096
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1096
ctgtaagtgg gcctacaaac                                                    20

<210> SEQ ID NO 1097
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1097
taactgtaag tgggcctaca                                                    20
```

<210> SEQ ID NO 1098
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1098
cattaactgt aagtgggcct                                           20

<210> SEQ ID NO 1099
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1099
tctcattaac tgtaagtggg                                           20

<210> SEQ ID NO 1100
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1100
ttttctcatt aactgtaagt                                           20

<210> SEQ ID NO 1101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1101
ttcttttctc attaactgta                                           20

<210> SEQ ID NO 1102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1102
atcttctttt ctcattaact                                           20

<210> SEQ ID NO 1103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1103
gcaatcttct tttctcatta                                           20

<210> SEQ ID NO 1104
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 1104
attgcaatct tcttttctca                                              20

<210> SEQ ID NO 1105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1105
tcaattgcaa tcttcttttc                                              20

<210> SEQ ID NO 1106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1106
taatcaattg caatcttctt                                              20

<210> SEQ ID NO 1107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1107
gcataatcaa ttgcaatctt                                              20

<210> SEQ ID NO 1108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1108
caggcataat caattgcaat                                              20

<210> SEQ ID NO 1109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1109
tagcaggcat aatcaattgc                                              20

<210> SEQ ID NO 1110
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1110
acctagcagg cataatcaat                                              20

<210> SEQ ID NO 1111
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 1111
aaaacctagc aggcataatc                                           20

<210> SEQ ID NO 1112
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1112
gataaaacct agcaggcata                                           20

<210> SEQ ID NO 1113
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1113
ttggataaaa cctagcaggc                                           20

<210> SEQ ID NO 1114
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1114
cctttggata aaacctagca                                           20

<210> SEQ ID NO 1115
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1115
taacctttgg ataaaaccta                                           20

<210> SEQ ID NO 1116
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1116
tggtaacctt tggataaaac                                           20

<210> SEQ ID NO 1117
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1117
atttggtaac ctttggataa                                           20
```

```
<210> SEQ ID NO 1118
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1118
aatatttggt aacctttgga                                              20

<210> SEQ ID NO 1119
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1119
gtaaatattt ggtaaccttt                                              20

<210> SEQ ID NO 1120
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1120
atggtaaata tttggtaacc                                              20

<210> SEQ ID NO 1121
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1121
ccaatggtaa atatttggta                                              20

<210> SEQ ID NO 1122
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1122
tatccaatgg taaatatttg                                              20

<210> SEQ ID NO 1123
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1123
ccttatccaa tggtaaatat                                              20

<210> SEQ ID NO 1124
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 1124 taccottatc caatggtaaa                                                      20

<210> SEQ ID NO 1125
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1125 taatacccttt atccaatggt                                                     20

<210> SEQ ID NO 1126
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1126
gtttaatacc cttatccaat                                                      20

<210> SEQ ID NO 1127
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1127
aaggtttaat acccttatcc                                                      20

<210> SEQ ID NO 1128
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1128
aataaggttt aatacccta                                                       20

<210> SEQ ID NO 1129
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1129
gataataagg tttaataccc                                                      20

<210> SEQ ID NO 1130
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1130
ctggataata aggtttaata                                                      20

<210> SEQ ID NO 1131
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 1131
gttctggata ataaggttta                                              20

<210> SEQ ID NO 1132
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1132
gatgttctgg ataataaggt                                              20

<210> SEQ ID NO 1133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1133
ctagatgttc tggataataa                                              20

<210> SEQ ID NO 1134
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1134
taactagatg ttctggataa                                              20

<210> SEQ ID NO 1135
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1135
gattaactag atgttctgga                                              20

<210> SEQ ID NO 1136
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1136
aatgattaac tagatgttct                                              20

<210> SEQ ID NO 1137
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1137
agtaatgatt aactagatgt                                              20
```

<210> SEQ ID NO 1138
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1138
ggaagtaatg attaactaga                                         20

<210> SEQ ID NO 1139
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1139
tttggaagta atgattaact                                         20

<210> SEQ ID NO 1140
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1140
tagtttggaa gtaatgatta                                         20

<210> SEQ ID NO 1141
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1141
gtctagtttg gaagtaatga                                         20

<210> SEQ ID NO 1142
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1142
agtgtctagt ttggaagtaa                                         20

<210> SEQ ID NO 1143
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1143
aatagtgtct agtttggaag                                         20

<210> SEQ ID NO 1144
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 1144
gtaaatagtg tctagtttgg                                              20

<210> SEQ ID NO 1145
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1145
tgtgtaaata gtgtctagtt                                              20

<210> SEQ ID NO 1146
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1146
gagtgtgtaa atagtgtcta                                              20

<210> SEQ ID NO 1147
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1147
atagagtgtg taaatagtgt                                              20

<210> SEQ ID NO 1148
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1148
tccatagagt gtgtaaatag                                              20

<210> SEQ ID NO 1149
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1149
ccttccatag agtgtgtaaa                                              20

<210> SEQ ID NO 1150
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1150
ccgccttcca tagagtgtgt                                              20

<210> SEQ ID NO 1151
<211> LENGTH: 20
```

<212> TYPE: DNA
<213> ORGANISM: Artificial Sequence
<220> FEATURE:
<223> OTHER INFORMATION: Synthetic oligonucleotide

<400> SEQUENCE: 1151
tacccgcctt ccatagagtg                                               20

<210> SEQ ID NO 1152
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1152
atatacccgc cttccataga                                               20

<210> SEQ ID NO 1153
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1153
ataatatacc cgccttccat                                               20

<210> SEQ ID NO 1154
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1154
tatataatat acccgccttc                                               20

<210> SEQ ID NO 1155
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1155
tcttatataa tacccgcc                                                 20

<210> SEQ ID NO 1156
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1156
ctctcttata taatataccc                                               20

<210> SEQ ID NO 1157
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1157
tttctctctt atataatata                                               20

<210> SEQ ID NO 1158
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1158
ttgtttctct cttatataat        20

<210> SEQ ID NO 1159
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1159
gtgttgtttc tctcttatat        20

<210> SEQ ID NO 1160
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1160
tatgtgttgt ttctctctta        20

<210> SEQ ID NO 1161
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1161
cgctatgtgt tgtttctctc        20

<210> SEQ ID NO 1162
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1162
tgacccacaa aatgaggcgc        20

<210> SEQ ID NO 1163
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1163
tggtgaccca caaaatgagg        20

<210> SEQ ID NO 1164
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 1164
atatggtgac ccacaaaatg                                          20

<210> SEQ ID NO 1165
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1165
agaatatggt gacccacaaa                                          20

<210> SEQ ID NO 1166
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1166
ccaagaatat ggtgacccac                                          20

<210> SEQ ID NO 1167
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1167
ttcccaagaa tatggtgacc                                          20

<210> SEQ ID NO 1168
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1168
ttgttcccaa gaatatggtg                                          20

<210> SEQ ID NO 1169
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1169
atcttgttcc caagaatatg                                          20

<210> SEQ ID NO 1170
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1170
tagatcttgt tcccaagaat                                          20

<210> SEQ ID NO 1171
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 1171
ctgtagatct tgttcccaag                                           20

<210> SEQ ID NO 1172
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1172
atgctgtaga tcttgttccc                                           20

<210> SEQ ID NO 1173
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1173
cccatgctgt agatcttgtt                                           20

<210> SEQ ID NO 1174
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1174
tgccccatgc tgtagatctt                                           20

<210> SEQ ID NO 1175
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1175
ttctgcccca tgctgtagat                                           20

<210> SEQ ID NO 1176
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1176
agattctgcc ccatgctgta                                           20

<210> SEQ ID NO 1177
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1177
gaaagattct gccccatgct                                           20
```

<210> SEQ ID NO 1178
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1178
gtggaaagat tctgccccat                                              20

<210> SEQ ID NO 1179
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1179
ctggtggaaa gattctgccc                                              20

<210> SEQ ID NO 1180
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1180
ttgctggtgg aaagattctg                                              20

<210> SEQ ID NO 1181
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1181
ggattgctgg tggaaagatt                                              20

<210> SEQ ID NO 1182
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1182
agaggattgc tggtggaaag                                              20

<210> SEQ ID NO 1183
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1183
cccagaggat tgctggtgga                                              20

<210> SEQ ID NO 1184
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 1184
aatcccagag gattgctggt                                              20

<210> SEQ ID NO 1185
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1185
aagaatccca gaggattgct                                              20

<210> SEQ ID NO 1186
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1186
ggaaagaatc ccagaggatt                                              20

<210> SEQ ID NO 1187
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1187
tcgggaaaga atcccagagg                                              20

<210> SEQ ID NO 1188
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1188
tggtcgggaa agaatcccag                                              20

<210> SEQ ID NO 1189
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1189
tggtggtcgg gaaagaatcc                                              20

<210> SEQ ID NO 1190
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1190
aactggtggt cgggaaagaa                                              20

<210> SEQ ID NO 1191
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 1191
tccaactggt ggtcgggaaa                                             20

<210> SEQ ID NO 1192
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1192
ggatccaact ggtggtcggg                                             20

<210> SEQ ID NO 1193
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1193
gctggatcca actggtggtc                                             20

<210> SEQ ID NO 1194
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1194
aaggctggat ccaactggtg                                             20

<210> SEQ ID NO 1195
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1195
ctgaaggctg gatccaactg                                             20

<210> SEQ ID NO 1196
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1196
gctctgaagg ctggatccaa                                             20

<210> SEQ ID NO 1197
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1197
tttgctctga aggctggatc                                             20
```

<210> SEQ ID NO 1198
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1198
gtgtttgctc tgaaggctgg                                              20

<210> SEQ ID NO 1199
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1199
gctgtgtttg ctctgaaggc                                              20

<210> SEQ ID NO 1200
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1200
tttgctgtgt tgctctgaa                                               20

<210> SEQ ID NO 1201
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1201
ggatttgctg tgtttgctct                                              20

<210> SEQ ID NO 1202
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1202
tctggatttg ctgtgtttgc                                              20

<210> SEQ ID NO 1203
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1203
caatctggat tgctgtgtt                                               20

<210> SEQ ID NO 1204
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1204
tcccaatctg gatttgctgt                                               20

<210> SEQ ID NO 1205
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1205
aagtcccaat ctggatttgc                                               20

<210> SEQ ID NO 1206
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1206
ttgaagtccc aatctggatt                                               20

<210> SEQ ID NO 1207
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1207
ggattgaagt cccaatctgg                                               20

<210> SEQ ID NO 1208
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1208
ttgggattga agtcccaatc                                               20

<210> SEQ ID NO 1209
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1209
ttgttgggat tgaagtccca                                               20

<210> SEQ ID NO 1210
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1210
tccttgttgg gattgaagtc                                               20

<210> SEQ ID NO 1211
<211> LENGTH: 20

-continued

```
<212> TYPE: DNA
<213> ORGANISM: Artificial Sequence
<220> FEATURE:
<223> OTHER INFORMATION: Synthetic oligonucleotide

<400> SEQUENCE: 1211
gtgtccttgt tgggattgaa                                              20

<210> SEQ ID NO 1212
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1212
caggtgtcct tgttgggatt                                              20

<210> SEQ ID NO 1213
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1213
ggccaggtgt ccttgttggg                                              20

<210> SEQ ID NO 1214
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1214
tctggccagg tgtccttgtt                                              20

<210> SEQ ID NO 1215
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1215
cagctcctac cttgttggcg                                              20

<210> SEQ ID NO 1216
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1216
ctccagctcc taccttgttg                                              20

<210> SEQ ID NO 1217
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1217
atgctccagc tcctaccttg                                              20
```

<210> SEQ ID NO 1218
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1218
cgaatgctcc agctcctacc                                                 20

<210> SEQ ID NO 1219
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1219
gcccgaatgc tccagctcct                                                 20

<210> SEQ ID NO 1220
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1220
ccagcccgaa tgctccagct                                                 20

<210> SEQ ID NO 1221
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1221
aacccagccc gaatgctcca                                                 20

<210> SEQ ID NO 1222
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1222
tgaaacccag cccgaatgct                                                 20

<210> SEQ ID NO 1223
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1223
gggtgaaacc cagcccgaat                                                 20

<210> SEQ ID NO 1224
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1224
aaaggcctcc gtgcggtggg					20

<210> SEQ ID NO 1225
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1225
ccaaaaggcc tccgtgcggt					20

<210> SEQ ID NO 1226
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1226
accccaaaag gcctccgtgc					20

<210> SEQ ID NO 1227
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1227
tccaccccaa aaggcctccg					20

<210> SEQ ID NO 1228
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1228
ggctccaccc caaaaggcct					20

<210> SEQ ID NO 1229
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1229
gagggctcca ccccaaaagg					20

<210> SEQ ID NO 1230
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1230
cctgagggct ccaccccaaa					20

<210> SEQ ID NO 1231
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 1231
gagcctgagg gctccacccc                                              20

<210> SEQ ID NO 1232
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1232
cctgagcctg agggctccac                                              20

<210> SEQ ID NO 1233
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1233
tgccctgagc ctgagggctc                                              20

<210> SEQ ID NO 1234
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1234
gtatgccctg agcctgaggg                                              20

<210> SEQ ID NO 1235
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1235
gtagtatgcc ctgagcctga                                              20

<210> SEQ ID NO 1236
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1236
tttgtagtat gccctgagcc                                              20

<210> SEQ ID NO 1237
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1237
aagtttgtag tatgccctga                                              20
```

<210> SEQ ID NO 1238
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1238
gcaaagtttg tagtatgccc                                          20

<210> SEQ ID NO 1239
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1239
ctggcaaagt ttgtagtatg                                          20

<210> SEQ ID NO 1240
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1240
ttgctggcaa agtttgtagt                                          20

<210> SEQ ID NO 1241
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1241
gatttgctgg caaagtttgt                                          20

<210> SEQ ID NO 1242
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1242
gcggatttgc tggcaaagtt                                          20

<210> SEQ ID NO 1243
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1243
gaggcggatt tgctggcaaa                                          20

<210> SEQ ID NO 1244
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1244
caggaggcgg atttgctggc                                                   20

<210> SEQ ID NO 1245
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1245
aggcaggagg cggatttgct                                                   20

<210> SEQ ID NO 1246
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1246
tggaggcagg aggcggattt                                                   20

<210> SEQ ID NO 1247
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1247
tggtggaggc aggaggcgga                                                   20

<210> SEQ ID NO 1248
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1248
gattggtgga ggcaggaggc                                                   20

<210> SEQ ID NO 1249
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1249
ggcgattggt ggaggcagga                                                   20

<210> SEQ ID NO 1250
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1250
tctggcgatt ggtggaggca                                                   20

<210> SEQ ID NO 1251
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 1251
ctgtctggcg attggtggag                                           20

<210> SEQ ID NO 1252
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1252
ttcctgtctg gcgattggtg                                           20

<210> SEQ ID NO 1253
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1253
gccttcctgt ctggcgattg                                           20

<210> SEQ ID NO 1254
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1254
gctgccttcc tgtctggcga                                           20

<210> SEQ ID NO 1255
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1255
taggctgcct tcctgtctgg                                           20

<210> SEQ ID NO 1256
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1256
gggtaggctg ccttcctgtc                                           20

<210> SEQ ID NO 1257
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1257
tcaaaggtgg agacagcggg                                           20
```

<210> SEQ ID NO 1258
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1258
ttctcaaagg tggagacagc                                         20

<210> SEQ ID NO 1259
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1259
tgtttctcaa aggtggagac                                         20

<210> SEQ ID NO 1260
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1260
gagtgtttct caaaggtgga                                         20

<210> SEQ ID NO 1261
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1261
gatgagtgtt tctcaaaggt                                         20

<210> SEQ ID NO 1262
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1262
gaggatgagt gtttctcaaa                                         20

<210> SEQ ID NO 1263
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1263
cctgaggatg agtgtttctc                                         20

<210> SEQ ID NO 1264
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 1264
tggcctgagg atgagtgttt                                              20

<210> SEQ ID NO 1265
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1265
gcatggcctg aggatgagtg                                              20

<210> SEQ ID NO 1266
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1266
cactgcatgg cctgaggatg                                              20

<210> SEQ ID NO 1267
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1267
ttccactgca tggcctgagg                                              20

<210> SEQ ID NO 1268
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1268
gaattccact gcatggcctg                                              20

<210> SEQ ID NO 1269
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1269
gtggaattcc actgcatggc                                              20

<210> SEQ ID NO 1270
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1270
gttgtggaat tccactgcat                                              20

<210> SEQ ID NO 1271
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 1271
aaggttgtgg aattccactg                                              20

<210> SEQ ID NO 1272
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1272
tgaaaggttg tggaattcca                                              20

<210> SEQ ID NO 1273
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1273
cctgctggtg gctccagttc                                              20

<210> SEQ ID NO 1274
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 1274
agagtctaga ctcgtggtgg acttctctca attttctagg gg                     42

<210> SEQ ID NO 1275
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 1275
tggatgtgtc tgcggcgttt tatcat                                       26

<210> SEQ ID NO 1276
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 1276
catcctgctg ctatgcctca tcttctt                                      27

<210> SEQ ID NO 1277
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1277
caaggtatgt tgcccgt                                                 17
```

```
<210> SEQ ID NO 1278
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1278
tgtattccca tcccatc                                                    17

<210> SEQ ID NO 1279
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1279
cctatgggag tgggcctcag                                                 20

<210> SEQ ID NO 1280
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1280
tggctcagtt tactagtgc                                                  19

<210> SEQ ID NO 1281
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1281
gggctttccc ccactgt                                                    17

<210> SEQ ID NO 1282
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 1282
tcctctgccg atccatactg cggaactcct                                      30

<210> SEQ ID NO 1283
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1283
cgcacctctc tttacgcgg                                                  19

<210> SEQ ID NO 1284
<211> LENGTH: 17
<212> TYPE: DNA
<213> ORGANISM: Artificial Sequence
<220> FEATURE:
<223> OTHER INFORMATION: Synthetic oligonucleotide
```

```
<400> SEQUENCE: 1284
ggagtgtgga ttcgcac                                                   17

<210> SEQ ID NO 1285
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1285
gaagaagaac tccctcgcct                                                20

<210> SEQ ID NO 1286
<211> LENGTH: 159
<212> TYPE: DNA
<213> ORGANISM: Hepatitis B virus

<400> SEQUENCE: 1286
ccagcaaatc cgcctcctgc ctccaccaat cgccagacag gaaggcagcc taccccgctg    60
tctccacctt tgagaaacac tcatcctcag gccatgcagt ggaattccac aacctttcac  120
caaactctgc aagatcccag agtgagaggc ctgtatttc                          159

<210> SEQ ID NO 1287
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 1287
tggctcagtt tactagtgcc atttgttcag tggttcg                             37

<210> SEQ ID NO 1288
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1288
ctggagccac cagcagg                                                   17

<210> SEQ ID NO 1289
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1289
actggagcca ccagcag                                                   17

<210> SEQ ID NO 1290
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1290
aactggagcc accagca                                                   17
```

```
<210> SEQ ID NO 1291
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1291
gaactggagc caccagc                                                  17

<210> SEQ ID NO 1292
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1292
actagtaaac tgagcca                                                  17

<210> SEQ ID NO 1293
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1293
cactagtaaa ctgagcc                                                  17

<210> SEQ ID NO 1294
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1294
gcactagtaa actgagc                                                  17

<210> SEQ ID NO 1295
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1295
cgcagtatgg atcggca                                                  17

<210> SEQ ID NO 1296
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1296
ccgcagtatg gatcggc                                                  17

<210> SEQ ID NO 1297
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1297
```
tccgcagtat ggatcgg                                                    17

<210> SEQ ID NO 1298
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1298
ttccgcagta tggatcg                                                    17

<210> SEQ ID NO 1299
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1299
gttccgcagt atggatc                                                    17

<210> SEQ ID NO 1300
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1300
agttccgcag tatggat                                                    17

<210> SEQ ID NO 1301
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1301
gagttccgca gtatgga                                                    17

<210> SEQ ID NO 1302
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1302
ggagttccgc agtatgg                                                    17

<210> SEQ ID NO 1303
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1303
aggagttccg cagtatg                                                    17

<210> SEQ ID NO 1304
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1304
aagcgaagtg cacacgg                                                     17

<210> SEQ ID NO 1305
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1305
gaagcgaagt gcacacg                                                     17

<210> SEQ ID NO 1306
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1306
tgaagcgaag tgcacac                                                     17

<210> SEQ ID NO 1307
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1307
gtgaagcgaa gtgcaca                                                     17

<210> SEQ ID NO 1308
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1308
ggtgaagcga agtgcac                                                     17

<210> SEQ ID NO 1309
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1309
aggtgaagcg aagtgca                                                     17

<210> SEQ ID NO 1310
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1310
gaggtgaagc gaagtgc                                                     17

```
<210> SEQ ID NO 1311
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1311
agaggtgaag cgaagtg                                              17

<210> SEQ ID NO 1312
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1312
cagaggtgaa gcgaagt                                              17

<210> SEQ ID NO 1313
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1313
gcagaggtga agcgaag                                              17

<210> SEQ ID NO 1314
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1314
tgcagaggtg aagcgaa                                              17

<210> SEQ ID NO 1315
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1315
gtgcagaggt gaagcga                                              17

<210> SEQ ID NO 1316
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1316
cgtgcagagg tgaagcg                                              17

<210> SEQ ID NO 1317
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1317
```
acgtgcagag gtgaagc    17

<210> SEQ ID NO 1318
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1318
tggagccacc agcagg    16

<210> SEQ ID NO 1319
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1319
ctggagccac cagcag    16

<210> SEQ ID NO 1320
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1320
actggagcca ccagca    16

<210> SEQ ID NO 1321
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1321
aactggagcc accagc    16

<210> SEQ ID NO 1322
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1322
actagtaaac tgagcc    16

<210> SEQ ID NO 1323
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1323
cactagtaaa ctgagc    16

<210> SEQ ID NO 1324
<211> LENGTH: 16
<212> TYPE: DNA
<213> ORGANISM: Artificial Sequence

```
<220> FEATURE:
<223> OTHER INFORMATION: Synthetic oligonucleotide

<400> SEQUENCE: 1324
gcactagtaa actgag                                                    16

<210> SEQ ID NO 1325
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1325
cgcagtatgg atcggc                                                    16

<210> SEQ ID NO 1326
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1326
ccgcagtatg gatcgg                                                    16

<210> SEQ ID NO 1327
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1327
tccgcagtat ggatcg                                                    16

<210> SEQ ID NO 1328
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1328
ttccgcagta tggatc                                                    16

<210> SEQ ID NO 1329
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1329
gttccgcagt atggat                                                    16

<210> SEQ ID NO 1330
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1330
agttccgcag tatgga                                                    16
```

```
<210> SEQ ID NO 1331
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1331
gagttccgca gtatgg                                                       16

<210> SEQ ID NO 1332
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1332
ggagttccgc agtatg                                                       16

<210> SEQ ID NO 1333
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1333
aggagttccg cagtat                                                       16

<210> SEQ ID NO 1334
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1334
agcgaagtgc acacgg                                                       16

<210> SEQ ID NO 1335
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1335
aagcgaagtg cacacg                                                       16

<210> SEQ ID NO 1336
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1336
gaagcgaagt gcacac                                                       16

<210> SEQ ID NO 1337
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1337
```
tgaagcgaag tgcaca                                          16

<210> SEQ ID NO 1338
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1338
gtgaagcgaa gtgcac                                          16

<210> SEQ ID NO 1339
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1339
ggtgaagcga agtgca                                          16

<210> SEQ ID NO 1340
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1340
aggtgaagcg aagtgc                                          16

<210> SEQ ID NO 1341
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1341
gaggtgaagc gaagtg                                          16

<210> SEQ ID NO 1342
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1342
agaggtgaag cgaagt                                          16

<210> SEQ ID NO 1343
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1343
cagaggtgaa gcgaag                                          16

<210> SEQ ID NO 1344
<211> LENGTH: 16
<212> TYPE: DNA
<213> ORGANISM: Artificial Sequence

```
<220> FEATURE:
<223> OTHER INFORMATION: Synthetic oligonucleotide

<400> SEQUENCE: 1344
gcagaggtga agcgaa                                                       16

<210> SEQ ID NO 1345
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1345
tgcagaggtg aagcga                                                       16

<210> SEQ ID NO 1346
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1346
gtgcagaggt gaagcg                                                       16

<210> SEQ ID NO 1347
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1347
cgtgcagagg tgaagc                                                       16

<210> SEQ ID NO 1348
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1348
acgtgcagag gtgaag                                                       16

<210> SEQ ID NO 1349
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1349
ggagttccgc agtatggatc                                                   20

<210> SEQ ID NO 1350
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1350
acgtgcagag gtgaagcgaa                                                   20
```

```
<210> SEQ ID NO 1351
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1351
cggtccttgg aggatgc                                                  17

<210> SEQ ID NO 1352
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 1352
ccgtgtgcac ttcgcttcac ctctgcacgt                                    30

<210> SEQ ID NO 1353
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 1353
ggaggctgta ggcataaatt ggt                                           23

<210> SEQ ID NO 1354
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 1354
agagtctaga ctcgtggtgg acttctctca                                    30

<210> SEQ ID NO 1355

<400> SEQUENCE: 1355

000

<210> SEQ ID NO 1356

<400> SEQUENCE: 1356

000

<210> SEQ ID NO 1357

<400> SEQUENCE: 1357

000

<210> SEQ ID NO 1358

<400> SEQUENCE: 1358

000

<210> SEQ ID NO 1359
<211> LENGTH: 17
<212> TYPE: DNA
<213> ORGANISM: Artificial Sequence
```

```
<220> FEATURE:
<223> OTHER INFORMATION: Synthetic oligonucleotide

<400> SEQUENCE: 1359
tatatggatg atgtggt                                                      17

<210> SEQ ID NO 1360
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1360
tgccaagtgt ttgctga                                                      17

<210> SEQ ID NO 1361
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1361
tgccgatcca tactgcggaa ctcct                                             25

<210> SEQ ID NO 1362
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 1362 cttttcacc tctgccta                                                      18

<210> SEQ ID NO 1363
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1363
ttcaagcctc caagctgtgc cttgg                                             25

<210> SEQ ID NO 1364
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1364
aaatggcact agtaaa                                                       16

<210> SEQ ID NO 1365
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1365
caaatggcac tagtaa                                                       16
```

```
<210> SEQ ID NO 1366
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1366
acaaatggca ctagta                                                 16

<210> SEQ ID NO 1367
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1367
aacaaatggc actagt                                                 16

<210> SEQ ID NO 1368
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1368
gaacaaatgg cactag                                                 16

<210> SEQ ID NO 1369
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1369
tgaacaaatg gcacta                                                 16

<210> SEQ ID NO 1370
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1370
ctgaacaaat ggcact                                                 16

<210> SEQ ID NO 1371
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1371
actgaacaaa tggcac                                                 16

<210> SEQ ID NO 1372
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1372
```
cactgaacaa atggca                                               16

<210> SEQ ID NO 1373
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1373
cctgatgtga tgttctccat g                                         21

<210> SEQ ID NO 1374
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1374
aaacgccgca gacacatcca                                           20

<210> SEQ ID NO 1375
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1375
gataaaacgc cgcagacaca                                           20

<210> SEQ ID NO 1376
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1376
atgataaaac gccgcagaca                                           20

<210> SEQ ID NO 1377
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1377
cacccaaggc acagcttgg                                            19

<210> SEQ ID NO 1378
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1378
gaatcctgat gtgatgttct c                                         21

<210> SEQ ID NO 1379
<211> LENGTH: 18
<212> TYPE: DNA
<213> ORGANISM: Artificial Sequence

```
<220> FEATURE:
<223> OTHER INFORMATION: Synthetic oligonucleotide

<400> SEQUENCE: 1379
aatttatgcc tacagcct                                              18

<210> SEQ ID NO 1380
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1380
ccaaagccac ccaagg                                                16

<210> SEQ ID NO 1381
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1381
caaattcttt ataagggtcg a                                          21
```

MODULATION OF HEPATITIS B VIRUS (HBV) EXPRESSION

RELATED APPLICATIONS

This application claims priority under 35 U.S.C. §119(e) to U.S. Provisional Patent Application No. 61/478,040, filed Apr. 21, 2011; U.S. Provisional Patent Application No. 61/478,038, filed Apr. 21, 2011; U.S. Provisional Patent Application No. 61/596,690, filed Feb. 8, 2012; and U.S. Provisional Patent Application No. 61/596,692, filed Feb. 8, 2012, each of which is incorporated herein by reference in its entirety.

Isis Pharmaceuticals, Inc. and GlaxoSmithKline LLC are parties to a joint research agreement under 35 U.S.C. § 103 (c)(3).

SEQUENCE LISTING

The present application is being filed along with a Sequence Listing in electronic format. The Sequence Listing is provided as a file entitled BIOL0175USSEQ.txt created Apr. 18, 2012, which is approximately 256 KB in size. The information in the electronic format of the sequence listing is incorporated herein by reference in its entirety.

FIELD

In certain embodiments provided are methods, compounds, and compositions for inhibiting expression of hepatitis B virus (HBV) mRNA and protein in an animal. Such methods, compounds, and compositions are useful to treat, prevent, or ameliorate HBV-related diseases and disorders.

BACKGROUND

Hepatitis B is a viral disease transmitted parenterally by contaminated material such as blood and blood products, contaminated needles, sexually and vertically from infected or carrier mothers to their offspring. It is estimated by the World Health Organization that more than 2 billion people have been infected worldwide, with about 4 million acute cases per year, 1 million deaths per year, and 350-400 million chronic carriers (World Health Organization: Geographic Prevalence of Hepatitis B Prevalence, 2004. http://www-.who.int/vaccines-surveillance/graphics/htmls/hepbpre-v.htm).

The virus, HBV, is a double-stranded hepatotropic virus which infects only humans and non-human primates. Viral replication takes place predominantly in the liver and, to a lesser extent, in the kidneys, pancreas, bone marrow and spleen (Hepatitis B virus biology. Microbiol. Mol Biol Rev. 64: 2000; 51-68.). Viral and immune markers are detectable in blood and characteristic antigen-antibody patterns evolve over time. The first detectable viral marker is HBsAg, followed by hepatitis B e antigen (HBeAg) and HBV DNA. Titers may be high during the incubation period, but HBV DNA and HBeAg levels begin to fall at the onset of illness and may be undetectable at the time of peak clinical illness (Hepatitis B virus infection—natural history and clinical consequences. N Engl J. Med. 350: 2004; 1118-1129). HBeAg is a viral marker detectable in blood and correlates with active viral replication, and therefore high viral load and infectivity (Hepatitis B e antigen—the dangerous end game of hepatitis B. N Engl J. Med. 347: 2002; 208-210). The presence of anti-HBsAb and anti-HBcAb (IgG) indicates recovery and immunity in a previously infected individual.

Currently the recommended therapies for chronic HBV infection by the American Association for the Study of Liver Diseases (AASLD) and the European Association for the Study of the Liver (EASL) include interferon alpha (INF$\alpha$), pegylated interferon alpha-2a (Peg-IFN2a), entecavir, and tenofovir. The nucleoside and nucleotide therapies, entecavir and tenofovir, are successful at reducing viral load, but the rates of HBeAg seroconversion and HBsAg loss are even lower than those obtained using IFN$\alpha$ therapy. Other similar therapies, including lamivudine (3TC), telbivudine (LdT), and adefovir are also used, but for nucleoside/nucleotide therapies in general, the emergence of resistance limits therapeutic efficacy.

Thus, there is a need in the art to discover and develop new anti-viral therapies. Additionally, there is a need for new anti-HBV therapies capable of increasing HBeAg and HBsAg seroconversion rates. Recent clinical research has found a correlation between seroconversion and reductions in HBeAg (Fried et al (2008) Hepatology 47:428) and reductions in HBsAg (Moucari et al (2009) Hepatology 49:1151). Reductions in antigen levels may have allowed immunological control of HBV infection because high levels of antigens are thought to induce immunological tolerance. Current nucleoside therapies for HBV are capable of dramatic reductions in serum levels of HBV but have little impact on HBeAg and HBsAg levels.

Antisense technology is emerging as an effective means for reducing the expression of specific gene products and may therefore prove to be uniquely useful in a number of therapeutic, diagnostic, and research applications for the modulation of HBV expression (See U.S. Patent Publication Nos. 2008/0039418 and 2007/0299027). Antisense therapy differs from nucleoside therapy in that it can directly target the transcripts for the HBV antigens and thereby reduce serum HBeAg and HBsAg levels. Because of the multiple, overlapping transcripts produced upon HBV infection, there is also an opportunity for a single antisense oligomer to reduce HBV DNA in addition to both HBeAg and HBsAg. Therefore, antisense technology is emerging as an effective means for reducing the expression of certain gene products and may therefore prove to be uniquely useful in a number of therapeutic, diagnostic, and research applications for the modulation of HBV.

SUMMARY

Provided herein are methods, compounds, and compositions for modulating expression of HBV mRNA and protein. In certain embodiments, compounds useful for modulating expression of HBV mRNA and protein are antisense compounds. In certain embodiments, the antisense compounds are antisense oligonucleotides.

In certain embodiments, modulation can occur in a cell or tissue. In certain embodiments, the cell or tissue is in an animal. In certain embodiments, the animal is a human. In certain embodiments, HBV mRNA levels are reduced. In certain embodiments, HBV DNA levels are reduced. In certain embodiments, HBV protein levels are reduced. In certain embodiments, HBV antigen levels are reduced. In certain embodiments, HBV s-antigen (HBsAg) levels are reduced. In certain embodiments, HBV e-antigen (HBeAg) levels are reduced. Such reduction can occur in a time-dependent manner or in a dose-dependent manner.

Also provided are methods, compounds, and compositions useful for preventing, treating, and ameliorating diseases, disorders, and conditions. In certain embodiments, such HBV related diseases, disorders, and conditions are liver diseases.

In certain embodiments, such liver diseases, disorders, and conditions includes jaundice, liver cancer, liver inflammation, liver fibrosis, inflammation, liver cirrhosis, liver failure, diffuse hepatocellular inflammatory disease, hemophagocytic syndrome, serum hepatitis, HBV viremia, and liver disease-related transplantation. In certain embodiments, such HBV related diseases, disorders, and conditions are hyperproliferative diseases, disorders, and conditions. In certain embodiments such hyperproliferative diseases, disorders, and conditions include cancer as well as associated malignancies and metastases. In certain embodiments, such cancers include liver cancer and hepatocellular cancer (HCC).

Such diseases, disorders, and conditions can have one or more risk factors, causes, or outcomes in common. Certain risk factors and causes for development of liver disease or a hyperproliferative disease include growing older; tobacco use; exposure to sunlight and ionizing radiation; contact with certain chemicals; infection with certain viruses and bacteria; certain hormone therapies; family history of cancer; alcohol use; and certain lifestyle choices including poor diet, lack of physical activity, and/or being overweight. Certain symptoms and outcomes associated with development of a liver disease or a hyperproliferative disease include but are not limited to: flu-like illness, weakness, aches, headache, fever, loss of appetite, diarrhea, jaundice, nausea and vomiting, pain over the liver area of the body, clay- or grey-colored stool, itching all over, and dark-colored urine.

In certain embodiments, methods of treatment include administering a HBV antisense compound to an individual in need thereof. In certain embodiments, methods of treatment include administering a HBV antisense oligonucleotide to an individual in need thereof.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification at the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of HBV", it is implied that the HBV levels are inhibited within a range of 63% and 77%.

"Acceptable safety profile" means a pattern of side effects that is within clinically acceptable limits.

"Active pharmaceutical agent" means the substance or substances in a pharmaceutical composition that provide a therapeutic benefit when administered to an individual. For example, in certain embodiments an antisense oligonucleotide targeted to HBV is an active pharmaceutical agent.

"Active target region" means a target region to which one or more active antisense compounds is targeted. "Active antisense compounds" means antisense compounds that reduce target nucleic acid levels or protein levels.

"Acute hepatitis B infection" results when a person exposed to the hepatitis B virus begins to develop the signs and symptoms of viral hepatitis. This period of time, called the incubation period, is an average of 90 days, but could be as short as 45 days or as long as 6 months. For most people this infection will cause mild to moderate discomfort but will go away by itself because of the body's immune response succeeds in fighting the virus. However, some people, particularly those with compromised immune systems, such as persons suffering from AIDS, undergoing chemotherapy, taking immunosuppressant drugs, or taking steroids, have very serious problems as a result of the acute HBV infection, and go on to more severe conditions such as fulminant liver failure.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Agent" means an active substance that can provide a therapeutic benefit when administered to an animal. "First Agent" means a therapeutic compound described herein. For example, a first agent can be an antisense oligonucleotide targeting HBV. "Second agent" means a second therapeutic compound described herein (e.g. a second antisense oligonucleotide targeting HBV) and/or a non-HBV therapeutic compound.

"Amelioration" refers to a lessening of at least one indicator of the severity of a condition or disease. The severity of indicators may be determined by subjective or objective measures which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, $F_{ab}$ region, and $F_c$ region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, snoRNAs, miRNAs, and satellite repeats.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two non-geminal carbon atoms. A bicyclic sugar is a modified sugar.

"Body weight" refers to an animal's whole body weight, inclusive of all tissues including adipose tissue.

"Cap structure" or "terminal cap moiety" means chemical modifications, which have been incorporated at either terminus of an antisense compound.

"cEt" or "constrained ethyl" means a bicyclic sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Chronic hepatitis B infection" occurs when a person initially suffers from an acute infection but is then unable to fight off the infection. Whether the disease becomes chronic or completely resolves depends mostly on the age of the infected person. About 90% of infants infected at birth will progress to chronic disease. However, as a person ages, the risk of chronic infection decreases such that between 20%-50% of children and less than 10% of older children or adults will progress from acute to chronic infection. Chronic HBV infections are the primary treatment goal for embodiments of the present invention, although ASO compositions of the present invention are also capable of treating HBV-related conditions, such as inflammation, fibrosis, cirrhosis, liver cancer, serum hepatitis, and more.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Complementarity" means the capacity for pairing between nucleobases of a first nucleic acid and a second nucleic acid.

"Comply" means the adherence with a recommended therapy by an individual.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Cure" means a method or course that restores health or a prescribed treatment for an illness.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dosage unit" means a form in which a pharmaceutical agent is provided, e.g. pill, tablet, or other dosage unit known in the art.

"Dose" means a specified quantity of a pharmaceutical agent provided in a single administration, or in a specified time period. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual. In other embodiments, the pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Duration" means the period of time during which an activity or event continues. In certain embodiments, the duration of treatment is the period of time during which doses of a pharmaceutical agent are administered.

"Effective amount" in the context of modulating an activity or of treating or preventing a condition means the administration of that amount of active ingredient to a subject in need of such modulation, treatment or prophylaxis, either in a single dose or as part of a series, that is effective for modulation of that effect, or for treatment or prophylaxis or improvement of that condition. The effective amount will vary depending upon the health and physical condition of the subject to be treated, the taxonomic group of subjects to be treated, the formulation of the composition, the assessment of the medical situation, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Fully modified motif" refers to an antisense compound comprising a contiguous sequence of nucleosides wherein essentially each nucleoside is a sugar modified nucleoside having uniform modification.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Gap-widened" means an antisense compound having a gap segment of 12 or more contiguous 2'-deoxyribonucleotides positioned between 5' and 3' wing segments having from one to six nucleotides having modified sugar moieties.

"HBV" means mammalian hepatitis B virus, including human hepatitis B virus. The term encompasses geographical genotypes of hepatitis B virus, particularly human hepatitis B virus, as well as variant strains of geographical genotypes of hepatitis B virus.

"HBV antigen" means any hepatitis B virus antigen or protein, including core proteins such as "hepatitis B core antigen" or "HBcAG" and "hepatitis B E antigen" or "HBeAG" and envelope proteins such as "HBV surface antigen", or "HBsAg" or "HBsAG".

"Hepatitis B E antigen" or "HBeAg" or "HBeAG" is a secreted, non-particulate form of HBV core protein. HBV antigens HBeAg and HBcAg share primary amino acid sequences, so show cross-reactivity at the T cell level. HBeAg is not required for viral assembly or replication, although studies suggest they may be required for establishment of chronic infection. Neonatal infection with HBeAg-negative mutant often results in fulminant acute rather than chronic HBV infection (Terezawa et al (1991) Pediatr. Res. 29:5), whereas infection of young woodchucks with WHeAg-negative mutant results in a much lower rate of chronic WHV infection (Cote et al (2000) Hepatology 31:190). HBeAg may possibly function as a toleragen by inactivating core specific T cells through deletion or clonal anergy (Milich et al (1998) J. Immunol. 160:8102). There is a positive correlation between reduction of HBV viral load and antigens, and a decrease of expression, by T cells, of the inhibitory receptor programmed death-1 (PD-1; also known as PDCD1), a negative regulator of activated T cells, upon antiviral therapy and HBeAg seroconversion (Evans et al (2008) Hepatology 48:759).

"HBV mRNA" means any messenger RNA expressed by hepatitis B virus.

"HBV nucleic acid" or 'HBV DNA" means any nucleic acid encoding HBV. For example, in certain embodiments, a HBV nucleic acid includes, without limitation, any viral DNA sequence encoding a HBV genome or portion thereof, any RNA sequence transcribed from a viral DNA including any mRNA sequence encoding a HBV protein.

"HBV protein" means any protein secreted by hepatitis B virus The term encompasses various HBV antigens, including core proteins such as "Hepatitis E antigen", "HBeAg" or "HBeAG" and envelope proteins such as "HBV surface antigen", or "HBsAg".

"HBV surface antigen", or "HBsAg", or "HBsAG" is the envelope protein of infectious HBV viral particles but is also secreted as a non-infectious particle with serum levels 1000-fold higher than HBV viral particles. The serum levels of HBsAg in an infected person or animal can be as high as 1000 μg/mL (Kann and Gehrlich (1998) Topley & Wilson's Microbiology and Microbial Infections, $9^{th}$ ed. 745). In acute HBV infections, the half-life of HBsAg in the serum, or serum $t_{1/2}$, is 8.3 days (Chulanov et al (2003) J. Med. Virol. 69: 313). Internalization of HBsAg by myeloid dendritic cells inhibits up-regulation of co-stimulatory molecules (i.e. B7) and inhibits T cell stimulatory capacity (den Brouw et al (2008) Immunology 126:280), and dendritic cells from chronically infected patients also show deficits in expression of co-stimulatory molecules, secretion of IL-12, and stimulation of T cells in the presence of HBsAg (Zheng et al (2004) J. Viral Hepatitis 11:217). HBsAg specific CD8 cells from CHB patients show altered tetramer binding. These CD8 cells are not anergic but may have TCR topology that confers partial tolerance or ignorance (Reignat et al (2002) J. Exp. Med. 195:1089). Moreover, reduction in serum HBsAg >1 log at week 24 has a high predictive value (92%) for sustained virological response (SVR—defined as nondetectable HBV DNA by PCR at 1 year after treatment) during Peg-IFNα2a therapy (Moucari et al (2009) Hepatology 49:1151).

"Hepatitis B-related condition" or "HBV-related condition" means any disease, biological condition, medical condition, or event which is exacerbated, caused by, related to, associated with, or traceable to a hepatitis B infection, exposure, or illness. The term hepatitis B-related condition includes chronic HBV infection, inflammation, fibrosis, cirrhosis, liver cancer, serum hepatitis, jaundice, liver cancer, liver inflammation, liver fibrosis, liver cirrhosis, liver failure, diffuse hepatocellular inflammatory disease, hemophagocytic syndrome, serum hepatitis, HBV viremia, liver disease related to transplantation, and conditions having symptoms which may include any or all of the following: flu-like illness, weakness, aches, headache, fever, loss of appetite, diarrhea, nausea and vomiting, pain over the liver area of the body, clay- or grey-colored stool, itching all over, and dark-colored urine, when coupled with a positive test for presence of a hepatitis B virus, a hepatitis B viral antigen, or a positive test for the presence of an antibody specific for a hepatitis B viral antigen.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Identifying an animal having an HBV infection" means identifying an animal having been diagnosed with an HBV; or, identifying an animal having any symptom of an HBV infection including, but not limited to chronic HBV infection, inflammation, fibrosis, cirrhosis, liver cancer, serum hepatitis, jaundice, liver cancer, liver inflammation, liver fibrosis, liver cirrhosis, liver failure, diffuse hepatocellular inflammatory disease, hemophagocytic syndrome, serum hepatitis, HBV viremia, liver disease related to transplantation, and conditions having symptoms which may include any or all of the following: flu-like illness, weakness, aches, headache, fever, loss of appetite, diarrhea, nausea and vomiting, pain over the liver area of the body, clay- or grey-colored stool, itching all over, and dark-colored urine, when coupled with a positive test for presence of a hepatitis B virus, a hepatitis B viral antigen, or a positive test for the presence of an antibody specific for a hepatitis B viral antigen, when coupled with a positive test for presence of a hepatitis B virus, a hepatitis B viral antigen, or a positive test for the presence of an antibody specific for a hepatitis B viral antigen.

"Immediately adjacent" means there are no intervening elements between the immediately adjacent elements.

"Individual" means a human or non-human animal selected for treatment or therapy.

"Individual compliance" means adherence to a recommended or prescribed therapy by an individual.

"Induce", "inhibit", "potentiate", "elevate", "increase", "decrease" or the like, generally denote quantitative differences between two states. Such terms may refer to a statistically significant difference between the two states. For example, "an amount effective to inhibit the activity or expression of HBV" means that the level of activity or expression of HBV in a treated sample will quantitatively differ, and may be statistically significant, from the level of HBV activity or expression in untreated cells. Such terms are applied to, for example, levels of expression, and levels of activity.

"Inhibiting HBV" means reducing the level or expression of an HBV mRNA, DNA and/or protein. In certain embodiments, HBV is inhibited in the presence of an antisense compound targeting HBV, including an antisense oligonucleotide targeting HBV, as compared to expression of HBV mRNA, DNA and/or protein levels in the absence of a HBV antisense compound, such as an antisense oligonucleotide.

"Inhibiting the expression or activity" refers to a reduction, blockade of the expression or activity and does not necessarily indicate a total elimination of expression or activity.

"Injection site reaction" means inflammation or abnormal redness of skin at a site of injection in an individual.

"Internucleoside linkage" refers to the chemical bond between nucleosides.

"Intraperitoneal administration" means administration through infusion or injection into the peritoneum.

"Intravenous administration" means administration into a vein.

"Lengthened" antisense oligonucleotides are those that have one or more additional nucleosides relative to an antisense oligonucleotide disclosed herein.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2' position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

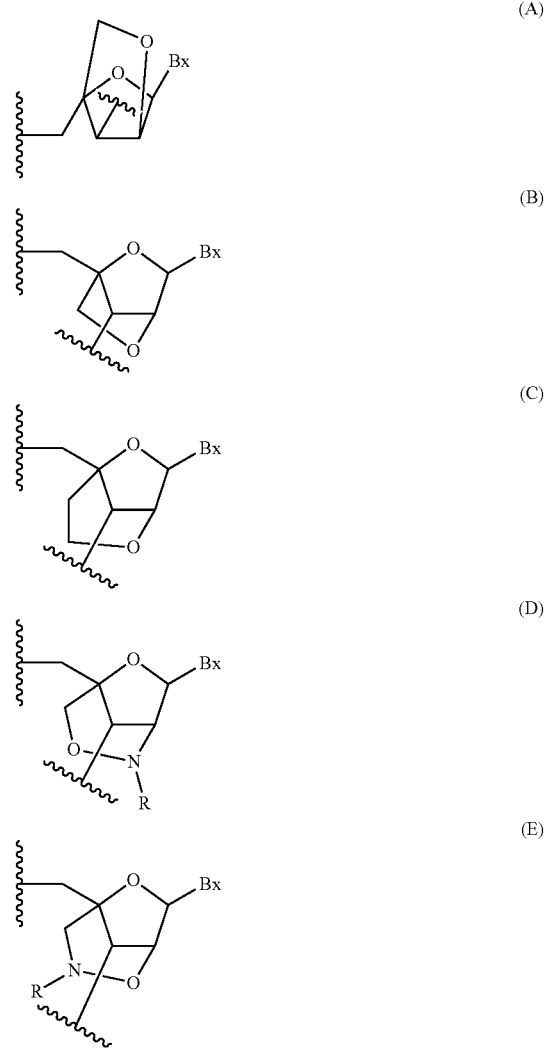

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)═C(R$_2$)—, —C(R$_1$)═N—, —C(═NR$_1$)—, —C(═O)—, —C(=S)—, —O—, —Si(R$_1$)$_2$—, —S(=O)$_x$— and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

Examples of 4'-2' bridging groups encompassed within the definition of LNA include, but are not limited to one of formulae: —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2',4'-(CH$_2$)$_2$—O-2', 4'-CH$_2$—O—N(R$_1$)-2' and 4'-CH$_2$—N(R$_1$)—O-2'-bridges, wherein each R$_1$ and R$_2$ is, independently, H, a protecting group or C$_1$-C$_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicylic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Monomer" refers to a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, "peptide" refers to polypeptides and proteins.

"Pharmaceutically acceptable carrier" means a medium or diluent that does not interfere with the structure of the oligonucleotide. Certain such carriers enable pharmaceutical compositions to be formulated as, for example, tablets, pills, dragees, capsules, liquids, gels, syrups, slurries, suspension and lozenges for the oral ingestion by a subject.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Pharmaceutical agent" means a substance that provides a therapeutic benefit when administered to an individual. For example, in certain embodiments, an antisense oligonucleotide targeted to HBV is a pharmaceutical agent.

"Pharmaceutical composition" means a mixture of substances suitable for administering to a subject. For example, a pharmaceutical composition may comprise an antisense oligonucleotide and a sterile aqueous solution. In certain embodiments, a pharmaceutical composition shows activity in free uptake assay in certain cell lines.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevention" or "preventing" refers to delaying or forestalling the onset or development of a condition or disease for a period of time from hours to days, preferably weeks to months.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Recommended therapy" means a therapeutic regimen recommended by a medical professional for the treatment, amelioration, or prevention of a disease.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Seroconversion" is defined as serum HBeAg absence plus serum HBeAb presence, if monitoring HBeAg as the determinant for seroconversion, or defined as serum HBsAg absence, if monitoring HBsAg as the determinant for seroconversion, as determined by currently available detection limits of commercial ELISA systems.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

"Significant," as used herein means measurable or observable, e.g, a significant result, such as, a significant improvement or significant reduction generally refers to a measurable or observable result, such as a measurable or observable improvement or reduction.

"Sites," as used herein, are defined as unique nucleobase positions within a target nucleic acid.

"Slows progression" means decrease in the development of the said disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Statistically Significant," as used herein means a measurable or observable parameter that is unlikely to occur by chance.

"Subcutaneous administration" means administration just below the skin.

"Subject" means a human or non-human animal selected for treatment or therapy.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treatment" refers to administering a composition to effect an alteration or improvement of the disease or condition.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Validated target segment" is defined as at least an 8-nucleobase portion (i.e. 8 consecutive nucleobases) of a target region to which an active oligomeric compound is targeted.

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide methods, compounds, and compositions for inhibiting HBV mRNA expression.

Certain embodiments provide antisense compounds targeted to a HBV nucleic acid. In certain embodiments, the HBV nucleic acid is the sequences set forth in GENBANK Accession No. U95551.1 (incorporated herein as SEQ ID NO: 1).

In certain embodiments, the compounds provided herein are or comprise a modified oligonucleotide. In certain embodiments the compounds comprise a modified oligonucleotide and a conjugate as described herein. In certain embodiments, the modified oligonucleotide is a pharmaceutically acceptable derivative.

In certain embodiments, the compounds or compositions comprise a modified oligonucleotide 10 to 30 linked nucleosides in length targeted to HBV. The HBV target can have a sequence recited in SEQ ID NO: 1 or a portion thereof or a variant thereof.

In certain embodiments, the compounds or modified oligonucleotides provided herein are 10 to 30 linked nucleosides in length and are targeted to HBV. In certain embodiments, the HBV target has the sequence recited in SEQ ID NO: 1. In certain embodiments, such compounds or oligonucleotides target one of the following nucleotide regions of HBV: CCTGCTGGTGGCTCCAGTTC (SEQ ID NO: 1273); AGAGTCTAGACTCGTGGTGGACTTCTCTCA (SEQ ID NO: 1354); CATCCTGCTGCTATGCCTCATCTTCTT (SEQ ID NO: 1276); CAAGGTATGTTGCCCGT (SEQ ID NO: 1277); CCTATGGGAGTGGGCCTCAG (SEQ ID NO: 1279; TGGCTCAGTTTACTAGTGCCATTTGTTCAGTGGTTCG (SEQ ID NO: 1287); TATATGGATGATGTGGT (SEQ ID NO:1359); TGCCAAGTGTTTGCTGA (SEQ ID NO:1360); TGCCGATCCATACTGCGGAACTCCT (SEQ ID NO: 1361); CCGTGTGCACTTCGCTTCACCTCTGCACGT (SEQ ID NO:1352); GGAGGCTGTAGGCATAAATTGGT (SEQ ID NO:1353); CTTTTTCACCTCTGCCTA (SEQ ID NO:1362); TTCAAGCCTCCAAGCTGTGCCTTGG (SEQ ID NO:1363); AGAGTCTAGACTCGTGGTGGACTTCTCTCAATTTTCTAGGGG (SEQ ID NO: 1274); TGGATGTGTCTGCGGCGTTTTATCAT (SEQ ID NO: 1275); TGTATTCCCATCCCATC (SEQ ID NO: 1278); TGGCTCAGTTTACTAGTGC (SEQ ID NO: 1280); GGGCTTTCCCCCACTGT (SEQ ID NO: 1281); TCCTCTGCCGATCCATACTGCGGAACTCCT (SEQ ID NO: 1282); CGCACCTCTCTTTACGCGG (SEQ ID NO: 1283); GGAGTGTGGATTCGCAC (SEQ ID NO: 1284); or GAAGAAGAACTCCCTCGCCT (SEQ ID NO: 1285). In certain embodiments, such compounds or oligonucleotides have a gap segment of 9, 10, or more linked deoxynucleosides. In certain embodiments, such compounds or oligonucleotides have a gap segment of 6, 7, 8, 9, 10, 11, 12, 13, 14, 15, or 16 linked nucleosides. In certain embodiments, such gap segment is between two wing segments that independently have 1, 2, 3, 4, 5, 6, 7, or 8 linked modified nucleosides. In certain embodiments, one or more modified nucleosides in the wing segment have a modified sugar. In certain embodiments, the modified sugar is a bicyclic sugar. In certain embodiments, the modified nucleoside is an LNA nucleoside. In certain embodiments, the modified nucleoside is a 2'-substituted nucleoside. In certain embodiments, 2' substituted nucleosides include nucleosides with bicyclic sugar modifications. In certain embodiments, the modified nucleoside is a 2'-MOE nucleoside. In certain embodiments, the modified nucleoside is a constrained ethyl (cEt) nucleoside.

In certain embodiments, the compounds or compositions comprise modified oligonucleotides consisting of 10 to 30 linked nucleosides and having a nucleobase sequence comprising a portion at least 8, 9, 10, 11, 12, 13, 14, 15, 16, 17, 18, 19, 20, 21, 22, 23, 24, 25, 26, 27, 28, 29 or 30 contiguous nucleobases complementary to an equal length portion of any of the nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1. In certain embodiments, such oligonucleotides have a gap segment of 9, 10, or more linked deoxynucleosides. In certain embodiments, such gap segment is between two wing segments that independently have 1, 2, 3, 4, 5, 6, 7, or 8 linked modified nucleosides. In certain embodiments, one or more modified nucleosides in the wing segment have a modified sugar. In certain embodiments, the modified sugar is a bicyclic sugar. In certain embodiments, the modified nucleoside is an LNA nucleoside. In certain embodiments, the modified nucleoside is a 2'-substituted nucleoside. In certain embodiments, 2' substituted nucleosides include nucleosides with bicyclic sugar modifications. In certain embodiments, the modified nucleoside is a 2'-MOE nucleoside. In certain embodiments, the modified nucleoside is a constrained ethyl (cEt) nucleoside. In certain embodiments, each modified nucleoside in each wing segment is independently a 2'-MOE nucleoside or a nucleoside with a bicyclic sugar modification such as a constrained ethyl (cEt) nucleoside or LNA nucleoside.

In certain embodiments, the compounds or compositions comprise a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 5-310, 321-802, 804-1272, 1288-1350, 1364-1372, 1375, 1376, or 1379. In certain embodiments, such oligonucleotides have a gap segment of 9, 10, or more linked deoxynucleosides. In certain embodiments, such gap segment is between two wing segments that independently have 1-5, 1-4, 1-3, 2-5, 2-4 or 2-3 linked modified nucleosides. In certain embodiments, such gap segment is between two wing segments that independently have 1, 2, 3, 4, 5, 6, 7, or 8 linked modified nucleosides. In certain embodiments, one or more modified nucleosides in the wing segment have a modified sugar. In certain embodiments, the modified sugar is a bicyclic sugar. In certain embodiments, the modified nucleoside is an LNA nucleoside. In certain embodiments, the modified nucleoside is a 2'-substituted nucleoside. In certain embodiments, 2' substituted nucleosides include nucleosides with bicyclic sugar modifications. In certain embodiments, the modified nucleoside is a 2'-MOE nucleoside. In certain embodiments, the modified nucleoside is a constrained ethyl (cEt) nucleoside.

In certain embodiments, the modified oligonucleotide is 16 nucleosides in length and has a gap segment of 10 linked nucleosides. In certain embodiments, the modified oligonucleotide has a wing segment on the 5' end and 3' end of the gap each independently having 2, 3, or 4 sugar modified nucleosides. In certain embodiments, each sugar modified nucleoside is independently a 2'-MOE nucleoside or a nucleoside with a bicyclic sugar moiety such as a constrained ethyl (cEt) nucleoside or LNA nucleoside. In certain embodiments, the modified oligonucleotide is 16 nucleosides in length and has a gap segment of 9 linked nucleosides. In certain embodiments, the modified oligonucleotide has a wing segment on the 5' end and 3' end of the gap each independently having 2, 3, 4, or 5 sugar modified nucleosides. In certain embodiments, each sugar modified nucleoside is independently a 2'-MOE nucleoside or a bicyclic nucleoside such as a constrained ethyl (cEt) nucleoside or LNA nucleoside.

In certain embodiments, the compounds or compositions comprise a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 5-310, 321-802, 804-1272, 1288-1350, 1364-1372, 1375, 1376, or 1379. In certain embodiments, such oligonucleotides have a gap segment of 10 or more linked deoxynucleosides. In certain embodiments, such gap segment is between two wing segments that independently have 1-5, 1-4, 1-3, 2-5, 2-4 or 2-3 linked modified nucleosides. In certain embodiments, such gap segment is between two wing segments that independently have 2, 3, 4, 5, 6, 7, or 8 linked modified nucleosides. In certain embodiments, one or more modified nucleosides in the wing segment have a modified sugar. In certain embodiments, the modified sugar is a bicyclic sugar. In certain embodiments, the modified nucleoside is an LNA nucleoside. In certain embodiments, the modified nucleoside is a 2'-substituted nucleoside. In certain embodiments, 2' substituted nucleosides include nucleosides with bicyclic sugar modifications. In certain embodiments, the modified nucleoside is a 2'-MOE nucleoside.

In certain embodiments, the compounds or compositions comprise a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 5, 15, 16, 33, 39-95, 123-135, 163-175, 180-310, 321-406, 413-455, 461-802, or 804-1272. In certain embodiments, such oligonucleotides have a gap segment of 10 or more linked deoxynucleosides. In certain embodiments, such gap segment is between two wing segments that independently have 1-5, 1-4, 1-3, 2-5, 2-4 or 2-3 linked modified nucleosides. In certain embodiments, one or more modified nucleosides in the wing segment have a modified sugar. In certain embodiments, the modified sugar is a bicyclic sugar. In certain embodiments, the modified nucleoside is an LNA nucleoside. In certain embodiments, the modified nucleoside is a 2'-substituted nucleoside. In certain embodiments, 2' substituted nucleosides include nucleosides with bicyclic sugar modifications. In certain embodiments, the modified nucleoside is a 2'-MOE nucleoside.

In certain embodiments, the compounds or compositions comprise a modified oligonucleotide consisting of 10 to 30 linked nucleosides and having a nucleobase sequence comprising at least 8, 9, 10, 11, 12, 13, 14, 15, 16, 17, 18, 19, or 20 contiguous nucleobases of any of SEQ ID NOs: 6-14, 17-32, 34-38, 96-122, 136-162, 176-179, 407-412, 456-462, 523-538. In certain embodiments, such oligonucleotides have a gap segment of 10 or more linked deoxynucleosides. In certain embodiments, such gap segment is between two wing segments that independently have 1-5, 1-4, 1-3, 2-5, 2-4 or 2-3 linked modified nucleosides. In certain embodiments, one or more modified nucleosides in the wing segment have a modified sugar. In certain embodiments, the modified nucleoside is a 2'-substituted nucleoside. In certain embodiments, the modified nucleoside is a 2'-MOE nucleoside. In certain embodiments, the modified oligonucleotide is 14 nucleosides in length and has a gap segment of 10 linked nucleosides. In certain embodiments, the modified oligonucleotide has a wing segment on the 5' end and 3' end of the gap each independently having 1-3 or 2 sugar modified nucleosides.

In certain embodiments, the modified oligonucleotide is 16 nucleosides in length and has a gap segment of 10 linked nucleosides. In certain embodiments, the modified oligonucleotide has a wing segment on the 5' end and 3' end of the gap each independently having 1-5, 2-4 or 3 sugar modified nucleosides. In certain embodiments, the modified oligonucleotide is 16 nucleosides in length and has a gap segment of 9 linked nucleosides. In certain embodiments, the modified oligonucleotide has a wing segment on the 5' end and 3' end of the gap each independently having 2, 3, 4, or 5 sugar modified nucleosides, such as 2'-MOE nucleosides.

In certain embodiments, the modified oligonucleotide is 17 nucleosides in length and has a gap segment of 9 or 10 linked nucleosides. In certain embodiments, the modified oligonucleotide has a wing segment on the 5' end and 3' end of the gap each independently having 1-5, 2-4 or 3-4 sugar modified nucleosides. In certain embodiments, the modified oligonucleotide has a wing segment on the 5' end and 3' end of the gap each independently having 2, 3, 4, 5, or 6 sugar modified nucleosides, such as 2'-MOE nucleosides.

In certain embodiments, the modified oligonucleotide is 18 nucleosides in length and has a gap segment of 10 linked nucleosides. In certain embodiments, the modified oligonucleotide has a wing segment on the 5' end and 3' end of the gap each independently having 1-5, 3-5, or 4 sugar modified nucleosides.

In certain embodiments, the modified oligonucleotide is 20 nucleosides in length and has a gap segment of 10 linked nucleosides. In certain embodiments, the modified oligonucleotide has a wing segment on the 5' end and 3' end of the gap each independently having 1-5, or 5 sugar modified nucleosides. In certain embodiments, the modified oligonucleotide has a wing segment on the 5' end and 3' end of the gap each independently having 2, 3, 4, 5, 6, 7, or 8 sugar modified nucleosides, such as 2'-MOE nucleosides.

In certain embodiments, the compounds or compositions comprise a salt of the modified oligonucleotide.

In certain embodiments, the compounds or compositions further comprise a pharmaceutically acceptable carrier or diluent.

In certain embodiments, the nucleobase sequence of the modified oligonucleotide is at least 70%, 75%, 80%, 85%, 90%, 95% or 100% complementary to SEQ ID NO: 1, as measured over the entirety of the modified oligonucleotide.

In certain embodiments, the nucleobase sequence of the modified oligonucleotide is at least 70%, 75%, 80%, 85%, 90%, 95% or 100% complementary to any one of SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, as measured over the entirety of the modified oligonucleotide.

In certain embodiments, the compound or modified oligonucleotide is single-stranded.

In certain embodiments, the modified oligonucleotide consists of 8, 9, 10, 11, 12, 13, 14, 15, 16, 17, 18, 19, 20, 21, 22, 23, 24, 25, 26, 27, 28, 29 or 30 linked nucleosides. In certain embodiments, the modified oligonucleotide consists of 20 linked nucleosides. In certain embodiments, the modified oligonucleotide consists of 18 linked nucleosides. In certain embodiments, the modified oligonucleotide consists of 17 linked nucleosides. In certain embodiments, the modified oligonucleotide consists of 16 linked nucleosides. In certain embodiments, the modified oligonucleotide consists of 14 linked nucleosides.

In certain embodiments, at least one internucleoside linkage of the modified oligonucleotide is a modified internucleoside linkage. In certain embodiments, each internucleoside linkage is a phosphorothioate internucleoside linkage.

In certain embodiments, at least one nucleoside of the modified oligonucleotide comprises a modified sugar. In certain embodiments, at least one modified sugar comprises a 2'-O-methoxyethyl group (2'—O(CH$_2$)$_2$—OCH$_3$). In certain embodiments, the modified sugar comprises a 2'-O—CH$_3$ group.

In certain embodiments, at least one modified sugar is a bicyclic sugar. In certain embodiments, at least one modified sugar the bicyclic sugar comprises a 4'-(CH$_2$)$_n$—O-2' bridge, wherein n is 1 or 2. In certain embodiments, the bicyclic sugar comprises a 4'-CH$_2$—O-2' bridge. In certain embodiments, the bicyclic sugar comprises a 4'-CH(CH$_3$)—O-2' bridge.

In certain embodiments, at least one nucleoside of said modified oligonucleotide comprises a modified nucleobase. In certain embodiments, the modified nucleobase is a 5-methylcytosine.

In certain embodiments, the modified oligonucleotide consists of a single-stranded modified oligonucleotide.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 16 linked nucleosides, the gap segment consisting of 10 linked deoxynucleosides, the 5' wing segment consisting of three linked nucleosides, the 3' wing segment consisting of three linked nucleosides, each nucleoside of each wing segment comprises a 2'-O-methoxyethyl sugar and/or a constrained ethyl (cEt) sugar, each internucleoside linkage is a phosphorothioate linkage and each cytosine is a 5-methylcytosine. In some aspects, each of the three linked nucleosides of the 5' wing segment is a 2'-O-methoxyethyl sugar and each of the three linked nucleosides of the 3' wing segment is a constrained ethyl (cEt) sugar. In other aspects, the three linked nucleosides of the 5' wing segment are a 2'-O-methoxyethyl sugar, a constrained ethyl (cEt) sugar, and a constrained ethyl (cEt) sugar in the 5' to 3' direction, and the three linked nucleosides of the 3' wing segment are a constrained ethyl (cEt) sugar, a constrained ethyl (cEt) sugar, and a 2'-O-methoxyethyl sugar in the 5' to 3' direction. In other aspects, the three linked nucleosides of the 5' wing segment are a constrained ethyl (cEt) sugar, a 2'-O-methoxyethyl sugar, and a constrained ethyl (cEt) sugar in the 5' to 3' direction, and the three linked nucleosides of the 3' wing segment are a constrained ethyl (cEt) sugar, a 2'-O-methoxyethyl sugar, and a constrained ethyl (cEt) sugar in the 5' to 3' direction.

In certain embodiments, the modified oligonucleotide consists of 16 linked nucleosides, the gap segment consisting of 10 linked deoxynucleosides, the 5' wing segment consisting of two linked nucleosides, the 3' wing segment consisting of four linked nucleosides, each nucleoside of each wing segment comprises a 2'-O-methoxyethyl sugar and a constrained ethyl (cEt) sugar, each internucleoside linkage is a phosphorothioate linkage and each cytosine is a 5-methylcytosine. In some aspects, the two linked nucleosides of the 5' wing segment are a 2'-O-methoxyethyl sugar and a constrained ethyl (cEt) sugar in the 5' to 3' direction, and the four linked nucleosides of the 3' wing segment are a constrained ethyl (cEt) sugar, a 2'-O-methoxyethyl sugar, a constrained ethyl (cEt) sugar, and a 2'-O-methoxyethyl sugar in the 5' to 3' direction.

In certain embodiments, the modified oligonucleotide consists of 16 linked nucleosides, the gap segment consisting of 9 linked deoxynucleosides, the 5' wing segment consisting of five linked nucleosides, the 3' wing segment consisting of two linked nucleosides; the five linked nucleosides of the 5' wing segment are a constrained ethyl (cEt) sugar, a 2'-deoxynucleoside, a constrained ethyl (cEt) sugar, a 2'-deoxynucleoside, and a constrained ethyl (cEt) sugar in the 5' to 3' direction; the two linked nucleosides of the 3' wing segment are a 2'-O-methoxyethyl sugar and a 2'-O-methoxyethyl sugar in the 5' to 3' direction; each internucleoside linkage is a phosphorothioate linkage; and each cytosine is a 5-methylcytosine.

In certain embodiments, the modified oligonucleotide consists of 16 linked nucleosides, the gap segment consisting of 8 linked deoxynucleosides, the 5' wing segment consisting of three linked nucleosides, the 3' wing segment consisting of five linked nucleosides; the three linked nucleosides of the 5' wing segment are a constrained ethyl (cEt) sugar, a 2'-O-methoxyethyl sugar, and a constrained ethyl (cEt) sugar in the 5' to 3' direction; each of the five linked nucleosides of the 3' wing segment is a 2'-O-methoxyethyl sugar; each internucleoside linkage is a phosphorothioate linkage; and each cytosine is a 5-methylcytosine.

In certain embodiments, the modified oligonucleotide consists of 16 linked nucleosides, the gap segment consisting of 8 linked deoxynucleosides, the 5' wing segment consisting of three linked nucleosides, the 3' wing segment consisting of five linked nucleosides; each of the three linked nucleosides of the 5' wing segment is a constrained ethyl (cEt) sugar; each of the five linked nucleosides of the 3' wing segment is a 2'-O-methoxyethyl sugar; each internucleoside linkage is a phosphorothioate linkage; and each cytosine is a 5-methylcytosine.

In certain embodiments, the modified oligonucleotide consists of 17 linked nucleosides, the gap segment consisting of 9 linked deoxynucleosides, the 5' wing segment consisting of four linked nucleosides, the 3' wing segment consisting of four linked nucleosides, each nucleoside of each wing segment comprises a 2'-O-methoxyethyl sugar and a constrained ethyl (cEt) sugar, each internucleoside linkage is a phosphorothioate linkage and each cytosine is a 5-methylcytosine. In some aspects, the four linked nucleosides of the 5' wing segment are a 2'-O-methoxyethyl sugar, a 2'-O-methoxyethyl sugar, a constrained ethyl (cEt) sugar, and a constrained ethyl (cEt) sugar in the 5' to 3' direction, and the four linked nucleosides of the 3' wing segment are a 2'-O-methoxyethyl sugar, constrained ethyl (cEt) sugar, a 2'-O-methoxyethyl sugar, and a 2'-O-methoxyethyl sugar in the 5' to 3' direction.

In certain embodiments, the modified oligonucleotide consists of 17 linked nucleosides, the gap segment consisting of 9 linked deoxynucleosides, the 5' wing segment consisting of four linked nucleosides, the 3' wing segment consisting of four linked nucleosides; the four linked nucleosides of the 5' wing segment are a 2'-O-methoxyethyl sugar, a 2'-O-methoxyethyl sugar, a 2'-O-methoxyethyl sugar, and a constrained ethyl (cEt) sugar in the 5' to 3' direction; the four linked nucleosides of the 3' wing segment are a constrained ethyl (cEt) sugar, a 2'-O-methoxyethyl sugar, a 2'-O-methoxyethyl sugar, and a 2'-O-methoxyethyl sugar; each internucleoside linkage is a phosphorothioate linkage; and each cytosine is a 5-methylcytosine.

In certain embodiments, the modified oligonucleotide consists of 17 linked nucleosides, the gap segment consisting of 9 linked deoxynucleosides, the 5' wing segment consisting of four linked nucleosides, the 3' wing segment consisting of four linked nucleosides; the four linked nucleosides of the 5' wing segment are a 2'-O-methoxyethyl sugar, a constrained ethyl (cEt) sugar, a 2'-O-methoxyethyl sugar, and a constrained ethyl (cEt) sugar in the 5' to 3' direction; each of the four linked nucleosides of the 3' wing segment is a 2'-O-methoxyethyl sugar; each internucleoside linkage is a phosphorothioate linkage; and each cytosine is a 5-methylcytosine.

In certain embodiments, the modified oligonucleotide consists of 17 linked nucleosides, the gap segment consisting of 8 linked deoxynucleosides, the 5' wing segment consisting of five linked nucleosides, the 3' wing segment consisting of four linked nucleosides; the five linked nucleosides of the 5' wing segment are a constrained ethyl (cEt) sugar, a 2'-deoxynucleoside, a constrained ethyl (cEt) sugar, a 2'-deoxynucleoside, and a constrained ethyl (cEt) sugar in the 5' to 3' direction; each of the four linked nucleosides of the 3' wing segment is a 2'-O-methoxyethyl sugar; each internucleoside linkage is a phosphorothioate linkage; and each cytosine is a 5-methylcytosine.

In certain embodiments, the modified oligonucleotide consists of 17 linked nucleosides, the gap segment consisting of 8 linked deoxynucleosides, the 5' wing segment consisting of five linked nucleosides, the 3' wing segment consisting of four linked nucleosides; the five linked nucleosides of the 5' wing segment are a 2'-O-methoxyethyl sugar, a 2'-O-methoxyethyl sugar, 2'-O-methoxyethyl sugar, a constrained ethyl (cEt) sugar, and a constrained ethyl (cEt) sugar in the 5' to 3' direction; each of the four linked nucleosides of the 3' wing segment is a 2'-O-methoxyethyl sugar; each internucleoside linkage is a phosphorothioate linkage; and each cytosine is a 5-methylcytosine.

In certain embodiments, the modified oligonucleotide consists of 17 linked nucleosides, the gap segment consisting of 7 linked deoxynucleosides, the 5' wing segment consisting of five linked nucleosides, the 3' wing segment consisting of five linked nucleosides; the five linked nucleosides of the 5' wing segment are a 2'-O-methoxyethyl sugar, a 2'-O-methoxyethyl sugar, a 2'-O-methoxyethyl sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a 2'-O-methoxyethyl sugar, a 2'-O-methoxyethyl sugar, and a 2'-O-methoxyethyl sugar; each internucleoside linkage is a phosphorothioate linkage; and each cytosine is a 5-methylcytosine.

In certain embodiments, the modified oligonucleotide consists of 17 linked nucleosides, the gap segment consisting of 7 linked deoxynucleosides, the 5' wing segment consisting of six linked nucleosides, the 3' wing segment consisting of four linked nucleosides; the six linked nucleosides of the 5' wing segment are a 2'-O-methoxyethyl sugar, a 2'-O-methoxyethyl sugar, a 2'-O-methoxyethyl sugar, a 2'-O-methoxyethyl sugar, a constrained ethyl (cEt) sugar, and a constrained ethyl (cEt) sugar in the 5' to 3' direction; each of the four linked nucleosides of the 3' wing segment is a 2'-O-methoxyethyl sugar; each internucleoside linkage is a phosphorothioate linkage; and each cytosine is a 5-methylcytosine.

In certain embodiments, the modified oligonucleotide consists of 17 linked nucleosides, the gap segment consisting of 7 linked deoxynucleosides, the 5' wing segment consisting of six linked nucleosides, the 3' wing segment consisting of four linked nucleosides; the six linked nucleosides of the 5' wing segment are a 2'-O-methoxyethyl sugar, a constrained ethyl (cEt) sugar, a 2'-O-methoxyethyl sugar, a constrained ethyl (cEt) sugar, a 2'-deoxynucleoside, and a constrained ethyl (cEt) sugar in the 5' to 3' direction; each of the four linked nucleosides of the 3' wing segment is a 2'-O-methoxyethyl sugar; each internucleoside linkage is a phosphorothioate linkage; and each cytosine is a 5-methylcytosine.

In certain embodiments, the modified oligonucleotide consists of 20 linked nucleosides, the gap segment consisting of 10 linked deoxynucleosides, the 5' wing segment consisting of five linked nucleosides, the 3' wing segment consisting of five linked nucleosides, each nucleoside of each wing segment comprises a constrained ethyl (cEt) sugar, each internucleoside linkage is a phosphorothioate linkage and each cytosine is a 5-methylcytosine.

In certain embodiments, the modified oligonucleotide consists of 20 linked nucleosides, the gap segment consisting of 10 linked deoxynucleosides, the 5' wing segment consisting of five linked nucleosides, the 3' wing segment consisting of five linked nucleosides, each internucleoside linkage is a phosphorothioate linkage and each cytosine is a 5-methylcytosine, wherein the five linked nucleosides of the 5' wing are a constrained ethyl (cEt) sugar, a 2'-deoxynucleoside, a constrained ethyl (cEt) sugar, a 2'-deoxynucleoside, and a constrained ethyl (cEt) sugar in the 5' to 3' direction, and each of the five linked nucleosides of the 3' wing are a 2'-O-methoxyethyl sugar.

In certain embodiments, the compounds or compositions comprise a modified oligonucleotide consisting of 16 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of three linked nucleosides; and c) a 3' wing segment consisting of three linked nucleosides. In some aspects, the gap segment is positioned between the 5' wing segment and the 3' wing segment; each of the three linked nucleosides of the 5' wing segment is a 2'-O-methoxyethyl sugar and each of the three linked nucleosides of the 3' wing segment is a constrained ethyl (cEt) sugar; each internucleoside linkage is a phosphorothioate linkage; and each cytosine residue is a 5-methylcytosine. In other aspects, the gap segment is positioned between the 5' wing segment and the 3' wing segment; the three linked nucleosides of the 5' wing segment are a 2'-O-methoxyethyl sugar, a constrained ethyl (cEt) sugar, and a constrained ethyl (cEt) sugar in the 5' to 3' direction; the three linked nucleosides of the 3' wing segment are a constrained ethyl (cEt) sugar, a constrained ethyl (cEt) sugar, and a 2'-O-methoxyethyl sugar in the 5' to 3' direction; each internucleoside linkage is a phosphorothioate linkage; and each cytosine residue is a 5-methylcytosine. In other aspects, the three linked nucleosides of the 5' wing segment are a constrained ethyl (cEt) sugar, a 2'-O-methoxyethyl sugar, and a constrained ethyl (cEt) sugar in the 5' to 3' direction, and the three linked nucleosides of the 3' wing segment are a constrained ethyl (cEt) sugar, a 2'-O-methoxyethyl sugar, and a constrained ethyl (cEt) sugar in the 5' to 3' direction.

In certain embodiments, the compounds or compositions comprise a modified oligonucleotide consisting of 16 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises a) a gap segment consisting of ten linked deoxynucleosides; b) a 5' wing segment consisting of two linked nucleosides; and c) a 3' wing segment consisting of four linked nucleosides. In some aspects, the gap segment is positioned between the 5' wing segment and the 3' wing segment; the two linked nucleosides of the 5' wing segment are a 2'-O-methoxyethyl sugar and a constrained ethyl (cEt) sugar in the 5' to 3' direction; the four linked nucleosides of the 3' wing segment are a constrained ethyl (cEt) sugar, 2'-O-methoxyethyl sugar, constrained ethyl (cEt) sugar, and 2'-O-methoxyethyl sugar in the 5' to 3' direction; each internucleoside linkage is a phosphorothioate linkage; and each cytosine residue is a 5-methylcytosine.

In certain embodiments, the compounds or compositions comprise a modified oligonucleotide consisting of 16 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) gap segment consisting of 9 linked deoxynucleosides; b) a 5' wing segment consisting of five linked nucleosides; and c) a 3' wing segment consisting of two linked nucleosides, wherein the five linked nucleosides of the 5' wing segment are a constrained ethyl (cEt) sugar, a 2'-deoxynucleoside, a constrained ethyl (cEt) sugar, a 2'-deoxynucleoside, and a constrained ethyl (cEt) sugar in the 5' to 3' direction; the two linked nucleosides of the 3' wing segment are a 2'-O-methoxyethyl sugar and a 2'-O-methoxyethyl sugar in the 5' to 3' direction; each internucleoside linkage is a phosphorothioate linkage; and each cytosine is a 5-methylcytosine.

In certain embodiments, the compounds or compositions comprise a modified oligonucleotide consisting of 16 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ED NO: 1 and wherein the modified oligonucleotide comprises: a) a gap segment consisting of 8 linked deoxynucleosides; b) a 5' wing segment consisting of three linked nucleosides; and c) a 3' wing segment consisting of five linked nucleosides, wherein the three linked nucleosides of the 5' wing segment are a constrained ethyl (cEt) sugar, a 2'-O-methoxyethyl sugar, and a constrained ethyl (cEt) sugar in the 5' to 3' direction; each of the five linked nucleosides of the 3' wing segment is a 2'-O-methoxyethyl sugar; each internucleoside linkage is a phosphorothioate linkage; and each cytosine is a 5-methylcytosine.

In certain embodiments, the compounds or compositions comprise a modified oligonucleotide consisting of 16 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of 8 linked deoxynucleosides; b) a 5' wing segment consisting of three linked nucleosides; and c) a 3' wing segment consisting of five linked nucleosides, wherein each of the three linked nucleosides of the 5' wing segment is a constrained ethyl (cEt) sugar; each of the five linked nucleosides of the 3' wing segment is a 2'-O-methoxyethyl sugar; each internucleoside linkage is a phosphorothioate linkage; and each cytosine is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of 9 linked deoxynucleosides; b) a 5' wing segment consisting of four linked nucleosides; and c) a 3' wing segment consisting of four linked nucleosides, each nucleoside of each wing segment comprises a 2'-O-methoxyethyl sugar and a constrained ethyl (cEt) sugar, each internucleoside linkage is a phosphorothioate linkage and each cytosine is a 5-methylcytosine. In some aspects, the four linked nucleosides of the 5' wing segment are a 2'-O-methoxyethyl sugar, a 2'-O-methoxyethyl sugar, a constrained ethyl (cEt) sugar, and a constrained ethyl (cEt) sugar in the 5' to 3' direction, and the four linked nucleosides of the 3' wing segment are a 2'-O-methoxyethyl sugar, constrained ethyl (cEt) sugar, a 2'-O-methoxyethyl sugar, and a 2'-O-methoxyethyl sugar in the 5' to 3' direction.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of 9 linked deoxynucleosides; b) a 5' wing segment consisting of four linked nucleosides; and c) a 3' wing segment consisting of four linked nucleosides, wherein the four linked nucleosides of the 5' wing segment are a 2'-O-methoxyethyl sugar, a 2'-O-methoxyethyl sugar, a 2'-O-methoxyethyl sugar, and a constrained ethyl (cEt) sugar in the 5' to 3' direction; the four linked nucleosides of the 3' wing segment are a constrained ethyl (cEt) sugar, a 2'-O-methoxyethyl sugar, a 2'-O-methoxyethyl sugar, and a 2'-O-methoxyethyl sugar; each internucleoside linkage is a phosphorothioate linkage; and each cytosine is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of 9 linked deoxynucleosides; b) a 5' wing segment consisting of four linked nucleosides; and c) the 3' wing segment consisting of four linked nucleosides, wherein the four linked nucleosides of the 5' wing segment are a 2'-O-methoxyethyl sugar, a constrained ethyl (cEt) sugar, a 2'-O-methoxyethyl sugar, and a constrained ethyl (cEt) sugar in the 5' to 3' direction; each of the four linked nucleosides of the 3' wing segment is a 2'-O-methoxyethyl sugar; each internucleoside linkage is a phosphorothioate linkage; and each cytosine is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of 8 linked deoxynucleosides; b) a 5' wing segment consisting of five linked nucleosides; and c) a 3' wing segment consisting of four linked nucleosides, wherein the five linked nucleosides of the 5' wing segment are a constrained ethyl (cEt) sugar, a 2'-deoxynucleoside, a constrained ethyl (cEt) sugar, a 2'-deoxynucleoside, and a constrained ethyl (cEt) sugar in the 5' to 3' direction; each of the four linked nucleosides of the 3' wing segment is a 2'-O-methoxyethyl sugar; each internucleoside linkage is a phosphorothioate linkage; and each cytosine is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of 8 linked deoxynucleosides; b) a 5' wing segment consisting of five linked nucleosides; and c) a 3' wing segment consisting of four linked nucleosides, wherein the five linked nucleosides of the 5' wing segment are a 2'-O-methoxyethyl sugar, a 2'-O-methoxyethyl sugar, 2'-O-methoxyethyl sugar, a constrained ethyl (cEt) sugar, and a constrained ethyl (cEt) sugar in the 5' to 3' direction; each of the four linked nucleosides of the 3' wing segment is a 2'-O-methoxyethyl sugar; each internucleoside linkage is a phosphorothioate linkage; and each cytosine is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of 7 linked deoxynucleosides; b) a 5' wing segment consisting of five linked nucleosides; and c) a 3' wing segment consisting of five linked nucleosides, wherein the five linked nucleosides of the 5' wing segment are a 2'-O-methoxyethyl sugar, a 2'-O-methoxyethyl sugar, a 2'-O-methoxyethyl sugar, a constrained ethyl (cEt) sugar, and a constrained ethyl (cEt) sugar in the 5' to 3' direction; the five linked nucleosides of the 3' wing segment are a constrained ethyl (cEt) sugar, a constrained ethyl (cEt) sugar, a 2'-O-methoxyethyl sugar, 2'-O-methoxyethyl sugar, and a 2'-O-methoxyethyl sugar; each internucleoside linkage is a phosphorothioate linkage; and each cytosine is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of 7 linked deoxynucleosides; b) a 5' wing segment consisting of six linked nucleosides; and c) a 3' wing segment consisting of four linked nucleosides, wherein the six linked nucleosides of the 5' wing segment are a 2'-O-methoxyethyl sugar, a 2'-O-methoxyethyl sugar, a 2'-O-methoxyethyl sugar, a 2'-O-methoxyethyl sugar, a constrained ethyl (cEt) sugar, and a constrained ethyl (cEt) sugar in the 5' to 3' direction; each of the four linked nucleosides of the 3' wing segment is a 2'-O-methoxyethyl sugar; each internucleoside linkage is a phosphorothioate linkage; and each cytosine is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of 7 linked deoxynucleosides; b) a 5' wing segment consisting of six linked nucleosides; and c) a 3' wing segment consisting of four linked nucleosides, wherein the six linked nucleosides of the 5' wing segment are a 2'-O-methoxyethyl sugar, a constrained ethyl (cEt) sugar, a 2'-O-methoxyethyl sugar, a constrained ethyl (cEt) sugar, a 2'-deoxynucleoside, and a constrained ethyl (cEt) sugar in the 5' to 3' direction; each of the four linked nucleosides of the 3' wing segment is a 2'-O-methoxyethyl sugar; each internucleoside linkage is a phosphorothioate linkage; and each cytosine is a 5-methylcytosine.

In certain embodiments, the compounds or compositions comprise a modified oligonucleotide consisting of 20 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of 10 linked deoxynucleosides; b) a 5' wing segment consisting of five linked nucleosides; and c) a 3' wing segment consisting of five linked nucleosides, each nucleoside of each wing segment comprises a constrained ethyl (cEt) sugar, each internucleoside linkage is a phosphorothioate linkage and each cytosine is a 5-methylcytosine.

In certain embodiments, the compounds or compositions comprise a modified oligonucleotide consisting of 20 linked nucleosides having a nucleobase sequence comprising a portion of at least 8 contiguous nucleobases complementary to an equal length portion of any of nucleobases set forth in SEQ ID NOs: 1, 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of 10 linked deoxynucleosides; b) a 5' wing segment consisting of five linked nucleosides; and c) a 3' wing segment consisting of five linked nucleosides, each internucleoside linkage is a phosphorothioate linkage and each cytosine is a 5-methylcytosine, wherein the five linked nucleosides of the 5' wing are a constrained ethyl (cEt) sugar, a 2'-deoxynucleoside, a constrained ethyl (cEt) sugar, a 2'-deoxynucleoside, and a constrained ethyl (cEt) sugar in the 5' to 3' direction, and each of the five linked nucleosides of the 3' wing are a 2'-O-methoxyethyl sugar.

In certain embodiments, the modified oligonucleotide consists of 20 linked nucleosides, the gap segment consisting of ten linked deoxynucleosides, the 5' wing segment consisting of five linked nucleosides, the 3' wing segment consisting of five linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 20 linked nucleosides, the gap segment consisting of ten linked deoxynucleosides, the 5' wing segment consisting of two linked nucleosides, the 3' wing segment consisting of eight linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 20 linked nucleosides, the gap segment consisting of ten linked deoxynucleosides, the 5' wing segment consisting of eight linked nucleosides, the 3' wing segment consisting of two linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 20 linked nucleosides, the gap segment consisting of ten linked deoxynucleosides, the 5' wing segment consisting of three linked nucleosides, the 3' wing segment consisting of seven linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 20 linked nucleosides, the gap segment consisting of ten linked deoxynucleosides, the 5' wing segment consisting of seven linked nucleosides, the 3' wing segment consisting of three linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 20 linked nucleosides, the gap segment consisting of ten linked deoxynucleosides, the 5' wing segment consisting of four linked nucleosides, the 3' wing segment consisting of six linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 20 linked nucleosides, the gap segment consisting of ten linked deoxynucleosides, the 5' wing segment consisting of six linked nucleosides, the 3' wing segment consisting of four linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 18 linked nucleosides, the gap segment consisting of ten linked deoxynucleosides, the 5' wing segment consisting of four linked nucleosides, the 3' wing segment consisting of four linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 17 linked nucleosides, the gap segment consisting of ten linked deoxynucleosides, the 5' wing segment consisting of three linked nucleosides, the 3' wing segment consisting of four linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 17 linked nucleosides, the gap segment consisting of nine linked deoxynucleosides, the 5' wing segment consisting of two linked nucleosides, the 3' wing segment consisting of six linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 17 linked nucleosides, the gap segment consisting of nine linked deoxynucleosides, the 5' wing segment consisting of six linked nucleosides, the 3' wing segment consisting of two linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 17 linked nucleosides, the gap segment consisting of nine linked deoxynucleosides, the 5' wing segment consisting of four linked nucleosides, the 3' wing segment consisting of four linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 17 linked nucleosides, the gap segment consisting of nine linked deoxynucleosides, the 5' wing segment consisting of five linked nucleosides, the 3' wing segment consisting of three linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 17 linked nucleosides, the gap segment consisting of nine linked deoxynucleosides, the 5' wing segment consisting of three linked nucleosides, the 3' wing segment consisting of five linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 16 linked nucleosides, the gap segment consisting of ten linked deoxynucleosides, the 5' wing segment consisting of three linked nucleosides, the 3' wing segment consisting of three linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 16 linked nucleosides, the gap segment consisting of nine linked deoxynucleosides, the 5' wing segment consisting of five linked nucleosides, the 3' wing segment consisting of two linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 16 linked nucleosides, the gap segment consisting of nine linked deoxynucleosides, the 5' wing segment consisting of two linked nucleosides, the 3' wing segment consisting of five linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 16 linked nucleosides, the gap segment consisting of nine linked deoxynucleosides, the 5' wing segment consisting of four linked nucleosides, the 3' wing segment consisting of three linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 16 linked nucleosides, the gap segment consisting of nine linked deoxynucleosides, the 5' wing segment consisting of three linked nucleosides, the 3' wing segment consisting of four linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the modified oligonucleotide consists of 14 linked nucleosides, the gap segment consisting of ten linked deoxynucleosides, the 5' wing segment consisting of two linked nucleosides, the 3' wing segment consisting of two linked nucleosides, each nucleoside of each wing segment comprises a 2'-O-methoxyethyl sugar, each internucleoside linkage is a phosphorothioate linkage and each cytosine is a 5-methylcytosine.

In certain embodiments, the compounds or compositions comprise a modified oligonucleotide consisting of 20 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between, the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 20 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of two linked nucleosides; and c) a 3' wing segment consisting of eight linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 20 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of eight linked nucleosides; and c) a 3' wing segment consisting of two linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 20 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of three linked nucleosides; and c) a 3' wing segment consisting of seven linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 20 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of seven linked nucleosides; and c) a 3' wing segment consisting of three linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 20 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of four linked nucleosides; and c) a 3' wing segment consisting of six linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 20 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of six linked nucleosides; and c) a 3' wing segment consisting of four linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 18 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of four linked nucleosides; and c) a 3' wing segment consisting of four linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of three linked nucleosides; and c) a 3' wing segment consisting of four linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of nine linked deoxynucleosides; b) a 5' wing segment consisting of two linked nucleosides; and c) a 3' wing segment consisting of six linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of nine linked deoxynucleosides; b) a 5' wing segment consisting of six linked nucleosides; and c) a 3' wing segment consisting of two linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of nine linked deoxynucleosides; b) a 5' wing segment consisting of four linked nucleosides; and c) a 3' wing segment consisting of four linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of nine linked deoxynucleosides; b) a 5' wing segment consisting of five linked nucleosides; and c) a 3' wing segment consisting of three linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 17 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of nine linked deoxynucleosides; b) a 5' wing segment consisting of three linked nucleosides; and c) a 3' wing segment consisting of five linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 16 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of three linked nucleosides; and c) a 3' wing segment consisting of three linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 16 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of nine linked deoxynucleosides; b) a 5' wing segment consisting of five linked nucleosides; and c) a 3' wing segment consisting of two linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 16 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of nine linked deoxynucleosides; b) a 5' wing segment consisting of two linked nucleosides; and c) a 3' wing segment consisting of five linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 16 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of nine linked deoxynucleosides; b) a 5' wing segment consisting of four linked nucleosides; and c) a 3' wing segment consisting of three linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 16 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of nine linked deoxynucleosides; b) a 5' wing segment consisting of three linked nucleosides; and c) a 3' wing segment consisting of four linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the compounds or compositions comprise a modified oligonucleotide consisting of 14 linked nucleosides having a nucleobase sequence comprising a portion of at least 8 contiguous nucleobases complementary to an equal length portion of any of nucleobases set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, wherein the nucleobase sequence is complementary to SEQ ID NO: 1 and wherein the modified oligonucleotide comprises: a) a gap segment consisting of ten linked deoxynucleosides; b) a 5' wing segment consisting of two linked nucleosides; and c) a 3' wing segment consisting of two linked nucleosides. The gap segment is positioned between the 5' wing segment and the 3' wing segment, each nucleoside of each wing segment comprises a 2'-O-methoxyethyl sugar, each internucleoside linkage is a phosphorothioate linkage and each cytosine residue is a 5-methylcytosine.

In certain embodiments, the provided methods, compounds, and compositions inhibit HBV mRNA expression and/or DNA levels and or protein levels and/or antigen levels.

Another embodiment provides a method for treating a HBV-related diseases, disorders, and conditions in a mammal, the method comprising administering a therapeutically effective amount of any pharmaceutical composition as described above to a mammal in need thereof, so as to treat the HBV-related diseases, disorders, and condition. In related embodiments, the mammal is a human and the HBV-related disease, disorder, and condition is a hepatitis B virus infection from a human hepatitis B virus. More particularly, the human hepatitis B virus may be any of the human geographical genotypes: A (Northwest Europe, North America, Central America); B (Indonesia, China, Vietnam); C (East Asia, Korea, China, Japan, Polynesia, Vietnam); D (Mediterranean area, Middle East, India); E (Africa); F (Native Americans, Polynesia); G (United States, France); or H (Central America).

In certain embodiments, an antisense compound or oligonucleotide targeted to a HBV nucleic acid is complementary within the following nucleotide regions of SEQ ID NO: 1: 1-20, 10-29, 10-56, 13-38, 13-35, 19-38, 25-47, 25-50, 25-56, 43-68, 43-63, 55-74, 58-73, 58-74, 58-77, 58-79, 58-80, 58-84, 59-74, 59-75, 59-80, 60-75, 60-76, 60-79, 61-76, 61-77, 61-80, 62-77, 63-84, 68-114, 101-123, 98-123, 113-138, 116-138, 131-150, 137-162, 152-186, 158-177, 167-186, 191-215, 196-224, 196-215, 196-218, 199-228, 199-218, 199-224, 200-224, 205-224, 206-228, 218-237, 224-243, 233-264, 242-263, 243-262, 244-263, 245-274; 245-260, 245-264, 246-266, 247-266, 247-269, 247-270, 245-267, 251-267, 245-266, 250-269, 251-266, 251-268, 251-269, 245-269, 245-266, 245-261, 250-265, 250-266, 250-267, 250-268, 250-269, 251-270, 252-267, 253-268, 253-269, 253-272, 253-274, 254-269, 254-270, 254-274, 255-270, 255-271, 255-274, 255-401, 255-400, 255-274, 255-273, 255-272, 255-271, 256-271, 256-275, 255-276, 256-272, 256-276, 253-275, 256-279, 257-276, 258-273, 259-274, 260-279, 262-281, 262-321, 262-315, 262-312, 265-312, 266-288, 266-291, 266-285, 281-321, 281-303, 290-321, 290-312, 292-311, 290-312, 293-312, 293-315, 293-321, 296-321, 302-321, 324-343, 339-361, 339-367, 348-367, 342-367, 358-392, 358-378, 360-392, 360-383, 360-388, 360-385, 362-381, 366-388, 369-388, 366-385, 366-392, 370-389, 370-392, 380-399, 382-401, 384-433, 384-400, 384-401, 385-401, 405-424, 409-428, 405-428, 411-426, 411-427, 411-430, 411-431, 411-437, 412-431, 411-426, 411-427, 412-428, 412-431, 412-427, 413-433, 413-432, 413-428, 413-429, 413-432, 413-433, 414-427, 415-427, 414-429, 414-430, 414-433, 415-428, 415-429, 415-430, 415-431, 415-434, 416-431, 416-432, 416-429, 416-435, 417-432, 417-433, 417-436, 418-433, 418-435, 418-434, 418-437, 419-435, 419-434, 420-435, 419-432, 419-434, 421-436, 422-437, 422-441, 423-436, 425-465, 454-473, 454-472, 457-476, 457-472, 457-473, 454-476, 455-472, 457-485, 458-485, 458-483, 458-477, 458-473, 459-485, 460-485, 463-498, 463-485, 466-485, 463-482, 457-491, 458-491, 459-491, 460-491, 463-491, 466-491, 472-491, 472-493, 473-492, 475-491, 459-494, 460-494, 463-494, 466-494, 467-498, 472-494, 475-494, 457-473, 457-472, 458-494, 454-494, 457-494, 457-473, 485-513, 470-493, 476-519, 485-519, 500-519, 512-534, 512-550, 524-546, 536-559, 548-567, 548-570, 550-570, 548-594, 554-573, 548-576, 560-594, 584-606, 611-645, 617-363, 623-642, 617-645, 639-754, 639-658, 639-654, 641-656, 642-657, 643-658, 642-754, 653-672, 662-685, 665-685, 665-689, 668-687, 670-754, 670-706, 670-685, 670-686, 670-689, 671-690, 671-691, 671-686, 671-687, 672-693, 672-697, 672-707, 672-687, 672-688, 673-688, 674-693, 678-693, 679-694, 679-707, 679-698, 679-701, 679-702, 679-707, 680-695, 680-699, 679-699, 681-706, 681-696, 682-697, 682-706, 682-707, 682-702, 682-701, 683-698, 684-699, 685-700, 686-701, 687-754, 688-704, 689-709, 689-710, 690-705, 679-705, 679-710, 679-706, 690-710, 691-710, 690-754, 690-706, 684-703, 687-705, 687-702, 687-703, 687-706, 688-703, 688-704, 688-705, 689-704, 689-705, 689-708, 690-705, 690-706, 690-709, 691-706, 692-711, 693-716, 693-712, 695-715, 697-716, 697-716, 690-716, 724-746, 724-752, 724-754, 724-758, 733-752, 738-754, 738-753, 739-758, 739-754, 739-775, 739-754, 740-754, 742-785, 742-773, 757-776, 757-785, 790-815, 793-812, 811-833, 811-844, 814-833, 811-906, 820-839, 822-844, 822-867, 823-842, 845-864, 845-867, 854-906, 845-909, 845-906, 854-876, 863-882, 863-885, 878-900, 887-906, 899-918, 899-933, 899-958, 905-927, 905-933, 914-933, 936-958, 936-955, 945-964, 951-970, 951-985, 951-1044, 951-1024, 951-1056, 951-997, 960-985, 963-1044, 963-1024, 963-997, 972-1015, 1025-1044, 1031-1056, 1037-1056, 1046-1083, 1049-1068, 1070-1089, 1070-1095, 1082-1101, 1081-1134, 1081-1143, 1082-1101, 1088-1107, 1088-1134, 1094-1119, 1097-1119, 1112-1134, 1118-1143, 1118-1146, 1088-1146, 1121-1140, 1127-1146, 1127-1193, 1150-1193, 1156-1187, 1165-1187, 1170-1192, 1171-1191, 1172-1191, 1176-1192, 1176-1285, 1177-1192, 1176-1191, 1203-1297, 1206-1228, 1206-1255, 1209-1228, 1215-1255, 1245-1265, 1251-1280, 1262-1285, 1251-1285, 1259-1296, 1259-1290, 1259-1287, 1261-1296, 1261-1285, 1261-1276, 1261-1277, 1261-1280, 1262-1296, 1262-1277, 1262-1278, 1262-1281, 1263-1278, 1263-1279, 1263-1282, 1264-1279, 1264-1280, 1264-1283, 1264-1297, 1265-1280, 1265-1281, 1265-1284, 1266-1281, 1266-1282, 1266-1285, 1267-1282, 1267-1283, 1268-1283, 1268-1284, 1268-1296, 1269-1284, 1269-1285, 1269-1288, 1270-1285, 1271-1290, 1271-1296, 1277-1296, 1261-1290, 1262-1290, 1268-1290, 1263-1305, 1259-1305, 1259-1305, 1266-1305, 1259-1302, 1275-1294, 1281-1306, 1281-1324, 1281-1336, 1282-1301, 1286-1306, 1290-1324, 1293-1318, 1290-1324, 1293-1315, 1296-1315, 1311-1336, 1311-1333, 1326-1345, 1353-1381, 1359-1378, 1395-1414, 1498-1532, 1498-1523, 1498-1535, 1510-1529, 1515-1535, 1515-1563, 1515-1596, 1515-1605, 1515-1602, 1515-1540, 1515-1535, 1518-1605, 1518-1602, 1518-1537, 1521-1563, 1521-1540, 1550-1655, 1550-1563, 1550-1569, 1553-1578, 1553-1599, 1553-1590, 1565-1584, 1571-1595, 1577-1605, 1577-1606, 1577-1592, 1577-1593, 1577-1596, 1578-1593, 1578-1594, 1578-1597, 1578-1598, 1571-1598, 1579-1594, 1579-1594, 1579-1598, 1580-1595, 1580-1596, 1580-1599, 1580-1605, 1580-1602, 1581-1596, 1581-1597, 1581-1600, 1582-1597, 1582-1598, 1582-1601, 1582-1602, 1553-1655, 1583-1598, 1583-1599, 1583-1602, 1584-1599, 1584-1600, 1584-1603, 1585-1600, 1585-1601, 1585-1604, 1586-1601, 1586-1602, 1586-1605, 1587-1602, 1587-1603, 1587-1606, 1588-1603, 1588-1604, 1589-1604, 1589-1605, 1590-1605, 1590-1606, 1591-1606, 1586-1652, 1642-1664, 1651-1720, 1651-1673, 1655-1679, 1695-1720, 1716-1738, 1743-1763, 1743-1768, 1764-1783, 1773-1792, 1777-1796, 1777-1800, 1778-1800, 1778-1793, 1778-1794, 1778-1797, 1779-1798, 1779-1797, 1779-1796, 1779-1795, 1779-1794, 1780-1799, 1780-1796, 1780-1795, 1781-1797, 1781-1796, 1781-1796, 1781-1800, 1781-1797, 1782-1799, 1782-1797, 1782-1798, 1783-1798, 1783-1799, 1784-1800, 1784-1799, 1779-

1799, 1778-1889, 1778-1794, 1779-1795, 1780-1799, 1785-1800, 1794-1813, 1806-1837, 1806-1828, 1806-1825, 1809-1828, 1812-1843, 1812-1837, 1812-1831, 1815-1843, 1815-1844, 1815-1840, 1815-1834, 1818-1837, 1821-1840, 1821-1844, 1821-1837, 1822-1843, 1822-1839, 1822-1837, 1823-1843, 1823-1838, 1824-1839, 1827-1846, 1861-1884, 1861-1880, 1865-1885, 1866-1881, 1867-1882, 1867-1886, 1868-1883, 1869-1885, 1869-1884, 1870-1885, 1871-1886, 1872-1887, 1874-1889, 1876-1895, 1888-1914, 1888-1908, 1891-1910, 1891-1914, 1895-1938, 1895-1935, 1913-1935, 1898-1920, 1907-1929, 1913-1935, 1918-1934, 1919-1938, 1919-1934, 1921-1934, 1928-1956, 1957-1976, 2035-2057, 2083-2141, 2230-2261, 2368-2393, 2381-2397, 2368-2394, 2379-2394, 2381-2396, 2368-2397, 2368-2396, 2420-2439, 2458-2476, 2459-2478, 2819-2838, 2818-2838, 2873-2892, and 3161-3182.

In certain embodiments, an antisense compound or oligonucleotide targeted to a HBV nucleic acid target the following nucleotide regions of SEQ ID NO: 1: 1-20, 10-29, 10-56, 13-38, 13-35, 19-38, 25-47, 25-50, 25-56, 43-68, 43-63, 55-74, 58-73, 58-74, 58-77, 58-79, 58-80, 58-84, 59-74, 59-75, 59-80, 60-75, 60-76, 60-79, 61-76, 61-77, 61-80, 62-77, 63-84, 68-114, 101-123, 98-123, 113-138, 116-138, 131-150, 137-162, 152-186, 158-177, 167-186, 191-215, 196-224, 196-215, 196-218, 199-228, 199-218, 199-224, 200-224, 205-224, 206-228, 218-237, 224-243, 233-264, 242-263, 243-262, 244-263, 245-274; 245-260, 245-264, 246-266, 247-266, 247-269, 247-270, 245-267, 251-267, 245-266, 250-269, 251-266, 251-268, 251-269, 245-269, 245-266, 245-261, 250-265, 250-266, 250-267, 250-268, 250-269, 251-270, 252-267, 253-268, 253-269, 253-272, 253-274, 254-269, 254-270, 254-274, 255-270, 255-271, 255-274, 255-401, 255-400, 255-274, 255-273, 255-272, 255-271, 256-271, 256-275, 255-276, 256-272, 256-276, 253-275, 256-279, 257-276, 258-273, 259-274, 260-279, 262-281, 262-321, 262-315, 262-312, 265-312, 266-288, 266-291, 266-285, 281-321, 281-303, 290-321, 290-312, 292-311, 290-312, 293-312, 293-315, 293-321, 296-321, 302-321, 324-343, 339-361, 339-367, 348-367, 342-367, 358-392, 358-378, 360-392, 360-383, 360-388, 360-385, 362-381, 366-388, 369-388, 366-385, 366-392, 370-389, 370-392, 380-399, 382-401, 384-433, 384-400, 384-401, 385-401, 405-424, 409-428, 405-428, 411-426, 411-427, 411-430, 411-431, 411-437, 412-431, 411-426, 411-427, 412-428, 412-431, 412-427, 413-433, 413-432, 413-428, 413-429, 413-432, 413-433, 414-427, 415-427, 414-429, 414-430, 414-433, 415-428, 415-429, 415-430, 415-431, 415-434, 416-431, 416-432, 416-429, 416-435, 417-432, 417-433, 417-436, 418-433, 418-435, 418-434, 418-437, 419-435, 419-434, 420-435, 419-432, 419-434, 421-436, 422-437, 422-441, 423-436, 425-465, 454-473, 454-472, 457-476, 457-472, 457-473, 454-476, 455-472, 457-485, 458-485, 458-483, 458-477, 458-473, 459-485, 460-485, 463-498, 463-485, 466-485, 463-482, 457-491, 458-491, 459-491, 460-491, 463-491, 466-491, 472-491, 472-493, 473-492, 475-491, 459-494, 460-494, 463-494, 466-494, 467-498, 472-494, 475-494, 457-473, 457-472, 458-494, 454-494, 457-494, 457-473, 485-513, 470-493, 476-519, 485-519, 500-519, 512-534, 512-550, 524-546, 536-559, 548-567, 548-570, 550-570, 548-594, 554-573, 548-576, 560-594, 584-606, 611-645, 617-363, 623-642, 617-645, 639-754, 639-658, 639-654, 641-656, 642-657, 643-658, 642-754, 653-672, 662-685, 665-685, 665-689, 668-687, 670-754, 670-685, 670-685, 670-686, 670-689, 671-690, 671-691, 671-686, 671-687, 672-693, 672-697, 672-707, 672-687, 672-688, 673-688, 674-693, 678-693, 679-694, 679-707, 679-698, 679-701, 679-702, 679-707, 680-695, 680-699, 679-699, 681-706, 681-696, 682-697, 682-706, 682-707, 682-702, 682-701, 683-698, 684-699, 685-700, 686-701, 687-754, 688-704, 689-709, 689-710, 690-705, 679-705, 679-710, 679-706, 690-710, 691-710, 690-754, 690-706, 684-703, 687-705, 687-702, 687-703, 687-706, 688-703, 688-704, 688-705, 689-704, 689-705, 689-708, 690-705, 690-706, 690-709, 691-706, 692-711, 693-716, 693-712, 695-715, 697-716, 697-716, 690-716, 724-746, 724-752, 724-754, 724-758, 733-752, 738-754, 738-753, 739-758, 739-754, 739-775, 739-754, 740-754, 742-785, 742-773, 757-776, 757-785, 790-815, 793-812, 811-833, 811-844, 814-833, 811-906, 820-839, 822-844, 822-867, 823-842, 845-864, 845-867, 854-906, 845-909, 845-906, 854-876, 863-882, 863-885, 878-900, 887-906, 899-918, 899-933, 899-958, 905-927, 905-933, 914-933, 936-958, 936-955, 945-964, 951-970, 951-985, 951-1044, 951-1024, 951-1056, 951-997, 960-985, 963-1044, 963-1024, 963-997, 972-1015, 1025-1044, 1031-1056, 1037-1056, 1046-1083, 1049-1068, 1070-1089, 1070-1095, 1082-1101, 1081-1134, 1081-1143, 1082-1101, 1088-1107, 1088-1134, 1094-1119, 1097-1119, 1112-1134, 1118-1143, 1118-1146, 1088-1146, 1121-1140, 1127-1146, 1127-1193, 1150-1193, 1156-1187, 1165-1187, 1170-1192, 1171-1191, 1172-1191, 1176-1192, 1176-1285, 1177-1192, 1176-1191, 1203-1297, 1206-1228, 1206-1255, 1209-1228, 1215-1255, 1245-1265, 1251-1280, 1262-1285, 1251-1285, 1259-1296, 1259-1290, 1259-1287, 1261-1296, 1261-1285, 1261-1276, 1261-1277, 1261-1280, 1262-1296, 1262-1277, 1262-1278, 1262-1281, 1263-1278, 1263-1279, 1263-1282, 1264-1279, 1264-1280, 1264-1283, 1264-1297, 1265-1280, 1265-1281, 1265-1284, 1266-1281, 1266-1282, 1266-1285, 1267-1282, 1267-1283, 1268-1283, 1268-1284, 1268-1296, 1269-1284, 1269-1285, 1269-1288, 1270-1285, 1271-1290, 1271-1296, 1277-1296, 1261-1290, 1262-1290, 1268-1290, 1263-1305, 1259-1305, 1259-1305, 1266-1305, 1259-1302, 1275-1294, 1281-1306, 1281-1324, 1281-1336, 1282-1301, 1286-1306, 1290-1324, 1293-1318, 1290-1324, 1293-1315, 1296-1315, 1311-1336, 1311-1333, 1326-1345, 1353-1381, 1359-1378, 1395-1414, 1498-1532, 1498-1523, 1498-1535, 1510-1529, 1515-1535, 1515-1563, 1515-1596, 1515-1605, 1515-1602, 1515-1540, 1515-1535, 1518-1605, 1518-1602, 1518-1537, 1521-1563, 1521-1540, 1550-1655, 1550-1563, 1550-1569, 1553-1578, 1553-1599, 1553-1590, 1565-1584, 1571-1595, 1577-1605, 1577-1606, 1577-1592, 1577-1593, 1577-1596, 1578-1593, 1578-1594, 1578-1597, 1578-1598, 1571-1598, 1579-1594, 1579-1594, 1579-1598, 1580-1595, 1580-1596, 1580-1599, 1580-1605, 1580-1602, 1581-1596, 1581-1597, 1581-1600, 1582-1597, 1582-1598, 1582-1601, 1582-1602, 1553-1655, 1583-1598, 1583-1599, 1583-1602, 1584-1599, 1584-1600, 1584-1603, 1585-1600, 1585-1601, 1585-1604, 1586-1601, 1586-1602, 1586-1605, 1587-1602, 1587-1603, 1587-1606, 1588-1603, 1588-1604, 1589-1604, 1589-1605, 1590-1605, 1590-1606, 1591-1606, 1586-1652, 1642-1664, 1651-1720, 1651-1673, 1655-1679, 1695-1720, 1716-1738, 1743-1763, 1743-1768, 1764-1783, 1773-1792, 1777-1796, 1777-1800, 1778-1800, 1778-1793, 1778-1794, 1778-1797, 1779-1798, 1779-1797, 1779-1796, 1779-1795, 1779-1794, 1780-1799, 1780-1796, 1780-1795, 1781-1797, 1781-1796, 1781-1796, 1781-1800, 1781-1797, 1782-1799, 1782-1797, 1782-1798, 1783-1798, 1783-1799, 1784-1800, 1784-1799, 1779-1799, 1778-1889, 1778-1794, 1779-1795, 1780-1799, 1785-1800, 1794-1813, 1806-1837, 1806-1828, 1806-1825, 1809-1828, 1812-1843, 1812-1837, 1812-1831, 1815-1843, 1815-1844, 1815-1840, 1815-1834, 1818-1837, 1821-1840, 1821-1844, 1821-1837, 1822-1843, 1822-1839, 1822-1837, 1823-1843, 1823-1838, 1824-1839, 1827-1846, 1861-1884, 1861-1880, 1865-1885, 1866-1881, 1867-1882, 1867-1886, 1868-1883, 1869-1885, 1869-1884, 1870-1885, 1871-1886, 1872-1887, 1874-1889, 1876-1895, 1888-1914, 1888-1908, 1891-1910, 1891-1914, 1895-1938, 1895-1935, 1913-1935, 1898-1920, 1907-1929, 1913-1935, 1918-1934, 1919-1938, 1919-1934, 1921-1934, 1928-1956, 1957-1976, 2035-2057, 2083-2141, 2230-2261, 2368-2393, 2381-2397, 2368-2394, 2379-2394, 2381-2396, 2368-2397, 2368-2396, 2420-2439, 2458-2476, 2459-2478, 2819-2838, 2818-2838, 2873-2892, and 3161-3182.

In certain embodiments, an antisense compound or oligonucleotide targeted to a HBV nucleic acid is complementary within the HBV pre-S1 second portion gene region corresponding to nucleotide region 1-1932 of SEQ ID NO: 1. In certain embodiments, an antisense compound or oligonucleotide targeted to a HBV nucleic acid is complementary within the HBV pre-S1 first portion gene region corresponding to nucleotide region 2831-3182 of SEQ ID NO: 1.

In certain embodiments, an antisense compound or oligonucleotide targeted to a HBV nucleic acid target the HBV pre-S1 second portion gene region corresponding to nucleotide region 1-1932 of SEQ ID NO: 1. In certain embodiments, an antisense compound or oligonucleotide targeted to a HBV nucleic acid target the HBV pre-S1 first portion gene region corresponding to nucleotide region 2831-3182 of SEQ ID NO: 1.

In certain embodiments, antisense compounds or oligonucleotides target a region of a HBV nucleic acid. In certain embodiments, such compounds or oligonucleotides targeted to a region of a HBV nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide regions of SEQ ID NO: 1: 1-20, 10-29, 10-56, 13-38, 13-35, 19-38, 25-47, 25-50, 25-56, 43-68, 43-63, 55-74, 58-73, 58-74, 58-77, 58-79, 58-80, 58-84, 59-74, 59-75, 59-80, 60-75, 60-76, 60-79, 61-76, 61-77, 61-80, 62-77, 63-84, 68-114, 101-123, 98-123, 113-138, 116-138, 131-150, 137-162, 152-186, 158-177, 167-186, 191-215, 196-224, 196-215, 196-218, 199-228, 199-218, 199-224, 200-224, 205-224, 206-228, 218-237, 224-243, 233-264, 242-263, 243-262, 244-263, 245-274; 245-260, 245-264, 246-266, 247-266, 247-269, 247-270, 245-267, 251-267, 245-266, 250-269, 251-266, 251-268, 251-269, 245-269, 245-266, 245-261, 250-265, 250-266, 250-267, 250-268, 250-269, 251-270, 252-267, 253-268, 253-269, 253-272, 253-274, 254-269, 254-270, 254-274, 255-270, 255-271, 255-274, 255-401, 255-400, 255-274, 255-273, 255-272, 255-271, 256-271, 256-275, 255-276, 256-272, 256-276, 253-275, 256-279, 257-276, 258-273, 259-274, 260-279, 262-281, 262-321, 262-315, 262-312, 265-312, 266-288, 266-291, 266-285, 281-321, 281-303, 290-321, 290-312, 292-311, 290-312, 293-312, 293-315, 293-321, 296-321, 302-321, 324-343, 339-361, 339-367, 348-367, 342-367, 358-392, 358-378, 360-392, 360-383, 360-388, 360-385, 362-381, 366-388, 369-388, 366-385, 366-392, 370-389, 370-392, 380-399, 382-401, 384-433, 384-400, 384-401, 385-401, 405-424, 409-428, 405-428, 411-426, 411-427, 411-430, 411-431, 411-437, 412-431, 411-426, 411-427, 412-428, 412-431, 412-427, 413-433, 413-432, 413-428, 413-429, 413-432, 413-433, 414-427, 415-427, 414-429, 414-430, 414-433, 415-428, 415-429, 415-430, 415-431, 415-434, 416-431, 416-432, 416-429, 416-435, 417-432, 417-433, 417-436, 418-433, 418-435, 418-434, 418-437, 419-435, 419-434, 420-435, 419-432, 419-434, 421-436, 422-437, 422-441, 423-436, 425-465, 454-473, 454-472, 457-476, 457-472, 457-473, 454-476, 455-472, 457-485, 458-485, 458-483, 458-477, 458-473, 459-485, 460-485, 463-498, 463-485, 466-485, 463-482, 457-491, 458-491, 459-491, 460-491, 463-491, 466-491, 472-491, 472-493, 473-492, 475-491, 459-494, 460-494, 463-494, 466-494, 467-498, 472-494, 475-494, 457-473, 457-472, 458-494, 454-494, 457-494, 457-473, 485-513, 470-493, 476-519, 485-519, 500-519, 512-534, 512-550, 524-546, 536-559, 548-567, 548-570, 550-570, 548-594, 554-573, 548-576, 560-594, 584-606, 611-645, 617-363, 623-642, 617-645, 639-754, 639-658, 639-654, 641-656, 642-657, 643-658, 642-754, 653-672, 662-685, 665-685, 665-689, 668-687, 670-754, 670-706, 670-685, 670-686, 670-689, 671-690, 671-691, 671-686, 671-687, 672-693, 672-697, 672-707, 672-687, 672-688, 673-688, 674-693, 678-693, 679-694, 679-707, 679-698, 679-701, 679-702, 679-707, 680-695, 680-699, 679-699, 681-706, 681-696, 682-697, 682-706, 682-707, 682-702, 682-701, 683-698, 684-699, 685-700, 686-701, 687-754, 688-704, 689-709, 689-710, 690-705, 679-705, 679-710, 679-706, 690-710, 691-710, 690-754, 690-706, 684-703, 687-705, 687-702, 687-703, 687-706, 688-703, 688-704, 688-705, 689-704, 689-705, 689-708, 690-705, 690-706, 690-709, 691-706, 692-711, 693-716, 693-712, 695-715, 697-716, 697-716, 690-716, 724-746, 724-752, 724-754, 724-758, 733-752, 738-754, 738-753, 739-758, 739-754, 739-775, 739-754, 740-754, 742-785, 742-773, 757-776, 757-785, 790-815, 793-812, 811-833, 811-844, 814-833, 811-906, 820-839, 822-844, 822-867, 823-842, 845-864, 845-867, 854-906, 845-909, 845-906, 854-876, 863-882, 863-885, 878-900, 887-906, 899-918, 899-933, 899-958, 905-927, 905-933, 914-933, 936-958, 936-955, 945-964, 951-970, 951-985, 951-1044, 951-1024, 951-1056, 951-997, 960-985, 963-1044, 963-1024, 963-997, 972-1015, 1025-1044, 1031-1056, 1037-1056, 1046-1083, 1049-1068, 1070-1089, 1070-1095, 1082-1101, 1081-1134, 1081-1143, 1082-1101, 1088-1107, 1088-1134, 1094-1119, 1097-1119, 1112-1134, 1118-1143, 1118-1146, 1088-1146, 1121-1140, 1127-1146, 1127-1193, 1150-1193, 1156-1187, 1165-1187, 1170-1192, 1171-1191, 1172-1191, 1176-1192, 1176-1285, 1177-1192, 1176-1191, 1203-1297, 1206-1228, 1206-1255, 1209-1228, 1215-1255, 1245-1265, 1251-1280, 1262-1285, 1251-1285, 1259-1296, 1259-1290, 1259-1287, 1261-1296, 1261-1285, 1261-1276, 1261-1277, 1261-1280, 1262-1296, 1262-1277, 1262-1278, 1262-1281, 1263-1278, 1263-1279, 1263-1282, 1264-1279, 1264-1280, 1264-1283, 1264-1297, 1265-1280, 1265-1281, 1265-1284, 1266-1281, 1266-1282, 1266-1285, 1267-1282, 1267-1283, 1268-1283, 1268-1284, 1268-1296, 1269-1284, 1269-1285, 1269-1288, 1270-1285, 1271-1290, 1271-1296, 1277-1296, 1261-1290, 1262-1290, 1268-1290, 1263-1305, 1259-1305, 1259-1305, 1266-1305, 1259-1302, 1275-1294, 1281-1306, 1281-1324, 1281-1336, 1282-1301, 1286-1306, 1290-1324, 1293-1318, 1290-1324, 1293-1315, 1296-1315, 1311-1336, 1311-1333, 1326-1345, 1353-1381, 1359-1378, 1395-1414, 1498-1532, 1498-1523, 1498-1535, 1510-1529, 1515-1535, 1515-1563, 1515-1596, 1515-1605, 1515-1602, 1515-1540, 1515-1535, 1518-1605, 1518-1602, 1518-1537, 1521-1563, 1521-1540, 1550-1655, 1550-1563, 1550-1569, 1553-1578, 1553-1599, 1553-1590, 1565-1584, 1571-1595, 1577-1605, 1577-1606, 1577-1592, 1577-1593, 1577-1596, 1578-1593, 1578-1594, 1578-1597, 1578-1598, 1571-1598, 1579-1594, 1579-1594, 1579-1598, 1580-1595, 1580-1596, 1580-1599, 1580-1605, 1580-1602, 1581-1596, 1581-1597, 1581-1600, 1582-1597, 1582-1598, 1582-1601, 1582-1602, 1553-1655, 1583-1598, 1583-1599, 1583-1602, 1584-1599, 1584-1600, 1584-1603, 1585-1600, 1585-1601, 1585-1604, 1586-1601, 1586-1602, 1586-1605, 1587-1602, 1587-1603, 1587-1606, 1588-1603, 1588-1604, 1589-1604, 1589-1605, 1590-1605, 1590-1606, 1591-1606, 1586-1652, 1642-1664, 1651-1720, 1651-1673, 1655-1679, 1695-1720, 1716-1738, 1743-1763, 1743-1768, 1764-1783, 1773-1792, 1777-1796, 1777-1800, 1778-1800, 1778-1793, 1778-1794, 1778-1797, 1779-1798, 1779-1797, 1779-1796, 1779-1795, 1779-1794, 1780-1799, 1780-1796, 1780-1795, 1781-1797, 1781-1796, 1781-1796, 1781-1800, 1781-1797, 1782-1799, 1782-1797, 1782-1798, 1783-1798, 1783-1799, 1784-1800, 1784-1799, 1779-1799, 1778-1889, 1778-1794, 1779-1795, 1780-1799, 1785-1800, 1794-1813, 1806-1837, 1806-1828, 1806-1825, 1809-1828, 1812-1843, 1812-1837, 1812-1831, 1815-1843, 1815-1844, 1815-1840, 1815-1834, 1818-1837, 1821-1840, 1821-1844, 1821-1837, 1822-1843, 1822-1839, 1822-1837, 1823-1843, 1823-1838, 1824-1839, 1827-1846, 1861-1884, 1861-1880, 1865-1885, 1866-1881, 1867-1882, 1867-1886, 1868-1883, 1869-1885, 1869-1884, 1870-1885, 1871-1886, 1872-1887, 1874-1889, 1876-1895, 1888-1914, 1888-1908, 1891-1910, 1891-1914, 1895-1938, 1895-1935, 1913-1935, 1898-1920, 1907-1929, 1913-1935, 1918-1934, 1919-1938, 1919-1934, 1921-1934, 1928-1956, 1957-1976, 2035-2057, 2083-2141, 2230-2261, 2368-2393, 2381-2397, 2368-2394, 2379-2394, 2381-2396, 2368-2397, 2368-2396, 2420-2439, 2458-2476, 2459-2478, 2819-2838, 2818-2838, 2873-2892, and 3161-3182.

In certain embodiments, antisense compounds or oligonucleotides target a region of a HBV nucleic acid. In certain embodiments, such compounds or oligonucleotides targeted to a region of a HBV nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide regions of SEQ ID NO: 1: 58-73, 58-74, 58-77, 59-74, 60-75, 61-76, 62-77, 245-274; 245-260, 250-265, 251-266, 252-267, 253-268, 254-269, 255-270, 256-271, 256-272, 258-273, 259-274, 380-399, 382-401, 411-437, 411-427, 411-426, 412-427, 413-428, 413-432, 414-429, 415-430, 416-431, 417-432, 418-433, 419-434, 420-435, 421-436, 422-437, 457-472, 458-473, 639-754, 639-658, 639-654, 641-656, 642-657, 643-658, 670-754, 670-706, 670-685, 671-686, 672-687, 673-688, 678-693, 679-694, 680-695, 681-706, 681-696, 682-697, 683-698, 684-699, 685-700, 686-701, 687-702, 688-703, 689-704, 690-705, 691-706, 738-754, 738-753, 739-754, 1176-1285, 1176-1191, 1177-1192, 1261-1285, 1261-1276, 1262-1277, 1263-1278, 1264-1279, 1265-1280, 1266-1281, 1267-1282, 1268-1283, 1269-1284, 1270-1285, 1577-1606, 1577-1592, 1578-1593, 1579-1594, 1580-1595, 1581-1596, 1582-1597, 1583-1598, 1584-1599, 1585-1600, 1586-1601, 1587-1602, 1588-1603, 1589-1604, 1590-1605, 1591-1606, 1778-1889, 1778-1800, 1778-1793, 1779-1794, 1780-1799, 1780-1796, 1780-1795, 1781-1796, 1782-1797, 1783-1798, 1784-1799, 1785-1800, 1822-1839, 1822-1837, 1823-1838, 1824-1839, 1866-1881, 1867-1882, 1868-1883, 1869-1884, 1870-1885, 1871-1886, 1872-1887, or 1874-1889, and wherein at least one nucleoside of the compound or modified oligonucleotide comprises at least one 2'-O-methoxyethyl or constrained ethyl (cEt) sugar.

In certain embodiments, an antisense compound or oligonucleotide targeted to a HBV nucleic acid is complementary within the following nucleotide regions of SEQ ID NO: 1: 58-73, 58-74, 58-77, 59-74, 59-75, 60-75, 60-76, 61-76, 61-77, 62-77, 253-272, 253-269, 254-270, 255-271, 256-272, 411-437, 411-426, 411-427, 411-430, 412-427, 412-428, 412-431, 413-428, 413-429, 413-432, 414-429, 414-430, 414-433, 415-430, 415-431, 415-434, 416-431, 416-432, 416-435, 417-432, 417-433, 417-436, 418-433, 418-434, 418-437, 457-472, 457-473, 458-473, 670-706, 670-685, 670-686, 671-686, 671-687, 672-687, 672-688, 673-688, 687-702, 687-703, 687-706, 688-703, 688-704, 689-704, 689-705, 690-705, 690-706, 691-706, 1261-1285, 1261-1276, 1261-1277, 1261-1280, 1262-1277, 1262-1278, 1262-1281, 1263-1278, 1263-1279, 1263-1282, 1264-1279, 1264-1280, 1264-1283, 1265-1280, 1265-1281, 1265-1284, 1266-1281, 1266-1282, 1266-1285, 1267-1282, 1267-1283, 1268-1283, 1268-1284, 1269-1284, 1269-1285, 1270-1285, 1577-1606, 1577-1592, 1577-1593, 1577-1596, 1578-1593, 1578-1594, 1578-1597, 1579-1594, 1579-1594, 1579-1598, 1580-1595, 1580-1596, 1580-1599, 1581-1596, 1581-1597, 1581-1600, 1582-1597, 1582-1598, 1582-1601, 1583-1598, 1583-1599, 1583-1602, 1584-1599, 1584-1600, 1584-1603, 1585-1600, 1585-1601, 1585-1604, 1586-1601, 1586-1602, 1586-1605, 1587-1602, 1587-1603, 1587-1606, 1588-1603, 1588-1604, 1589-1604, 1589-1605, 1590-1605, 1590-1606, 1591-1606, 1778-1800, 1778-1793, 1778-1794, 1778-1797, 1779-1794, 1779-1795, 1779-1798, 1780-1795, 1780-1796, 1780-1799, 1781-1796, 1781-1797, 1781-1800, 1782-1797, 1782-1798, 1783-1798, 1783-1799, 1784-1799, and 1784-1800.

In certain embodiments, an antisense compound or oligonucleotide targeted to a HBV nucleic acid target the following nucleotide regions of SEQ ID NO: 1: 58-73, 58-74, 58-77, 59-74, 59-75, 60-75, 60-76, 61-76, 61-77, 62-77, 253-272, 253-269, 254-270, 255-271, 256-272, 411-437, 411-426, 411-427, 411-430, 412-427, 412-428, 412-431, 413-428, 413-429, 413-432, 414-429, 414-430, 414-433, 415-430, 415-431, 415-434, 416-431, 416-432, 416-435, 417-432, 417-433, 417-436, 418-433, 418-434, 418-437, 457-472, 457-473, 458-473, 670-706, 670-685, 670-686, 671-686, 671-687, 672-687, 672-688, 673-688, 687-702, 687-703, 687-706, 688-703, 688-704, 689-704, 689-705, 690-705, 690-706, 691-706, 1261-1285, 1261-1276, 1261-1277, 1261-1280, 1262-1277, 1262-1278, 1262-1281, 1263-1278, 1263-1279, 1263-1282, 1264-1279, 1264-1280, 1264-1283, 1265-1280, 1265-1281, 1265-1284, 1266-1281, 1266-1282, 1266-1285, 1267-1282, 1267-1283, 1268-1283, 1268-1284, 1269-1284, 1269-1285, 1270-1285, 1577-1606, 1577-1592, 1577-1593, 1577-1596, 1578-1593, 1578-1594, 1578-1597, 1579-1594, 1579-1594, 1579-1598, 1580-1595, 1580-1596, 1580-1599, 1581-1596, 1581-1597, 1581-1600, 1582-1597, 1582-1598, 1582-1601, 1583-1598, 1583-1599, 1583-1602, 1584-1599, 1584-1600, 1584-1603, 1585-1600, 1585-1601, 1585-1604, 1586-1601, 1586-1602, 1586-1605, 1587-1602, 1587-1603, 1587-1606, 1588-1603, 1588-1604, 1589-1604, 1589-1605, 1590-1605, 1590-1606, 1591-1606, 1778-1800, 1778-1793, 1778-1794, 1778-1797, 1779-1794, 1779-1795, 1779-1798, 1780-1795, 1780-1796, 1780-1799, 1781-1796, 1781-1797, 1781-1800, 1782-1797, 1782-1798, 1783-1798, 1783-1799, 1784-1799, and 1784-1800.

In certain embodiments, antisense compounds or oligonucleotides target a region of a HBV nucleic acid. In certain embodiments, such compounds or oligonucleotides targeted to a region of a HBV nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide regions of SEQ ID NO: 1: 1-20, 10-29, 10-56, 13-38, 13-35, 19-38, 25-47, 25-50, 25-56, 43-68, 43-63, 55-74, 58-73, 58-74, 58-77, 58-79, 58-80, 58-84, 59-74, 59-75, 59-80, 60-75, 60-76, 60-79, 61-76, 61-77, 61-80, 62-77, 63-84, 68-114, 101-123, 98-123, 113-138, 116-138, 131-150, 137-162, 152-186, 158-177, 167-186, 191-215, 196-224, 196-215, 196-218, 199-228, 199-218, 199-224, 200-224, 205-224, 206-228, 218-237, 224-243, 233-264, 242-263, 243-262, 244-263, 245-264, 246-266, 247-266, 247-269, 247-270, 245-267, 251-267, 245-266, 250-269, 251-268, 251-269, 245-269, 245-266, 245-261, 250-266, 250-267, 250-268, 250-269, 251-270, 253-269, 253-272, 253-274, 254-270, 254-274, 255-271, 255-274, 255-401, 255-400, 255-274, 255-273, 255-272, 255-271, 256-275, 255-276, 256-272, 256-276, 253-275, 256-279, 257-276, 260-279, 262-281, 262-321, 262-315, 262-312, 265-312, 266-288, 266-291, 266-285, 281-321, 281-303, 290-321, 290-312, 292-311, 290-312, 293-312, 293-315, 293-321, 296-321, 302-321, 324-343, 339-361, 339-367, 348-367, 342-367, 358-392, 358-378, 360-392, 360-383, 360-388, 360-385, 362-381, 366-388, 369-388, 366-385, 366-392, 370-389, 370-392, 384-433, 384-400, 384-401, 385-401, 405-424, 409-428, 405-428, 411-426, 411-427, 411-430, 411-431, 411-437, 412-431, 411-426, 411-427, 412-428, 412-431, 412-427, 413-433, 413-432, 413-428, 413-429, 413-432, 413-433, 414-427, 415-427, 414-429, 414-430, 414-433, 415-428, 415-429, 415-430, 415-431, 415-434, 416-431, 416-432, 416-429, 416-435, 417-432, 417-433, 417-436, 418-433, 418-435, 418-434, 418-437, 419-435, 419-434, 420-435, 419-432, 419-434, 422-441, 423-436, 425-465, 454-473, 454-472, 457-476, 457-472, 457-473, 454-476, 455-472, 457-485, 458-485, 458-483, 458-477, 458-473, 459-485, 460-485, 463-498, 463-485, 466-485, 463-482, 457-491, 458-491, 459-491, 460-491, 463-491, 466-491, 472-491, 472-493, 473-492, 475-491, 459-494, 460-494, 463-494, 466-494, 467-498, 472-494, 475-494, 457-473, 457-472, 458-494, 454-494, 457-494, 457-473, 485-513, 470-493, 476-519, 485-519, 500-519, 512-534, 512-550, 524-546, 536-559, 548-567, 548-570, 550-570, 548-594, 554-573, 548-576, 560-594, 584-606, 611-645, 617-363, 623-642, 617-645, 642-754, 653-672, 662-685, 665-685, 665-689, 668-687, 670-706, 670-685, 670-686, 670-689, 671-690, 671-691, 671-686, 671-687, 672-693, 672-697, 672-707, 672-687, 672-688, 673-688, 674-693, 679-707, 679-698, 679-701, 679-702, 679-707, 680-699, 679-699, 682-706, 682-707, 682-702, 682-701, 687-754, 688-704, 689-709, 689-710, 690-705, 679-705, 679-710, 679-706, 690-710, 691-710, 690-754, 690-706, 684-703, 687-705, 687-702, 687-703, 687-706, 688-703, 688-704, 688-705, 689-704, 689-705, 689-708, 690-705, 690-706, 690-709, 691-706, 692-711, 693-716, 693-712, 695-715, 697-716, 697-716, 690-716, 724-746, 724-752, 724-754, 724-758, 733-752, 738-754, 739-758, 739-754, 739-775, 739-754, 740-754, 742-785, 742-773, 757-776, 757-785, 790-815, 793-812, 811-833, 811-844, 814-833, 811-906, 820-839, 822-844, 822-867, 823-842, 845-864, 845-867, 854-906, 845-909, 845-906, 854-876, 863-882, 863-885, 878-900, 887-906, 899-918, 899-933, 899-958, 905-927, 905-933, 914-933, 936-958, 936-955, 945-964, 951-970, 951-985, 951-1044, 951-1024, 951-1056, 951-997, 960-985, 963-1044, 963-1024, 963-997, 972-1015, 1025-1044, 1031-1056, 1037-1056, 1046-1083, 1049-1068, 1070-1089, 1070-1095, 1082-1101, 1081-1134, 1081-1143, 1082-1101, 1088-1107, 1088-1134, 1094-1119, 1097-1119, 1112-1134, 1118-1143, 1118-1146, 1088-1146, 1121-1140, 1127-1146, 1127-1193, 1150-1193, 1156-1187, 1165-1187, 1170-1192, 1171-1191, 1172-1191, 1176-1192, 1177-1192, 1176-1191, 1203-1297, 1206-1228, 1206-1255, 1209-1228, 1215-1255, 1245-1265, 1251-1280, 1262-1285, 1251-1285, 1259-1296, 1259-1290, 1259-1287, 1261-1296, 1261-1285, 1261-1276, 1261-1277, 1261-1280, 1262-1296, 1262-1277, 1262-1278, 1262-1281, 1263-1278, 1263-1279, 1263-1282, 1264-1279, 1264-1280, 1264-1283, 1264-1297, 1265-1280, 1265-1281, 1265-1284, 1266-1281, 1266-1282, 1266-1285, 1267-1282, 1267-1283, 1268-1283, 1268-1284, 1268-1296, 1269-1284, 1269-1285, 1269-1288, 1270-1285, 1271-1290, 1271-1296, 1277-1296, 1261-1290, 1262-1290, 1268-1290, 1263-1305, 1259-1305, 1259-1305, 1266-1305, 1259-1302, 1275-1294, 1281-1306, 1281-1324, 1281-1336, 1282-1301, 1286-1306, 1290-1324, 1293-1318, 1290-1324, 1293-1315, 1296-1315, 1311-1336, 1311-1333, 1326-1345, 1353-1381, 1359-1378, 1395-1414, 1498-1532, 1498-1523, 1498-1535, 1510-1529, 1515-1535, 1515-1563, 1515-1596, 1515-1605, 1515-1602, 1515-1540, 1515-1535, 1518-1605, 1518-1602, 1518-1537, 1521-1563, 1521-1540, 1550-1655, 1550-1563, 1550-1569, 1553-1578, 1553-1599, 1553-1590, 1565-1584, 1571-1595, 1577-1605, 1577-1606, 1577-1592, 1577-1593, 1577-1596, 1578-1593, 1578-1594, 1578-1597, 1578-1598, 1571-1598, 1579-1594, 1579-1594, 1579-1598, 1580-1595, 1580-1596, 1580-1599, 1580-1605, 1580-1602, 1581-1596, 1581-1597, 1581-1600, 1582-1597, 1582-1598, 1582-1601, 1582-1602, 1553-1655, 1583-1598, 1583-1599, 1583-1602, 1584-1599, 1584-1600, 1584-1603, 1585-1600, 1585-1601, 1585-1604, 1586-1601, 1586-1602, 1586-1605, 1587-1602, 1587-1603, 1587-1606, 1588-1603, 1588-1604, 1589-1604, 1589-1605, 1590-1605, 1590-1606, 1591-1606, 1586-1652, 1642-1664, 1651-1720, 1651-1673, 1655-1679, 1695-1720, 1716-1738, 1743-1763, 1743-1768, 1764-1783, 1773-1792, 1777-1796, 1777-1800, 1778-1800, 1778-1793, 1778-1794, 1778-1797, 1779-1798, 1779-1797, 1779-1796, 1779-1795, 1779-1794, 1780-1799, 1780-1796, 1780-1795, 1781-1797, 1781-1796, 1781-1796, 1781-1800, 1781-1797, 1782-1799, 1782-1797, 1782-1798, 1783-1798, 1783-1799, 1784-1800, 1784-1799, 1779-1799, 1778-1794, 1779-1795, 1780-1799, 1794-1813, 1806-1837, 1806-1828, 1806-1825, 1809-1828, 1812-1843, 1812-1837, 1812-1831, 1815-1843, 1815-1844, 1815-1840, 1815-1834, 1818-1837, 1821-1840, 1821-1844, 1821-1837, 1822-1843, 1822-1839, 1823-1843, 1827-1846, 1861-1884, 1861-1880, 1865-1885, 1867-1886, 1869-1885, 1876-1895, 1888-1914, 1888-1908, 1891-1910, 1891-1914, 1895-1938, 1895-1935, 1913-1935, 1898-1920, 1907-1929, 1913-1935, 1918-1934, 1919-1938, 1919-1934, 1921-1934, 1928-1956, 1957-1976, 2035-2057, 2083-2141, 2230-2261, 2368-2393, 2381-2397, 2368-2394, 2379-2394, 2381-2396, 2368-2397, 2368-2396, 2420-2439, 2458-2476, 2459-2478, 2819-2838, 2818-2838, 2873-2892, and 3161-3182.

In certain embodiments, antisense compounds or oligonucleotides target a region of a HBV nucleic acid. In certain embodiments, such compounds or oligonucleotides targeted to a region of a HBV nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide regions of SEQ ID NO: 1: 233-264, 242-263, 243-262, 244-263, 245-264, 246-266, 247-266, 247-269, 247-270, 245-267, 251-267, 245-266, 250-269, 251-268, 251-269, 245-269, 245-266, 245-261, 250-266, 250-267, 250-268, 250-269, 251-270, 253-272, 253-274, 254-274, 255-274, 255-401, 255-400, 255-274, 255-273, 255-272, 255-271, 256-275, 255-276, 256-276, 253-275, 256-279, 257-276, 260-279, 262-281, 262-321, 262-315, 262-312, 265-312, 266-288, 266 291, 266 285, 281 321, 281-303, 405-424, 409-428, 405-428, 411-430, 411-431, 411-431, 412-431, 411-426, 411-427, 412-428, 412-431, 412-427, 413-433, 413-432, 413-428, 413-433, 411-427, 414-427, 415-427, 415-428, 415-429, 416-432, 416-429, 418-435, 418-434, 419-435, 419-434, 420-435, 419-432, 419-434, 422-441, 423-436, 425-465, 584-606, 611-645, 617-363, 623-642, 617-645, 642-754, 653-672, and wherein at least one nucleoside of the compound or modified oligonucleotide comprises at least one 2'-O-methoxyethyl sugar.

In certain embodiments, the following nucleotide regions of SEQ ID NO: 1, when targeted by antisense compounds or oligonucleotides, display at least 50% inhibition: 1-20, 10-29, 10-56, 13-38, 13-35, 19-38, 25-47, 25-50, 25-56, 43-68, 43-63, 55-74, 58-77, 58-74, 58-73, 58-79, 58-80, 58-84, 59-74, 59-75, 59-80, 60-79, 60-75, 60-76, 61-80, 61-76, 61-77, 62-77, 63-84, 68-114, 101-123, 98-123, 113-138, 116-138, 131-150, 137-162, 152-186, 158-177, 167-186, 191-215, 196-224, 196-215, 196-218, 199-228, 199-218, 199-224, 200-224, 205-224, 206-228, 218-237, 224-243, 233-264, 242-263, 243-262, 244-263, 245-264, 246-266, 247-266, 247-269, 247-270, 245-267, 251-267, 245-266, 250-269, 251-268, 251-269, 245-269, 245-266, 245-261, 250-265, 250-266, 250-267, 250-268, 250-269, 251-266, 251-270, 252-267, 253-268, 253-269, 253-272, 253-274, 254-269, 254-270, 254-274, 255-274, 255-401, 255-400, 255-274, 255-273, 255-272, 255-271, 255-270, 256-271, 256-272, 256-275, 255-276, 256-276, 253-275, 256-279, 257-276, 258-273, 259-274, 260-279, 262-281, 262-321, 262-315, 262-312, 265-312, 266-288, 266-291, 266-285, 281-321, 281-303, 290-321, 290-312, 292-311, 290-312, 293-312, 293-315, 293-321, 296-321, 302-321, 324-343, 339-361, 339-367, 348-367, 342-367, 358-392, 358-378, 360-392, 360-383, 360-388, 360-385, 362-381, 366-388, 369-388, 366-385, 366-392, 370-389, 370-392, 380-399, 382-401, 384-433, 384-400, 384-401, 385-401, 405-424, 409-428, 405-428, 411-430, 411-431, 411-431, 412-431, 411-426, 411-427, 411-430, 411-437, 412-428, 412-431, 412-427, 413-432, 413-428, 413-429, 413-433, 411-427, 414-427, 414-429, 414-430, 414-433, 415-427, 415-428, 415-429, 415-430, 415-431, 415-434, 416-435, 416-432, 416-431, 416-429, 417-432, 417-433, 417-436, 418-437, 418-435, 418-434, 418-433, 419-435, 419-434, 420-435, 419-432, 419-434, 421-436, 422-441, 422-437, 423-436, 425-465, 454-473, 454-472, 457-476, 454-476, 455-472, 457-485, 457-473, 457-472, 458-485, 458-483, 458-477, 458-473, 459-485, 460-485, 463-498, 463-485, 466-485, 463-482, 457-491, 458-491, 459-491, 460-491, 463-491, 466-491, 472-491, 472-493, 473-492, 475-491, 459-494, 460-494, 463-494, 466-494, 467-498, 472-494, 475-494, 457-473, 457-472, 458-494, 454-494, 457-494, 457-473, 485-513, 470-493, 476-519, 485-519, 500-519, 512-534, 512-550, 524-546, 536-559, 548-567, 548-570, 550-570, 548-594, 554-573, 548-576, 560-594, 584-606, 611-645, 617-363, 623-642, 617-645, 639-654, 641-656, 642-657, 642-754, 643-658, 653-672, 662-685, 665-685, 665-689, 668-687, 670-689, 670-706, 670-685, 670-686, 671-686, 671-687, 671-690, 671-691, 672-687, 672-688, 672-693, 672-697, 672-707, 673-688, 674-693, 678-693, 679-707, 679-694, 679-698, 679-701, 679-702, 679-707, 680-699, 679-699, 680-695, 681-696, 682-706, 682-707, 682-702, 682-701, 682-697, 683-698, 684-699, 685-700, 686-701, 687-702, 687-703, 687-706, 687-754, 688-703, 688-704, 689-704, 689-705, 689-709, 689-710, 690-705, 690-706, 691-706, 679-705, 679-710, 679-706, 690-710, 691-710, 690-754, 690-706, 684-703, 687-705, 687-703, 687-706, 688-705, 689-708, 690-709, 692-711, 693-716, 693-712, 695-715, 697-716, 697-716, 690-716, 724-746, 724-752, 724-754, 724-758, 733-752, 738-753, 738-754, 739-758, 739-754, 739-775, 739-754, 740-754, 742-785, 742-773, 757-776, 757-785, 790-815, 793-812, 811-833, 811-844, 814-833, 811-906, 820-839, 822-844, 822-867, 823-842, 845-864, 845-867, 854-906, 845-909, 845-906, 854-876, 854-873, 863-882, 863-885, 878-900, 878-897, 887-906, 899-918, 899-933, 899-958, 905-927, 905-933, 914-933, 936-958, 936-955, 945-964, 951-970, 951-985, 951-1044, 951-1024, 951-1056, 951-997, 960-985, 963-1044, 963-1024, 963-997, 966-985, 972-1015, 978-997, 1025-1044, 1031-1056, 1037-1056, 1046-1083, 1049-1068, 1070-1089, 1070-1095, 1082-1101, 1081-1134, 1081-1143, 1082-1101, 1088-1107, 1088-1134, 1094-1119, 1097-1119, 1112-1134, 1118-1143, 1118-1146, 1088-1146, 1121-1140, 1127-1146, 1127-1193, 1150-1193, 1156-1187, 1165-1187, 1170-1192, 1171-1191, 1172-1191, 1176-1192, 1177-1192, 1176-1191, 1203-1297, 1206-1228, 1206-1255, 1209-1228, 1215-1255, 1215-1234, 1218-1237, 1221-1240, 1224-1243, 1227-1246, 1230-1249, 1233-1252, 1236-1255, 1245-1265, 1251-1280, 1251-1285, 1251-1270, 1254-1273, 1254-1279, 1257-1276, 1258-1277, 1259-1296, 1259-1290, 1259-1287, 1260-1279, 1261-1285, 1261-1276, 1261-1277, 1261-1280, 1261-1296, 1262-1277, 1262-1278, 1262-1281, 1262-1285, 1262-1296, 1263-1278, 1263-1279, 1263-1282, 1264-1279, 1264-1280, 1264-1283, 1264-1297, 1265-1280, 1265-1281, 1265-1284, 1266-1281, 1266-1282, 1266-1285, 1267-1282, 1267-1283, 1268-1283, 1268-1284, 1268-1296, 1269-1284, 1269-1285, 1269-1288, 1270-1285, 1271-1290, 1271-1296, 1277-1296, 1261-1290, 1262-1290, 1268-1290, 1263-1305, 1259-1305, 1259-1305, 1266-1305, 1259-1302, 1275-1294, 1281-1306, 1281-1324, 1281-1336, 1782-1797, 1282-1301, 1286-1306, 1290-1324, 1293-1318, 1290-1324, 1293-1315, 1296-1315, 1311-1336, 1311-1333, 1326-1345, 1353-1381, 1359-1378, 1395-1414, 1498-1532, 1498-1523, 1498-1535, 1510-1529, 1515-1535, 1515-1563, 1515-1596, 1515-1605, 1515-1602, 1515-1540, 1515-1535, 1518-1605, 1518-1602, 1518-1537, 1521-1563, 1521-1540, 1550-1655, 1550-1563, 1550-1569, 1553-1578, 1553-1599, 1553-1590, 1565-1584, 1571-1595, 1577-1606, 1577-1605, 1577-1596, 1577-1592, 1577-1593, 1578-1593, 1578-1594, 1578-1597, 1578-1598, 1579-1594, 1579-1595, 1579-1598, 1571-1598, 1580-1605, 1580-1602, 1580-1595, 1580-1596, 1580-1599, 1581-1596, 1581-1597, 1581-1600, 1582-1597, 1582-1598, 1582-1601, 1582-1602, 1553-1655, 1583-1598, 1583-1599, 1583-1602, 1584-1599, 1584-1600, 1584-1603, 1585-1600, 1585-1601, 1585-1602, 1586-1601, 1586-1602, 1586-1605, 1586-1652, 1587-1602, 1587-1603, 1587-1606, 1588-1603, 1588-1604, 1589-1604, 1589-1605, 1590-1605, 1590-1606, 1591-1606, 1642-1664, 1651-1720, 1651-1673, 1655-1679, 1695-1720, 1716-1738, 1743-1763, 1743-1768, 1764-1783, 1773-1792, 1777-1796, 1777-1800, 1778-1800, 1778-1793, 1778-1794, 1778-1797, 1779-1798, 1779-1797, 1779-1796, 1779-1795, 1779-1794, 1780-1796, 1781-1797, 1781-1796, 1781-1800, 1781-1797, 1782-1799, 1784-1800, 1779-1799, 1778-1794, 1779-1795, 1780-1799, 1794-1813, 1780-1795, 1780-1796, 1780-1799, 1781-1796, 1781-1797, 1781-1800, 1782-1798, 1783-1799, 1784-1799, 1784-1800, 1785-1800, 1806-1837, 1806-1828, 1806-1825, 1809-1828, 1812-1843, 1812-1837, 1812-1831, 1815-1843, 1815-1844, 1815-1840, 1815-1834, 1818-1837, 1821-1840, 1821-1844, 1821-1837, 1822-1843, 1822-1839, 1823-1843, 1827-1846, 1861-1884, 1861-1880, 1865-1885, 1867-1886, 1869-1885, 1876-1895, 1888-1914, 1888-1908, 1891-1910, 1891-1914, 1895-1938, 1895-1935, 1913-1935, 1898-1920, 1907-1929, 1913-1935, 1918-1934, 1919-1938, 1919-1934, 1921-1934, 1928-1956, 1957-1976, 2035-2057, 2083-2141, 2230-2261, 2278-2297, 2281-2300, 2284-2303, 2368-2393, 2381-2397, 2368-2394, 2379-2394, 2381-2396, 2368-2397, 2368-2396, 2420-2439, 2458-2476, 2459-2478, 2819-2838, 2818-2838, 2873-2892, and 3161-3182.

In certain embodiments, the following nucleotide regions of SEQ ID NO: 1, when targeted by antisense compounds or oligonucleotides, display at least 60% inhibition: 1-20, 10-29, 10-53, 13-38, 25-50, 43-68, 55-74, 58-84, 58-77, 58-74, 58-73, 58-79, 59-80, 59-74, 59-75, 60-75, 60-76, 61-77, 61-76, 61-80, 62-77, 68-114, 98-123, 101-123, 113-138, 116-138, 131-150, 137-162, 152-186, 191-215, 196-224, 196-215, 199-228, 199-218, 200-223, 199-218, 205-224, 206-228, 218-237, 224-243, 233-263, 244-263, 245-264, 247-266, 250-265, 251-266, 252-267, 253-272, 253-269, 251-267, 253-274, 254-270, 255-276, 256-279, 256-276, 256-274, 256-272, 256-271, 258-273, 259-274, 265-388, 265-284, 266-291, 266-288, 260-279, 281-321, 281-303, 290-321, 290-312, 293-312, 296-315, 302-321, 324-343, 339-367, 339-361, 342-367, 348-367, 358-392, 358-378, 360-392, 360-379, 366-392, 366-385, 369-388, 370-392, 382-401, 405-428, 405-424, 409-428, 411-436, 411-433, 411-431, 411-426, 411-430, 411-427, 412-431, 412-428, 412-427, 413-428, 413-429, 413-433, 414-433, 414-430, 414-429, 414-433, 415-430, 415-431, 415-434, 415-435, 415-436, 416-429, 416-434, 416-431, 416-432, 416-436, 416-435, 417-436, 417-433, 417-432, 418-434, 418-433, 418-437, 419-434, 420-435, 421-436, 422-437, 423-436, 425-465, 454-472, 455-472, 457-476, 457-472, 457-473, 458-485, 458-473, 458-483, 463-498, 467-498, 463-482, 470-493, 472-491, 485-519, 485-513, 500-519, 512-534, 524-546, 536-558, 548-567, 554-573, 548-576, 560-594, 584-606, 608-648, 639-654, 640-656, 641-656, 642-657, 642-658, 643-658, 653-672, 662-685, 665-685, 670-706, 670-689, 670-685, 670-686, 671-690, 671-686, 671-687, 672-707, 672-697, 672-693, 672-687, 672-688, 673-688, 679-707, 679-698, 679-694, 680-695, 681-696, 682-697, 682-701, 683-698, 684-699, 685-700, 686-701, 687-754, 687-702, 687-705, 687-703, 687-706, 688-704, 688-703, 688-704, 688-705, 688-707, 689-710, 689-709, 689-705, 689-704, 690-754, 690-705, 690-706, 691-706, 691-710, 692-711, 697-716, 724-758, 724-754, 724-752, 724-746, 738-754, 738-753, 739-754, 742-785, 757-785, 790-815, 811-906, 811-844, 811-833, 822-867, 822-844, 823-842, 845-867, 854-906, 854-873, 878-897, 899-958, 899-933, 936-958, 945-964, 951-1044, 951-1024, 951-985, 951-997, 963-1044, 963-1024, 963-997, 966-985, 978-997, 1031-1056, 1046-1083, 1070-1095, 1081-1143, 1081-1134, 1082-1101, 1088-1146, 1088-1134, 1118-1146, 1118-1143, 1127-1193, 1170-1189, 1176-1192, 1176-1191, 1177-1192, 1203-1297, 1206-1255, 1209-1228, 1215-1234, 1218-1237, 1221-1240, 1224-1243, 1227-1246, 1230-1249, 1233-1252, 1236-1255, 1251-1270, 1251-1285, 1254-1273, 1254-1279, 1257-1276, 1258-1277, 1259-1278, 1260-1279, 1261-1276, 1261-1285, 1261-1276, 1261-1277, 1261-1280, 1262-1281, 1262-1277, 1262-1278, 1262-1281, 1263-1278, 1263-1279, 1263-1282, 1264-1297, 1264-1279, 1264-1280, 1264-1283, 1265-1280, 1265-1281, 1265-1284, 1266-1281, 1266-1282, 1266-1285, 1267-1282, 1267-1283, 1268-1283, 1268-1284, 1268-1287, 1269-1284, 1269-1285, 1270-1285, 1281-1336, 1281-1324, 1281-1306, 1286-1305, 1290-1324, 1311-1336, 1326-1345, 1353-1381, 1395-1414, 1498-1535, 1498-1532, 1515-1535, 1515-1534, 1521-1540, 1550-1655, 1553-1599, 1553-1590, 1577-1606, 1577-1592, 1577-1593, 1577-1596, 1578-1593, 1578-1594, 1578-1597, 1579-1594, 1579-1595, 1579-1598, 1580-1595, 1580-1596, 1580-1599, 1581-1596, 1581-1597, 1581-1600, 1582-1597, 1582-1598, 1582-1601, 1583-1598, 1583-1599, 1583-1602, 1584-1599, 1584-1600, 1584-1603, 1585-1600, 1585-1601, 1585-1604, 1586-1601, 1586-1602, 1586-1605, 1587-1602, 1587-1603, 1587-1606, 1588-1603, 1588-1604, 1589-1604, 1589-1605, 1590-1605, 1590-1606, 1591-1606, 1642-1664, 1651-1720, 1716-1738, 1743-1763, 1764-1783, 1773-1792, 1777-1800, 1777-1797, 1655-1674, 1778-1794, 1778-1800, 1781-1800, 1781-1797, 1784-1800, 1779-1799, 1778-1794, 1778-1797, 1779-1795, 1779-1798, 1780-1795, 1780-1796, 1780-1799, 1781-1796, 1781-1797, 1781-1800, 1782-1797, 1794-1813, 1806-1837, 1806-1825, 1812-1837, 1812-1831, 1815-1844, 1815-1834, 1818-1837, 1821-1837, 1822-1838, 1827-1846, 1861-1884, 1821-1840, 1866-1885, 1867-1886, 1888-1914, 1888-1907, 1891-1914, 1895-1938, 1895-1935, 1919-1938, 1928-1956, 1957-1976, 2035-2057, 2083-2141, 2230-2261, 2278-2297, 2281-2300, 2284-2303, 2368-2397, 2368-2396, 2368-2394, 2368-2393, 2379-2394, 2381-2396, 2420-2439, 2458-2476, 2819-2838, 2873-2892, and 3161-3182.

In certain embodiments, the following nucleotide regions of SEQ ID NO: 1, when targeted by antisense compounds or oligonucleotides, display at least 65% inhibition: 1-20, 10-29, 10-53, 13-38, 25-50, 43-68, 55-74, 58-84, 58-79, 58-74, 58-73, 58-77, 59-75, 59-80, 58-77, 60-75, 60-76, 61-77, 61-76, 61-80, 62-77, 68-114, 98-123, 101-123, 113-138, 116-138, 131-150, 137-162, 152-186, 191-215, 196-215, 199-228, 199-218, 200-223, 199-218, 205-224, 206-228, 218-237, 224-243, 233-263, 244-263, 245-264, 250-265, 251-266, 253-269, 253-274, 255-276, 256-279, 256-276, 256-274, 256-272, 256-271, 247-266, 253-272, 258-273, 266-291, 266-288, 260-279, 281-321, 281-303, 290-321, 290-312, 296-315, 293-312, 302-321, 324-343, 339-367, 339-361, 342-367, 348-367, 358-392, 358-378, 360-392, 360-379, 366-392, 366-385, 369-388, 370-392, 382-401, 405-428, 405-424, 409-428, 411-433, 411-431, 411-430, 411-427, 411-426, 412-431, 412-428, 412-427, 413-433, 413-428, 413-429, 413-432, 414-433, 414-430, 414-429, 415-430, 415-431, 415-434, 415-435, 415-436, 416-434, 416-436, 416-435, 416-432, 416-431, 417-436, 417-433, 417-432, 418-433, 418-434, 418-437, 420-435, 422-437, 423-436, 425-465, 454-472, 455-472, 457-472, 458-485, 458-483, 458-473, 463-498, 467-498, 457-476, 470-493, 472-491, 485-519, 485-513, 500-519, 512-534, 524-546, 536-558, 548-567, 554-573, 548-576, 560-594, 584-606, 608-648, 639-654, 640-656, 641-656, 642-657, 642-658, 643-658, 653-672, 662-685, 665-685, 670-685, 670-706, 670-689, 670-686, 670-685, 671-686, 671-687, 690, 672-688, 672-687, 672-707, 672-697, 672-693, 673-688, 679-698, 680-695, 681-696, 682-697, 682-701, 683-698, 684-699, 685-700, 686-701, 687-702, 687-703, 688-707, 687-754, 690-754, 690-706, 690-705, 687-705, 687-703, 687-706, 687-702, 688-705, 688-703, 688-704, 689-705, 691-706, 692-711, 697-716, 724-758, 724-754, 724-752, 724-746, 738-754, 739-754, 742-785, 757-785, 790-815, 811-906, 811-844, 811-833, 822-867, 822-844, 823-842, 845-867, 854-906, 854-873, 878-897, 899-958, 899-933, 936-958, 945-964, 951-1044, 951-1024, 951-985, 951-997, 963-1044, 963-1024, 963-997, 966-985, 978-997, 1031-1056, 1046-1083, 1070-1095, 1081-1143, 1081-1134, 1082-1101, 1088-1146, 1088-1134, 1118-1146, 1118-1143, 1127-1193, 1170-1189, 1176-1192, 1177-1192, 1203-1297, 1206-1255, 1209-1228, 1215-1234, 1218-1237, 1221-1240, 1224-1243, 1227-1246, 1230-1249, 1233-1252, 1236-1255, 1251-1270, 1251-1285, 1254-1273, 1254-1279, 1257-1276, 1258-1277, 1259-1278, 1260-1279, 1261-1285, 1261-1276, 1261-1277, 1261-1280, 1262-1281, 1262-1277, 1262-1278, 1263-1278, 1263-1279, 1263-1282, 1264-1297, 1264-1279, 1264-1280, 1264-1283, 1265-1280, 1265-1281, 1265-1284, 1266-1281, 1266-1282, 1266-1285, 1267-1282, 1267-1283, 1268-1283, 1268-1284, 1268-1287, 1269-1284, 1269-1285, 1270-1285, 1281-1336, 1281-1324, 1281-1306, 1290-1324, 1311-1336, 1326-1345, 1353-1381, 1395-1414, 1498-1535, 1498-1532, 1515-1535, 1515-1534, 1550-1655, 1553-1599, 1553-

1590, 1577-1606, 1577-1592, 1577-1593, 1577-1596, 1578-1593, 1578-1594, 1578-1597, 1579-1594, 1579-1595, 1579-1598, 1580-1595, 1580-1596, 1580-1599, 1581-1596, 1581-1597, 1581-1600, 1582-1597, 1582-1598, 1582-1601, 1583-1598, 1583-1599, 1583-1602, 1584-1599, 1584-1600, 1584-1603, 1585-1600, 1585-1601, 1585-1604, 1586-1601, 1586-1602, 1586-1605, 1587-1602, 1587-1603, 1587-1606, 1588-1603, 1588-1604, 1589-1604, 1589-1605, 1590-1605, 1590-1606, 1591-1606, 1642-1664, 1651-1720, 1655-1674, 1716-1738, 1743-1763, 1764-1783, 1773-1792, 1777-1800, 1777-1797, 1778-1800, 1778-1797, 1779-1799, 1778-1794, 1779-1794, 1779-1795, 1779-1798, 1780-1796, 1780-1799, 1780-1795, 1781-1796, 1781-1797, 1781-1800, 1782-1797, 1794-1813, 1806-1837, 1806-1825, 1812-1837, 1812-1831, 1815-1844, 1815-1834, 1818-1837, 1821-1837, 1822-1838, 1827-1846, 1861-1884, 1866-1885, 1867-1886, 1888-1914, 1888-1907, 1891-1914, 1895-1938, 1895-1935, 1919-1938, 1928-1956, 1957-1976, 2035-2057, 2083-2141, 2230-2261, 2278-2297, 2281-2300, 2284-2303, 2368-2397, 2368-2396, 2368-2394, 2368-2393, 2379-2394, 2381-2396, 2420-2439, 2458-2476, 2819-2838, 2873-2892, and 3161-3182.

In certain embodiments, the following nucleotide regions of SEQ ID NO: 1, when targeted by antisense compounds or oligonucleotides, display at least 70% inhibition: 1-20, 10-29, 10-53, 13-38, 25-50, 43-68, 55-74, 58-84, 58-79, 58-74, 59-75, 59-80, 58-77, 60-75, 60-76, 61-77, 68-114, 98-123, 101-123, 113-138, 116-138, 131-150, 137-162, 152-186, 191-215, 199-228, 199-218, 200-223, 205-224, 206-228, 218-237, 224-243, 233-263, 244-263, 245-264, 253-269, 253-274, 255-276, 256-279, 256-276, 256-274, 256-272, 247-266, 250-265, 251-266, 253-272, 256-271, 266-291, 266-288, 260-279, 281-321, 281-303, 290-321, 290-312, 293-312, 302-321, 324-343, 339-367, 339-361, 342-367, 348-367, 358-392, 358-378, 360-392, 360-379, 366-392, 366-385, 370-392, 382-401, 405-428, 405-424, 409-428, 411-433, 411-431, 411-430, 411-427, 411-426, 412-431, 412-428, 412-427, 413-428, 413-429, 413-432, 414-433, 414-430, 414-429, 415-430, 414-433, 415-434, 415-435, 415-436, 416-431, 416-434, 416-436, 416-435, 416-432, 417-436, 417-433, 418-433, 418-437, 423-436, 425-465, 454-472, 455-472, 457-472, 457-476, 458-473, 458-485, 458-483, 463-498, 467-498, 457-476, 470-493, 470-493, 472-491, 485-519, 485-513, 485-519, 485-513, 500-519, 512-534, 524-546, 536-558, 548-567, 554-573, 548-576, 560-594, 584-606, 608-648, 639-654, 640-656, 641-656, 642-657, 642-658, 643-658, 653-672, 662-685, 665-685, 670-706, 670-689, 670-685, 670-686, 671-690, 671-686, 671-687, 672-687, 672-688, 672-707, 672-697, 672-693, 673-688, 679-698, 681-696, 682-697, 682-701, 683-698, 684-699, 686-701, 687-702, 687-754, 687-702, 688-703, 690-754, 690-706, 687-705, 687-703, 687-706, 692-711, 697-716, 724-758, 724-754, 724-752, 724-746, 738-754, 739-754, 738-754, 742-785, 757-785, 790-815, 811-906, 811-844, 811-833, 822-867, 822-844, 845-867, 854-906, 854-873, 878-897, 899-958, 899-933, 936-958, 945-964, 951-1044, 951-1024, 951-985, 951-997, 963-1044, 963-1024, 963-997, 966-985, 978-997, 1031-1056, 1046-1083, 1070-1095, 1081-1143, 1081-1134, 1082-1101, 1088-1146, 1088-1134, 1118-1146, 1118-1143, 1127-1193, 1170-1189, 1176-1192, 1177-1192, 1203-1297, 1206-1255, 1209-1228, 1215-1234, 1218-1237, 1221-1240, 1224-1243, 1227-1246, 1230-1249, 1233-1252, 1236-1255, 1251-1285, 1251-1270, 1254-1273, 1254-1279, 1257-1276, 1258-1277, 1259-1278, 1260-1279, 1261-1285, 1261-1276, 1261-1277, 1261-1280, 1262-1281, 1262-1277, 1262-1278, 1263-1278, 1263-1279, 1263-1282, 1264-1297, 1264-1279, 1264-1280, 1264-1283, 1265-1281, 1265-1284, 1266-1282, 1266-1285, 1267-1282, 1267-1283, 1268-1283, 1268-1284, 1268-1287, 1269-1284, 1269-1285, 1270-1285, 1281-1336, 1281-1324, 1281-1306, 1290-1324, 1311-1336, 1326-1345, 1353-1381, 1395-1414, 1498-1535, 1498-1532, 1515-1535, 1550-1655, 1553-1599, 1553-1590, 1577-1606, 1577-1592, 1577-1593, 1577-1596, 1578-1593, 1578-1594, 1578-1597, 1579-1594, 1579-1595, 1579-1598, 1580-1595, 1580-1596, 1580-1599, 1581-1596, 1581-1597, 1581-1600, 1582-1597, 1582-1598, 1582-1601, 1583-1598, 1583-1599, 1583-1602, 1584-1599, 1584-1600, 1584-1603, 1585-1600, 1585-1601, 1585-1604, 1586-1602, 1586-1605, 1587-1602, 1587-1603, 1587-1606, 1588-1603, 1588-1604, 1589-1604, 1589-1605, 1590-1605, 1590-1606, 1591-1606, 1642-1664, 1651-1720, 1716-1738, 1743-1763, 1764-1783, 1773-1792, 1777-1800, 1777-1797, 1778-1800, 1778-1797, 1779-1799, 1778-1794, 1779-1795, 1779-1798, 1780-1795, 1780-1796, 1780-1799, 1781-1800, 1782-1797, 1794-1813, 1806-1837, 1806-1825, 1812-1837, 1812-1831, 1815-1844, 1815-1834, 1818-1837, 1821-1837, 1822-1838, 1827-1846, 1861-1884, 1866-1885, 1867-1886, 1888-1914, 1888-1907, 1891-1914, 1895-1938, 1895-1935, 1919-1938, 1928-1956, 1957-1976, 2035-2057, 2083-2141, 2230-2261, 2278-2297, 2281-2300, 2284-2303, 2368-2397, 2368-2396, 2368-2394, 2368-2393, 2379-2394, 2381-2396, 2420-2439, 2458-2476, 2819-2838, 2873-2892, and 3161-3182.

In certain embodiments, the following nucleotide regions of SEQ ID NO: 1, when targeted by antisense compounds or oligonucleotides, display at least 75% inhibition: 13-32, 16-35, 19-38, 25-44, 28-47, 31-50, 43-62, 46-65, 49-68, 55-74, 58-82, 58-74, 58-77, 59-75, 60-75, 60-76, 61-77, 65-84, 98-117, 101-120, 104-123, 116-135, 119-138, 131-150, 137-156, 140-159, 143-162, 158-177, 161-180, 164-183, 167-186, 200-219, 203-226, 209-228, 218-237, 233-252, 236-255, 239-258, 242-264, 247-266, 251-266, 253-272, 255-276, 266-285, 269-288, 281-300, 284-303, 290-313, 298-317, 302-321, 324-343, 339-358, 342-361, 348-367, 358-381, 364-383, 366-386, 370-389, 373-392, 382-401, 405-424, 409-428, 411-430, 411-426, 411-427, 412-427, 412-431, 413-428, 413-429, 413-432, 414-436, 414-430, 414-429, 415-430, 416-431, 416-432, 417-433, 418-437, 422-441, 425-444, 428-447, 434-453, 440-459, 443-462, 446-465, 456-477, 458-473, 464-483, 470-493, 476-495, 479-498, 488-507, 491-510, 494-513, 500-519, 512-531, 515-534, 524-543, 527-546, 536-555, 539-558, 560-579, 566-585, 569-588, 572-591, 575-594, 584-603, 587-606, 608-627, 614-633, 617-636, 620-639, 623-642, 626-645, 629-648, 639-654, 641-656, 642-657, 643-658, 653-672, 665-684, 668-688, 670-706, 670-686, 670-685, 671-691, 671-687, 671-686, 672-688, 673-688, 679-703, 681-696, 682-697, 686-701, 686-706, 687-702, 687-703, 688-703, 689-708, 693-712, 695-714, 696-715, 697-716, 727-746, 739-754, 742-761, 748-767, 751-770, 754-773, 757-776, 760-779, 763-782, 766-785, 790-809, 793-812, 796-815, 811-830, 814-833, 817-836, 820-839, 822-844, 845-864, 854-873, 857-876, 863-882, 866-885, 872-891, 875-894, 878-897, 881-900, 884-903, 887-906, 899-918, 902-921, 905-924, 908-927, 911-930, 914-933, 936-955, 939-958, 951-970, 954-973, 957-976, 960-979, 963-982, 966-985, 969-988, 972-991, 975-994, 978-997, 996-1015, 1002-1021, 1025-1044, 1031-1050, 1034-1053, 1037-1056, 1046-1065, 1049-1068, 1052-1071, 1055-1074, 1058-1077, 1061-1080, 1064-1083, 1070-1089, 1073-1092, 1076-1095, 1082-1101, 1088-1107, 1094-1113, 1097-1116, 1100-1119, 1103-1122, 1106-1125, 1109-1128, 1112-1131, 1115-1134, 1121-1140, 1127-1146, 1153-1172, 1156-1175, 1159-1178, 1162-1181, 1165-1184, 1168-1191, 1174-1193, 1206-1225, 1209-1228, 1212-1231, 1215-1234, 1218-1237, 1221-1240, 1224-1243, 1227-1246, 1230-1249, 1233-1252, 1236-1255, 1239-

1258, 1242-1261, 1245-1264, 1251-1270, 1254-1273, 1254-1279, 1257-1283, 1257-1276, 1258-1277, 1260-1279, 1261-1285, 1261-1276, 1261-1277, 1261-1280, 1262-1277, 1262-1278, 1263-1278, 1263-1279, 1263-1282, 1264-1279, 1264-1280, 1264-1283, 1265-1281, 1265-1284, 1266-1281, 1266-1282, 1266-1285, 1267-1282, 1267-1283, 1268-1283, 1268-1284, 1268-1287, 1269-1284, 1269-1285, 1270-1285, 1272-1291, 1275-1294, 1282-1303, 1286-1306, 1290-1309, 1293-1312, 1296-1315, 1299-1318, 1305-1324, 1311-1330, 1314-1333, 1317-1336, 1353-1381, 1356-1375, 1359-1378, 1498-1517, 1501-1520, 1504-1523, 1510-1529, 1553-1572, 1556-1575, 1559-1578, 1562-1581, 1565-1584, 1571-1590, 1574-1599, 1577-1606, 1577-1592, 1577-1593, 1577-1596, 1578-1593, 1578-1594, 1578-1597, 1579-1594, 1579-1595, 1579-1598, 1580-1595, 1580-1596, 1581-1596, 1581-1597, 1581-1600, 1582-1597, 1582-1598, 1582-1601, 1582-1602, 1583-1598, 1583-1599, 1583-1602, 1584-1599, 1584-1600, 1584-1603, 1585-1600, 1585-1601, 1585-1604, 1586-1601, 1586-1605, 1586-1602, 1587-1602, 1587-1603, 1587-1606, 1588-1603, 1588-1604, 1589-1604, 1589-1605, 1590-1605, 1590-1606, 1591-1606, 1604-1623, 1607-1626, 1630-1649, 1633-1652, 1645-1664, 1651-1670, 1654-1674, 1657-1676, 1660-1679, 1663-1682, 1666-1685, 1689-1708, 1695-1714, 1698-1717, 1701-1720, 1716-1735, 1778-1797, 1778-1794, 1778-1797, 1779-1795, 1779-1798, 1780-1795, 1780-1796, 1780-1799, 1781-1800, 1794-1813, 1895-1914, 1898-1917, 1901-1920, 1907-1926, 1910-1929, 1913-1932, 1916-1935, 1919-1938, 2278-2297, 2281-2300, and 2284-2303.

In certain embodiments, the following nucleotide regions of SEQ ID NO: 1, when targeted by antisense compounds or oligonucleotides, display at least 80% inhibition: 13-32, 16-35, 19-38, 25-44, 28-47, 46-65, 49-68, 58-77, 59-80, 63-82, 98-120, 116-135, 137-159, 158-177, 167-186, 203-224, 205-224, 209-228, 218-237, 233-252, 236-263, 245-264, 253-272, 256-275, 257-276, 266-288, 281-300, 290-312, 293-312, 324-343, 339-358, 348-367, 358-378, 360-379, 361-383, 366-385, 373-392, 382-401, 405-424, 411-431, 411-426, 411-427, 411-430, 413-428, 414-433, 414-434, 415-430, 415-434, 416-431, 416-435, 417-436, 418-437, 422-441, 425-444, 434-453, 456-476, 458-473, 458-477, 464-483, 471-493, 488-507, 494-513, 512-531, 524-543, 527-546, 536-558, 560-579, 566-585, 572-591, 575-594, 584-603, 587-606, 608-627, 614-633, 617-636, 620-639, 623-642, 626-645, 629-648, 639-654, 641-656, 642-657, 643-658, 665-688, 670-687, 670-686, 671-686, 671-687, 671-691, 673-688, 679-699, 682-697, 682-706, 686-701, 687-702, 687-706, 687-703, 693-715, 727-746, 742-761, 748-767, 757-776, 766-785, 790-815, 814-833, 820-839, 822-844, 845-864, 854-873, 854-876, 863-885, 872-906, 878-897, 899-918, 905-933, 936-955, 951-979, 963-985, 966-985, 972-1015, 978-997, 1002-1021, 1025-1044, 1031-1056, 1049-1074, 1061-1083, 1070-1089, 1082-1101, 1088-11107, 1094-1119, 1109-1134, 1121-1140, 1127-1146, 1159-1187, 1171-1191, 1206-1228, 1209-1228, 1215-1255, 1215-1234, 1218-1237, 1221-1240, 1224-1243, 1227-1246, 1230-1249, 1233-1252, 1236-1255, 1245-1264, 1251-1279, 1251-1270, 1254-1273, 1254-1279, 1257-1276, 1258-1277, 1259-1278, 1260-1279, 1261-1285, 1261-1276, 1261-1277, 1261-1280, 1262-1277, 1262-1278, 1262-1281, 1263-1278, 1263-1282, 1264-1279, 1264-1283, 1265-1284, 1266-1285, 1267-1282, 1267-1283, 1268-1283, 1268-1284, 1269-1284, 1269-1285, 1269-1288, 1270-1285, 1275-1294, 1282-1301, 1286-1306, 1293-1318, 1311-1333, 1326-1345, 1359-1378, 1553-1578, 1565-1584, 1571-1590, 1574-1599, 1577-1592, 1577-1596, 1577-1593, 1577-1596, 1578-1593, 1578-1594, 1578-1597, 1579-1595, 1579-1598, 1580-1596, 1580-1599, 1581-1596, 1581-1597, 1581-1600, 1582-1597, 1582-1601, 1582-1602, 1583-1598, 1583-1599, 1583-1602, 1584-1599, 1584-1603, 1585-1601, 1585-1604, 1586-1605, 1587-1602, 1587-1606, 1588-1603, 1589-1604, 1589-1605, 1657-1679, 1780-1795, 1780-1796, 1780-1799, 1913-1935, 2278-2297, 2281-2300, and 2284-2303.

In certain embodiments, the following nucleotide regions of SEQ ID NO: 1, when targeted by antisense compounds or oligonucleotides, display at least 85% inhibition: 13-32, 16-35, 19-38, 25-44, 46-65, 59-80, 101-120, 140-159, 158-177, 167-186, 200-219, 205-224, 209-228, 233-252, 242-263, 253-272, 266-285, 281-300, 290-311, 293-312, 359-379, 361-381, 370-389, 382-401, 411-426, 411-430, 411-427, 413-428, 414-433, 415-430, 416-435, 417-436, 422-441, 456-476, 458-473, 470-493, 512-531, 524-543, 536-558, 566-585, 575-594, 587-606, 608-627, 614-636, 623-645, 639-654, 665-687, 671-686, 671-687, 680-699, 682-703, 687-706, 687-703, 727-746, 742-761, 757-776, 793-812, 822-843, 854-876, 854-873, 863-885, 878-900, 878-897, 887-906, 899-918, 905-927, 914-933, 936-955, 951-985, 966-985, 972-1015, 978-997, 1002-1021, 1025-1044, 1037-1056, 1049-1074, 1064-1083, 1070-1089, 1088-1107, 1094-1119, 1109-1128, 1121-1140, 1156-1175, 1162-1187, 1172-1191, 1206-1228, 1209-1228, 1215-1255, 1215-1234, 1218-1237, 1221-1240, 1224-1243, 1227-1246, 1230-1249, 1233-1252, 1236-1255, 1245-1264, 1251-1279, 1251-1270, 1254-1273, 1254-1279, 1257-1276, 1258-1277, 1259-1278, 1260-1279, 1261-1285, 1261-1276, 1261-1277, 1261-1280, 1262-1277, 1262-1278, 1262-1281, 1263-1278, 1263-1282, 1264-1279, 1264-1283, 1265-1284, 1266-1285, 1267-1282, 1267-1283, 1268-1284, 1269-1284, 1269-1285, 1269-1288, 1270-1285, 1275-1294, 1282-1301, 1293-1315, 1311-1330, 1359-1378, 1574-1593, 1577-1592, 1577-1593, 1577-1596, 1577-1606, 1578-1593, 1578-1594, 1578-1597, 1579-1598, 1580-1596, 1580-1599, 1581-1597, 1581-1600, 1582-1601, 1583-1598, 1583-1602, 1584-1603, 1585-1601, 1585-1604, 1586-1605, 1587-1602, 1588-1603, 1780-1799, 1780-1796, and 2278-2297, 2281-2300, and 2284-2303.

In certain embodiments, the following nucleotide regions of SEQ ID NO: 1, when targeted by antisense compounds or oligonucleotides, display at least 90% inhibition: 13-32, 16-35, 60-80, 140-159, 158-177, 167-186, 242-261, 292-311, 362-381, 370-389, 382-401, 411-427, 411-426, 413-428, 415-430, 416-435, 422-441, 473-492, 617-636, 623-642, 639-654, 668-687, 680-699, 682-701, 684-703, 687-706, 727-746, 757-776, 824-843, 854-873, 854-876, 863-882, 878-897, 878-900, 887-906, 899-918, 905-927, 914-933, 936-955, 951-970, 960-985, 966-985, 972-1015, 978-997, 1025-1044, 1037-1056, 1070-1089, 1097-1119, 1109-1128, 1121-1140, 1165-1187, 1172-1191, 1206-1228, 1209-1228, 1215-1234, 1215-1234, 1215-1255, 1218-1237, 1221-1240, 1224-1243, 1227-1246, 1230-1249, 1233-1252, 1236-1255, 1245-1264, 1251-1279, 1251-1270, 1254-1273, 1254-1279, 1257-1276, 1258-1277, 1259-1278, 1260-1279, 1261-1285, 1261-1280, 1262-1278, 1261-1276, 1262-1281, 1262-1277, 1263-1282, 1263-1278, 1264-1283, 1265-1284, 1266-1285, 1268-1284, 1269-1284, 1269-1285, 1269-1288, 1296-1315, 1577-1605, 1577-1596, 1577-1593, 1577-1592, 1578-1597, 1581-1600, 1582-1601, 1583-1602, 1583-1598, 1585-1601, 1585-1604, 1586-1605, 1588-1603, 1780-1799, 1780-1796, 2278-2297, 2281-2300, and 2284-2303.

In certain embodiments, the following nucleotide regions of SEQ ID NO: 1, when targeted by antisense compounds or oligonucleotides, display at least 95% inhibition: 411-426, 411-427, 413-428, 617-636, 623-642, 668-687, 680-699, 682-701, 854-873, 878-897, 887-906, 914-933, 966-985, 978-997, 1209-1228, 1215-1234, 1218-1237, 1221-1240, 1224-1243, 1227-1246, 1230-1249, 1233-1252, 1236-1255, 1245-1264, 1251-1270, 1254-1273, 1254-1279, 1257-1276, 1258-1277, 1259-1278, 1260-1279, 1261-1285, 1261-1280, 1262-1281, 1263-1282, 1263-1278, 1264-1283, 1265-1284, 1266-1285, 1268-1284, 1269-1288, 1577-1592, 1577-1596, 1577-1601, 1583-1598, 1585-1601, 1588-1603, 1780-1799, 2278-2297, 2281-2300, and 2284-2303.

In certain embodiments, the following antisense compounds or oligonucleotides target a region of a HBV nucleic acid and effect at least a 50% inhibition of a HBV mRNA, ISIS IDs: 510088, 510089, 510090, 510092, 510096, 510097, 510098, 510099, 510100, 510101, 510102, 505330, 509928, 510104, 509929, 510105, 509930, 510106, 510107, 510108, 510111, 510115, 509931, 510116, 510117, 510118, 510119, 510120, 510121, 509932, 510122, 509933, 510123, 509934, 510124, 509935, 510125, 510126, 510127, 510128, 510140, 146779, 505314, 505315, 505316, 505317, 146821, 505318, 509922, 505319, 509925, 505320, 509952, 505321, 505322, 505323, 505324, 505325, 505326, 505327, 505328, 505329, 509956, 509957, 509927, 509958, 510038, 505330, 509959, 510039, 509960, 510040, 509961, 510041, 509962, 509963, 505331, 505332, 509968, 509969, 510050, 510052, 505333, 505334, 505335, 505336, 509972, 146823, 509974, 505338, 505339, 509975, 505340, 509978, 505341, 509979, 510058, 505342, 509981, 510061, 505344, 505345, 509983, 505346, 509984, 505347, 505348, 505350, 505352, 505353, 505354, 505355, 505356, 146786, 505357, 505358, 505359, 505360, 509985, 509986, 509987, 509988, 505363, 505364, 505365, 505366, 146787, 510079, 524410, 524411, 524413, 524414, 524415, 524416, 524417, 524418, 524419, 524420, 524421, 524422, 524424, 524425, 524426, 524427, 524428, 524429, 524431, 524432, 524433, 524434, 524435, 524436, 524439, 524440, 524442, 524444, 524446, 524447, 524448, 524450, 524451, 524452, 524453, 524454, 524455, 524456, 524457, 524458, 524459, 524460, 524461, 524462, 524464, 524466, 524467, 524468, 524469, 524470, 524471, 524472, 524473, 524474, 524475, 524477, 524478, 524479, 524480, 524481, 524482, 524483, 524484, 524485, 524486, 524487, 524489, 524490, 524491, 524492, 524493, 524494, 524495, 524496, 524498, 524499, 524500, 524501, 524502, 524503, 524504, 524506, 524507, 524508, 524509, 524510, 524511, 524512, 524513, 524514, 524515, 524516, 524517, 524518, 524519, 524520, 524521, 524522, 524523, 524524, 524525, 524526, 524527, 524528, 524529, 524530, 524531, 524532, 524533, 524534, 524535, 524536, 524537, 524538, 524539, 524540, 524541, 524543, 524544, 524546, 524547, 524548, 524549, 524550, 524551, 524552, 524553, 524554, 524555, 524556, 524557, 524558, 524559, 524560, 524561, 524562, 524563, 524564, 524565, 524568, 524569, 524570, 524571, 524572, 524573, 524574, 524575, 524576, 524577, 524578, 524579, 524580, 524581, 524582, 524584, 524585, 524586, 524587, 524588, 524589, 524590, 524591, 524592, 524593, 524594, 524595, 524598, 524599, 524600, 524601, 524602, 524603, 524604, 524605, 524606, 524607, 524608, 524609, 524610, 524611, 524614, 524615, 524616, 524617, 524618, 524619, 524620, 524621, 524622, 524623, 524624, 524625, 524626, 524627, 524629, 524632, 524633, 524634, 524635, 524636, 524637, 524638, 524639, 524640, 524641, 524642, 524643, 524644, 524646, 524647, 524648, 524649, 524650, 524651, 524652, 524654, 524656, 524657, 524658, 524659, 524660, 524661, 524662, 524663, 524664, 524665, 524666, 524667, 524668, 524669, 524670, 524672, 524673, 524675, 524676, 524678, 524679, 524680, 524682, 524683, 524684, 524685, 524686, 524687, 524688, 524689, 524690, 524691, 524692, 524693, 524694, 524695, 524696, 524697, 524698, 524699, 524700, 524701, 524702, 524703, 524704, 524705, 524706, 524707, 524708, 524709, 524710, 524712, 524713, 524714, 524715, 524716, 524717, 524718, 524719, 524721, 524722, 524723, 524724, 524726, 524727, 524728, 524729, 524730, 524731, 524732, 524733, 524734, 524735, 524736, 524737, 524738, 524739, 524740, 524741, 524742, 524743, 524744, 524745, 524746, 524747, 524748, 524749, 524750, 524751, 524752, 524753, 524754, 524755, 524756, 524757, 524758, 524759, 524760, 524761, 524762, 524763, 524764, 524765, 524766, 524767, 524768, 524769, 524770, 524771, 524772, 524773, 524774, 524775, 524776, 524777, 524778, 524779, 524780, 524781, 524782, 524783, 524784, 524785, 524786, 524787, 524788, 524789, 524790, 524791, 524792, 524793, 524794, 524795, 524796, 524797, 524798, 524799, 524800, 524801, 524802, 524803, 524804, 524805, 524806, 524807, 524808, 524809, 524810, 524811, 524812, 524813, 524814, 524815, 524816, 524817, 524818, 524819, 524820, 524821, 524822, 524823, 524824, 524825, 524826, 524827, 524828, 524829, 524830, 524831, 524632, 524833, 524834, 524835, 524842, 524843, 524844, 524845, 524847, 524848, 524856, 524857, 524861, 524866, 524867, 524868, 524869, 524870, 524871, 524872, 524873, 524875, 524876, 524877, 524878, 524879, 524880, 524881, 524882, 524883, 524884, 524885, 524886, 524887, 524888, 524889, 524890, 524891, 524892, 524893, 524894, 524895, 524896, 524897, 524898, 524899, 524900, 524901, 524902, 524903, 524904, 524905, 524906, 524907, 524908, 524909, 524910, 524911, 524912, 524913, 524914, 524915, 524916, 524917, 524918, 524919, 524921, 524922, 524923, 524924, 524925, 524926, 524927, 524928, 524929, 524930, 524931, 524932, 524933, 524934, 524935, 524936, 524937, 524938, 524939, 524940, 524941, 524942, 524943, 524944, 524945, 524946, 524947, 524948, 524949, 524950, 524951, 524952, 524953, 524954, 524955, 524956, 524957, 524958, 524959, 524960, 524961, 524962, 524964, 524965, 524976, 524977, 524978, 524979, 524980, 524981, 524982, 524983, 524984, 524985, 524986, 524987, 524988, 524989, 524991, 524992, 524993, 524994, 524997, 524998, 525021, 525022, 525037, 525039, 525043, 525050, 525052, 525086, 525090, 525100, 551909, 551910, 551911, 551912, 551913, 551916, 551917, 551918, 551919, 551920, 551921, 551922, 551923, 551924, 551925, 551926, 551927, 551928, 551929, 551930, 551932, 551933, 551934, 551935, 551936, 551937, 551939, 551940, 551941, 551942, 551943, 551944, 551945, 551946, 551947, 551948, 551949, 551950, 551951, 551952, 551953, 551954, 551955, 551956, 551957, 551958, 551959, 551960, 551962, 551963, 551964, 551965, 551966, 551967, 551968, 551971, 551972, 551973, 551974, 551975, 551976, 551977, 551978, 551979, 551980, 551981, 551982, 551983, 551984, 551985, 551986, 551987, 551988, 551989, 551990, 551992, 551993, 551994, 551995, 551996, 551997, 551998, 551999, 552000, 552001, 552002, 552003, 552004, 552005, 552006, 552007, 552009, 552010, 552011, 552012, 552013, 552014, 552015, 552016, 552017, 552018, 552019, 552020, 552021, 552022, 552023, 552024, 552025, 552026, 552027, 552028, 552029, 552030, 552031, 552032, 552033, 552034, 552035, 552036, 552037, 552038, 552039, 552040, 552041, 552042, 552043, 552044, 552045, 552046, 552047, 552048, 552049, 552050, 552051, 552052, 552053, 552054, 552055, 552056, 552057, 552058, 552059, 552060, 552061, 552062, 552063, 552064, 552065, 552067, 552068, 552069, 552070, 552071, 552072, 552073, 552074, 552075, 552076, 552077, 552078, 552079, 552080, 552081, 552082, 552083, 552084, 552085, 552086, 552087, 552088, 552089, 552090, 552091, 552092, 552093, 552094, 552095, 552096, 552097, 552098, 552099, 552100, 552101, 552102, 552114, 552115, 552116, 552117, 552118, 552119, 552122, 552123, 552124, 552125, 552126, 552127, 552128, 552129, 552131, 552132, 552133, 552134, 552135, 552136, 552137, 552138, 552139, 552140, 552141, 552142, 552143, 552144, 552145, 552146, 552147, 552148, 552149, 552150, 552151, 552152, 552153, 552154, 552155, 552158, 552159, 552160, 552161, 552162, 552163, 552164, 552165, 552167, 552168, 552169, 552170, 552171, 552175, 552176, 552177, 552178, 552179, 552180, 552181, 552182, 552183, 552185, 552186, 552187, 552188, 552189, 552191, 552192, 552193, 552194, 552195, 552196, 552197, 552198, 552199, 552200, 552201, 552202, 552203, 552204, 552205, 552206, 552207, 552208, 552209, 552210, 552211, 552212, 552213, 552214, 552215, 552216, 552217, 552218, 552220, 552222, 552224, 552225, 552230, 552239, 552240, 552241, 552242, 552243, 552246, 552247, 552248, 552249, 552250, 552251, 552252, 552253, 552254, 552255, 552256, 552257, 552258, 552259, 552260, 552261, 552262, 552263, 552264, 552265, 552266, 552267, 552268, 552269, 552270, 552271, 552279, 552285, 552288, 552293, 552294, 552295, 552296, 552297, 552300, 552301, 552302, 552303, 552304, 552305, 552306, 552307, 552308, 552309, 552310, 552312, 552313, 552314, 552315, 552316, 552317, 552318, 552319, 552320, 552321, 552322, 552323, 552325, 552326, 552330, 552331, 552332, 552333, 552337, 552338, 552339, 552340, 552341, 552342, 552343, 552344, 552345, 552347, 552348, 552349, 552350, 552351, 552352, 552354, 552355, 552356, 552357, 552358, 552359, 552360, 552361, 552362, 552363, 552364, 552365, 552366, 552367, 552368, 552369, 552370, 552371, 552372, 552373, 552374, 552375, 552376, 552377, 552378, 552379, 552380, 552385, 552386, 552390, 552391, 552393, 552394, 552395, 552396, 552397, 552398, 552399, 552400, 552401, 552402, 552403, 552408, 552409, 552410, 552411, 552412, 552413, 552414, 552415, 552416, 552417, 552418, 552419, 552420, 552421, 552422, 552423, 552424, 552425, 552428, 552430, 5521131, 552432, 552433, 552440, 552442, 552443, 552444, 552445, 552446, 552447, 552448, 552449, 552450, 552452, 552453, 552455, 552456, 552458, 552459, 552464, 552465, 552466, 552467, 552468, 552469, 552470, 552471, 552472, 552473, 552474, 552475, 552476, 552477, 552478, 552479, 552480, 552481, 552482, 552484, 552485, 552486, 552487, 552488, 552490, 552491, 552493, 552497, 552499, 552500, 552501, 552502, 552503, 552504, 552505, 552506, 552508, 552509, 552510, 552511, 552512, 552513, 552514, 552515, 552516, 552517, 552520, 552521, 552522, 552523, 552525, 552526, 552527, 552528, 552529, 552530, 552531, 552532, 552533, 552534, 552535, 552538, 552539, 552540, 552541, 552542, 552544, 552547, 552548, 552553, 552554, 552555, 552557, 552558, 552559, 552561, 552562, 552565, 552566, 552567, 552568, 552569, 552570, 552571, 552572, 552576, 552577, 552578, 552579, 552580, 552581, 552582, 552583, 552584, 552585, 552586, 552587, 552588, 552589, 552590, 552591, 552592, 552594, 552595, 552596, 552597, 552598, 552600, 552606, 552608, 552787, 552788, 552789, 552790, 552791, 552794, 552795, 552796, 552797, 552798, 552799, 552800, 552801, 552802, 552803, 552804, 552805, 552806, 552807, 552808, 552809, 552810, 552811, 552812, 552813, 552814, 552815, 552816, 552817, 552818, 552819, 552820, 552821, 552822, 552823, 552824, 552825, 552826, 552827, 552828, 552829, 552830, 552831, 552832, 552833, 552834, 552835, 552836, 552837, 552838, 552839, 552840, 552841, 552842, 552843, 552844, 552845, 552846, 552847, 552848, 552849, 552850, 552851, 552852, 552853, 552854, 552855, 552856, 552857, 552858, 552859, 552860, 552861, 552862, 552863, 552864, 552865, 552866, 552868, 552870, 552871, 552872, 552876, 552889, 552890, 552891, 552892, 552893, 552894, 552895, 552896, 552898, 552899, 552901, 552902, 552903, 552904, 552905, 552907, 552908, 552909, 552910, 552911, 552912, 552913, 552914, 552915, 552916, 552917, 552918, 552919, 552922, 552923, 552925, 552926, 552927, 552928, 552929, 552930, 552931, 552932, 552933, 552934, 552935, 552936, 552937, 552938, 552939, 552940, 552941, 552942, 552943, 552944, 552945, 552946, 552947, 552948, 552950, 552951, 552953, 552954, 552955, 552956, 552957, 552958, 552959, 552960, 552961, 552965, 552966, 552969, 552970, 552971, 552972, 552973, 552974, 552975, 552976, 552977, 552979, 552980, 552981, 552982, 552983, 552984, 552987, 552988, 552989, 552990, 552991, 552992, 552993, 552994, 552995, 552996, 552997, 552998, 552999, 553000, 553001, 553002, 553003, 553004, 553005, 553006, 553007, 553008, 553009, 553010, 553011, 553012, 553014, 553015, 553016, 566828, 566829, 566830, 566831, 566832, 577120, 577121, 577122, 577123, 577124, 577125, 577126, 577127, 577128, 577129, 577130, 577131, 577132, 577133, 577134, 577135, 577136, 582665, and 582666.

In certain embodiments, the following antisense compounds or oligonucleotides target a region of a HBV nucleic acid and effect at least a 50% inhibition of a HBV mRNA, SEQ ID NOs: 5, 6, 7, 9, 10, 12, 13, 14, 15, 16, 17, 18, 19, 20, 21, 22, 23, 24, 25, 26, 27, 28, 29, 30, 33, 38, 39, 40, 41, 42, 43, 44, 45, 46, 47, 48, 49, 50, 51, 52, 53, 54, 55, 56, 74, 83, 85, 86, 87, 88, 89, 92, 96, 98, 99, 100, 102, 103, 104, 106, 108, 109, 111, 112, 115, 117, 121, 122, 123, 124, 125, 126, 127, 128, 136, 137, 139, 140, 142, 143, 144, 145, 146, 147, 148, 149, 150, 151, 153, 155, 157, 159, 161, 165, 166, 167, 168, 169, 171, 172, 173, 174, 175, 176, 177, 178, 179, 180, 181, 186, 187, 188, 189, 190, 191, 192, 193, 194, 197, 198, 199, 201, 203, 206, 207, 208, 209, 210, 211, 212, 213, 215, 217, 218, 220, 221, 222, 224, 225, 226, 227, 228, 230, 231, 232, 233, 234, 235, 236, 237, 240, 241, 242, 243, 244, 250, 283, 321, 322, 324, 325, 326, 327, 328, 329, 330, 331, 332, 333, 335, 336, 337, 338, 339, 340, 342, 343, 344, 345, 346, 347, 350, 351, 353, 355, 357, 358, 359, 361, 362, 363, 364, 365, 366, 367, 368, 369, 370, 371, 372, 373, 375, 376, 377, 378, 379, 380, 381, 382, 383, 384, 387, 388, 389, 390, 391, 392, 393, 394, 395, 396, 397, 399, 400, 401, 402, 403, 404, 405, 406, 408, 409, 410, 411, 412, 413, 414, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 453, 454, 456, 457, 458, 459, 460, 461, 462, 463, 464, 465, 466, 467, 468, 469, 470, 471, 473, 474, 475, 478, 479, 480, 481, 482, 483, 484, 485, 486, 487, 488, 489, 490, 491, 492, 494, 495, 496, 497, 498, 499, 500, 501, 502, 503, 504, 505, 508, 509, 510, 511, 512, 513, 514, 515, 516, 517, 518, 519, 520, 521, 524, 525, 526, 527, 528, 529, 530, 531, 532, 533, 534, 535, 536, 537, 539, 542, 543, 544, 545, 546, 547, 548, 549, 550, 551, 552, 553, 554, 555, 556, 557, 558, 559, 560, 561, 562, 564, 566, 567, 568, 569, 570, 571, 572, 573, 574, 575, 576, 577, 578, 579, 580, 582, 583, 585, 586, 588, 589, 590, 592, 593, 594, 595, 596, 597, 598, 599, 600, 601, 602, 603, 604, 605, 606, 607, 608, 609, 610, 611, 612, 613, 614, 615, 616, 617, 618, 619, 620, 622, 623, 624, 625, 626, 627, 628, 629, 631, 632, 633, 634, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 754, 755, 756, 757, 759, 760, 768, 769, 773, 777, 778, 779, 780, 781, 782, 783, 784, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 876, 877, 888, 889, 890, 891, 892, 893, 894, 895, 896, 897, 898, 899, 900, 901, 903, 904, 905, 906, 909, 910, 933, 934, 949, 951, 955, 962, 964, 998, 1002, 1013, 1052, 1267, 1271, 1272, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1364, 1365, 1366, 1367, 1368, 1369, 1370, 1371, 1372, 1375, and 1376.

In certain embodiments, the following antisense compounds or oligonucleotides target a region of a HBV nucleic acid and effect at least a 60% inhibition of a HBV mRNA, ISIS IDs: 510090, 510100, 510102, 505330, 509928, 510104, 509929, 510105, 509930, 510106, 510107, 510111, 509931, 510116, 510117, 510118, 510119, 510120, 510121, 509932, 510122, 509933, 510123, 509934, 510124, 509935, 510125, 510128, 146779, 505314, 505315, 505316, 505317, 146821, 505318, 505319, 505322, 505323, 505324, 505325, 505326, 505327, 505328, 505329, 509956, 509957, 509958, 505330, 509959, 510041, 505332, 509968, 505333, 505335, 146823, 509974, 505338, 505339, 509975, 505340, 505341, 509979, 505342, 509981, 505344, 505345, 509983, 505346, 509984, 505347, 505348, 505353, 505354, 505356, 146786, 505357, 505358, 505359, 505360, 509985, 509986, 505363, 505366, 524410, 524413, 524414, 524415, 524416, 524417, 524418, 524419, 524420, 524421, 524422, 524424, 524425, 524426, 524428, 524431, 524432, 524433, 524434, 524435, 524439, 524440, 524446, 524447, 524448, 524451, 524452, 524453, 524454, 524455, 524456, 524457, 524459, 524460, 524461, 524464, 524466, 524467, 524468, 524469, 524471, 524472, 524473, 524474, 524475, 524477, 524478, 524479, 524480, 524481, 524482, 524485, 524486, 524487, 524489, 524490, 524491, 524492, 524493, 524494, 524495, 524496, 524499, 524500, 524501, 524502, 524503, 524504, 524506, 524507, 524508, 524509, 524510, 524511, 524512, 524513, 524514, 524515, 524516, 524517, 524519, 524520, 524521, 524523, 524525, 524526, 524527, 524528, 524529, 524532, 524533, 524534, 524535, 524536, 524537, 524538, 524539, 524540, 524541, 524543, 524546, 524547, 524549, 524550, 524552, 524553, 524554, 524555, 524556, 524557, 524558, 524559, 524560, 524561, 524562, 524563, 524564, 524565, 524568, 524569, 524570, 524571, 524572, 524573, 524574, 524575, 524576, 524577, 524578, 524579, 524580, 524581, 524582, 524585, 524586, 524587, 524588, 524589, 524590, 524591, 524593, 524594, 524595, 524598, 524599, 524600, 524602, 524603, 524604, 524605, 524606, 524607, 524610, 524611, 524614, 524615, 524616, 524617, 524618, 524619, 524620, 524621, 524622, 524623, 524625, 524627, 524629, 524632, 524633, 524634, 524635, 524636, 524637, 524638, 524639, 524640, 524641, 524642, 524643, 524644, 524646, 524647, 524648, 524649, 524650, 524651, 524654, 524656, 524657, 524658, 524659, 524661, 524662, 524663, 524664, 524665, 524666, 524667, 524668, 524669, 524670, 524673, 524675, 524676, 524678, 524679, 524680, 524683, 524684, 524685, 524686, 524687, 524688, 524689, 524690, 524691, 524692, 524694, 524695, 524696, 524697, 524698, 524699, 524700, 524701, 524702, 524703, 524704, 524705, 524706, 524707, 524708, 524709, 524710, 524713, 524714, 524715, 524716, 524717, 524718, 524719, 524721, 524722, 524724, 524726, 524727, 524728, 524729, 524730, 524731, 524732, 524733, 524734, 524735, 524736, 524737, 524738, 524739, 524741, 524742, 524743, 524744, 524746, 524747, 524748, 524749, 524750, 524751, 524752, 524753, 524754, 524755, 524756, 524757, 524758, 524759, 524760, 524761, 524762, 524763, 524764, 524765, 524766, 524767, 524768, 524769, 524770, 524771, 524772, 524773, 524774, 524775, 524776, 524777, 524778, 524779, 524780, 524781, 524782, 524783, 524784, 524785, 524787, 524788, 524789, 524790, 524791, 524792, 524793, 524794, 524795, 524796, 524797, 524798, 524799, 524800, 524801, 524802, 524803, 524804, 524805, 524806, 524807, 524808, 524809, 524810, 524811, 524812, 524813, 524814, 524815, 524816, 524817, 524818, 524819, 524820, 524821, 524822, 524823, 524824, 524825, 524826, 524827, 524828, 524829, 524830, 524632, 524833, 524842, 524843, 524844, 524845, 524847, 524856, 524866, 524867, 524868, 524869, 524870, 524871, 524872, 524873, 524876, 524878, 524879, 524880, 524881, 524882, 524883, 524884, 524885, 524886, 524887, 524888, 524889, 524890, 524891, 524892, 524893, 524894, 524895, 524896, 524897, 524898, 524899, 524900, 524901, 524902, 524903, 524904, 524905, 524906, 524907, 524908, 524909, 524910, 524911, 524912, 524913, 524914, 524915, 524916, 524921, 524922, 524923, 524924, 524925, 524926, 524928, 524929, 524930, 524931, 524932, 524933, 524936, 524937, 524938, 524939, 524940, 524941, 524942, 524944, 524946, 524947, 524948, 524949, 524950, 524952, 524953, 524954, 524955, 524961, 524977, 524978, 524979, 524980, 524981, 524982, 524983, 524984, 524985, 524986, 524987, 524988, 524991, 524992, 524993, 524994, 525037, 525052, 551909, 551911, 551919, 551920, 551921, 551922, 551924, 551925, 551926, 551927, 551928, 551932, 551933, 551934, 551935, 551936, 551941, 551943, 551944, 551948, 551949, 551950, 551951, 551952, 551953, 551954, 551955, 551956, 551957, 551958, 551959, 551960, 551962, 551963, 551965, 551966, 551967, 551968, 551973, 551975, 551979, 551981, 551982, 551983, 551984, 551985, 551986, 551987, 551989, 551990, 551992, 551993, 551994, 551995, 551996, 551997, 551998, 551999, 552000, 552001, 552002, 552003, 552005, 552006, 552007, 552009, 552010, 552012, 552013, 552014, 552015, 552016, 552017, 552018, 552019, 552020, 552021, 552022, 552023, 552024, 552025, 552026, 552027, 552028, 552029, 552030, 552031, 552032, 552033, 552034, 552035, 552036, 552038, 552039, 552041, 552042, 552044, 552045, 552046, 552047, 552048, 552049, 552050, 552051, 552052, 552053, 552054, 552055, 552056, 552057, 552058, 552059, 552060, 552061, 552062, 552063, 552064, 552065, 552068, 552069, 552070, 552071, 552073, 552074, 552075, 552076, 552077, 552078, 552079, 552080, 552081, 552082, 552083, 552084, 552085, 552086, 552087, 552088, 552089, 552090, 552091, 552092, 552093, 552094, 552095, 552096, 552097, 552098, 552099, 552100, 552101, 552102, 552114, 552115, 552116, 552117, 552118, 552119, 552123, 552124, 552125, 552126, 552127, 552128, 552129, 552131, 552132, 552133, 552134, 552135, 552136, 552138, 552139, 552140, 552141, 552143, 552144, 552145, 552146, 552147, 552148, 552149, 552150, 552151, 552152, 552153, 552155, 552158, 552159, 552160, 552162, 552163, 552168, 552169, 552170, 552171, 552176, 552178, 552179, 552180, 552182, 552183, 552185, 552187, 552188, 552191, 552192, 552193, 552194, 552195, 552196, 552197, 552198, 552199, 552200, 552201, 552202, 552203, 552204, 552205, 552206, 552207, 552208, 552209, 552210, 552211, 552212, 552213, 552214, 552215, 552216, 552222, 552224, 552225, 552239, 552240, 552242, 552246, 552247, 552248, 552252, 552253, 552254, 552255, 552256, 552257, 552258, 552259, 552261, 552263, 552265, 552266, 552268, 552285, 552293, 552294, 552295, 552296, 552301, 552302, 552303, 552306, 552307, 552308, 552309, 552310, 552312, 552313, 552314, 552315, 552316, 552317, 552318, 552320, 552321, 552322, 552323, 552325, 552326, 552331, 552332, 552337, 552338, 552339, 552340, 552343, 552345, 552347, 552348, 552349, 552351, 552354, 552355, 552356, 552358, 552359, 552360, 552361, 552362, 552363, 552364, 552365, 552366, 552367, 552368, 552369, 552370, 552371, 552372, 552373, 552374, 552375, 552376, 552377, 552378, 552379, 552396, 552397, 552398, 552403, 552408, 552409, 552410, 552411, 552412, 552414, 552416, 552418, 552419, 552420, 552421, 552422, 552423, 552424, 552431, 552442, 552445, 552449, 552455, 552456, 552459, 552464, 552465, 552466, 552467, 552469, 552472, 552473, 552474, 552475, 552477, 552478, 552479, 552480, 552484, 552487, 552497, 552508, 552509, 552511, 552512, 552515, 552516, 552520, 552521, 552522, 552523, 552526, 552527, 552528, 552529, 552530, 552531, 552534, 552540, 552541, 552542, 552559, 552567, 552568, 552569, 552570, 552572, 552576, 552577, 552578, 552579, 552582, 552583, 552584, 552585, 552586, 552587, 552588, 552590, 552595, 552596, and 552597, 552788, 552789, 552790, 552791, 552796, 552800, 552801, 552803, 552804, 552805, 552806, 552807, 552808, 552809, 552811, 552812, 552813, 552814, 552815, 552816, 552817, 552818, 552819, 552820, 552821, 552822, 552823, 552824, 552826, 552827, 552828, 552829, 552830, 552831, 552832, 552833, 552834, 552835, 552836, 552837, 552838, 552839, 552841, 552842, 552843, 552844, 552845, 552846, 552847, 552848, 552849, 552850, 552851, 552852, 552853, 552854, 552855, 552856, 552857, 552858, 552859, 552860, 552861, 552862, 552863, 552864, 552865, 552866, 552872, 552891, 552892, 552893, 552894, 552902, 552903, 552904, 552905, 552907, 552908, 552909, 552910, 552911, 552912, 552913, 552914, 552915, 552916, 552917, 552918, 552922, 552923, 552925, 552927, 552928, 552929, 552930, 552931, 552932, 552933, 552934, 552935, 552936, 552937, 552938, 552939, 552940, 552941, 552942, 552943, 552944, 552945, 552946, 552951, 552955, 552956, 552957, 552958, 552960, 552961, 552966, 552969, 552971, 552972, 552973, 552974, 552975, 552976, 552977, 552979, 552980, 552981, 552982, 552983, 552984, 552988, 552989, 552990, 552991, 552992, 552993, 552994, 552995, 552996, 552998, 552999, 553000, 553001, 553002, 553003, 553004, 553005, 553006, 553007, 553008, 553009, 553010, 553011, 553012, 553016, 566828, 566829, 566830, 566831, 566832, 577120, 577121, 577122, 577123, 577124, 577125, 577126, 577127, 577128, 577129, 577130, 577131, 577132, 577133, 577134, 577135, 577136, and 582666.

In certain embodiments, the following antisense compounds or oligonucleotides target a region of a HBV nucleic acid and effect at least a 60% inhibition of a HBV mRNA, SEQ ID NOs: 7, 9, 10, 12, 17, 18, 19, 20, 21, 22, 23, 24, 25, 26, 27, 28, 29, 33, 39, 40, 41, 42, 43, 44, 45, 46, 47, 48, 49, 50, 51, 52, 53, 56, 83, 85, 86, 87, 88, 89, 92, 96, 98, 100, 102, 103, 112, 115, 117, 122, 123, 124, 125, 126, 127, 128, 136, 137, 139, 140, 142, 143, 145, 147, 149, 150, 151, 153, 155, 157, 159, 161, 166, 167, 168, 172, 174, 176, 177, 178, 179, 180, 181, 186, 187, 188, 189, 190, 191, 192, 193, 194, 198, 199, 201, 206, 207, 208, 209, 210, 211, 212, 213, 218, 220, 222, 224, 225, 226, 227, 228, 230, 231, 232, 233, 234, 240, 243, 321, 324, 325, 326, 327, 328, 329, 330, 331, 332, 333, 335, 336, 337, 339, 342, 343, 344, 345, 346, 350, 351, 357, 358, 359, 362, 363, 364, 365, 366, 367, 368, 370, 371, 372, 375, 376, 377, 378, 379, 381, 382, 383, 384, 387, 388, 389, 390, 391, 392, 395, 396, 397, 399, 400, 401, 402, 403, 404, 405, 406, 409, 410, 411, 412, 413, 414, 416, 417, 418, 419, 420, 421, 422, 423, 424, 425, 426, 427, 429, 430, 431, 433, 435, 436, 437, 438, 439, 442, 443, 444, 445, 446, 447, 448, 449, 450, 451, 453, 456, 457, 459, 460, 462, 463, 464, 465, 466, 467, 468, 469, 470, 471, 473, 474, 475, 478, 479, 480, 481, 482, 483, 484, 485, 486, 487, 488, 489, 490, 491, 492, 495, 496, 497, 498, 499, 500, 501, 503, 504, 505, 508, 509, 510, 512, 513, 514, 515, 516, 517, 520, 521, 524, 525, 526, 527, 528, 529, 530, 531, 532, 533, 535, 537, 539, 542, 543, 544, 545, 546, 547, 548, 549, 550, 551, 552, 553, 554, 555, 556, 557, 558, 559, 560, 561, 564, 566, 567, 568, 569, 571, 572, 573, 574, 575, 576, 577, 578, 579, 580, 583, 585, 586, 588, 589, 590, 593, 594, 595, 596, 597, 598, 599, 600, 601, 602, 604, 605, 606, 607, 608, 609, 610, 611, 612, 613, 614, 615, 616, 617, 618, 619, 620, 623, 624, 625, 626, 627, 628, 629, 631, 632, 634, 636, 637, 638, 639, 640, 641, 642, 643, 644, 645, 646, 647, 648, 649, 650, 652, 653, 654, 655, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 740, 741, 742, 744, 745, 754, 755, 756, 757, 759, 768, 777, 778, 779, 780, 781, 782, 783, 784, 787, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 833, 834, 835, 836, 837, 838, 840, 841, 842, 843, 844, 845, 848, 849, 850, 851, 852, 853, 854, 856, 858, 859, 860, 861, 862, 864, 865, 866, 867, 873, 889, 890, 891, 892, 893, 894, 895, 896, 897, 898, 899, 900, 903, 904, 905, 906, 949, 964, 1271, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1365, 1366, 1367, 1368, 1369, 1370, 1371, 1372, and 1376.

In certain embodiments, the following antisense compounds or oligonucleotides target a region of a HBV nucleic acid and effect at least a 70% inhibition of a HBV mRNA, ISIS IDs: 510100, 505330, 509928, 509929, 509930, 510106, 509931, 510116, 510119, 510120, 510121, 509932, 510122, 509933, 510123, 509934, 510124, 509935, 146779, 505317, 146821, 505318, 505319, 505323, 505325, 505326, 505327, 509957, 505330, 505332, 505335, 509974, 505338, 505339, 509975, 505342, 509981, 505345, 505346, 505347, 505348, 146786, 505357, 505358, 505359, 505363, 524410, 524413, 524414, 524415, 524416, 524418, 524419, 524420, 524421, 524424, 524425, 524426, 524428, 524431, 524432, 524433, 524434, 524435, 524446, 524447, 524448, 524452, 524453, 524457, 524459, 524460, 524461, 524464, 524466, 524467, 524468, 524469, 524472, 524473, 524474, 524475, 524477, 524478, 524479, 524480, 524481, 524482, 524485, 524487, 524490, 524491, 524492, 524493, 524494, 524495, 524499, 524500, 524502, 524503, 524507, 524508, 524510, 524511, 524512, 524513, 524514, 524515, 524516, 524517, 524520, 524525, 524526, 524528, 524532, 524533, 524534, 524535, 524536, 524537, 524538, 524539, 524540, 524541, 524547, 524549, 524552, 524553, 524554, 524555, 524556, 524557, 524558, 524559, 524560, 524561, 524563, 524564, 524565, 524568, 524569, 524570, 524571, 524572, 524573, 524574, 524575, 524577, 524578, 524579, 524580, 524582, 524586, 524587, 524590, 524591, 524594, 524595, 524598, 524600, 524602, 524603, 524604, 524605, 524606, 524607, 524610, 524611, 524614, 524615, 524616, 524617, 524618, 524619, 524620, 524621, 524629, 524633, 524634, 524635, 524636, 524637, 524638, 524641, 524642, 524643, 524644, 524646, 524647, 524648, 524649, 524650, 524651, 524656, 524657, 524659, 524661, 524662, 524663, 524664, 524665, 524666, 524667, 524668, 524669, 524670, 524678, 524679, 524680, 524685, 524686, 524687, 524688, 524689, 524690, 524691, 524692, 524695, 524696, 524698, 524699, 524700, 524701, 524702, 524703, 524704, 524705, 524706, 524707, 524708, 524709, 524713, 524714, 524715, 524716, 524717, 524718, 524721, 524722, 524724, 524726, 524727, 524728, 524729, 524730, 524731, 524732, 524733, 524734, 524735, 524736, 524737, 524738, 524739, 524741, 524742, 524743, 524746, 524747, 524748, 524749, 524750, 524751, 524752, 524754, 524755, 524756, 524758, 524760, 524761, 524762, 524763, 524764, 524765, 524766, 524767, 524768, 524769, 524771, 524773, 524775, 524776, 524777, 524778, 524779, 524780, 524781, 524782, 524783, 524784, 524785, 524787, 524788, 524789, 524790, 524791, 524792, 524793, 524794, 524795, 524796, 524797, 524798, 524799, 524800, 524801, 524802, 524803, 524804, 524805, 524806, 524807, 524808, 524809, 524810, 524811, 524812, 524813, 524814, 524815, 524816, 524817, 524818, 524819, 524821, 524822, 524823, 524824, 524825, 524826, 524827, 524828, 524829, 524830, 524833, 524842, 524843, 524844, 524845, 524856, 524866, 524867, 524868, 524869, 524870, 524871, 524873, 524879, 524880, 524881, 524882, 524883, 524884, 524885, 524886, 524887, 524888, 524889, 524890, 524891, 524892, 524893, 524894, 524895, 524896, 524897, 524898, 524899, 524900, 524902, 524903, 524905, 524906, 524907, 524908, 524909, 524910, 524911, 524912, 524913, 524914, 524915, 524916, 524921, 524922, 524930, 524931, 524932, 524937, 524940, 524942, 524948, 524980, 524981, 524982, 524983, 524984, 524985, 524986, 524987, 524988, 551919, 551921, 551922, 551924, 551925, 551926, 551933, 551941, 551950, 551951, 551952, 551953, 551955, 551956, 551957, 551958, 551966, 551983, 551984, 551985, 551986, 551987, 551989, 551990, 551992, 551993, 551994, 551995, 551996, 551997, 551998, 551999, 552000, 552005, 552006, 552009, 552012, 552013, 552014, 552015, 552017, 552018, 552019, 552020, 552021, 552022, 552023, 552024, 552025, 552026, 552027, 552028, 552029, 552030, 552031, 552032, 552033, 552034, 552038, 552039, 552041, 552044, 552046, 552047, 552049, 552050, 552051, 552052, 552053, 552054, 552055, 552056, 552057, 552058, 552059, 552060, 552061, 552062, 552063, 552064, 552065, 552068, 552069, 552070, 552071, 552073, 552074, 552075, 552076, 552077, 552078, 552079, 552080, 552081, 552082, 552083, 552084, 552085, 552086, 552087, 552088, 552089, 552090, 552091, 552092, 552093, 552094, 552095, 552096, 552097, 552098, 552099, 552100, 552101, 552115, 552117, 552123, 552125, 552127, 552128, 552129, 552132, 552133, 552138, 552139, 552140, 552141, 552143, 552144, 552145, 552146, 552147, 552148, 552149, 552150, 552151, 552152, 552158, 552159, 552160, 552163, 552168, 552179, 552187, 552188, 552192, 552193, 552195, 552199, 552200, 552201, 552202, 552203, 552204, 552205, 552206, 552207, 552208, 552210, 552211, 552213, 552214, 552222, 552246, 552247, 552248, 552253, 552254, 552255, 552258, 552294, 552301, 552302, 552306, 552307, 552308, 552309, 552310, 552312, 552314, 552315, 552317, 552318, 552321, 552322, 552323, 552325, 552332, 552337, 552339, 552347, 552348, 552349, 552354, 552355, 552358, 552359, 552360, 552361, 552362, 552363, 552364, 552365, 552366, 552367, 552368, 552369, 552371, 552373, 552374, 552375, 552376, 552377, 552378, 552379, 552403, 552408, 552409, 552411, 552418, 552419, 552420, 552424, 552442, 552464, 552465, 552466, 552467, 552472, 552474, 552475, 552477, 552478, 552521, 552522, 552523, 552527, 552528, 552529, 552530, 552534, 552567, 552578, 552579, 552584, 552586, 552587, 552588, 552590, 552789, 552803, 552804, 552805, 552808, 552816, 552817, 552818, 552819, 552820, 552821, 552822, 552823, 552824, 552828, 552829, 552830, 552833, 552834, 552835, 552842, 552843, 552844, 552846, 552848, 552849, 552850, 552851, 552852, 552853, 552854, 552855, 552856, 552857, 552858, 552859, 552860, 552861, 552863, 552864, 552865, 552872, 552894, 552903, 552904, 552907, 552909, 552910, 552911, 552913, 552914, 552915, 552916, 552917, 552918, 552922, 552923, 552925, 552927, 552928, 552929, 552930, 552931, 552932, 552933, 552934, 552935, 552936, 552937, 552938, 552939, 552940, 552941, 552942, 552943, 552944, 552945, 552946, 552957, 552961, 552966, 552969, 552971, 552972, 552974, 552976, 552979, 552980, 552981, 552983, 552984, 552988, 552989, 552990, 552991, 552995, 552996, 552998, 552999, 553001, 553002, 553003, 553004, 553006, 553008, 553009, 553010, 553011, 553012, 566828, 566829, 566830, 566831, 566832, 577120, 577121, 577122, 577123, 577124, 577125, 577126, 577127, 577128, 577129, 577130, 577131, 577132, 577133, 577134, 577135, 577136, and 582666.

In certain embodiments, the following antisense compounds or oligonucleotides target a region of a HBV nucleic acid and effect at least a 70% inhibition of a HBV mRNA, SEQ ID NOs: 12, 17, 18, 20, 21, 22, 24, 25, 26, 27, 28, 29, 39, 40, 43, 44, 45, 46, 47, 48, 49, 50, 51, 52, 83, 89, 92, 96, 98, 100, 103, 112, 123, 125, 126, 127, 136, 137, 139, 140, 142, 143, 145, 147, 149, 151, 153, 166, 167, 168, 174, 176, 177, 178, 179, 181, 186, 187, 188, 190, 198, 201, 207, 209, 210, 211, 212, 213, 224, 225, 226, 227, 232, 234, 240, 321, 324, 325, 326, 327, 329, 330, 331, 332, 335, 336, 337, 339, 342, 343, 344, 345, 346, 357, 358, 359, 363, 364, 368, 370, 371, 372, 375, 376, 377, 378, 379, 382, 383, 384, 387, 388, 389, 390, 391, 392, 395, 397, 400, 401, 402, 403, 404, 405, 409, 410, 412, 413, 417, 418, 420 421, 422, 423, 424, 425, 426, 427, 430, 435, 436, 438, 442, 443, 444, 445, 446, 447, 448, 449, 450, 451, 457, 459, 462, 463, 464, 465, 466, 467, 468, 469, 470, 473, 474, 475, 478, 479, 480, 481, 482, 483, 484, 485, 487, 488, 489, 490, 492, 496, 497, 500, 501, 504, 505, 508, 510, 512, 513, 514, 515, 516, 517, 520, 521, 524, 525, 526, 527, 528, 529, 530, 531, 539, 543, 544, 545, 546, 547, 548, 551, 552, 553, 554, 555, 556, 557, 558, 559, 560, 561, 566, 567, 569, 571, 572, 573, 574, 575, 576, 577, 578, 579, 580, 588, 589, 590, 595, 596, 597, 598, 599, 600, 601, 602, 605, 606, 608, 609, 610, 611, 612, 613, 614, 615, 616, 617, 618, 619, 623, 624, 625, 626, 627, 628, 631, 632, 634, 636, 637, 638, 639, 640, 641, 642, 643, 644, 645, 646, 647, 648, 649, 650, 652, 653, 654, 657, 658, 659, 660, 661, 662, 663, 665, 666, 667, 669, 671, 672, 673, 674, 675, 676, 677, 678, 679, 680, 682, 684, 686, 687, 688, 689, 690, 691, 692, 693, 694, 695, 696, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 733, 734, 735, 736, 737, 738, 740, 741, 742, 745, 754, 755, 756, 757, 768, 777, 778, 779, 780, 781, 782, 784, 790, 791, 792, 793, 794, 795, 796, 797, 798, 799, 800, 801, 802, 803, 804, 805, 806, 807, 808, 809, 810, 811, 812, 814, 815, 817, 818, 819, 820, 821, 822, 823, 824, 825, 826, 827, 828, 833, 834, 842, 843, 844, 849, 852, 854, 860, 892, 893, 894, 895, 896, 897, 898, 899, 900, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1320, 1322, 1323, 1324, 1325, 1326, 1327, 1329, 1330, 1331, 1332, 1333, 1334, 1335, 1336, 1337, 1338, 1340, 1341, 1342, 1343, 1344, 1345, 1346, 1347, 1348, 1349, and 1350, 1367, 1368, 1369, 1370, 1372, and 1376.

In certain embodiments, the following antisense compounds or oligonucleotides target a region of a HBV nucleic acid and effect at least a 80% inhibition of a HBV mRNA, ISIS IDs: 510100, 509931, 510116, 505317, 505319, 505323, 505326, 505327, 505330, 505339, 505346, 505347, 505358, 509934, 146786, 524414, 524415, 524416, 524418, 524419, 524425, 524426, 524431, 524432, 524434, 524446, 524447, 524452, 524459, 524460, 524466, 524469, 524475, 524477, 524478, 524479, 524482, 524485, 524490, 524491, 524492, 524493, 524494, 524495, 524499, 524502, 524503, 524507, 524510, 524511, 524512, 524520, 524525, 524528, 524532, 524533, 524534, 524535, 524536, 524540, 524541, 524547, 524552, 524553, 524556, 524561, 524564, 524565, 524568, 524570, 524571, 524572, 524573, 524578, 524580, 524586, 524590, 524591, 524594, 524595, 524602, 524604, 524606, 524607, 524610, 524611, 524614, 524616, 524617, 524618, 524619, 524620, 524621, 524633, 524634, 524635, 524636, 524637, 524641, 524643, 524644, 524646, 524649, 524650, 524651, 524657, 524662, 524664, 524667, 524670, 524678, 524679, 524680, 524686, 524688, 524690, 524691, 524692, 524695, 524698, 524699, 524701, 524702, 524704, 524705, 524706, 524707, 524708, 524709, 524713, 524715, 524716, 524717, 524718, 524721, 524726, 524727, 524728, 524729, 524730, 524731, 524733, 524734, 524735, 524737, 524739, 524741, 524742, 524743, 524747, 524748, 524749, 524751, 524752, 524754, 524758, 524760, 524762, 524763, 524764, 524767, 524768, 524769, 524771, 524773, 524777, 524778, 524779, 524780, 524781, 524783, 524784, 524788, 524789, 524791, 524792, 524793, 524794, 524795, 524796, 524797, 524798, 524801, 524803, 524804, 524805, 524806, 524807, 524808, 524809, 524810, 524811, 524813, 524816, 524819, 524822, 524823, 524824, 524827, 524828, 524829, 524833, 524842, 524844, 524880, 524881, 524882, 524884, 524886, 524887, 524888, 524889, 524890, 524891, 524893, 524907, 524908, 524980, 524986, 524987, 551921, 551924, 551925, 551953, 551956, 551957, 551984, 551986, 551987, 551989, 551990, 551993, 551994, 551995, 551996, 551997, 551998, 551999, 552000, 552005, 552006, 552018, 552019, 552020, 552021, 552022, 552023, 552024, 552025, 552026, 552027, 552028, 552029, 552030, 552031, 552032, 552033, 552034, 552039, 552044, 552046, 552050, 552051, 552052, 552053, 552054, 552055, 552056, 552057, 552058, 552059, 552060, 552061, 552062, 552063, 552064, 552065, 552073, 552077, 552078, 552079, 552080, 552082, 552083, 552084, 552085, 552086, 552087, 552088, 552089, 552090, 552091, 552092, 552093, 552094, 552095, 552096, 552097, 552098, 552138, 552139, 552145, 552146, 552147, 552149, 552192, 552193, 552199, 552200, 552201, 552207, 552246, 552247, 552253, 552301, 552307, 552308, 552310, 552317, 552347, 552348, 552354, 552355, 552360, 552361, 552362, 552363, 552364, 552365, 552366, 552367, 552371, 552375, 552464, 552465, 552521, 552808, 552816, 552817, 552818, 552819, 552820, 552822, 552824, 552834, 552844, 552849, 552850, 552851, 552852, 552853, 552854, 552916, 552922, 552923, 552925, 552930, 552931, 552932, 552933, 552936, 552937, 552938, 552939, 552942, 552943, 552944, 552980, 552988, 552989, 552996, 552998, 553002, 553003, 566828, 566829, 566830, 566831, 566832, 577120, 577121, 577122, 577123, 577124, 577125, 577126, 577127, 577128, 577130, 577131, 577132, 577133, 577134, 577135, 577136, and 582666.

In certain embodiments, the following antisense compounds or oligonucleotides target a region of a HBV nucleic acid and effect at least a 80% inhibition of a HBV mRNA, SEQ ID NOs: 17, 20, 22, 24, 26, 28, 39, 40, 50, 51, 83, 89, 103, 123, 126, 127, 136, 137, 143, 147, 149, 168, 176, 177, 178, 179, 187, 188, 210, 211, 212, 224, 225, 226, 227, 232, 325, 326, 327, 329, 330, 336, 337, 342, 343, 345, 357, 358, 363, 370, 371, 376, 379, 387, 388, 389, 392, 395, 400, 401, 402, 403, 404, 405, 409, 412, 413, 417, 420 421, 422, 430, 435, 438, 442, 443, 444, 445, 446, 450, 451, 457, 462, 463, 466, 474, 475, 478, 480, 481, 482, 483, 488, 490, 496, 500, 501, 504, 505, 512, 514, 516, 517, 520, 521, 524, 526, 527, 528, 529, 530, 531, 543, 544, 545, 546, 547, 551, 553, 554, 555, 559, 560, 561, 567, 572, 574, 577, 580, 588, 589, 590, 596, 598, 600, 601, 602, 605, 608, 609, 611, 612, 614, 615, 616, 617, 618, 619, 623, 625, 626, 627, 628, 631, 636, 637, 638, 639, 640, 641, 643, 644, 645, 646, 648, 650, 652, 653, 654, 658, 659, 660, 662, 663, 665, 669, 671, 673, 674, 675, 678, 679, 680, 682, 684, 688, 689, 690, 691, 692, 694, 695, 699, 700, 702, 703, 704, 705, 706, 707, 708, 709, 712, 714, 715, 716, 717, 718, 719, 720, 721, 722, 723, 725, 728, 731, 734, 735, 736, 740, 741, 745, 756, 791, 792, 793, 795, 797, 798, 799, 800, 801, 802, 804, 805, 806, 807, 819, 820, 892, 898, 899, 1292, 1293, 1295, 1296, 1301, 1302, 1303, 1304, 1305, 1306, 1307, 1308, 1310, 1312, 1316, 1322, 1324, 1325, 1326, 1327, 1330, 1331, 1332, 1333, 1334, 1335, 1338, 1339, 1340, 1341, 1344, 1345, 1349, 1350, 1368, 1372, and 1376.

In certain embodiments, the following antisense compounds or oligonucleotides target a region of a HBV nucleic acid and effect at least a 90% inhibition of a HBV mRNA, ISIS IDs: 524414, 524415, 524432, 524460, 524466, 524469, 524475, 524477, 524493, 524512, 524535, 524540, 524552, 524561, 524572, 524617, 524619, 524634, 524641, 524644, 524657, 524667, 524691, 524698, 524699, 524701, 524706, 524707, 524709, 524713, 524715, 524716, 524718, 524721, 524726, 524729, 524730, 524731, 524733, 524734, 524735, 524739, 524743, 524754, 524763, 524764, 524767, 524771, 524780, 524781, 524784, 524788, 524789, 524791, 524792, 524793, 524794, 524795, 524796, 524797, 524798, 524801, 524803, 524804, 524805, 524806, 524807, 524808, 524809, 524810, 524811, 524822, 524827, 524842, 551986, 551987, 551989, 552005, 552018, 552019, 552020, 552021, 552022, 552023, 552025, 552046, 552050, 552051, 552052, 552053, 552054, 552055, 552057, 552082, 552083, 552084, 552085, 552086, 552087, 552088, 552089, 552092, 552093, 552096, 552097, 552307, 552317, 552355, 552361, 552362, 552363, 552817, 552851, 552922, 552923, 566828, 566829, 566830, 566831, 566832, 577120, 577121, 577122, 577123, 577124, 577125, 577126, 577127, 577128, 577130, 577131, 577132, 577134, 577135, 577136, and 582666.

In certain embodiments, the following antisense compounds or oligonucleotides target a region of a HBV nucleic acid and effect at least a 90% inhibition of a HBV mRNA, SEQ ID NOs: 17, 24, 50, 51, 137, 143, 147, 176, 211, 212, 224, 226, 227, 325, 326, 343, 371, 376, 379, 403, 422, 445, 450, 462, 482, 527, 529, 544, 551, 554, 567, 577, 601, 608, 609, 611, 616, 617, 619, 623, 625, 626, 628, 631, 636, 639, 640, 641, 643, 644, 645, 646, 650, 654, 665, 674, 675, 678, 682, 691, 692, 695, 699, 700, 702, 703, 704, 705, 706, 707, 708, 709, 712, 714, 715, 716, 717, 718, 719, 720, 721, 722, 723, 735, 801, 804, 805, 807, 1296, 1302, 1303, 1304, 1312, 1325, 1326, 1332, 1334, 1340, 1345, 1349, and 1376.

In certain embodiments, the following antisense compounds or oligonucleotides target a region of a HBV nucleic acid and effect at least a 95% inhibition of a HBV mRNA, ISIS IDs: 524619, 524634, 524641, 505339, 524698, 524709, 524718, 524731, 524734, 524789, 524791, 524792, 524793, 524794, 524795, 524796, 524797, 524798, 524801, 524803, 524804, 524805, 524806, 505346, 146785, 524807, 505347, 524808, 524809, 524810, 524811, 146786, 525101, 525102, 525103, 525107, 525108, 525109, 525110, 525111, 525112, 525113, 525114, 525115, 525116, 525117, 525118, 525119, 525120, 552018, 552050, 552019, 552051, 552020, 552052, 551987, 552021, 552053, 552005, 552022, 552054, 551989, 552023, 552055, 552084, 552085, 552086, 552087, 552088, 552361, 552317, 566831, 577123, 577124, 566830, 566828, 566829, 577127, 577135, 577132, 577136, 566832, and 577122.

In certain embodiments, the following antisense compounds or oligonucleotides target a region of a HBV nucleic acid and effect at least a 95% inhibition of a HBV mRNA, SEQ ID NOs: 17, 50, 137, 143, 187, 210, 212, 224, 529, 544, 551, 608, 619, 628, 641, 645, 700, 702, 703, 704, 705, 706, 707, 708, 709, 712, 715, 716, 717, 718, 719, 720, 721, 722, 723, 1014, 1015, 1016, 1020, 1021, 1022, 1023, 1024, 1025, 1026, 1027, 1028, 1029, 1030, 1031, 1032, 1033, 1236, 1302, 1312, 1334, 1340, 1345, 1349.

Certain embodiments provide methods of treating HBV related disease, disorder, or condition in an animal, comprising administering to an animal in need thereof a compound or composition described herein. In certain embodiments, the compound or composition comprises a modified oligonucleotide consisting of 10 to 30 linked nucleosides and having a nucleobase sequence comprising at least 10 contiguous nucleobases of any of the nucleobase sequences of SEQ ID NOs: 5-310, 321-802, 804-1272, 1288-1350, 1364-1372, 1375, 1376, and 1379.

Certain embodiments provide methods of treating HBV related disease, disorder, or condition in an animal, comprising administering to an animal in need thereof a compound or composition described herein. In certain embodiments, the compound or composition comprises a modified oligonucleotide consisting of 10 to 30 linked nucleosides and having a nucleobase sequence comprising at least 10 contiguous nucleobases of any of the nucleobase sequences of SEQ ID NOs: 17, 51, 86, 93, 95, 98, 100, 102, 104, 106, 109, 112, 115, 117, 137, 140, 143, 145, 147, 149, 151, 153, 155, 157, 159, 161, 167, 168, 176, 177-179, 181, 188, 190-192, 194, 199, 201, 208, 209, 211, 226, 230-237, 244, 245, 247, 252, 254, 256, 258, 260, 262, 264, 266, 271, 1318-1347, 1364-1372, 1375, 1376, and 1379, wherein at least one nucleoside of the modified oligonucleotide comprises at least one 2'-O-methoxyethyl sugar and/or constrained ethyl (cEt) sugar. In certain embodiments, the modified oligonucleotide is 16 nucleosides in length and has a gap segment of 10 linked nucleosides. In certain embodiments, the modified oligonucleotide has a wing segment on the 5' end and 3' end of the gap each independently having 2, 3, or 4 sugar modified nucleosides.

Certain embodiments provide a method of reducing HBV expression in an animal comprising administering to the animal a compound or composition described herein. In certain embodiments, the compound or composition comprises a modified oligonucleotide 10 to 30 linked nucleosides in length targeted to HBV and having a nucleobase sequence comprising at least 10 contiguous nucleobases of any of the nucleobase sequences of SEQ ID NOs: 5-310, 321-802, 804-1272, 1288-1350, 1364-1372, 1375, 1376, and 1379.

Certain embodiments provide a method of reducing HBV expression in an animal comprising administering to the animal a compound or composition described herein. In certain embodiments, the compound or composition comprises a modified oligonucleotide 10 to 30 linked nucleosides in length targeted to HBV and having a nucleobase sequence comprising at least 10 contiguous nucleobases of any of the nucleobase sequences of SEQ ID NOs: 17, 51, 86, 93, 95, 98, 100, 102, 104, 106, 109, 112, 115, 117, 137, 140, 143, 145, 147, 149, 151, 153, 155, 157, 159, 161, 167, 168, 176, 177-179, 181, 188, 190-192, 194, 199, 201, 208, 209, 211, 226, 230-237, 244, 245, 247, 252, 254, 256, 258, 260, 262, 264, 266, 271, 1318-1347, 1364-1372, 1375, and 1376, wherein at least one nucleoside of the modified oligonucleotide comprises at least one 2'-O-methoxyethyl sugar and/or constrained ethyl (cEt) sugar. In certain embodiments, the modified oligonucleotide is 16 nucleosides in length and has a gap segment of 9 or 10 linked nucleosides. In certain embodiments, the modified oligonucleotide has a wing segment on the 5' end and 3' end of the gap each independently having 2, 3, 4, or 5 sugar modified nucleosides.

Certain embodiments provide a method of preventing, ameliorating or treating an HBV-related disease, disorder or condition in an animal comprising administering to the animal a compound or composition described herein. In certain embodiments, the compound or composition comprises a modified oligonucleotide 10 to 30 linked nucleosides in length targeted to HBV and having a nucleobase sequence comprising at least 10 contiguous nucleobases of any of the nucleobase sequences of SEQ ID NOs: 17, 51, 86, 93, 95, 98, 100, 102, 104, 106, 109, 112, 115, 117, 137, 140, 143, 145, 147, 149, 151, 153, 155, 157, 159, 161, 167, 168, 176, 177-179, 181, 188, 190-192, 194, 199, 201, 208, 209, 211, 226, 230-237, 244, 245, 247, 252, 254, 256, 258, 260, 262, 264, 266, 271, 1318-1347, 1364-1372, 1375, and 1376, wherein at least one nucleoside of the modified oligonucleotide comprises at least one 2'-O-methoxyethyl sugar and/or constrained ethyl (cEt) sugar. In certain embodiments, the modified oligonucleotide is 16 nucleosides in length and has a gap segment of 9 or 10 linked nucleosides. In certain embodiments, the modified oligonucleotide has a wing segment on the 5' end and 3' end of the gap each independently having 2, 3, 4, or 5 sugar modified nucleosides.

Certain embodiments provide methods of treating HBV related disease, disorder, or condition in an animal, comprising administering to an animal in need thereof a compound or composition described herein. In certain embodiments, the compound or composition comprises a modified oligonucleotide consisting of 10 to 30 linked nucleosides and having a nucleobase sequence comprising at least 10 contiguous nucleobases of any of the nucleobase sequences of SEQ ID NOs: 5, 15, 16, 33, 39-95, 123-135, 163-175, 180-310, 321-406, 413-455, 461-802, or 804-1272.

Certain embodiments provide methods of treating HBV related disease, disorder, or condition in an animal, comprising administering to an animal in need thereof a compound or composition described herein. In certain embodiments, the compound or composition comprises a modified oligonucleotide consisting of 10 to 30 linked nucleosides and having a nucleobase sequence comprising at least 10 contiguous nucleobases of any of the nucleobase sequences of SEQ ID NOs: 6-14, 17-32, 34-38, 96-122, 136-162, 176-179, 407-412, 456-462, 523-538 wherein at least one nucleoside of the modified oligonucleotide comprises at least one 2'-O-methoxyethyl sugar.

In certain embodiments, the modified oligonucleotide is 14 nucleosides in length and has a gap segment of 10 linked nucleosides. In certain embodiments, the modified oligonucleotide has a wing segment on the 5' end and 3' end of the gap each independently having 1-3 or 2 sugar modified nucleosides. In certain embodiments, the modified oligonucleotide is 16 nucleosides in length and has a gap segment of 9 or 10 linked nucleosides. In certain embodiments, the modified oligonucleotide has a wing segment on the 5' end and 3' end of the gap each independently having 1-5, 2-4 or 3 sugar modified nucleosides. In certain embodiments, the modified oligonucleotide has a wing segment on the 5' end and 3' end of the gap each independently having 2, 3, 4, or 5 sugar modified nucleosides. In certain embodiments, the modified oligonucleotide is 17 nucleosides in length and has a gap segment of 9 or 10 linked nucleosides. In certain embodiments, the modified oligonucleotide has a wing segment on the 5' end and 3' end of the gap each independently having 1-5, 2-4 or 3-4 sugar modified nucleosides. In certain embodiments, the modified oligonucleotide has a wing segment on the 5' end and 3' end of the gap each independently having 2, 3, 4, 5, or 6 sugar modified nucleosides. In certain embodiments, the modified oligonucleotide is 18 nucleosides in length and has a gap segment of 10 linked nucleosides. In certain embodiments, the modified oligonucleotide has a wing segment on the 5' end and 3' end of the gap each independently having 1-5, 3-5, or 4 sugar modified nucleosides. In certain embodiments, the modified oligonucleotide is 20 nucleosides in length and has a gap segment of 10 linked nucleosides. In certain embodiments, the modified oligonucleotide has a wing segment on the 5' end and 3' end of the gap each independently having 1-5, or 5 sugar modified nucleosides. In certain embodiments, the modified oligonucleotide has a wing segment on the 5' end and 3' end of the gap each independently having 2, 3, 4, 5, 6, 7, or 8 sugar modified nucleosides.

Certain embodiments provide a method of reducing HBV expression in an animal comprising administering to the animal a compound or composition described herein. In certain embodiments, the compound or composition comprises a modified oligonucleotide 10 to 30 linked nucleosides in length targeted to HBV and having a nucleobase sequence comprising at least 10 contiguous nucleobases of any of the nucleobase sequences of SEQ ID NOs: 5-310, 321-802, 804-1272, or 1288-1350.

Certain embodiments provide a method of reducing HBV expression in an animal comprising administering to the animal a compound or composition described herein. In certain embodiments, the compound or composition comprises a modified oligonucleotide 10 to 30 linked nucleosides in length targeted to HBV and having a nucleobase sequence comprising at least 10 contiguous nucleobases of any of the nucleobase sequences of SEQ ID NOs: 5, 15, 16, 33, 39-95, 123-135, 163-175, 180-310, 321-406, 413-455, 461-802, or 804-1272.

Certain embodiments provide a method of reducing HBV expression in an animal comprising administering to the animal a compound or composition described herein. In certain embodiments, the compound or composition comprises a modified oligonucleotide 10 to 30 linked nucleosides in length targeted to HBV and having a nucleobase sequence comprising at least 10 contiguous nucleobases of any of the nucleobase sequences of SEQ ID NOs: 6-14, 17-32, 34-38, 96-122, 136-162, 176-179, 407-412, 456-462, 523-538 wherein at least one nucleoside of the modified oligonucleotide comprises at least one 2'-O-methoxyethyl sugar.

In certain embodiments, the modified oligonucleotide is 14 nucleosides in length and has a gap segment of 10 linked nucleosides. In certain embodiments, the modified oligonucleotide has a wing segment on the 5' end and 3' end of the gap each independently having 1-3 or 2 sugar modified nucleosides. In certain embodiments, the modified oligonucleotide is 16 nucleosides in length and has a gap segment of 9 or 10 linked nucleosides. In certain embodiments, the modified oligonucleotide has a wing segment on the 5' end and 3' end of the gap each independently having 2, 3, 4, or 5 sugar modified nucleosides. In certain embodiments, the modified oligonucleotide is 16 nucleosides in length and has a gap segment of 10 linked nucleosides. In certain embodiments, the modified oligonucleotide has a wing segment on the 5' end and 3' end of the gap each independently having 1-5, 2-4 or 3 sugar modified nucleosides. In certain embodiments, the modified oligonucleotide is 17 nucleosides in length and has a gap segment of 9 or 10 linked nucleosides. In certain embodiments, the modified oligonucleotide has a wing segment on the 5' end and 3' end of the gap each independently having 2, 3, 4, 5, or 6 sugar modified nucleosides. In certain embodiments, the modified oligonucleotide is 17 nucleosides in length and has a gap segment of 10 linked nucleosides. In certain embodiments, the modified oligonucleotide has a wing segment on the 5' end and 3' end of the gap each independently having 1-5, 2-4 or 3-4 sugar modified nucleosides. In certain embodiments, the modified oligonucleotide is 18 nucleosides in length and has a gap segment of 10 linked nucleosides. In certain embodiments, the modified oligonucleotide has a wing segment on the 5' end and 3' end of the gap each independently having 1-5, 3-5, or 4 sugar modified nucleosides. In certain embodiments, the modified oligonucleotide is 20 nucleosides in length and has a gap segment of 10 linked nucleosides. In certain embodiments, the modified oligonucleotide has a wing segment on the 5' end and 3' end of the gap each independently having 2, 3, 4, 5, 6, 7, or 8 sugar modified nucleosides. In certain embodiments, the modified oligonucleotide is 20 nucleosides in length and has a gap segment of 10 linked nucleosides. In certain embodiments, the modified oligonucleotide has a wing segment on the 5' end and 3' end of the gap each independently having 1-5, or 5 sugar modified nucleosides.

Certain embodiments provide a method of preventing, ameliorating or treating an HBV-related disease, disorder or condition in an animal comprising administering to the animal a compound or composition described herein. In certain embodiments, the compound or composition comprises a modified oligonucleotide 10 to 30 linked nucleosides in length targeted to HBV. In certain embodiments, the compound or composition comprises a modified oligonucleotide 10 to 30 linked nucleosides in length targeted to HBV and having a nucleobase sequence comprising at least 10 contiguous nucleobases of any of the nucleobase sequences of SEQ ID NOs: 5-310, 321-802, 804-1272, or 1288-1350, wherein at least one nucleoside of the modified oligonucleotide comprises at least one 2'-O-methoxyethyl sugar. In certain embodiments, the modified oligonucleotide has a nucleobase sequence comprising at least 10 contiguous nucleobases of any of the nucleobase sequences of SEQ ID NOs: 5-310, 321-802, or 804-1272. In certain embodiments, the modified oligonucleotide has a nucleobase sequence comprising at least 10 contiguous nucleobases of any of the nucleobase sequences of SEQ ID NOs: 5, 15, 16, 33, 39-95, 123-135, 163-175, 180-310, 321-406, 413-455, 461-802, or 804-1272. In certain embodiments, the modified oligonucleotide has a nucleobase sequence comprising at least 10 contiguous nucleobases of any of the nucleobase sequences of SEQ ID NOs: 6-14, 17-32, 34-38, 96-122, 136-162, 176-179, 407-412, 456-462, 523-538 wherein at least one nucleoside of the modified oligonucleotide comprises at least one 2'-O-methoxyethyl sugar. In certain embodiments, the modified oligonucleotide is 14 nucleosides in length and has a gap segment of 10 linked nucleosides. In certain embodiments, the modified oligonucleotide has a wing segment on the 5' end and 3' end of the gap each independently having 1-3 or 2 sugar modified nucleosides. In certain embodiments, the modified oligonucleotide is 16 nucleosides in length and has a gap segment of 9 or 10 linked nucleosides. In certain embodiments, the modified oligonucleotide has a wing segment on the 5' end and 3' end of the gap each independently having 2, 3, 4, or 5 sugar modified nucleosides. In certain embodiments, the modified oligonucleotide is 16 nucleosides in length and has a gap segment of 10 linked nucleosides. In certain embodiments, the modified oligonucleotide has a wing segment on the 5' end and 3' end of the gap each independently having 1-5, 2-4 or 3 sugar modified nucleosides. In certain embodiments, the modified oligonucleotide is 17 nucleosides in length and has a gap segment of 9 or 10 linked nucleosides. In certain embodiments, the modified oligonucleotide has a wing segment on the 5' end and 3' end of the gap each independently having 2, 3, 4, 5, or 6 sugar modified nucleosides. In certain embodiments, the modified oligonucleotide is 17 nucleosides in length and has a gap segment of 10 linked nucleosides. In certain embodiments, the modified oligonucleotide has a wing segment on the 5' end and 3' end of the gap each independently having 1-5, 2-4 or 3-4 sugar modified nucleosides. In certain embodiments, the modified oligonucleotide is 18 nucleosides in length and has a gap segment of 10 linked nucleosides. In certain embodiments, the modified oligonucleotide has a wing segment on the 5' end and 3' end of the gap each independently having 1-5, 3-5, or 4 sugar modified nucleosides. In certain embodiments, the modified oligonucleotide is 20 nucleosides in length and has a gap segment of 10 linked nucleosides. In certain embodiments, the modified oligonucleotide has a wing segment on the 5' end and 3' end of the gap each independently having 2, 3, 4, 5, 6, 7, or 8 sugar modified nucleosides. In certain embodiments, the modified oligonucleotide is 20 nucleosides in length and has a gap segment of 10 linked nucleosides. In certain embodiments, the modified oligonucleotide has a wing segment on the 5' end and 3' end of the gap each independently having 1-5, or 5 sugar modified nucleosides.

Examples of HBV-related diseases, disorders or conditions include, but are not limited to chronic HBV infection, jaundice, liver cancer, liver inflammation, liver fibrosis, liver cirrhosis, liver failure, diffuse hepatocellular inflammatory disease, hemophagocytic syndrome, serum hepatitis, HBV viremia, and conditions having symptoms which may include any or all of the following: flu-like illness, weakness, aches, headache, fever, loss of appetite, diarrhea, nausea and vomiting, pain over the liver area of the body, clay- or grey-colored stool, itching all over, and dark-colored urine, when coupled with a positive test for presence of a hepatitis B virus, a hepatitis B viral antigen, or a positive test for the presence of an antibody specific for a hepatitis B viral antigen.

Certain embodiments provide a method of reducing HBV mRNA expression in an animal comprising administering to the animal a compound or composition described herein. In certain embodiments, the compound or composition comprises a modified oligonucleotide 10 to 30 linked nucleosides in length targeted to HBV. In certain embodiments, reduction of HBV mRNA expression in an animal prevents, ameliorates or treats an HBV-related disease, disorder or condition. In certain embodiments, reduction of HBV mRNA expression in an animal prevents, ameliorates or treats liver disease. In certain embodiments, the HBV mRNA expression is reduced by at least 5%, 10%, 20%, 30%, 35%, 40%, 45%, 50%, 55%, 60%, 65%, 70%, 75%, 80%, 85%, 90%, 95% or 100%.

Certain embodiments provide a method of reducing HBV protein levels in an animal comprising administering to the animal a compound or composition described herein. In certain embodiments, the compound or composition comprises a modified oligonucleotide 10 to 30 linked nucleosides in length targeted to HBV. In certain embodiments, reduction of HBV protein levels in an animal prevents, ameliorates or treats an HBV-related disease, disorder or condition. In certain embodiments, reduction of HBV protein levels in an animal prevents, ameliorates or treats liver disease. In certain embodiments, the HBV protein level is reduced by at least 5%, 10%, 20%, 30%, 35%, 40%, 45%, 50%, 55%, 60%, 65%, 70%, 75%, 80%, 85%, 90%, 95% or 100%.

Certain embodiments provide a method of reducing HBV DNA levels in an animal comprising administering to the animal a compound or composition described herein. In certain embodiments, the compound or composition comprises a modified oligonucleotide 10 to 30 linked nucleosides in length targeted to HBV. In certain embodiments, reduction of HBV DNA levels in an animal prevents, ameliorates or treats an HBV-related disease, disorder or condition. In certain embodiments, the mammal may be human, and the hepatitis B virus may be a human hepatitis B virus. More particularly, the human hepatitis B virus may be any of the human geographical genotypes: A (Northwest Europe, North America, Central America); B (Indonesia, China, Vietnam); C (East Asia, Korea, China, Japan, Polynesia, Vietnam); D (Mediterranean area, Middle East, India); E (Africa); F (Native Americans, Polynesia); G (United States, France); or H (Central America). In certain embodiments, reduction of HBV DNA levels in an animal prevents, ameliorates or treats liver disease. In certain embodiments, the HBV DNA level is reduced by at least 5%, 10%, 20%, 30%, 35%, 40%, 45%, 50%, 55%, 60%, 65%, 70%, 75%, 80%, 85%, 90%, 95% or 100%.

Certain embodiments provide a method of reducing HBV antigen levels in an animal comprising administering to the animal a compound or composition described herein. In certain embodiments, the compound or composition comprises a modified oligonucleotide 10 to 30 linked nucleosides in length targeted to HBV. In certain embodiments, the antigen is HBsAG or HBeAG. In certain embodiments, reduction of HBV antigen levels in an animal prevents, ameliorates or treats an HBV-related disease, disorder or condition. In certain embodiments, reduction of HBV antigen levels in an animal prevents, ameliorates or treats liver disease. In certain embodiments, the HBV antigen levels are reduced by at least 5%, 10%, 20%, 30%, 35%, 40%, 45%, 50%, 55%, 60%, 65%, 70%, 75%, 80%, 85%, 90%, 95% or 100%.

Certain embodiments provide a method of reducing HBV DNA and HBV antigen in a animal infected with a hepatitis B virus, comprising administering to the animal a compound or composition described herein. In certain embodiments, the compound or composition comprises a modified oligonucleotide 10 to 30 linked nucleosides in length targeted to HBV. In certain embodiments, the antigen is HBsAG or HBeAG. In certain embodiments, the amount of HBV antigen may be sufficiently reduced to result in seroconversion, defined as serum HBeAg absence plus serum HBeAb presence if monitoring HBeAg as the determinant for seroconversion, or defined as serum HBsAg absence if monitoring HBsAg as the determinant for seroconversion, as determined by currently available detection limits of commercial ELISA systems.

Certain embodiments provide a method for treating an animal with a HBV related disease, disorder or condition comprising: a) identifying said animal with the HBV related disease, disorder or condition, and b) administering to said animal a therapeutically effective amount of a compound or composition comprising a modified oligonucleotide consisting of 14 to 20 linked nucleosides and having a nucleobase sequence at least 90% complementary to any of SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363, as measured over the entirety of said modified oligonucleotide. In certain embodiments, the therapeutically effective amount of the compound or composition administered to the animal treats or reduces the HBV related disease, disorder or condition, or a symptom thereof, in the animal. In certain embodiments, the HBV related disease, disorder or condition is a liver disease. In certain embodiments, the related disease, disorder or condition is chronic HBV infection, jaundice, liver cancer, liver inflammation, liver fibrosis, liver cirrhosis, liver failure, diffuse hepatocellular inflammatory disease, hemophagocytic syndrome, serum hepatitis, HBV viremia, or liver disease-related to transplantation.

Certain embodiments provide a method for treating an animal with a HBV related disease, disorder or condition comprising: a) identifying said animal with the HBV related disease, disorder or condition, and b) administering to said animal a therapeutically effective amount of a compound or composition comprising a modified oligonucleotide consisting of 14 to 20 linked nucleosides and having a nucleobase sequence at least 90% complementary to SEQ ID NO: 1, as measured over the entirety of said modified oligonucleotide. In certain embodiments, the therapeutically effective amount of the compound or composition administered to the animal treats or reduces the HBV related disease, disorder or condition, or a symptom thereof, in the animal. In certain embodiments, the HBV related disease, disorder or condition is a liver disease. In certain embodiments, the related disease, disorder or condition is chronic HBV infection, jaundice, liver cancer, liver inflammation, liver fibrosis, liver cirrhosis, liver failure, diffuse hepatocellular inflammatory disease, hemophagocytic syndrome, serum hepatitis, HBV viremia, or liver disease-related to transplantation.

In certain embodiments, HBV has the sequence as set forth in GenBank Accession Numbers U95551.1 (incorporated herein as SEQ ID NO: 1) or any variant or fragment thereof. In certain embodiments, HBV has truncated portions of the human sequence as set forth in SEQ ID NOs: 1273, 1274, 1275, 1276, 1277, 1278, 1279, 1280, 1281, 1282, 1283, 1284, 1285, 1287, 1352, 1353, 1354, 1359, 1360, 1361, 1362, and 1363.

In certain embodiments, the animal is a human.

In certain embodiments, the compounds or compositions are designated as a first agent. In certain embodiments, the methods comprise administering a first agent and one or more second agents. In certain embodiments, the methods comprise administering a first agent and one or more second agents. In certain embodiments, the first agent and one or more second agents are co-administered. In certain embodiments the first agent and one or more second agents are co-administered sequentially or concomitantly.

In certain embodiments, the one or more second agents are also a compound or composition described herein. In certain embodiments, the one or more second agents are different from a compound or composition described herein. Examples of one or more second agents include, but are not limited to, an anti-inflammatory agent, chemotherapeutic agent or anti-infection agent.

In other related embodiments, the additional therapeutic agent may be an HBV agent, an HCV agent, a chemotherapeutic agent, an antibiotic, an analgesic, a non-steroidal anti-inflammatory (NSAID) agent, an antifungal agent, an antiparasitic agent, an anti-nausea agent, an anti-diarrheal agent, or an immunosuppressant agent.

In certain embodiments, the one or more second agents are an HBV agent. In certain embodiments the HBV agent can include, but is not limited to, interferon alpha-2b, interferon alpha-2a, and interferon alphacon-1 (pegylated and unpegylated), ribavirin; an HBV RNA replication inhibitor; a second antisense oligomer; an HBV therapeutic vaccine; an HBV prophylactic vaccine; lamivudine (3TC); entecavir (ETV); tenofovir diisoproxil fumarate (TDF); telbivudine (LdT); adefovir; or an HBV antibody therapy (monoclonal or polyclonal).

In certain embodiments, the one or more second agents are an HCV agent. In certain embodiments the HBV agent can include, but is not limited to interferon alpha-2b, interferon alpha-2a, and interferon alphacon-1 (pegylated and unpegylated); ribavirin; an HCV RNA replication inhibitor (e.g., ViroPharma's VP50406 series); an HCV antisense agent; an HCV therapeutic vaccine; an HCV protease inhibitor; an HCV helicase inhibitor; or an HCV monoclonal or polyclonal antibody therapy.

In certain embodiments, the one or more second agents are an anti-inflammatory agent (i.e., an inflammation lowering therapy). In certain embodiments the inflammation lowering therapy can include, but is not limited to, a therapeutic lifestyle change, a steroid, a NSAID or a DMARD. The steroid can be a corticosteroid. The NSAID can be an aspirin, acetaminophen, ibuprofen, naproxen, COX inhibitors, indomethacin and the like. The DMARD can be a TNF inhibitor, purine synthesis inhibitor, calcineurin inhibitor, pyrimidine synthesis inhibitor, a sulfasalazine, methotrexate and the like.

In certain embodiments, the one or more second agents are a chemotherapeutic agent (i.e., a cancer treating agent). Chemotherapeutic agents can include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin, gemcitabine and diethylstilbestrol (DES).

In certain embodiments, the one or more second agents are an anti-infection agent. Examples of anti-infection agents include, but are not limited to, antibiotics, antifungal drugs and antiviral drugs.

In certain embodiments, administration comprises parenteral administration.

Certain embodiment provides a method for reducing an amount of HBV mRNA, DNA, protein and/or an amount of HBV antigen in a mammal infected with a hepatitis B virus, the method comprising administering a therapeutically effective amount of a pharmaceutical composition as described above to a mammal in need thereof so as to reduce the hepatitis B virus infection and the hepatitis B antigen, compared to the amount of HBV mRNA, protein and an amount of HBV antigen in the mammal before treatment. In some embodiments, the mammal may be human, and the hepatitis B virus may be a human hepatitis B virus. More particularly, the human hepatitis B virus may be any of the human geographical genotypes: A (Northwest Europe, North America, Central America); B (Indonesia, China, Vietnam); C (East Asia, Korea, China, Japan, Polynesia, Vietnam); D (Mediterranean area, Middle East, India); E (Africa); F (Native Americans, Polynesia); G (United States, France); or H (Central America).

In certain embodiments, a method is provided for reducing an amount of HBV mRNA, DNA, protein and/or an amount of HBV antigen in a mammal infected with a hepatitis B virus, the method comprising administering a therapeutically effective amount of a pharmaceutical composition as described above to a mammal in need thereof so as to reduce the hepatitis B virus infection and the hepatitis B antigen, compared to the amount of HBV mRNA, protein and an amount of HBV antigen in the mammal before treatment, wherein the amount of mRNA is reduced at least 70% compared to the amount before administration of the modified antisense oligonucleotide. In certain embodiments, a method is provided for reducing an amount of HBV mRNA, DNA, protein and/or an amount of HBV antigen in a mammal infected with a hepatitis B virus, the method comprising administering a therapeutically effective amount of a pharmaceutical composition as described above to a mammal in need thereof so as to reduce the hepatitis B virus infection and the hepatitis B antigen, compared to the amount of HBV mRNA, protein and an amount of HBV antigen in the mammal before treatment, wherein the amount of mRNA is reduced at least 75% compared to the amount before administration of the modified antisense oligonucleotide. In certain embodiments, a method is provided for reducing an amount of HBV mRNA, DNA, protein and/or an amount of HBV antigen in a mammal infected with a hepatitis B virus, the method comprising administering a therapeutically effective amount of a pharmaceutical composition as described above to a mammal in need thereof so as to reduce the hepatitis B virus infection and the hepatitis B antigen, compared to the amount of HBV mRNA, protein and an amount of HBV antigen in the mammal before treatment, wherein the amount of mRNA is reduced at least 80% compared to the amount before administration of the modified antisense oligonucleotide. In certain embodiments, a method is provided for reducing an amount of HBV mRNA, DNA, protein and/or an amount of HBV antigen in a mammal infected with a hepatitis B virus, the method comprising administering a therapeutically effective amount of a pharmaceutical composition as described above to a mammal in need thereof so as to reduce the hepatitis B virus infection and the hepatitis B antigen, compared to the amount of HBV mRNA, protein and an amount of HBV antigen in the mammal before treatment, wherein the amount of mRNA is reduced at least 85% compared to the amount before administration of the modified antisense oligonucleotide. In certain embodiments, a method is provided for reducing an amount of HBV mRNA, DNA, protein and/or an amount of HBV antigen in a mammal infected with a hepatitis B virus, the method comprising administering a therapeutically effective amount of a pharmaceutical composition as described above to a mammal in need thereof so as to reduce the hepatitis B virus infection and the hepatitis B antigen, compared to the amount of HBV mRNA, protein and an amount of HBV antigen in the mammal before treatment, wherein the amount of mRNA is reduced at least 90% compared to the amount before administration of the modified antisense oligonucleotide. In certain embodiments, a method is provided for reducing an amount of HBV mRNA, DNA, protein and/or an amount of HBV antigen in a mammal infected with a hepatitis B virus, the method comprising administering a therapeutically effective amount of a pharmaceutical composition as described above to a mammal in need thereof so as to reduce the hepatitis B virus infection and the hepatitis B antigen, compared to the amount of HBV mRNA, protein and an amount of HBV antigen in the mammal before treatment, wherein the amount of mRNA is reduced at least 95% compared to the amount before administration of the modified antisense oligonucleotide. In related methods, the HBV antigen may be HBsAg or may be HBeAg, and more particularly, the amount of HBV antigen may be sufficiently reduced to result in seroconversion, defined as serum HBeAg absence plus serum HBeAb presence if monitoring HBeAg as the determinant for seroconversion, or defined as serum HBsAg absence if monitoring HBsAg as the determinant for seroconversion, as determined by currently available detection limits of commercial ELISA systems.

Certain embodiment provides a method for promoting seroconversion of a hepatitis B virus in a mammal infected with HBV, the method comprising administering a therapeutically effective amount of a pharmaceutical composition as described above to a mammal infected with hepatitis B; monitoring for presence of HBeAg plus HBeAb in a serum sample of the mammal, or monitoring for presence of HBsAg in a serum sample of the mammal, such that the absence of HBeAg plus the presence of HBeAb in the serum sample if monitoring HBeAg as the determinant for seroconversion, or the absence of HBsAg in the serum sample if monitoring HBsAg as the determinant for seroconversion, as determined by current detection limits of commercial ELISA systems, is indication of seroconversion in the mammal.

Certain embodiments provide the use of a compound or composition as described herein for preventing, ameliorating or treating liver disease, or symptom thereof, in an animal. In certain embodiments, the compound or composition comprises a modified oligonucleotide 10 to 30 linked nucleosides in length targeted to HBV. In certain embodiments, the modified oligonucleotide has a nucleobase sequence comprising at least 10 contiguous nucleobases of any of the nucleobase sequences of SEQ ID NOs: 17, 51, 86, 93, 95, 98, 100, 102, 104, 106, 109, 112, 115, 117, 137, 140, 143, 145, 147, 149, 151, 153, 155, 157, 159, 161, 167, 168, 176, 177-179, 181, 188, 190-192, 194, 199, 201, 208, 209, 211, 226, 230-237, 244, 245, 247, 252, 254, 256, 258, 260, 262, 264, 266, 271, 1318-1347, 1364-1372, 1375, 1376, and 1379.

In certain embodiments, the compounds or compositions as described herein are efficacious by virtue of having at least one of an in vitro $IC_{50}$ of less than 250 nM, less than 200 nM, less than 150 nM, less than 100 nM, less than 90 nM, less than 80 nM, less than 70 nM, less than 65 nM, less than 60 nM, less than 55 nM, less than 50 nM, less than 49 nM, less than 47 nM, less than 46 nM, when delivered to HepG2.2.1 cells. In certain embodiments inhibition is measured with primer probe set RTS3370, as described herein.

In certain embodiments, the compounds or compositions as described herein are efficacious by virtue of having at least one of an in vitro $IC_{50}$ of less than 250 nM, less than 200 nM, less than 100 nM, less than 90 nM, less than 80 nM, less than 70 nM, less than 60 nM, less than 50 nM, less than 40 nM, less than 35 nM, less than 34 nM, less than 33 nM, less than 32 nM, less than 31 nM, when delivered to HepG2.2.1 cells. In certain embodiments inhibition is measured with primer probe set RTS3371, as described herein.

In certain embodiments, the compounds or compositions as described herein are efficacious by virtue of having at least one of an in vitro $IC_{50}$ of less than 20 µM, less than 10 µM, less than 9.5 µM, less than 9.0 µM, less than 8.5 µM, less than 8.0 µM, less than 7.5 less than 7.0 µM, less than 6.5 µM, less than 6.0 less than 5.5 µM, less than 5.0 µM, less than 4.5 µM, less than 4.0 µM, less than 3.5 µM, less than 3.0 µM, less than 2.5 µM, when delivered to HepG2.2.1 cells as described herein.

In certain embodiments, the compounds or compositions as described herein are highly tolerable as demonstrated by having at least one of an increase an ALT or AST value of no more than 4 fold, 3 fold, or 2 fold over saline treated animals or an increase in liver, spleen, or kidney weight of no more than 30%, 20%, 15%, 12%, 10%, 5%, or 2%. In certain embodiments, the compounds or compositions as described herein are highly tolerable as demonstrated by having no increase of ALT or AST over saline treated animals. In certain embodiments, the compounds or compositions as described herein are highly tolerable as demonstrated by having no increase in liver, spleen, or kidney weight over saline treated animals. In certain embodiments, these compounds or compositions include ISIS 146779, ISIS 146786, ISIS 505317, ISIS 505329, ISIS 505332, ISIS 505346, ISIS 505347, ISIS 505358, ISIS 509926, ISIS 509927, ISIS 509932, ISIS 509934, ISIS 509960, ISIS 509974, ISIS 510038, ISIS 510039, ISIS 510040, ISIS 510041, ISIS 5100501SIS 509975, ISIS 510100, ISIS 510106, and ISIS 510116. In certain embodiments, such compounds or compositions include compounds comprising the nucleobase sequence of any one of SEQ ID NOs: 5-310, 321-802, or 804-1272. In certain embodiments, such compounds or compositions include compounds comprising the nucleobase sequence of any one of SEQ ID NOs: 5, 15, 16, 33, 39-95, 123-135, 163-175, 180-310, 321-406, 413-455, 461-802, or 804-1272. In certain embodiments, such compounds or compositions include compounds comprising the nucleobase sequence of any one of SEQ ID NOs: 6-14, 17-32, 34-38, 96-122, 136-162, 176-179, 407-412, 456-462, 523-538 (update SEQ ID NOs) wherein at least one nucleoside of the modified oligonucleotide comprises at least one 2'-O-methoxyethyl sugar. In certain embodiments, the modified oligonucleotide is 14 nucleosides in length and has a gap segment of 10 linked nucleosides. In certain embodiments, the modified oligonucleotide has a wing segment on the 5' end and 3' end of the gap each independently having 1-3 or 2 sugar modified nucleosides. In certain embodiments, the modified oligonucleotide is 16 nucleosides in length and has a gap segment of 10 linked nucleosides. In certain embodiments, the modified oligonucleotide has a wing segment on the 5' end and 3' end of the gap each independently having 1-5, 2-4 or 3 sugar modified nucleosides. In certain embodiments, the modified oligonucleotide is 17 nucleosides in length and has a gap segment of 10 linked nucleosides. In certain embodiments, the modified oligonucleotide has a wing segment on the 5' end and 3' end of the gap each independently having 1-5, 2-4 or 3-4 sugar modified nucleosides. In certain embodiments, the modified oligonucleotide is 18 nucleosides in length and has a gap segment of 10 linked nucleosides. In certain embodiments, the modified oligonucleotide has a wing segment on the 5' end and 3' end of the gap each independently having 1-5, 3-5, or 4 sugar modified nucleosides. In certain embodiments, the modified oligonucleotide is 20 nucleosides in length and has a gap segment of 10 linked nucleosides. In certain embodiments, the modified oligonucleotide has a wing segment on the 5' end and 3' end of the gap each independently having 1-5, or 5 sugar modified nucleosides.

Certain embodiments provide the use of a compound or composition as described herein in the manufacture of a medicament for treating, ameliorating, delaying or preventing an HBV-related disease, disorder or condition in an animal.

Certain embodiments provide the use of a compound or composition as described herein in the manufacture of a medicament for treating, ameliorating, delaying or preventing liver disease in an animal.

Certain embodiments provide a kit for treating, preventing, or ameliorating an HBV-related disease, disorder or condition, or a symptom thereof, as described herein wherein the kit comprises: a) a compound or compositions as described herein; and optionally b) an additional agent or therapy as described herein. The kit can further include instructions or a label for using the kit to treat, prevent, or ameliorate the HBV-related disease, disorder or condition.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a HBV nucleic acid is 10-30 subunits in length. In certain embodiments, an antisense compound targeted to a HBV nucleic acid is 12 to 30 subunits in length. In certain embodiments, an antisense compound targeted to a HBV nucleic acid is 12 to 22 subunits in length. In certain embodiments, an antisense compound targeted to a HBV nucleic acid is 14 to 30 subunits in length. In certain embodiments, an antisense compound targeted to a HBV nucleic acid is 14 to 20 subunits in length. In certain embodiments, an antisense compound targeted to a HBV nucleic acid is 15 to 30 subunits in length. In certain embodiments, an antisense compound targeted to a HBV nucleic acid is 15 to 20 subunits in length. In certain embodiments, an antisense compound targeted to a HBV nucleic acid is 16 to 30 subunits in length. In certain embodiments, an antisense compound targeted to a HBV nucleic acid is 16 to 20 subunits in length. In certain embodiments, an antisense compound targeted to a HBV nucleic acid is 17 to 30 subunits in length. In certain embodiments, an antisense compound targeted to a HBV nucleic acid is 17 to 20 subunits in length. In certain embodiments, an antisense compound targeted to a HBV nucleic acid is 18 to 30 subunits in length. In certain embodiments, an antisense compound targeted to a HBV nucleic acid is 18 to 21 subunits in length. In certain embodiments, an antisense compound targeted to a HBV nucleic acid is 18 to 20 subunits in length. In certain embodiments, an antisense compound targeted to a HBV nucleic acid is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound targeted to a HBV nucleic acid is 14 subunits in length. In certain embodiments, an antisense compound targeted to a HBV nucleic acid is 16 subunits in length. In certain embodiments, an antisense compound targeted to a HBV nucleic acid is 17 subunits in length. In certain embodiments, an antisense compound targeted to a HBV nucleic acid is 18 subunits in length. In certain embodiments, an antisense compound targeted to a HBV nucleic acid is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides targeted to a HBV nucleic acid may be shortened or truncated. For example, a single subunit may be deleted from the 5' end (5' truncation), or alternatively from the 3' end (3' truncation). A shortened or truncated antisense compound targeted to a HBV nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a HBV nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X—Y—Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X—Y—Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, gapmers provided herein include, for example, 11-mers having a motif of 1-9-1.

In certain embodiments, gapmers provided herein include, for example, 12-mers having a motif of 1-9-2, 2-9-1, or 1-10-1.

In certain embodiments, gapmers provided herein include, for example, 13-mers having a motif of 1-9-3, 2-9-2, 3-9-1, 1-10-2, or 2-10-1.

In certain embodiments, gapmers provided herein include, for example, 14-mers having a motif of 1-9-4, 2-9-3, 3-9-2, 4-9-1, 1-10-3, 2-10-2, or 3-10-1.

In certain embodiments, gapmers provided herein include, for example, 15-mers having a motif of 1-9-5, 2-9-4, 3-9-3, 4-9-2, 5-9-1, 1-10-4, 2-10-3, 3-10-2, or 4-10-1.

In certain embodiments, gapmers provided herein include, for example, 16-mers having a motif of 4-8-4, 2-9-5, 3-9-4, 4-9-3, 5-9-2, 1-10-5, 2-10-4, 3-10-3, 4-10-2, 3-8-5, or 5-10-1.

In certain embodiments, gapmers provided herein include, for example, 17-mers having a motif of 3-9-5, 3-10-4, 4-9-4, 5-9-3, 2-10-5, 3-10-4, 4-10-3, 5-10-2, 2-9-6, 5-8-4, 5-7-5, 6-7-4, or 6-9-2.

In certain embodiments, gapmers provided herein include, for example, 18-mers having a motif of 4-9-5, 5-9-4, 3-10-5, 4-10-4, or 5-10-3.

In certain embodiments, gapmers provided herein include, for example, 19-mers having a motif of 5-9-5, 4-10-5, or 5-10-4.

In certain embodiments, gapmers provided herein include, for example, 20-mers having a motif of 5-10-5, 2-10-8, 8-10-2, 3-10-7, 7-10-3, 4-10-6, or 6-10-4.

In certain embodiments, the antisense compound has a "wingmer" motif, having a wing-gap or gap-wing configuration, i.e. an X—Y or Y—Z configuration as described above for the gapmer configuration. Thus, wingmer configurations provided herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, the antisense compound targeted to a HBV nucleic acid has a 2-10-2 gapmer motif.

In certain embodiments, the antisense compound targeted to a HBV nucleic acid has a 3-10-3 gapmer motif.

In certain embodiments, the antisense compound targeted to a HBV nucleic acid has a 4-10-4 gapmer motif.

In certain embodiments, the antisense compound targeted to a HBV nucleic acid has a 5-10-5 gapmer motif.

In certain embodiments, the antisense compound targeted to a HBV nucleic acid has a 3-10-4 gapmer motif.

In certain embodiments, the antisense compound targeted to a HBV nucleic acid has a 2-10-4 gapmer motif.

In certain embodiments, the antisense compound targeted to a HBV nucleic acid has a 2-10-8 gapmer motif.

In certain embodiments, the antisense compound targeted to a HBV nucleic acid has a 8-10-2 gapmer motif.

In certain embodiments, the antisense compound targeted to a HBV nucleic acid has a 3-10-7 gapmer motif.

In certain embodiments, the antisense compound targeted to a HBV nucleic acid has a 7-10-3 gapmer motif.

In certain embodiments, the antisense compound targeted to a HBV nucleic acid has a 4-10-6 gapmer motif.

In certain embodiments, the antisense compound targeted to a HBV nucleic acid has a 6-10-4 gapmer motif.

In certain embodiments, the antisense compound targeted to a HBV nucleic acid has a 2-9-6 gapmer motif.

In certain embodiments, the antisense compound targeted to a HBV nucleic acid has a 6-9-2 gapmer motif.

In certain embodiments, the antisense compound targeted to a HBV nucleic acid has a 4-9-4 gapmer motif.

In certain embodiments, the antisense compound targeted to a HBV nucleic acid has a 5-9-3 gapmer motif.

In certain embodiments, the antisense compound targeted to a HBV nucleic acid has a 3-9-5 gapmer motif.

In certain embodiments, the antisense compound targeted to a HBV nucleic acid has a 5-9-2 gapmer motif.

In certain embodiments, the antisense compound targeted to a HBV nucleic acid has a 2-9-5 gapmer motif.

In certain embodiments, the antisense compound targeted to a HBV nucleic acid has a 4-9-3 gapmer motif.

In certain embodiments, the antisense compound targeted to a HBV nucleic acid has a 3-9-4 gapmer motif.

In certain embodiments, the antisense compound targeted to a HBV nucleic acid has a gap-widened motif.

In certain embodiments, the antisense compound targeted to a HBV nucleic acid has a gapmer motif in which the gap consists of 6, 7, 8, 9, 10, 11, 12, 13, 14, 15, or 16 linked nucleosides.

In certain embodiments, the antisense compounds targeted to a HBV nucleic acid has any of the following sugar motifs:
k-d(10)-k
e-d(10)-k
k-d(10)-e
k-k-d(10)-k-k
k-k-d(10)-e-e
e-e-d(10)-k-k
k-k-k-d(10)-k-k-k
e-e-e-d(10)-k-k-k
k-k-k-d(10)-e-e-e
k-k-k-d(10)-k-k-k
e-k-k-d(10)-k-k-e
e-e-k-d(10)-k-k-e
e-d-k-d(10)-k-k-e
e-k-d(10)-k-e-k-e
k-d(10)-k-e-k-e-e
e-e-k-d(10)-k-e-k-e
e-d-d-k-d(9)-k-k-e
e-e-e-d(9)-k-k-e
e-e-e-e-e-d(10)-e-e-e-e-e
k-d-k-d-k-d(9)-e-e
e-e-k-k-d(9)-e-k-e-e
k-d-k-d-k-d(10)-e-e-e-e-e
k-e-k-d(10)-k-e-k
e-e-e-k-k-d(8)-e-e-e-e
e-e-e-k-k-d(7)-k-k-e-e-e
e-e-e-k-d(9)-k-e-e-e
e-e-e-k-k-d(7)-k-k-e-e-e
e-e-e-e-k-k-d(7)-e-e-e-e
e-k-e-k-d(9)-e-e-e-e
e-k-e-k-d-k-d(7)-e-e-e-e
e-e-e-k-k-d(7)-k-k-e-e-e
k-d-k-d-k-d(8)-e-e-e-e-e
wherein, k is a constrained ethyl nucleoside, e is a 2'-MOE substituted nucleoside, and d is a 2'-deoxynucleoside.

In certain embodiments, the antisense oligonucleotide has a sugar motif described by Formula A as follows: $(J)_m$-$(B)_n$-$(J)_p$-$(B)_r$-$(A)_t$-$(D)_g$-$(A)_v$-$(B)_w$-$(J)_x$-$(B)_y$-$(J)_z$ wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14;
provided that:
at least one of m, n, and r is other than 0;
at least one of w and y is other than 0;
the sum of m, n, p, r, and t is from 2 to 5; and
the sum of v, w, x, y, and z is from 2 to 5.

Target Nucleic Acids, Target Regions and Nucleotide Sequences

Nucleotide sequences that encode HBV include, without limitation, the following: GENBANK Accession U95551.1 (incorporated herein as SEQ ID NO: 1).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for HBV can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in HBV mRNA levels are indicative of inhibition of HBV expression. Reductions in levels of a HBV protein are also indicative of inhibition of target mRNA expression. Further, phenotypic changes are indicative of inhibition of HBV expression. In certain embodiments, reduced fatigue, reduced flu-like symptoms, increase in appetite, reduced nausea, reduced joint pain, reduced jaundice, reduced pain in the abdomen, reduced weakness, reduced weight loss, reduction in breast enlargement in men, reduced rash on the palms, reduced difficulty with blood clotting, reduced cirrhosis, reduced spider-like blood vessels on the skin, increased Vitamins A and D absorption, reduced tumor growth, reduced tumor volume, reduced headache, reduced fever, reduced diarrhea, reduced pain over the liver area of the body, reduced clay- or grey-colored stool, reduced itching, reduced dark-colored urine, and reduced nausea and vomiting can be indicative of inhibition of HBV expression, In certain embodiments, amelioration of symptoms associated with HBV-related conditions, disease, and disorders can be indicative of inhibition of HBV expression. In certain embodiments, reduction of cirrhosis is indicative of inhibition of HBV expression. In certain embodiments, reduction of liver cancer markers can be indicative of inhibition of HBV expression.

Hybridization

In some embodiments, hybridization occurs between an antisense compound disclosed herein and a HBV nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a HBV nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a HBV nucleic acid).

Non-complementary nucleobases between an antisense compound and a HBV nucleic acid may be tolerated provided that the antisense compound remains able to specifically hybridize to a target nucleic acid. Moreover, an antisense compound may hybridize over one or more segments of a HBV nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a HBV nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools)

and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to a HBV nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a HBV nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a HBV nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a HBV nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds provided herein can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise a chemically modified ribofuranose ring moiety. Examples of chemically modified ribofuranose rings include, without limitation, addition of substituent groups (including 5' and 2' substituent groups); bridging of non-geminal ring atoms to form bicyclic nucleic acids (BNA); replacement of the ribosyl ring oxygen atom with S, N(R), or C(R1)(R)2 (R=H, $C_1$-$C_{12}$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5',2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-$OCH_3$, and 2'-$O(CH_2)2OCH_3$ substituent groups. The substituent at the 2' position can also be selected from allyl, amino, azido, thio, O-allyl, O—$C_1$-$C_{10}$ alkyl, $OCF_3$, $O(CH_2)2SCH_3$, $O(CH_2)2$-O—N(Rm)(Rn), and O—$CH_2$—C(=O)—N(Rm)(Rn), where each Rm and Rn is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-($CH_2$)—O-2' (LNA); 4'-($CH_2$)—S-2'; 4'-($CH_2$)$_2$—O-2' (ENA); 4'-CH($CH_3$)—O-2' (cEt) and 4'-CH($CH_2OCH_3$)—O-2', and analogs thereof (see, U.S. Pat. No. 7,399,845, issued on Jul. 15, 2008); 4'-C($CH_3$)($CH_3$)—O-2', and analogs thereof (see, published PCT International Application WO2009/006478, published Jan. 8, 2009); 4'-$CH_2$—N($OCH_3$)-2', and analogs thereof (see, published PCT International Application WO2008/150729, published Dec. 11, 2008); 4'-$CH_2$—O—N($CH_3$)-2' (see, published U.S. Patent Application US2004/0171570, published Sep. 2, 2004); 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, Chattopadhyaya, et al., *J. Org. Chem.,* 2009, 74, 118-134); and 4'-$CH_2$—C(=$CH_2$)-2', and analogs thereof (see, published PCT International Application WO 2008/154401, published on Dec. 8, 2008). Also see, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129(26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=N$R_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

In certain embodiments, the bridge of a bicyclic sugar moiety is, —[C($R_a$)($R_b$)]$_n$—, —[C($R_a$)($R_b$)]$_n$—O—, —C($R_aR_b$)—N(R)—O— or, —C($R_aR_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2', and 4'-CH$_2$—N(R)—O-2'-, wherein each R is, independently, H, a protecting group, or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-Methyleneoxy (4'-CH$_2$—O-2') BNA, (B) β-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA, (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

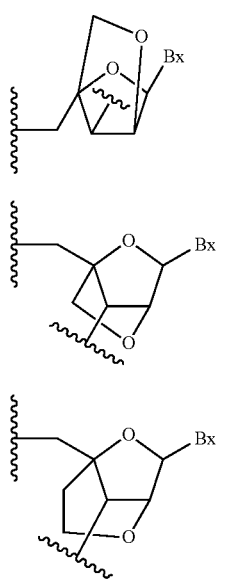

(A)

(B)

(C)

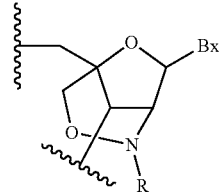

(D)

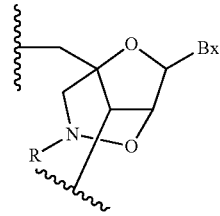

(E)

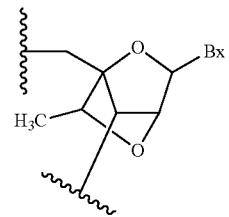

(F)

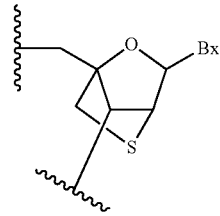

(G)

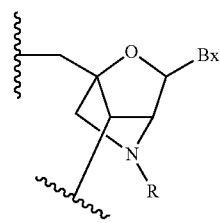

(H)

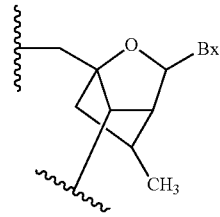

(I)

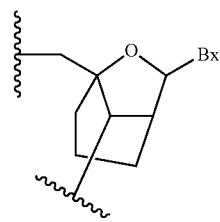

(J)

wherein Bx is the base moiety and R is, independently, H, a protecting group or $C_1$-$C_{12}$ alkyl.

In certain embodiments, bicyclic nucleoside having Formula I:

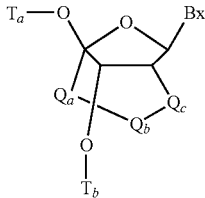

wherein:
Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O—, or —N($R_c$)—O—$CH_2$;
$R_c$ is $C_1$-$C_{12}$ alkyl or an amino protecting group; and
$T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

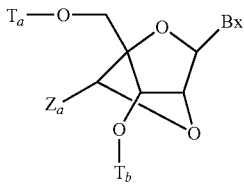

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC$(=X)$NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

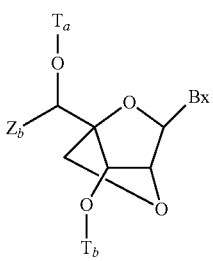

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In certain embodiments, bicyclic nucleoside having Formula IV:

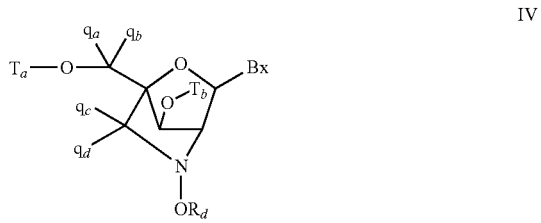

wherein:
Bx is a heterocyclic base moiety;
$T_a$ and $T_b$ are each, independently H, a hydroxyl protecting group, a conjugate group, a reactive phosphorus group, a phosphorus moiety, or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl, or substituted $C_1$-$C_6$ aminoalkyl;

In certain embodiments, bicyclic nucleoside having Formula V:

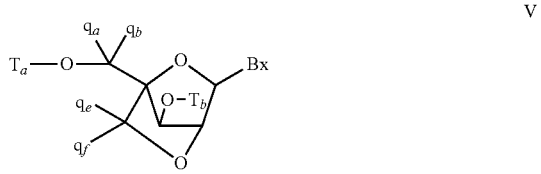

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;
or $q_e$ and $q_f$ together are =C($q_g$)($q_h$);
$q_g$ and $q_h$ are each, independently, H, halogen, $C_1$-$C_{12}$ alkyl, or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron*, 1998, 54, 3607-3630). BNAs and preparation thereof are also described in WO 98/39352 and WO 99/14226.

Analogs of methyleneoxy (4'-CH$_2$—O-2') BNA, methyleneoxy (4'-CH$_2$—O-2') BNA, and 2'-thio-BNAs, have also been prepared (see, e.g., Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleoside having Formula VI:

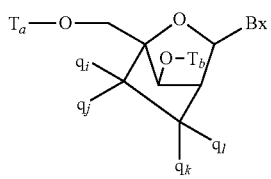

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, OJ$_j$, SJ$_j$, SOJ$_j$, SO$_2$J$_j$, NJ$_j$J$_k$, N$_3$, CN, C(=O)OJ$_j$, C(=O)NJ$_j$J$_k$, C(=O)J$_j$, O—C(=O)NJ$_j$J$_k$, N(H)C(=NH)NJ$_j$J$_k$, N(H)C(=O)NJ$_j$J$_k$, or N(H)C(=S)NJ$_j$J$_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl, or substituted $C_1$-$C_{12}$ alkyl.

One carbocyclic bicyclic nucleoside having a 4'-(CH$_2$)$_3$-2' bridge and the alkenyl analog, bridge 4'-CH=CH—CH$_2$-2', have been described (see, e.g., Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

As used herein, "bicyclic nucleoside" refers to a nucleoside comprising a bridge connecting two carbon atoms of the sugar ring, thereby forming a bicyclic sugar moiety. In certain embodiments, the bridge connects the 2' carbon and another carbon of the sugar ring.

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; SCH$_3$; OCN; Cl; Br; CN; CF$_3$; OCF$_3$; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (see, e.g., Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), or those compounds having Formula X:

Formula X:

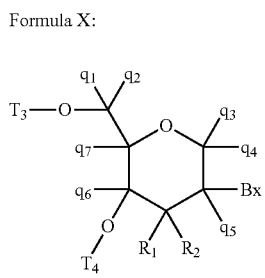

wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S, or $NJ_1$, and each $J_1$, $J_2$, and $J_3$ is, independently, H or $C_1$-$C_6$ alkyl.

In certain embodiments, the modified THP nucleosides of Formula X are provided wherein $q_m$, $q_n$, $q_p$, $q_r$, $q_s$, $q_t$, and $q_u$ are each H. In certain embodiments, at least one of $q_m$, $q_n$, $q_p$, $q_r$, $q_s$, $q_t$, and $q_u$ is other than H. In certain embodiments, at least one of $q_m$, $q_n$, $q_p$, $q_r$, $q_s$, $q_t$ and $q_u$ is methyl. In certain embodiments, THP nucleosides of Formula X are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

As used herein, "2'-modified nucleoside" or "2'-substituted nucleoside" refers to a nucleoside comprising a sugar comprising a substituent at the 2' position of a furanose ring other than H or OH. 2'-modified nucleosides, include, but are not limited to, bicyclic nucleosides wherein the bridge connecting two carbon atoms of the sugar ring connects the 2' carbon and another carbon of the sugar ring and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—$C(=O)$—$N(R_m)(R_n)$, where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE.

In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a HBV nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a HBV nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of HBV nucleic acids can be tested in vitro in a variety of cell types. Cell types used for such analyses are available from commerical vendors (e.g. American Type Culture Collection, Manassus, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HuVEC cells, b.END cells, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a HBV nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a HBV nucleic acid. Methods for designing real-time PCR probes and primers are well known in the art, and may include the use of software such as PRIMER EXPRESS Software (Applied Biosystems, Foster City, Calif.).

Quantitative Real-Time PCR Analysis of Target DNA Levels

Quantitation of target DNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Gene (or DNA) target quantities obtained by real time PCR are normalized using either the expression level of a gene whose expression is constant, such as cyclophilin A, or by quantifying total DNA using RIBOGREEN (Invitrogen, Inc. Carlsbad, Calif.). Cyclophilin A expression is quantified by real time PCR, by being run simultaneously with the target, multiplexing, or separately. Total DNA is quantified using RIBOGREEN RNA quantification reagent (Invetrogen, Inc. Eugene, Oreg.). Methods of DNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a HBV nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of HBV nucleic acids can be assessed by measuring HBV protein levels. Protein levels of HBV can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of HBV and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, subcutaneous, intrathecal, and intracerebroventricular. Calculation of antisense oligonucleotide dosage and dosing frequency is within the abilities of those skilled in the art, and depends upon factors such as route of administration and animal body weight. Following a period of treatment with antisense oligonucleotides, RNA is isolated from liver tissue and changes in HBV nucleic acid expression are measured. Changes in HBV DNA levels are also measured. Changes in HBV protein levels are also measured. Changes in HBV HBeAg levels are also measured. Changes in HBV HBsAg levels are also measured.

Certain Indications

In certain embodiments, provided herein are methods, compounds, and compositions of treating an individual comprising administering one or more pharmaceutical compositions provided herein. In certain embodiments, the individual has an HBV-related condition. In certain embodiments, chronic HBV infection, inflammation, fibrosis, cirrhosis, liver cancer, serum hepatitis, jaundice, liver cancer, liver inflammation, liver fibrosis, liver cirrhosis, liver failure, diffuse hepatocellular inflammatory disease, hemophagocytic syndrome, serum hepatitis, and HBV viremia. In certain embodiments, the HBV-related condition may have which may include any or all of the following: flu-like illness, weakness, aches, headache, fever, loss of appetite, diarrhea, jaundice, nausea and vomiting, pain over the liver area of the body, clay- or grey-colored stool, itching all over, and dark-colored urine, when coupled with a positive test for presence of a hepatitis B virus, a hepatitis B viral antigen, or a positive test for the presence of an antibody specific for a hepatitis B viral antigen. In certain embodiments, the individual is at risk for an HBV-related condition. This includes individuals having one or more risk factors for developing an HBV-related condition, including sexual exposure to an individual infected with Hepatitis B virus, living in the same house as an individual with a lifelong hepatitis B virus infection, exposure to human blood infected with the hepatitis B virus, injection of illicit drugs, being a person who has hemophilia, and visiting an area where hepatitis B is common. In certain embodiments, the individual has been identified as in need of treatment for an HBV-related condition. In certain embodiments provided herein are methods for prophylactically reducing HBV expression in an individual. Certain embodiments include treating an individual in need thereof by administering to an individual a therapeutically effective amount of an antisense compound targeted to an HBV nucleic acid.

Due to overlapping transmission routes, many people have been exposed to both hepatitis B virus (HBV) and hepatitis C virus (HCV), and a smaller proportion are chronically infected with both viruses, especially in regions such as Asia where HBV is endemic. Estimates suggest that up to 10% of people with HCV may also have HBV, while perhaps 20% of people with HBV are co-infected with HCV. However, treatment of hepatitis B or hepatitis B in HBV-HCV co-infected individuals has not been well studied. Treatment is complicated by the fact that HCV and HBV appear to inhibit each other's replication (though not all studied have observed this interaction). Therefore, treatment that fully suppresses HBV could potentially allow HCV to re-emerge, or vice versa. Therefore, the compounds and compositions described herein may advantageously be used for treating patients infected with both HBV and HCV. Exemplary treatment options for hepatitis C(HCV) include interferons, e.g., interferon alpha-2b, interferon alpha-2a, and interferon alphacon-1. Less frequent interferon dosing can be achieved using pegylated interferon (interferon attached to a polyethylene glycol moiety which improves its pharmacokinetic profile). Combination therapy with interferon alpha-2b (pegylated and unpegylated) and ribavirin has also been shown to be efficacious for some patient populations. Other agents currently being developed include HCV RNA replication inhibitors (e.g., ViroPharma's VP50406 series), HCV antisense agents, HCV therapeutic vaccines, HCV protease inhibitors, HCV helicase inhibitors and HCV antibody therapy (monoclonal or polyclonal).

In certain embodiments, treatment with the methods, compounds, and compositions described herein is useful for preventing an HBV-related condition associated with the presence of the hepatitis B virus. In certain embodiments, treatment with the methods, compounds, and compositions described herein is useful for preventing an HBV-related condition.

In one embodiment, administration of a therapeutically effective amount of an antisense compound targeted to an HBV nucleic acid is accompanied by monitoring of HBV mRNA levels in the serum of an individual to determine an individual's response to administration of the antisense compound. In certain embodiments, administration of a therapeutically effective amount of an antisense compound targeted to an HBV nucleic acid is accompanied by monitoring of HBV DNA levels in the serum of an individual to determine an individual's response to administration of the antisense compound. In certain embodiments, administration of a therapeutically effective amount of an antisense compound targeted to an HBV nucleic acid is accompanied by monitoring of HBV protein levels in the serum of an individual to determine an individual's response to administration of the antisense compound. In certain embodiments, administration of a therapeutically effective amount of an antisense compound targeted to an HBV nucleic acid is accompanied by monitoring of HBV S antigen (HBsAg) levels in the serum of an individual to determine an individual's response to administration of the antisense compound. In certain embodiments, administration of a therapeutically effective amount of an antisense compound targeted to an HBV nucleic acid is accompanied by monitoring of HBV E antigen (HBeAg) levels in the serum of an individual to determine an individual's response to administration of the antisense compound. An individual's response to administration of the antisense compound is used by a physician to determine the amount and duration of therapeutic intervention.

In certain embodiments, administration of an antisense compound targeted to an HBV nucleic acid results in reduction of HBV expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to an HBV nucleic acid results in reduced symptoms associated with the HBV-related condition and reduced HBV-related markers in the blood. In certain embodiments, administration of an HBV antisense compound decreases HBV RNA levels, HBV DNA levels, HBV protein levels, HBsAg levels, or HBeAg levels by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to HBV are used for the preparation of a medicament for treating a patient suffering or susceptible to an HBV-related condition.

Certain Combination Therapies

In certain embodiments, one or more pharmaceutical compositions provided herein are co-administered with one or more other pharmaceutical agents. In certain embodiments, such one or more other pharmaceutical agents are designed to treat the same disease, disorder, or condition as the one or more pharmaceutical compositions provided herein. In certain embodiments, such one or more other pharmaceutical agents are designed to treat a different disease, disorder, or condition as the one or more pharmaceutical compositions provided herein. In certain embodiments, such one or more other pharmaceutical agents are designed to treat an undesired side effect of one or more pharmaceutical compositions provided herein. In certain embodiments, one or more pharmaceutical compositions provided herein are co-administered with another pharmaceutical agent to treat an undesired effect of that other pharmaceutical agent. In certain embodiments, one or more pharmaceutical compositions provided herein are co-administered with another pharmaceutical agent to produce a combinational effect. In certain embodiments, one or more pharmaceutical compositions provided herein are co-administered with another pharmaceutical agent to produce a synergistic effect.

In certain embodiments, one or more pharmaceutical compositions provided herein and one or more other pharmaceutical agents are administered at the same time. In certain embodiments, one or more pharmaceutical compositions provided herein and one or more other pharmaceutical agents are administered at different times. In certain embodiments, one or more pharmaceutical compositions provided herein and one or more other pharmaceutical agents are prepared together in a single formulation. In certain embodiments, one or more pharmaceutical compositions provided herein and one or more other pharmaceutical agents are prepared separately. In certain embodiments the antisense oligonucleotides disclosed is administered in combination with an HCV agent. In further embodiments, the HCV compound is administered simultaneously as the antisense compound; in other embodiments, the HCV compound is administered separately; so that a dose of each of the HCV agent and the antisense compound overlap, in time, within the patient's body. In related embodiments, the HCV agent may be selected from interferon alpha-2b, interferon alpha-2a, and interferon alphacon-1 (pegylated and unpegylated); ribavirin; an HCV RNA replication inhibitor (e.g., ViroPharma's VP50406 series); an HCV antisense agent; an HCV therapeutic vaccine; an HCV protease inhibitor; an HCV helicase inhibitor; and an HCV antibody therapy (monoclonal or polyclonal).

In other embodiments, an HBV antisense compound of the present invention may be administered to a patient infected with HBV, in combination with one or more HBV therapeutic agents, wherein the one or more HBV therapeutic agents may be administered in the same drug formulation as the HBV ASO compound, or may be administered in a separate formulation. The one or more HBV therapeutic agents may be administered simultaneously with the ASO HBV compound, or may be administered separately, so that a dose of each of the HBV ASO compound and the HBV therapeutic agent overlap, in time, within the patient's body. In related embodiments, the one or more HBV therapeutic agent may be selected from interferon alpha-2b, interferon alpha-2a, and interferon alphacon-1 (pegylated and unpegylated), ribavirin; an HBV RNA replication inhibitor; a second HBV antisense compound; an HBV therapeutic vaccine; an HBV prophylactic vaccine; lamivudine (3TC); entecavir; tenofovir; telbivudine (LdT); adefovir; and an HBV antibody therapy (monoclonal or polyclonal).

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of HBV Viral mRNA in HepG2.2.15 Cells by MOE Gapmers

Antisense oligonucleotides were designed targeting a HBV viral nucleic acid and were tested for their effects on HBV mRNA in vitro. Cultured HepG2.2.15 cells at a density of 25,000 cells per well were transfected using electroporation with 15,000 nM antisense oligonucleotide. After a treatment period of approximately 24 hours, RNA was isolated from the cells and HBV mRNA levels were measured by quantitative real-time PCR. Viral primer probe set RTS3370 (forward sequence CTTGGTCATGGGCCATCAG, designated herein as SEQ ID NO: 2; reverse sequence CGGCTAG-GAGTTCCGCAGTA, designated herein as SEQ ID NO: 3; probe sequence TGCGTGGAACCTTTTCGGCTCC, designated herein as SEQ ID NO: 4) was used to measure mRNA levels. HBV mRNA levels were adjusted according to total RNA content, as measured by RIBOGREEN®. Results are presented as percent inhibition of HBV, relative to untreated control cells.

The newly designed chimeric antisense oligonucleotides in Table 1 were designed as either 5-10-5 MOE gapmers or 3-10-4 MOE gapmers. The 5-10-5 MOE gapmers are 20 nucleosides in length, wherein the central gap segment comprises of ten 2'-deoxynucleosides and is flanked on both sides (in the 5' and 3' directions) by wings comprising five nucleosides each. The 3-10-4 MOE gapmers are 17 nucleosides in length, wherein the central gap segment comprises of ten 2'-deoxynucleosides and is flanked on both sides (in the 5' and 3' directions) by wings comprising three and 4 nucleosides respectively. Each nucleoside in the 5' wing segment and each nucleoside in the 3' wing segment has an MOE sugar modification. Each nucleoside in the central gap segment has a deoxy sugar modification. The internucleoside linkages throughout each gapmer are phosphorothioate (P=S) linkages. All cytosine residues throughout each gapmer are 5-methylcytosines.

"Viral Target start site" indicates the 5'-most nucleotide to which the gapmer is targeted in the viral gene sequence. "Viral Target stop site" indicates the 3'-most nucleotide to which the gapmer is targeted viral gene sequence. The 'Motif' column indicates the gap and wing structure of each gapmer. Each gapmer listed in Table 1 is targeted to the viral genomic sequence, designated herein as SEQ ID NO: 1 (GENBANK Accession No. U95551.1).

TABLE 1

Inhibition of viral HBV mRNA levels by MOE gapmers targeted to SEQ ID NO: 1

| Viral Start Site | Viral Stop Site | ISIS No | Sequence | Motif | % inhibition | SEQ ID NO |
|---|---|---|---|---|---|---|
| 245 | 261 | 510088 | CCACGAGTCTAGACTCT | 3-10-4 | 55 | 5 |
| 250 | 266 | 510089 | GTCCACCACGAGTCTAG | 3-10-4 | 59 | 6 |
| 251 | 267 | 510090 | AGTCCACCACGAGTCTA | 3-10-4 | 60 | 7 |
| 252 | 268 | 510091 | AAGTCCACCACGAGTCT | 3-10-4 | 47 | 8 |
| 253 | 269 | 510092 | GAAGTCCACCACGAGTC | 3-10-4 | 59 | 9 |
| 254 | 270 | 510093 | AGAAGTCCACCACGAGT | 3-10-4 | 32 | 10 |
| 255 | 271 | 510094 | GAGAAGTCCACCACGAG | 3-10-4 | 41 | 11 |
| 256 | 272 | 510095 | AGAGAAGTCCACCACGA | 3-10-4 | 44 | 12 |
| 257 | 273 | 510096 | GAGAGAAGTCCACCACG | 3-10-4 | 54 | 13 |
| 258 | 274 | 510097 | TGAGAGAAGTCCACCAC | 3-10-4 | 57 | 14 |
| 384 | 400 | 510098 | TGATAAAACGCCGCAGA | 3-10-4 | 55 | 15 |
| 385 | 401 | 510099 | ATGATAAAACGCCGCAG | 3-10-4 | 59 | 16 |
| 411 | 427 | 510100 | GGCATAGCAGCAGGATG | 3-10-4 | 85 | 17 |
| 412 | 428 | 510101 | AGGCATAGCAGCAGGAT | 3-10-4 | 51 | 18 |
| 413 | 429 | 510102 | GAGGCATAGCAGCAGGA | 3-10-4 | 69 | 19 |
| 414 | 433 | 505330 | AGATGAGGCATAGCAGCAGG | 5-10-5 | 74 | 20 |
| 414 | 430 | 510103 | TGAGGCATAGCAGCAGG | 3-10-4 | 12 | 21 |
| 415 | 434 | 509928 | AAGATGAGGCATAGCAGCAG | 5-10-5 | 71 | 22 |
| 415 | 431 | 510104 | ATGAGGCATAGCAGCAG | 3-10-4 | 69 | 23 |
| 416 | 435 | 509929 | GAAGATGAGGCATAGCAGCA | 5-10-5 | 78 | 24 |
| 416 | 432 | 510105 | GATGAGGCATAGCAGCA | 3-10-4 | 69 | 25 |
| 417 | 436 | 509930 | AGAAGATGAGGCATAGCAGC | 5-10-5 | 72 | 26 |
| 417 | 433 | 510106 | AGATGAGGCATAGCAGC | 3-10-4 | 77 | 27 |
| 418 | 437 | 146783 | AAGAAGATGAGGCATAGCAG | 5-10-5 | 15 | 28 |
| 418 | 434 | 510107 | AAGATGAGGCATAGCAG | 3-10-4 | 69 | 29 |
| 419 | 435 | 510108 | GAAGATGAGGCATAGCA | 3-10-4 | 59 | 30 |
| 420 | 436 | 510109 | AGAAGATGAGGCATAGC | 3-10-4 | 0 | 31 |
| 421 | 437 | 510110 | AAGAAGATGAGGCATAG | 3-10-4 | 38 | 32 |
| 457 | 473 | 510111 | ACGGGCAACATACCTTG | 3-10-4 | 62 | 33 |
| 639 | 658 | 146784 | CTGAGGCCCACTCCCATAGG | 5-10-5 | 5 | 34 |
| 639 | 655 | 510112 | AGGCCCACTCCCATAGG | 3-10-4 | 44 | 35 |
| 640 | 656 | 510113 | GAGGCCCACTCCCATAG | 3-10-4 | 27 | 36 |

TABLE 1-continued

Inhibition of viral HBV mRNA levels by MOE gapmers targeted to SEQ ID NO: 1

| Viral Start Site | Viral Stop Site | ISIS No | Sequence | Motif | % inhibition | SEQ ID NO |
|---|---|---|---|---|---|---|
| 641 | 657 | 510114 | TGAGGCCCACTCCCATA | 3-10-4 | 44 | 37 |
| 642 | 658 | 510115 | CTGAGGCCCACTCCCAT | 3-10-4 | 52 | 38 |
| 687 | 706 | 509931 | CGAACCACTGAACAAATGGC | 5-10-5 | 89 | 39 |
| 687 | 703 | 510116 | ACCACTGAACAAATGGC | 3-10-4 | 89 | 40 |
| 688 | 704 | 510117 | AACCACTGAACAAATGG | 3-10-4 | 69 | 41 |
| 689 | 705 | 510118 | GAACCACTGAACAAATG | 3-10-4 | 63 | 42 |
| 690 | 706 | 510119 | CGAACCACTGAACAAAT | 3-10-4 | 74 | 43 |
| 738 | 754 | 510120 | ACCACATCATCCATATA | 3-10-4 | 71 | 44 |
| 1176 | 1192 | 510121 | TCAGCAAACACTTGGCA | 3-10-4 | 73 | 45 |
| 1778 | 1797 | 509932 | AATTTATGCCTACAGCCTCC | 5-10-5 | 76 | 46 |
| 1778 | 1794 | 510122 | TTATGCCTACAGCCTCC | 3-10-4 | 76 | 47 |
| 1779 | 1798 | 509933 | CAATTTATGCCTACAGCCTC | 5-10-5 | 72 | 48 |
| 1779 | 1795 | 510123 | TTTATGCCTACAGCCTC | 3-10-4 | 75 | 49 |
| 1780 | 1799 | 509934 | CCAATTTATGCCTACAGCCT | 5-10-5 | 75 | 50 |
| 1780 | 1796 | 510124 | ATTTATGCCTACAGCCT | 3-10-4 | 73 | 51 |
| 1781 | 1800 | 509935 | ACCAATTTATGCCTACAGCC | 5-10-5 | 72 | 52 |
| 1781 | 1797 | 510125 | AATTTATGCCTACAGCC | 3-10-4 | 69 | 53 |
| 1782 | 1798 | 510126 | CAATTTATGCCTACAGC | 3-10-4 | 59 | 54 |
| 1783 | 1799 | 510127 | CCAATTTATGCCTACAG | 3-10-4 | 58 | 55 |
| 1784 | 1800 | 510128 | ACCAATTTATGCCTACA | 3-10-4 | 60 | 56 |
| 1822 | 1838 | 510129 | AGGCAGAGGTGAAAAAG | 3-10-4 | 47 | 57 |
| 1823 | 1839 | 510130 | TAGGCAGAGGTGAAAAA | 3-10-4 | 30 | 58 |
| 1865 | 1884 | 509936 | GCACAGCTTGGAGGCTTGAA | 5-10-5 | 39 | 59 |
| 1865 | 1881 | 510131 | CAGCTTGGAGGCTTGAA | 3-10-4 | 4 | 60 |
| 1866 | 1885 | 509937 | GGCACAGCTTGGAGGCTTGA | 5-10-5 | 35 | 61 |
| 1866 | 1882 | 510132 | ACAGCTTGGAGGCTTGA | 3-10-4 | 0 | 62 |
| 1867 | 1886 | 505370 | AGGCACAGCTTGGAGGCTTG | 5-10-5 | 36 | 63 |
| 1867 | 1883 | 510133 | CACAGCTTGGAGGCTTG | 3-10-4 | 12 | 64 |
| 1868 | 1887 | 509938 | AAGGCACAGCTTGGAGGCTT | 5-10-5 | 7 | 65 |
| 1868 | 1884 | 510134 | GCACAGCTTGGAGGCTT | 3-10-4 | 20 | 66 |
| 1869 | 1888 | 509939 | CAAGGCACAGCTTGGAGGCT | 5-10-5 | 36 | 67 |
| 1869 | 1885 | 510135 | GGCACAGCTTGGAGGCT | 3-10-4 | 22 | 68 |
| 1870 | 1889 | 505371 | CCAAGGCACAGCTTGGAGGC | 5-10-5 | 35 | 69 |
| 1870 | 1886 | 510136 | AGGCACAGCTTGGAGGC | 3-10-4 | 14 | 70 |

TABLE 1-continued

Inhibition of viral HBV mRNA levels by MOE gapmers targeted to SEQ ID NO: 1

| Viral Start Site | Viral Stop Site | ISIS No | Sequence | Motif | % inhibition | SEQ ID NO |
|---|---|---|---|---|---|---|
| 1871 | 1887 | 510137 | AAGGCACAGCTTGGAGG | 3-10-4 | 0 | 71 |
| 1872 | 1888 | 510138 | CAAGGCACAGCTTGGAG | 3-10-4 | 6 | 72 |
| 1873 | 1889 | 510139 | CCAAGGCACAGCTTGGA | 3-10-4 | 17 | 73 |
| 1918 | 1934 | 510140 | GCTCCAAATTCTTTATA | 3-10-4 | 59 | 74 |
| 2378 | 2397 | 509940 | TCTGCGAGGCGAGGGAGTTC | 3-10-4 | 10 | 75 |
| 2378 | 2394 | 510141 | GCGAGGCGAGGGAGTTC | 3-10-4 | 5 | 76 |
| 2379 | 2395 | 510142 | TGCGAGGCGAGGGAGTT | 3-10-4 | 0 | 77 |
| 2380 | 2396 | 510143 | CTGCGAGGCGAGGGAGT | 3-10-4 | 8 | 78 |
| 2381 | 2397 | 510144 | TCTGCGAGGCGAGGGAG | 3-10-4 | 17 | 79 |
| 2820 | 2836 | 510145 | TTCCCAAGAATATGGTG | 3-10-4 | 22 | 80 |
| 2821 | 2837 | 510146 | GTTCCCAAGAATATGGT | 3-10-4 | 11 | 81 |
| 2822 | 2838 | 510147 | TGTTCCCAAGAATATGG | 3-10-4 | 21 | 82 |

Example 2

Antisense Inhibition of HBV Viral mRNA in HepG2.2.15 Cells by MOE Gapmers

Additional antisense oligonucleotides were designed targeting a HBV viral nucleic acid and were tested for their effects on HBV mRNA in vitro. Cultured HepG2.2.15 cells at a density of 25,000 cells per well were transfected using electroporation with 15,000 nM antisense oligonucleotide. After a treatment period of approximately 24 hours, RNA was isolated from the cells and HBV mRNA levels were measured by quantitative real-time PCR. Viral primer probe set RTS3370 was used to measure mRNA levels. RTS3370 detects the full length mRNA and the second portions of the pre-S1, pre-S2 and pre-C mRNA transcripts. The gapmers were also probed with additional primer probe sets. Viral primer probe set RTS3371 (forward sequence CCAAACCTTCGGACGGAAA, designated herein as SEQ ID NO: 311; reverse sequence TGAGGCCCACTCCCATAGG, designated herein as SEQ ID NO: 312; probe sequence CCCATCATCCTGGGCTTTCGGAAAAT, designated herein as SEQ ID NO: 313) was used also to measure mRNA levels. RTS3371 detects the full length mRNA and the second portions of the pre-S1, pre-S2 and pre-C mRNA transcripts, similar to RTS3370, but at different regions. Viral primer probe set RTS3372 (forward sequence ATCCTATCAACACTTCCGGAAACT, designated herein as SEQ ID NO: 314; reverse sequence CGACGCGGCGATTGAG, designated herein as SEQ ID NO: 315; probe sequence AAGAACTCCCTCGCCTCGCAGACG, designated herein as SEQ ID NO: 316) was used to measure mRNA levels. RTS3372 detects the full length genomic sequence. Viral primer probe set RTS3373MGB (forward sequence CCGACCTTGAGGCATACTTCA, designated herein as SEQ ID NO: 317; reverse sequence AATTTATGCCTACAGCCTCCTAGTACA, designated herein as SEQ ID NO: 318; probe sequence TTAAAGACTGGGAGGAGTTG, designated herein as SEQ ID NO: 319) was used to measure mRNA levels. RTS3373MGB detects the full length mRNA and the second portions of the pre-S1, pre-S2, pre-C, and pre-X mRNA transcripts.

HBV mRNA levels were adjusted according to total RNA content, as measured by RIBOGREEN®. Results are presented as percent inhibition of HBV, relative to untreated control cells.

The newly designed chimeric antisense oligonucleotides in Table 2 were designed as either 5-10-5 MOE gapmers, 3-10-3 MOE gapmers, or 2-10-2 MOE gapmers. The 5-10-5 MOE gapmers are 20 nucleosides in length, wherein the central gap segment comprises of ten 2'-deoxynucleosides and is flanked on both sides (in the 5' and 3' directions) by wings comprising five nucleosides each. The 3-10-3 MOE gapmers are 16 nucleosides in length, wherein the central gap segment comprises of ten 2'-deoxynucleosides and is flanked on both sides (in the 5' and 3' directions) by wings comprising three nucleosides each. The 2-10-2 MOE gapmers are 14 nucleosides in length, wherein the central gap segment comprises of ten 2'-deoxynucleosides and is flanked on both sides (in the 5' and 3' directions) by wings comprising two nucleosides each. Each nucleoside in the 5' wing segment and each nucleoside in the 3' wing segment has an MOE sugar modification. Each nucleoside in the central gap segment has a deoxy sugar modification. The internucleoside linkages throughout each gapmer are phosphorothioate (P=S) linkages. All cytosine residues throughout each gapmer are 5'-methylcytosines.

"Start site" indicates the 5'-most nucleotide to which the gapmer is targeted in the viral gene sequence. "Stop site" indicates the 3'-most nucleotide to which the gapmer is targeted viral gene sequence. The 'Motif' column indicates the gap and wing structure of each gapmer. Each gapmer listed in Table 2 is targeted to the viral genomic sequence, designated herein as SEQ ID NO: 1 (GENBANK Accession No. U95551.1).

TABLE 2

Inhibition of viral HBV mRNA levels by MOE gapmers targeted to SEQ ID NO: 1
(detected by RTS3370, RTS3371, RTS3372, and RTS3373MGB)

| Start Site | Stop Site | ISIS No | Sequence | RTS3370 % inhibition | RTS3371 % inhibition | RTS3372 % inhibition | RTS3373 MGB % inhibition | Motif | SEQ ID NO |
|---|---|---|---|---|---|---|---|---|---|
| 58 | 77 | 146779 | GAACTGGAGCCACCAGCAGG | 76 | 80 | 82 | 81 | 5-10-5 | 83 |
| 58 | 71 | 510019 | GAGCCACCAGCAGG | 38 | 32 | 45 | 31 | 2-10-2 | 84 |
| 61 | 80 | 505314 | CCTGAACTGGAGCCACCAGC | 68 | 71 | 67 | 66 | 5-10-5 | 85 |
| 62 | 77 | 509941 | GAACTGGAGCCACCAG | 36 | 32 | 71 | 53 | 3-10-3 | 86 |
| 196 | 215 | 505315 | AAAAACCCCGCCTGTAACAC | 69 | 74 | 80 | 88 | 5-10-5 | 87 |
| 199 | 218 | 505316 | AAGAAAAACCCCGCCTGTAA | 60 | 60 | 64 | 64 | 5-10-5 | 88 |
| 205 | 224 | 505317 | GTCAACAAGAAAACCCCGC | 85 | 83 | 79 | 85 | 5-10-5 | 89 |
| 228 | 241 | 510020 | GTATTGTGAGGATT | 28 | 18 | 0 | 16 | 2-10-2 | 90 |
| 229 | 242 | 510021 | GGTATTGTGAGGAT | 40 | 37 | 19 | 34 | 2-10-2 | 91 |
| 244 | 263 | 146821 | CACCACGAGTCTAGACTCTG | 74 | 73 | 62 | 75 | 5-10-5 | 92 |
| 245 | 260 | 509942 | CACGAGTCTAGACTCT | 18 | 15 | 45 | 46 | 3-10-3 | 93 |
| 245 | 258 | 510022 | CGAGTCTAGACTCT | 32 | 26 | 23 | 19 | 2-10-2 | 94 |
| 246 | 261 | 509943 | CCACGAGTCTAGACTC | 34 | 35 | 63 | 60 | 3-10-3 | 95 |
| 247 | 266 | 505318 | GTCCACCACGAGTCTAGACT | 75 | 77 | 64 | 75 | 5-10-5 | 96 |
| 250 | 269 | 509921 | GAAGTCCACCACGAGTCTAG | 46 | 46 | 39 | 40 | 5-10-5 | 97 |
| 250 | 265 | 509944 | TCCACCACGAGTCTAG | 38 | 39 | 65 | 59 | 3-10-3 | 98 |
| 251 | 270 | 509922 | AGAAGTCCACCACGAGTCTA | 55 | 56 | 17 | 38 | 5-10-5 | 99 |
| 251 | 266 | 509945 | GTCCACCACGAGTCTA | 34 | 35 | 64 | 51 | 3-10-3 | 100 |
| 252 | 271 | 509923 | GAGAAGTCCACCACGAGTCT | 39 | 38 | 39 | 33 | 5-10-5 | 101 |
| 252 | 267 | 509946 | AGTCCACCACGAGTCT | 47 | 51 | 50 | 45 | 3-10-3 | 102 |
| 253 | 272 | 505319 | AGAGAAGTCCACCACGAGTC | 88 | 83 | 80 | 78 | 5-10-5 | 103 |

TABLE 2-continued

Inhibition of viral HBV mRNA levels by MOE gapmers targeted to SEQ ID NO: 1
(detected by RTS3370, RTS3371, RTS3372, and RTS3373MGB)

| Start Site | Stop Site | ISIS No | Sequence | RTS3370 % inhibition | RTS3371 % inhibition | RTS3372 % inhibition | RTS3373 MGB % inhibition | Motif | SEQ ID NO |
|---|---|---|---|---|---|---|---|---|---|
| 253 | 268 | 509947 | AAGTCCACCACGAGTC | 46 | 50 | 56 | 46 | 3-10-3 | 104 |
| 254 | 273 | 509924 | GAGAGAAGTCCACCACGAGT | 43 | 40 | 49 | 44 | 5-10-5 | 105 |
| 254 | 269 | 509948 | GAAGTCCACCACGAGT | 41 | 46 | 51 | 44 | 3-10-3 | 106 |
| 254 | 267 | 510023 | AGTCCACCACGAGT | 41 | 32 | 47 | 48 | 2-10-2 | 107 |
| 255 | 274 | 509925 | TGAGAGAAGTCCACCACGAG | 50 | 57 | 55 | 55 | 5-10-5 | 108 |
| 255 | 270 | 509949 | AGAAGTCCACCACGAG | 40 | 41 | 52 | 34 | 3-10-3 | 109 |
| 255 | 268 | 510024 | AAGTCCACCACGAG | 26 | 29 | 19 | 23 | 2-10-2 | 110 |
| 256 | 275 | 505320 | TTGAGAGAAGTCCACCACGA | 51 | 57 | 55 | 66 | 5-10-5 | 111 |
| 256 | 271 | 509950 | GAGAAGTCCACCACGA | 30 | 31 | 43 | 33 | 3-10-3 | 112 |
| 256 | 269 | 510025 | GAAGTCCACCACGA | 44 | 38 | 53 | 54 | 2-10-2 | 113 |
| 257 | 270 | 510026 | AGAAGTCCACCACG | 39 | 42 | 32 | 25 | 2-10-2 | 114 |
| 258 | 273 | 509952 | GAGAGAAGTCCACCAC | 54 | 52 | 60 | 48 | 3-10-3 | 115 |
| 258 | 271 | 510027 | GAGAAGTCCACCAC | 29 | 30 | 25 | 19 | 2-10-2 | 116 |
| 259 | 274 | 509953 | TGAGAGAAGTCCACCA | 39 | 44 | 47 | 38 | 3-10-3 | 117 |
| 259 | 272 | 510028 | AGAGAAGTCCACCA | 31 | 29 | 3 | 15 | 2-10-2 | 118 |
| 260 | 273 | 510029 | GAGAGAAGTCCACC | 21 | 19 | 23 | 18 | 2-10-2 | 119 |
| 261 | 274 | 510030 | TGAGAGAAGTCCAC | 16 | 22 | 21 | 20 | 2-10-2 | 120 |
| 262 | 281 | 505321 | AGAAAATTGAGAGAAGTCCA | 53 | 58 | 52 | 56 | 5-10-5 | 121 |
| 265 | 284 | 505322 | CCTAGAAAATTGAGAGAAGT | 62 | 65 | 69 | 67 | 5-10-5 | 122 |
| 293 | 312 | 505323 | ATTTTGGCCAAGACACACGG | 86 | 84 | 81 | 85 | 5-10-5 | 123 |
| 296 | 315 | 505324 | CGAATTTTGGCCAAGACACA | 67 | 67 | 69 | 64 | 5-10-5 | 124 |

TABLE 2-continued

Inhibition of viral HBV mRNA levels by MOE gapmers targeted to SEQ ID NO: 1
(detected by RTS3370, RTS3371, RTS3372, and RTS3373MGB)

| Start Site | Stop Site | ISIS No | Sequence | RTS3370 % inhibition | RTS3371 % inhibition | RTS3372 % inhibition | RTS3373 MGB % inhibition | Motif | SEQ ID NO |
|---|---|---|---|---|---|---|---|---|---|
| 302 | 321 | 505325 | GGACTGCGAATTTTGGCCAA | 77 | 75 | 73 | 76 | 5-10-5 | 125 |
| 360 | 379 | 505326 | TCCAGCGATAACCAGGACAA | 89 | 90 | 77 | 91 | 5-10-5 | 126 |
| 366 | 385 | 505327 | GACACATCCAGCGATAACCA | 83 | 85 | 75 | 86 | 5-10-5 | 127 |
| 369 | 388 | 505328 | GCAGACACATCCAGCGATAA | 65 | 68 | 49 | 57 | 5-10-5 | 128 |
| 384 | 399 | 509954 | GATAAAACGCCGCAGA | 37 | 46 | 53 | 35 | 3-10-3 | 129 |
| 384 | 397 | 510031 | TAAAACGCCGCAGA | 36 | 36 | 33 | 33 | 2-10-2 | 130 |
| 385 | 398 | 510032 | ATAAAACGCCGCAG | 12 | 7 | 19 | 15 | 2-10-2 | 131 |
| 386 | 401 | 509955 | ATGATAAAACGCCGCA | 49 | 55 | 57 | 53 | 3-10-3 | 132 |
| 386 | 399 | 510033 | GATAAAACGCCGCA | 39 | 39 | 45 | 37 | 2-10-2 | 133 |
| 387 | 400 | 510034 | TGATAAAACGCCGC | 40 | 37 | 29 | 39 | 2-10-2 | 134 |
| 388 | 401 | 510035 | ATGATAAAACGCCG | 22 | 24 | 9 | 22 | 2-10-2 | 135 |
| 411 | 430 | 505329 | TGAGGCATAGCAGCAGGATG | 60 | 64 | 47 | 55 | 5-10-5 | 136 |
| 411 | 426 | 509956 | GCATAGCAGCAGGATG | 62 | 64 | 71 | 60 | 3-10-3 | 137 |
| 411 | 424 | 510036 | ATAGCAGCAGGATG | 44 | 34 | 30 | 48 | 2-10-2 | 138 |
| 412 | 431 | 509926 | ATGAGGCATAGCAGCAGGAT | 45 | 54 | 71 | 62 | 5-10-5 | 139 |
| 412 | 427 | 509957 | GGCATAGCAGCAGGAT | 72 | 75 | 80 | 71 | 3-10-3 | 140 |
| 412 | 425 | 510037 | CATAGCAGCAGGAT | 29 | 24 | 24 | 20 | 2-10-2 | 141 |
| 413 | 432 | 509927 | GATGAGGCATAGCAGCAGGA | 54 | 58 | 54 | 49 | 5-10-5 | 142 |
| 413 | 428 | 509958 | AGGCATAGCAGCAGGA | 63 | 66 | 68 | 64 | 3-10-3 | 143 |
| 413 | 426 | 510038 | GCATAGCAGCAGGA | 55 | 54 | 37 | 46 | 2-10-2 | 144 |
| 414 | 433 | 505330 | AGATGAGGCATAGCAGCAGG | 85 | 87 | 74 | 82 | 5-10-5 | 20 |

TABLE 2-continued

Inhibition of viral HBV mRNA levels by MOE gapmers targeted to SEQ ID NO: 1
(detected by RTS3370, RTS3371, RTS3372, and RTS3373MGB)

| Start Site | Stop Site | ISIS No | Sequence | RTS3370 % inhibition | RTS3371 % inhibition | RTS3372 % inhibition | RTS3373 MGB % inhibition | Motif | SEQ ID NO |
|---|---|---|---|---|---|---|---|---|---|
| 414 | 429 | 509959 | GAGGCATAGCAGCAGG | 64 | 64 | 80 | 68 | 3-10-3 | 145 |
| 414 | 427 | 510039 | GGCATAGCAGCAGG | 58 | 54 | 41 | 45 | 2-10-2 | 146 |
| 415 | 430 | 509960 | TGAGGCATAGCAGCAG | 59 | 59 | 66 | 64 | 3-10-3 | 147 |
| 415 | 428 | 510040 | AGGCATAGCAGCAG | 58 | 55 | 38 | 41 | 2-10-2 | 148 |
| 416 | 431 | 509961 | ATGAGGCATAGCAGCA | 56 | 54 | 65 | 56 | 3-10-3 | 149 |
| 416 | 429 | 510041 | GAGGCATAGCAGCA | 64 | 62 | 64 | 57 | 2-10-2 | 150 |
| 417 | 432 | 509962 | GATGAGGCATAGCAGC | 57 | 52 | 58 | 49 | 3-10-3 | 151 |
| 417 | 430 | 510042 | TGAGGCATAGCAGC | 48 | 50 | 55 | 48 | 2-10-2 | 152 |
| 418 | 433 | 509963 | AGATGAGGCATAGCAG | 50 | 52 | 64 | 51 | 3-10-3 | 153 |
| 418 | 431 | 510043 | ATGAGGCATAGCAG | 36 | 31 | 36 | 26 | 2-10-2 | 154 |
| 419 | 434 | 509964 | AAGATGAGGCATAGCA | 48 | 47 | 72 | 65 | 3-10-3 | 155 |
| 419 | 432 | 510044 | GATGAGGCATAGCA | 44 | 28 | 0 | 14 | 2-10-2 | 156 |
| 420 | 435 | 509965 | GAAGATGAGGCATAGC | 45 | 41 | 65 | 62 | 3-10-3 | 157 |
| 420 | 433 | 510045 | AGATGAGGCATAGC | 41 | 43 | 37 | 29 | 2-10-2 | 158 |
| 421 | 436 | 509966 | AGAAGATGAGGCATAG | 32 | 29 | 64 | 51 | 3-10-3 | 159 |
| 421 | 434 | 510046 | AAGATGAGGCATAG | 21 | 18 | 26 | 27 | 2-10-2 | 160 |
| 422 | 437 | 509967 | AAGAAGATGAGGCATA | 21 | 17 | 55 | 46 | 3-10-3 | 161 |
| 422 | 435 | 510047 | GAAGATGAGGCATA | 25 | 24 | 23 | 25 | 2-10-2 | 162 |
| 423 | 436 | 510048 | AGAAGATGAGGCAT | 21 | 17 | 25 | 19 | 2-10-2 | 163 |
| 424 | 437 | 510049 | AAGAAGATGAGGCA | 17 | 11 | 38 | 27 | 2-10-2 | 164 |
| 454 | 473 | 505331 | ACGGGCAACATACCTTGATA | 55 | 57 | 65 | 60 | 5-10-5 | 165 |
| 457 | 476 | 505332 | CAAACGGGCAACATACCTTG | 73 | 77 | 77 | 74 | 5-10-5 | 166 |
| 457 | 472 | 509968 | CGGGCAACATACCTTG | 60 | 61 | 73 | 70 | 3-10-3 | 167 |

TABLE 2-continued

Inhibition of viral HBV mRNA levels by MOE gapmers targeted to SEQ ID NO: 1
(detected by RTS3370, RTS3371, RTS3372, and RTS3373MGB)

| Start Site | Stop Site | ISIS No | Sequence | RTS3370 % inhibition | RTS3371 % inhibition | RTS3372 % inhibition | RTS3373 MGB % inhibition | Motif | SEQ ID NO |
|---|---|---|---|---|---|---|---|---|---|
| 458 | 473 | 509969 | ACGGGCAACATACCTT | 58 | 63 | 64 | 58 | 3-10-3 | 168 |
| 458 | 471 | 510050 | GGGCAACATACCTT | 58 | 56 | 57 | 46 | 2-10-2 | 169 |
| 459 | 472 | 510051 | CGGGCAACATACCT | 49 | 43 | 47 | 37 | 2-10-2 | 170 |
| 460 | 473 | 510052 | ACGGGCAACATACC | 50 | 50 | 54 | 51 | 2-10-2 | 171 |
| 463 | 482 | 505333 | AGAGGACAAACGGGCAACAT | 64 | 68 | 64 | 71 | 5-10-5 | 172 |
| 466 | 485 | 505334 | ATTAGAGGACAAACGGGCAA | 59 | 62 | 42 | 69 | 5-10-5 | 173 |
| 472 | 491 | 505335 | CCTGGAATTAGAGGACAAAC | 78 | 81 | 73 | 86 | 5-10-5 | 174 |
| 475 | 494 | 505336 | GATCCTGGAATTAGAGGACA | 56 | 65 | 61 | 72 | 5-10-5 | 175 |
| 639 | 654 | 509970 | GGCCCACTCCCATAGG | 38 | 55 | 74 | 48 | 3-10-3 | 176 |
| 641 | 656 | 509971 | GAGGCCCACTCCCATA | 30 | 46 | 77 | 54 | 3-10-3 | 177 |
| 642 | 657 | 509972 | TGAGGCCCACTCCCAT | 58 | 57 | 84 | 66 | 3-10-3 | 178 |
| 643 | 658 | 509973 | CTGAGGCCCACTCCCA | 38 | 53 | 70 | 66 | 3-10-3 | 179 |
| 670 | 689 | 146823 | GGCACTAGTAAACTGAGCCA | 61 | 64 | 63 | 63 | 5-10-5 | 180 |
| 670 | 685 | 509974 | CTAGTAAACTGAGCCA | 71 | 71 | 78 | 80 | 3-10-3 | 181 |
| 670 | 683 | 510053 | AGTAAACTGAGCCA | 49 | 48 | 52 | 53 | 2-10-2 | 182 |
| 671 | 684 | 510054 | TAGTAAACTGAGCC | 41 | 38 | 19 | 30 | 2-10-2 | 183 |
| 672 | 685 | 510055 | CTAGTAAACTGAGC | 25 | 27 | 42 | 47 | 2-10-2 | 184 |
| 673 | 692 | 505337 | AATGGCACTAGTAAACTGAG | 34 | 46 | 49 | 52 | 5-10-5 | 185 |
| 679 | 698 | 505338 | TGAACAAATGGCACTAGTAA | 74 | 77 | 71 | 80 | 5-10-5 | 186 |
| 682 | 701 | 505339 | CACTGAACAAATGGCACTAG | 82 | 83 | 71 | 82 | 5-10-5 | 187 |
| 687 | 702 | 509975 | CCACTGAACAAATGGC | 72 | 73 | 76 | 80 | 3-10-3 | 188 |

TABLE 2-continued

Inhibition of viral HBV mRNA levels by MOE gapmers targeted to SEQ ID NO: 1
(detected by RTS3370, RTS3371, RTS3372, and RTS3373MGB)

| Start Site | Stop Site | ISIS No | Sequence | RTS3370 % inhibition | RTS3371 % inhibition | RTS3372 % inhibition | RTS3373 MGB % inhibition | Motif | SEQ ID NO |
|---|---|---|---|---|---|---|---|---|---|
| 688 | 707 | 505340 | ACGAACCACTGAACAAATGG | 69 | 69 | 78 | 76 | 5-10-5 | 189 |
| 688 | 703 | 509976 | ACCACTGAACAAATGG | 47 | 48 | 67 | 65 | 3-10-3 | 190 |
| 689 | 704 | 509977 | AACCACTGAACAAATG | 33 | 33 | 39 | 41 | 3-10-3 | 191 |
| 690 | 705 | 509978 | GAACCACTGAACAAAT | 50 | 49 | 63 | 48 | 3-10-3 | 192 |
| 691 | 710 | 505341 | CCTACGAACCACTGAACAAA | 64 | 70 | 70 | 72 | 5-10-5 | 193 |
| 691 | 706 | 509979 | CGAACCACTGAACAAA | 67 | 66 | 78 | 77 | 3-10-3 | 194 |
| 691 | 704 | 510056 | AACCACTGAACAAA | 36 | 36 | 23 | 32 | 2-10-2 | 195 |
| 692 | 705 | 510057 | GAACCACTGAACAA | 45 | 44 | 51 | 43 | 2-10-2 | 196 |
| 693 | 706 | 510058 | CGAACCACTGAACA | 59 | 52 | 48 | 49 | 2-10-2 | 197 |
| 697 | 716 | 505342 | GAAAGCCCTACGAACCACTG | 76 | 80 | 73 | 83 | 5-10-5 | 198 |
| 738 | 753 | 509980 | CCACATCATCCATATA | 40 | 33 | 62 | 54 | 3-10-3 | 199 |
| 738 | 751 | 510059 | ACATCATCCATATA | 19 | 9 | 30 | 27 | 2-10-2 | 200 |
| 739 | 754 | 509981 | ACCACATCATCCATAT | 76 | 78 | 93 | 85 | 3-10-3 | 201 |
| 739 | 752 | 510060 | CACATCATCCATAT | 45 | 35 | 24 | 17 | 2-10-2 | 202 |
| 740 | 753 | 510061 | CCACATCATCCATA | 52 | 49 | 43 | 40 | 2-10-2 | 203 |
| 741 | 754 | 510062 | ACCACATCATCCAT | 44 | 45 | 48 | 47 | 2-10-2 | 204 |
| 756 | 775 | 505343 | TGTACAGACTTGGCCCCCAA | 47 | 56 | 55 | 68 | 5-10-5 | 205 |
| 823 | 842 | 505344 | AGGGTTTAAATGTATACCCA | 66 | 71 | 64 | 72 | 5-10-5 | 206 |
| 1170 | 1189 | 505345 | GCAAACACTTGGCACAGACC | 76 | 80 | 35 | 70 | 5-10-5 | 207 |
| 1176 | 1191 | 509982 | CAGCAAACACTTGGCA | 42 | 44 | 56 | 54 | 3-10-3 | 208 |
| 1177 | 1192 | 509983 | TCAGCAAACACTTGGC | 60 | 54 | 74 | 70 | 3-10-3 | 209 |
| 1259 | 1278 | 505346 | CCGCAGTATGGATCGGCAGA | 88 | 82 | 57 | 80 | 5-10-5 | 210 |

TABLE 2-continued

Inhibition of viral HBV mRNA levels by MOE gapmers targeted to SEQ ID NO: 1
(detected by RTS3370, RTS3371, RTS3372, and RTS3373MGB)

| Start Site | Stop Site | ISIS No | Sequence | RTS3370 % inhibition | RTS3371 % inhibition | RTS3372 % inhibition | RTS3373 MGB % inhibition | Motif | SEQ ID NO |
|---|---|---|---|---|---|---|---|---|---|
| 1261 | 1276 | 509984 | GCAGTATGGATCGGCA | 61 | 58 | 65 | 72 | 3-10-3 | 211 |
| 1262 | 1281 | 505347 | GTTCCGCAGTATGGATCGGC | 84 | 81 | 71 | 83 | 5-10-5 | 212 |
| 1268 | 1287 | 505348 | CTAGGAGTTCCGCAGTATGG | 78 | 68 | 70 | 79 | 5-10-5 | 213 |
| 1271 | 1290 | 505349 | CGGCTAGGAGTTCCGCAGTA | 47 | 54 | 59 | 61 | 5-10-5 | 214 |
| 1277 | 1296 | 505350 | AACAAGCGGCTAGGAGTTCC | 55 | 62 | 69 | 69 | 5-10-5 | 215 |
| 1280 | 1299 | 505351 | CAAAACAAGCGGCTAGGAGT | 20 | 49 | 49 | 54 | 5-10-5 | 216 |
| 1283 | 1302 | 505352 | GAGCAAAACAAGCGGCTAGG | 53 | 83 | 73 | 87 | 5-10-5 | 217 |
| 1286 | 1305 | 505353 | TGCGAGCAAAACAAGCGGCT | 64 | 73 | 68 | 78 | 5-10-5 | 218 |
| 1413 | 1426 | 510063 | ACAAAGGACGTCCC | 14 | 8 | 0 | 0 | 2-10-2 | 219 |
| 1515 | 1534 | 505354 | GAGGTGCGCCCCGTGGTCGG | 68 | 81 | 61 | 80 | 5-10-5 | 220 |
| 1518 | 1537 | 505355 | AGAGAGGTGCGCCCCGTGGT | 59 | 75 | 75 | 84 | 5-10-5 | 221 |
| 1521 | 1540 | 505356 | TAAAGAGAGGTGCGCCCCGT | 63 | 76 | 83 | 78 | 5-10-5 | 222 |
| 1550 | 1563 | 510064 | AAGGCACAGACGGG | 35 | 38 | 25 | 32 | 2-10-2 | 223 |
| 1577 | 1596 | 146786 | GTGAAGCGAAGTGCACACGG | 88 | 91 | 84 | 93 | 5-10-5 | 224 |
| 1580 | 1599 | 505357 | GAGGTGAAGCGAAGTGCACA | 70 | 75 | 71 | 82 | 5-10-5 | 225 |
| 1583 | 1602 | 505358 | GCAGAGGTGAAGCGAAGTGC | 77 | 82 | 72 | 84 | 5-10-5 | 226 |
| 1586 | 1605 | 505359 | CGTGCAGAGGTGAAGCGAAG | 72 | 73 | 67 | 80 | 5-10-5 | 227 |
| 1655 | 1674 | 505360 | AGTCCAAGAGTCCTCTTATG | 66 | 68 | 54 | 68 | 5-10-5 | 228 |
| 1706 | 1719 | 510065 | CAGTCTTTGAAGTA | 19 | 19 | 26 | 17 | 2-10-2 | 229 |

TABLE 2-continued

Inhibition of viral HBV mRNA levels by MOE gapmers targeted to SEQ ID NO: 1
(detected by RTS3370, RTS3371, RTS3372, and RTS3373MGB)

| Start Site | Stop Site | ISIS No | Sequence | RTS3370 % inhibition | RTS3371 % inhibition | RTS3372 % inhibition | RTS3373 MGB % inhibition | Motif | SEQ ID NO |
|---|---|---|---|---|---|---|---|---|---|
| 1778 | 1793 | 509985 | TATGCCTACAGCCTCC | 64 | 60 | 64 | 63 | 3-10-3 | 230 |
| 1779 | 1794 | 509986 | TTATGCCTACAGCCTC | 66 | 66 | 77 | 73 | 3-10-3 | 231 |
| 1780 | 1795 | 509987 | TTTATGCCTACAGCCT | 56 | 55 | 68 | 67 | 3-10-3 | 232 |
| 1781 | 1796 | 509988 | ATTTATGCCTACAGCC | 52 | 52 | 68 | 63 | 3-10-3 | 233 |
| 1782 | 1797 | 509989 | AATTTATGCCTACAGC | 48 | 44 | 70 | 59 | 3-10-3 | 234 |
| 1783 | 1798 | 509990 | CAATTTATGCCTACAG | 24 | 18 | 39 | 40 | 3-10-3 | 235 |
| 1784 | 1799 | 509991 | CCAATTTATGCCTACA | 37 | 37 | 55 | 55 | 3-10-3 | 236 |
| 1785 | 1800 | 509992 | ACCAATTTATGCCTAC | 35 | 36 | 60 | 55 | 3-10-3 | 237 |
| 1806 | 1825 | 505361 | AAAGTTGCATGGTGCTGGTG | 42 | 55 | 75 | 61 | 5-10-5 | 238 |
| 1809 | 1828 | 505362 | GAAAAGTTGCATGGTGCTG | 45 | 56 | 64 | 53 | 5-10-5 | 239 |
| 1812 | 1831 | 505363 | GGTGAAAAAGTTGCATGGTG | 71 | 70 | 80 | 72 | 5-10-5 | 240 |
| 1815 | 1834 | 505364 | AGAGGTGAAAAAGTTGCATG | 51 | 57 | 77 | 82 | 5-10-5 | 241 |
| 1818 | 1837 | 505365 | GGCAGAGGTGAAAAAGTTGC | 54 | 63 | 76 | 78 | 5-10-5 | 242 |
| 1821 | 1840 | 505366 | TTAGGCAGAGGTGAAAAAGT | 61 | 65 | 80 | 66 | 5-10-5 | 243 |
| 1822 | 1837 | 509993 | GGCAGAGGTGAAAAAG | 47 | 51 | 74 | 54 | 3-10-3 | 244 |
| 1823 | 1838 | 509994 | AGGCAGAGGTGAAAAA | 47 | 40 | 76 | 54 | 3-10-3 | 245 |
| 1824 | 1843 | 505367 | TGATTAGGCAGAGGTGAAAA | 41 | 39 | 62 | 29 | 5-10-5 | 246 |
| 1824 | 1839 | 509995 | TAGGCAGAGGTGAAAA | 46 | 42 | 79 | 59 | 3-10-3 | 247 |
| 1826 | 1839 | 510066 | TAGGCAGAGGTGAA | 40 | 33 | 44 | 31 | 2-10-2 | 248 |
| 1827 | 1846 | 505368 | AGATGATTAGGCAGAGGTGA | 27 | 46 | 62 | 51 | 5-10-5 | 249 |
| 1861 | 1880 | 146787 | AGCTTGGAGGCTTGAACAGT | 59 | 61 | 65 | 72 | 5-10-5 | 250 |

TABLE 2-continued

Inhibition of viral HBV mRNA levels by MOE gapmers targeted to SEQ ID NO: 1
(detected by RTS3370, RTS3371, RTS3372, and RTS3373MGB)

| Start Site | Stop Site | ISIS No | Sequence | RTS3370 % inhibition | RTS3371 % inhibition | RTS3372 % inhibition | RTS3373 MGB % inhibition | Motif | SEQ ID NO |
|---|---|---|---|---|---|---|---|---|---|
| 1864 | 1883 | 505369 | CACAGCTTGGAGGCTTGAAC | 11 | 21 | 48 | 31 | 5-10-5 | 251 |
| 1865 | 1880 | 509996 | AGCTTGGAGGCTTGAA | 13 | 1 | 45 | 40 | 3-10-3 | 252 |
| 1865 | 1878 | 510067 | CTTGGAGGCTTGAA | 22 | 17 | 20 | 14 | 2-10-2 | 253 |
| 1866 | 1881 | 509997 | CAGCTTGGAGGCTTGA | 29 | 19 | 51 | 45 | 3-10-3 | 254 |
| 1866 | 1879 | 510068 | GCTTGGAGGCTTGA | 24 | 25 | 37 | 32 | 2-10-2 | 255 |
| 1867 | 1886 | 505370 | AGGCACAGCTTGGAGGCTTG | 32 | 36 | 58 | 33 | 5-10-5 | 63 |
| 1867 | 1882 | 509998 | ACAGCTTGGAGGCTTG | 1 | 4 | 23 | 12 | 3-10-3 | 256 |
| 1867 | 1880 | 510069 | AGCTTGGAGGCTTG | 23 | 24 | 17 | 23 | 2-10-2 | 257 |
| 1868 | 1883 | 509999 | CACAGCTTGGAGGCTT | 5 | 1 | 48 | 41 | 3-10-3 | 258 |
| 1868 | 1881 | 510070 | CAGCTTGGAGGCTT | 21 | 20 | 0 | 18 | 2-10-2 | 259 |
| 1869 | 1884 | 510000 | GCACAGCTTGGAGGCT | 14 | 10 | 50 | 37 | 3-10-3 | 260 |
| 1869 | 1882 | 510071 | ACAGCTTGGAGGCT | 19 | 22 | 24 | 27 | 2-10-2 | 261 |
| 1870 | 1889 | 505371 | CCAAGGCACAGCTTGGAGGC | 27 | 40 | 68 | 38 | 5-10-5 | 69 |
| 1870 | 1885 | 510001 | GGCACAGCTTGGAGGC | 10 | 12 | 43 | 16 | 3-10-3 | 262 |
| 1870 | 1883 | 510072 | CACAGCTTGGAGGC | 28 | 31 | 33 | 30 | 2-10-2 | 263 |
| 1871 | 1886 | 510002 | AGGCACAGCTTGGAGG | 24 | 20 | 46 | 25 | 3-10-3 | 264 |
| 1871 | 1884 | 510073 | GCACAGCTTGGAGG | 20 | 18 | 22 | 15 | 2-10-2 | 265 |
| 1872 | 1887 | 510003 | AAGGCACAGCTTGGAG | 6 | 0 | 45 | 24 | 3-10-3 | 266 |
| 1872 | 1885 | 510074 | GGCACAGCTTGGAG | 18 | 18 | 32 | 23 | 2-10-2 | 267 |
| 1873 | 1892 | 505372 | CACCCAAGGCACAGCTTGGA | 18 | 8 | 55 | 16 | 5-10-5 | 268 |
| 1873 | 1888 | 510004 | CAAGGCACAGCTTGGA | 9 | 0 | 31 | 15 | 3-10-3 | 269 |
| 1873 | 1886 | 510075 | AGGCACAGCTTGGA | 23 | 9 | 27 | 10 | 2-10-2 | 270 |
| 1874 | 1889 | 510005 | CCAAGGCACAGCTTGG | 0 | 0 | 39 | 25 | 3-10-3 | 271 |

TABLE 2-continued

Inhibition of viral HBV mRNA levels by MOE gapmers targeted to SEQ ID NO: 1
(detected by RTS3370, RTS3371, RTS3372, and RTS3373MGB)

| Start Site | Stop Site | ISIS No | Sequence | RTS3370 % inhibition | RTS3371 % inhibition | RTS3372 % inhibition | RTS3373 MGB % inhibition | Motif | SEQ ID NO |
|---|---|---|---|---|---|---|---|---|---|
| 1876 | 1895 | 505373 | AGCCACCCAAGGCACAGCTT | 47 | 50 | 69 | 56 | 5-10-5 | 272 |
| 1879 | 1898 | 505374 | CAAAGCCACCCAAGGCACAG | 27 | 27 | 55 | 30 | 5-10-5 | 273 |
| 1882 | 1901 | 505375 | CCCCAAAGCCACCCAAGGCA | 34 | 40 | 54 | 39 | 5-10-5 | 274 |
| 1885 | 1904 | 505376 | ATGCCCCAAAGCCACCCAAG | 41 | 43 | 54 | 52 | 5-10-5 | 275 |
| 1888 | 1907 | 505377 | TCCATGCCCCAAAGCCACCC | 40 | 42 | 72 | 40 | 5-10-5 | 276 |
| 1891 | 1910 | 505378 | ATGTCCATGCCCCAAAGCCA | 35 | 33 | 70 | 40 | 5-10-5 | 277 |
| 1918 | 1933 | 510006 | CTCCAAATTCTTTATA | 9 | 2 | 53 | 41 | 3-10-3 | 278 |
| 1918 | 1931 | 510076 | CCAAATTCTTTATA | 28 | 22 | 7 | 22 | 2-10-2 | 279 |
| 1919 | 1934 | 510007 | GCTCCAAATTCTTTAT | 43 | 39 | 72 | 57 | 3-10-3 | 280 |
| 1919 | 1932 | 510077 | TCCAAATTCTTTAT | 19 | 11 | 0 | 2 | 2-10-2 | 281 |
| 1920 | 1933 | 510078 | CTCCAAATTCTTTA | 19 | 11 | 0 | 0 | 2-10-2 | 282 |
| 1921 | 1934 | 510079 | GCTCCAAATTCTTT | 50 | 48 | 61 | 55 | 2-10-2 | 283 |
| 1957 | 1976 | 505379 | GGAAAGAAGTCAGAAGGCAA | 17 | 14 | 81 | 39 | 5-10-5 | 284 |
| 2270 | 2285 | 510008 | GTGCGAATCCACACTC | 21 | 4 | 36 | 11 | 3-10-3 | 285 |
| 2270 | 2283 | 510080 | GCGAATCCACACTC | 32 | 29 | 41 | 33 | 2-10-2 | 286 |
| 2271 | 2284 | 510081 | TGCGAATCCACACT | 28 | 20 | 25 | 11 | 2-10-2 | 287 |
| 2272 | 2285 | 510082 | GTGCGAATCCACAC | 28 | 20 | 32 | 22 | 2-10-2 | 288 |
| 2368 | 2387 | 505380 | GAGGGAGTTCTTCTTCTAGG | 24 | 22 | 90 | 48 | 5-10-5 | 289 |
| 2378 | 2393 | 510009 | CGAGGCGAGGGAGTTC | 12 | 1 | 65 | 10 | 3-10-3 | 290 |
| 2378 | 2391 | 510083 | AGGCGAGGGAGTTC | 17 | 18 | 29 | 25 | 2-10-2 | 291 |
| 2379 | 2394 | 510010 | GCGAGGCGAGGGAGTT | 18 | 13 | 82 | 37 | 3-10-3 | 292 |

TABLE 2-continued

Inhibition of viral HBV mRNA levels by MOE gapmers targeted to SEQ ID NO: 1
(detected by RTS3370, RTS3371, RTS3372, and RTS3373MGB)

| Start Site | Stop Site | ISIS No | Sequence | RTS3370 % inhibition | RTS3371 % inhibition | RTS3372 % inhibition | RTS3373 MGB % inhibition | Motif | SEQ ID NO |
|---|---|---|---|---|---|---|---|---|---|
| 2379 | 2392 | 510084 | GAGGCGAGGGAGTT | 29 | 22 | 54 | 30 | 2-10-2 | 293 |
| 2380 | 2395 | 510011 | TGCGAGGCGAGGGAGT | 13 | 11 | 69 | 44 | 3-10-3 | 294 |
| 2380 | 2393 | 510085 | CGAGGCGAGGGAGT | 25 | 20 | 53 | 42 | 2-10-2 | 295 |
| 2381 | 2396 | 510012 | CTGCGAGGCGAGGGAG | 17 | 14 | 79 | 53 | 3-10-3 | 296 |
| 2381 | 2394 | 510086 | GCGAGGCGAGGGAG | 33 | 29 | 66 | 48 | 2-10-2 | 297 |
| 2382 | 2397 | 510013 | TCTGCGAGGCGAGGGA | 18 | 4 | 77 | 47 | 3-10-3 | 298 |
| 2420 | 2439 | 505381 | CCGAGATTGAGATCTTCTGC | 12 | 18 | 83 | 28 | 5-10-5 | 299 |
| 2459 | 2478 | 505382 | CCCACCTTATGAGTCCAAGG | 14 | 19 | 80 | 36 | 5-10-5 | 300 |
| 2819 | 2838 | 505383 | TGTTCCCAAGAATATGGTGA | 29 | 32 | 78 | 44 | 5-10-5 | 301 |
| 2820 | 2835 | 510014 | TCCCAAGAATATGGTG | 10 | 10 | 68 | 40 | 3-10-3 | 302 |
| 2821 | 2836 | 510015 | TTCCCAAGAATATGGT | 5 | 0 | 62 | 24 | 3-10-3 | 303 |
| 2822 | 2837 | 510016 | GTTCCCAAGAATATGG | 6 | 2 | 42 | 16 | 3-10-3 | 304 |
| 2823 | 2838 | 510017 | TGTTCCCAAGAATATG | 18 | 18 | 47 | 18 | 3-10-3 | 305 |
| 2824 | 2839 | 510018 | TTGTTCCCAAGAATAT | 7 | 5 | 57 | 19 | 3-10-3 | 306 |
| 2825 | 2838 | 510087 | TGTTCCCAAGAATA | 25 | 20 | 44 | 25 | 2-10-2 | 307 |
| 2873 | 2892 | 505384 | GAAAGAATCCCAGAGGATTG | 8 | 4 | 61 | 22 | 5-10-5 | 308 |
| 3161 | 3180 | 146833 | ACTGCATGGCCTGAGGATGA | 47 | 46 | 82 | 54 | 5-10-5 | 309 |
| 3163 | 3182 | 505385 | CCACTGCATGGCCTGAGGAT | 25 | 34 | 69 | 19 | 5-10-5 | 310 |

Example 3

Antisense Inhibition of HBV Viral mRNA in HepAD38 (Tet-HBV) Cells by MOE Gapmers Certain antisense oligonucleotides selected from the study described in Example 2 were tested for their effects on HBV mRNA in another cell line, human hepatoma HepAD38 cells, in which HBV production is under the control of a tetracycline-regulated promoter. Cultured HepAD38 (Tet-HBV) cells at a density of 45,000 cells per well were transfected using electroporation with 15,000 nM antisense oligonucleotide. After a treatment period of approximately 24 hours, RNA was isolated from the cells and HBV mRNA levels were measured by quantitative real-time PCR. Viral primer probe sets RTS3372 and RTS3373MGB were used individually to measure mRNA levels. HBV mRNA levels were adjusted according to total RNA content, as measured by RIBOGREEN®. Results are presented in Table 3 as percent inhibition of HBV, relative to untreated control cells.

TABLE 3

Inhibition of viral HBV mRNA levels by MOE gapmers in HepAD38 (Tet-HBV) cells (detected by RTS3372 and RTS3373MGB)

| Start Site | Stop Site | ISIS No | Motif | RTS3373MGB % inhibition | RTS3372 % inhibition | SEQ ID NO |
|---|---|---|---|---|---|---|
| 58 | 77 | 146779 | 5-10-5 | 76 | 82 | 83 |
| 58 | 71 | 510019 | 5-10-5 | 0 | 9 | 84 |
| 61 | 80 | 505314 | 5-10-5 | 65 | 75 | 85 |
| 196 | 215 | 505315 | 5-10-5 | 46 | 65 | 87 |
| 199 | 218 | 505316 | 5-10-5 | 57 | 71 | 88 |
| 205 | 224 | 505317 | 5-10-5 | 83 | 87 | 89 |
| 228 | 241 | 510020 | 2-10-2 | 6 | 0 | 90 |
| 229 | 242 | 510021 | 2-10-2 | 19 | 24 | 91 |
| 244 | 263 | 146821 | 5-10-5 | 72 | 71 | 92 |
| 245 | 258 | 510022 | 2-10-2 | 6 | 24 | 94 |
| 247 | 266 | 505318 | 5-10-5 | 68 | 77 | 96 |
| 250 | 269 | 509921 | 5-10-5 | 25 | 47 | 97 |
| 251 | 270 | 509922 | 5-10-5 | 28 | 46 | 99 |
| 252 | 271 | 509923 | 5-10-5 | 19 | 40 | 101 |
| 253 | 272 | 505319 | 5-10-5 | 69 | 66 | 103 |
| 254 | 273 | 509924 | 5-10-5 | 9 | 39 | 105 |
| 254 | 267 | 510023 | 2-10-2 | 19 | 15 | 107 |
| 255 | 274 | 509925 | 5-10-5 | 26 | 55 | 108 |
| 255 | 268 | 510024 | 2-10-2 | 0 | 5 | 110 |
| 256 | 275 | 505320 | 5-10-5 | 62 | 68 | 111 |
| 256 | 269 | 510025 | 2-10-2 | 0 | 8 | 113 |
| 257 | 270 | 510026 | 2-10-2 | 7 | 21 | 114 |
| 258 | 271 | 510027 | 2-10-2 | 0 | 0 | 116 |
| 259 | 272 | 510028 | 2-10-2 | 0 | 0 | 118 |
| 260 | 273 | 510029 | 2-10-2 | 0 | 9 | 119 |
| 261 | 274 | 510030 | 2-10-2 | 0 | 0 | 120 |
| 262 | 281 | 505321 | 5-10-5 | 53 | 54 | 121 |
| 265 | 284 | 505322 | 5-10-5 | 59 | 60 | 122 |
| 293 | 312 | 505323 | 5-10-5 | 65 | 77 | 123 |
| 296 | 315 | 505324 | 5-10-5 | 78 | 83 | 124 |
| 302 | 321 | 505325 | 5-10-5 | 71 | 80 | 125 |
| 360 | 379 | 505326 | 5-10-5 | 76 | 84 | 126 |
| 366 | 385 | 505327 | 5-10-5 | 77 | 83 | 127 |
| 369 | 388 | 505328 | 5-10-5 | 65 | 78 | 128 |
| 384 | 397 | 510031 | 2-10-2 | 0 | 16 | 130 |
| 385 | 398 | 510032 | 2-10-2 | 0 | 0 | 131 |
| 386 | 399 | 510033 | 2-10-2 | 1 | 21 | 133 |
| 387 | 400 | 510034 | 2-10-2 | 8 | 28 | 134 |
| 388 | 401 | 510035 | 2-10-2 | 0 | 0 | 135 |
| 411 | 430 | 505329 | 5-10-5 | 58 | 72 | 136 |
| 411 | 424 | 510036 | 2-10-2 | 6 | 11 | 138 |
| 412 | 431 | 509926 | 5-10-5 | 20 | 54 | 139 |
| 412 | 425 | 510037 | 2-10-2 | 0 | 10 | 141 |
| 413 | 432 | 509927 | 5-10-5 | 56 | 76 | 142 |
| 413 | 426 | 510038 | 2-10-2 | 54 | 68 | 144 |
| 414 | 433 | 505330 | 5-10-5 | 66 | 81 | 20 |
| 414 | 427 | 510039 | 2-10-2 | 60 | 74 | 146 |
| 415 | 428 | 510040 | 2-10-2 | 33 | 39 | 148 |
| 416 | 429 | 510041 | 2-10-2 | 30 | 58 | 150 |
| 417 | 430 | 510042 | 2-10-2 | 34 | 57 | 152 |
| 418 | 431 | 510043 | 2-10-2 | 0 | 2 | 154 |
| 419 | 432 | 510044 | 2-10-2 | 0 | 29 | 156 |
| 420 | 433 | 510045 | 2-10-2 | 3 | 31 | 158 |
| 421 | 434 | 510046 | 2-10-2 | 0 | 0 | 160 |
| 422 | 435 | 510047 | 2-10-2 | 0 | 0 | 162 |
| 423 | 436 | 510048 | 2-10-2 | 0 | 0 | 163 |
| 424 | 437 | 510049 | 2-10-2 | 0 | 0 | 164 |
| 454 | 473 | 505331 | 5-10-5 | 60 | 77 | 165 |
| 457 | 476 | 505332 | 5-10-5 | 55 | 74 | 166 |
| 458 | 471 | 510050 | 2-10-2 | 47 | 47 | 169 |
| 459 | 472 | 510051 | 2-10-2 | 35 | 55 | 170 |
| 460 | 473 | 510052 | 2-10-2 | 27 | 41 | 171 |
| 463 | 482 | 505333 | 5-10-5 | 66 | 78 | 172 |
| 466 | 485 | 505334 | 5-10-5 | 53 | 63 | 173 |
| 472 | 491 | 505335 | 5-10-5 | 70 | 76 | 174 |
| 475 | 494 | 505336 | 5-10-5 | 64 | 77 | 175 |
| 670 | 689 | 146823 | 5-10-5 | 74 | 79 | 180 |
| 670 | 683 | 510053 | 2-10-2 | 18 | 20 | 182 |
| 671 | 684 | 510054 | 2-10-2 | 13 | 21 | 183 |
| 672 | 685 | 510055 | 2-10-2 | 4 | 2 | 184 |
| 673 | 692 | 505337 | 5-10-5 | 60 | 72 | 185 |
| 679 | 698 | 505338 | 5-10-5 | 62 | 75 | 186 |
| 682 | 701 | 505339 | 5-10-5 | 81 | 90 | 187 |
| 688 | 707 | 505340 | 5-10-5 | 67 | 81 | 189 |
| 691 | 710 | 505341 | 5-10-5 | 68 | 80 | 193 |
| 691 | 704 | 510056 | 2-10-2 | 0 | 0 | 195 |
| 692 | 705 | 510057 | 2-10-2 | 37 | 48 | 196 |
| 693 | 706 | 510058 | 2-10-2 | 44 | 59 | 197 |
| 697 | 716 | 505342 | 5-10-5 | 80 | 87 | 198 |
| 738 | 751 | 510059 | 2-10-2 | 0 | 0 | 200 |
| 739 | 752 | 510060 | 2-10-2 | 0 | 0 | 202 |
| 740 | 753 | 510061 | 2-10-2 | 23 | 19 | 203 |
| 741 | 754 | 510062 | 2-10-2 | 25 | 30 | 204 |
| 756 | 775 | 505343 | 5-10-5 | 62 | 71 | 205 |
| 823 | 842 | 505344 | 5-10-5 | 52 | 66 | 206 |
| 1170 | 1189 | 505345 | 5-10-5 | 83 | 81 | 207 |
| 1259 | 1278 | 505346 | 5-10-5 | 84 | 81 | 210 |
| 1262 | 1281 | 505347 | 5-10-5 | 89 | 84 | 212 |
| 1268 | 1287 | 505348 | 5-10-5 | 78 | 78 | 213 |
| 1271 | 1290 | 505349 | 5-10-5 | 74 | 77 | 214 |
| 1277 | 1296 | 505350 | 5-10-5 | 75 | 77 | 215 |
| 1280 | 1299 | 505351 | 5-10-5 | 49 | 62 | 216 |
| 1283 | 1302 | 505352 | 5-10-5 | 70 | 66 | 217 |
| 1286 | 1305 | 505353 | 5-10-5 | 62 | 60 | 218 |
| 1413 | 1426 | 510063 | 2-10-2 | 0 | 0 | 219 |
| 1515 | 1534 | 505354 | 5-10-5 | 85 | 75 | 220 |
| 1518 | 1537 | 505355 | 5-10-5 | 81 | 74 | 221 |
| 1521 | 1540 | 505356 | 5-10-5 | 57 | 52 | 222 |
| 1550 | 1563 | 510064 | 2-10-2 | 0 | 0 | 223 |
| 1577 | 1596 | 146786 | 5-10-5 | 94 | 85 | 224 |
| 1580 | 1599 | 505357 | 5-10-5 | 86 | 79 | 225 |
| 1583 | 1602 | 505358 | 5-10-5 | 89 | 79 | 226 |
| 1586 | 1605 | 505359 | 5-10-5 | 82 | 68 | 227 |
| 1655 | 1674 | 505360 | 5-10-5 | 84 | 74 | 228 |
| 1706 | 1719 | 510065 | 2-10-2 | 0 | 0 | 229 |
| 1806 | 1825 | 505361 | 5-10-5 | 66 | 66 | 238 |
| 1809 | 1828 | 505362 | 5-10-5 | 52 | 59 | 239 |
| 1812 | 1831 | 505363 | 5-10-5 | 72 | 75 | 240 |
| 1815 | 1834 | 505364 | 5-10-5 | 73 | 80 | 241 |
| 1818 | 1837 | 505365 | 5-10-5 | 68 | 82 | 242 |
| 1821 | 1840 | 505366 | 5-10-5 | 50 | 76 | 243 |
| 1824 | 1843 | 505367 | 5-10-5 | 58 | 76 | 246 |
| 1826 | 1839 | 510066 | 2-10-2 | 0 | 31 | 248 |
| 1827 | 1846 | 505368 | 5-10-5 | 71 | 84 | 249 |
| 1861 | 1880 | 146787 | 5-10-5 | 25 | 35 | 250 |
| 1864 | 1883 | 505369 | 5-10-5 | 29 | 65 | 251 |
| 1865 | 1878 | 510067 | 2-10-2 | 0 | 0 | 253 |
| 1866 | 1879 | 510068 | 2-10-2 | 0 | 20 | 255 |
| 1867 | 1886 | 505370 | 5-10-5 | 45 | 70 | 63 |
| 1867 | 1880 | 510069 | 2-10-2 | 0 | 0 | 257 |
| 1868 | 1881 | 510070 | 2-10-2 | 0 | 0 | 259 |
| 1869 | 1882 | 510071 | 2-10-2 | 0 | 0 | 261 |
| 1870 | 1889 | 505371 | 5-10-5 | 48 | 66 | 69 |
| 1870 | 1883 | 510072 | 2-10-2 | 0 | 0 | 263 |
| 1871 | 1884 | 510073 | 2-10-2 | 0 | 0 | 265 |
| 1872 | 1885 | 510074 | 2-10-2 | 0 | 2 | 267 |
| 1873 | 1892 | 505372 | 5-10-5 | 48 | 67 | 268 |
| 1873 | 1886 | 510075 | 2-10-2 | 0 | 0 | 270 |
| 1876 | 1895 | 505373 | 5-10-5 | 23 | 48 | 272 |
| 1879 | 1898 | 505374 | 5-10-5 | 0 | 34 | 273 |
| 1882 | 1901 | 505375 | 5-10-5 | 39 | 66 | 274 |
| 1885 | 1904 | 505376 | 5-10-5 | 0 | 40 | 275 |
| 1888 | 1907 | 505377 | 5-10-5 | 4 | 47 | 276 |
| 1891 | 1910 | 505378 | 5-10-5 | 65 | 77 | 277 |
| 1918 | 1931 | 510076 | 2-10-2 | 0 | 0 | 279 |
| 1919 | 1932 | 510077 | 2-10-2 | 0 | 0 | 281 |
| 1920 | 1933 | 510078 | 2-10-2 | 0 | 0 | 282 |
| 1921 | 1934 | 510079 | 2-10-2 | 18 | 50 | 283 |
| 1957 | 1976 | 505379 | 5-10-5 | 42 | 84 | 284 |
| 2270 | 2283 | 510080 | 2-10-2 | 0 | 0 | 286 |
| 2271 | 2284 | 510081 | 2-10-2 | 0 | 0 | 287 |
| 2272 | 2285 | 510082 | 2-10-2 | 0 | 10 | 288 |
| 2368 | 2387 | 505380 | 5-10-5 | 29 | 79 | 289 |
| 2378 | 2391 | 510083 | 2-10-2 | 0 | 0 | 291 |

TABLE 3-continued

Inhibition of viral HBV mRNA levels by MOE gapmers in HepAD38 (Tet-HBV) cells (detected by RTS3372 and RTS3373MGB)

| Start Site | Stop Site | ISIS No | Motif | RTS3373MGB % inhibition | RTS3372 % inhibition | SEQ ID NO |
|---|---|---|---|---|---|---|
| 2379 | 2392 | 510084 | 2-10-2 | 31 | 17 | 293 |
| 2380 | 2393 | 510085 | 2-10-2 | 0 | 8 | 295 |
| 2381 | 2394 | 510086 | 2-10-2 | 10 | 2 | 297 |
| 2420 | 2439 | 505381 | 5-10-5 | 30 | 86 | 299 |
| 2459 | 2478 | 505382 | 5-10-5 | 16 | 87 | 300 |
| 2819 | 2838 | 505383 | 5-10-5 | 26 | 81 | 301 |
| 2825 | 2838 | 510087 | 2-10-2 | 0 | 0 | 307 |
| 2873 | 2892 | 505384 | 5-10-5 | 31 | 59 | 308 |
| 3161 | 3180 | 146833 | 5-10-5 | 55 | 76 | 309 |
| 3163 | 3182 | 505385 | 5-10-5 | 58 | 83 | 310 |

Example 4

Antisense Inhibition of HBV Viral mRNA in HepAD38 (Tet-HBV) Cells by MOE Gapmers Certain antisense oligonucleotides from the study described in Examples 1 and 2 were tested for their effects on HBV mRNA in vitro. Cultured HepAD38 (Tet-HBV) cells at a density of 45,000 cells per well were transfected using electroporation with 15,000 nM antisense oligonucleotide. After a treatment period of approximately 24 hours, RNA was isolated from the cells and HBV mRNA levels were measured by quantitative real-time PCR. Viral primer probe set RTS3372 was used to measure mRNA levels. The mRNA levels were also measured using the RTS3373MGB primer probe set. HBV mRNA levels were adjusted according to total RNA content, as measured by RIBOGREEN®. Results are presented in Table 4 as percent inhibition of HBV, relative to untreated control cells.

TABLE 4

Inhibition of viral HBV mRNA levels by MOE gapmers (RTS3372 and RTS3373MGB)

| Start Site | Stop Site | ISIS No | Motif | RTS3372 % inhibition | RTS3373MGB % inhibition | SEQ ID NO |
|---|---|---|---|---|---|---|
| 62 | 77 | 509941 | 3-10-3 | 36 | 5 | 86 |
| 245 | 260 | 509942 | 3-10-3 | 3 | 0 | 93 |
| 245 | 261 | 510088 | 3-10-4 | 24 | 10 | 5 |
| 246 | 261 | 509943 | 3-10-3 | 27 | 13 | 95 |
| 250 | 265 | 509944 | 3-10-3 | 46 | 34 | 98 |
| 250 | 266 | 510089 | 3-10-4 | 61 | 33 | 6 |
| 251 | 266 | 509945 | 3-10-3 | 54 | 43 | 100 |
| 251 | 267 | 510090 | 3-10-4 | 58 | 32 | 7 |
| 252 | 267 | 509946 | 3-10-3 | 50 | 28 | 102 |
| 252 | 268 | 510091 | 3-10-4 | 60 | 42 | 8 |
| 253 | 268 | 509947 | 3-10-3 | 49 | 40 | 104 |
| 253 | 269 | 510092 | 3-10-4 | 40 | 9 | 9 |
| 254 | 269 | 509948 | 3-10-3 | 13 | 22 | 106 |
| 254 | 270 | 510093 | 3-10-4 | 39 | 2 | 10 |
| 255 | 270 | 509949 | 3-10-3 | 33 | 24 | 109 |
| 255 | 271 | 510094 | 3-10-4 | 40 | 16 | 11 |
| 256 | 271 | 509950 | 3-10-3 | 31 | 23 | 112 |
| 256 | 272 | 510095 | 3-10-4 | 24 | 6 | 12 |
| 257 | 273 | 510096 | 3-10-4 | 62 | 44 | 13 |
| 258 | 273 | 509952 | 3-10-3 | 42 | 40 | 115 |
| 258 | 274 | 510097 | 3-10-4 | 65 | 48 | 14 |
| 259 | 274 | 509953 | 3-10-3 | 35 | 29 | 117 |
| 384 | 399 | 509954 | 3-10-3 | 35 | 18 | 129 |
| 384 | 400 | 510098 | 3-10-4 | 62 | 43 | 15 |
| 385 | 401 | 510099 | 3-10-4 | 67 | 50 | 16 |
| 386 | 401 | 509955 | 3-10-3 | 44 | 37 | 132 |
| 411 | 426 | 509956 | 3-10-3 | 67 | 53 | 137 |
| 411 | 427 | 510100 | 3-10-4 | 88 | 69 | 17 |

TABLE 4-continued

Inhibition of viral HBV mRNA levels by MOE gapmers (RTS3372 and RTS3373MGB)

| Start Site | Stop Site | ISIS No | Motif | RTS3372 % inhibition | RTS3373MGB % inhibition | SEQ ID NO |
|---|---|---|---|---|---|---|
| 412 | 427 | 509957 | 3-10-3 | 86 | 76 | 140 |
| 412 | 428 | 510101 | 3-10-4 | 71 | 46 | 18 |
| 413 | 428 | 509958 | 3-10-3 | 78 | 74 | 143 |
| 413 | 429 | 510102 | 3-10-4 | 77 | 52 | 19 |
| 414 | 433 | 505330 | 5-10-5 | 81 | 60 | 20 |
| 414 | 429 | 509959 | 3-10-3 | 62 | 49 | 145 |
| 414 | 430 | 510103 | 3-10-4 | 9 | 5 | 21 |
| 415 | 434 | 509928 | 5-10-5 | 81 | 66 | 22 |
| 415 | 430 | 509960 | 3-10-3 | 67 | 57 | 147 |
| 415 | 431 | 510104 | 3-10-4 | 71 | 57 | 23 |
| 416 | 435 | 509929 | 5-10-5 | 82 | 69 | 24 |
| 416 | 431 | 509961 | 3-10-3 | 62 | 43 | 149 |
| 416 | 432 | 510105 | 3-10-4 | 81 | 64 | 25 |
| 417 | 436 | 509930 | 5-10-5 | 74 | 45 | 26 |
| 417 | 432 | 509962 | 3-10-3 | 59 | 48 | 151 |
| 417 | 433 | 510106 | 3-10-4 | 86 | 70 | 27 |
| 418 | 437 | 146783 | 5-10-5 | 19 | 3 | 28 |
| 418 | 433 | 509963 | 3-10-3 | 48 | 28 | 153 |
| 418 | 434 | 510107 | 3-10-4 | 74 | 51 | 29 |
| 419 | 434 | 509964 | 3-10-3 | 50 | 39 | 155 |
| 419 | 435 | 510108 | 3-10-4 | 67 | 50 | 30 |
| 420 | 435 | 509965 | 3-10-3 | 49 | 38 | 157 |
| 420 | 436 | 510109 | 3-10-4 | 12 | 13 | 31 |
| 421 | 436 | 509966 | 3-10-3 | 23 | 22 | 159 |
| 421 | 437 | 510110 | 3-10-4 | 34 | 16 | 32 |
| 422 | 437 | 509967 | 3-10-3 | 3 | 12 | 161 |
| 457 | 472 | 509968 | 3-10-3 | 56 | 38 | 167 |
| 457 | 473 | 510111 | 3-10-4 | 68 | 51 | 33 |
| 458 | 473 | 509969 | 3-10-3 | 53 | 39 | 168 |
| 639 | 658 | 146784 | 5-10-5 | 0 | 0 | 34 |
| 639 | 654 | 509970 | 3-10-3 | 51 | 15 | 176 |
| 639 | 655 | 510112 | 3-10-4 | 66 | 32 | 35 |
| 640 | 656 | 510113 | 3-10-4 | 70 | 31 | 36 |
| 641 | 656 | 509971 | 3-10-3 | 54 | 31 | 177 |
| 641 | 657 | 510114 | 3-10-4 | 67 | 45 | 37 |
| 642 | 657 | 509972 | 3-10-3 | 51 | 25 | 178 |
| 642 | 658 | 510115 | 3-10-4 | 73 | 50 | 38 |
| 643 | 658 | 509973 | 3-10-3 | 49 | 32 | 179 |
| 670 | 685 | 509974 | 3-10-3 | 74 | 67 | 181 |
| 687 | 706 | 509931 | 5-10-5 | 92 | 83 | 39 |
| 687 | 702 | 509975 | 3-10-3 | 72 | 71 | 188 |
| 687 | 703 | 510116 | 3-10-4 | 83 | 74 | 40 |
| 688 | 703 | 509976 | 3-10-3 | 46 | 52 | 190 |
| 688 | 704 | 510117 | 3-10-4 | 71 | 57 | 41 |
| 689 | 704 | 509977 | 3-10-3 | 18 | 22 | 191 |
| 689 | 705 | 510118 | 3-10-4 | 71 | 50 | 42 |
| 690 | 705 | 509978 | 3-10-3 | 57 | 37 | 192 |
| 690 | 706 | 510119 | 3-10-4 | 80 | 64 | 43 |
| 691 | 706 | 509979 | 3-10-3 | 65 | 55 | 194 |
| 738 | 753 | 509980 | 3-10-3 | 48 | 44 | 199 |
| 738 | 754 | 510120 | 3-10-4 | 70 | 54 | 44 |
| 739 | 754 | 509981 | 3-10-3 | 54 | 45 | 201 |
| 1176 | 1191 | 509982 | 3-10-3 | 44 | 36 | 208 |
| 1176 | 1192 | 510121 | 3-10-4 | 74 | 69 | 45 |
| 1177 | 1192 | 509983 | 3-10-3 | 57 | 53 | 209 |
| 1261 | 1276 | 509984 | 3-10-3 | 57 | 50 | 211 |
| 1778 | 1797 | 509932 | 5-10-5 | 30 | 76 | 46 |
| 1778 | 1793 | 509985 | 3-10-3 | 0 | 46 | 230 |
| 1778 | 1794 | 510122 | 3-10-4 | 0 | 60 | 47 |
| 1779 | 1798 | 509933 | 5-10-5 | 54 | 78 | 48 |
| 1779 | 1794 | 509986 | 3-10-3 | 56 | 81 | 231 |
| 1779 | 1795 | 510123 | 3-10-4 | 74 | 85 | 49 |
| 1780 | 1799 | 509934 | 5-10-5 | 69 | 84 | 50 |
| 1780 | 1795 | 509987 | 3-10-3 | 52 | 78 | 232 |
| 1780 | 1796 | 510124 | 3-10-4 | 75 | 84 | 51 |
| 1781 | 1800 | 509935 | 5-10-5 | 72 | 85 | 52 |
| 1781 | 1796 | 509988 | 3-10-3 | 57 | 68 | 232 |
| 1781 | 1797 | 510125 | 3-10-4 | 68 | 72 | 53 |
| 1782 | 1797 | 509989 | 3-10-3 | 46 | 41 | 234 |
| 1782 | 1798 | 510126 | 3-10-4 | 56 | 51 | 54 |
| 1783 | 1798 | 509990 | 3-10-3 | 16 | 25 | 234 |
| 1783 | 1799 | 510127 | 3-10-4 | 61 | 69 | 55 |
| 1784 | 1799 | 509991 | 3-10-3 | 41 | 41 | 236 |
| 1784 | 1800 | 510128 | 3-10-4 | 61 | 68 | 56 |

TABLE 4-continued

Inhibition of viral HBV mRNA levels by
MOE gapmers (RTS3372 and RTS3373MGB)

| Start Site | Stop Site | ISIS No | Motif | RTS3372 % inhibition | RTS3373MGB % inhibition | SEQ ID NO |
|---|---|---|---|---|---|---|
| 1785 | 1800 | 509992 | 3-10-3 | 43 | 43 | 237 |
| 1822 | 1837 | 509993 | 3-10-3 | 72 | 44 | 244 |
| 1822 | 1838 | 510129 | 3-10-4 | 66 | 33 | 57 |
| 1823 | 1838 | 509994 | 3-10-3 | 79 | 32 | 245 |
| 1823 | 1839 | 510130 | 3-10-4 | 49 | 31 | 58 |
| 1824 | 1839 | 509995 | 3-10-3 | 63 | 30 | 247 |
| 1865 | 1884 | 509936 | 5-10-5 | 74 | 59 | 59 |
| 1865 | 1880 | 509996 | 3-10-3 | 36 | 0 | 252 |
| 1865 | 1881 | 510131 | 3-10-4 | 26 | 0 | 60 |
| 1866 | 1885 | 509937 | 5-10-5 | 78 | 63 | 61 |
| 1866 | 1881 | 509997 | 3-10-3 | 5 | 0 | 254 |
| 1866 | 1882 | 510132 | 3-10-4 | 37 | 4 | 62 |
| 1867 | 1886 | 505370 | 5-10-5 | 54 | 17 | 63 |
| 1867 | 1882 | 509998 | 3-10-3 | 13 | 0 | 256 |
| 1867 | 1883 | 510133 | 3-10-4 | 42 | 25 | 64 |
| 1868 | 1887 | 509938 | 5-10-5 | 9 | 6 | 65 |
| 1868 | 1883 | 509999 | 3-10-3 | 47 | 6 | 258 |
| 1868 | 1884 | 510134 | 3-10-4 | 56 | 27 | 66 |
| 1869 | 1888 | 509939 | 5-10-5 | 64 | 29 | 67 |
| 1869 | 1884 | 510000 | 3-10-3 | 24 | 1 | 260 |
| 1869 | 1885 | 510135 | 3-10-4 | 70 | 43 | 68 |
| 1870 | 1889 | 505371 | 5-10-5 | 63 | 46 | 69 |
| 1870 | 1885 | 510001 | 3-10-3 | 39 | 12 | 262 |
| 1870 | 1886 | 510136 | 3-10-4 | 52 | 23 | 70 |
| 1871 | 1886 | 510002 | 3-10-3 | 10 | 0 | 264 |
| 1871 | 1887 | 510137 | 3-10-4 | 28 | 0 | 71 |
| 1872 | 1887 | 510003 | 3-10-3 | 21 | 0 | 266 |
| 1872 | 1888 | 510138 | 3-10-4 | 25 | 7 | 72 |
| 1873 | 1888 | 510004 | 3-10-3 | 21 | 38 | 269 |
| 1873 | 1889 | 510139 | 3-10-4 | 18 | 0 | 73 |
| 1874 | 1889 | 510005 | 3-10-3 | 8 | 0 | 271 |
| 1918 | 1933 | 510006 | 3-10-3 | 0 | 0 | 278 |
| 1918 | 1934 | 510140 | 3-10-4 | 81 | 67 | 74 |
| 1919 | 1934 | 510007 | 3-10-3 | 69 | 66 | 280 |
| 2270 | 2285 | 510008 | 3-10-3 | 23 | 0 | 285 |
| 2378 | 2397 | 509940 | 3-10-4 | 66 | 7 | 75 |
| 2378 | 2393 | 510009 | 3-10-3 | 23 | 0 | 290 |
| 2378 | 2394 | 510141 | 3-10-4 | 10 | 11 | 76 |
| 2379 | 2394 | 510010 | 3-10-3 | 39 | 6 | 292 |
| 2379 | 2395 | 510142 | 3-10-4 | 46 | 24 | 77 |
| 2380 | 2395 | 510011 | 3-10-3 | 33 | 23 | 294 |
| 2380 | 2396 | 510143 | 3-10-4 | 59 | 36 | 78 |
| 2381 | 2396 | 510012 | 3-10-3 | 38 | 22 | 296 |
| 2381 | 2397 | 510144 | 3-10-4 | 54 | 20 | 79 |
| 2382 | 2397 | 510013 | 3-10-3 | 42 | 0 | 298 |
| 2820 | 2835 | 510014 | 3-10-3 | 51 | 9 | 302 |
| 2820 | 2836 | 510145 | 3-10-4 | 68 | 19 | 80 |
| 2821 | 2836 | 510015 | 3-10-3 | 35 | 2 | 303 |
| 2821 | 2837 | 510146 | 3-10-4 | 65 | 15 | 81 |
| 2822 | 2837 | 510016 | 3-10-3 | 9 | 0 | 304 |
| 2822 | 2838 | 510147 | 3-10-4 | 30 | 0 | 85 |
| 2823 | 2838 | 510017 | 3-10-3 | 18 | 0 | 305 |
| 2824 | 2839 | 510018 | 3-10-3 | 24 | 5 | 306 |

Example 5

Dose-Dependent Inhibition of Viral BEV RNA in HepG2.2.15 Cells by MOE Gapmers

Certain gapmers from the study described in Examples 3 and 4 were tested at various doses in human HepG2.2.15 cells. Cells were plated at a density of 25,000 cells per well and transfected using electroporation with 2.5 µM, 5.0 µM, 10.0 µM, and 20.0 µM concentrations of antisense oligonucleotide, as specified in Table 5. After a treatment period of approximately 16 hours, RNA was isolated from the cells and HBV mRNA levels were measured by quantitative real-time PCR. Viral primer probe set RTS3370 was used to measure mRNA levels. HBV mRNA levels were adjusted according to total RNA content, as measured by RIBOGREEN®. Results are presented as percent inhibition of HBV, relative to untreated control cells.

The half maximal inhibitory concentration ($IC_{50}$) of each oligonucleotide is also presented in Table 5. As illustrated in Table 5, HBV mRNA levels were significantly reduced in a dose-dependent manner in antisense oligonucleotide treated cells.

TABLE 5

Dose-dependent antisense inhibition of HBV RNA in HepG2.2.15 cells using RTS3370

| ISIS No | 2.5 µM | 5.0 µM | 10.0 µM | 20.0 µM | $IC_{50}$ (µM) |
|---|---|---|---|---|---|
| 146786 | 33 | 50 | 54 | 81 | 5.7 |
| 505317 | 35 | 40 | 63 | 67 | 6.6 |
| 505323 | 16 | 33 | 48 | 63 | 11.1 |
| 505326 | 27 | 44 | 64 | 67 | 6.9 |
| 509929 | 21 | 44 | 60 | 62 | 8.4 |
| 509931 | 51 | 63 | 75 | 75 | <2.5 |
| 509957 | 37 | 53 | 57 | 70 | 5.4 |
| 509974 | 25 | 35 | 54 | 63 | 9.5 |
| 509975 | 36 | 55 | 62 | 81 | 4.7 |
| 509981 | 7 | 23 | 35 | 52 | 18.8 |
| 510039 | 27 | 46 | 60 | 69 | 6.9 |
| 510040 | 10 | 28 | 43 | 59 | 13.4 |
| 510041 | 29 | 41 | 53 | 66 | 8.3 |
| 510058 | 9 | 34 | 42 | 63 | 11.9 |

Example 6

Dose-Dependent Inhibition of Viral HBV RNA in HepG2.2.15 Cells by MOE Gapmers

Additional gapmers from the study described in Examples 3 and 4 were further tested at various doses in human HepG2.2.15 cells. Cells were plated at a density of 28,000 cells per well and transfected using LipofectAMINE 2000® reagent with 15.625 nM, 31.25 nM, 62.5 nM, 125.0 nM, and 250.0 nM concentrations of antisense oligonucleotide, as specified in Table 6. After a treatment period of approximately 16 hours, RNA was isolated from the cells and HBV mRNA levels were measured by quantitative real-time PCR. Viral primer probe set RTS3370 was used to measure mRNA levels. HBV mRNA levels were adjusted according to total RNA content, as measured by RIBOGREEN®. Results are presented as percent inhibition of HBV, relative to untreated control cells.

The half maximal inhibitory concentration ($IC_{50}$) of each oligonucleotide is also presented in Table 6. As illustrated in Table 6, HBV mRNA levels were significantly reduced in a dose-dependent manner in some antisense oligonucleotide treated cells.

TABLE 6

Dose-dependent antisense inhibition of HBV RNA in HepG2.2.15 cells using RTS3370

| ISIS No | 15.625 nM | 31.25 nM | 62.5 nM | 125.0 nM | 250.0 nM | $IC_{50}$ (nM) |
|---|---|---|---|---|---|---|
| 146779 | 14 | 25 | 44 | 70 | 78 | 73.1 |
| 146786 | 10 | 35 | 64 | 85 | 93 | 49.4 |
| 146833 | 12 | 16 | 32 | 62 | 72 | 99.8 |
| 505317 | 19 | 31 | 44 | 69 | 83 | 65.2 |
| 505319 | 5 | 11 | 24 | 39 | 69 | 152.8 |
| 505323 | 2 | 11 | 26 | 68 | 90 | 85.4 |

TABLE 6-continued

Dose-dependent antisense inhibition of HBV RNA in HepG2.2.15 cells using RTS3370

| ISIS No | 15.625 nM | 31.25 nM | 62.5 nM | 125.0 nM | 250.0 nM | IC$_{50}$ (nM) |
|---|---|---|---|---|---|---|
| 505326 | 1 | 15 | 45 | 72 | 89 | 73.7 |
| 505327 | 0 | 4 | 12 | 56 | 74 | 128.5 |
| 505329 | 3 | 16 | 33 | 51 | 64 | 130.4 |
| 505339 | 26 | 32 | 59 | 82 | 92 | 46.0 |
| 505342 | 10 | 4 | 34 | 69 | 74 | 95.7 |
| 505347 | 20 | 26 | 41 | 70 | 92 | 63.0 |
| 505356 | 0 | 0 | 0 | 38 | 69 | 182.0 |
| 505358 | 8 | 28 | 47 | 71 | 84 | 67.9 |
| 505382 | 5 | 0 | 3 | 26 | 19 | >250.0 |
| 509926 | 0 | 6 | 18 | 42 | 67 | 159.3 |
| 509927 | 3 | 17 | 33 | 55 | 76 | 103.2 |
| 509929 | 7 | 19 | 36 | 60 | 69 | 102.9 |
| 509931 | 18 | 28 | 52 | 76 | 87 | 57.4 |
| 509934 | 14 | 14 | 40 | 61 | 76 | 89.3 |
| 509957 | 20 | 28 | 51 | 71 | 79 | 63.1 |
| 509958 | 12 | 17 | 37 | 56 | 76 | 96.4 |
| 509959 | 12 | 11 | 18 | 59 | 70 | 121.7 |
| 509960 | 9 | 19 | 30 | 57 | 74 | 103.4 |
| 509972 | 15 | 6 | 17 | 27 | 45 | >250.0 |
| 509974 | 25 | 35 | 57 | 83 | 92 | 45.3 |
| 509975 | 33 | 44 | 45 | 61 | 80 | 53.1 |
| 509981 | 0 | 15 | 11 | 35 | 60 | 224.4 |
| 510007 | 0 | 0 | 15 | 31 | 45 | >250.0 |
| 510038 | 12 | 19 | 48 | 73 | 84 | 68.9 |
| 510039 | 17 | 25 | 44 | 69 | 72 | 77.3 |
| 510040 | 17 | 20 | 23 | 59 | 72 | 108.6 |
| 510041 | 11 | 21 | 43 | 64 | 79 | 80.5 |
| 510050 | 3 | 21 | 16 | 51 | 70 | 132.4 |
| 510058 | 7 | 9 | 16 | 22 | 46 | >250.0 |
| 510079 | 0 | 6 | 11 | 29 | 32 | >250.0 |
| 510100 | 18 | 34 | 50 | 79 | 83 | 56.1 |
| 510106 | 23 | 25 | 35 | 69 | 74 | 78.4 |
| 510116 | 20 | 44 | 65 | 79 | 91 | 42.6 |
| 510140 | 7 | 28 | 30 | 55 | 58 | 136.5 |

The mRNA levels were also measured with primer probe set RTS3371. The results are presented in Table 7.

TABLE 7

Dose-dependent antisense inhibition of HBV RNA in HepG2.2.15 cells using RTS3371

| ISIS No | 15.625 nM | 31.25 nM | 62.5 nM | 125.0 nM | 250.0 nM | IC$_{50}$ (nM) |
|---|---|---|---|---|---|---|
| 146779 | 16 | 7 | 38 | 69 | 68 | 96.9 |
| 146786 | 28 | 39 | 65 | 86 | 93 | 35 |
| 146833 | 26 | 22 | 52 | 61 | 65 | 82.3 |
| 505317 | 18 | 33 | 40 | 77 | 84 | 61.4 |
| 505319 | 0 | 0 | 0 | 15 | 55 | >250.0 |
| 505323 | 0 | 0 | 33 | 66 | 87 | 100.5 |
| 505326 | 0 | 21 | 7 | 57 | 85 | 114.6 |
| 505327 | 0 | 0 | 40 | 50 | 63 | 132.3 |
| 505329 | 11 | 22 | 35 | 66 | 77 | 90.7 |
| 505342 | 15 | 0 | 1 | 40 | 59 | 190.1 |
| 505347 | 3 | 35 | 44 | 65 | 90 | 68.4 |
| 505356 | 0 | 0 | 3 | 42 | 76 | 153.2 |
| 505358 | 20 | 11 | 39 | 71 | 78 | 79.7 |
| 505382 | 0 | 0 | 0 | 0 | 0 | >250.0 |
| 509926 | 0 | 4 | 14 | 55 | 72 | 130.6 |
| 509927 | 11 | 25 | 31 | 61 | 78 | 88.4 |
| 509929 | 11 | 26 | 41 | 70 | 77 | 75.8 |
| 509931 | 25 | 39 | 55 | 79 | 85 | 46.6 |
| 509934 | 0 | 25 | 32 | 54 | 65 | 119.9 |
| 509957 | 25 | 44 | 48 | 74 | 80 | 50.6 |
| 509958 | 24 | 18 | 20 | 57 | 72 | 114.5 |
| 509959 | 2 | 9 | 31 | 52 | 65 | 132.3 |
| 509960 | 16 | 28 | 22 | 57 | 75 | 101.8 |
| 509972 | 3 | 5 | 1 | 39 | 60 | 236.3 |
| 509974 | 38 | 46 | 65 | 83 | 94 | 31.2 |
| 509975 | 30 | 7 | 24 | 49 | 67 | 148.2 |
| 509981 | 22 | 22 | 23 | 46 | 58 | 194.7 |
| 510007 | 3 | 0 | 15 | 33 | 39 | >250.0 |
| 510038 | 16 | 22 | 50 | 76 | 84 | 62.9 |
| 510039 | 23 | 36 | 32 | 70 | 68 | 79.7 |
| 510040 | 18 | 15 | 41 | 59 | 67 | 101.9 |
| 510041 | 0 | 27 | 38 | 62 | 81 | 84.5 |
| 510050 | 1 | 16 | 17 | 52 | 63 | 149 |
| 510058 | 20 | 19 | 40 | 44 | 51 | 214.1 |
| 510079 | 0 | 2 | 5 | 41 | 49 | >250.0 |
| 510100 | 35 | 52 | 61 | 86 | 90 | 30.7 |
| 510106 | 27 | 23 | 5 | 75 | 81 | 87.9 |
| 510116 | 11 | 44 | 70 | 72 | 94 | 46.5 |
| 510140 | 0 | 18 | 26 | 45 | 41 | >250.0 |

Example 7

Tolerability of MOE Gapmers Targeting HBV in BALB/c Mice

BALB/c mice (Charles River, Mass.) are a multipurpose model of mice, frequently utilized for safety and efficacy testing. The mice were treated with ISIS antisense oligonucleotides selected from studies described above and evaluated for changes in the levels of various metabolic markers.

Study 1

Groups of four BALB/c mice each were injected subcutaneously twice a week for 3 weeks with 50 mg/kg of ISIS 146779, ISIS 146786, ISIS 505317, ISIS 505319, ISIS 505330, ISIS 505332, ISIS 505339, ISIS 505346, ISIS 505347, ISIS 505358, ISIS 509929, ISIS 509931, ISIS 509932, ISIS 509934, ISIS 509957, ISIS 510100, ISIS 510106, ISIS 510116, and ISIS 510140. A group of four BALB/c mice were injected subcutaneously twice a week for 3 weeks with 50 mg/kg of ISIS 141923 (CCTTCCCTGAAG-GTTCCTCC (SEQ ID NO: 320)), a 5-10-5 MOE gapmer with no known homology to any human or mouse gene sequence. Another group of 4 BALB/c mice was injected subcutaneously twice a week for 3 weeks with PBS. This group of mice served as the control group. Three days after the last dose at each time point, body weights were taken, mice were euthanized and organs and plasma were harvested for further analysis.

Body and Organ Weights

The body weights of the mice were measured pre-dose and at the end of each treatment period. The body weights are presented in Table 8, and are expressed as percent change from the weight taken before the start of treatment. Liver, spleen and kidney weights were measured at the end of the study, and are presented in Table 9 as a percentage difference from the respective organ weights of the PBS control. The results indicate that most of the ISIS oligonucleotides did not cause any adverse effects on body or organ weights.

TABLE 8

Change in body weights of BALB/c mice after antisense oligonucleotide treatment (%)

| | Body weight |
|---|---|
| PBS | 9 |
| ISIS 141923 | 9 |

TABLE 8-continued

Change in body weights of BALB/c mice after antisense oligonucleotide treatment (%)

|  | Body weight |
|---|---|
| ISIS 146779 | 11 |
| ISIS 146786 | 9 |
| ISIS 505317 | 10 |
| ISIS 505319 | 14 |
| ISIS 505330 | 11 |
| ISIS 505332 | 10 |
| ISIS 505339 | 14 |
| ISIS 505346 | 12 |
| ISIS 505347 | 16 |
| ISIS 505358 | 12 |
| ISIS 509929 | 8 |
| ISIS 509931 | 9 |
| ISIS 509932 | 21 |
| ISIS 509934 | 14 |
| ISIS 509957 | 10 |
| ISIS 510100 | 10 |
| ISIS 510106 | 15 |
| ISIS 510116 | 16 |
| ISIS 510140 | 19 |

TABLE 9

Change in organ weights of BALB/c mice after antisense oligonucleotide treatment (%)

|  | Liver | Kidney | Spleen |
|---|---|---|---|
| PBS | — | — | — |
| ISIS 141923 | 3 | −3 | −9 |
| ISIS 146779 | 10 | 1 | 13 |
| ISIS 146786 | 19 | −3 | 4 |
| ISIS 505317 | −4 | −7 | 9 |
| ISIS 505319 | 1 | −16 | 23 |
| ISIS 505330 | 12 | −4 | 9 |
| ISIS 505332 | 7 | −2 | 14 |
| ISIS 505339 | 5 | −6 | 7 |
| ISIS 505346 | 7 | −6 | 0 |
| ISIS 505347 | 12 | −7 | 5 |
| ISIS 505358 | 8 | 0 | 3 |
| ISIS 509929 | 17 | 14 | 200 |
| ISIS 509931 | −4 | −9 | 3 |
| ISIS 509932 | 18 | −9 | 79 |
| ISIS 509934 | 6 | −6 | 2 |
| ISIS 509957 | 0 | −2 | 15 |
| ISIS 510100 | 2 | 1 | 8 |
| ISIS 510106 | 5 | −2 | 58 |
| ISIS 510116 | 12 | −8 | 7 |
| ISIS 510140 | 20 | −8 | 49 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 10 expressed in IU/L. Plasma levels of cholesterol and triglycerides were also measured using the same clinical chemistry analyzer and the results are also presented in Table 10.

TABLE 10

Effect of antisense oligonucleotide treatment on metabolic markers in the liver of BALB/c mice

|  | ALT (IU/L) | AST (IU/L) | Cholesterol (mg/dL) | Triglycerides (mg/dL) |
|---|---|---|---|---|
| PBS | 37 | 58 | 114 | 238 |
| ISIS 141923 | 36 | 57 | 114 | 234 |
| ISIS 146779 | 43 | 56 | 121 | 221 |
| ISIS 146786 | 53 | 76 | 118 | 327 |
| ISIS 505317 | 68 | 103 | 117 | 206 |
| ISIS 505319 | 136 | 152 | 144 | 168 |
| ISIS 505330 | 281 | 194 | 119 | 188 |
| ISIS 505332 | 67 | 70 | 123 | 226 |
| ISIS 505339 | 113 | 111 | 135 | 249 |
| ISIS 505346 | 56 | 63 | 128 | 234 |
| ISIS 505347 | 79 | 83 | 122 | 347 |
| ISIS 505358 | 78 | 175 | 112 | 214 |
| ISIS 509929 | 111 | 166 | 61 | 175 |
| ISIS 509931 | 635 | 508 | 110 | 179 |
| ISIS 509932 | 92 | 113 | 118 | 131 |
| ISIS 509934 | 38 | 89 | 97 | 176 |
| ISIS 509957 | 159 | 229 | 85 | 173 |
| ISIS 510100 | 90 | 87 | 86 | 222 |
| ISIS 510106 | 61 | 88 | 79 | 239 |
| ISIS 510116 | 70 | 95 | 124 | 214 |
| ISIS 510140 | 1247 | 996 | 161 | 167 |

Kidney Function

To evaluate the effect of ISIS oligonucleotides on kidney function, plasma concentrations of blood urea nitrogen (BUN) were measured using an automated clinical chemistry analyzer (Hitachi Olympus AU400e, Melville, N.Y.). Results are presented in Table 11, expressed in mg/dL.

TABLE 11

Effect of antisense oligonucleotide treatment on kidney markers of BALB/c mice

|  | BUN (mg/dL) |
|---|---|
| PBS | 29 |
| ISIS 141923 | 29 |
| ISIS 146779 | 28 |
| ISIS 146786 | 30 |
| ISIS 505317 | 30 |
| ISIS 505319 | 30 |
| ISIS 505330 | 29 |
| ISIS 505332 | 28 |
| ISIS 505339 | 29 |
| ISIS 505346 | 27 |
| ISIS 505347 | 26 |
| ISIS 505358 | 26 |
| ISIS 509929 | 25 |
| ISIS 509931 | 23 |
| ISIS 509932 | 28 |
| ISIS 509934 | 25 |
| ISIS 509957 | 24 |
| ISIS 510100 | 27 |
| ISIS 510106 | 27 |
| ISIS 510116 | 25 |
| ISIS 510140 | 22 |

Study 2

Groups of four BALB/c mice each were injected subcutaneously twice a week for 3 weeks with 50 mg/kg of ISIS 505329, ISIS 509926, ISIS 509927, ISIS 509958, ISIS 509959, ISIS 509960, ISIS 509974, ISIS 509975, ISIS 510038, ISIS 510039, ISIS 510040, ISIS 510041, and ISIS 510050. A group of 4 BALB/c mice was injected subcutaneously twice a week for 3 weeks with PBS. This group of mice served as the control group. Three days after the last dose at each time point, body weights were taken, mice were euthanized and organs and plasma were harvested for further analysis.

Organ Weights

Liver, spleen and kidney weights were measured at the end of the study, and are also presented in Table 12 as a percentage change over the respective organ weights of the PBS control.

TABLE 12

Change in organ weights of BALB/c mice after antisense oligonucleotide treatment (%)

| ISIS No | Liver | Kidney | Spleen |
|---|---|---|---|
| 505329 | 12 | 2 | 12 |
| 509926 | 23 | 3 | 30 |
| 509927 | 8 | −4 | 27 |
| 509958 | 1 | −4 | 9 |
| 509959 | 7 | 0 | 26 |
| 509960 | 16 | 6 | 30 |
| 509974 | 5 | 8 | 7 |
| 509975 | 1 | −1 | 7 |
| 510038 | 6 | 4 | 23 |
| 510039 | 0 | 15 | 9 |
| 510040 | 3 | 1 | 2 |
| 510041 | 6 | 6 | 10 |
| 510050 | 5 | 5 | 18 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 13 expressed in IU/L.

TABLE 13

Effect of antisense oligonucleotide treatment on transaminases (IU/L) in the liver of BALB/c mice

|  | ALT | AST |
|---|---|---|
| PBS | 37 | 78 |
| ISIS 505329 | 48 | 65 |
| ISIS 509926 | 77 | 120 |
| ISIS 509927 | 71 | 92 |
| ISIS 509958 | 106 | 105 |
| ISIS 509959 | 119 | 122 |
| ISIS 509960 | 40 | 66 |
| ISIS 509974 | 38 | 43 |
| ISIS 509975 | 33 | 45 |
| ISIS 510038 | 69 | 66 |
| ISIS 510039 | 32 | 61 |
| ISIS 510040 | 83 | 113 |
| ISIS 510041 | 32 | 45 |
| ISIS 510050 | 26 | 47 |

Kidney Function

To evaluate the effect of ISIS oligonucleotides on kidney function, plasma concentrations of blood urea nitrogen (BUN) were measured using an automated clinical chemistry analyzer (Hitachi Olympus AU400e, Melville, N.Y.). Results are presented in Table 14, expressed in mg/dL.

TABLE 14

Effect of antisense oligonucleotide treatment on kidney markers of BALB/c mice

|  | BUN |
|---|---|
| PBS | 21 |
| ISIS 505329 | 22 |
| ISIS 509926 | 20 |
| ISIS 509927 | 20 |
| ISIS 509958 | 22 |
| ISIS 509959 | 21 |
| ISIS 509960 | 20 |
| ISIS 509974 | 19 |
| ISIS 509975 | 19 |
| ISIS 510038 | 19 |
| ISIS 510039 | 19 |
| ISIS 510040 | 22 |
| ISIS 510041 | 18 |
| ISIS 510050 | 22 |

Example 8

Dose Response Confirmation of MOE Gapmers Targeting HBV in HepG2.2.15 Cells

Gapmers were chosen based on sequence conservation, activity and tolerability, as measured in the study described in Examples 7 and 8, and tested at various doses in HepG2.2.15 cells. Cells were plated at a density of 28,000 cells per well and transfected using LipofectAMINE 2000 reagent with 15.625 nM, 31.25 nM, 62.5 nM, 125.0 nM and 250.0 nM concentrations of antisense oligonucleotide. Two days post-transfection, the media was replaced with fresh media. Samples were collected 4 days post-transfection. DNA, RNA, HBsAg and HBeAg levels were measured in the supernatant.

HBV mRNA levels were measured by quantitative real-time PCR. HBV primer probe set RTS3370 was used to measure mRNA levels. HBV mRNA levels were adjusted according to total RNA content, as measured by RIBOGREEN®. Results are presented as percent inhibition of HBV, relative to untreated control cells. As illustrated in Table 15, HBV mRNA levels were reduced in a dose-dependent manner in most of the antisense oligonucleotide treated cells.

HBV antigens in the supernatants were detected with the ELISA technique. HBs antigen (HBsAg) levels were detected by ELISA from Abazyme LLC, MA. As presented in Table 16, treatment with ISIS oligonucleotides 146779, 146786, 505329, 505330, 505339, 505347, 505358, 509927, 509934, 509958, 509959, 509960, 509974, 5100038, 510039, 510040, 510041, 510100, 510106, and 510116 caused significant reduction in HBsAg levels. HBe antigen (HBeAg) levels were detected by ELISA from International Immunodiagnostics, CA. As presented in Table 17, treatment with ISIS oligonucleotides 146779, 146786, 505329, 505330, 505339, 505347, 505358, 509927, 509934, 509958, 509959, 509960, 509974, 5100038, 510039, 510040, 510041, 510100, 510106, and 510116 caused significant reduction in HBeAg levels. HBV DNA levels were measured using primer probe set RTS3370. As presented in Table 18, treatment with ISIS oligonucleotides 146779, 146786, 505329, 505330, 505339, 505347, 505358, 509927, 509934, 509958, 509959, 509960, 509974, 5100038, 510039, 510040, 510041, 510100, 510106, and 510116 caused significant reduction in HBV DNA levels. The total protein in the supernatants was measured by a DC protein assay (BioRad), as presented in Table 19.

TABLE 15

Dose-dependent antisense inhibition of HBV RNA in HepG2.2.15 cells

| ISIS No | 15.625 nM | 31.25 nM | 62.5 nM | 125 nM | 250 nM |
|---|---|---|---|---|---|
| 146779 | 10 | 25 | 42 | 64 | 95 |
| 146786 | 23 | 59 | 78 | 84 | 90 |
| 505329 | 45 | 49 | 57 | 69 | 83 |
| 505330 | 31 | 61 | 65 | 80 | 93 |
| 505339 | 31 | 56 | 78 | 89 | 97 |
| 505347 | 30 | 50 | 72 | 87 | 96 |
| 505358 | 28 | 52 | 75 | 86 | 95 |
| 509927 | 41 | 61 | 67 | 61 | 76 |
| 509934 | 38 | 61 | 64 | 82 | 58 |
| 509958 | 50 | 67 | 72 | 79 | 89 |
| 509959 | 50 | 63 | 73 | 80 | 86 |
| 509960 | 63 | 61 | 72 | 82 | 74 |
| 509974 | 29 | 44 | 75 | 91 | 96 |
| 510038 | 29 | 40 | 85 | 89 | 93 |
| 510039 | 32 | 34 | 63 | 84 | 84 |
| 510040 | 18 | 0 | 51 | 71 | 77 |
| 510041 | 34 | 53 | 67 | 76 | 71 |
| 510100 | 29 | 64 | 70 | 89 | 93 |
| 510106 | 28 | 65 | 64 | 81 | 85 |
| 510116 | 13 | 34 | 78 | 89 | 95 |

TABLE 16

Dose-dependent reduction of S antigen in HepG2.2.15 cell supernatant

| ISIS No | 15.625 nM | 31.25 nM | 62.5 nM | 125 nM |
|---|---|---|---|---|
| 146779 | 40 | 58 | 80 | 92 |
| 146786 | 47 | 75 | 92 | 98 |
| 505329 | 37 | 58 | 71 | 89 |
| 505330 | 45 | 66 | 84 | 95 |
| 505339 | 62 | 79 | 93 | 96 |
| 505347 | 68 | 71 | 89 | 97 |
| 505358 | 69 | 83 | 92 | 96 |
| 509927 | 54 | 74 | 88 | 94 |
| 509934 | 40 | 59 | 78 | 89 |
| 509958 | 57 | 77 | 91 | 93 |
| 509959 | 54 | 72 | 84 | 100 |
| 509960 | 44 | 72 | 91 | 91 |
| 509974 | 58 | 77 | 92 | 95 |
| 510038 | 58 | 78 | 94 | 98 |
| 510039 | 53 | 74 | 89 | 95 |
| 510040 | 39 | 70 | 80 | 90 |
| 510041 | 47 | 65 | 82 | 92 |
| 510100 | 74 | 83 | 95 | 96 |
| 510106 | 54 | 75 | 86 | 92 |
| 510116 | 61 | 74 | 91 | 94 |

TABLE 17

Dose-dependent reduction of E antigen in HepG2.2.15 cell supernatant

| ISIS No | 15.625 nM | 31.25 nM | 62.5 nM | 125 nM |
|---|---|---|---|---|
| 146779 | 14 | 45 | 66 | 76 |
| 146786 | 26 | 58 | 75 | 80 |
| 505329 | 19 | 26 | 60 | 73 |
| 505330 | 28 | 70 | 69 | 80 |
| 505339 | 31 | 57 | 77 | 82 |
| 505347 | 24 | 33 | 64 | 77 |
| 505358 | 26 | 45 | 72 | 81 |
| 509927 | 34 | 54 | 72 | 79 |
| 509934 | 21 | 42 | 59 | 73 |
| 509958 | 29 | 45 | 72 | 77 |
| 509959 | 60 | 64 | 77 | 80 |
| 509960 | 19 | 36 | 67 | 77 |
| 509974 | 16 | 48 | 72 | 80 |
| 510038 | 20 | 35 | 79 | 80 |
| 510039 | 14 | 41 | 64 | 78 |
| 510040 | 0 | 8 | 37 | 69 |
| 510041 | 9 | 34 | 63 | 76 |
| 510100 | 26 | 52 | 73 | 81 |
| 510106 | 7 | 42 | 62 | 76 |
| 510116 | 27 | 56 | 76 | 81 |

TABLE 18

Dose-dependent antisense inhibition of HBV DNA in HepG2.2.15 cells

| ISIS No | 15.625 nM | 31.25 nM | 62.5 nM | 125 nM |
|---|---|---|---|---|
| 146779 | 71 | 71 | 84 | 85 |
| 146786 | 67 | 81 | 82 | 75 |
| 505329 | 53 | 65 | 72 | 67 |
| 505330 | 72 | 76 | 86 | 90 |
| 505339 | 83 | 85 | 89 | 88 |
| 505347 | 76 | 78 | 81 | 87 |
| 505358 | 79 | 82 | 90 | 87 |
| 509927 | 51 | 75 | 78 | 69 |
| 509934 | 61 | 60 | 64 | 75 |
| 509958 | 57 | 73 | 69 | 71 |
| 509959 | 59 | 54 | 73 | 73 |
| 509960 | 48 | 66 | 63 | 54 |
| 509974 | 76 | 90 | 84 | 85 |
| 510038 | 69 | 76 | 90 | 87 |
| 510039 | 70 | 79 | 81 | 86 |
| 510040 | 40 | 67 | 68 | 68 |
| 510041 | 53 | 71 | 62 | 68 |
| 510100 | 76 | 81 | 87 | 87 |
| 510106 | 46 | 74 | 73 | 76 |
| 510116 | 79 | 84 | 89 | 86 |

TABLE 19

Total protein levels in HepG2.2.15 cell supernatant

| | 15.625 nM | 31.25 nM | 62.5 nM | 125 nM |
|---|---|---|---|---|
| PBS | 5601 | 5601 | 5601 | 5601 |
| 146779 | 6491 | 6631 | 6027 | 5067 |
| 146786 | 5408 | 5328 | 4839 | 3518 |
| 505329 | 5719 | 5285 | 5384 | 4994 |
| 505330 | 7514 | 7262 | 6627 | 5179 |
| 505339 | 6572 | 6343 | 5349 | 4550 |
| 505347 | 7315 | 6602 | 6378 | 5908 |
| 505358 | 6357 | 6871 | 5798 | 5720 |
| 509927 | 5581 | 5487 | 5145 | 3601 |
| 509934 | 5476 | 5610 | 5394 | 4127 |
| 509958 | 5193 | 5492 | 5071 | 3957 |
| 509959 | 5051 | 5312 | 5144 | 3893 |
| 509960 | 4726 | 5160 | 5071 | 3305 |
| 509974 | 6913 | 7624 | 5798 | 5389 |
| 510038 | 5707 | 6381 | 5772 | 6733 |
| 510039 | 5981 | 7629 | 4802 | 6156 |
| 510040 | 4302 | 5209 | 5049 | 4188 |
| 510041 | 5565 | 5607 | 5205 | 3757 |
| 510100 | 8466 | 8378 | 7985 | 6402 |
| 510106 | 5703 | 5940 | 5231 | 4005 |
| 510116 | 5880 | 5380 | 4797 | 4757 |

Example 9

In Vivo Inhibition of HBV mRNA by MOE Gapmers in HBV-Transgenic Mice

ISIS 146786, a 5-10-5 MOE gapmer, and ISIS 510100, a 3-10-4 MOE gapmer, both demonstrating significant inhibition of HBV mRNA, were tested in transgenic mice containing the HBV gene (Chisari 1.3.32 line) (Guidotti, L. G. et al., *J. Virol.* 1995, 69, 6158-6169) and the efficacy of the gapmers was evaluated.

Treatment

Two groups of ten-eleven HBV-transgenic male and female mice each were administered subcutaneously twice a week for four weeks with 25 mg/kg of ISIS 146786 or ISIS 510100. Another group of 14 male and female HBV-transgenic mice was administered Entecavir, an oral antiviral drug used to treat Hepatitis B infection, at 1 mg/kg daily for two weeks. Another group of 10 male and female HBV-transgenic female mice were injected subcutaneously with PBS twice a week for four weeks. The mice injected with PBS served as a control group. Liver HBV mRNA and DNA levels, plasma ALT, and body and organ weights were measured.

RNA Analysis

RNA was extracted from liver tissue for real-time PCR analysis of HBV using primer probe sets RTS3370, RTS3371, and RTS3372. Results are presented as percent inhibition of HBV mRNA, relative to PBS control. As shown in Table 20, treatment with ISIS antisense oligonucleotides resulted in significant reduction of HBV mRNA in comparison to the PBS control, irrespective of the primer probe set used for measurement. Entecavir did not decrease HBV mRNA expression.

TABLE 20

Inhibition of HBV mRNA in HBV-transgenic mice liver relative to the PBS control

| ISIS No | RTS3370 | RTS3371 | RTS3372 |
|---|---|---|---|
| 146786 | 82 | 75 | 81 |
| 510100 | 93 | 83 | 89 |

DNA Analysis

DNA was extracted from liver tissue for real-time PCR analysis of HBV using primer probe sets RTS3370 and RTS3371. The levels were normalized to RIBOGREEN®. Results are presented as percent inhibition of HBV DNA, relative to PBS control. As shown in Table 21, treatment with ISIS antisense oligonucleotides resulted in significant reduction of HBV DNA in comparison to the PBS control, irrespective of the primer probe set used for measurement. Treatment with Entecavir also reduced DNA levels, as expected.

TABLE 21

Inhibition of HBV DNA in HBV-transgenic mice liver relative to the PBS control

| ISIS No | RTS3370 | RTS3371 |
|---|---|---|
| 146786 | 65 | 69 |
| 510100 | 67 | 73 |
| Entecavir | 75 | 96 |

Liver Function

To evaluate the effect of ISIS oligonucleotides on hepatic function, plasma concentrations of transaminase was measured using a manual clinical chemistry analyzer (Teco Diagnostics, Anaheim, Calif.) Plasma concentrations of ALT (alanine transaminase) were measured and the results are presented in Table 22, expressed in IU/L. The results indicate that antisense inhibition of HBV had no adverse effects on the liver function of the mice.

TABLE 22

Effect of antisense oligonucleotide treatment on liver ALT of transgenic mice

|  | IU/mL |
|---|---|
| PBS | 12.7 |
| ISIS 146786 | 24.1 |
| ISIS 510100 | 25.8 |
| Entecavir | 23.7 |

The data from the study indicates that both ISIS 146786 and ISIS 510100 caused robust reductions in liver HBV RNA and DNA and treatment with these oligonucleotides were well tolerated in the transgenic mice.

Example 10

Antisense Inhibition of HBV Viral mRNA in HepG2.2.15 Cells by MOE Gapmers

Additional antisense oligonucleotides were designed targeting a HBV viral nucleic acid and were tested for their effects on HBV mRNA in vitro. Several of the antisense oligonucleotides from the studies described above were also included in the assay. Cultured HepG2.2.15 cells at a density of 28,000 cells per well were transfected using LipofectAMINE 2000® reagent with 100 nM antisense oligonucleotide. After a treatment period of approximately 24 hours, RNA was isolated from the cells and HBV mRNA levels were measured by quantitative real-time PCR. Viral primer probe set RTS3370 was used to measure mRNA levels. HBV mRNA levels were adjusted according to total RNA content, as measured by RIBOGREEN®. Results are presented as percent inhibition of HBV, relative to untreated control cells.

The newly designed chimeric antisense oligonucleotides in Table 23 were designed as 5-10-5 MOE gapmers. The gapmers are 20 nucleosides in length, wherein the central gap segment comprises of ten 2'-deoxynucleosides and is flanked on both sides (in the 5' and 3' directions) by wings comprising five nucleosides each. Each nucleoside in the 5' wing segment and each nucleoside in the 3' wing segment has an MOE sugar modification. Each nucleoside in the central gap segment has a deoxy sugar modification. The internucleoside linkages throughout each gapmer are phosphorothioate (P=S) linkages. All cytosine residues throughout each gapmer are 5-methylcytosines.

"Viral Target start site" indicates the 5'-most nucleotide to which the gapmer is targeted in the viral gene sequence. "Viral Target stop site" indicates the 3'-most nucleotide to which the gapmer is targeted viral gene sequence. Each gapmer listed in Table 23 is targeted to the viral genomic sequence, designated herein as SEQ ID NO: 1 (GENBANK Accession No. U95551.1).

TABLE 23

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 1 | 20 | 524410 | TGGTGAAAGGTTGTGGAATT | 70 | 321 |
| 4 | 23 | 524411 | GTTTGGTGAAAGGTTGTGGA | 51 | 322 |
| 7 | 26 | 524412 | AGAGTTTGGTGAAAGGTTGT | 47 | 323 |
| 10 | 29 | 524413 | TGCAGAGTTTGGTGAAAGGT | 74 | 324 |
| 13 | 32 | 524414 | TCTTGCAGAGTTTGGTGAAA | 91 | 325 |
| 16 | 35 | 524415 | GGATCTTGCAGAGTTTGGTG | 93 | 326 |
| 19 | 38 | 524416 | CTGGGATCTTGCAGAGTTTG | 85 | 327 |
| 22 | 41 | 524417 | ACTCTGGGATCTTGCAGAGT | 66 | 328 |
| 25 | 44 | 524418 | CTCACTCTGGGATCTTGCAG | 86 | 329 |
| 28 | 47 | 524419 | CCTCTCACTCTGGGATCTTG | 81 | 330 |
| 31 | 50 | 524420 | AGGCCTCTCACTCTGGGATC | 77 | 331 |
| 34 | 53 | 524421 | TACAGGCCTCTCACTCTGGG | 71 | 332 |
| 37 | 56 | 524422 | AAATACAGGCCTCTCACTCT | 68 | 333 |
| 40 | 59 | 524423 | GGGAAATACAGGCCTCTCAC | 43 | 334 |
| 43 | 62 | 524424 | GCAGGGAAATACAGGCCTCT | 76 | 335 |
| 46 | 65 | 524425 | CCAGCAGGGAAATACAGGCC | 89 | 336 |
| 49 | 68 | 524426 | CCACCAGCAGGGAAATACAG | 82 | 337 |
| 52 | 71 | 524427 | GAGCCACCAGCAGGGAAATA | 53 | 338 |
| 55 | 74 | 524428 | CTGGAGCCACCAGCAGGGAA | 76 | 339 |
| 56 | 75 | 524429 | ACTGGAGCCACCAGCAGGGA | 55 | 340 |
| 57 | 76 | 524430 | AACTGGAGCCACCAGCAGGG | 45 | 341 |
| 58 | 77 | 146779 | GAACTGGAGCCACCAGCAGG | 57 | 83 |
| 59 | 78 | 524431 | TGAACTGGAGCCACCAGCAG | 85 | 342 |
| 60 | 79 | 524432 | CTGAACTGGAGCCACCAGCA | 90 | 343 |
| 61 | 80 | 505314 | CCTGAACTGGAGCCACCAGC | 93 | 85 |
| 62 | 81 | 524433 | TCCTGAACTGGAGCCACCAG | 79 | 344 |
| 63 | 82 | 524434 | CTCCTGAACTGGAGCCACCA | 82 | 345 |
| 65 | 84 | 524435 | TGCTCCTGAACTGGAGCCAC | 78 | 346 |
| 68 | 87 | 524436 | TACTGCTCCTGAACTGGAGC | 58 | 347 |
| 71 | 90 | 524437 | GTTTACTGCTCCTGAACTGG | 40 | 348 |
| 74 | 93 | 524438 | AGGGTTTACTGCTCCTGAAC | 45 | 349 |
| 77 | 96 | 524439 | AACAGGGTTTACTGCTCCTG | 69 | 350 |
| 80 | 99 | 524440 | CGGAACAGGGTTTACTGCTC | 67 | 351 |
| 83 | 102 | 524441 | AGTCGGAACAGGGTTTACTG | 47 | 352 |
| 86 | 105 | 524442 | AGTAGTCGGAACAGGGTTTA | 59 | 353 |
| 89 | 108 | 524443 | GGCAGTAGTCGGAACAGGGT | 47 | 354 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 92 | 111 | 524444 | AGAGGCAGTAGTCGGAACAG | 54 | 355 |
| 95 | 114 | 524445 | GGGAGAGGCAGTAGTCGGAA | 49 | 356 |
| 98 | 117 | 524446 | TAAGGGAGAGGCAGTAGTCG | 81 | 357 |
| 101 | 120 | 524447 | CGATAAGGGAGAGGCAGTAG | 86 | 358 |
| 104 | 123 | 524448 | TGACGATAAGGGAGAGGCAG | 79 | 359 |
| 107 | 126 | 524449 | GATTGACGATAAGGGAGAGG | 27 | 360 |
| 110 | 129 | 524450 | GAAGATTGACGATAAGGGAG | 53 | 361 |
| 113 | 132 | 524451 | CGAGAAGATTGACGATAAGG | 67 | 362 |
| 116 | 135 | 524452 | CCTCGAGAAGATTGACGATA | 84 | 363 |
| 119 | 138 | 524453 | AATCCTCGAGAAGATTGACG | 79 | 364 |
| 122 | 141 | 524454 | CCCAATCCTCGAGAAGATTG | 65 | 365 |
| 125 | 144 | 524455 | GTCCCCAATCCTCGAGAAGA | 66 | 366 |
| 128 | 147 | 524456 | AGGGTCCCCAATCCTCGAGA | 67 | 367 |
| 131 | 150 | 524457 | CGCAGGGTCCCCAATCCTCG | 76 | 368 |
| 134 | 153 | 524458 | CAGCGCAGGGTCCCCAATCC | 59 | 369 |
| 137 | 156 | 524459 | GTTCAGCGCAGGGTCCCCAA | 80 | 370 |
| 140 | 159 | 524460 | CATGTTCAGCGCAGGGTCCC | 90 | 371 |
| 143 | 162 | 524461 | CTCCATGTTCAGCGCAGGGT | 75 | 372 |
| 146 | 165 | 524462 | GTTCTCCATGTTCAGCGCAG | 54 | 373 |
| 149 | 168 | 524463 | GATGTTCTCCATGTTCAGCG | 27 | 374 |
| 152 | 171 | 524464 | TGTGATGTTCTCCATGTTCA | 72 | 375 |
| 158 | 177 | 524466 | TCCTGATGTGATGTTCTCCA | 91 | 376 |
| 161 | 180 | 524467 | GAATCCTGATGTGATGTTCT | 77 | 377 |
| 164 | 183 | 524468 | TAGGAATCCTGATGTGATGT | 77 | 378 |
| 167 | 186 | 524469 | TCCTAGGAATCCTGATGTGA | 94 | 379 |
| 170 | 189 | 524470 | GGGTCCTAGGAATCCTGATG | 56 | 380 |
| 188 | 207 | 524471 | CGCCTGTAACACGAGAAGGG | 65 | 381 |
| 191 | 210 | 524472 | CCCCGCCTGTAACACGAGAA | 71 | 382 |
| 194 | 213 | 524473 | AAACCCCGCCTGTAACACGA | 74 | 383 |
| 195 | 214 | 524474 | AAAACCCCGCCTGTAACACG | 72 | 384 |
| 196 | 215 | 505315 | AAAAACCCCGCCTGTAACAC | 52 | 87 |
| 197 | 216 | 524475 | GAAAAACCCCGCCTGTAACA | 38 | 385 |
| 198 | 217 | 524476 | AGAAAAACCCCGCCTGTAAC | 18 | 386 |
| 200 | 219 | 524477 | CAAGAAAAACCCCGCCTGTA | 86 | 387 |
| 203 | 222 | 524478 | CAACAAGAAAAACCCCGCCT | 84 | 388 |
| 204 | 223 | 524479 | TCAACAAGAAAAACCCCGCC | 80 | 389 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 205 | 224 | 505317 | GTCAACAAGAAAAACCCGC | 84 | 89 |
| 206 | 225 | 524480 | TGTCAACAAGAAAAACCCG | 79 | 390 |
| 207 | 226 | 524481 | TTGTCAACAAGAAAAACCC | 76 | 391 |
| 209 | 228 | 524482 | TCTTGTCAACAAGAAAACC | 86 | 392 |
| 212 | 231 | 524483 | GATTCTTGTCAACAAGAAAA | 57 | 393 |
| 215 | 234 | 524484 | GAGGATTCTTGTCAACAAGA | 51 | 394 |
| 218 | 237 | 524485 | TGTGAGGATTCTTGTCAACA | 83 | 395 |
| 221 | 240 | 524486 | TATTGTGAGGATTCTTGTCA | 61 | 396 |
| 224 | 243 | 524487 | CGGTATTGTGAGGATTCTTG | 74 | 397 |
| 227 | 246 | 524488 | CTGCGGTATTGTGAGGATTC | 49 | 398 |
| 230 | 249 | 524489 | ACTCTGCGGTATTGTGAGGA | 67 | 399 |
| 233 | 252 | 524490 | TAGACTCTGCGGTATTGTGA | 88 | 400 |
| 236 | 255 | 524491 | GTCTAGACTCTGCGGTATTG | 84 | 401 |
| 239 | 258 | 524492 | CGAGTCTAGACTCTGCGGTA | 82 | 402 |
| 242 | 261 | 524493 | CCACGAGTCTAGACTCTGCG | 94 | 403 |
| 243 | 262 | 524494 | ACCACGAGTCTAGACTCTGC | 87 | 404 |
| 244 | 263 | 146821 | CACCACGAGTCTAGACTCTG | 87 | 92 |
| 245 | 264 | 524495 | CCACCACGAGTCTAGACTCT | 80 | 405 |
| 246 | 265 | 524496 | TCCACCACGAGTCTAGACTC | 65 | 406 |
| 247 | 266 | 505318 | GTCCACCACGAGTCTAGACT | 65 | 96 |
| 248 | 267 | 524497 | AGTCCACCACGAGTCTAGAC | 46 | 407 |
| 249 | 268 | 524498 | AAGTCCACCACGAGTCTAGA | 54 | 408 |
| 250 | 269 | 509921 | GAAGTCCACCACGAGTCTAG | 35 | 97 |
| 251 | 270 | 509922 | AGAAGTCCACCACGAGTCTA | 51 | 99 |
| 252 | 271 | 509923 | GAGAAGTCCACCACGAGTCT | 49 | 101 |
| 253 | 272 | 505319 | AGAGAAGTCCACCACGAGTC | 60 | 103 |
| 254 | 273 | 509924 | GAGAGAAGTCCACCACGAGT | 46 | 105 |
| 255 | 274 | 509925 | TGAGAGAAGTCCACCACGAG | 79 | 108 |
| 256 | 275 | 505320 | TTGAGAGAAGTCCACCACGA | 84 | 111 |
| 257 | 276 | 524499 | ATTGAGAGAAGTCCACCACG | 83 | 409 |
| 260 | 279 | 524500 | AAAATTGAGAGAAGTCCACC | 71 | 410 |
| 263 | 282 | 524501 | TAGAAAATTGAGAGAAGTCC | 67 | 411 |
| 266 | 285 | 524502 | CCCTAGAAAATTGAGAGAAG | 88 | 412 |
| 269 | 288 | 524503 | TCCCCCTAGAAAATTGAGAG | 82 | 413 |
| 272 | 291 | 524504 | AGTTCCCCCTAGAAAATTGA | 66 | 414 |
| 275 | 294 | 524505 | GGTAGTTCCCCCTAGAAAAT | 0 | 415 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 278 | 297 | 524506 | CACGGTAGTTCCCCCTAGAA | 65 | 416 |
| 281 | 300 | 524507 | ACACACGGTAGTTCCCCTA | 87 | 417 |
| 284 | 303 | 524508 | AAGACACACGGTAGTTCCCC | 76 | 418 |
| 287 | 306 | 524509 | GCCAAGACACACGGTAGTTC | 61 | 419 |
| 290 | 309 | 524510 | TTGGCCAAGACACACGGTAG | 87 | 420 |
| 291 | 310 | 524511 | TTTGGCCAAGACACACGGTA | 87 | 421 |
| 292 | 311 | 524512 | TTTTGGCCAAGACACACGGT | 93 | 422 |
| 293 | 312 | 505323 | ATTTTGGCCAAGACACACGG | 83 | 123 |
| 294 | 313 | 524513 | AATTTTGGCCAAGACACACG | 79 | 423 |
| 295 | 314 | 524514 | GAATTTTGGCCAAGACACAC | 74 | 424 |
| 298 | 317 | 524515 | TGCGAATTTTGGCCAAGACA | 78 | 425 |
| 300 | 319 | 524516 | ACTGCGAATTTTGGCCAAGA | 71 | 426 |
| 301 | 320 | 524517 | GACTGCGAATTTTGGCCAAG | 71 | 427 |
| 302 | 321 | 505325 | GGACTGCGAATTTTGGCCAA | 50 | 125 |
| 303 | 322 | 524518 | GGGACTGCGAATTTTGGCCA | 55 | 428 |
| 321 | 340 | 524519 | GTGAGTGATTGGAGGTTGGG | 68 | 429 |
| 324 | 343 | 524520 | TTGGTGAGTGATTGGAGGTT | 84 | 430 |
| 327 | 346 | 524521 | AGGTTGGTGAGTGATTGGAG | 64 | 431 |
| 330 | 349 | 524522 | AGGAGGTTGGTGAGTGATTG | 58 | 432 |
| 333 | 352 | 524523 | GACAGGAGGTTGGTGAGTGA | 62 | 433 |
| 336 | 355 | 524524 | GAGGACAGGAGGTTGGTGAG | 56 | 434 |
| 339 | 358 | 524525 | TTGGAGGACAGGAGGTTGGT | 81 | 435 |
| 342 | 361 | 524526 | AAGTTGGAGGACAGGAGGTT | 77 | 436 |
| 345 | 364 | 524527 | GACAAGTTGGAGGACAGGAG | 69 | 437 |
| 348 | 367 | 524528 | CAGGACAAGTTGGAGGACAG | 82 | 438 |
| 351 | 370 | 524529 | AACCAGGACAAGTTGGAGGA | 67 | 439 |
| 354 | 373 | 524530 | GATAACCAGGACAAGTTGGA | 53 | 440 |
| 357 | 376 | 524531 | AGCGATAACCAGGACAAGTT | 55 | 441 |
| 358 | 377 | 524532 | CAGCGATAACCAGGACAAGT | 84 | 442 |
| 359 | 378 | 524533 | CCAGCGATAACCAGGACAAG | 86 | 443 |
| 360 | 379 | 505326 | TCCAGCGATAACCAGGACAA | 79 | 126 |
| 361 | 380 | 524534 | ATCCAGCGATAACCAGGACA | 85 | 444 |
| 362 | 381 | 524535 | CATCCAGCGATAACCAGGAC | 90 | 445 |
| 364 | 383 | 524536 | CACATCCAGCGATAACCAGG | 82 | 446 |
| 365 | 384 | 524537 | ACACATCCAGCGATAACCAG | 72 | 447 |
| 366 | 385 | 505327 | GACACATCCAGCGATAACCA | 61 | 127 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 367 | 386 | 524538 | AGACACATCCAGCGATAACC | 79 | 448 |
| 368 | 387 | 524539 | CAGACACATCCAGCGATAAC | 73 | 449 |
| 370 | 389 | 524540 | CGCAGACACATCCAGCGATA | 94 | 450 |
| 373 | 392 | 524541 | CGCCGCAGACACATCCAGCG | 84 | 451 |
| 390 | 409 | 524542 | AGAGGAAGATGATAAAACGC | 45 | 452 |
| 393 | 412 | 524543 | TGAAGAGGAAGATGATAAAA | 62 | 453 |
| 396 | 415 | 524544 | GGATGAAGAGGAAGATGATA | 58 | 454 |
| 399 | 418 | 524545 | GCAGGATGAAGAGGAAGATG | 48 | 455 |
| 402 | 421 | 524546 | GCAGCAGGATGAAGAGGAAG | 60 | 456 |
| 405 | 424 | 524547 | ATAGCAGCAGGATGAAGAGG | 84 | 457 |
| 408 | 427 | 524548 | GGCATAGCAGCAGGATGAAG | 56 | 458 |
| 409 | 428 | 524549 | AGGCATAGCAGCAGGATGAA | 78 | 459 |
| 410 | 429 | 524550 | GAGGCATAGCAGCAGGATGA | 67 | 460 |
| 411 | 430 | 505329 | TGAGGCATAGCAGCAGGATG | 85 | 136 |
| 412 | 431 | 509926 | ATGAGGCATAGCAGCAGGAT | 84 | 139 |
| 413 | 432 | 509927 | GATGAGGCATAGCAGCAGGA | 68 | 142 |
| 414 | 433 | 505330 | AGATGAGGCATAGCAGCAGG | 82 | 20 |
| 415 | 434 | 509928 | AAGATGAGGCATAGCAGCAG | 83 | 22 |
| 416 | 435 | 509929 | GAAGATGAGGCATAGCAGCA | 80 | 24 |
| 417 | 436 | 509930 | AGAAGATGAGGCATAGCAGC | 78 | 26 |
| 418 | 437 | 146783 | AAGAAGATGAGGCATAGCAG | 80 | 28 |
| 419 | 438 | 524551 | CAAGAAGATGAGGCATAGCA | 55 | 461 |
| 422 | 441 | 524552 | CAACAAGAAGATGAGGCATA | 90 | 462 |
| 425 | 444 | 524553 | AACCAACAAGAAGATGAGGC | 82 | 463 |
| 428 | 447 | 524554 | AAGAACCAACAAGAAGATGA | 79 | 464 |
| 431 | 450 | 524555 | CAGAAGAACCAACAAGAAGA | 72 | 465 |
| 434 | 453 | 524556 | GTCCAGAAGAACCAACAAGA | 87 | 466 |
| 437 | 456 | 524557 | ATAGTCCAGAAGAACCAACA | 72 | 467 |
| 440 | 459 | 524558 | TTGATAGTCCAGAAGAACCA | 76 | 468 |
| 443 | 462 | 524559 | ACCTTGATAGTCCAGAAGAA | 78 | 469 |
| 446 | 465 | 524560 | CATACCTTGATAGTCCAGAA | 77 | 470 |
| 449 | 468 | 524561 | CAACATACCTTGATAGTCCA | 69 | 471 |
| 452 | 471 | 524562 | GGGCAACATACCTTGATAGT | 39 | 472 |
| 455 | 474 | 524563 | AACGGGCAACATACCTTGAT | 72 | 473 |
| 456 | 475 | 524564 | AAACGGGCAACATACCTTGA | 86 | 474 |
| 457 | 476 | 505332 | CAAACGGGCAACATACCTTG | 85 | 166 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 458 | 477 | 524565 | ACAAACGGGCAACATACCTT | 80 | 475 |
| 459 | 478 | 524566 | GACAAACGGGCAACATACCT | 42 | 476 |
| 461 | 480 | 524567 | AGGACAAACGGGCAACATAC | 47 | 477 |
| 464 | 483 | 524568 | TAGAGGACAAACGGGCAACA | 81 | 478 |
| 467 | 486 | 524569 | AATTAGAGGACAAACGGGCA | 72 | 479 |
| 470 | 489 | 524570 | TGGAATTAGAGGACAAACGG | 84 | 480 |
| 471 | 490 | 524571 | CTGGAATTAGAGGACAAACG | 86 | 481 |
| 472 | 491 | 505335 | CCTGGAATTAGAGGACAAAC | 89 | 174 |
| 473 | 492 | 524572 | TCCTGGAATTAGAGGACAAA | 92 | 482 |
| 474 | 493 | 524573 | ATCCTGGAATTAGAGGACAA | 86 | 483 |
| 476 | 495 | 524574 | GGATCCTGGAATTAGAGGAC | 76 | 484 |
| 479 | 498 | 524575 | TGAGGATCCTGGAATTAGAG | 77 | 485 |
| 482 | 501 | 524576 | GGTTGAGGATCCTGGAATTA | 62 | 486 |
| 485 | 504 | 524577 | GGTGGTTGAGGATCCTGGAA | 73 | 487 |
| 488 | 507 | 524578 | GCTGGTGGTTGAGGATCCTG | 84 | 488 |
| 491 | 510 | 524579 | CGTGCTGGTGGTTGAGGATC | 79 | 489 |
| 494 | 513 | 524580 | TCCCGTGCTGGTGGTTGAGG | 83 | 490 |
| 497 | 516 | 524581 | TGGTCCCGTGCTGGTGGTTG | 66 | 491 |
| 500 | 519 | 524582 | GCATGGTCCCGTGCTGGTGG | 77 | 492 |
| 503 | 522 | 524583 | TCGGCATGGTCCCGTGCTGG | 0 | 493 |
| 506 | 525 | 524584 | GGTTCGGCATGGTCCCGTGC | 56 | 494 |
| 509 | 528 | 524585 | GCAGGTTCGGCATGGTCCCG | 61 | 495 |
| 512 | 531 | 524586 | CATGCAGGTTCGGCATGGTC | 87 | 496 |
| 515 | 534 | 524587 | AGTCATGCAGGTTCGGCATG | 77 | 497 |
| 518 | 537 | 524588 | AGTAGTCATGCAGGTTCGGC | 64 | 498 |
| 521 | 540 | 524589 | AGCAGTAGTCATGCAGGTTC | 61 | 499 |
| 524 | 543 | 524590 | TTGAGCAGTAGTCATGCAGG | 86 | 500 |
| 527 | 546 | 524591 | TCCTTGAGCAGTAGTCATGC | 80 | 501 |
| 530 | 549 | 524592 | GGTTCCTTGAGCAGTAGTCA | 50 | 502 |
| 533 | 552 | 524593 | AGAGGTTCCTTGAGCAGTAG | 61 | 503 |
| 536 | 555 | 524594 | CATAGAGGTTCCTTGAGCAG | 89 | 504 |
| 539 | 558 | 524595 | ATACATAGAGGTTCCTTGAG | 87 | 505 |
| 542 | 561 | 524596 | GGGATACATAGAGGTTCCTT | 0 | 506 |
| 545 | 564 | 524597 | GGAGGGATACATAGAGGTTC | 38 | 507 |
| 548 | 567 | 524598 | ACAGGAGGGATACATAGAGG | 73 | 508 |
| 551 | 570 | 524599 | GCAACAGGAGGGATACATAG | 67 | 509 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 554 | 573 | 524600 | ACAGCAACAGGAGGGATACA | 72 | 510 |
| 557 | 576 | 524601 | GGTACAGCAACAGGAGGGAT | 59 | 511 |
| 560 | 579 | 524602 | TTTGGTACAGCAACAGGAGG | 81 | 512 |
| 563 | 582 | 524603 | AGGTTTGGTACAGCAACAGG | 74 | 513 |
| 566 | 585 | 524604 | CGAAGGTTTGGTACAGCAAC | 85 | 514 |
| 569 | 588 | 524605 | GTCCGAAGGTTTGGTACAGC | 76 | 515 |
| 572 | 591 | 524606 | TCCGTCCGAAGGTTTGGTAC | 80 | 516 |
| 575 | 594 | 524607 | ATTTCCGTCCGAAGGTTTGG | 88 | 517 |
| 578 | 597 | 524608 | GCAATTTCCGTCCGAAGGTT | 50 | 518 |
| 581 | 600 | 524609 | GGTGCAATTTCCGTCCGAAG | 55 | 519 |
| 584 | 603 | 524610 | ACAGGTGCAATTTCCGTCCG | 81 | 520 |
| 587 | 606 | 524611 | AATACAGGTGCAATTTCCGT | 88 | 521 |
| 590 | 609 | 524612 | GGGAATACAGGTGCAATTTC | 32 | 522 |
| 593 | 612 | 524613 | GATGGGAATACAGGTGCAAT | 49 | 523 |
| 608 | 627 | 524614 | AGCCCAGGATGATGGGATGG | 89 | 524 |
| 611 | 630 | 524615 | GAAAGCCCAGGATGATGGGA | 71 | 525 |
| 614 | 633 | 524616 | TCCGAAAGCCCAGGATGATG | 86 | 526 |
| 617 | 636 | 524617 | TTTTCCGAAAGCCCAGGATG | 97 | 527 |
| 620 | 639 | 524618 | GAATTTTCCGAAAGCCCAGG | 80 | 528 |
| 623 | 642 | 524619 | TAGGAATTTTCCGAAAGCCC | 95 | 529 |
| 626 | 645 | 524620 | CCATAGGAATTTTCCGAAAG | 88 | 530 |
| 629 | 648 | 524621 | CTCCCATAGGAATTTTCCGA | 83 | 531 |
| 632 | 651 | 524622 | CCACTCCCATAGGAATTTTC | 68 | 532 |
| 635 | 654 | 524623 | GGCCCACTCCCATAGGAATT | 60 | 533 |
| 638 | 657 | 524624 | TGAGGCCCACTCCCATAGGA | 57 | 534 |
| 641 | 660 | 524625 | GGCTGAGGCCCACTCCCATA | 62 | 535 |
| 644 | 663 | 524626 | ACGGGCTGAGGCCCACTCCC | 57 | 536 |
| 647 | 666 | 524627 | GAAACGGGCTGAGGCCCACT | 62 | 537 |
| 650 | 669 | 524628 | GGAGAAACGGGCTGAGGCCC | 31 | 538 |
| 653 | 672 | 524629 | CCAGGAGAAACGGGCTGAGG | 77 | 539 |
| 656 | 675 | 524630 | GAGCCAGGAGAAACGGGCTG | 48 | 540 |
| 659 | 678 | 524631 | ACTGAGCCAGGAGAAACGGG | 43 | 541 |
| 662 | 681 | 524632 | TAAACTGAGCCAGGAGAAAC | 67 | 542 |
| 665 | 684 | 524633 | TAGTAAACTGAGCCAGGAGA | 86 | 543 |
| 668 | 687 | 524634 | CACTAGTAAACTGAGCCAGG | 96 | 544 |
| 669 | 688 | 524635 | GCACTAGTAAACTGAGCCAG | 83 | 545 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 671 | 690 | 524636 | TGGCACTAGTAAACTGAGCC | 84 | 546 |
| 672 | 691 | 524637 | ATGGCACTAGTAAACTGAGC | 82 | 547 |
| 674 | 693 | 524638 | AAATGGCACTAGTAAACTGA | 74 | 548 |
| 677 | 696 | 524639 | AACAAATGGCACTAGTAAAC | 63 | 549 |
| 678 | 697 | 524640 | GAACAAATGGCACTAGTAAA | 67 | 550 |
| 679 | 698 | 505338 | TGAACAAATGGCACTAGTAA | 84 | 186 |
| 680 | 699 | 524641 | CTGAACAAATGGCACTAGTA | 95 | 551 |
| 681 | 700 | 524642 | ACTGAACAAATGGCACTAGT | 77 | 552 |
| 682 | 701 | 505339 | CACTGAACAAATGGCACTAG | 95 | 187 |
| 683 | 702 | 524643 | CCACTGAACAAATGGCACTA | 89 | 553 |
| 684 | 703 | 524644 | ACCACTGAACAAATGGCACT | 90 | 554 |
| 686 | 705 | 524646 | GAACCACTGAACAAATGGCA | 82 | 555 |
| 687 | 706 | 509931 | CGAACCACTGAACAAATGGC | 90 | 39 |
| 689 | 708 | 524647 | TACGAACCACTGAACAAATG | 79 | 556 |
| 690 | 709 | 146824 | CTACGAACCACTGAACAAAT | 72 | 557 |
| 692 | 711 | 524648 | CCCTACGAACCACTGAACAA | 73 | 558 |
| 693 | 712 | 524649 | GCCCTACGAACCACTGAACA | 83 | 559 |
| 695 | 714 | 524650 | AAGCCCTACGAACCACTGAA | 82 | 560 |
| 696 | 715 | 524651 | AAAGCCCTACGAACCACTGA | 81 | 561 |
| 697 | 716 | 505342 | GAAAGCCCTACGAACCACTG | 66 | 198 |
| 698 | 717 | 524652 | GGAAAGCCCTACGAACCACT | 59 | 562 |
| 699 | 718 | 524653 | GGGAAAGCCCTACGAACCAC | 46 | 563 |
| 718 | 737 | 524654 | ACTGAAAGCCAAACAGTGGG | 64 | 564 |
| 721 | 740 | 524655 | ATAACTGAAAGCCAAACAGT | 0 | 565 |
| 724 | 743 | 524656 | CATATAACTGAAAGCCAAAC | 70 | 566 |
| 727 | 746 | 524657 | ATCCATATAACTGAAAGCCA | 91 | 567 |
| 730 | 749 | 524658 | ATCATCCATATAACTGAAAG | 69 | 568 |
| 733 | 752 | 524659 | CACATCATCCATATAACTGA | 70 | 569 |
| 736 | 755 | 524660 | TACCACATCATCCATATAAC | 57 | 570 |
| 739 | 758 | 524661 | CAATACCACATCATCCATAT | 70 | 571 |
| 742 | 761 | 524662 | CCCCAATACCACATCATCCA | 85 | 572 |
| 745 | 764 | 524663 | GGCCCCAATACCACATCAT | 70 | 573 |
| 748 | 767 | 524664 | CTTGGCCCCAATACCACAT | 82 | 574 |
| 751 | 770 | 524665 | AGACTTGGCCCCAATACCA | 77 | 575 |
| 754 | 773 | 524666 | TACAGACTTGGCCCCAATA | 77 | 576 |
| 757 | 776 | 524667 | CTGTACAGACTTGGCCCCA | 90 | 577 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 760 | 779 | 524668 | ATGCTGTACAGACTTGGCCC | 79 | 578 |
| 763 | 782 | 524669 | AAGATGCTGTACAGACTTGG | 79 | 579 |
| 766 | 785 | 524670 | CTCAAGATGCTGTACAGACT | 84 | 580 |
| 769 | 788 | 524671 | GGACTCAAGATGCTGTACAG | 24 | 581 |
| 772 | 791 | 524672 | AAGGGACTCAAGATGCTGTA | 57 | 582 |
| 775 | 794 | 524673 | AAAAGGGACTCAAGATGCT | 66 | 583 |
| 778 | 797 | 524674 | GGTAAAAGGGACTCAAGAT | 30 | 584 |
| 781 | 800 | 524675 | AGCGGTAAAAGGGACTCAA | 68 | 585 |
| 784 | 803 | 524676 | AACAGCGGTAAAAGGGACT | 67 | 586 |
| 787 | 806 | 524677 | GGTAACAGCGGTAAAAGGG | 48 | 587 |
| 790 | 809 | 524678 | ATTGGTAACAGCGGTAAAAA | 81 | 588 |
| 793 | 812 | 524679 | AAAATTGGTAACAGCGGTAA | 89 | 589 |
| 796 | 815 | 524680 | AAGAAAATTGGTAACAGCGG | 84 | 590 |
| 799 | 818 | 524681 | CAAAAGAAAATTGGTAACAG | 41 | 591 |
| 802 | 821 | 524682 | AGACAAAAGAAAATTGGTAA | 51 | 592 |
| 805 | 824 | 524683 | CAAAGACAAAAGAAAATTGG | 66 | 593 |
| 808 | 827 | 524684 | ACCCAAAGACAAAAGAAAAT | 61 | 594 |
| 811 | 830 | 524685 | TATACCCAAAGACAAAAGAA | 79 | 595 |
| 814 | 833 | 524686 | ATGTATACCCAAAGACAAAA | 84 | 596 |
| 817 | 836 | 524687 | TAAATGTATACCCAAAGACA | 77 | 597 |
| 820 | 839 | 524688 | GTTTAAATGTATACCCAAAG | 80 | 598 |
| 821 | 840 | 524689 | GGTTTAAATGTATACCCAAA | 71 | 599 |
| 822 | 841 | 524690 | GGGTTTAAATGTATACCCAA | 85 | 600 |
| 823 | 842 | 505344 | AGGGTTTAAATGTATACCCA | 85 | 206 |
| 824 | 843 | 524691 | TAGGGTTTAAATGTATACCC | 90 | 601 |
| 825 | 844 | 524692 | TTAGGGTTTAAATGTATACC | 83 | 602 |
| 827 | 846 | 524693 | TGTTAGGGTTTAAATGTATA | 53 | 603 |
| 830 | 849 | 524694 | TTTTGTTAGGGTTTAAATGT | 67 | 604 |
| 845 | 864 | 524695 | AACCCCATCTCTTTGTTTTG | 81 | 605 |
| 848 | 867 | 524696 | AGTAACCCCATCTCTTTGTT | 71 | 606 |
| 851 | 870 | 524697 | GAGAGTAACCCCATCTCTTT | 65 | 607 |
| 854 | 873 | 524698 | TCAGAGAGTAACCCCATCTC | 96 | 608 |
| 857 | 876 | 524699 | AATTCAGAGAGTAACCCCAT | 94 | 609 |
| 860 | 879 | 524700 | TAAAATTCAGAGAGTAACCC | 71 | 610 |
| 863 | 882 | 524701 | CCATAAAATTCAGAGAGTAA | 90 | 611 |
| 866 | 885 | 524702 | AACCCATAAAATTCAGAGAG | 86 | 612 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 869 | 888 | 524703 | CATAACCCATAAAATTCAGA | 72 | 613 |
| 872 | 891 | 524704 | TGACATAACCCATAAAATTC | 81 | 614 |
| 875 | 894 | 524705 | CAATGACATAACCCATAAAA | 81 | 615 |
| 878 | 897 | 524706 | TTCCAATGACATAACCCATA | 95 | 616 |
| 881 | 900 | 524707 | AACTTCCAATGACATAACCC | 91 | 617 |
| 884 | 903 | 524708 | CATAACTTCCAATGACATAA | 83 | 618 |
| 887 | 906 | 524709 | ACCCATAACTTCCAATGACA | 95 | 619 |
| 890 | 909 | 524710 | AGGACCCATAACTTCCAATG | 66 | 620 |
| 893 | 912 | 524711 | GCAAGGACCCATAACTTCCA | 41 | 621 |
| 896 | 915 | 524712 | GTGGCAAGGACCCATAACTT | 53 | 622 |
| 899 | 918 | 524713 | CTTGTGGCAAGGACCCATAA | 91 | 623 |
| 902 | 921 | 524714 | GTTCTTGTGGCAAGGACCCA | 77 | 624 |
| 905 | 924 | 524715 | TGTGTTCTTGTGGCAAGGAC | 90 | 625 |
| 908 | 927 | 524716 | TGATGTGTTCTTGTGGCAAG | 90 | 626 |
| 911 | 930 | 524717 | GTATGATGTGTTCTTGTGGC | 82 | 627 |
| 914 | 933 | 524718 | TTTGTATGATGTGTTCTTGT | 95 | 628 |
| 930 | 949 | 524719 | AAACATTCTTTGATTTTTG | 61 | 629 |
| 933 | 952 | 524720 | CTAAAACATTCTTTGATTTT | 43 | 630 |
| 936 | 955 | 524721 | TTTCTAAAACATTCTTTGAT | 90 | 631 |
| 939 | 958 | 524722 | AGTTTTCTAAAACATTCTTT | 75 | 632 |
| 942 | 961 | 524723 | GGAAGTTTTCTAAAACATTC | 52 | 633 |
| 945 | 964 | 524724 | ATAGGAAGTTTTCTAAAACA | 74 | 634 |
| 948 | 967 | 524725 | TTAATAGGAAGTTTTCTAAA | 40 | 635 |
| 951 | 970 | 524726 | CTGTTAATAGGAAGTTTTCT | 93 | 636 |
| 954 | 973 | 524727 | GGCCTGTTAATAGGAAGTTT | 87 | 637 |
| 957 | 976 | 524728 | ATAGGCCTGTTAATAGGAAG | 85 | 638 |
| 960 | 979 | 524729 | TCAATAGGCCTGTTAATAGG | 92 | 639 |
| 963 | 982 | 524730 | CAATCAATAGGCCTGTTAAT | 90 | 640 |
| 966 | 985 | 524731 | TTCCAATCAATAGGCCTGTT | 96 | 641 |
| 969 | 988 | 524732 | ACTTTCCAATCAATAGGCCT | 77 | 642 |
| 972 | 991 | 146826 | CATACTTTCCAATCAATAGG | 92 | 643 |
| 975 | 994 | 524733 | TGACATACTTTCCAATCAAT | 91 | 644 |
| 978 | 997 | 524734 | CGTTGACATACTTTCCAATC | 95 | 645 |
| 996 | 1015 | 524735 | CCCAAAAGACCCACAATTCG | 92 | 646 |
| 999 | 1018 | 524736 | AAACCCAAAAGACCCACAAT | 74 | 647 |
| 1002 | 1021 | 524737 | GCAAACCCAAAAGACCCAC | 85 | 648 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 1005 | 1024 | 524738 | GCAGCAAAACCCAAAAGACC | 70 | 649 |
| 1025 | 1044 | 524739 | AACCACATTGTGTAAATGGG | 90 | 650 |
| 1028 | 1047 | 524740 | GATAACCACATTGTGTAAAT | 58 | 651 |
| 1031 | 1050 | 524741 | CAGGATAACCACATTGTGTA | 83 | 652 |
| 1034 | 1053 | 524742 | ACGCAGGATAACCACATTGT | 84 | 653 |
| 1037 | 1056 | 524743 | TTAACGCAGGATAACCACAT | 93 | 654 |
| 1040 | 1059 | 524744 | GCATTAACGCAGGATAACCA | 60 | 655 |
| 1043 | 1062 | 524745 | AGGGCATTAACGCAGGATAA | 58 | 656 |
| 1046 | 1065 | 524746 | ACAAGGGCATTAACGCAGGA | 75 | 657 |
| 1049 | 1068 | 524747 | CATACAAGGGCATTAACGCA | 89 | 658 |
| 1052 | 1071 | 524748 | ATGCATACAAGGGCATTAAC | 87 | 659 |
| 1055 | 1074 | 524749 | TACATGCATACAAGGGCATT | 86 | 660 |
| 1058 | 1077 | 524750 | GAATACATGCATACAAGGGC | 75 | 661 |
| 1061 | 1080 | 524751 | ATTGAATACATGCATACAAG | 81 | 662 |
| 1064 | 1083 | 524752 | TAGATTGAATACATGCATAC | 85 | 663 |
| 1067 | 1086 | 524753 | GCTTAGATTGAATACATGCA | 69 | 664 |
| 1070 | 1089 | 524754 | CCTGCTTAGATTGAATACAT | 90 | 665 |
| 1073 | 1092 | 524755 | AAGCCTGCTTAGATTGAATA | 76 | 666 |
| 1076 | 1095 | 524756 | TGAAAGCCTGCTTAGATTGA | 76 | 667 |
| 1079 | 1098 | 524757 | AAGTGAAAGCCTGCTTAGAT | 68 | 668 |
| 1082 | 1101 | 524758 | AGAAAGTGAAAGCCTGCTTA | 81 | 669 |
| 1085 | 1104 | 524759 | GCGAGAAAGTGAAAGCCTGC | 61 | 670 |
| 1088 | 1107 | 524760 | TTGGCGAGAAAGTGAAAGCC | 89 | 671 |
| 1091 | 1110 | 524761 | AAGTTGGCGAGAAAGTGAAA | 74 | 672 |
| 1094 | 1113 | 524762 | TGTAAGTTGGCGAGAAAGTG | 85 | 673 |
| 1097 | 1116 | 524763 | CCTTGTAAGTTGGCGAGAAA | 90 | 674 |
| 1100 | 1119 | 524764 | AGGCCTTGTAAGTTGGCGAG | 93 | 675 |
| 1103 | 1122 | 524765 | GAAAGGCCTTGTAAGTTGGC | 78 | 676 |
| 1106 | 1125 | 524766 | ACAGAAAGGCCTTGTAAGTT | 76 | 677 |
| 1109 | 1128 | 524767 | TACACAGAAAGGCCTTGTAA | 94 | 678 |
| 1112 | 1131 | 524768 | GTTTACACAGAAAGGCCTTG | 80 | 679 |
| 1115 | 1134 | 524769 | ATTGTTTACACAGAAAGGCC | 83 | 680 |
| 1118 | 1137 | 524770 | GGTATTGTTTACACAGAAAG | 63 | 681 |
| 1121 | 1140 | 524771 | TCAGGTATTGTTTACACAGA | 93 | 682 |
| 1124 | 1143 | 524772 | GGTTCAGGTATTGTTTACAC | 68 | 683 |
| 1127 | 1146 | 524773 | AAAGGTTCAGGTATTGTTTA | 82 | 684 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 1130 | 1149 | 524774 | GGTAAAGGTTCAGGTATTGT | 68 | 685 |
| 1150 | 1169 | 524775 | TGGCCGTTGCCGGGCAACGG | 74 | 686 |
| 1153 | 1172 | 524776 | ACCTGGCCGTTGCCGGGCAA | 77 | 687 |
| 1156 | 1175 | 524777 | CAGACCTGGCCGTTGCCGGG | 88 | 688 |
| 1159 | 1178 | 524778 | GCACAGACCTGGCCGTTGCC | 80 | 689 |
| 1162 | 1181 | 524779 | TTGGCACAGACCTGGCCGTT | 85 | 690 |
| 1165 | 1184 | 524780 | CACTTGGCACAGACCTGGCC | 93 | 691 |
| 1168 | 1187 | 524781 | AAACACTTGGCACAGACCTG | 90 | 692 |
| 1169 | 1188 | 524782 | CAAACACTTGGCACAGACCT | 75 | 693 |
| 1170 | 1189 | 505345 | GCAAACACTTGGCACAGACC | 78 | 207 |
| 1171 | 1190 | 524783 | AGCAAACACTTGGCACAGAC | 84 | 694 |
| 1172 | 1191 | 524784 | CAGCAAACACTTGGCACAGA | 90 | 695 |
| 1174 | 1193 | 524785 | GTCAGCAAACACTTGGCACA | 79 | 696 |
| 1200 | 1219 | 524786 | ACCAAGCCCCAGCCAGTGGG | 57 | 697 |
| 1203 | 1222 | 524787 | ATGACCAAGCCCCAGCCAGT | 74 | 698 |
| 1206 | 1225 | 524788 | CCCATGACCAAGCCCCAGCC | 90 | 699 |
| 1209 | 1228 | 524789 | TGGCCCATGACCAAGCCCCA | 96 | 700 |
| 1212 | 1231 | 524790 | TGATGGCCCATGACCAAGCC | 79 | 701 |
| 1215 | 1234 | 542791 | CGCTGATGGCCCATGACCAA | 97 | 702 |
| 1218 | 1237 | 542792 | ACGCGCTGATGGCCCATGAC | 98 | 703 |
| 1221 | 1240 | 524793 | CGCACGCGCTGATGGCCCAT | 98 | 704 |
| 1224 | 1243 | 524794 | CCACGCACGCGCTGATGGCC | 98 | 705 |
| 1227 | 1246 | 524795 | GTTCCACGCACGCGCTGATG | 98 | 706 |
| 1230 | 1249 | 524796 | AAGGTTCCACGCACGCGCTG | 99 | 707 |
| 1233 | 1252 | 524797 | GAAAAGGTTCCACGCACGCG | 97 | 708 |
| 1236 | 1255 | 524798 | GCCGAAAAGGTTCCACGCAC | 98 | 709 |
| 1239 | 1258 | 524799 | GGAGCCGAAAAGGTTCCACG | 75 | 710 |
| 1242 | 1261 | 524800 | AGAGGAGCCGAAAAGGTTCC | 79 | 711 |
| 1245 | 1264 | 524801 | GGCAGAGGAGCCGAAAAGGT | 98 | 712 |
| 1248 | 1267 | 524802 | ATCGGCAGAGGAGCCGAAAA | 73 | 713 |
| 1251 | 1270 | 524803 | TGGATCGGCAGAGGAGCCGA | 91 | 714 |
| 1254 | 1273 | 524804 | GTATGGATCGGCAGAGGAGC | 98 | 715 |
| 1257 | 1276 | 524805 | GCAGTATGGATCGGCAGAGG | 98 | 716 |
| 1258 | 1277 | 524806 | CGCAGTATGGATCGGCAGAG | 98 | 717 |
| 1259 | 1278 | 505346 | CCGCAGTATGGATCGGCAGA | 98 | 210 |
| 1260 | 1279 | 146785 | TCCGCAGTATGGATCGGCAG | 98 | 718 |

TABLE 23-continued

Inhibition of viral HBV mRNA levels by chimeric antisense oligonucleotides targeted to SEQ ID NO: 1 (RTS3370)

| Viral Start Site | Viral Stop Site | ISIS No | Sequence | % inhibition | SEQ ID NO |
|---|---|---|---|---|---|
| 1261 | 1280 | 524807 | TTCCGCAGTATGGATCGGCA | 98 | 719 |
| 1262 | 1281 | 505347 | GTTCCGCAGTATGGATCGGC | 98 | 212 |
| 1263 | 1282 | 524808 | AGTTCCGCAGTATGGATCGG | 96 | 720 |
| 1264 | 1283 | 524809 | GAGTTCCGCAGTATGGATCG | 97 | 721 |
| 1266 | 1285 | 524810 | AGGAGTTCCGCAGTATGGAT | 96 | 722 |
| 1269 | 1288 | 524811 | GCTAGGAGTTCCGCAGTATG | 96 | 723 |
| 1272 | 1291 | 524812 | GCGGCTAGGAGTTCCGCAGT | 75 | 724 |
| 1275 | 1294 | 524813 | CAAGCGGCTAGGAGTTCCGC | 86 | 725 |
| 1278 | 1297 | 524814 | AAACAAGCGGCTAGGAGTTC | 73 | 726 |
| 1281 | 1300 | 524815 | GCAAAACAAGCGGCTAGGAG | 71 | 727 |
| 1282 | 1301 | 524816 | AGCAAAACAAGCGGCTAGGA | 89 | 728 |
| 1283 | 1302 | 505352 | GAGCAAAACAAGCGGCTAGG | 76 | 217 |
| 1284 | 1303 | 524817 | CGAGCAAAACAAGCGGCTAG | 78 | 729 |
| 1285 | 1304 | 524818 | GCGAGCAAAACAAGCGGCTA | 71 | 730 |
| 1286 | 1305 | 505353 | TGCGAGCAAAACAAGCGGCT | 82 | 218 |
| 1287 | 1306 | 524819 | CTGCGAGCAAAACAAGCGGC | 82 | 731 |
| 1288 | 1307 | 524820 | GCTGCGAGCAAAACAAGCGG | 67 | 732 |
| 1290 | 1309 | 524821 | CTGCTGCGAGCAAAACAAGC | 79 | 733 |
| 1293 | 1312 | 524822 | GACCTGCTGCGAGCAAAACA | 87 | 734 |
| 1296 | 1315 | 524823 | CCAGACCTGCTGCGAGCAAA | 94 | 735 |
| 1299 | 1318 | 524824 | GCTCCAGACCTGCTGCGAGC | 80 | 736 |
| 1302 | 1321 | 524825 | TTTGCTCCAGACCTGCTGCG | 70 | 737 |
| 1305 | 1324 | 524826 | ATGTTTGCTCCAGACCTGCT | 75 | 738 |
| 1308 | 1327 | 524827 | ATAATGTTTGCTCCAGACCT | 55 | 739 |
| 1311 | 1330 | 524828 | CCGATAATGTTTGCTCCAGA | 87 | 740 |
| 1314 | 1333 | 524829 | GTCCCGATAATGTTTGCTCC | 80 | 741 |
| 1317 | 1336 | 524830 | TCAGTCCCGATAATGTTTGC | 76 | 742 |
| 1320 | 1339 | 524831 | TTATCAGTCCCGATAATGTT | 53 | 743 |
| 1577 | 1596 | 146786 | GTGAAGCGAAGTGCACACGG | 96 | 224 |

Example 11

Antisense Inhibition of HBV Viral mRNA in HepG2.2.15 Cells by MOE Gapmers

Additional antisense oligonucleotides were designed targeting a HBV viral nucleic acid and were tested for their effects on HBV mRNA in vitro. Several of the antisense oligonucleotides from the studies described above were also included in the assay. Cultured HepG2.2.15 cells at a density of 28,000 cells per well were transfected using Lipo-fectAMINE 2000® reagent with 70 nM antisense oligonucleotide. After a treatment period of approximately 24 hours, RNA was isolated from the cells and HBV mRNA levels were measured by quantitative real-time PCR. Viral primer probe set RTS3370 was used to measure mRNA levels. The mRNA levels of some of the gapmers were also measured using RTS3372. HBV mRNA levels were adjusted according to total RNA content, as measured by RIBOGREEN®. Results are presented as percent inhibition of HBV, relative to untreated control cells.

The newly designed chimeric antisense oligonucleotides in Tables 24 and 25 were designed as 5-10-5 MOE gapmers. The gapmers are 20 nucleotides in length, wherein the central gap segment comprises of ten 2'-deoxynucleosides and is flanked on both sides (in the 5' and 3' directions) by wings comprising five nucleosides each. Each nucleoside in the 5' wing segment and each nucleoside in the 3' wing segment has an MOE sugar modification. Each nucleoside in the central gap segment has a deoxy sugar modification. The internucleoside linkages throughout each gapmer are phosphorothioate (P=S) linkages. All cytosine residues throughout each gapmer are 5-methylcytosines.

"Viral Target start site" indicates the 5'-most nucleotide to which the gapmer is targeted in the viral gene sequence. "Viral Target stop site" indicates the 3'-most nucleotide to which the gapmer is targeted viral gene sequence. Each gapmer listed in Table 24 is targeted to the viral genomic sequence, designated herein as SEQ ID NO: 1 (GENBANK Accession No. U95551.1). Each gapmer listed in Table 25 is targeted to the viral genomic sequence, designated herein as SEQ ID NO: 1286 (a permuted version of GENBANK Accession No. U95551.1). 'n/a' indicates that the inhibition data for that particular gapmer was not measured with that particular primer probe set.

TABLE 24

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 1323 | 1342 | 524832 | GAGTTATCAGTCCCGATAAT | 63 | n/a | 744 |
| 1326 | 1345 | 524833 | ACAGAGTTATCAGTCCCGAT | 82 | n/a | 745 |
| 1329 | 1348 | 524834 | ACAACAGAGTTATCAGTCCC | 52 | n/a | 746 |
| 1332 | 1351 | 524835 | AGGACAACAGAGTTATCAGT | 57 | n/a | 747 |
| 1335 | 1354 | 524836 | GAGAGGACAACAGAGTTATC | 49 | n/a | 748 |
| 1338 | 1357 | 524837 | CGGGAGAGGACAACAGAGTT | 0 | n/a | 749 |
| 1341 | 1360 | 524838 | TTGCGGGAGAGGACAACAGA | 17 | n/a | 750 |
| 1344 | 1363 | 524839 | TATTTGCGGGAGAGGACAAC | 30 | n/a | 751 |
| 1347 | 1366 | 524840 | GTATATTTGCGGGAGAGGAC | 22 | n/a | 752 |
| 1350 | 1369 | 524841 | GATGTATATTTGCGGGAGAG | 32 | n/a | 753 |
| 1353 | 1372 | 524842 | TACGATGTATATTTGCGGGA | 76 | n/a | 754 |
| 1356 | 1375 | 524843 | GGATACGATGTATATTTGCG | 76 | n/a | 755 |
| 1359 | 1378 | 524844 | CATGGATACGATGTATATTT | 87 | n/a | 756 |
| 1362 | 1381 | 524845 | AGCCATGGATACGATGTATA | 70 | n/a | 757 |
| 1365 | 1384 | 524846 | AGCAGCCATGGATACGATGT | 22 | n/a | 758 |
| 1368 | 1387 | 524847 | CCTAGCAGCCATGGATACGA | 67 | n/a | 759 |
| 1371 | 1390 | 524848 | CAGCCTAGCAGCCATGGATA | 56 | n/a | 760 |
| 1374 | 1393 | 524849 | GCACAGCCTAGCAGCCATGG | 38 | n/a | 761 |
| 1377 | 1396 | 524850 | GCAGCACAGCCTAGCAGCCA | 11 | n/a | 762 |
| 1380 | 1399 | 524851 | TTGGCAGCACAGCCTAGCAG | 34 | n/a | 763 |
| 1383 | 1402 | 524852 | CAGTTGGCAGCACAGCCTAG | 47 | n/a | 764 |
| 1386 | 1405 | 524853 | ATCCAGTTGGCAGCACAGCC | 45 | n/a | 765 |
| 1389 | 1408 | 524854 | AGGATCCAGTTGGCAGCACA | 36 | n/a | 766 |
| 1392 | 1411 | 524855 | CGCAGGATCCAGTTGGCAGC | 41 | n/a | 767 |
| 1395 | 1414 | 524856 | CCGCGCAGGATCCAGTTGGC | 72 | n/a | 768 |
| 1398 | 1417 | 524857 | GTCCCGCGCAGGATCCAGTT | 55 | n/a | 769 |
| 1457 | 1476 | 524858 | AGCGACCCCGAGAAGGGTCG | 17 | n/a | 770 |
| 1460 | 1479 | 524859 | CCAAGCGACCCCGAGAAGGG | 45 | n/a | 771 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 1463 | 1482 | 524860 | GTCCCAAGCGACCCCGAGAA | 8 | n/a | 772 |
| 1466 | 1485 | 524861 | AGAGTCCCAAGCGACCCCGA | 51 | n/a | 773 |
| 1469 | 1488 | 524862 | GAGAGAGTCCCAAGCGACCC | 28 | n/a | 774 |
| 1472 | 1491 | 524863 | GACGAGAGAGTCCCAAGCGA | 37 | n/a | 775 |
| 1492 | 1511 | 524864 | GAACGGCAGACGGAGAAGGG | 27 | n/a | 776 |
| 1498 | 1517 | 524866 | CGGTCGGAACGGCAGACGGA | 78 | n/a | 777 |
| 1501 | 1520 | 524867 | GGTCGGTCGGAACGGCAGAC | 78 | n/a | 778 |
| 1504 | 1523 | 524868 | CGTGGTCGGTCGGAACGGCA | 79 | n/a | 779 |
| 1507 | 1526 | 524869 | CCCCGTGGTCGGTCGGAACG | 70 | n/a | 780 |
| 1510 | 1529 | 524870 | GCGCCCCGTGGTCGGTCGGA | 78 | n/a | 781 |
| 1513 | 1532 | 524871 | GGTGCGCCCCGTGGTCGGTC | 74 | n/a | 782 |
| 1514 | 1533 | 524872 | AGGTGCGCCCCGTGGTCGGT | 63 | n/a | 783 |
| 1515 | 1534 | 505354 | GAGGTGCGCCCCGTGGTCGG | 70 | n/a | 220 |
| 1516 | 1535 | 524873 | AGAGGTGCGCCCCGTGGTCG | 72 | n/a | 784 |
| 1517 | 1536 | 524874 | GAGAGGTGCGCCCCGTGGTC | 49 | n/a | 785 |
| 1518 | 1537 | 505355 | AGAGAGGTGCGCCCCGTGGT | 64 | n/a | 221 |
| 1519 | 1538 | 524875 | AAGAGAGGTGCGCCCCGTGG | 57 | n/a | 786 |
| 1520 | 1539 | 524876 | AAAGAGAGGTGCGCCCCGTG | 63 | n/a | 787 |
| 1521 | 1540 | 505356 | TAAAGAGAGGTGCGCCCCGT | 68 | n/a | 222 |
| 1522 | 1541 | 524877 | GTAAAGAGAGGTGCGCCCCG | 50 | n/a | 788 |
| 1523 | 1542 | 524878 | CGTAAAGAGAGGTGCGCCCC | 64 | n/a | 789 |
| 1550 | 1569 | 524879 | GATGAGAAGGCACAGACGGG | 70 | n/a | 790 |
| 1553 | 1572 | 524880 | GCAGATGAGAAGGCACAGAC | 81 | n/a | 791 |
| 1556 | 1575 | 524881 | CCGGCAGATGAGAAGGCACA | 80 | n/a | 792 |
| 1559 | 1578 | 524882 | GGTCCGGCAGATGAGAAGGC | 84 | n/a | 793 |
| 1562 | 1581 | 524883 | CACGGTCCGGCAGATGAGAA | 79 | n/a | 794 |
| 1565 | 1584 | 524884 | GCACACGGTCCGGCAGATGA | 83 | n/a | 795 |
| 1568 | 1587 | 524885 | AGTGCACACGGTCCGGCAGA | 77 | n/a | 796 |
| 1571 | 1590 | 524886 | CGAAGTGCACACGGTCCGGC | 89 | n/a | 797 |
| 1574 | 1593 | 524887 | AAGCGAAGTGCACACGGTCC | 85 | n/a | 798 |
| 1575 | 1594 | 524888 | GAAGCGAAGTGCACACGGTC | 83 | n/a | 799 |
| 1576 | 1595 | 524889 | TGAAGCGAAGTGCACACGGT | 83 | n/a | 800 |
| 1577 | 1596 | 146786 | GTGAAGCGAAGTGCACACGG | 88 | 85 | 224 |
| 1578 | 1597 | 524890 | GGTGAAGCGAAGTGCACACG | 83 | n/a | 801 |
| 1579 | 1598 | 524891 | AGGTGAAGCGAAGTGCACAC | 82 | n/a | 802 |
| 1580 | 1599 | 505357 | GAGGTGAAGCGAAGTGCACA | 79 | n/a | 803 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 1581 | 1600 | 524892 | AGAGGTGAAGCGAAGTGCAC | 73 | n/a | 804 |
| 1582 | 1601 | 524893 | CAGAGGTGAAGCGAAGTGCA | 80 | n/a | 805 |
| 1583 | 1602 | 505358 | GCAGAGGTGAAGCGAAGTGC | 84 | n/a | 226 |
| 1584 | 1603 | 524894 | TGCAGAGGTGAAGCGAAGTG | 74 | n/a | 806 |
| 1585 | 1604 | 524895 | GTGCAGAGGTGAAGCGAAGT | 72 | n/a | 807 |
| 1586 | 1605 | 505359 | CGTGCAGAGGTGAAGCGAAG | 78 | n/a | 227 |
| 1604 | 1623 | 524896 | ACGGTGGTCTCCATGCGACG | 79 | n/a | 808 |
| 1607 | 1626 | 524897 | TTCACGGTGGTCTCCATGCG | 75 | n/a | 809 |
| 1630 | 1649 | 524898 | CCTTGGGCAACATTCGGTGG | 77 | n/a | 810 |
| 1633 | 1652 | 524899 | AGACCTTGGGCAACATTCGG | 76 | n/a | 811 |
| 1636 | 1655 | 524900 | GTAAGACCTTGGGCAACATT | 73 | n/a | 812 |
| 1639 | 1658 | 524901 | TATGTAAGACCTTGGGCAAC | 60 | n/a | 813 |
| 1642 | 1661 | 524902 | TCTTATGTAAGACCTTGGGC | 72 | n/a | 814 |
| 1645 | 1664 | 524903 | TCCTCTTATGTAAGACCTTG | 75 | n/a | 815 |
| 1648 | 1667 | 524904 | GAGTCCTCTTATGTAAGACC | 65 | n/a | 816 |
| 1651 | 1670 | 524905 | CAAGAGTCCTCTTATGTAAG | 76 | n/a | 817 |
| 1654 | 1673 | 524906 | GTCCAAGAGTCCTCTTATGT | 78 | n/a | 818 |
| 1657 | 1676 | 524907 | AGAGTCCAAGAGTCCTCTTA | 82 | n/a | 819 |
| 1660 | 1679 | 524908 | CAGAGAGTCCAAGAGTCCTC | 82 | n/a | 820 |
| 1663 | 1682 | 524909 | TTGCAGAGAGTCCAAGAGTC | 76 | n/a | 821 |
| 1666 | 1685 | 524910 | ACATTGCAGAGAGTCCAAGA | 76 | n/a | 822 |
| 1669 | 1688 | 524911 | TTGACATTGCAGAGAGTCCA | 74 | n/a | 823 |
| 1689 | 1708 | 524912 | GTATGCCTCAAGGTCGGTCG | 76 | n/a | 824 |
| 1692 | 1711 | 524913 | GAAGTATGCCTCAAGGTCGG | 73 | n/a | 825 |
| 1695 | 1714 | 524914 | TTTGAAGTATGCCTCAAGGT | 76 | n/a | 826 |
| 1698 | 1717 | 524915 | GTCTTTGAAGTATGCCTCAA | 75 | n/a | 827 |
| 1701 | 1720 | 524916 | ACAGTCTTTGAAGTATGCCT | 77 | n/a | 828 |
| 1704 | 1723 | 524917 | CAAACAGTCTTTGAAGTATG | 55 | n/a | 829 |
| 1707 | 1726 | 524918 | AAACAAACAGTCTTTGAAGT | 59 | n/a | 830 |
| 1710 | 1729 | 524919 | TTTAAACAAACAGTCTTTGA | 53 | n/a | 831 |
| 1713 | 1732 | 524920 | GTCTTTAAACAAACAGTCTT | 3 | n/a | 832 |
| 1716 | 1735 | 524921 | CCAGTCTTTAAACAAACAGT | 75 | n/a | 833 |
| 1719 | 1738 | 524922 | CTCCCAGTCTTTAAACAAAC | 70 | n/a | 834 |
| 1722 | 1741 | 524923 | CTCCTCCCAGTCTTTAAACA | 68 | n/a | 835 |
| 1725 | 1744 | 524924 | CAACTCCTCCCAGTCTTTAA | 62 | n/a | 836 |
| 1728 | 1747 | 524925 | CCCCAACTCCTCCCAGTCTT | 63 | n/a | 837 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 1731 | 1750 | 524926 | CTCCCCCAACTCCTCCCAGT | 62 | n/a | 838 |
| 1734 | 1753 | 524927 | CTCCTCCCCCAACTCCTCCC | 55 | n/a | 839 |
| 1737 | 1756 | 524928 | AATCTCCTCCCCCAACTCCT | 61 | n/a | 840 |
| 1740 | 1759 | 524929 | TCTAATCTCCTCCCCCAACT | 61 | n/a | 841 |
| 1743 | 1762 | 524930 | TAATCTAATCTCCTCCCCCA | 70 | n/a | 842 |
| 1746 | 1765 | 524931 | CTTTAATCTAATCTCCTCCC | 74 | n/a | 843 |
| 1749 | 1768 | 524932 | GACCTTTAATCTAATCTCCT | 74 | n/a | 844 |
| 1752 | 1771 | 524933 | AAAGACCTTTAATCTAATCT | 60 | n/a | 845 |
| 1755 | 1774 | 524934 | TACAAAGACCTTTAATCTAA | 55 | n/a | 846 |
| 1758 | 1777 | 524935 | TAGTACAAAGACCTTTAATC | 54 | n/a | 847 |
| 1761 | 1780 | 524936 | TCCTAGTACAAAGACCTTTA | 69 | n/a | 848 |
| 1764 | 1783 | 524937 | GCCTCCTAGTACAAAGACCT | 72 | n/a | 849 |
| 1767 | 1786 | 524938 | ACAGCCTCCTAGTACAAAGA | 60 | n/a | 850 |
| 1770 | 1789 | 524939 | CCTACAGCCTCCTAGTACAA | 66 | n/a | 851 |
| 1773 | 1792 | 524940 | ATGCCTACAGCCTCCTAGTA | 70 | n/a | 852 |
| 1776 | 1795 | 524941 | TTTATGCCTACAGCCTCCTA | 63 | n/a | 853 |
| 1777 | 1796 | 524942 | ATTTATGCCTACAGCCTCCT | 70 | n/a | 854 |
| 1778 | 1797 | 509932 | AATTTATGCCTACAGCCTCC | 68 | n/a | 46 |
| 1779 | 1798 | 509933 | CAATTTATGCCTACAGCCTC | 68 | n/a | 48 |
| 1780 | 1799 | 509934 | CCAATTTATGCCTACAGCCT | 65 | n/a | 50 |
| 1781 | 1800 | 509935 | ACCAATTTATGCCTACAGCC | 64 | n/a | 52 |
| 1782 | 1801 | 524943 | GACCAATTTATGCCTACAGC | 57 | n/a | 855 |
| 1783 | 1802 | 524944 | AGACCAATTTATGCCTACAG | 60 | n/a | 856 |
| 1785 | 1804 | 524945 | GCAGACCAATTTATGCCTAC | 54 | n/a | 857 |
| 1788 | 1807 | 524946 | TGCGCAGACCAATTTATGCC | 68 | n/a | 858 |
| 1791 | 1810 | 524947 | TGGTGCGCAGACCAATTTAT | 64 | n/a | 859 |
| 1794 | 1813 | 524948 | TGCTGGTGCGCAGACCAATT | 75 | n/a | 860 |
| 1797 | 1816 | 524949 | TGGTGCTGGTGCGCAGACCA | 68 | n/a | 861 |
| 1800 | 1819 | 524950 | GCATGGTGCTGGTGCGCAGA | 69 | n/a | 862 |
| 1803 | 1822 | 524951 | GTTGCATGGTGCTGGTGCGC | 59 | n/a | 863 |
| 1807 | 1826 | 524952 | AAAGTTGCATGGTGCTGGT | 61 | n/a | 864 |
| 1810 | 1829 | 524953 | TGAAAAGTTGCATGGTGCT | 60 | n/a | 865 |
| 1813 | 1832 | 524954 | AGGTGAAAAGTTGCATGGT | 61 | n/a | 866 |
| 1816 | 1835 | 524955 | CAGAGGTGAAAAGTTGCAT | 63 | n/a | 867 |
| 1819 | 1838 | 524956 | AGGCAGAGGTGAAAAGTTG | 57 | n/a | 868 |
| 1822 | 1841 | 524957 | ATTAGGCAGAGGTGAAAAG | 50 | n/a | 869 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 1823 | 1842 | 524958 | GATTAGGCAGAGGTGAAAAA | 57 | n/a | 870 |
| 1825 | 1844 | 524959 | ATGATTAGGCAGAGGTGAAA | 54 | n/a | 871 |
| 1828 | 1847 | 524960 | GAGATGATTAGGCAGAGGTG | 59 | n/a | 872 |
| 1831 | 1850 | 524961 | CAAGAGATGATTAGGCAGAG | 61 | n/a | 873 |
| 1834 | 1853 | 524962 | GAACAAGAGATGATTAGGCA | 56 | n/a | 874 |
| 1837 | 1856 | 524963 | CATGAACAAGAGATGATTAG | 24 | n/a | 875 |
| 1840 | 1859 | 524964 | GGACATGAACAAGAGATGAT | 54 | n/a | 876 |
| 1843 | 1862 | 524965 | GTAGGACATGAACAAGAGAT | 52 | n/a | 877 |
| 1846 | 1865 | 524966 | ACAGTAGGACATGAACAAGA | 47 | n/a | 878 |
| 1849 | 1868 | 524967 | TGAACAGTAGGACATGAACA | 33 | n/a | 879 |
| 1852 | 1871 | 524968 | GCTTGAACAGTAGGACATGA | 44 | n/a | 880 |
| 1855 | 1874 | 524969 | GAGGCTTGAACAGTAGGACA | 43 | n/a | 881 |
| 1858 | 1877 | 524970 | TTGGAGGCTTGAACAGTAGG | 28 | n/a | 882 |
| 1862 | 1881 | 524971 | CAGCTTGGAGGCTTGAACAG | 30 | n/a | 883 |
| 1871 | 1890 | 524972 | CCCAAGGCACAGCTTGGAGG | 38 | n/a | 884 |
| 1874 | 1893 | 524973 | CCACCCAAGGCACAGCTTGG | 47 | n/a | 885 |
| 1877 | 1896 | 524974 | AAGCCACCCAAGGCACAGCT | 49 | n/a | 886 |
| 1880 | 1899 | 524975 | CCAAAGCCACCCAAGGCACA | 32 | n/a | 887 |
| 1883 | 1902 | 524976 | GCCCAAAGCCACCCAAGGC | 56 | n/a | 888 |
| 1886 | 1905 | 524977 | CATGCCCCAAAGCCACCCAA | 63 | n/a | 889 |
| 1889 | 1908 | 524978 | GTCCATGCCCCAAAGCCACC | 64 | n/a | 890 |
| 1892 | 1911 | 524979 | GATGTCCATGCCCCAAAGCC | 65 | n/a | 891 |
| 1895 | 1914 | 524980 | GTCGATGTCCATGCCCCAAA | 80 | n/a | 892 |
| 1898 | 1917 | 524981 | AGGGTCGATGTCCATGCCCC | 79 | n/a | 893 |
| 1901 | 1920 | 524982 | ATAAGGGTCGATGTCCATGC | 79 | n/a | 894 |
| 1904 | 1923 | 524983 | TTTATAAGGGTCGATGTCCA | 71 | n/a | 895 |
| 1907 | 1926 | 524984 | TTCTTTATAAGGGTCGATGT | 77 | n/a | 896 |
| 1910 | 1929 | 524985 | AAATTCTTTATAAGGGTCGA | 79 | n/a | 897 |
| 1913 | 1932 | 524986 | TCCAAATTCTTTATAAGGGT | 80 | n/a | 898 |
| 1916 | 1935 | 524987 | AGCTCCAAATTCTTTATAAG | 80 | n/a | 899 |
| 1919 | 1938 | 524988 | AGTAGCTCCAAATTCTTTAT | 76 | n/a | 900 |
| 1922 | 1941 | 524989 | CACAGTAGCTCCAAATTCTT | 59 | n/a | 901 |
| 1925 | 1944 | 524990 | CTCCACAGTAGCTCCAAATT | 46 | n/a | 902 |
| 1928 | 1947 | 524991 | TAACTCCACAGTAGCTCCAA | 63 | n/a | 903 |
| 1931 | 1950 | 524992 | GAGTAACTCCACAGTAGCTC | 65 | n/a | 904 |
| 1934 | 1953 | 524993 | CGAGAGTAACTCCACAGTAG | 69 | n/a | 905 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 1937 | 1956 | 524994 | AAACGAGAGTAACTCCACAG | 61 | n/a | 906 |
| 1940 | 1959 | 524995 | CAAAAACGAGAGTAACTCCA | 46 | n/a | 907 |
| 1943 | 1962 | 524996 | AGGCAAAAACGAGAGTAACT | 39 | n/a | 908 |
| 1946 | 1965 | 524997 | AGAAGGCAAAAACGAGAGTA | 53 | n/a | 909 |
| 1949 | 1968 | 524998 | GTCAGAAGGCAAAAACGAGA | 56 | n/a | 910 |
| 1952 | 1971 | 524999 | GAAGTCAGAAGGCAAAAACG | 49 | n/a | 911 |
| 1955 | 1974 | 525000 | AAAGAAGTCAGAAGGCAAAA | 29 | n/a | 912 |
| 1958 | 1977 | 525001 | AGGAAAGAAGTCAGAAGGCA | 41 | n/a | 913 |
| 1961 | 1980 | 525002 | TGAAGGAAAGAAGTCAGAAG | 34 | n/a | 914 |
| 1964 | 1983 | 525003 | TACTGAAGGAAAGAAGTCAG | 26 | n/a | 915 |
| 1984 | 2003 | 525004 | GCGGTATCTAGAAGATCTCG | 24 | n/a | 916 |
| 1987 | 2006 | 525005 | GAGGCGGTATCTAGAAGATC | 29 | n/a | 917 |
| 1990 | 2009 | 525006 | GCTGAGGCGGTATCTAGAAG | 29 | n/a | 918 |
| 1993 | 2012 | 525007 | AGAGCTGAGGCGGTATCTAG | 13 | n/a | 919 |
| 1996 | 2015 | 525008 | TACAGAGCTGAGGCGGTATC | 6 | n/a | 920 |
| 1999 | 2018 | 525009 | CGATACAGAGCTGAGGCGGT | 3 | n/a | 921 |
| 2002 | 2021 | 525010 | TCCCGATACAGAGCTGAGGC | 27 | n/a | 922 |
| 2005 | 2024 | 525011 | GCTTCCCGATACAGAGCTGA | 43 | n/a | 923 |
| 2008 | 2027 | 525012 | AAGGCTTCCCGATACAGAGC | 33 | n/a | 924 |
| 2011 | 2030 | 525013 | TCTAAGGCTTCCCGATACAG | 34 | n/a | 925 |
| 2014 | 2033 | 525014 | GACTCTAAGGCTTCCCGATA | 38 | n/a | 926 |
| 2017 | 2036 | 525015 | GGAGACTCTAAGGCTTCCCG | 16 | n/a | 927 |
| 2020 | 2039 | 525016 | TCAGGAGACTCTAAGGCTTC | 16 | n/a | 928 |
| 2023 | 2042 | 525017 | TGCTCAGGAGACTCTAAGGC | 14 | n/a | 929 |
| 2026 | 2045 | 525018 | CAATGCTCAGGAGACTCTAA | 34 | n/a | 930 |
| 2029 | 2048 | 525019 | GAACAATGCTCAGGAGACTC | 32 | n/a | 931 |
| 2032 | 2051 | 525020 | GGTGAACAATGCTCAGGAGA | 9 | n/a | 932 |
| 2035 | 2054 | 525021 | TGAGGTGAACAATGCTCAGG | 50 | n/a | 933 |
| 2038 | 2057 | 525022 | TGGTGAGGTGAACAATGCTC | 54 | n/a | 934 |
| 2041 | 2060 | 525023 | GTATGGTGAGGTGAACAATG | 47 | n/a | 935 |
| 2044 | 2063 | 525024 | GCAGTATGGTGAGGTGAACA | 40 | n/a | 936 |
| 2047 | 2066 | 525025 | AGTGCAGTATGGTGAGGTGA | 35 | n/a | 937 |
| 2050 | 2069 | 525026 | CTGAGTGCAGTATGGTGAGG | 43 | n/a | 938 |
| 2053 | 2072 | 525027 | TGCCTGAGTGCAGTATGGTG | 45 | n/a | 939 |
| 2056 | 2075 | 525028 | GCTTGCCTGAGTGCAGTATG | 42 | n/a | 940 |
| 2059 | 2078 | 525029 | ATTGCTTGCCTGAGTGCAGT | 39 | n/a | 941 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 2062 | 2081 | 525030 | AGAATTGCTTGCCTGAGTGC | 27 | n/a | 942 |
| 2065 | 2084 | 525031 | CAAAGAATTGCTTGCCTGAG | 42 | n/a | 943 |
| 2068 | 2087 | 525032 | CAGCAAAGAATTGCTTGCCT | 49 | n/a | 944 |
| 2071 | 2090 | 525033 | CCCCAGCAAAGAATTGCTTG | 41 | n/a | 945 |
| 2074 | 2093 | 525034 | TCCCCCCAGCAAAGAATTGC | 39 | n/a | 946 |
| 2077 | 2096 | 525035 | AGTTCCCCCCAGCAAAGAAT | 39 | n/a | 947 |
| 2080 | 2099 | 525036 | ATTAGTTCCCCCCAGCAAAG | 43 | n/a | 948 |
| 2083 | 2102 | 525037 | GTCATTAGTTCCCCCCAGCA | 64 | n/a | 949 |
| 2086 | 2105 | 525038 | AGAGTCATTAGTTCCCCCCA | 45 | n/a | 950 |
| 2089 | 2108 | 525039 | GCTAGAGTCATTAGTTCCCC | 58 | n/a | 951 |
| 2092 | 2111 | 525040 | GTAGCTAGAGTCATTAGTTC | 45 | n/a | 952 |
| 2095 | 2114 | 525041 | CAGGTAGCTAGAGTCATTAG | 44 | n/a | 953 |
| 2098 | 2117 | 525042 | ACCCAGGTAGCTAGAGTCAT | 39 | n/a | 954 |
| 2101 | 2120 | 525043 | CCCACCCAGGTAGCTAGAGT | 51 | n/a | 955 |
| 2104 | 2123 | 525044 | ACACCCACCCAGGTAGCTAG | 27 | n/a | 956 |
| 2107 | 2126 | 525045 | TTAACACCCACCCAGGTAGC | 41 | n/a | 957 |
| 2110 | 2129 | 525046 | AAATTAACACCCACCCAGGT | 44 | n/a | 958 |
| 2113 | 2132 | 525047 | TCCAAATTAACACCCACCCA | 29 | n/a | 959 |
| 2116 | 2135 | 525048 | TCTTCCAAATTAACACCCAC | 31 | n/a | 960 |
| 2119 | 2138 | 525049 | GGATCTTCCAAATTAACACC | 42 | n/a | 961 |
| 2122 | 2141 | 525050 | GCTGGATCTTCCAAATTAAC | 53 | n/a | 962 |
| 2125 | 2144 | 525051 | GATGCTGGATCTTCCAAATT | 41 | n/a | 963 |
| 2128 | 2147 | 525052 | CTAGATGCTGGATCTTCCAA | 62 | n/a | 964 |
| 2131 | 2150 | 525053 | TCTCTAGATGCTGGATCTTC | 41 | 83 | 965 |
| 2134 | 2153 | 525054 | AGGTCTCTAGATGCTGGATC | 26 | 73 | 966 |
| 2137 | 2156 | 525055 | ACTAGGTCTCTAGATGCTGG | 36 | 74 | 967 |
| 2140 | 2159 | 525056 | ACTACTAGGTCTCTAGATGC | 22 | 63 | 968 |
| 2143 | 2162 | 525057 | CTGACTACTAGGTCTCTAGA | 28 | 80 | 969 |
| 2146 | 2165 | 525058 | TAACTGACTACTAGGTCTCT | 47 | 83 | 970 |
| 2149 | 2168 | 525059 | ACATAACTGACTACTAGGTC | 31 | 77 | 971 |
| 2152 | 2171 | 525060 | TTGACATAACTGACTACTAG | 34 | 75 | 972 |
| 2155 | 2174 | 525061 | GTGTTGACATAACTGACTAC | 42 | 75 | 973 |
| 2158 | 2177 | 525062 | TTAGTGTTGACATAACTGAC | 48 | 81 | 974 |
| 2161 | 2180 | 525063 | ATATTAGTGTTGACATAACT | 33 | 73 | 975 |
| 2164 | 2183 | 525064 | CCCATATTAGTGTTGACATA | 41 | 82 | 976 |
| 2167 | 2186 | 525065 | AGGCCCATATTAGTGTTGAC | 39 | 77 | 977 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 2170 | 2189 | 525066 | TTTAGGCCCATATTAGTGTT | 46 | 83 | 978 |
| 2173 | 2192 | 525067 | AACTTTAGGCCCATATTAGT | 38 | 69 | 979 |
| 2176 | 2195 | 525068 | CTGAACTTTAGGCCCATATT | 41 | 85 | 980 |
| 2179 | 2198 | 525069 | TGCCTGAACTTTAGGCCCAT | 38 | 81 | 981 |
| 2182 | 2201 | 525070 | AGTTGCCTGAACTTTAGGCC | 17 | 67 | 982 |
| 2185 | 2204 | 525071 | AAGAGTTGCCTGAACTTTAG | 27 | 62 | 983 |
| 2188 | 2207 | 525072 | CACAAGAGTTGCCTGAACTT | 27 | 64 | 984 |
| 2191 | 2210 | 525073 | AACCACAAGAGTTGCCTGAA | 41 | 80 | 985 |
| 2194 | 2213 | 525074 | TGAAACCACAAGAGTTGCCT | 32 | 75 | 986 |
| 2197 | 2216 | 525075 | ATGTGAAACCACAAGAGTTG | 43 | 67 | 987 |
| 2200 | 2219 | 525076 | GAAATGTGAAACCACAAGAG | 34 | 74 | 988 |
| 2203 | 2222 | 525077 | CAAGAAATGTGAAACCACAA | 22 | 65 | 989 |
| 2206 | 2225 | 525078 | AGACAAGAAATGTGAAACCA | 39 | 70 | 990 |
| 2209 | 2228 | 525079 | GTGAGACAAGAAATGTGAAA | 32 | 74 | 991 |
| 2212 | 2231 | 525080 | AAAGTGAGACAAGAAATGTG | 30 | 63 | 992 |
| 2215 | 2234 | 525081 | CCAAAAGTGAGACAAGAAAT | 25 | 58 | 993 |
| 2218 | 2237 | 525082 | CTTCCAAAAGTGAGACAAGA | 36 | 74 | 994 |
| 2221 | 2240 | 525083 | TCTCTTCCAAAAGTGAGACA | 42 | 84 | 995 |
| 2224 | 2243 | 525084 | GTTTCTCTTCCAAAAGTGAG | 33 | 75 | 996 |
| 2227 | 2246 | 525085 | ACGGTTTCTCTTCCAAAAGT | 32 | 68 | 997 |
| 2230 | 2249 | 525086 | ATAACGGTTTCTCTTCCAAA | 51 | 80 | 998 |
| 2233 | 2252 | 525087 | TCTATAACGGTTTCTCTTCC | 36 | 77 | 999 |
| 2236 | 2255 | 525088 | TACTCTATAACGGTTTCTCT | 23 | 69 | 1000 |
| 2239 | 2258 | 525089 | AAATACTCTATAACGGTTTC | 45 | 77 | 1001 |
| 2242 | 2261 | 525090 | ACCAAATACTCTATAACGGT | 57 | 82 | 1002 |
| 2245 | 2264 | 525091 | GACACCAAATACTCTATAAC | 36 | 77 | 1003 |
| 2248 | 2267 | 525092 | AAAGACACCAAATACTCTAT | 42 | 80 | 1004 |
| 2251 | 2270 | 525093 | CCGAAAGACACCAAATACTC | 41 | 89 | 1005 |
| 2254 | 2273 | 525094 | ACTCCGAAAGACACCAAATA | 29 | 73 | 1006 |
| 2257 | 2276 | 525095 | CACACTCCGAAAGACACCAA | 33 | 92 | 1007 |
| 2260 | 2279 | 525096 | ATCCACACTCCGAAAGACAC | 18 | 74 | 1008 |
| 2263 | 2282 | 525097 | CGAATCCACACTCCGAAAGA | 30 | 57 | 1009 |
| 2266 | 2285 | 525098 | GTGCGAATCCACACTCCGAA | 28 | 67 | 1010 |
| 2269 | 2288 | 146789 | GGAGTGCGAATCCACACTCC | 37 | 72 | 1011 |
| 2272 | 2291 | 525099 | GGAGGAGTGCGAATCCACAC | 36 | 64 | 1012 |
| 2275 | 2294 | 525100 | GCTGGAGGAGTGCGAATCCA | 52 | 90 | 1013 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 2278 | 2297 | 525101 | TAAGCTGGAGGAGTGCGAAT | 49 | 96 | 1014 |
| 2281 | 2300 | 525102 | CTATAAGCTGGAGGAGTGCG | 37 | 96 | 1015 |
| 2284 | 2303 | 525103 | GGTCTATAAGCTGGAGGAGT | 30 | 97 | 1016 |
| 2287 | 2306 | 525104 | GGTGGTCTATAAGCTGGAGG | 22 | 77 | 1017 |
| 2290 | 2309 | 525105 | TTTGGTGGTCTATAAGCTGG | 41 | 76 | 1018 |
| 2293 | 2312 | 525106 | GCATTTGGTGGTCTATAAGC | 39 | 76 | 1019 |
| 2313 | 2332 | 525107 | GAAGTGTTGATAGGATAGGG | 27 | 97 | 1020 |
| 2316 | 2335 | 525108 | CCGGAAGTGTTGATAGGATA | 42 | 97 | 1021 |
| 2319 | 2338 | 525109 | TTTCCGGAAGTGTTGATAGG | 48 | 99 | 1022 |
| 2322 | 2341 | 525110 | TAGTTTCCGGAAGTGTTGAT | 18 | 98 | 1023 |
| 2325 | 2344 | 525111 | CAGTAGTTTCCGGAAGTGTT | 19 | 98 | 1024 |
| 2328 | 2347 | 525112 | CAACAGTAGTTTCCGGAAGT | 29 | 96 | 1025 |
| 2331 | 2350 | 525113 | TAACAACAGTAGTTTCCGGA | 39 | 95 | 1026 |
| 2334 | 2353 | 525114 | GTCTAACAACAGTAGTTTCC | 40 | 99 | 1027 |
| 2369 | 2388 | 525115 | CGAGGGAGTTCTTCTTCTAG | 42 | 98 | 1028 |
| 2372 | 2391 | 525116 | AGGCGAGGGAGTTCTTCTTC | 31 | 97 | 1029 |
| 2375 | 2394 | 525117 | GCGAGGCGAGGGAGTTCTTC | 22 | 98 | 1030 |
| 2379 | 2398 | 525118 | GTCTGCGAGGCGAGGGAGTT | 20 | 99 | 1031 |
| 2398 | 2417 | 525119 | CGCGGCGATTGAGACCTTCG | 26 | 97 | 1032 |
| 2401 | 2420 | 525120 | CGACGCGGCGATTGAGACCT | 23 | 97 | 1033 |
| 2404 | 2423 | 525121 | CTGCGACGCGGCGATTGAGA | 47 | 92 | 1034 |
| 2407 | 2426 | 525122 | CTTCTGCGACGCGGCGATTG | 27 | 74 | 1035 |
| 2410 | 2429 | 525123 | GATCTTCTGCGACGCGGCGA | 36 | 87 | 1036 |
| 2413 | 2432 | 146790 | TGAGATCTTCTGCGACGCGG | 25 | 85 | 1037 |
| 2416 | 2435 | 525124 | GATTGAGATCTTCTGCGACG | 17 | 84 | 1038 |
| 2419 | 2438 | 525125 | CGAGATTGAGATCTTCTGCG | 24 | 82 | 1039 |
| 2422 | 2441 | 525126 | TCCCGAGATTGAGATCTTCT | 29 | 74 | 1040 |
| 2425 | 2444 | 525127 | GGTTCCCGAGATTGAGATCT | 14 | 79 | 1041 |
| 2428 | 2447 | 525128 | TGAGGTTCCCGAGATTGAGA | 41 | 76 | 1042 |
| 2431 | 2450 | 525129 | CATTGAGGTTCCCGAGATTG | 39 | 72 | 1043 |
| 2434 | 2453 | 525130 | TAACATTGAGGTTCCCGAGA | 37 | 71 | 1044 |
| 2437 | 2456 | 525131 | TACTAACATTGAGGTTCCCG | 42 | 76 | 1045 |
| 2440 | 2459 | 525132 | GAATACTAACATTGAGGTTC | 21 | 75 | 1046 |
| 2443 | 2462 | 525133 | AAGGAATACTAACATTGAGG | 36 | 75 | 1047 |
| 2446 | 2465 | 525134 | TCCAAGGAATACTAACATTG | 29 | 77 | 1048 |
| 2449 | 2468 | 525135 | GAGTCCAAGGAATACTAACA | 32 | 76 | 1049 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 2452 | 2471 | 525136 | TATGAGTCCAAGGAATACTA | 23 | 62 | 1050 |
| 2455 | 2474 | 525137 | CCTTATGAGTCCAAGGAATA | 27 | 57 | 1051 |
| 2458 | 2477 | 525138 | CCACCTTATGAGTCCAAGGA | 52 | 82 | 1052 |
| 2461 | 2480 | 525139 | TCCCCACCTTATGAGTCCAA | 46 | 80 | 1053 |
| 2464 | 2483 | 525140 | AGTTCCCCACCTTATGAGTC | 14 | 59 | 1054 |
| 2467 | 2486 | 525141 | TAAAGTTCCCCACCTTATGA | 20 | 45 | 1055 |
| 2470 | 2489 | 525142 | CAGTAAAGTTCCCCACCTTA | 14 | 72 | 1056 |
| 2473 | 2492 | 525143 | GACCAGTAAAGTTCCCCACC | 30 | 77 | 1057 |
| 2476 | 2495 | 525144 | AAAGACCAGTAAAGTTCCCC | 19 | 72 | 1058 |
| 2479 | 2498 | 525145 | AATAAAGACCAGTAAAGTTC | 18 | 55 | 1059 |
| 2482 | 2501 | 525146 | AAGAATAAAGACCAGTAAAG | 16 | 51 | 1060 |
| 2485 | 2504 | 525147 | TAGAAGAATAAAGACCAGTA | 22 | 68 | 1061 |
| 2488 | 2507 | 525148 | CAGTAGAAGAATAAAGACCA | 13 | 59 | 1062 |
| 2491 | 2510 | 525149 | GTACAGTAGAAGAATAAAGA | 0 | 45 | 1063 |
| 2494 | 2513 | 525150 | CAGGTACAGTAGAAGAATAA | 31 | 62 | 1064 |
| 2497 | 2516 | 525151 | AGACAGGTACAGTAGAAGAA | 8 | 62 | 1065 |
| 2500 | 2519 | 525152 | TAAAGACAGGTACAGTAGAA | 29 | 61 | 1066 |
| 2503 | 2522 | 525153 | GATTAAAGACAGGTACAGTA | 28 | 67 | 1067 |
| 2506 | 2525 | 525154 | GAGGATTAAAGACAGGTACA | 38 | 76 | 1068 |
| 2509 | 2528 | 525155 | AATGAGGATTAAAGACAGGT | 30 | 72 | 1069 |
| 2512 | 2531 | 525156 | TCCAATGAGGATTAAAGACA | 24 | 67 | 1070 |
| 2515 | 2534 | 525157 | TTTTCCAATGAGGATTAAAG | 0 | 44 | 1071 |
| 2518 | 2537 | 525158 | GTGTTTTCCAATGAGGATTA | 20 | 74 | 1072 |
| 2521 | 2540 | 525159 | ATGGTGTTTTCCAATGAGGA | 30 | 71 | 1073 |
| 2524 | 2543 | 525160 | AAGATGGTGTTTTCCAATGA | 22 | 68 | 1074 |
| 2527 | 2546 | 525161 | GAAAAGATGGTGTTTTCCAA | 19 | 61 | 1075 |
| 2530 | 2549 | 525162 | TAGGAAAAGATGGTGTTTTC | 14 | 52 | 1076 |
| 2533 | 2552 | 525163 | TATTAGGAAAAGATGGTGTT | 1 | 47 | 1077 |
| 2536 | 2555 | 525164 | GTATATTAGGAAAAGATGGT | 0 | 60 | 1078 |
| 2539 | 2558 | 525165 | AATGTATATTAGGAAAAGAT | 0 | 30 | 1079 |
| 2542 | 2561 | 525166 | GTAAATGTATATTAGGAAAA | 1 | 18 | 1080 |
| 2545 | 2564 | 525167 | GGTGTAAATGTATATTAGGA | 23 | 72 | 1081 |
| 2548 | 2567 | 525168 | CTTGGTGTAAATGTATATTA | 32 | 75 | 1082 |
| 2551 | 2570 | 525169 | TGTCTTGGTGTAAATGTATA | 12 | 65 | 1083 |
| 2554 | 2573 | 525170 | TAATGTCTTGGTGTAAATGT | 3 | 51 | 1084 |
| 2557 | 2576 | 525171 | TGATAATGTCTTGGTGTAAA | 24 | 62 | 1085 |

TABLE 24-continued

Inhibition of viral HBV mRNA levels by chimeric antisense
oligonucleotides targeted to SEQ ID NO: 1
(RTS3370 and RTS3372)

| Start Site | Stop Site | ISIS No | Sequence | RTS3370 % inhibition | RTS3372 % inhibition | SEQ ID NO |
|---|---|---|---|---|---|---|
| 2560 | 2579 | 525172 | TTTTGATAATGTCTTGGTGT | 18 | 66 | 1086 |
| 2563 | 2582 | 525173 | ATTTTTTGATAATGTCTTGG | 11 | 63 | 1087 |
| 2566 | 2585 | 525174 | CACATTTTTTGATAATGTCT | 20 | 68 | 1088 |
| 2569 | 2588 | 525175 | GTTCACATTTTTTGATAATG | 38 | 68 | 1089 |
| 2572 | 2591 | 525176 | ACTGTTCACATTTTTTGATA | 12 | 61 | 1090 |
| 2575 | 2594 | 525177 | CAAACTGTTCACATTTTTTG | 25 | 56 | 1091 |
| 2578 | 2597 | 525178 | CTACAAACTGTTCACATTTT | 21 | 47 | 1092 |
| 2581 | 2600 | 525179 | GGCCTACAAACTGTTCACAT | 28 | 83 | 1093 |
| 2584 | 2603 | 525180 | GTGGGCCTACAAACTGTTCA | 7 | 72 | 1094 |
| 2587 | 2606 | 525181 | TAAGTGGGCCTACAAACTGT | 26 | 75 | 1095 |
| 2590 | 2609 | 525182 | CTGTAAGTGGGCCTACAAAC | 35 | 78 | 1096 |
| 2593 | 2612 | 525183 | TAACTGTAAGTGGGCCTACA | 29 | 69 | 1097 |
| 2596 | 2615 | 525184 | CATTAACTGTAAGTGGGCCT | 22 | 73 | 1098 |
| 2599 | 2618 | 525185 | TCTCATTAACTGTAAGTGGG | 31 | 81 | 1099 |
| 2602 | 2621 | 525186 | TTTTCTCATTAACTGTAAGT | 15 | 58 | 1100 |
| 2605 | 2624 | 525187 | TTCTTTTCTCATTAACTGTA | 14 | 71 | 1101 |
| 2608 | 2627 | 525188 | ATCTTCTTTTCTCATTAACT | 19 | 71 | 1102 |
| 2611 | 2630 | 525189 | GCAATCTTCTTTTCTCATTA | 36 | 79 | 1103 |
| 2614 | 2633 | 525190 | ATTGCAATCTTCTTTTCTCA | 38 | 82 | 1104 |
| 2617 | 2636 | 525191 | TCAATTGCAATCTTCTTTTC | 23 | 61 | 1105 |
| 2620 | 2639 | 525192 | TAATCAATTGCAATCTTCTT | 10 | 67 | 1106 |
| 2623 | 2642 | 525193 | GCATAATCAATTGCAATCTT | 27 | 71 | 1107 |
| 2626 | 2645 | 525194 | CAGGCATAATCAATTGCAAT | 23 | 71 | 1108 |
| 2629 | 2648 | 525195 | TAGCAGGCATAATCAATTGC | 30 | 77 | 1109 |
| 2632 | 2651 | 525196 | ACCTAGCAGGCATAATCAAT | 7 | 70 | 1110 |
| 2635 | 2654 | 525197 | AAAACCTAGCAGGCATAATC | 47 | 70 | 1111 |
| 2638 | 2657 | 525198 | GATAAAACCTAGCAGGCATA | 41 | 81 | 1112 |
| 2641 | 2660 | 525199 | TTGGATAAAACCTAGCAGGC | 30 | 78 | 1113 |
| 2644 | 2663 | 525200 | CCTTTGGATAAAACCTAGCA | 31 | 76 | 1114 |
| 2647 | 2666 | 525201 | TAACCTTTGGATAAAACCTA | 25 | 63 | 1115 |
| 2650 | 2669 | 525202 | TGGTAACCTTTGGATAAAAC | 24 | 76 | 1116 |
| 2653 | 2672 | 525203 | ATTTGGTAACCTTTGGATAA | 20 | 64 | 1117 |
| 2656 | 2675 | 525204 | AATATTTGGTAACCTTTGGA | 16 | 77 | 1118 |
| 2659 | 2678 | 525205 | GTAAATATTTGGTAACCTTT | 39 | 80 | 1119 |
| 2662 | 2681 | 525206 | ATGGTAAATATTTGGTAACC | 40 | 75 | 1120 |
| 2665 | 2684 | 525207 | CCAATGGTAAATATTTGGTA | 38 | 75 | 1121 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 2668 | 2687 | 525208 | TATCCAATGGTAAATATTTG | 0 | 0 | 1122 |
| 2671 | 2690 | 525209 | CCTTATCCAATGGTAAATAT | 28 | 57 | 1123 |
| 2674 | 2693 | 525210 | TACCCTTATCCAATGGTAAA | 18 | 71 | 1124 |
| 2677 | 2696 | 525211 | TAATACCCTTATCCAATGGT | 35 | 76 | 1125 |
| 2680 | 2699 | 525212 | GTTTAATACCCTTATCCAAT | 41 | 77 | 1126 |
| 2683 | 2702 | 525213 | AAGGTTTAATACCCTTATCC | 11 | 79 | 1127 |
| 2686 | 2705 | 525214 | AATAAGGTTTAATACCCTTA | 35 | 75 | 1128 |
| 2689 | 2708 | 525215 | GATAATAAGGTTTAATACCC | 22 | 54 | 1129 |
| 2692 | 2711 | 525216 | CTGGATAATAAGGTTTAATA | 19 | 35 | 1130 |
| 2695 | 2714 | 525217 | GTTCTGGATAATAAGGTTTA | 24 | 58 | 1131 |
| 2698 | 2717 | 525218 | GATGTTCTGGATAATAAGGT | 20 | 73 | 1132 |
| 2701 | 2720 | 525219 | CTAGATGTTCTGGATAATAA | 26 | 66 | 1133 |
| 2704 | 2723 | 525220 | TAACTAGATGTTCTGGATAA | 21 | 66 | 1134 |
| 2707 | 2726 | 525221 | GATTAACTAGATGTTCTGGA | 30 | 78 | 1135 |
| 2710 | 2729 | 525222 | AATGATTAACTAGATGTTCT | 30 | 61 | 1136 |
| 2713 | 2732 | 525223 | AGTAATGATTAACTAGATGT | 9 | 57 | 1137 |
| 2716 | 2735 | 525224 | GGAAGTAATGATTAACTAGA | 18 | 72 | 1138 |
| 2719 | 2738 | 525225 | TTTGGAAGTAATGATTAACT | 7 | 67 | 1139 |
| 2722 | 2741 | 525226 | TAGTTTGGAAGTAATGATTA | 2 | 30 | 1140 |
| 2725 | 2744 | 525227 | GTCTAGTTTGGAAGTAATGA | 27 | 78 | 1141 |
| 2728 | 2747 | 525228 | AGTGTCTAGTTTGGAAGTAA | 27 | 75 | 1142 |
| 2731 | 2750 | 525229 | AATAGTGTCTAGTTTGGAAG | 34 | 73 | 1143 |
| 2734 | 2753 | 525230 | GTAAATAGTGTCTAGTTTGG | 28 | 68 | 1144 |
| 2737 | 2756 | 525231 | TGTGTAAATAGTGTCTAGTT | 27 | 79 | 1145 |
| 2740 | 2759 | 525232 | GAGTGTGTAAATAGTGTCTA | 27 | 71 | 1146 |
| 2743 | 2762 | 525233 | ATAGAGTGTGTAAATAGTGT | 17 | 75 | 1147 |
| 2746 | 2765 | 525234 | TCCATAGAGTGTGTAAATAG | 18 | 75 | 1148 |
| 2749 | 2768 | 525235 | CCTTCCATAGAGTGTGTAAA | 23 | 80 | 1149 |
| 2752 | 2771 | 525236 | CCGCCTTCCATAGAGTGTGT | 26 | 82 | 1150 |
| 2755 | 2774 | 525237 | TACCCGCCTTCCATAGAGTG | 19 | 80 | 1151 |
| 2758 | 2777 | 525238 | ATATACCCGCCTTCCATAGA | 0 | 67 | 1152 |
| 2761 | 2780 | 525239 | ATAATATACCCGCCTTCCAT | 19 | 70 | 1153 |
| 2764 | 2783 | 525240 | TATATAATATACCCGCCTTC | 9 | 73 | 1154 |
| 2767 | 2786 | 525241 | TCTTATATAATATACCCGCC | 20 | 80 | 1155 |
| 2770 | 2789 | 525242 | CTCTCTTATATAATATACCC | 29 | 76 | 1156 |
| 2773 | 2792 | 525243 | TTTCTCTCTTATATAATATA | 16 | 58 | 1157 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 2776 | 2795 | 525244 | TTGTTTCTCTCTTATATAAT | 26 | 57 | 1158 |
| 2779 | 2798 | 525245 | GTGTTGTTTCTCTCTTATAT | 35 | 85 | 1159 |
| 2782 | 2801 | 525246 | TATGTGTTGTTTCTCTCTTA | 34 | 82 | 1160 |
| 2785 | 2804 | 525247 | CGCTATGTGTTGTTTCTCTC | 34 | 86 | 1161 |
| 2802 | 2821 | 525248 | TGACCCACAAAATGAGGCGC | 17 | 71 | 1162 |
| 2805 | 2824 | 525249 | TGGTGACCCACAAAATGAGG | 31 | 67 | 1163 |
| 2808 | 2827 | 525250 | ATATGGTGACCCACAAAATG | 38 | 69 | 1164 |
| 2811 | 2830 | 525251 | AGAATATGGTGACCCACAAA | 37 | 77 | 1165 |
| 2814 | 2833 | 525252 | CCAAGAATATGGTGACCCAC | 35 | 79 | 1166 |
| 2817 | 2836 | 146831 | TTCCCAAGAATATGGTGACC | 27 | 75 | 1167 |
| 2820 | 2839 | 525253 | TTGTTCCCAAGAATATGGTG | 33 | 69 | 1168 |
| 2823 | 2842 | 525254 | ATCTTGTTCCCAAGAATATG | 27 | 65 | 1169 |
| 2826 | 2845 | 525255 | TAGATCTTGTTCCCAAGAAT | 31 | 70 | 1170 |
| 2829 | 2848 | 525256 | CTGTAGATCTTGTTCCCAAG | 42 | 81 | 1171 |
| 2832 | 2851 | 525257 | ATGCTGTAGATCTTGTTCCC | 34 | 80 | 1172 |
| 2835 | 2854 | 525258 | CCCATGCTGTAGATCTTGTT | 38 | 80 | 1173 |
| 2838 | 2857 | 525259 | TGCCCCATGCTGTAGATCTT | 36 | 80 | 1174 |
| 2841 | 2860 | 525260 | TTCTGCCCCATGCTGTAGAT | 32 | 74 | 1175 |
| 2844 | 2863 | 525261 | AGATTCTGCCCCATGCTGTA | 27 | 75 | 1176 |
| 2847 | 2866 | 525262 | GAAAGATTCTGCCCCATGCT | 34 | 70 | 1177 |
| 2850 | 2869 | 525263 | GTGGAAAGATTCTGCCCCAT | 22 | 76 | 1178 |
| 2853 | 2872 | 525264 | CTGGTGGAAAGATTCTGCCC | 36 | 72 | 1179 |
| 2856 | 2875 | 525265 | TTGCTGGTGGAAAGATTCTG | 32 | 71 | 1180 |
| 2859 | 2878 | 525266 | GGATTGCTGGTGGAAAGATT | 20 | 74 | 1181 |
| 2862 | 2881 | 525267 | AGAGGATTGCTGGTGGAAAG | 25 | 73 | 1182 |
| 2865 | 2884 | 525268 | CCCAGAGGATTGCTGGTGGA | 40 | 82 | 1183 |
| 2868 | 2887 | 525269 | AATCCCAGAGGATTGCTGGT | 32 | 79 | 1184 |
| 2871 | 2890 | 525270 | AAGAATCCCAGAGGATTGCT | 23 | 69 | 1185 |
| 2874 | 2893 | 525271 | GGAAAGAATCCCAGAGGATT | 10 | 66 | 1186 |
| 2877 | 2896 | 525272 | TCGGGAAAGAATCCCAGAGG | 29 | 73 | 1187 |
| 2880 | 2899 | 525273 | TGGTCGGGAAAGAATCCCAG | 31 | 77 | 1188 |
| 2883 | 2902 | 525274 | TGGTGGTCGGGAAAGAATCC | 38 | 71 | 1189 |
| 2886 | 2905 | 525275 | AACTGGTGGTCGGGAAAGAA | 33 | 78 | 1190 |
| 2889 | 2908 | 525276 | TCCAACTGGTGGTCGGGAAA | 29 | 76 | 1191 |
| 2892 | 2911 | 525277 | GGATCCAACTGGTGGTCGGG | 19 | 81 | 1192 |
| 2895 | 2914 | 525278 | GCTGGATCCAACTGGTGGTC | 24 | 74 | 1193 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 2898 | 2917 | 525279 | AAGGCTGGATCCAACTGGTG | 33 | 83 | 1194 |
| 2901 | 2920 | 525280 | CTGAAGGCTGGATCCAACTG | 18 | 81 | 1195 |
| 2904 | 2923 | 525286 | GCTCTGAAGGCTGGATCCAA | 40 | 79 | 1196 |
| 2907 | 2926 | 525287 | TTTGCTCTGAAGGCTGGATC | 34 | 69 | 1197 |
| 2910 | 2929 | 525288 | GTGTTTGCTCTGAAGGCTGG | 38 | 72 | 1198 |
| 2913 | 2932 | 525289 | GCTGTGTTTGCTCTGAAGGC | 40 | 82 | 1199 |
| 2916 | 2935 | 525290 | TTTGCTGTGTTTGCTCTGAA | 44 | 78 | 1200 |
| 2919 | 2938 | 525291 | GGATTTGCTGTGTTTGCTCT | 38 | 76 | 1201 |
| 2922 | 2941 | 525292 | TCTGGATTTGCTGTGTTTGC | 28 | 79 | 1202 |
| 2925 | 2944 | 525293 | CAATCTGGATTTGCTGTGTT | 26 | 61 | 1203 |
| 2928 | 2947 | 525294 | TCCCAATCTGGATTTGCTGT | 32 | 68 | 1204 |
| 2931 | 2950 | 525295 | AAGTCCCAATCTGGATTTGC | 33 | 59 | 1205 |
| 2934 | 2953 | 146832 | TTGAAGTCCCAATCTGGATT | 17 | 35 | 1206 |
| 2937 | 2956 | 525296 | GGATTGAAGTCCCAATCTGG | 35 | 62 | 1207 |
| 2940 | 2959 | 525297 | TTGGGATTGAAGTCCCAATC | 10 | 36 | 1208 |
| 2943 | 2962 | 525298 | TTGTTGGGATTGAAGTCCCA | 24 | 49 | 1209 |
| 2946 | 2965 | 525299 | TCCTTGTTGGGATTGAAGTC | 16 | 52 | 1210 |
| 2949 | 2968 | 525300 | GTGTCCTTGTTGGGATTGAA | 18 | 71 | 1211 |
| 2952 | 2971 | 525301 | CAGGTGTCCTTGTTGGGATT | 25 | 73 | 1212 |
| 2955 | 2974 | 525302 | GGCCAGGTGTCCTTGTTGGG | 31 | 70 | 1213 |
| 2958 | 2977 | 525303 | TCTGGCCAGGTGTCCTTGTT | 29 | 75 | 1214 |
| 2978 | 2997 | 525304 | CAGCTCCTACCTTGTTGGCG | 29 | 71 | 1215 |
| 2981 | 3000 | 525305 | CTCCAGCTCCTACCTTGTTG | 19 | 63 | 1216 |
| 2984 | 3003 | 525306 | ATGCTCCAGCTCCTACCTTG | 35 | 75 | 1217 |
| 2987 | 3006 | 525307 | CGAATGCTCCAGCTCCTACC | 13 | 77 | 1218 |
| 2990 | 3009 | 525308 | GCCCGAATGCTCCAGCTCCT | 28 | 72 | 1219 |
| 2993 | 3012 | 525309 | CCAGCCCGAATGCTCCAGCT | 32 | 77 | 1220 |
| 2996 | 3015 | 525310 | AACCCAGCCCGAATGCTCCA | 34 | 72 | 1221 |
| 2999 | 3018 | 525311 | TGAAACCCAGCCCGAATGCT | 28 | 69 | 1222 |
| 3002 | 3021 | 525312 | GGGTGAAACCCAGCCCGAAT | 18 | 68 | 1223 |
| 3020 | 3039 | 525313 | AAAGGCCTCCGTGCGGTGGG | 36 | 77 | 1224 |
| 3023 | 3042 | 525314 | CCAAAAGGCCTCCGTGCGGT | 34 | 83 | 1225 |
| 3026 | 3045 | 525315 | ACCCCAAAAGGCCTCCGTGC | 28 | 70 | 1226 |
| 3029 | 3048 | 525316 | TCCACCCCAAAAGGCCTCCG | 26 | 65 | 1227 |
| 3032 | 3051 | 525317 | GGCTCCACCCCAAAAGGCCT | 19 | 36 | 1228 |
| 3035 | 3054 | 525318 | GAGGGCTCCACCCCAAAAGG | 14 | 36 | 1229 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 3038 | 3057 | 525319 | CCTGAGGGCTCCACCCCAAA | 32 | 71 | 1230 |
| 3041 | 3060 | 525320 | GAGCCTGAGGGCTCCACCCC | 37 | 61 | 1231 |
| 3044 | 3063 | 525321 | CCTGAGCCTGAGGGCTCCAC | 42 | 70 | 1232 |
| 3047 | 3066 | 525322 | TGCCCTGAGCCTGAGGGCTC | 24 | 56 | 1233 |
| 3050 | 3069 | 525323 | GTATGCCCTGAGCCTGAGGG | 14 | 75 | 1234 |
| 3053 | 3072 | 525324 | GTAGTATGCCCTGAGCCTGA | 29 | 83 | 1235 |
| 3056 | 3075 | 525325 | TTTGTAGTATGCCCTGAGCC | 32 | 61 | 1236 |
| 3059 | 3078 | 525326 | AAGTTTGTAGTATGCCCTGA | 35 | 70 | 1237 |
| 3062 | 3081 | 525327 | GCAAAGTTTGTAGTATGCCC | 37 | 61 | 1238 |
| 3065 | 3084 | 525328 | CTGGCAAAGTTTGTAGTATG | 26 | 63 | 1239 |
| 3068 | 3087 | 525329 | TTGCTGGCAAAGTTTGTAGT | 37 | 74 | 1240 |
| 3071 | 3090 | 525330 | GATTTGCTGGCAAAGTTTGT | 20 | 56 | 1241 |
| 3074 | 3093 | 525331 | GCGGATTTGCTGGCAAAGTT | 28 | 80 | 1242 |
| 3077 | 3096 | 525332 | GAGGCGGATTTGCTGGCAAA | 38 | 74 | 1243 |
| 3080 | 3099 | 525333 | CAGGAGGCGGATTTGCTGGC | 41 | 66 | 1244 |
| 3083 | 3102 | 525334 | AGGCAGGAGGCGGATTTGCT | 27 | 55 | 1245 |
| 3086 | 3105 | 525335 | TGGAGGCAGGAGGCGGATTT | 13 | 17 | 1246 |
| 3089 | 3108 | 525336 | TGGTGGAGGCAGGAGGCGGA | 7 | 21 | 1247 |
| 3092 | 3111 | 525337 | GATTGGTGGAGGCAGGAGGC | 21 | 44 | 1248 |
| 3095 | 3114 | 525338 | GGCGATTGGTGGAGGCAGGA | 31 | 65 | 1249 |
| 3098 | 3117 | 525339 | TCTGGCGATTGGTGGAGGCA | 15 | 76 | 1250 |
| 3101 | 3120 | 525340 | CTGTCTGGCGATTGGTGGAG | 35 | 73 | 1251 |
| 3104 | 3123 | 525341 | TTCCTGTCTGGCGATTGGTG | 32 | 72 | 1252 |
| 3107 | 3126 | 525342 | GCCTTCCTGTCTGGCGATTG | 28 | 64 | 1253 |
| 3110 | 3129 | 525343 | GCTGCCTTCCTGTCTGGCGA | 25 | 69 | 1254 |
| 3113 | 3132 | 525344 | TAGGCTGCCTTCCTGTCTGG | 32 | 79 | 1255 |
| 3116 | 3135 | 525345 | GGGTAGGCTGCCTTCCTGTC | 35 | 80 | 1256 |
| 3134 | 3153 | 525346 | TCAAAGGTGGAGACAGCGGG | 4 | 57 | 1257 |
| 3137 | 3156 | 525347 | TTCTCAAAGGTGGAGACAGC | 32 | 72 | 1258 |
| 3140 | 3159 | 525348 | TGTTTCTCAAAGGTGGAGAC | 32 | 66 | 1259 |
| 3143 | 3162 | 525349 | GAGTGTTTCTCAAAGGTGGA | 34 | 63 | 1260 |
| 3146 | 3165 | 525350 | GATGAGTGTTTCTCAAAGGT | 35 | 68 | 1261 |
| 3149 | 3168 | 525351 | GAGGATGAGTGTTTCTCAAA | 36 | 84 | 1262 |
| 3152 | 3171 | 525352 | CCTGAGGATGAGTGTTTCTC | 44 | 77 | 1263 |
| 3155 | 3174 | 525353 | TGGCCTGAGGATGAGTGTTT | 32 | 72 | 1264 |

TABLE 24-continued

Inhibition of viral HBV mRNA levels by chimeric antisense oligonucleotides targeted to SEQ ID NO: 1 (RTS3370 and RTS3372)

| Start Site | Stop Site | ISIS No | Sequence | RTS3370 % inhibition | RTS3372 % inhibition | SEQ ID NO |
|---|---|---|---|---|---|---|
| 3158 | 3177 | 525354 | GCATGGCCTGAGGATGAGTG | 27 | 73 | 1265 |
| 3162 | 3181 | 525355 | CACTGCATGGCCTGAGGATG | 40 | 69 | 1266 |

TABLE 25

Inhibition of viral HBV mRNA levels by chimeric antisense oligonucleotides targeted to SEQ ID NO: 1286 (RTS3370 and RTS3372)

| Viral Start Site | Viral Stop Site | ISIS No | Sequence | RTS3370 % inhibition | RTS3372 % inhibition | SEQ ID NO |
|---|---|---|---|---|---|---|
| 85 | 104 | 525356 | TTCCACTGCATGGCCTGAGG | 53 | 78 | 1267 |
| 88 | 107 | 525357 | GAATTCCACTGCATGGCCTG | 44 | 68 | 1268 |
| 91 | 110 | 525358 | GTGGAATTCCACTGCATGGC | 42 | 80 | 1269 |
| 94 | 113 | 525359 | GTTGTGGAATTCCACTGCAT | 45 | 77 | 1270 |
| 97 | 116 | 525360 | AAGGTTGTGGAATTCCACTG | 65 | 67 | 1271 |
| 100 | 119 | 525361 | TGAAAGGTTGTGGAATTCCA | 56 | 61 | 1272 |

Example 12

Dose-Dependent Inhibition of Viral HBV RNA in HepG2.2.15 Cells by MOE Gapmers Certain gapmers from the study described in Examples 11 and 12 were tested at various doses in human HepG2.2.15 cells. Cells were plated at a density of 28,000 cells per well and transfected using LipofectAMINE 2000® reagent with 5.56 nM, 16.67 nM, 50.0 nM, and 150.0 nM concentrations of antisense oligonucleotide, as specified in Table 26. After a treatment period of approximately 16 hours, RNA was isolated from the cells and HBV mRNA levels were measured by quantitative real-time PCR. Viral primer probe set RTS3370 was used to measure mRNA levels. HBV mRNA levels were adjusted according to total RNA content, as measured by RIBOGREEN®. Results are presented as percent inhibition of HBV, relative to untreated control cells.

The half maximal inhibitory concentration ($IC_{50}$) of each oligonucleotide is also presented in Table 26. As illustrated in Table 26, HBV mRNA levels were reduced in a dose-dependent manner in antisense oligonucleotide treated cells.

TABLE 26

Dose-dependent antisense inhibition of HBV RNA in HepG2.2.15 cells using RTS3370

| ISIS No | 5.5556 nM | 16.6667 nM | 50.0 nM | 150.0 nM | $IC_{50}$ (nM) |
|---|---|---|---|---|---|
| 146785 | 0 | 0 | 14 | 66 | 120.8 |
| 146786 | 40 | 64 | 78 | 88 | 8.5 |
| 505314 | 23 | 35 | 58 | 84 | 28.8 |
| 505339 | 28 | 42 | 62 | 84 | 23.2 |
| 505347 | 9 | 21 | 45 | 75 | 53.5 |
| 514469 | 11 | 22 | 69 | 79 | 35.4 |
| 524493 | 13 | 39 | 56 | 81 | 32.8 |
| 524540 | 15 | 38 | 54 | 80 | 34.0 |
| 524617 | 14 | 32 | 78 | 83 | 27.1 |
| 524619 | 33 | 42 | 60 | 84 | 21.3 |
| 524634 | 20 | 45 | 63 | 80 | 26.3 |
| 524641 | 39 | 49 | 62 | 86 | 14.9 |
| 524698 | 34 | 34 | 49 | 64 | 47.4 |
| 524699 | 25 | 31 | 44 | 63 | 66.1 |
| 524706 | 29 | 20 | 36 | 58 | 128.8 |
| 524709 | 32 | 26 | 48 | 56 | 89.1 |
| 524718 | 46 | 41 | 61 | 79 | 15.8 |
| 524731 | 49 | 53 | 68 | 83 | 8.1 |
| 524734 | 42 | 31 | 35 | 64 | 87.2 |
| 524767 | 19 | 38 | 62 | 84 | 27.8 |
| 524768 | 35 | 38 | 62 | 75 | 23.5 |
| 524769 | 16 | 26 | 61 | 75 | 38.1 |
| 524806 | 0 | 0 | 0 | 35 | >150.0 |
| 524807 | 3 | 22 | 39 | 74 | 60.2 |
| 524907 | 22 | 35 | 63 | 80 | 29.1 |
| 524908 | 25 | 45 | 67 | 78 | 22.9 |
| 524976 | 7 | 3 | 0 | 16 | >150.0 |
| 524978 | 6 | 0 | 0 | 27 | >150.0 |
| 524979 | 3 | 0 | 11 | 34 | >150.0 |
| 524980 | 18 | 51 | 48 | 59 | 51.5 |
| 524981 | 16 | 27 | 49 | 61 | 65.8 |
| 524982 | 21 | 19 | 29 | 54 | >150.0 |

TABLE 26-continued

Dose-dependent antisense inhibition of HBV RNA in HepG2.2.15 cells using RTS3370

| ISIS No | 5.5556 nM | 16.6667 nM | 50.0 nM | 150.0 nM | IC$_{50}$ (nM) |
|---|---|---|---|---|---|
| 524983 | 23 | 40 | 50 | 60 | 53.2 |
| 524984 | 19 | 25 | 45 | 74 | 50.0 |
| 524985 | 13 | 19 | 40 | 56 | 107.2 |
| 524986 | 29 | 48 | 46 | 64 | 39.3 |
| 524987 | 17 | 0 | 43 | 61 | 102.8 |
| 524988 | 22 | 39 | 52 | 63 | 47.6 |
| 524991 | 0 | 7 | 19 | 20 | >150.0 |
| 524997 | 17 | 0 | 1 | 9 | >150.0 |
| 524998 | 1 | 5 | 8 | 34 | >150.0 |
| 525095 | 5 | 0 | 0 | 18 | >150.0 |
| 525100 | 14 | 5 | 14 | 26 | >150.0 |
| 525101 | 0 | 0 | 15 | 19 | >150.0 |
| 525102 | 0 | 0 | 18 | 23 | >150.0 |
| 525103 | 0 | 0 | 3 | 15 | >150.0 |
| 525179 | 18 | 7 | 9 | 18 | >150.0 |
| 525245 | 0 | 0 | 8 | 8 | >150.0 |
| 525247 | 12 | 15 | 16 | 23 | >150.0 |
| 525289 | 1 | 1 | 15 | 30 | >150.0 |
| 525314 | 17 | 0 | 18 | 25 | >150.0 |
| 525324 | 0 | 6 | 13 | 16 | >150.0 |
| 525351 | 28 | 13 | 22 | 30 | >150.0 |

Some of the ISIS-oligonucleotides were also tested using primer probe set RTS3372. The results are presented in Table 27.

TABLE 27

Dose-dependent antisense inhibition of HBV RNA in HepG2.2.15 cells using RTS3372

| ISIS No | 5.5556 nM | 16.6667 nM | 50.0 nM | 150.0 nM | IC$_{50}$ (nM) |
|---|---|---|---|---|---|
| 146785 | 0 | 0 | 0 | 51 | >150.0 |
| 146786 | 41 | 68 | 81 | 91 | 7.9 |
| 505347 | 0 | 13 | 44 | 75 | 59.7 |
| 524103 | 0 | 0 | 1 | 9 | >150.0 |
| 524245 | 0 | 0 | 6 | 10 | >150.0 |
| 524767 | 18 | 46 | 60 | 85 | 25.8 |
| 524768 | 34 | 41 | 66 | 79 | 20.5 |
| 524769 | 12 | 38 | 60 | 77 | 34.5 |
| 524806 | 0 | 0 | 0 | 0 | >150.0 |
| 524807 | 0 | 9 | 34 | 70 | 78.6 |
| 524907 | 20 | 41 | 62 | 84 | 26.4 |
| 524908 | 27 | 45 | 66 | 82 | 21.3 |
| 524976 | 0 | 0 | 0 | 16 | >150.0 |
| 524978 | 3 | 0 | 0 | 22 | >150.0 |
| 524979 | 0 | 0 | 0 | 33 | >150.0 |
| 524980 | 28 | 51 | 52 | 67 | 30.1 |
| 524981 | 7 | 29 | 51 | 66 | 55.8 |
| 524982 | 22 | 29 | 37 | 63 | 83.5 |
| 524983 | 20 | 51 | 43 | 62 | 50.9 |
| 524984 | 20 | 30 | 38 | 75 | 51.7 |
| 524985 | 30 | 33 | 40 | 60 | 83.6 |
| 524986 | 25 | 51 | 51 | 66 | 33.8 |
| 524987 | 19 | 0 | 24 | 65 | 157.6 |
| 524988 | 12 | 41 | 45 | 62 | 59.2 |
| 524991 | 0 | 0 | 4 | 8 | >150.0 |
| 524997 | 19 | 0 | 0 | 15 | >150.0 |
| 524998 | 0 | 0 | 1 | 42 | >150.0 |
| 525095 | 0 | 0 | 0 | 17 | >150.0 |
| 525100 | 10 | 0 | 4 | 19 | >150.0 |
| 525101 | 10 | 0 | 21 | 25 | >150.0 |
| 525102 | 0 | 0 | 10 | 15 | >150.0 |
| 525247 | 11 | 12 | 15 | 28 | >150.0 |
| 525289 | 0 | 9 | 11 | 33 | >150.0 |
| 525314 | 1 | 0 | 18 | 24 | >150.0 |
| 525324 | 9 | 8 | 15 | 10 | >150.0 |

Example 13

Dose-Dependent Inhibition of Viral HBV RNA in HepG2.2.15 Cells by MOE Gapmers Certain gapmers from the studies described above were tested at various doses in human HepG2.2.15 cells. Cells were plated at a density of 30,000 cells per well and transfected using LipofectAMINE 2000® reagent with 7.8125 nM, 15.625 nM, 31.25 nM, 62.5 nM, 125.0 nM and 250.0 nM concentrations of antisense oligonucleotide, as specified in Table 28. After a treatment period of approximately 16 hours, RNA was isolated from the cells and HBV mRNA levels were measured by quantitative real-time PCR. Viral primer probe set RTS3370 was used to measure mRNA levels. HBV mRNA levels were adjusted according to total RNA content, as measured by RIBOGREEN®. Results are presented as percent inhibition of HBV, relative to untreated control cells.

The half maximal inhibitory concentration (IC$_{50}$) of each oligonucleotide is also presented in Table 28. As illustrated in Table 28, HBV mRNA levels were reduced in a dose-dependent manner in several antisense oligonucleotide treated cells.

TABLE 28

Dose-dependent antisense inhibition of HBV RNA in HepG2.2.15 cells using RTS3370

| ISIS No | 7.8125 nM | 15.625 nM | 31.25 nM | 62.5 nM | 125.0 nM | 250.0 nM | IC$_{50}$ (nM) |
|---|---|---|---|---|---|---|---|
| 146786 | 0 | 0 | 14 | 49 | 33 | 50 | 161.2 |
| 510100 | 0 | 17 | 30 | 28 | 44 | 53 | 177.8 |
| 510106 | 0 | 4 | 0 | 0 | 29 | 0 | >250.0 |
| 509934 | 0 | 0 | 0 | 7 | 16 | 0 | >250.0 |
| 510116 | 0 | 0 | 8 | 21 | 27 | 25 | >250.0 |
| 505347 | 31 | 3 | 30 | 63 | 80 | 81 | 48.7 |

Example 14

Antisense Inhibition of HBV Viral mRNA in HepG2 Cells by MOE Gapmers

Antisense oligonucleotides were designed targeting a HBV viral nucleic acid and were tested for their effects on HBV mRNA in vitro. The antisense oligonucleotides were tested in a series of experiments that had similar culture conditions. The results for each experiment are presented in separate tables. ISIS 146786, 509934, ISIS 509959, and ISIS 510100, from the studies described above, were also included. Cultured HepG2 cells at a density of 28,000 cells per well were transfected using LipofectAMINE2000® with 70 nM antisense oligonucleotide. After a treatment period of approximately 24 hours, RNA was isolated from the cells and HBV mRNA levels were measured by quantitative real-time PCR. Viral primer probe set RTS3370 (forward sequence CTTGGTCATGGGCCATCAG, designated herein as SEQ ID NO: 2; reverse sequence CGGCTAGGAGTTCCGCAGTA, designated herein as SEQ ID NO: 3; probe sequence TGCGTGGAACCTTTTCGGCTCC, designated herein as SEQ ID NO: 4) was used to measure mRNA levels. Levels were also measured using primer probe set RTS3371 (forward sequence CCAAACCTTCGGACGGAAA, designated herein as SEQ ID NO: 311; reverse sequence TGAGGCCCACTCCCATAGG, designated herein as SEQ ID NO: 312; probe sequence CCCATCATCCTGGGCTTTCGGAAAAT, designated herein as SEQ ID NO: 313). HBV mRNA levels were adjusted according to total RNA content, as measured by RIBOGREEN®. Results are presented as percent inhibition of HBV, relative to untreated control cells. In some of the assays shown in Tables 32, 35, 42, 45, and 46, the potency of ISIS 146786 was measured in two wells in a single plate. In those cases, the values of inhibition levels in both wells have been presented.

The newly designed chimeric antisense oligonucleotides in Tables below were designed as either 2-9-5 MOE gapmers, 2-9-6 MOE gapmers, 2-10-8 MOE gapmers, 3-9-4 MOE gapmers, 3-9-5 MOE gapmers, 3-10-3 MOE gapmers, 3-10-4 MOE gapmers, 3-10-7 MOE gapmers, 4-9-3 MOE gapmers, 4-9-4 MOE gapmers, 4-10-6 MOE gapmers, 5-9-2 MOE gapmers, 5-9-3 MOE gapmers, 5-10-5 MOE gapmers, 6-9-2 MOE gapmers, 6-10-4 MOE gapmers, 7-10-3 MOE gapmers, or 8-10-2 MOE gapmers. The 2-9-5 MOE gapmers are 16 nucleosides in length, wherein the central gap segment comprises of nine 2'-deoxynucleosides and is flanked on both sides (in the 5' and 3' directions) by wings comprising two and five nucleosides respectively. The 2-9-6 MOE gapmers are 17 nucleosides in length, wherein the central gap segment comprises of nine 2'-deoxynucleosides and is flanked on both sides (in the 5' and 3' directions) by wings comprising two and six nucleosides respectively. The 2-10-8 MOE gapmers are 20 nucleosides in length, wherein the central gap segment comprises of ten 2'-deoxynucleosides and is flanked on both sides (in the 5' and 3' directions) by wings comprising two and eight nucleosides respectively. The 3-9-4 MOE gapmers are 16 nucleosides in length, wherein the central gap segment comprises of nine 2'-deoxynucleosides and is flanked on both sides (in the 5' and 3' directions) by wings comprising three and four nucleosides respectively. The 3-9-5 MOE gapmers are 17 nucleosides in length, wherein the central gap segment comprises of nine 2'-deoxynucleosides and is flanked on both sides (in the 5' and 3' directions) by wings comprising three and five nucleosides respectively. The 3-10-3 MOE gapmers are 16 nucleosides in length, wherein the central gap segment comprises of ten 2'-deoxynucleosides and is flanked on both sides (in the 5' and 3' directions) by wings comprising three nucleosides each. The 3-10-4 MOE gapmers are 17 nucleosides in length, wherein the central gap segment comprises of ten 2'-deoxynucleosides and is flanked on both sides (in the 5' and 3' directions) by wings comprising three and four nucleosides respectively. The 3-10-7 MOE gapmers are 20 nucleosides in length, wherein the central gap segment comprises of ten 2'-deoxynucleosides and is flanked on both sides (in the 5' and 3' directions) by wings comprising three and seven nucleosides respectively. The 4-9-3 MOE gapmers are 16 nucleosides in length, wherein the central gap segment comprises of nine 2'-deoxynucleosides and is flanked on both sides (in the 5' and 3' directions) by wings comprising four and three nucleosides respectively. The 4-9-4 MOE gapmers are 17 nucleosides in length, wherein the central gap segment comprises of nine 2'-deoxynucleosides and is flanked on both sides (in the 5' and 3' directions) by wings comprising four nucleosides each. The 4-10-6 MOE gapmers are 20 nucleosides in length, wherein the central gap segment comprises of ten 2'-deoxynucleosides and is flanked on both sides (in the 5' and 3' directions) by wings comprising four and six nucleosides respectively. The 5-9-2 MOE gapmers are 16 nucleosides in length, wherein the central gap segment comprises of nine 2'-deoxynucleosides and is flanked on both sides (in the 5' and 3' directions) by wings comprising five and two nucleosides respectively. The 5-9-3 MOE gapmers are 17 nucleosides in length, wherein the central gap segment comprises of nine 2'-deoxynucleosides and is flanked on both sides (in the 5' and 3' directions) by wings comprising five and three nucleosides respectively. The 5-10-5 MOE gapmers are 20 nucleosides in length, wherein the central gap segment comprises of ten 2'-deoxynucleosides and is flanked on both sides (in the 5' and 3' directions) by wings comprising five nucleosides each. The 6-9-2 MOE gapmers are 17 nucleosides in length, wherein the central gap segment comprises of nine 2'-deoxynucleosides and is flanked on both sides (in the 5' and 3' directions) by wings comprising six and two nucleosides respectively. The 6-10-4 MOE gapmers are 20 nucleosides in length, wherein the central gap segment comprises of ten 2'-deoxynucleosides and is flanked on both sides (in the 5' and 3' directions) by wings comprising six and four nucleosides respectively. The 7-10-3 MOE gapmers are 20 nucleosides in length, wherein the central gap segment comprises of ten 2'-deoxynucleosides and is flanked on both sides (in the 5' and 3' directions) by wings comprising seven and three nucleosides respectively. The 8-10-2 MOE gapmers are 20 nucleosides in length, wherein the central gap segment comprises of ten 2'-deoxynucleosides and is flanked on both sides (in the 5' and 3' directions) by wings comprising eight and two nucleosides respectively. Each nucleoside in the 5' wing segment and each nucleoside in the 3' wing segment has an MOE sugar modification. The 'Motif' column indicates the motifs with the number of nucleosides in the wings and the gap segment of each of the oligonucleotides. The internucleoside linkages throughout each gapmer are phosphorothioate (P=S) linkages. All cytosine residues throughout each oligonucleotide are 5-methylcytosines.

"Viral Target start site" indicates the 5'-most nucleotide to which the gapmer is targeted in the viral gene sequence. "Viral Target stop site" indicates the 3'-most nucleotide to which the gapmer is targeted viral gene sequence. The 'Motif' column indicates the gap and wing structure of each gapmer. Each gapmer listed in the Tables is targeted to the viral genomic sequence, designated herein as SEQ ID NO: 1 (GENBANK Accession No. U95551.1). The potency of the newly designed oligonucleotides was compared with ISIS 146786, 509934, ISIS 509959, and ISIS 510100, the information of which have been placed at the top of each table.

TABLE 29

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 50 | 224 |
| 411 | 427 | GGCATAGCAGCAGGATG | 510100 | 3-10-4 | 62 | 17 |
| 58 | 74 | CTGGAGCCACCAGCAGG | 552276 | 5-9-3 | 42 | 1288 |

TABLE 29-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 59 | 75 | ACTGGAGCCACCAGCAG | 552277 | 5-9-3 | 46 | 1289 |
| 60 | 76 | AACTGGAGCCACCAGCA | 552278 | 5-9-3 | 31 | 1290 |
| 61 | 77 | GAACTGGAGCCACCAGC | 552279 | 5-9-3 | 41 | 1291 |
| 253 | 269 | GAAGTCCACCACGAGTC | 552280 | 5-9-3 | 5 | 9 |
| 254 | 270 | AGAAGTCCACCACGAGT | 552281 | 5-9-3 | 11 | 10 |
| 255 | 271 | GAGAAGTCCACCACGAG | 552282 | 5-9-3 | 20 | 11 |
| 256 | 272 | AGAGAAGTCCACCACGA | 552283 | 5-9-3 | 28 | 12 |
| 411 | 427 | GGCATAGCAGCAGGATG | 552230 | 4-9-4 | 57 | 17 |
| 411 | 427 | GGCATAGCAGCAGGATG | 552284 | 5-9-3 | 0 | 17 |
| 412 | 428 | AGGCATAGCAGCAGGAT | 552231 | 4-9-4 | 29 | 18 |
| 412 | 428 | AGGCATAGCAGCAGGAT | 552285 | 5-9-3 | 61 | 18 |
| 413 | 429 | GAGGCATAGCAGCAGGA | 552232 | 4-9-4 | 35 | 19 |
| 413 | 429 | GAGGCATAGCAGCAGGA | 552286 | 5-9-3 | 47 | 19 |
| 414 | 430 | TGAGGCATAGCAGCAGG | 552233 | 4-9-4 | 38 | 21 |
| 414 | 430 | TGAGGCATAGCAGCAGG | 552287 | 5-9-3 | 45 | 21 |
| 415 | 431 | ATGAGGCATAGCAGCAG | 552234 | 4-9-4 | 0 | 23 |
| 415 | 431 | ATGAGGCATAGCAGCAG | 552288 | 5-9-3 | 50 | 23 |
| 416 | 432 | GATGAGGCATAGCAGCA | 552235 | 4-9-4 | 0 | 25 |
| 416 | 432 | GATGAGGCATAGCAGCA | 552289 | 5-9-3 | 46 | 25 |
| 417 | 433 | AGATGAGGCATAGCAGC | 552236 | 4-9-4 | 45 | 27 |
| 417 | 433 | AGATGAGGCATAGCAGC | 552290 | 5-9-3 | 41 | 27 |
| 418 | 434 | AAGATGAGGCATAGCAG | 552237 | 4-9-4 | 44 | 29 |
| 418 | 434 | AAGATGAGGCATAGCAG | 552291 | 5-9-3 | 26 | 29 |
| 670 | 686 | ACTAGTAAACTGAGCCA | 552239 | 4-9-4 | 62 | 1292 |
| 670 | 686 | ACTAGTAAACTGAGCCA | 552293 | 5-9-3 | 67 | 1292 |
| 671 | 687 | CACTAGTAAACTGAGCC | 552240 | 4-9-4 | 61 | 1293 |
| 671 | 687 | CACTAGTAAACTGAGCC | 552294 | 5-9-3 | 71 | 1293 |
| 672 | 688 | GCACTAGTAAACTGAGC | 552241 | 4-9-4 | 55 | 1294 |
| 672 | 688 | GCACTAGTAAACTGAGC | 552295 | 5-9-3 | 58 | 1294 |
| 687 | 703 | ACCACTGAACAAATGGC | 552242 | 4-9-4 | 60 | 40 |
| 687 | 703 | ACCACTGAACAAATGGC | 552296 | 5-9-3 | 59 | 40 |
| 688 | 704 | AACCACTGAACAAATGG | 552243 | 4-9-4 | 57 | 41 |
| 688 | 704 | AACCACTGAACAAATGG | 552297 | 5-9-3 | 55 | 41 |
| 689 | 705 | GAACCACTGAACAAATG | 552244 | 4-9-4 | 33 | 42 |
| 689 | 705 | GAACCACTGAACAAATG | 552298 | 5-9-3 | 48 | 42 |
| 690 | 706 | CGAACCACTGAACAAAT | 552245 | 4-9-4 | 48 | 43 |

TABLE 29-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 690 | 706 | CGAACCACTGAACAAAT | 552299 | 5-9-3 | 34 | 43 |
| 1261 | 1277 | CGCAGTATGGATCGGCA | 552246 | 4-9-4 | 81 | 1295 |
| 1261 | 1277 | CGCAGTATGGATCGGCA | 552300 | 5-9-3 | 56 | 1295 |
| 1262 | 1278 | CCGCAGTATGGATCGGC | 552247 | 4-9-4 | 87 | 1296 |
| 1262 | 1278 | CCGCAGTATGGATCGGC | 552301 | 5-9-3 | 86 | 1296 |
| 1263 | 1279 | TCCGCAGTATGGATCGG | 552248 | 4-9-4 | 72 | 1297 |
| 1263 | 1279 | TCCGCAGTATGGATCGG | 552302 | 5-9-3 | 77 | 1297 |
| 1264 | 1280 | TTCCGCAGTATGGATCG | 552249 | 4-9-4 | 56 | 1298 |
| 1264 | 1280 | TTCCGCAGTATGGATCG | 552303 | 5-9-3 | 65 | 1298 |
| 1265 | 1281 | GTTCCGCAGTATGGATC | 552250 | 4-9-4 | 52 | 1299 |
| 1265 | 1281 | GTTCCGCAGTATGGATC | 552304 | 5-9-3 | 57 | 1299 |
| 1266 | 1282 | AGTTCCGCAGTATGGAT | 552251 | 4-9-4 | 43 | 1300 |
| 1266 | 1282 | AGTTCCGCAGTATGGAT | 552305 | 5-9-3 | 56 | 1300 |
| 1267 | 1283 | GAGTTCCGCAGTATGGA | 552252 | 4-9-4 | 62 | 1301 |
| 1267 | 1283 | GAGTTCCGCAGTATGGA | 552306 | 5-9-3 | 75 | 1301 |
| 1268 | 1284 | GGAGTTCCGCAGTATGG | 552253 | 4-9-4 | 82 | 1302 |
| 1268 | 1284 | GGAGTTCCGCAGTATGG | 552307 | 5-9-3 | 90 | 1302 |
| 1269 | 1285 | AGGAGTTCCGCAGTATG | 552254 | 4-9-4 | 74 | 1303 |
| 1577 | 1593 | AAGCGAAGTGCACACGG | 552255 | 4-9-4 | 78 | 1304 |
| 1578 | 1594 | GAAGCGAAGTGCACACG | 552256 | 4-9-4 | 65 | 1305 |
| 1579 | 1595 | TGAAGCGAAGTGCACAC | 552257 | 4-9-4 | 62 | 1306 |
| 1580 | 1596 | GTGAAGCGAAGTGCACA | 552258 | 4-9-4 | 72 | 1307 |
| 1581 | 1597 | GGTGAAGCGAAGTGCAC | 552259 | 4-9-4 | 63 | 1308 |
| 1582 | 1598 | AGGTGAAGCGAAGTGCA | 552260 | 4-9-4 | 58 | 1309 |
| 1583 | 1599 | GAGGTGAAGCGAAGTGC | 552261 | 4-9-4 | 63 | 1310 |
| 1584 | 1600 | AGAGGTGAAGCGAAGTG | 552262 | 4-9-4 | 50 | 1311 |
| 1585 | 1601 | CAGAGGTGAAGCGAAGT | 552263 | 4-9-4 | 60 | 1312 |
| 1586 | 1602 | GCAGAGGTGAAGCGAAG | 552264 | 4-9-4 | 52 | 1313 |
| 1587 | 1603 | TGCAGAGGTGAAGCGAA | 552265 | 4-9-4 | 68 | 1314 |
| 1588 | 1604 | GTGCAGAGGTGAAGCGA | 552266 | 4-9-4 | 62 | 1315 |
| 1589 | 1605 | CGTGCAGAGGTGAAGCG | 552267 | 4-9-4 | 58 | 1316 |
| 1590 | 1606 | ACGTGCAGAGGTGAAGC | 552268 | 4-9-4 | 62 | 1317 |
| 1778 | 1794 | TTATGCCTACAGCCTCC | 552269 | 4-9-4 | 52 | 47 |
| 1779 | 1795 | TTTATGCCTACAGCCTC | 552270 | 4-9-4 | 54 | 49 |
| 1780 | 1796 | ATTTATGCCTACAGCCT | 552271 | 4-9-4 | 58 | 51 |
| 1781 | 1797 | AATTTATGCCTACAGCC | 552272 | 4-9-4 | 40 | 53 |

TABLE 29-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1782 | 1798 | CAATTTATGCCTACAGC | 552273 | 4-9-4 | 34 | 54 |
| 1783 | 1799 | CCAATTTATGCCTACAG | 552274 | 4-9-4 | 34 | 55 |
| 1784 | 1800 | ACCAATTTATGCCTACA | 552275 | 4-9-4 | 39 | 56 |

TABLE 30

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 49 | 224 |
| 414 | 429 | GAGGCATAGCAGCAGG | 509959 | 3-10-3 | 43 | 145 |
| 411 | 427 | GGCATAGCAGCAGGATG | 510100 | 3-10-4 | 54 | 17 |
| 58 | 73 | TGGAGCCACCAGCAGG | 552384 | 2-9-5 | 29 | 1318 |
| 58 | 73 | TGGAGCCACCAGCAGG | 552440 | 3-9-4 | 58 | 1318 |
| 59 | 74 | CTGGAGCCACCAGCAG | 552385 | 2-9-5 | 57 | 1319 |
| 59 | 74 | CTGGAGCCACCAGCAG | 552441 | 3-9-4 | 42 | 1319 |
| 60 | 75 | ACTGGAGCCACCAGCA | 552386 | 2-9-5 | 53 | 1320 |
| 60 | 75 | ACTGGAGCCACCAGCA | 552442 | 3-9-4 | 53 | 1320 |
| 61 | 76 | AACTGGAGCCACCAGC | 552387 | 2-9-5 | 48 | 1321 |
| 61 | 76 | AACTGGAGCCACCAGC | 552443 | 3-9-4 | 59 | 1321 |
| 62 | 77 | GAACTGGAGCCACCAG | 552388 | 2-9-5 | 40 | 86 |
| 62 | 77 | GAACTGGAGCCACCAG | 552444 | 3-9-4 | 51 | 86 |
| 411 | 426 | GCATAGCAGCAGGATG | 552389 | 2-9-5 | 39 | 137 |
| 411 | 426 | GCATAGCAGCAGGATG | 552445 | 3-9-4 | 60 | 137 |
| 412 | 427 | GGCATAGCAGCAGGAT | 552390 | 2-9-5 | 52 | 140 |
| 412 | 427 | GGCATAGCAGCAGGAT | 552446 | 3-9-4 | 54 | 140 |
| 413 | 428 | AGGCATAGCAGCAGGA | 552391 | 2-9-5 | 57 | 143 |
| 413 | 428 | AGGCATAGCAGCAGGA | 552447 | 3-9-4 | 54 | 143 |
| 414 | 429 | GAGGCATAGCAGCAGG | 552392 | 2-9-5 | 0 | 145 |
| 414 | 429 | GAGGCATAGCAGCAGG | 552448 | 3-9-4 | 58 | 145 |
| 415 | 430 | TGAGGCATAGCAGCAG | 552393 | 2-9-5 | 59 | 147 |
| 415 | 430 | TGAGGCATAGCAGCAG | 552449 | 3-9-4 | 60 | 147 |
| 416 | 431 | ATGAGGCATAGCAGCA | 552394 | 2-9-5 | 53 | 149 |
| 416 | 431 | ATGAGGCATAGCAGCA | 552450 | 3-9-4 | 53 | 149 |
| 417 | 432 | GATGAGGCATAGCAGC | 552395 | 2-9-5 | 57 | 151 |

TABLE 30-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 417 | 432 | GATGAGGCATAGCAGC | 552451 | 3-9-4 | 39 | 151 |
| 418 | 433 | AGATGAGGCATAGCAG | 552396 | 2-9-5 | 62 | 153 |
| 418 | 433 | AGATGAGGCATAGCAG | 552452 | 3-9-4 | 57 | 153 |
| 457 | 473 | ACGGGCAACATACCTTG | 552238 | 4-9-4 | 38 | 33 |
| 457 | 473 | ACGGGCAACATACCTTG | 552292 | 5-9-3 | 48 | 33 |
| 457 | 473 | ACGGGCAACATACCTTG | 552346 | 6-9-2 | 0 | 33 |
| 457 | 472 | CGGGCAACATACCTTG | 552397 | 2-9-5 | 63 | 167 |
| 457 | 472 | CGGGCAACATACCTTG | 552453 | 3-9-4 | 56 | 167 |
| 458 | 473 | ACGGGCAACATACCTT | 552398 | 2-9-5 | 61 | 168 |
| 458 | 473 | ACGGGCAACATACCTT | 552454 | 3-9-4 | 48 | 168 |
| 670 | 685 | CTAGTAAACTGAGCCA | 552399 | 2-9-5 | 52 | 181 |
| 671 | 686 | ACTAGTAAACTGAGCC | 552400 | 2-9-5 | 57 | 1322 |
| 672 | 687 | CACTAGTAAACTGAGC | 552401 | 2-9-5 | 52 | 1323 |
| 673 | 688 | GCACTAGTAAACTGAG | 552402 | 2-9-5 | 54 | 1324 |
| 687 | 702 | CCACTGAACAAATGGC | 552403 | 2-9-5 | 74 | 188 |
| 688 | 703 | ACCACTGAACAAATGG | 552404 | 2-9-5 | 43 | 190 |
| 689 | 704 | AACCACTGAACAAATG | 552405 | 2-9-5 | 15 | 191 |
| 690 | 705 | GAACCACTGAACAAAT | 552406 | 2-9-5 | 37 | 192 |
| 691 | 706 | CGAACCACTGAACAAA | 552407 | 2-9-5 | 37 | 194 |
| 1261 | 1276 | GCAGTATGGATCGGCA | 552408 | 2-9-5 | 76 | 211 |
| 1262 | 1277 | CGCAGTATGGATCGGC | 552409 | 2-9-5 | 76 | 1325 |
| 1263 | 1278 | CCGCAGTATGGATCGG | 552410 | 2-9-5 | 63 | 1326 |
| 1264 | 1279 | TCCGCAGTATGGATCG | 552411 | 2-9-5 | 70 | 1327 |
| 1265 | 1280 | TTCCGCAGTATGGATC | 552412 | 2-9-5 | 62 | 1328 |
| 1266 | 1281 | GTTCCGCAGTATGGAT | 552413 | 2-9-5 | 56 | 1329 |
| 1267 | 1282 | AGTTCCGCAGTATGGA | 552414 | 2-9-5 | 63 | 1330 |
| 1268 | 1283 | GAGTTCCGCAGTATGG | 552415 | 2-9-5 | 52 | 1331 |
| 1269 | 1284 | GGAGTTCCGCAGTATG | 552416 | 2-9-5 | 67 | 1332 |
| 1270 | 1285 | AGGAGTTCCGCAGTAT | 552417 | 2-9-5 | 50 | 1333 |
| 1577 | 1592 | AGCGAAGTGCACACGG | 552418 | 2-9-5 | 79 | 1334 |
| 1578 | 1593 | AAGCGAAGTGCACACG | 552419 | 2-9-5 | 70 | 1335 |
| 1579 | 1594 | GAAGCGAAGTGCACAC | 552420 | 2-9-5 | 71 | 1336 |
| 1580 | 1595 | TGAAGCGAAGTGCACA | 552421 | 2-9-5 | 69 | 1337 |
| 1581 | 1596 | GTGAAGCGAAGTGCAC | 552422 | 2-9-5 | 68 | 1338 |
| 1582 | 1597 | GGTGAAGCGAAGTGCA | 552423 | 2-9-5 | 65 | 1339 |
| 1583 | 1598 | AGGTGAAGCGAAGTGC | 552424 | 2-9-5 | 70 | 1340 |

TABLE 30-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1584 | 1599 | GAGGTGAAGCGAAGTG | 552425 | 2-9-5 | 51 | 1341 |
| 1585 | 1600 | AGAGGTGAAGCGAAGT | 552426 | 2-9-5 | 40 | 1342 |
| 1586 | 1601 | CAGAGGTGAAGCGAAG | 552427 | 2-9-5 | 35 | 1343 |
| 1587 | 1602 | GCAGAGGTGAAGCGAA | 552428 | 2-9-5 | 58 | 1344 |
| 1588 | 1603 | TGCAGAGGTGAAGCGA | 552429 | 2-9-5 | 46 | 1345 |
| 1589 | 1604 | GTGCAGAGGTGAAGCG | 552430 | 2-9-5 | 53 | 1346 |
| 1590 | 1605 | CGTGCAGAGGTGAAGC | 552431 | 2-9-5 | 51 | 1347 |
| 1591 | 1606 | ACGTGCAGAGGTGAAG | 552432 | 2-9-5 | 57 | 1348 |
| 1778 | 1793 | TATGCCTACAGCCTCC | 552433 | 2-9-5 | 54 | 230 |
| 1779 | 1794 | TTATGCCTACAGCCTC | 552434 | 2-9-5 | 44 | 231 |
| 1780 | 1795 | TTTATGCCTACAGCCT | 552435 | 2-9-5 | 46 | 232 |
| 1781 | 1796 | ATTTATGCCTACAGCC | 552436 | 2-9-5 | 36 | 233 |
| 1782 | 1797 | AATTTATGCCTACAGC | 552437 | 2-9-5 | 27 | 234 |
| 1783 | 1798 | CAATTTATGCCTACAG | 552438 | 2-9-5 | 27 | 235 |
| 1784 | 1799 | CCAATTTATGCCTACA | 552439 | 2-9-5 | 13 | 236 |

TABLE 31

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 35 | 224 |
| 414 | 429 | GAGGCATAGCAGCAGG | 509959 | 3-10-3 | 52 | 145 |
| 58 | 73 | TGGAGCCACCAGCAGG | 552496 | 4-9-3 | 47 | 1318 |
| 59 | 74 | CTGGAGCCACCAGCAG | 552497 | 4-9-3 | 57 | 1319 |
| 60 | 75 | ACTGGAGCCACCAGCA | 552498 | 4-9-3 | 45 | 1320 |
| 61 | 76 | AACTGGAGCCACCAGC | 552499 | 4-9-3 | 52 | 1321 |
| 62 | 77 | GAACTGGAGCCACCAG | 552500 | 4-9-3 | 46 | 86 |
| 411 | 426 | GCATAGCAGCAGGATG | 552501 | 4-9-3 | 44 | 137 |
| 412 | 427 | GGCATAGCAGCAGGAT | 552502 | 4-9-3 | 57 | 140 |
| 413 | 428 | AGGCATAGCAGCAGGA | 552503 | 4-9-3 | 52 | 143 |
| 414 | 429 | GAGGCATAGCAGCAGG | 552504 | 4-9-3 | 45 | 145 |
| 415 | 430 | TGAGGCATAGCAGCAG | 552505 | 4-9-3 | 56 | 147 |
| 416 | 431 | ATGAGGCATAGCAGCA | 552506 | 4-9-3 | 54 | 149 |
| 417 | 432 | GATGAGGCATAGCAGC | 552507 | 4-9-3 | 34 | 151 |
| 418 | 433 | AGATGAGGCATAGCAG | 552508 | 4-9-3 | 34 | 153 |

TABLE 31-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 457 | 472 | CGGGCAACATACCTTG | 552509 | 4-9-3 | 48 | 167 |
| 458 | 473 | ACGGGCAACATACCTT | 552510 | 4-9-3 | 50 | 168 |
| 670 | 685 | CTAGTAAACTGAGCCA | 552455 | 3-9-4 | 66 | 181 |
| 670 | 685 | CTAGTAAACTGAGCCA | 552511 | 4-9-3 | 66 | 181 |
| 671 | 686 | ACTAGTAAACTGAGCC | 552456 | 3-9-4 | 64 | 1322 |
| 671 | 686 | ACTAGTAAACTGAGCC | 552512 | 4-9-3 | 62 | 1322 |
| 672 | 687 | CACTAGTAAACTGAGC | 552457 | 3-9-4 | 14 | 1323 |
| 672 | 687 | CACTAGTAAACTGAGC | 552513 | 4-9-3 | 56 | 1323 |
| 673 | 688 | GCACTAGTAAACTGAG | 552458 | 3-9-4 | 59 | 1324 |
| 673 | 688 | GCACTAGTAAACTGAG | 552514 | 4-9-3 | 52 | 1324 |
| 687 | 702 | CCACTGAACAAATGGC | 552459 | 3-9-4 | 69 | 188 |
| 687 | 702 | CCACTGAACAAATGGC | 552515 | 4-9-3 | 57 | 188 |
| 688 | 703 | ACCACTGAACAAATGG | 552460 | 3-9-4 | 0 | 190 |
| 688 | 703 | ACCACTGAACAAATGG | 552516 | 4-9-3 | 54 | 190 |
| 689 | 704 | AACCACTGAACAAATG | 552461 | 3-9-4 | 20 | 191 |
| 689 | 704 | AACCACTGAACAAATG | 552517 | 4-9-3 | 52 | 191 |
| 690 | 705 | GAACCACTGAACAAAT | 552462 | 3-9-4 | 46 | 192 |
| 690 | 705 | GAACCACTGAACAAAT | 552518 | 4-9-3 | 34 | 192 |
| 691 | 706 | CGAACCACTGAACAAA | 552463 | 3-9-4 | 48 | 194 |
| 691 | 706 | CGAACCACTGAACAAA | 552519 | 4-9-3 | 44 | 194 |
| 1261 | 1276 | GCAGTATGGATCGGCA | 552464 | 3-9-4 | 81 | 211 |
| 1261 | 1276 | GCAGTATGGATCGGCA | 552520 | 4-9-3 | 69 | 211 |
| 1262 | 1277 | CGCAGTATGGATCGGC | 552465 | 3-9-4 | 84 | 1325 |
| 1262 | 1277 | CGCAGTATGGATCGGC | 552521 | 4-9-3 | 80 | 1325 |
| 1263 | 1278 | CCGCAGTATGGATCGG | 552466 | 3-9-4 | 75 | 1326 |
| 1263 | 1278 | CCGCAGTATGGATCGG | 552522 | 4-9-3 | 76 | 1326 |
| 1264 | 1279 | TCCGCAGTATGGATCG | 552467 | 3-9-4 | 65 | 1327 |
| 1264 | 1279 | TCCGCAGTATGGATCG | 552523 | 4-9-3 | 71 | 1327 |
| 1265 | 1280 | TTCCGCAGTATGGATC | 552468 | 3-9-4 | 53 | 1328 |
| 1265 | 1280 | TTCCGCAGTATGGATC | 552524 | 4-9-3 | 43 | 1328 |
| 1266 | 1281 | GTTCCGCAGTATGGAT | 552469 | 3-9-4 | 51 | 1329 |
| 1266 | 1281 | GTTCCGCAGTATGGAT | 552525 | 4-9-3 | 57 | 1329 |
| 1267 | 1282 | AGTTCCGCAGTATGGA | 552470 | 3-9-4 | 46 | 1330 |
| 1267 | 1282 | AGTTCCGCAGTATGGA | 552526 | 4-9-3 | 60 | 1330 |
| 1268 | 1283 | GAGTTCCGCAGTATGG | 552471 | 3-9-4 | 54 | 1331 |
| 1268 | 1283 | GAGTTCCGCAGTATGG | 552527 | 4-9-3 | 72 | 1331 |

TABLE 31-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1269 | 1284 | GGAGTTCCGCAGTATG | 552472 | 3-9-4 | 78 | 1332 |
| 1269 | 1284 | GGAGTTCCGCAGTATG | 552528 | 4-9-3 | 78 | 1332 |
| 1270 | 1285 | AGGAGTTCCGCAGTAT | 552473 | 3-9-4 | 67 | 1333 |
| 1270 | 1285 | AGGAGTTCCGCAGTAT | 552529 | 4-9-3 | 77 | 1333 |
| 1577 | 1592 | AGCGAAGTGCACACGG | 552474 | 3-9-4 | 79 | 1334 |
| 1577 | 1592 | AGCGAAGTGCACACGG | 552530 | 4-9-3 | 78 | 1334 |
| 1578 | 1593 | AAGCGAAGTGCACACG | 552475 | 3-9-4 | 74 | 1335 |
| 1578 | 1593 | AAGCGAAGTGCACACG | 552531 | 4-9-3 | 68 | 1335 |
| 1579 | 1594 | GAAGCGAAGTGCACAC | 552476 | 3-9-4 | 52 | 1336 |
| 1580 | 1595 | TGAAGCGAAGTGCACA | 552477 | 3-9-4 | 76 | 1337 |
| 1581 | 1596 | GTGAAGCGAAGTGCAC | 552478 | 3-9-4 | 70 | 1338 |
| 1582 | 1597 | GGTGAAGCGAAGTGCA | 552479 | 3-9-4 | 67 | 1339 |
| 1583 | 1598 | AGGTGAAGCGAAGTGC | 552480 | 3-9-4 | 68 | 1340 |
| 1584 | 1599 | GAGGTGAAGCGAAGTG | 552481 | 3-9-4 | 57 | 1341 |
| 1585 | 1600 | AGAGGTGAAGCGAAGT | 552482 | 3-9-4 | 51 | 1342 |
| 1586 | 1601 | CAGAGGTGAAGCGAAG | 552483 | 3-9-4 | 48 | 1343 |
| 1587 | 1602 | GCAGAGGTGAAGCGAA | 552484 | 3-9-4 | 58 | 1344 |
| 1588 | 1603 | TGCAGAGGTGAAGCGA | 552485 | 3-9-4 | 51 | 1345 |
| 1589 | 1604 | GTGCAGAGGTGAAGCG | 552486 | 3-9-4 | 55 | 1346 |
| 1590 | 1605 | CGTGCAGAGGTGAAGC | 552487 | 3-9-4 | 62 | 1347 |
| 1591 | 1606 | ACGTGCAGAGGTGAAG | 552488 | 3-9-4 | 51 | 1348 |
| 1778 | 1793 | TATGCCTACAGCCTCC | 552489 | 3-9-4 | 49 | 230 |
| 1779 | 1794 | TTATGCCTACAGCCTC | 552490 | 3-9-4 | 51 | 231 |
| 1780 | 1795 | TTTATGCCTACAGCCT | 552491 | 3-9-4 | 51 | 232 |
| 1781 | 1796 | ATTTATGCCTACAGCC | 552492 | 3-9-4 | 38 | 233 |
| 1782 | 1797 | AATTTATGCCTACAGC | 552493 | 3-9-4 | 52 | 234 |
| 1783 | 1798 | CAATTTATGCCTACAG | 552494 | 3-9-4 | 17 | 235 |
| 1784 | 1799 | CCAATTTATGCCTACA | 552495 | 3-9-4 | 49 | 236 |

TABLE 32

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 43 52 | 224 |

TABLE 32-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 414 | 429 | GAGGCATAGCAGCAGG | 509959 | 3-10-3 | 38 | 145 |
| 58 | 73 | TGGAGCCACCAGCAGG | 552552 | 5-9-2 | 33 | 1318 |
| 59 | 74 | CTGGAGCCACCAGCAG | 552553 | 5-9-2 | 46 | 1319 |
| 60 | 75 | ACTGGAGCCACCAGCA | 552554 | 5-9-2 | 54 | 1320 |
| 61 | 76 | AACTGGAGCCACCAGC | 552555 | 5-9-2 | 50 | 1321 |
| 62 | 77 | GAACTGGAGCCACCAG | 552556 | 5-9-2 | 46 | 86 |
| 411 | 426 | GCATAGCAGCAGGATG | 552557 | 5-9-2 | 57 | 137 |
| 412 | 427 | GGCATAGCAGCAGGAT | 552558 | 5-9-2 | 55 | 140 |
| 413 | 428 | AGGCATAGCAGCAGGA | 552559 | 5-9-2 | 66 | 143 |
| 414 | 429 | GAGGCATAGCAGCAGG | 552560 | 5-9-2 | 44 | 145 |
| 415 | 430 | TGAGGCATAGCAGCAG | 552561 | 5-9-2 | 48 | 147 |
| 416 | 431 | ATGAGGCATAGCAGCA | 552562 | 5-9-2 | 52 | 149 |
| 417 | 432 | GATGAGGCATAGCAGC | 552563 | 5-9-2 | 45 | 151 |
| 418 | 433 | AGATGAGGCATAGCAG | 552564 | 5-9-2 | 41 | 153 |
| 457 | 472 | CGGGCAACATACCTTG | 552565 | 5-9-2 | 54 | 167 |
| 458 | 473 | ACGGGCAACATACCTT | 552566 | 5-9-2 | 56 | 168 |
| 670 | 685 | CTAGTAAACTGAGCCA | 552567 | 5-9-2 | 71 | 181 |
| 671 | 686 | ACTAGTAAACTGAGCC | 552568 | 5-9-2 | 64 | 1322 |
| 672 | 687 | CACTAGTAAACTGAGC | 552569 | 5-9-2 | 59 | 1323 |
| 673 | 688 | GCACTAGTAAACTGAG | 552570 | 5-9-2 | 60 | 1324 |
| 687 | 702 | CCACTGAACAAATGGC | 552571 | 5-9-2 | 55 | 188 |
| 688 | 703 | ACCACTGAACAAATGG | 552572 | 5-9-2 | 60 | 190 |
| 689 | 704 | AACCACTGAACAAATG | 552573 | 5-9-2 | 24 | 191 |
| 690 | 705 | GAACCACTGAACAAAT | 552574 | 5-9-2 | 34 | 192 |
| 691 | 706 | CGAACCACTGAACAAA | 552575 | 5-9-2 | 36 | 194 |
| 1261 | 1276 | GCAGTATGGATCGGCA | 552576 | 5-9-2 | 67 | 211 |
| 1262 | 1277 | CGCAGTATGGATCGGC | 552577 | 5-9-2 | 64 | 1325 |
| 1263 | 1278 | CCGCAGTATGGATCGG | 552578 | 5-9-2 | 75 | 1326 |
| 1264 | 1279 | TCCGCAGTATGGATCG | 552579 | 5-9-2 | 75 | 1327 |
| 1265 | 1280 | TTCCGCAGTATGGATC | 552580 | 5-9-2 | 59 | 1328 |
| 1266 | 1281 | GTTCCGCAGTATGGAT | 552581 | 5-9-2 | 54 | 1329 |
| 1267 | 1282 | AGTTCCGCAGTATGGA | 552582 | 5-9-2 | 61 | 1330 |
| 1268 | 1283 | GAGTTCCGCAGTATGG | 552583 | 5-9-2 | 69 | 1331 |
| 1269 | 1284 | GGAGTTCCGCAGTATG | 552584 | 5-9-2 | 74 | 1332 |
| 1270 | 1285 | AGGAGTTCCGCAGTAT | 552585 | 5-9-2 | 62 | 1333 |
| 1577 | 1592 | AGCGAAGTGCACACGG | 552586 | 5-9-2 | 79 | 1334 |

TABLE 32-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1578 | 1593 | AAGCGAAGTGCACACG | 552587 | 5-9-2 | 71 | 1335 |
| 1579 | 1594 | GAAGCGAAGTGCACAC | 552532 | 4-9-3 | 48 | 1336 |
| 1579 | 1594 | GAAGCGAAGTGCACAC | 552588 | 5-9-2 | 70 | 1336 |
| 1580 | 1595 | TGAAGCGAAGTGCACA | 552533 | 4-9-3 | 43 | 1337 |
| 1580 | 1595 | TGAAGCGAAGTGCACA | 552589 | 5-9-2 | 59 | 1337 |
| 1581 | 1596 | GTGAAGCGAAGTGCAC | 552534 | 4-9-3 | 62 | 1338 |
| 1581 | 1596 | GTGAAGCGAAGTGCAC | 552590 | 5-9-2 | 70 | 1338 |
| 1582 | 1597 | GGTGAAGCGAAGTGCA | 552535 | 4-9-3 | 55 | 1339 |
| 1582 | 1597 | GGTGAAGCGAAGTGCA | 552591 | 5-9-2 | 51 | 1339 |
| 1583 | 1598 | AGGTGAAGCGAAGTGC | 552536 | 4-9-3 | 3 | 1340 |
| 1583 | 1598 | AGGTGAAGCGAAGTGC | 552592 | 5-9-2 | 50 | 1340 |
| 1584 | 1599 | GAGGTGAAGCGAAGTG | 552537 | 4-9-3 | 14 | 1341 |
| 1584 | 1599 | GAGGTGAAGCGAAGTG | 552593 | 5-9-2 | 46 | 1341 |
| 1585 | 1600 | AGAGGTGAAGCGAAGT | 552538 | 4-9-3 | 52 | 1342 |
| 1585 | 1600 | AGAGGTGAAGCGAAGT | 552594 | 5-9-2 | 55 | 1342 |
| 1586 | 1601 | CAGAGGTGAAGCGAAG | 552539 | 4-9-3 | 47 | 1343 |
| 1586 | 1601 | CAGAGGTGAAGCGAAG | 552595 | 5-9-2 | 60 | 1343 |
| 1587 | 1602 | GCAGAGGTGAAGCGAA | 552540 | 4-9-3 | 60 | 1344 |
| 1587 | 1602 | GCAGAGGTGAAGCGAA | 552596 | 5-9-2 | 63 | 1344 |
| 1588 | 1603 | TGCAGAGGTGAAGCGA | 552541 | 4-9-3 | 60 | 1345 |
| 1588 | 1603 | TGCAGAGGTGAAGCGA | 552597 | 5-9-2 | 61 | 1345 |
| 1589 | 1604 | GTGCAGAGGTGAAGCG | 552542 | 4-9-3 | 64 | 1346 |
| 1589 | 1604 | GTGCAGAGGTGAAGCG | 552598 | 5-9-2 | 57 | 1346 |
| 1590 | 1605 | CGTGCAGAGGTGAAGC | 552543 | 4-9-3 | 46 | 1347 |
| 1590 | 1605 | CGTGCAGAGGTGAAGC | 552600 | 5-9-2 | 59 | 1347 |
| 1591 | 1606 | ACGTGCAGAGGTGAAG | 552544 | 4-9-3 | 53 | 1348 |
| 1591 | 1606 | ACGTGCAGAGGTGAAG | 552602 | 5-9-2 | 6 | 1348 |
| 1778 | 1793 | TATGCCTACAGCCTCC | 552545 | 4-9-3 | 33 | 230 |
| 1778 | 1793 | TATGCCTACAGCCTCC | 552604 | 5-9-2 | 47 | 230 |
| 1779 | 1794 | TTATGCCTACAGCCTC | 552546 | 4-9-3 | 42 | 231 |
| 1779 | 1794 | TTATGCCTACAGCCTC | 552606 | 5-9-2 | 53 | 231 |
| 1780 | 1795 | TTTATGCCTACAGCCT | 552547 | 4-9-3 | 51 | 232 |
| 1780 | 1795 | TTTATGCCTACAGCCT | 552608 | 5-9-2 | 53 | 232 |
| 1781 | 1796 | ATTTATGCCTACAGCC | 552548 | 4-9-3 | 52 | 233 |
| 1781 | 1796 | ATTTATGCCTACAGCC | 552610 | 5-9-2 | 47 | 233 |
| 1782 | 1797 | AATTTATGCCTACAGC | 552549 | 4-9-3 | 38 | 234 |

TABLE 32-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1782 | 1797 | AATTTATGCCTACAGC | 552612 | 5-9-2 | 39 | 234 |
| 1783 | 1798 | CAATTTATGCCTACAG | 552550 | 4-9-3 | 19 | 235 |
| 1783 | 1798 | CAATTTATGCCTACAG | 552614 | 5-9-2 | 24 | 235 |
| 1784 | 1799 | CCAATTTATGCCTACA | 552551 | 4-9-3 | 24 | 236 |
| 1784 | 1799 | CCAATTTATGCCTACA | 552616 | 5-9-2 | 15 | 236 |

TABLE 33

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 51 | 224 |
| 1780 | 1799 | CCAATTTATGCCTACAGCCT | 509934 | 5-10-5 | 76 | 50 |
| 58 | 77 | GAACTGGAGCCACCAGCAGG | 552007 | 6-10-4 | 61 | 83 |
| 58 | 77 | GAACTGGAGCCACCAGCAGG | 552039 | 7-10-3 | 84 | 83 |
| 253 | 272 | AGAGAAGTCCACCACGAGTC | 552008 | 6-10-4 | 48 | 103 |
| 253 | 272 | AGAGAAGTCCACCACGAGTC | 552040 | 7-10-3 | 48 | 103 |
| 411 | 430 | TGAGGCATAGCAGCAGGATG | 552009 | 6-10-4 | 77 | 136 |
| 411 | 430 | TGAGGCATAGCAGCAGGATG | 552041 | 7-10-3 | 73 | 136 |
| 412 | 431 | ATGAGGCATAGCAGCAGGAT | 552010 | 6-10-4 | 63 | 139 |
| 412 | 431 | ATGAGGCATAGCAGCAGGAT | 552042 | 7-10-3 | 66 | 139 |
| 413 | 432 | GATGAGGCATAGCAGCAGGA | 552011 | 6-10-4 | 52 | 142 |
| 413 | 432 | GATGAGGCATAGCAGCAGGA | 552043 | 7-10-3 | 54 | 142 |
| 414 | 433 | AGATGAGGCATAGCAGCAGG | 552012 | 6-10-4 | 73 | 20 |
| 414 | 433 | AGATGAGGCATAGCAGCAGG | 552044 | 7-10-3 | 86 | 20 |
| 415 | 434 | AAGATGAGGCATAGCAGCAG | 552013 | 6-10-4 | 73 | 22 |
| 415 | 434 | AAGATGAGGCATAGCAGCAG | 552045 | 7-10-3 | 65 | 22 |
| 416 | 435 | GAAGATGAGGCATAGCAGCA | 552014 | 6-10-4 | 76 | 24 |
| 416 | 435 | GAAGATGAGGCATAGCAGCA | 552046 | 7-10-3 | 93 | 24 |
| 417 | 436 | AGAAGATGAGGCATAGCAGC | 552015 | 6-10-4 | 70 | 26 |
| 417 | 436 | AGAAGATGAGGCATAGCAGC | 552047 | 7-10-3 | 77 | 26 |
| 418 | 437 | AAGAAGATGAGGCATAGCAG | 552016 | 6-10-4 | 61 | 28 |
| 418 | 437 | AAGAAGATGAGGCATAGCAG | 552048 | 7-10-3 | 66 | 28 |
| 687 | 706 | CGAACCACTGAACAAATGGC | 552017 | 6-10-4 | 73 | 39 |
| 687 | 706 | CGAACCACTGAACAAATGGC | 552049 | 7-10-3 | 73 | 39 |

TABLE 33-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1261 | 1280 | TTCCGCAGTATGGATCGGCA | 552018 | 6-10-4 | 98 | 719 |
| 1261 | 1280 | TTCCGCAGTATGGATCGGCA | 552050 | 7-10-3 | 98 | 719 |
| 1262 | 1281 | GTTCCGCAGTATGGATCGGC | 552019 | 6-10-4 | 98 | 212 |
| 1262 | 1281 | GTTCCGCAGTATGGATCGGC | 552051 | 7-10-3 | 99 | 212 |
| 1263 | 1282 | AGTTCCGCAGTATGGATCGG | 551986 | 4-10-6 | 92 | 720 |
| 1263 | 1282 | AGTTCCGCAGTATGGATCGG | 552020 | 6-10-4 | 97 | 720 |
| 1263 | 1282 | AGTTCCGCAGTATGGATCGG | 552052 | 7-10-3 | 98 | 720 |
| 1264 | 1283 | GAGTTCCGCAGTATGGATCG | 551987 | 4-10-6 | 95 | 721 |
| 1264 | 1283 | GAGTTCCGCAGTATGGATCG | 552021 | 6-10-4 | 97 | 721 |
| 1264 | 1283 | GAGTTCCGCAGTATGGATCG | 552053 | 7-10-3 | 98 | 721 |
| 1265 | 1284 | GGAGTTCCGCAGTATGGATC | 551988 | 4-10-6 | 50 | 1349 |
| 1265 | 1284 | GGAGTTCCGCAGTATGGATC | 552005 | 5-10-5 | 99 | 1349 |
| 1265 | 1284 | GGAGTTCCGCAGTATGGATC | 552022 | 6-10-4 | 99 | 1349 |
| 1265 | 1284 | GGAGTTCCGCAGTATGGATC | 552054 | 7-10-3 | 99 | 1349 |
| 1266 | 1285 | AGGAGTTCCGCAGTATGGAT | 551989 | 4-10-6 | 96 | 722 |
| 1266 | 1285 | AGGAGTTCCGCAGTATGGAT | 552023 | 6-10-4 | 99 | 722 |
| 1266 | 1285 | AGGAGTTCCGCAGTATGGAT | 552055 | 7-10-3 | 98 | 722 |
| 1577 | 1596 | GTGAAGCGAAGTGCACACGG | 551990 | 4-10-6 | 86 | 224 |
| 1577 | 1596 | GTGAAGCGAAGTGCACACGG | 552024 | 6-10-4 | 89 | 224 |
| 1577 | 1596 | GTGAAGCGAAGTGCACACGG | 552056 | 7-10-3 | 88 | 224 |
| 1578 | 1597 | GGTGAAGCGAAGTGCACACG | 551991 | 4-10-6 | 0 | 801 |
| 1578 | 1597 | GGTGAAGCGAAGTGCACACG | 552025 | 6-10-4 | 90 | 801 |
| 1578 | 1597 | GGTGAAGCGAAGTGCACACG | 552057 | 7-10-3 | 92 | 801 |
| 1579 | 1598 | AGGTGAAGCGAAGTGCACAC | 551992 | 4-10-6 | 72 | 802 |
| 1579 | 1598 | AGGTGAAGCGAAGTGCACAC | 552026 | 6-10-4 | 88 | 802 |
| 1579 | 1598 | AGGTGAAGCGAAGTGCACAC | 552058 | 7-10-3 | 86 | 802 |
| 1580 | 1599 | GAGGTGAAGCGAAGTGCACA | 551993 | 4-10-6 | 82 | 225 |
| 1580 | 1599 | GAGGTGAAGCGAAGTGCACA | 552027 | 6-10-4 | 87 | 225 |
| 1580 | 1599 | GAGGTGAAGCGAAGTGCACA | 552059 | 7-10-3 | 88 | 225 |
| 1581 | 1600 | AGAGGTGAAGCGAAGTGCAC | 551994 | 4-10-6 | 85 | 804 |
| 1581 | 1600 | AGAGGTGAAGCGAAGTGCAC | 552028 | 6-10-4 | 83 | 804 |
| 1581 | 1600 | AGAGGTGAAGCGAAGTGCAC | 552060 | 7-10-3 | 82 | 804 |
| 1582 | 1601 | CAGAGGTGAAGCGAAGTGCA | 551995 | 4-10-6 | 84 | 805 |
| 1582 | 1601 | CAGAGGTGAAGCGAAGTGCA | 552029 | 6-10-4 | 88 | 805 |
| 1582 | 1601 | CAGAGGTGAAGCGAAGTGCA | 552061 | 7-10-3 | 85 | 805 |
| 1583 | 1602 | GCAGAGGTGAAGCGAAGTGC | 551996 | 4-10-6 | 87 | 226 |

TABLE 33-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1583 | 1602 | GCAGAGGTGAAGCGAAGTGC | 552030 | 6-10-4 | 88 | 226 |
| 1583 | 1602 | GCAGAGGTGAAGCGAAGTGC | 552062 | 7-10-3 | 85 | 226 |
| 1584 | 1603 | TGCAGAGGTGAAGCGAAGTG | 551997 | 4-10-6 | 83 | 806 |
| 1584 | 1603 | TGCAGAGGTGAAGCGAAGTG | 552031 | 6-10-4 | 82 | 806 |
| 1585 | 1604 | GTGCAGAGGTGAAGCGAAGT | 551998 | 4-10-6 | 85 | 807 |
| 1585 | 1604 | GTGCAGAGGTGAAGCGAAGT | 552032 | 6-10-4 | 87 | 807 |
| 1586 | 1605 | CGTGCAGAGGTGAAGCGAAG | 551999 | 4-10-6 | 82 | 227 |
| 1586 | 1605 | CGTGCAGAGGTGAAGCGAAG | 552033 | 6-10-4 | 87 | 227 |
| 1587 | 1606 | ACGTGCAGAGGTGAAGCGAA | 552000 | 4-10-6 | 83 | 1350 |
| 1587 | 1606 | ACGTGCAGAGGTGAAGCGAA | 552006 | 5-10-5 | 88 | 1350 |
| 1587 | 1606 | ACGTGCAGAGGTGAAGCGAA | 552034 | 6-10-4 | 89 | 1350 |
| 1778 | 1797 | AATTTATGCCTACAGCCTCC | 552001 | 4-10-6 | 65 | 46 |
| 1778 | 1797 | AATTTATGCCTACAGCCTCC | 552035 | 6-10-4 | 60 | 46 |
| 1779 | 1798 | CAATTTATGCCTACAGCCTC | 552002 | 4-10-6 | 63 | 48 |
| 1779 | 1798 | CAATTTATGCCTACAGCCTC | 552036 | 6-10-4 | 65 | 48 |
| 1780 | 1799 | CCAATTTATGCCTACAGCCT | 552003 | 4-10-6 | 65 | 50 |
| 1780 | 1799 | CCAATTTATGCCTACAGCCT | 552037 | 6-10-4 | 58 | 50 |
| 1781 | 1800 | ACCAATTTATGCCTACAGCC | 552004 | 4-10-6 | 58 | 52 |
| 1781 | 1800 | ACCAATTTATGCCTACAGCC | 552038 | 6-10-4 | 70 | 52 |

TABLE 34

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 64 | 224 |
| 411 | 427 | GGCATAGCAGCAGGATG | 510100 | 3-10-4 | 62 | 17 |
| 58 | 74 | CTGGAGCCACCAGCAGG | 552168 | 3-9-5 | 79 | 1288 |
| 58 | 74 | CTGGAGCCACCAGCAGG | 552222 | 4-9-4 | 79 | 1288 |
| 59 | 75 | ACTGGAGCCACCAGCAG | 552169 | 3-9-5 | 67 | 1289 |
| 59 | 75 | ACTGGAGCCACCAGCAG | 552223 | 4-9-4 | 40 | 1289 |
| 60 | 76 | AACTGGAGCCACCAGCA | 552170 | 3-9-5 | 69 | 1290 |
| 60 | 76 | AACTGGAGCCACCAGCA | 552224 | 4-9-4 | 64 | 1290 |
| 61 | 77 | GAACTGGAGCCACCAGC | 552171 | 3-9-5 | 65 | 1291 |
| 61 | 77 | GAACTGGAGCCACCAGC | 552225 | 4-9-4 | 69 | 1291 |
| 253 | 269 | GAAGTCCACCACGAGTC | 552172 | 3-9-5 | 33 | 9 |

TABLE 34-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 253 | 269 | GAAGTCCACCACGAGTC | 552226 | 4-9-4 | 48 | 9 |
| 254 | 270 | AGAAGTCCACCACGAGT | 552173 | 3-9-5 | 41 | 10 |
| 254 | 270 | AGAAGTCCACCACGAGT | 552227 | 4-9-4 | 32 | 10 |
| 255 | 271 | GAGAAGTCCACCACGAG | 552174 | 3-9-5 | 31 | 11 |
| 255 | 271 | GAGAAGTCCACCACGAG | 552228 | 4-9-4 | 42 | 11 |
| 256 | 272 | AGAGAAGTCCACCACGA | 552175 | 3-9-5 | 59 | 12 |
| 411 | 427 | GGCATAGCAGCAGGATG | 552176 | 3-9-5 | 68 | 17 |
| 412 | 428 | AGGCATAGCAGCAGGAT | 552177 | 3-9-5 | 55 | 18 |
| 413 | 429 | GAGGCATAGCAGCAGGA | 552178 | 3-9-5 | 66 | 19 |
| 414 | 430 | TGAGGCATAGCAGCAGG | 552179 | 3-9-5 | 70 | 21 |
| 415 | 431 | ATGAGGCATAGCAGCAG | 552180 | 3-9-5 | 66 | 23 |
| 416 | 432 | GATGAGGCATAGCAGCA | 552181 | 3-9-5 | 51 | 25 |
| 417 | 433 | AGATGAGGCATAGCAGC | 552182 | 3-9-5 | 69 | 27 |
| 418 | 434 | AAGATGAGGCATAGCAG | 552183 | 3-9-5 | 69 | 29 |
| 457 | 473 | ACGGGCAACATACCTTG | 552184 | 3-9-5 | 43 | 33 |
| 670 | 686 | ACTAGTAAACTGAGCCA | 552185 | 3-9-5 | 66 | 1292 |
| 671 | 687 | CACTAGTAAACTGAGCC | 552186 | 3-9-5 | 54 | 1293 |
| 672 | 688 | GCACTAGTAAACTGAGC | 552187 | 3-9-5 | 74 | 1294 |
| 687 | 703 | ACCACTGAACAAATGGC | 552188 | 3-9-5 | 78 | 40 |
| 688 | 704 | AACCACTGAACAAATGG | 552189 | 3-9-5 | 57 | 41 |
| 689 | 705 | GAACCACTGAACAAATG | 552190 | 3-9-5 | 39 | 42 |
| 690 | 706 | CGAACCACTGAACAAAT | 552191 | 3-9-5 | 60 | 43 |
| 1261 | 1277 | CGCAGTATGGATCGGCA | 552192 | 3-9-5 | 85 | 1295 |
| 1262 | 1278 | CCGCAGTATGGATCGGC | 552193 | 3-9-5 | 86 | 1296 |
| 1263 | 1279 | TCCGCAGTATGGATCGG | 552194 | 3-9-5 | 68 | 1297 |
| 1264 | 1280 | TTCCGCAGTATGGATCG | 552195 | 3-9-5 | 73 | 1298 |
| 1265 | 1281 | GTTCCGCAGTATGGATC | 552196 | 3-9-5 | 60 | 1299 |
| 1266 | 1282 | AGTTCCGCAGTATGGAT | 552197 | 3-9-5 | 60 | 1300 |
| 1267 | 1283 | GAGTTCCGCAGTATGGA | 552198 | 3-9-5 | 61 | 1301 |
| 1268 | 1284 | GGAGTTCCGCAGTATGG | 552199 | 3-9-5 | 89 | 1302 |
| 1269 | 1285 | AGGAGTTCCGCAGTATG | 552200 | 3-9-5 | 85 | 1303 |
| 1577 | 1593 | AAGCGAAGTGCACACGG | 552201 | 3-9-5 | 81 | 1304 |
| 1578 | 1594 | GAAGCGAAGTGCACACG | 552202 | 3-9-5 | 76 | 1305 |
| 1579 | 1595 | TGAAGCGAAGTGCACAC | 552203 | 3-9-5 | 74 | 1306 |
| 1580 | 1596 | GTGAAGCGAAGTGCACA | 552204 | 3-9-5 | 71 | 1307 |
| 1581 | 1597 | GGTGAAGCGAAGTGCAC | 552151 | 2-9-6 | 77 | 1308 |

TABLE 34-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1581 | 1597 | GGTGAAGCGAAGTGCAC | 552205 | 3-9-5 | 78 | 1308 |
| 1582 | 1598 | AGGTGAAGCGAAGTGCA | 552152 | 2-9-6 | 72 | 1309 |
| 1582 | 1598 | AGGTGAAGCGAAGTGCA | 552206 | 3-9-5 | 77 | 1309 |
| 1583 | 1599 | GAGGTGAAGCGAAGTGC | 552153 | 2-9-6 | 67 | 1310 |
| 1583 | 1599 | GAGGTGAAGCGAAGTGC | 552207 | 3-9-5 | 81 | 1310 |
| 1584 | 1600 | AGAGGTGAAGCGAAGTG | 552154 | 2-9-6 | 56 | 1311 |
| 1584 | 1600 | AGAGGTGAAGCGAAGTG | 552208 | 3-9-5 | 70 | 1311 |
| 1585 | 1601 | CAGAGGTGAAGCGAAGT | 552155 | 2-9-6 | 61 | 1312 |
| 1585 | 1601 | CAGAGGTGAAGCGAAGT | 552209 | 3-9-5 | 63 | 1312 |
| 1586 | 1602 | GCAGAGGTGAAGCGAAG | 552156 | 2-9-6 | 20 | 1313 |
| 1586 | 1602 | GCAGAGGTGAAGCGAAG | 552210 | 3-9-5 | 75 | 1313 |
| 1587 | 1603 | TGCAGAGGTGAAGCGAA | 552157 | 2-9-6 | 39 | 1314 |
| 1587 | 1603 | TGCAGAGGTGAAGCGAA | 552211 | 3-9-5 | 75 | 1314 |
| 1588 | 1604 | GTGCAGAGGTGAAGCGA | 552158 | 2-9-6 | 70 | 1315 |
| 1588 | 1604 | GTGCAGAGGTGAAGCGA | 552212 | 3-9-5 | 67 | 1315 |
| 1589 | 1605 | CGTGCAGAGGTGAAGCG | 552159 | 2-9-6 | 74 | 1316 |
| 1589 | 1605 | CGTGCAGAGGTGAAGCG | 552213 | 3-9-5 | 70 | 1316 |
| 1590 | 1606 | ACGTGCAGAGGTGAAGC | 552160 | 2-9-6 | 78 | 1317 |
| 1590 | 1606 | ACGTGCAGAGGTGAAGC | 552214 | 3-9-5 | 79 | 1317 |
| 1778 | 1794 | TTATGCCTACAGCCTCC | 552161 | 2-9-6 | 56 | 47 |
| 1778 | 1794 | TTATGCCTACAGCCTCC | 552215 | 3-9-5 | 61 | 47 |
| 1779 | 1795 | TTTATGCCTACAGCCTC | 552162 | 2-9-6 | 64 | 49 |
| 1779 | 1795 | TTTATGCCTACAGCCTC | 552216 | 3-9-5 | 62 | 49 |
| 1780 | 1796 | ATTTATGCCTACAGCCT | 552163 | 2-9-6 | 71 | 51 |
| 1780 | 1796 | ATTTATGCCTACAGCCT | 552217 | 3-9-5 | 58 | 51 |
| 1781 | 1797 | AATTTATGCCTACAGCC | 552164 | 2-9-6 | 52 | 53 |
| 1781 | 1797 | AATTTATGCCTACAGCC | 552218 | 3-9-5 | 56 | 53 |
| 1782 | 1798 | CAATTTATGCCTACAGC | 552165 | 2-9-6 | 53 | 54 |
| 1782 | 1798 | CAATTTATGCCTACAGC | 552219 | 3-9-5 | 33 | 54 |
| 1783 | 1799 | CCAATTTATGCCTACAG | 552166 | 2-9-6 | 41 | 55 |
| 1783 | 1799 | CCAATTTATGCCTACAG | 552220 | 3-9-5 | 53 | 55 |
| 1784 | 1800 | ACCAATTTATGCCTACA | 552167 | 2-9-6 | 54 | 56 |
| 1784 | 1800 | ACCAATTTATGCCTACA | 552221 | 3-9-5 | 31 | 56 |

TABLE 35

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 60 85 | 224 |
| 1780 | 1799 | CCAATTTATGCCTACAGCCT | 509934 | 5-10-5 | 76 | 50 |
| 411 | 427 | GGCATAGCAGCAGGATG | 510100 | 3-10-4 | 73 | 17 |
| 58 | 77 | GAACTGGAGCCACCAGCAGG | 552071 | 8-10-2 | 79 | 83 |
| 58 | 74 | CTGGAGCCACCAGCAGG | 552114 | 2-9-6 | 66 | 1288 |
| 59 | 75 | ACTGGAGCCACCAGCAG | 552115 | 2-9-6 | 70 | 1289 |
| 60 | 76 | AACTGGAGCCACCAGCA | 552116 | 2-9-6 | 68 | 1290 |
| 61 | 77 | GAACTGGAGCCACCAGC | 552117 | 2-9-6 | 70 | 1291 |
| 253 | 272 | AGAGAAGTCCACCACGAGTC | 552072 | 8-10-2 | 50 | 103 |
| 253 | 269 | GAAGTCCACCACGAGTC | 552118 | 2-9-6 | 66 | 9 |
| 254 | 270 | AGAAGTCCACCACGAGT | 552119 | 2-9-6 | 62 | 10 |
| 255 | 271 | GAGAAGTCCACCACGAG | 552120 | 2-9-6 | 35 | 11 |
| 256 | 272 | AGAGAAGTCCACCACGA | 552121 | 2-9-6 | 39 | 12 |
| 411 | 430 | TGAGGCATAGCAGCAGGATG | 552073 | 8-10-2 | 80 | 136 |
| 411 | 427 | GGCATAGCAGCAGGATG | 552122 | 2-9-6 | 55 | 17 |
| 412 | 431 | ATGAGGCATAGCAGCAGGAT | 552074 | 8-10-2 | 73 | 139 |
| 412 | 428 | AGGCATAGCAGCAGGAT | 552123 | 2-9-6 | 75 | 18 |
| 413 | 432 | GATGAGGCATAGCAGCAGGA | 552075 | 8-10-2 | 78 | 142 |
| 413 | 429 | GAGGCATAGCAGCAGGA | 552124 | 2-9-6 | 64 | 19 |
| 414 | 433 | AGATGAGGCATAGCAGCAGG | 552076 | 8-10-2 | 70 | 20 |
| 414 | 430 | TGAGGCATAGCAGCAGG | 552125 | 2-9-6 | 73 | 21 |
| 415 | 434 | AAGATGAGGCATAGCAGCAG | 552077 | 8-10-2 | 83 | 22 |
| 415 | 431 | ATGAGGCATAGCAGCAG | 552126 | 2-9-6 | 64 | 23 |
| 416 | 435 | GAAGATGAGGCATAGCAGCA | 552078 | 8-10-2 | 80 | 24 |
| 416 | 432 | GATGAGGCATAGCAGCA | 552127 | 2-9-6 | 72 | 25 |
| 417 | 436 | AGAAGATGAGGCATAGCAGC | 552079 | 8-10-2 | 86 | 26 |
| 417 | 433 | AGATGAGGCATAGCAGC | 552128 | 2-9-6 | 76 | 27 |
| 418 | 437 | AAGAAGATGAGGCATAGCAG | 552080 | 8-10-2 | 83 | 28 |
| 418 | 434 | AAGATGAGGCATAGCAG | 552129 | 2-9-6 | 72 | 29 |
| 670 | 686 | ACTAGTAAACTGAGCCA | 552131 | 2-9-6 | 61 | 1292 |
| 671 | 687 | CACTAGTAAACTGAGCC | 552132 | 2-9-6 | 73 | 1293 |
| 672 | 688 | GCACTAGTAAACTGAGC | 552133 | 2-9-6 | 75 | 1294 |
| 687 | 706 | CGAACCACTGAACAAATGGC | 552081 | 8-10-2 | 76 | 39 |
| 687 | 703 | ACCACTGAACAAATGGC | 552134 | 2-9-6 | 58 | 40 |
| 688 | 704 | AACCACTGAACAAATGG | 552135 | 2-9-6 | 67 | 41 |
| 689 | 705 | GAACCACTGAACAAATG | 552136 | 2-9-6 | 65 | 42 |

TABLE 35-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 690 | 706 | CGAACCACTGAACAAAT | 552137 | 2-9-6 | 55 | 43 |
| 1261 | 1280 | TTCCGCAGTATGGATCGGCA | 552082 | 8-10-2 | 98 | 719 |
| 1261 | 1277 | CGCAGTATGGATCGGCA | 552138 | 2-9-6 | 82 | 1295 |
| 1262 | 1281 | GTTCCGCAGTATGGATCGGC | 552083 | 8-10-2 | 99 | 212 |
| 1262 | 1278 | CCGCAGTATGGATCGGC | 552139 | 2-9-6 | 86 | 1296 |
| 1263 | 1282 | AGTTCCGCAGTATGGATCGG | 552084 | 8-10-2 | 99 | 720 |
| 1263 | 1279 | TCCGCAGTATGGATCGG | 552140 | 2-9-6 | 74 | 1297 |
| 1264 | 1283 | GAGTTCCGCAGTATGGATCG | 552085 | 8-10-2 | 100 | 721 |
| 1264 | 1280 | TTCCGCAGTATGGATCG | 552141 | 2-9-6 | 67 | 1298 |
| 1265 | 1284 | GGAGTTCCGCAGTATGGATC | 552086 | 8-10-2 | 100 | 1349 |
| 1265 | 1281 | GTTCCGCAGTATGGATC | 552142 | 2-9-6 | 45 | 1299 |
| 1266 | 1285 | AGGAGTTCCGCAGTATGGAT | 552087 | 8-10-2 | 100 | 722 |
| 1266 | 1282 | AGTTCCGCAGTATGGAT | 552143 | 2-9-6 | 68 | 1300 |
| 1267 | 1283 | GAGTTCCGCAGTATGGA | 552144 | 2-9-6 | 78 | 1301 |
| 1268 | 1284 | GGAGTTCCGCAGTATGG | 552145 | 2-9-6 | 88 | 1302 |
| 1269 | 1285 | AGGAGTTCCGCAGTATG | 552146 | 2-9-6 | 81 | 1303 |
| 1577 | 1596 | GTGAAGCGAAGTGCACACGG | 552088 | 8-10-2 | 95 | 224 |
| 1577 | 1593 | AAGCGAAGTGCACACGG | 552147 | 2-9-6 | 88 | 1304 |
| 1578 | 1597 | GGTGAAGCGAAGTGCACACG | 552089 | 8-10-2 | 93 | 801 |
| 1578 | 1594 | GAAGCGAAGTGCACACG | 552148 | 2-9-6 | 79 | 1305 |
| 1579 | 1598 | AGGTGAAGCGAAGTGCACAC | 552090 | 8-10-2 | 87 | 802 |
| 1579 | 1595 | TGAAGCGAAGTGCACAC | 552149 | 2-9-6 | 81 | 1306 |
| 1580 | 1599 | GAGGTGAAGCGAAGTGCACA | 552091 | 8-10-2 | 88 | 225 |
| 1581 | 1600 | AGAGGTGAAGCGAAGTGCAC | 552092 | 8-10-2 | 90 | 804 |
| 1582 | 1601 | CAGAGGTGAAGCGAAGTGCA | 552093 | 8-10-2 | 91 | 805 |
| 1583 | 1602 | GCAGAGGTGAAGCGAAGTGC | 552094 | 8-10-2 | 88 | 226 |
| 1584 | 1603 | TGCAGAGGTGAAGCGAAGTG | 552063 | 7-10-3 | 81 | 806 |
| 1584 | 1603 | TGCAGAGGTGAAGCGAAGTG | 552095 | 8-10-2 | 89 | 806 |
| 1585 | 1604 | GTGCAGAGGTGAAGCGAAGT | 552064 | 7-10-3 | 85 | 807 |
| 1585 | 1604 | GTGCAGAGGTGAAGCGAAGT | 552096 | 8-10-2 | 92 | 807 |
| 1586 | 1605 | CGTGCAGAGGTGAAGCGAAG | 552065 | 7-10-3 | 86 | 227 |
| 1586 | 1605 | CGTGCAGAGGTGAAGCGAAG | 552097 | 8-10-2 | 93 | 227 |
| 1587 | 1606 | ACGTGCAGAGGTGAAGCGAA | 552066 | 7-10-3 | 33 | 1350 |
| 1587 | 1606 | ACGTGCAGAGGTGAAGCGAA | 552098 | 8-10-2 | 88 | 1350 |
| 1778 | 1797 | AATTTATGCCTACAGCCTCC | 552067 | 7-10-3 | 50 | 46 |
| 1778 | 1797 | AATTTATGCCTACAGCCTCC | 552099 | 8-10-2 | 70 | 46 |

TABLE 35-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1779 | 1798 | CAATTTATGCCTACAGCCTC | 552068 | 7-10-3 | 73 | 48 |
| 1779 | 1798 | CAATTTATGCCTACAGCCTC | 552100 | 8-10-2 | 70 | 48 |
| 1780 | 1799 | CCAATTTATGCCTACAGCCT | 552069 | 7-10-3 | 73 | 50 |
| 1780 | 1799 | CCAATTTATGCCTACAGCCT | 552101 | 8-10-2 | 76 | 50 |
| 1781 | 1800 | ACCAATTTATGCCTACAGCC | 552070 | 7-10-3 | 71 | 52 |
| 1781 | 1800 | ACCAATTTATGCCTACAGCC | 552102 | 8-10-2 | 64 | 52 |

TABLE 36

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 84 | 224 |
| 411 | 427 | GGCATAGCAGCAGGATG | 510100 | 3-10-4 | 76 | 17 |
| 58 | 74 | CTGGAGCCACCAGCAGG | 552330 | 6-9-2 | 54 | 1288 |
| 59 | 75 | ACTGGAGCCACCAGCAG | 552331 | 6-9-2 | 66 | 1289 |
| 60 | 76 | AACTGGAGCCACCAGCA | 552332 | 6-9-2 | 70 | 1290 |
| 61 | 77 | GAACTGGAGCCACCAGC | 552333 | 6-9-2 | 55 | 1291 |
| 253 | 269 | GAAGTCCACCACGAGTC | 552334 | 6-9-2 | 42 | 9 |
| 254 | 270 | AGAAGTCCACCACGAGT | 552335 | 6-9-2 | 39 | 10 |
| 255 | 271 | GAGAAGTCCACCACGAG | 552336 | 6-9-2 | 27 | 11 |
| 256 | 272 | AGAGAAGTCCACCACGA | 552337 | 6-9-2 | 74 | 12 |
| 411 | 427 | GGCATAGCAGCAGGATG | 552338 | 6-9-2 | 68 | 17 |
| 412 | 428 | AGGCATAGCAGCAGGAT | 552339 | 6-9-2 | 71 | 18 |
| 413 | 429 | GAGGCATAGCAGCAGGA | 552340 | 6-9-2 | 61 | 19 |
| 414 | 430 | TGAGGCATAGCAGCAGG | 552341 | 6-9-2 | 58 | 21 |
| 415 | 431 | ATGAGGCATAGCAGCAG | 552342 | 6-9-2 | 55 | 23 |
| 416 | 432 | GATGAGGCATAGCAGCA | 552343 | 6-9-2 | 63 | 25 |
| 417 | 433 | AGATGAGGCATAGCAGC | 552344 | 6-9-2 | 51 | 27 |
| 418 | 434 | AAGATGAGGCATAGCAG | 552345 | 6-9-2 | 65 | 29 |
| 457 | 473 | ACGGGCAACATACCTTG | 552346 | 6-9-2 | 0 | 33 |
| 670 | 686 | ACTAGTAAACTGAGCCA | 552347 | 6-9-2 | 84 | 1292 |
| 671 | 687 | CACTAGTAAACTGAGCC | 552348 | 6-9-2 | 87 | 1293 |
| 672 | 688 | GCACTAGTAAACTGAGC | 552349 | 6-9-2 | 74 | 1294 |
| 687 | 703 | ACCACTGAACAAATGGC | 552350 | 6-9-2 | 59 | 40 |

TABLE 36-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 688 | 704 | AACCACTGAACAAATGG | 552351 | 6-9-2 | 60 | 41 |
| 689 | 705 | GAACCACTGAACAAATG | 552352 | 6-9-2 | 53 | 42 |
| 690 | 706 | CGAACCACTGAACAAAT | 552353 | 6-9-2 | 0 | 43 |
| 1261 | 1277 | CGCAGTATGGATCGGCA | 552354 | 6-9-2 | 83 | 1295 |
| 1262 | 1278 | CCGCAGTATGGATCGGC | 552355 | 6-9-2 | 90 | 1296 |
| 1263 | 1279 | TCCGCAGTATGGATCGG | 552356 | 6-9-2 | 0 | 1297 |
| 1264 | 1280 | TTCCGCAGTATGGATCG | 552357 | 6-9-2 | 45 | 1298 |
| 1265 | 1281 | GTTCCGCAGTATGGATC | 552358 | 6-9-2 | 74 | 1299 |
| 1266 | 1282 | AGTTCCGCAGTATGGAT | 552359 | 6-9-2 | 72 | 1300 |
| 1267 | 1283 | GAGTTCCGCAGTATGGA | 552360 | 6-9-2 | 87 | 1301 |
| 1268 | 1284 | GGAGTTCCGCAGTATGG | 552361 | 6-9-2 | 96 | 1302 |
| 1269 | 1285 | AGGAGTTCCGCAGTATG | 552308 | 5-9-3 | 81 | 1303 |
| 1269 | 1285 | AGGAGTTCCGCAGTATG | 552362 | 6-9-2 | 92 | 1303 |
| 1577 | 1593 | AAGCGAAGTGCACACGG | 552309 | 5-9-3 | 77 | 1304 |
| 1577 | 1593 | AAGCGAAGTGCACACGG | 552363 | 6-9-2 | 92 | 1304 |
| 1578 | 1594 | GAAGCGAAGTGCACACG | 552310 | 5-9-3 | 80 | 1305 |
| 1578 | 1594 | GAAGCGAAGTGCACACG | 552364 | 6-9-2 | 87 | 1305 |
| 1579 | 1595 | TGAAGCGAAGTGCACAC | 552311 | 5-9-3 | 13 | 1306 |
| 1579 | 1595 | TGAAGCGAAGTGCACAC | 552365 | 6-9-2 | 84 | 1306 |
| 1580 | 1596 | GTGAAGCGAAGTGCACA | 552150 | 2-9-6 | 73 | 1307 |
| 1580 | 1596 | GTGAAGCGAAGTGCACA | 552312 | 5-9-3 | 77 | 1307 |
| 1580 | 1596 | GTGAAGCGAAGTGCACA | 552366 | 6-9-2 | 87 | 1307 |
| 1581 | 1597 | GGTGAAGCGAAGTGCAC | 552313 | 5-9-3 | 64 | 1308 |
| 1581 | 1597 | GGTGAAGCGAAGTGCAC | 552367 | 6-9-2 | 85 | 1308 |
| 1582 | 1598 | AGGTGAAGCGAAGTGCA | 552314 | 5-9-3 | 73 | 1309 |
| 1582 | 1598 | AGGTGAAGCGAAGTGCA | 552368 | 6-9-2 | 77 | 1309 |
| 1583 | 1599 | GAGGTGAAGCGAAGTGC | 552315 | 5-9-3 | 75 | 1310 |
| 1583 | 1599 | GAGGTGAAGCGAAGTGC | 552369 | 6-9-2 | 75 | 1310 |
| 1584 | 1600 | AGAGGTGAAGCGAAGTG | 552316 | 5-9-3 | 64 | 1311 |
| 1584 | 1600 | AGAGGTGAAGCGAAGTG | 552370 | 6-9-2 | 63 | 1311 |
| 1585 | 1601 | CAGAGGTGAAGCGAAGT | 552317 | 5-9-3 | 99 | 1312 |
| 1585 | 1601 | CAGAGGTGAAGCGAAGT | 552371 | 6-9-2 | 81 | 1312 |
| 1586 | 1602 | GCAGAGGTGAAGCGAAG | 552318 | 5-9-3 | 76 | 1313 |
| 1586 | 1602 | GCAGAGGTGAAGCGAAG | 552372 | 6-9-2 | 65 | 1313 |
| 1587 | 1603 | TGCAGAGGTGAAGCGAA | 552319 | 5-9-3 | 55 | 1314 |
| 1587 | 1603 | TGCAGAGGTGAAGCGAA | 552373 | 6-9-2 | 74 | 1314 |

TABLE 36-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1588 | 1604 | GTGCAGAGGTGAAGCGA | 552320 | 5-9-3 | 68 | 1315 |
| 1588 | 1604 | GTGCAGAGGTGAAGCGA | 552374 | 6-9-2 | 78 | 1315 |
| 1589 | 1605 | CGTGCAGAGGTGAAGCG | 552321 | 5-9-3 | 74 | 1316 |
| 1589 | 1605 | CGTGCAGAGGTGAAGCG | 552375 | 6-9-2 | 81 | 1316 |
| 1590 | 1606 | ACGTGCAGAGGTGAAGC | 552322 | 5-9-3 | 73 | 1317 |
| 1590 | 1606 | ACGTGCAGAGGTGAAGC | 552376 | 6-9-2 | 78 | 1317 |
| 1778 | 1794 | TTATGCCTACAGCCTCC | 552323 | 5-9-3 | 75 | 47 |
| 1778 | 1794 | TTATGCCTACAGCCTCC | 552377 | 6-9-2 | 70 | 47 |
| 1779 | 1795 | TTTATGCCTACAGCCTC | 552324 | 5-9-3 | 0 | 49 |
| 1779 | 1795 | TTTATGCCTACAGCCTC | 552378 | 6-9-2 | 72 | 49 |
| 1780 | 1796 | ATTTATGCCTACAGCCT | 552325 | 5-9-3 | 70 | 51 |
| 1780 | 1796 | ATTTATGCCTACAGCCT | 552379 | 6-9-2 | 74 | 51 |
| 1781 | 1797 | AATTTATGCCTACAGCC | 552326 | 5-9-3 | 63 | 53 |
| 1781 | 1797 | AATTTATGCCTACAGCC | 552380 | 6-9-2 | 53 | 53 |
| 1782 | 1798 | CAATTTATGCCTACAGC | 552327 | 5-9-3 | 30 | 54 |
| 1782 | 1798 | CAATTTATGCCTACAGC | 552381 | 6-9-2 | 26 | 54 |
| 1783 | 1799 | CCAATTTATGCCTACAG | 552328 | 5-9-3 | 25 | 55 |
| 1783 | 1799 | CCAATTTATGCCTACAG | 552382 | 6-9-2 | 13 | 55 |
| 1784 | 1800 | ACCAATTTATGCCTACA | 552329 | 5-9-3 | 33 | 56 |
| 1784 | 1800 | ACCAATTTATGCCTACA | 552383 | 6-9-2 | 5 | 56 |

TABLE 37

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1780 | 1799 | CCAATTTATGCCTACAGCCT | 509934 | 5-10-5 | 30 | 50 |
| 58 | 77 | GAACTGGAGCCACCAGCAGG | 551909 | 2-10-8 | 62 | 83 |
| 58 | 77 | GAACTGGAGCCACCAGCAGG | 551941 | 3-10-7 | 74 | 83 |
| 58 | 77 | GAACTGGAGCCACCAGCAGG | 551973 | 4-10-6 | 64 | 83 |
| 253 | 272 | AGAGAAGTCCACCACGAGTC | 551910 | 2-10-8 | 52 | 103 |
| 253 | 272 | AGAGAAGTCCACCACGAGTC | 551942 | 3-10-7 | 54 | 103 |
| 253 | 272 | AGAGAAGTCCACCACGAGTC | 551974 | 4-10-6 | 51 | 103 |
| 411 | 430 | TGAGGCATAGCAGCAGGATG | 551911 | 2-10-8 | 58 | 136 |
| 411 | 430 | TGAGGCATAGCAGCAGGATG | 551943 | 3-10-7 | 64 | 136 |
| 411 | 430 | TGAGGCATAGCAGCAGGATG | 551975 | 4-10-6 | 57 | 136 |

TABLE 37-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 412 | 431 | ATGAGGCATAGCAGCAGGAT | 551912 | 2-10-8 | 59 | 139 |
| 412 | 431 | ATGAGGCATAGCAGCAGGAT | 551944 | 3-10-7 | 66 | 139 |
| 412 | 431 | ATGAGGCATAGCAGCAGGAT | 551976 | 4-10-6 | 57 | 139 |
| 413 | 432 | GATGAGGCATAGCAGCAGGA | 551913 | 2-10-8 | 58 | 142 |
| 413 | 432 | GATGAGGCATAGCAGCAGGA | 551945 | 3-10-7 | 56 | 142 |
| 413 | 432 | GATGAGGCATAGCAGCAGGA | 551977 | 4-10-6 | 56 | 142 |
| 414 | 433 | AGATGAGGCATAGCAGCAGG | 551914 | 2-10-8 | 0 | 20 |
| 414 | 433 | AGATGAGGCATAGCAGCAGG | 551946 | 3-10-7 | 48 | 20 |
| 414 | 433 | AGATGAGGCATAGCAGCAGG | 551978 | 4-10-6 | 53 | 20 |
| 415 | 434 | AAGATGAGGCATAGCAGCAG | 551915 | 2-10-8 | 44 | 22 |
| 415 | 434 | AAGATGAGGCATAGCAGCAG | 551947 | 3-10-7 | 53 | 22 |
| 415 | 434 | AAGATGAGGCATAGCAGCAG | 551979 | 4-10-6 | 64 | 22 |
| 416 | 435 | GAAGATGAGGCATAGCAGCA | 551916 | 2-10-8 | 57 | 24 |
| 416 | 435 | GAAGATGAGGCATAGCAGCA | 551948 | 3-10-7 | 68 | 24 |
| 416 | 435 | GAAGATGAGGCATAGCAGCA | 551980 | 4-10-6 | 56 | 24 |
| 417 | 436 | AGAAGATGAGGCATAGCAGC | 551917 | 2-10-8 | 58 | 26 |
| 417 | 436 | AGAAGATGAGGCATAGCAGC | 551949 | 3-10-7 | 64 | 26 |
| 417 | 436 | AGAAGATGAGGCATAGCAGC | 551981 | 4-10-6 | 63 | 26 |
| 418 | 437 | AAGAAGATGAGGCATAGCAG | 551918 | 2-10-8 | 59 | 28 |
| 418 | 437 | AAGAAGATGAGGCATAGCAG | 551950 | 3-10-7 | 71 | 28 |
| 418 | 437 | AAGAAGATGAGGCATAGCAG | 551982 | 4-10-6 | 63 | 28 |
| 687 | 706 | CGAACCACTGAACAAATGGC | 551919 | 2-10-8 | 76 | 39 |
| 687 | 706 | CGAACCACTGAACAAATGGC | 551951 | 3-10-7 | 71 | 39 |
| 687 | 706 | CGAACCACTGAACAAATGGC | 551983 | 4-10-6 | 73 | 39 |
| 1261 | 1280 | TTCCGCAGTATGGATCGGCA | 551920 | 2-10-8 | 68 | 719 |
| 1261 | 1280 | TTCCGCAGTATGGATCGGCA | 551952 | 3-10-7 | 76 | 719 |
| 1261 | 1280 | TTCCGCAGTATGGATCGGCA | 551984 | 4-10-6 | 81 | 719 |
| 1262 | 1281 | GTTCCGCAGTATGGATCGGC | 551921 | 2-10-8 | 83 | 212 |
| 1262 | 1281 | GTTCCGCAGTATGGATCGGC | 551953 | 3-10-7 | 82 | 212 |
| 1262 | 1281 | GTTCCGCAGTATGGATCGGC | 551985 | 4-10-6 | 76 | 212 |
| 1263 | 1282 | AGTTCCGCAGTATGGATCGG | 551922 | 2-10-8 | 73 | 720 |
| 1263 | 1282 | AGTTCCGCAGTATGGATCGG | 551954 | 3-10-7 | 68 | 720 |
| 1264 | 1283 | GAGTTCCGCAGTATGGATCG | 551923 | 2-10-8 | 59 | 721 |
| 1264 | 1283 | GAGTTCCGCAGTATGGATCG | 551955 | 3-10-7 | 71 | 721 |
| 1265 | 1284 | GGAGTTCCGCAGTATGGATC | 551924 | 2-10-8 | 80 | 1349 |
| 1265 | 1284 | GGAGTTCCGCAGTATGGATC | 551956 | 3-10-7 | 80 | 1349 |

TABLE 37-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1266 | 1285 | AGGAGTTCCGCAGTATGGAT | 551925 | 2-10-8 | 82 | 722 |
| 1266 | 1285 | AGGAGTTCCGCAGTATGGAT | 551957 | 3-10-7 | 88 | 722 |
| 1577 | 1596 | GTGAAGCGAAGTGCACACGG | 551926 | 2-10-8 | 71 | 224 |
| 1577 | 1596 | GTGAAGCGAAGTGCACACGG | 551958 | 3-10-7 | 74 | 224 |
| 1578 | 1597 | GGTGAAGCGAAGTGCACACG | 551927 | 2-10-8 | 68 | 801 |
| 1578 | 1597 | GGTGAAGCGAAGTGCACACG | 551959 | 3-10-7 | 69 | 801 |
| 1579 | 1598 | AGGTGAAGCGAAGTGCACAC | 551928 | 2-10-8 | 69 | 802 |
| 1579 | 1598 | AGGTGAAGCGAAGTGCACAC | 551960 | 3-10-7 | 62 | 802 |
| 1580 | 1599 | GAGGTGAAGCGAAGTGCACA | 551929 | 2-10-8 | 54 | 225 |
| 1580 | 1599 | GAGGTGAAGCGAAGTGCACA | 551961 | 3-10-7 | 20 | 225 |
| 1581 | 1600 | AGAGGTGAAGCGAAGTGCAC | 551930 | 2-10-8 | 53 | 804 |
| 1581 | 1600 | AGAGGTGAAGCGAAGTGCAC | 551962 | 3-10-7 | 60 | 804 |
| 1582 | 1601 | CAGAGGTGAAGCGAAGTGCA | 551931 | 2-10-8 | 47 | 805 |
| 1582 | 1601 | CAGAGGTGAAGCGAAGTGCA | 551963 | 3-10-7 | 63 | 805 |
| 1583 | 1602 | GCAGAGGTGAAGCGAAGTGC | 551932 | 2-10-8 | 68 | 226 |
| 1583 | 1602 | GCAGAGGTGAAGCGAAGTGC | 551964 | 3-10-7 | 56 | 226 |
| 1584 | 1603 | TGCAGAGGTGAAGCGAAGTG | 551933 | 2-10-8 | 72 | 806 |
| 1584 | 1603 | TGCAGAGGTGAAGCGAAGTG | 551965 | 3-10-7 | 67 | 806 |
| 1585 | 1604 | GTGCAGAGGTGAAGCGAAGT | 551934 | 2-10-8 | 64 | 807 |
| 1585 | 1604 | GTGCAGAGGTGAAGCGAAGT | 551966 | 3-10-7 | 73 | 807 |
| 1586 | 1605 | CGTGCAGAGGTGAAGCGAAG | 551935 | 2-10-8 | 68 | 227 |
| 1586 | 1605 | CGTGCAGAGGTGAAGCGAAG | 551967 | 3-10-7 | 60 | 227 |
| 1587 | 1606 | ACGTGCAGAGGTGAAGCGAA | 551936 | 2-10-8 | 67 | 1350 |
| 1587 | 1606 | ACGTGCAGAGGTGAAGCGAA | 551968 | 3-10-7 | 63 | 1350 |
| 1778 | 1797 | AATTTATGCCTACAGCCTCC | 551937 | 2-10-8 | 47 | 46 |
| 1778 | 1797 | AATTTATGCCTACAGCCTCC | 551969 | 3-10-7 | 36 | 46 |
| 1779 | 1798 | CAATTTATGCCTACAGCCTC | 551938 | 2-10-8 | 41 | 48 |
| 1779 | 1798 | CAATTTATGCCTACAGCCTC | 551970 | 3-10-7 | 43 | 48 |
| 1780 | 1799 | CCAATTTATGCCTACAGCCT | 551939 | 2-10-8 | 53 | 50 |
| 1780 | 1799 | CCAATTTATGCCTACAGCCT | 551971 | 3-10-7 | 55 | 50 |
| 1781 | 1800 | ACCAATTTATGCCTACAGCC | 551940 | 2-10-8 | 50 | 52 |
| 1781 | 1800 | ACCAATTTATGCCTACAGCC | 551972 | 3-10-7 | 58 | 52 |

TABLE 38

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1780 | 1799 | CCAATTTATGCCTACAGCCT | 509934 | 5-10-5 | 21 | 50 |
| 58 | 77 | GAACTGGAGCCACCAGCAGG | 551909 | 2-10-8 | 52 | 83 |
| 58 | 77 | GAACTGGAGCCACCAGCAGG | 551941 | 3-10-7 | 62 | 83 |
| 58 | 77 | GAACTGGAGCCACCAGCAGG | 551973 | 4-10-6 | 58 | 83 |
| 253 | 272 | AGAGAAGTCCACCACGAGTC | 551910 | 2-10-8 | 48 | 103 |
| 253 | 272 | AGAGAAGTCCACCACGAGTC | 551942 | 3-10-7 | 36 | 103 |
| 253 | 272 | AGAGAAGTCCACCACGAGTC | 551974 | 4-10-6 | 45 | 103 |
| 411 | 430 | TGAGGCATAGCAGCAGGATG | 551911 | 2-10-8 | 61 | 136 |
| 411 | 430 | TGAGGCATAGCAGCAGGATG | 551943 | 3-10-7 | 56 | 136 |
| 411 | 430 | TGAGGCATAGCAGCAGGATG | 551975 | 4-10-6 | 60 | 136 |
| 412 | 431 | ATGAGGCATAGCAGCAGGAT | 551912 | 2-10-8 | 53 | 139 |
| 412 | 431 | ATGAGGCATAGCAGCAGGAT | 551944 | 3-10-7 | 48 | 139 |
| 412 | 431 | ATGAGGCATAGCAGCAGGAT | 551976 | 4-10-6 | 48 | 139 |
| 413 | 432 | GATGAGGCATAGCAGCAGGA | 551913 | 2-10-8 | 53 | 142 |
| 413 | 432 | GATGAGGCATAGCAGCAGGA | 551945 | 3-10-7 | 54 | 142 |
| 413 | 432 | GATGAGGCATAGCAGCAGGA | 551977 | 4-10-6 | 48 | 142 |
| 414 | 433 | AGATGAGGCATAGCAGCAGG | 551914 | 2-10-8 | 0 | 20 |
| 414 | 433 | AGATGAGGCATAGCAGCAGG | 551946 | 3-10-7 | 56 | 20 |
| 414 | 433 | AGATGAGGCATAGCAGCAGG | 551978 | 4-10-6 | 36 | 20 |
| 415 | 434 | AAGATGAGGCATAGCAGCAG | 551915 | 2-10-8 | 47 | 22 |
| 415 | 434 | AAGATGAGGCATAGCAGCAG | 551947 | 3-10-7 | 45 | 22 |
| 415 | 434 | AAGATGAGGCATAGCAGCAG | 551979 | 4-10-6 | 54 | 22 |
| 416 | 435 | GAAGATGAGGCATAGCAGCA | 551916 | 2-10-8 | 44 | 24 |
| 416 | 435 | GAAGATGAGGCATAGCAGCA | 551948 | 3-10-7 | 59 | 24 |
| 416 | 435 | GAAGATGAGGCATAGCAGCA | 551980 | 4-10-6 | 49 | 24 |
| 417 | 436 | AGAAGATGAGGCATAGCAGC | 551917 | 2-10-8 | 48 | 26 |
| 417 | 436 | AGAAGATGAGGCATAGCAGC | 551949 | 3-10-7 | 60 | 26 |
| 417 | 436 | AGAAGATGAGGCATAGCAGC | 551981 | 4-10-6 | 57 | 26 |
| 418 | 437 | AAGAAGATGAGGCATAGCAG | 551918 | 2-10-8 | 53 | 28 |
| 418 | 437 | AAGAAGATGAGGCATAGCAG | 551950 | 3-10-7 | 57 | 28 |
| 418 | 437 | AAGAAGATGAGGCATAGCAG | 551982 | 4-10-6 | 57 | 28 |
| 687 | 706 | CGAACCACTGAACAAATGGC | 551919 | 2-10-8 | 65 | 39 |
| 687 | 706 | CGAACCACTGAACAAATGGC | 551951 | 3-10-7 | 57 | 39 |
| 687 | 706 | CGAACCACTGAACAAATGGC | 551983 | 4-10-6 | 53 | 39 |
| 1261 | 1280 | TTCCGCAGTATGGATCGGCA | 551920 | 2-10-8 | 57 | 719 |
| 1261 | 1280 | TTCCGCAGTATGGATCGGCA | 551952 | 3-10-7 | 67 | 719 |

TABLE 38-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1261 | 1280 | TTCCGCAGTATGGATCGGCA | 551984 | 4-10-6 | 62 | 719 |
| 1262 | 1281 | GTTCCGCAGTATGGATCGGC | 551921 | 2-10-8 | 60 | 212 |
| 1262 | 1281 | GTTCCGCAGTATGGATCGGC | 551953 | 3-10-7 | 57 | 212 |
| 1262 | 1281 | GTTCCGCAGTATGGATCGGC | 551985 | 4-10-6 | 58 | 212 |
| 1263 | 1282 | AGTTCCGCAGTATGGATCGG | 551922 | 2-10-8 | 63 | 720 |
| 1263 | 1282 | AGTTCCGCAGTATGGATCGG | 551954 | 3-10-7 | 61 | 720 |
| 1264 | 1283 | GAGTTCCGCAGTATGGATCG | 551923 | 2-10-8 | 50 | 721 |
| 1264 | 1283 | GAGTTCCGCAGTATGGATCG | 551955 | 3-10-7 | 44 | 721 |
| 1265 | 1284 | GGAGTTCCGCAGTATGGATC | 551924 | 2-10-8 | 52 | 1349 |
| 1265 | 1284 | GGAGTTCCGCAGTATGGATC | 551956 | 3-10-7 | 46 | 1349 |
| 1266 | 1285 | AGGAGTTCCGCAGTATGGAT | 551925 | 2-10-8 | 54 | 722 |
| 1266 | 1285 | AGGAGTTCCGCAGTATGGAT | 551957 | 3-10-7 | 51 | 722 |
| 1577 | 1596 | GTGAAGCGAAGTGCACACGG | 551926 | 2-10-8 | 70 | 224 |
| 1577 | 1596 | GTGAAGCGAAGTGCACACGG | 551958 | 3-10-7 | 72 | 224 |
| 1578 | 1597 | GGTGAAGCGAAGTGCACACG | 551927 | 2-10-8 | 60 | 801 |
| 1578 | 1597 | GGTGAAGCGAAGTGCACACG | 551959 | 3-10-7 | 61 | 801 |
| 1579 | 1598 | AGGTGAAGCGAAGTGCACAC | 551928 | 2-10-8 | 57 | 802 |
| 1579 | 1598 | AGGTGAAGCGAAGTGCACAC | 551960 | 3-10-7 | 58 | 802 |
| 1580 | 1599 | GAGGTGAAGCGAAGTGCACA | 551929 | 2-10-8 | 49 | 225 |
| 1580 | 1599 | GAGGTGAAGCGAAGTGCACA | 551961 | 3-10-7 | 26 | 225 |
| 1581 | 1600 | AGAGGTGAAGCGAAGTGCAC | 551930 | 2-10-8 | 54 | 804 |
| 1581 | 1600 | AGAGGTGAAGCGAAGTGCAC | 551962 | 3-10-7 | 57 | 804 |
| 1582 | 1601 | CAGAGGTGAAGCGAAGTGCA | 551931 | 2-10-8 | 46 | 805 |
| 1582 | 1601 | CAGAGGTGAAGCGAAGTGCA | 551963 | 3-10-7 | 56 | 805 |
| 1583 | 1602 | GCAGAGGTGAAGCGAAGTGC | 551932 | 2-10-8 | 57 | 226 |
| 1583 | 1602 | GCAGAGGTGAAGCGAAGTGC | 551964 | 3-10-7 | 53 | 226 |
| 1584 | 1603 | TGCAGAGGTGAAGCGAAGTG | 551933 | 2-10-8 | 65 | 806 |
| 1584 | 1603 | TGCAGAGGTGAAGCGAAGTG | 551965 | 3-10-7 | 54 | 806 |
| 1585 | 1604 | GTGCAGAGGTGAAGCGAAGT | 551934 | 2-10-8 | 58 | 807 |
| 1585 | 1604 | GTGCAGAGGTGAAGCGAAGT | 551966 | 3-10-7 | 69 | 807 |
| 1586 | 1605 | CGTGCAGAGGTGAAGCGAAG | 551935 | 2-10-8 | 63 | 227 |
| 1586 | 1605 | CGTGCAGAGGTGAAGCGAAG | 551967 | 3-10-7 | 53 | 227 |
| 1587 | 1606 | ACGTGCAGAGGTGAAGCGAA | 551936 | 2-10-8 | 67 | 1350 |
| 1587 | 1606 | ACGTGCAGAGGTGAAGCGAA | 551968 | 3-10-7 | 60 | 1350 |
| 1778 | 1797 | AATTTATGCCTACAGCCTCC | 551937 | 2-10-8 | 51 | 46 |
| 1778 | 1797 | AATTTATGCCTACAGCCTCC | 551969 | 3-10-7 | 42 | 46 |

TABLE 38-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1779 | 1798 | CAATTTATGCCTACAGCCTC | 551938 | 2-10-8 | 40 | 48 |
| 1779 | 1798 | CAATTTATGCCTACAGCCTC | 551970 | 3-10-7 | 38 | 48 |
| 1780 | 1799 | CCAATTTATGCCTACAGCCT | 551939 | 2-10-8 | 32 | 50 |
| 1780 | 1799 | CCAATTTATGCCTACAGCCT | 551971 | 3-10-7 | 46 | 50 |
| 1781 | 1800 | ACCAATTTATGCCTACAGCC | 551940 | 2-10-8 | 39 | 52 |
| 1781 | 1800 | ACCAATTTATGCCTACAGCC | 551972 | 3-10-7 | 51 | 52 |

TABLE 39

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 40 | 224 |
| 411 | 427 | GGCATAGCAGCAGGATG | 510100 | 3-10-4 | 60 | 17 |
| 58 | 74 | CTGGAGCCACCAGCAGG | 552276 | 5-9-3 | 44 | 1288 |
| 59 | 75 | ACTGGAGCCACCAGCAG | 552277 | 5-9-3 | 39 | 1289 |
| 60 | 76 | AACTGGAGCCACCAGCA | 552278 | 5-9-3 | 37 | 1290 |
| 61 | 77 | GAACTGGAGCCACCAGC | 552279 | 5-9-3 | 50 | 1291 |
| 253 | 269 | GAAGTCCACCACGAGTC | 552280 | 5-9-3 | 2 | 9 |
| 254 | 270 | AGAAGTCCACCACGAGT | 552281 | 5-9-3 | 0 | 10 |
| 255 | 271 | GAGAAGTCCACCACGAG | 552282 | 5-9-3 | 13 | 11 |
| 256 | 272 | AGAGAAGTCCACCACGA | 552229 | 4-9-4 | 17 | 12 |
| 256 | 272 | AGAGAAGTCCACCACGA | 552283 | 5-9-3 | 27 | 12 |
| 411 | 427 | GGCATAGCAGCAGGATG | 552230 | 4-9-4 | 53 | 17 |
| 411 | 427 | GGCATAGCAGCAGGATG | 552284 | 5-9-3 | 0 | 17 |
| 412 | 428 | AGGCATAGCAGCAGGAT | 552231 | 4-9-4 | 31 | 18 |
| 412 | 428 | AGGCATAGCAGCAGGAT | 552285 | 5-9-3 | 56 | 18 |
| 413 | 429 | GAGGCATAGCAGCAGGA | 552232 | 4-9-4 | 35 | 19 |
| 413 | 429 | GAGGCATAGCAGCAGGA | 552286 | 5-9-3 | 43 | 19 |
| 414 | 430 | TGAGGCATAGCAGCAGG | 552233 | 4-9-4 | 40 | 21 |
| 414 | 430 | TGAGGCATAGCAGCAGG | 552287 | 5-9-3 | 44 | 21 |
| 415 | 431 | ATGAGGCATAGCAGCAG | 552234 | 4-9-4 | 0 | 23 |
| 415 | 431 | ATGAGGCATAGCAGCAG | 552288 | 5-9-3 | 44 | 23 |
| 416 | 432 | GATGAGGCATAGCAGCA | 552235 | 4-9-4 | 13 | 25 |
| 416 | 432 | GATGAGGCATAGCAGCA | 552289 | 5-9-3 | 21 | 25 |
| 417 | 433 | AGATGAGGCATAGCAGC | 552236 | 4-9-4 | 40 | 27 |

TABLE 39-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 417 | 433 | AGATGAGGCATAGCAGC | 552290 | 5-9-3 | 34 | 27 |
| 418 | 434 | AAGATGAGGCATAGCAG | 552237 | 4-9-4 | 37 | 29 |
| 418 | 434 | AAGATGAGGCATAGCAG | 552291 | 5-9-3 | 34 | 29 |
| 670 | 686 | ACTAGTAAACTGAGCCA | 552239 | 4-9-4 | 58 | 1292 |
| 670 | 686 | ACTAGTAAACTGAGCCA | 552293 | 5-9-3 | 61 | 1292 |
| 671 | 687 | CACTAGTAAACTGAGCC | 552240 | 4-9-4 | 54 | 1293 |
| 671 | 687 | CACTAGTAAACTGAGCC | 552294 | 5-9-3 | 62 | 1293 |
| 672 | 688 | GCACTAGTAAACTGAGC | 552241 | 4-9-4 | 47 | 1294 |
| 672 | 688 | GCACTAGTAAACTGAGC | 552295 | 5-9-3 | 63 | 1294 |
| 687 | 703 | ACCACTGAACAAATGGC | 552242 | 4-9-4 | 61 | 40 |
| 687 | 703 | ACCACTGAACAAATGGC | 552296 | 5-9-3 | 61 | 40 |
| 688 | 704 | AACCACTGAACAAATGG | 552243 | 4-9-4 | 55 | 41 |
| 688 | 704 | AACCACTGAACAAATGG | 552297 | 5-9-3 | 52 | 41 |
| 689 | 705 | GAACCACTGAACAAATG | 552244 | 4-9-4 | 45 | 42 |
| 689 | 705 | GAACCACTGAACAAATG | 552298 | 5-9-3 | 27 | 42 |
| 690 | 706 | CGAACCACTGAACAAAT | 552245 | 4-9-4 | 41 | 43 |
| 690 | 706 | CGAACCACTGAACAAAT | 552299 | 5-9-3 | 32 | 43 |
| 1261 | 1277 | CGCAGTATGGATCGGCA | 552246 | 4-9-4 | 67 | 1295 |
| 1261 | 1277 | CGCAGTATGGATCGGCA | 552300 | 5-9-3 | 57 | 1295 |
| 1262 | 1278 | CCGCAGTATGGATCGGC | 552247 | 4-9-4 | 74 | 1296 |
| 1262 | 1278 | CCGCAGTATGGATCGGC | 552301 | 5-9-3 | 76 | 1296 |
| 1263 | 1279 | TCCGCAGTATGGATCGG | 552248 | 4-9-4 | 65 | 1297 |
| 1263 | 1279 | TCCGCAGTATGGATCGG | 552302 | 5-9-3 | 68 | 1297 |
| 1264 | 1280 | TTCCGCAGTATGGATCG | 552249 | 4-9-4 | 38 | 1298 |
| 1264 | 1280 | TTCCGCAGTATGGATCG | 552303 | 5-9-3 | 59 | 1298 |
| 1265 | 1281 | GTTCCGCAGTATGGATC | 552250 | 4-9-4 | 43 | 1299 |
| 1265 | 1281 | GTTCCGCAGTATGGATC | 552304 | 5-9-3 | 30 | 1299 |
| 1266 | 1282 | AGTTCCGCAGTATGGAT | 552251 | 4-9-4 | 52 | 1300 |
| 1266 | 1282 | AGTTCCGCAGTATGGAT | 552305 | 5-9-3 | 49 | 1300 |
| 1267 | 1283 | GAGTTCCGCAGTATGGA | 552252 | 4-9-4 | 51 | 1301 |
| 1267 | 1283 | GAGTTCCGCAGTATGGA | 552306 | 5-9-3 | 56 | 1301 |
| 1268 | 1284 | GGAGTTCCGCAGTATGG | 552253 | 4-9-4 | 47 | 1302 |
| 1268 | 1284 | GGAGTTCCGCAGTATGG | 552307 | 5-9-3 | 49 | 1302 |
| 1269 | 1285 | AGGAGTTCCGCAGTATG | 552254 | 4-9-4 | 50 | 1303 |
| 1577 | 1593 | AAGCGAAGTGCACACGG | 552255 | 4-9-4 | 64 | 1304 |
| 1578 | 1594 | GAAGCGAAGTGCACACG | 552256 | 4-9-4 | 57 | 1305 |

TABLE 39-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1579 | 1595 | TGAAGCGAAGTGCACAC | 552257 | 4-9-4 | 51 | 1306 |
| 1580 | 1596 | GTGAAGCGAAGTGCACA | 552258 | 4-9-4 | 62 | 1307 |
| 1581 | 1597 | GGTGAAGCGAAGTGCAC | 552259 | 4-9-4 | 59 | 1308 |
| 1582 | 1598 | AGGTGAAGCGAAGTGCA | 552260 | 4-9-4 | 56 | 1309 |
| 1583 | 1599 | GAGGTGAAGCGAAGTGC | 552261 | 4-9-4 | 54 | 1310 |
| 1584 | 1600 | AGAGGTGAAGCGAAGTG | 552262 | 4-9-4 | 47 | 1311 |
| 1585 | 1601 | CAGAGGTGAAGCGAAGT | 552263 | 4-9-4 | 45 | 1312 |
| 1586 | 1602 | GCAGAGGTGAAGCGAAG | 552264 | 4-9-4 | 52 | 1313 |
| 1587 | 1603 | TGCAGAGGTGAAGCGAA | 552265 | 4-9-4 | 58 | 1314 |
| 1588 | 1604 | GTGCAGAGGTGAAGCGA | 552266 | 4-9-4 | 54 | 1315 |
| 1589 | 1605 | CGTGCAGAGGTGAAGCG | 552267 | 4-9-4 | 43 | 1316 |
| 1590 | 1606 | ACGTGCAGAGGTGAAGC | 552268 | 4-9-4 | 57 | 1317 |
| 1778 | 1794 | TTATGCCTACAGCCTCC | 552269 | 4-9-4 | 34 | 47 |
| 1779 | 1795 | TTTATGCCTACAGCCTC | 552270 | 4-9-4 | 37 | 49 |
| 1780 | 1796 | ATTTATGCCTACAGCCT | 552271 | 4-9-4 | 42 | 51 |
| 1781 | 1797 | AATTTATGCCTACAGCC | 552272 | 4-9-4 | 36 | 53 |
| 1782 | 1798 | CAATTTATGCCTACAGC | 552273 | 4-9-4 | 25 | 54 |
| 1783 | 1799 | CCAATTTATGCCTACAG | 552274 | 4-9-4 | 11 | 55 |
| 1784 | 1800 | ACCAATTTATGCCTACA | 552275 | 4-9-4 | 38 | 56 |

TABLE 40

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 38 | 1354 |
| 414 | 429 | GAGGCATAGCAGCAGG | 509959 | 3-10-3 | 49 | 145 |
| 411 | 427 | GGCATAGCAGCAGGATG | 510100 | 3-10-4 | 55 | 17 |
| 58 | 73 | TGGAGCCACCAGCAGG | 552384 | 2-9-5 | 41 | 1318 |
| 58 | 73 | TGGAGCCACCAGCAGG | 552440 | 3-9-4 | 57 | 1318 |
| 59 | 74 | CTGGAGCCACCAGCAG | 552385 | 2-9-5 | 53 | 1319 |
| 59 | 74 | CTGGAGCCACCAGCAG | 552441 | 3-9-4 | 38 | 1319 |
| 60 | 75 | ACTGGAGCCACCAGCA | 552386 | 2-9-5 | 42 | 1320 |
| 60 | 75 | ACTGGAGCCACCAGCA | 552442 | 3-9-4 | 72 | 1320 |
| 61 | 76 | AACTGGAGCCACCAGC | 552387 | 2-9-5 | 43 | 1321 |

TABLE 40-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 61 | 76 | AACTGGAGCCACCAGC | 552443 | 3-9-4 | 56 | 1321 |
| 62 | 77 | GAACTGGAGCCACCAG | 552388 | 2-9-5 | 18 | 86 |
| 62 | 77 | GAACTGGAGCCACCAG | 552444 | 3-9-4 | 39 | 86 |
| 411 | 426 | GCATAGCAGCAGGATG | 552389 | 2-9-5 | 24 | 137 |
| 411 | 426 | GCATAGCAGCAGGATG | 552445 | 3-9-4 | 53 | 137 |
| 412 | 427 | GGCATAGCAGCAGGAT | 552390 | 2-9-5 | 40 | 140 |
| 412 | 427 | GGCATAGCAGCAGGAT | 552446 | 3-9-4 | 57 | 140 |
| 413 | 428 | AGGCATAGCAGCAGGA | 552391 | 2-9-5 | 51 | 143 |
| 413 | 428 | AGGCATAGCAGCAGGA | 552447 | 3-9-4 | 53 | 143 |
| 414 | 429 | GAGGCATAGCAGCAGG | 552392 | 2-9-5 | 0 | 145 |
| 414 | 429 | GAGGCATAGCAGCAGG | 552448 | 3-9-4 | 57 | 145 |
| 415 | 430 | TGAGGCATAGCAGCAG | 552393 | 2-9-5 | 52 | 147 |
| 415 | 430 | TGAGGCATAGCAGCAG | 552449 | 3-9-4 | 49 | 147 |
| 416 | 431 | ATGAGGCATAGCAGCA | 552394 | 2-9-5 | 32 | 149 |
| 416 | 431 | ATGAGGCATAGCAGCA | 552450 | 3-9-4 | 44 | 149 |
| 417 | 432 | GATGAGGCATAGCAGC | 552395 | 2-9-5 | 33 | 151 |
| 417 | 432 | GATGAGGCATAGCAGC | 552451 | 3-9-4 | 38 | 151 |
| 418 | 433 | AGATGAGGCATAGCAG | 552396 | 2-9-5 | 46 | 153 |
| 418 | 433 | AGATGAGGCATAGCAG | 552452 | 3-9-4 | 30 | 153 |
| 457 | 473 | ACGGGCAACATACCTTG | 552130 | 2-9-6 | 46 | 33 |
| 457 | 473 | ACGGGCAACATACCTTG | 552184 | 3-9-5 | 34 | 33 |
| 457 | 473 | ACGGGCAACATACCTTG | 552238 | 4-9-4 | 41 | 33 |
| 457 | 473 | ACGGGCAACATACCTTG | 552292 | 5-9-3 | 45 | 33 |
| 457 | 473 | ACGGGCAACATACCTTG | 552346 | 6-9-2 | 0 | 33 |
| 457 | 472 | CGGGCAACATACCTTG | 552397 | 2-9-5 | 37 | 167 |
| 457 | 472 | CGGGCAACATACCTTG | 552453 | 3-9-4 | 45 | 167 |
| 458 | 473 | ACGGGCAACATACCTT | 552398 | 2-9-5 | 42 | 168 |
| 458 | 473 | ACGGGCAACATACCTT | 552454 | 3-9-4 | 39 | 168 |
| 670 | 685 | CTAGTAAACTGAGCCA | 552399 | 2-9-5 | 34 | 181 |
| 671 | 686 | ACTAGTAAACTGAGCC | 552400 | 2-9-5 | 47 | 1322 |
| 672 | 687 | CACTAGTAAACTGAGC | 552401 | 2-9-5 | 53 | 1323 |
| 673 | 688 | GCACTAGTAAACTGAG | 552402 | 2-9-5 | 47 | 1324 |
| 687 | 702 | CCACTGAACAAATGGC | 552403 | 2-9-5 | 70 | 188 |
| 688 | 703 | ACCACTGAACAAATGG | 552404 | 2-9-5 | 44 | 190 |
| 689 | 704 | AACCACTGAACAAATG | 552405 | 2-9-5 | 0 | 191 |
| 690 | 705 | GAACCACTGAACAAAT | 552406 | 2-9-5 | 25 | 192 |

TABLE 40-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 691 | 706 | CGAACCACTGAACAAA | 552407 | 2-9-5 | 23 | 194 |
| 1261 | 1276 | GCAGTATGGATCGGCA | 552408 | 2-9-5 | 73 | 211 |
| 1262 | 1277 | CGCAGTATGGATCGGC | 552409 | 2-9-5 | 71 | 1325 |
| 1263 | 1278 | CCGCAGTATGGATCGG | 552410 | 2-9-5 | 52 | 1326 |
| 1264 | 1279 | TCCGCAGTATGGATCG | 552411 | 2-9-5 | 62 | 1327 |
| 1265 | 1280 | TTCCGCAGTATGGATC | 552412 | 2-9-5 | 50 | 1328 |
| 1266 | 1281 | GTTCCGCAGTATGGAT | 552413 | 2-9-5 | 55 | 1329 |
| 1267 | 1282 | AGTTCCGCAGTATGGA | 552414 | 2-9-5 | 64 | 1330 |
| 1268 | 1283 | GAGTTCCGCAGTATGG | 552415 | 2-9-5 | 45 | 1331 |
| 1269 | 1284 | GGAGTTCCGCAGTATG | 552416 | 2-9-5 | 45 | 1332 |
| 1270 | 1285 | AGGAGTTCCGCAGTAT | 552417 | 2-9-5 | 37 | 1333 |
| 1577 | 1592 | AGCGAAGTGCACACGG | 552418 | 2-9-5 | 73 | 1334 |
| 1578 | 1593 | AAGCGAAGTGCACACG | 552419 | 2-9-5 | 68 | 1335 |
| 1579 | 1594 | GAAGCGAAGTGCACAC | 552420 | 2-9-5 | 64 | 1336 |
| 1580 | 1595 | TGAAGCGAAGTGCACA | 552421 | 2-9-5 | 54 | 1337 |
| 1581 | 1596 | GTGAAGCGAAGTGCAC | 552422 | 2-9-5 | 60 | 1338 |
| 1582 | 1597 | GGTGAAGCGAAGTGCA | 552423 | 2-9-5 | 62 | 1339 |
| 1583 | 1598 | AGGTGAAGCGAAGTGC | 552424 | 2-9-5 | 60 | 1340 |
| 1584 | 1599 | GAGGTGAAGCGAAGTG | 552425 | 2-9-5 | 46 | 1341 |
| 1585 | 1600 | AGAGGTGAAGCGAAGT | 552426 | 2-9-5 | 48 | 1342 |
| 1586 | 1601 | CAGAGGTGAAGCGAAG | 552427 | 2-9-5 | 36 | 1343 |
| 1587 | 1602 | GCAGAGGTGAAGCGAA | 552428 | 2-9-5 | 57 | 1344 |
| 1588 | 1603 | TGCAGAGGTGAAGCGA | 552429 | 2-9-5 | 36 | 1345 |
| 1589 | 1604 | GTGCAGAGGTGAAGCG | 552430 | 2-9-5 | 42 | 1346 |
| 1590 | 1605 | CGTGCAGAGGTGAAGC | 552431 | 2-9-5 | 60 | 1347 |
| 1591 | 1606 | ACGTGCAGAGGTGAAG | 552432 | 2-9-5 | 44 | 1348 |
| 1778 | 1793 | TATGCCTACAGCCTCC | 552433 | 2-9-5 | 55 | 230 |
| 1779 | 1794 | TTATGCCTACAGCCTC | 552434 | 2-9-5 | 46 | 231 |
| 1780 | 1795 | TTTATGCCTACAGCCT | 552435 | 2-9-5 | 47 | 232 |
| 1781 | 1796 | ATTTATGCCTACAGCC | 552436 | 2-9-5 | 25 | 233 |
| 1782 | 1797 | AATTTATGCCTACAGC | 552437 | 2-9-5 | 19 | 234 |
| 1783 | 1798 | CAATTTATGCCTACAG | 552438 | 2-9-5 | 25 | 235 |
| 1784 | 1799 | CCAATTTATGCCTACA | 552439 | 2-9-5 | 22 | 236 |

TABLE 41

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 414 | 429 | GAGGCATAGCAGCAGG | 509959 | 3-10-3 | 49 | 145 |
| 58 | 73 | TGGAGCCACCAGCAGG | 552496 | 4-9-3 | 35 | 1318 |
| 59 | 74 | CTGGAGCCACCAGCAG | 552497 | 4-9-3 | 60 | 1319 |
| 60 | 75 | ACTGGAGCCACCAGCA | 552498 | 4-9-3 | 20 | 1320 |
| 61 | 76 | AACTGGAGCCACCAGC | 552499 | 4-9-3 | 45 | 1321 |
| 62 | 77 | GAACTGGAGCCACCAG | 552500 | 4-9-3 | 53 | 86 |
| 411 | 426 | GCATAGCAGCAGGATG | 552501 | 4-9-3 | 56 | 137 |
| 412 | 427 | GGCATAGCAGCAGGAT | 552502 | 4-9-3 | 50 | 140 |
| 413 | 428 | AGGCATAGCAGCAGGA | 552503 | 4-9-3 | 36 | 143 |
| 414 | 429 | GAGGCATAGCAGCAGG | 552504 | 4-9-3 | 50 | 145 |
| 415 | 430 | TGAGGCATAGCAGCAG | 552505 | 4-9-3 | 53 | 147 |
| 416 | 431 | ATGAGGCATAGCAGCA | 552506 | 4-9-3 | 49 | 149 |
| 417 | 432 | GATGAGGCATAGCAGC | 552507 | 4-9-3 | 35 | 151 |
| 418 | 433 | AGATGAGGCATAGCAG | 552508 | 4-9-3 | 62 | 153 |
| 457 | 472 | CGGGCAACATACCTTG | 552509 | 4-9-3 | 65 | 167 |
| 458 | 473 | ACGGGCAACATACCTT | 552510 | 4-9-3 | 54 | 168 |
| 670 | 685 | CTAGTAAACTGAGCCA | 552455 | 3-9-4 | 60 | 181 |
| 670 | 685 | CTAGTAAACTGAGCCA | 552511 | 4-9-3 | 65 | 181 |
| 671 | 686 | ACTAGTAAACTGAGCC | 552456 | 3-9-4 | 69 | 1322 |
| 671 | 686 | ACTAGTAAACTGAGCC | 552512 | 4-9-3 | 63 | 1322 |
| 672 | 687 | CACTAGTAAACTGAGC | 552457 | 3-9-4 | 4 | 1323 |
| 672 | 687 | CACTAGTAAACTGAGC | 552513 | 4-9-3 | 50 | 1323 |
| 673 | 688 | GCACTAGTAAACTGAG | 552458 | 3-9-4 | 59 | 1324 |
| 673 | 688 | GCACTAGTAAACTGAG | 552514 | 4-9-3 | 53 | 1324 |
| 687 | 702 | CCACTGAACAAATGGC | 552459 | 3-9-4 | 69 | 188 |
| 687 | 702 | CCACTGAACAAATGGC | 552515 | 4-9-3 | 68 | 188 |
| 688 | 703 | ACCACTGAACAAATGG | 552460 | 3-9-4 | 3 | 190 |
| 688 | 703 | ACCACTGAACAAATGG | 552516 | 4-9-3 | 65 | 190 |
| 689 | 704 | AACCACTGAACAAATG | 552461 | 3-9-4 | 37 | 191 |
| 689 | 704 | AACCACTGAACAAATG | 552517 | 4-9-3 | 54 | 191 |
| 690 | 705 | GAACCACTGAACAAAT | 552462 | 3-9-4 | 42 | 192 |
| 690 | 705 | GAACCACTGAACAAAT | 552518 | 4-9-3 | 23 | 192 |
| 691 | 706 | CGAACCACTGAACAAA | 552463 | 3-9-4 | 28 | 194 |
| 691 | 706 | CGAACCACTGAACAAA | 552519 | 4-9-3 | 32 | 194 |
| 1261 | 1276 | GCAGTATGGATCGGCA | 552464 | 3-9-4 | 72 | 211 |
| 1261 | 1276 | GCAGTATGGATCGGCA | 552520 | 4-9-3 | 61 | 211 |

TABLE 41-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1262 | 1277 | CGCAGTATGGATCGGC | 552465 | 3-9-4 | 68 | 1325 |
| 1262 | 1277 | CGCAGTATGGATCGGC | 552521 | 4-9-3 | 68 | 1325 |
| 1263 | 1278 | CCGCAGTATGGATCGG | 552466 | 3-9-4 | 76 | 1326 |
| 1263 | 1278 | CCGCAGTATGGATCGG | 552522 | 4-9-3 | 71 | 1326 |
| 1264 | 1279 | TCCGCAGTATGGATCG | 552467 | 3-9-4 | 72 | 1327 |
| 1264 | 1279 | TCCGCAGTATGGATCG | 552523 | 4-9-3 | 73 | 1327 |
| 1265 | 1280 | TTCCGCAGTATGGATC | 552468 | 3-9-4 | 50 | 1328 |
| 1265 | 1280 | TTCCGCAGTATGGATC | 552524 | 4-9-3 | 49 | 1328 |
| 1266 | 1281 | GTTCCGCAGTATGGAT | 552469 | 3-9-4 | 65 | 1329 |
| 1266 | 1281 | GTTCCGCAGTATGGAT | 552525 | 4-9-3 | 45 | 1329 |
| 1267 | 1282 | AGTTCCGCAGTATGGA | 552470 | 3-9-4 | 58 | 1330 |
| 1267 | 1282 | AGTTCCGCAGTATGGA | 552526 | 4-9-3 | 39 | 1330 |
| 1268 | 1283 | GAGTTCCGCAGTATGG | 552471 | 3-9-4 | 30 | 1331 |
| 1268 | 1283 | GAGTTCCGCAGTATGG | 552527 | 4-9-3 | 39 | 1331 |
| 1269 | 1284 | GGAGTTCCGCAGTATG | 552472 | 3-9-4 | 43 | 1332 |
| 1269 | 1284 | GGAGTTCCGCAGTATG | 552528 | 4-9-3 | 43 | 1332 |
| 1270 | 1285 | AGGAGTTCCGCAGTAT | 552473 | 3-9-4 | 25 | 1333 |
| 1270 | 1285 | AGGAGTTCCGCAGTAT | 552529 | 4-9-3 | 50 | 1333 |
| 1577 | 1592 | AGCGAAGTGCACACGG | 552474 | 3-9-4 | 70 | 1334 |
| 1577 | 1592 | AGCGAAGTGCACACGG | 552530 | 4-9-3 | 73 | 1334 |
| 1578 | 1593 | AAGCGAAGTGCACACG | 552475 | 3-9-4 | 64 | 1335 |
| 1578 | 1593 | AAGCGAAGTGCACACG | 552531 | 4-9-3 | 62 | 1335 |
| 1579 | 1594 | GAAGCGAAGTGCACAC | 552476 | 3-9-4 | 50 | 1336 |
| 1580 | 1595 | TGAAGCGAAGTGCACA | 552477 | 3-9-4 | 66 | 1337 |
| 1581 | 1596 | GTGAAGCGAAGTGCAC | 552478 | 3-9-4 | 68 | 1338 |
| 1582 | 1597 | GGTGAAGCGAAGTGCA | 552479 | 3-9-4 | 60 | 1339 |
| 1583 | 1598 | AGGTGAAGCGAAGTGC | 552480 | 3-9-4 | 58 | 1340 |
| 1584 | 1599 | GAGGTGAAGCGAAGTG | 552481 | 3-9-4 | 54 | 1341 |
| 1585 | 1600 | AGAGGTGAAGCGAAGT | 552482 | 3-9-4 | 44 | 1342 |
| 1586 | 1601 | CAGAGGTGAAGCGAAG | 552483 | 3-9-4 | 17 | 1343 |
| 1587 | 1602 | GCAGAGGTGAAGCGAA | 552484 | 3-9-4 | 64 | 1344 |
| 1588 | 1603 | TGCAGAGGTGAAGCGA | 552485 | 3-9-4 | 56 | 1345 |
| 1589 | 1604 | GTGCAGAGGTGAAGCG | 552486 | 3-9-4 | 26 | 1346 |
| 1590 | 1605 | CGTGCAGAGGTGAAGC | 552487 | 3-9-4 | 42 | 1347 |
| 1591 | 1606 | ACGTGCAGAGGTGAAG | 552488 | 3-9-4 | 35 | 1348 |
| 1778 | 1793 | TATGCCTACAGCCTCC | 552489 | 3-9-4 | 46 | 230 |

TABLE 41-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1779 | 1794 | TTATGCCTACAGCCTC | 552490 | 3-9-4 | 41 | 231 |
| 1780 | 1795 | TTTATGCCTACAGCCT | 552491 | 3-9-4 | 38 | 232 |
| 1781 | 1796 | ATTTATGCCTACAGCC | 552492 | 3-9-4 | 47 | 233 |
| 1782 | 1797 | AATTTATGCCTACAGC | 552493 | 3-9-4 | 49 | 234 |
| 1783 | 1798 | CAATTTATGCCTACAG | 552494 | 3-9-4 | 22 | 235 |
| 1784 | 1799 | CCAATTTATGCCTACA | 552495 | 3-9-4 | 0 | 236 |

TABLE 42

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 56 55 | 224 |
| 414 | 429 | GAGGCATAGCAGCAGG | 509959 | 3-10-3 | 54 | 145 |
| 58 | 73 | TGGAGCCACCAGCAGG | 552552 | 5-9-2 | 32 | 1355 |
| 59 | 74 | CTGGAGCCACCAGCAG | 552553 | 5-9-2 | 53 | 1319 |
| 60 | 75 | ACTGGAGCCACCAGCA | 552554 | 5-9-2 | 48 | 1320 |
| 61 | 76 | AACTGGAGCCACCAGC | 552555 | 5-9-2 | 39 | 1321 |
| 62 | 77 | GAACTGGAGCCACCAG | 552556 | 5-9-2 | 39 | 86 |
| 411 | 426 | GCATAGCAGCAGGATG | 552557 | 5-9-2 | 54 | 137 |
| 412 | 427 | GGCATAGCAGCAGGAT | 552558 | 5-9-2 | 41 | 140 |
| 413 | 428 | AGGCATAGCAGCAGGA | 552559 | 5-9-2 | 56 | 143 |
| 414 | 429 | GAGGCATAGCAGCAGG | 552560 | 5-9-2 | 39 | 145 |
| 415 | 430 | TGAGGCATAGCAGCAG | 552561 | 5-9-2 | 51 | 147 |
| 416 | 431 | ATGAGGCATAGCAGCA | 552562 | 5-9-2 | 56 | 149 |
| 417 | 432 | GATGAGGCATAGCAGC | 552563 | 5-9-2 | 31 | 151 |
| 418 | 433 | AGATGAGGCATAGCAG | 552564 | 5-9-2 | 31 | 153 |
| 457 | 472 | CGGGCAACATACCTTG | 552565 | 5-9-2 | 53 | 167 |
| 458 | 473 | ACGGGCAACATACCTT | 552566 | 5-9-2 | 46 | 168 |
| 670 | 685 | CTAGTAAACTGAGCCA | 552567 | 5-9-2 | 63 | 181 |
| 671 | 686 | ACTAGTAAACTGAGCC | 552568 | 5-9-2 | 66 | 1322 |
| 672 | 687 | CACTAGTAAACTGAGC | 552569 | 5-9-2 | 60 | 1323 |
| 673 | 688 | GCACTAGTAAACTGAG | 552570 | 5-9-2 | 60 | 1324 |
| 687 | 702 | CCACTGAACAAATGGC | 552571 | 5-9-2 | 44 | 188 |
| 688 | 703 | ACCACTGAACAAATGG | 552572 | 5-9-2 | 52 | 190 |

TABLE 42-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 689 | 704 | AACCACTGAACAAATG | 552573 | 5-9-2 | 20 | 191 |
| 690 | 705 | GAACCACTGAACAAAT | 552574 | 5-9-2 | 36 | 192 |
| 691 | 706 | CGAACCACTGAACAAA | 552575 | 5-9-2 | 19 | 194 |
| 1261 | 1276 | GCAGTATGGATCGGCA | 552576 | 5-9-2 | 61 | 211 |
| 1262 | 1277 | CGCAGTATGGATCGGC | 552577 | 5-9-2 | 57 | 1325 |
| 1263 | 1278 | CCGCAGTATGGATCGG | 552578 | 5-9-2 | 71 | 1326 |
| 1264 | 1279 | TCCGCAGTATGGATCG | 552579 | 5-9-2 | 59 | 1327 |
| 1265 | 1280 | TTCCGCAGTATGGATC | 552580 | 5-9-2 | 58 | 1328 |
| 1266 | 1281 | GTTCCGCAGTATGGAT | 552581 | 5-9-2 | 51 | 1329 |
| 1267 | 1282 | AGTTCCGCAGTATGGA | 552582 | 5-9-2 | 40 | 1330 |
| 1268 | 1283 | GAGTTCCGCAGTATGG | 552583 | 5-9-2 | 35 | 1331 |
| 1269 | 1284 | GGAGTTCCGCAGTATG | 552584 | 5-9-2 | 50 | 1332 |
| 1270 | 1285 | AGGAGTTCCGCAGTAT | 552585 | 5-9-2 | 48 | 1333 |
| 1577 | 1592 | AGCGAAGTGCACACGG | 552586 | 5-9-2 | 74 | 1334 |
| 1578 | 1593 | AAGCGAAGTGCACACG | 552587 | 5-9-2 | 68 | 1335 |
| 1579 | 1594 | GAAGCGAAGTGCACAC | 552532 | 4-9-3 | 59 | 1336 |
| 1579 | 1594 | GAAGCGAAGTGCACAC | 552588 | 5-9-2 | 67 | 1336 |
| 1580 | 1595 | TGAAGCGAAGTGCACA | 552533 | 4-9-3 | 52 | 1337 |
| 1580 | 1595 | TGAAGCGAAGTGCACA | 552589 | 5-9-2 | 47 | 1337 |
| 1581 | 1596 | GTGAAGCGAAGTGCAC | 552534 | 4-9-3 | 71 | 1338 |
| 1581 | 1596 | GTGAAGCGAAGTGCAC | 552590 | 5-9-2 | 58 | 1338 |
| 1582 | 1597 | GGTGAAGCGAAGTGCA | 552535 | 4-9-3 | 59 | 1339 |
| 1582 | 1597 | GGTGAAGCGAAGTGCA | 552591 | 5-9-2 | 46 | 1339 |
| 1583 | 1598 | AGGTGAAGCGAAGTGC | 552536 | 4-9-3 | 19 | 1340 |
| 1583 | 1598 | AGGTGAAGCGAAGTGC | 552592 | 5-9-2 | 44 | 1340 |
| 1584 | 1599 | GAGGTGAAGCGAAGTG | 552537 | 4-9-3 | 26 | 1341 |
| 1584 | 1599 | GAGGTGAAGCGAAGTG | 552593 | 5-9-2 | 39 | 1341 |
| 1585 | 1600 | AGAGGTGAAGCGAAGT | 552538 | 4-9-3 | 54 | 1342 |
| 1585 | 1600 | AGAGGTGAAGCGAAGT | 552594 | 5-9-2 | 52 | 1342 |
| 1586 | 1601 | CAGAGGTGAAGCGAAG | 552539 | 4-9-3 | 50 | 1343 |
| 1586 | 1601 | CAGAGGTGAAGCGAAG | 552595 | 5-9-2 | 57 | 1343 |
| 1587 | 1602 | GCAGAGGTGAAGCGAA | 552540 | 4-9-3 | 60 | 1344 |
| 1587 | 1602 | GCAGAGGTGAAGCGAA | 552596 | 5-9-2 | 58 | 1344 |
| 1588 | 1603 | TGCAGAGGTGAAGCGA | 552541 | 4-9-3 | 68 | 1345 |
| 1588 | 1603 | TGCAGAGGTGAAGCGA | 552597 | 5-9-2 | 52 | 1345 |
| 1589 | 1604 | GTGCAGAGGTGAAGCG | 552542 | 4-9-3 | 63 | 1346 |

TABLE 42-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1589 | 1604 | GTGCAGAGGTGAAGCG | 552598 | 5-9-2 | 51 | 1346 |
| 1590 | 1605 | CGTGCAGAGGTGAAGC | 552543 | 4-9-3 | 44 | 1347 |
| 1590 | 1605 | CGTGCAGAGGTGAAGC | 552600 | 5-9-2 | 51 | 1347 |
| 1591 | 1606 | ACGTGCAGAGGTGAAG | 552544 | 4-9-3 | 45 | 1348 |
| 1591 | 1606 | ACGTGCAGAGGTGAAG | 552602 | 5-9-2 | 13 | 1348 |
| 1778 | 1793 | TATGCCTACAGCCTCC | 552545 | 4-9-3 | 42 | 230 |
| 1778 | 1793 | TATGCCTACAGCCTCC | 552604 | 5-9-2 | 42 | 230 |
| 1779 | 1794 | TTATGCCTACAGCCTC | 552546 | 4-9-3 | 46 | 231 |
| 1779 | 1794 | TTATGCCTACAGCCTC | 552606 | 5-9-2 | 42 | 231 |
| 1780 | 1795 | TTTATGCCTACAGCCT | 552547 | 4-9-3 | 38 | 232 |
| 1780 | 1795 | TTTATGCCTACAGCCT | 552608 | 5-9-2 | 37 | 232 |
| 1781 | 1796 | ATTTATGCCTACAGCC | 552548 | 4-9-3 | 49 | 233 |
| 1781 | 1796 | ATTTATGCCTACAGCC | 552610 | 5-9-2 | 41 | 233 |
| 1782 | 1797 | AATTTATGCCTACAGC | 552549 | 4-9-3 | 34 | 234 |
| 1782 | 1797 | AATTTATGCCTACAGC | 552612 | 5-9-2 | 23 | 234 |
| 1783 | 1798 | CAATTTATGCCTACAG | 552550 | 4-9-3 | 13 | 235 |
| 1783 | 1798 | CAATTTATGCCTACAG | 552614 | 5-9-2 | 11 | 235 |
| 1784 | 1799 | CCAATTTATGCCTACA | 552551 | 4-9-3 | 8 | 236 |
| 1784 | 1799 | CCAATTTATGCCTACA | 552616 | 5-9-2 | 6 | 236 |

TABLE 43

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 47 | 224 |
| 1780 | 1799 | CCAATTTATGCCTACAGCCT | 509934 | 5-10-5 | 67 | 50 |
| 58 | 77 | GAACTGGAGCCACCAGCAGG | 552007 | 6-10-4 | 53 | 83 |
| 58 | 77 | GAACTGGAGCCACCAGCAGG | 552039 | 7-10-3 | 74 | 83 |
| 253 | 272 | AGAGAAGTCCACCACGAGTC | 552008 | 6-10-4 | 47 | 103 |
| 253 | 272 | AGAGAAGTCCACCACGAGTC | 552040 | 7-10-3 | 57 | 103 |
| 411 | 430 | TGAGGCATAGCAGCAGGATG | 552009 | 6-10-4 | 70 | 136 |
| 411 | 430 | TGAGGCATAGCAGCAGGATG | 552041 | 7-10-3 | 65 | 136 |
| 412 | 431 | ATGAGGCATAGCAGCAGGAT | 552010 | 6-10-4 | 51 | 139 |
| 412 | 431 | ATGAGGCATAGCAGCAGGAT | 552042 | 7-10-3 | 59 | 139 |
| 413 | 432 | GATGAGGCATAGCAGCAGGA | 552011 | 6-10-4 | 47 | 142 |

TABLE 43-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 413 | 432 | GATGAGGCATAGCAGCAGGA | 552043 | 7-10-3 | 36 | 142 |
| 414 | 433 | AGATGAGGCATAGCAGCAGG | 552012 | 6-10-4 | 62 | 20 |
| 414 | 433 | AGATGAGGCATAGCAGCAGG | 552044 | 7-10-3 | 82 | 20 |
| 415 | 434 | AAGATGAGGCATAGCAGCAG | 552013 | 6-10-4 | 72 | 22 |
| 415 | 434 | AAGATGAGGCATAGCAGCAG | 552045 | 7-10-3 | 62 | 22 |
| 416 | 435 | GAAGATGAGGCATAGCAGCA | 552014 | 6-10-4 | 73 | 24 |
| 416 | 435 | GAAGATGAGGCATAGCAGCA | 552046 | 7-10-3 | 74 | 24 |
| 417 | 436 | AGAAGATGAGGCATAGCAGC | 552015 | 6-10-4 | 66 | 26 |
| 417 | 436 | AGAAGATGAGGCATAGCAGC | 552047 | 7-10-3 | 60 | 26 |
| 418 | 437 | AAGAAGATGAGGCATAGCAG | 552016 | 6-10-4 | 67 | 28 |
| 418 | 437 | AAGAAGATGAGGCATAGCAG | 552048 | 7-10-3 | 60 | 28 |
| 687 | 706 | CGAACCACTGAACAAATGGC | 552017 | 6-10-4 | 72 | 39 |
| 687 | 706 | CGAACCACTGAACAAATGGC | 552049 | 7-10-3 | 68 | 39 |
| 1261 | 1280 | TTCCGCAGTATGGATCGGCA | 552018 | 6-10-4 | 89 | 719 |
| 1261 | 1280 | TTCCGCAGTATGGATCGGCA | 552050 | 7-10-3 | 86 | 719 |
| 1262 | 1281 | GTTCCGCAGTATGGATCGGC | 552019 | 6-10-4 | 87 | 212 |
| 1262 | 1281 | GTTCCGCAGTATGGATCGGC | 552051 | 7-10-3 | 86 | 212 |
| 1263 | 1282 | AGTTCCGCAGTATGGATCGG | 551986 | 4-10-6 | 64 | 720 |
| 1263 | 1282 | AGTTCCGCAGTATGGATCGG | 552020 | 6-10-4 | 86 | 720 |
| 1263 | 1282 | AGTTCCGCAGTATGGATCGG | 552052 | 7-10-3 | 87 | 720 |
| 1264 | 1283 | GAGTTCCGCAGTATGGATCG | 551987 | 4-10-6 | 76 | 721 |
| 1264 | 1283 | GAGTTCCGCAGTATGGATCG | 552021 | 6-10-4 | 84 | 721 |
| 1264 | 1283 | GAGTTCCGCAGTATGGATCG | 552053 | 7-10-3 | 75 | 721 |
| 1265 | 1284 | GGAGTTCCGCAGTATGGATC | 551988 | 4-10-6 | 5 | 1349 |
| 1265 | 1284 | GGAGTTCCGCAGTATGGATC | 552005 | 5-10-5 | 72 | 1349 |
| 1265 | 1284 | GGAGTTCCGCAGTATGGATC | 552022 | 6-10-4 | 80 | 1349 |
| 1265 | 1284 | GGAGTTCCGCAGTATGGATC | 552054 | 7-10-3 | 83 | 1349 |
| 1266 | 1285 | AGGAGTTCCGCAGTATGGAT | 551989 | 4-10-6 | 64 | 722 |
| 1266 | 1285 | AGGAGTTCCGCAGTATGGAT | 552023 | 6-10-4 | 78 | 722 |
| 1266 | 1285 | AGGAGTTCCGCAGTATGGAT | 552055 | 7-10-3 | 57 | 722 |
| 1577 | 1596 | GTGAAGCGAAGTGCACACGG | 551990 | 4-10-6 | 83 | 224 |
| 1577 | 1596 | GTGAAGCGAAGTGCACACGG | 552024 | 6-10-4 | 89 | 224 |
| 1577 | 1596 | GTGAAGCGAAGTGCACACGG | 552056 | 7-10-3 | 82 | 224 |
| 1578 | 1597 | GGTGAAGCGAAGTGCACACG | 551991 | 4-10-6 | 0 | 801 |
| 1578 | 1597 | GGTGAAGCGAAGTGCACACG | 552025 | 6-10-4 | 89 | 801 |
| 1578 | 1597 | GGTGAAGCGAAGTGCACACG | 552057 | 7-10-3 | 89 | 801 |

TABLE 43-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1579 | 1598 | AGGTGAAGCGAAGTGCACAC | 551992 | 4-10-6 | 67 | 802 |
| 1579 | 1598 | AGGTGAAGCGAAGTGCACAC | 552026 | 6-10-4 | 84 | 802 |
| 1579 | 1598 | AGGTGAAGCGAAGTGCACAC | 552058 | 7-10-3 | 82 | 802 |
| 1580 | 1599 | GAGGTGAAGCGAAGTGCACA | 551993 | 4-10-6 | 78 | 225 |
| 1580 | 1599 | GAGGTGAAGCGAAGTGCACA | 552027 | 6-10-4 | 85 | 225 |
| 1580 | 1599 | GAGGTGAAGCGAAGTGCACA | 552059 | 7-10-3 | 85 | 225 |
| 1581 | 1600 | AGAGGTGAAGCGAAGTGCAC | 551994 | 4-10-6 | 82 | 804 |
| 1581 | 1600 | AGAGGTGAAGCGAAGTGCAC | 552028 | 6-10-4 | 82 | 804 |
| 1581 | 1600 | AGAGGTGAAGCGAAGTGCAC | 552060 | 7-10-3 | 74 | 804 |
| 1582 | 1601 | CAGAGGTGAAGCGAAGTGCA | 551995 | 4-10-6 | 81 | 805 |
| 1582 | 1601 | CAGAGGTGAAGCGAAGTGCA | 552029 | 6-10-4 | 81 | 805 |
| 1582 | 1601 | CAGAGGTGAAGCGAAGTGCA | 552061 | 7-10-3 | 81 | 805 |
| 1583 | 1602 | GCAGAGGTGAAGCGAAGTGC | 551996 | 4-10-6 | 79 | 226 |
| 1583 | 1602 | GCAGAGGTGAAGCGAAGTGC | 552030 | 6-10-4 | 86 | 226 |
| 1583 | 1602 | GCAGAGGTGAAGCGAAGTGC | 552062 | 7-10-3 | 85 | 226 |
| 1584 | 1603 | TGCAGAGGTGAAGCGAAGTG | 551997 | 4-10-6 | 80 | 806 |
| 1584 | 1603 | TGCAGAGGTGAAGCGAAGTG | 552031 | 6-10-4 | 86 | 806 |
| 1585 | 1604 | GTGCAGAGGTGAAGCGAAGT | 551998 | 4-10-6 | 74 | 807 |
| 1585 | 1604 | GTGCAGAGGTGAAGCGAAGT | 552032 | 6-10-4 | 78 | 807 |
| 1586 | 1605 | CGTGCAGAGGTGAAGCGAAG | 551999 | 4-10-6 | 79 | 227 |
| 1586 | 1605 | CGTGCAGAGGTGAAGCGAAG | 552033 | 6-10-4 | 80 | 227 |
| 1587 | 1606 | ACGTGCAGAGGTGAAGCGAA | 552000 | 4-10-6 | 84 | 1350 |
| 1587 | 1606 | ACGTGCAGAGGTGAAGCGAA | 552006 | 5-10-5 | 86 | 1350 |
| 1587 | 1606 | ACGTGCAGAGGTGAAGCGAA | 552034 | 6-10-4 | 81 | 1350 |
| 1778 | 1797 | AATTTATGCCTACAGCCTCC | 552001 | 4-10-6 | 66 | 46 |
| 1778 | 1797 | AATTTATGCCTACAGCCTCC | 552035 | 6-10-4 | 55 | 46 |
| 1779 | 1798 | CAATTTATGCCTACAGCCTC | 552002 | 4-10-6 | 54 | 48 |
| 1779 | 1798 | CAATTTATGCCTACAGCCTC | 552036 | 6-10-4 | 58 | 48 |
| 1780 | 1799 | CCAATTTATGCCTACAGCCT | 552003 | 4-10-6 | 50 | 50 |
| 1780 | 1799 | CCAATTTATGCCTACAGCCT | 552037 | 6-10-4 | 43 | 50 |
| 1781 | 1800 | ACCAATTTATGCCTACAGCC | 552004 | 4-10-6 | 56 | 52 |
| 1781 | 1800 | ACCAATTTATGCCTACAGCC | 552038 | 6-10-4 | 66 | 52 |

TABLE 44

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 61 | 224 |
| 411 | 427 | GGCATAGCAGCAGGATG | 510100 | 3-10-4 | 66 | 17 |
| 58 | 74 | CTGGAGCCACCAGCAGG | 552168 | 3-9-5 | 64 | 1288 |
| 58 | 74 | CTGGAGCCACCAGCAGG | 552222 | 4-9-4 | 76 | 1288 |
| 59 | 75 | ACTGGAGCCACCAGCAG | 552169 | 3-9-5 | 65 | 1289 |
| 59 | 75 | ACTGGAGCCACCAGCAG | 552223 | 4-9-4 | 41 | 1289 |
| 60 | 76 | AACTGGAGCCACCAGCA | 552170 | 3-9-5 | 58 | 1290 |
| 60 | 76 | AACTGGAGCCACCAGCA | 552224 | 4-9-4 | 58 | 1290 |
| 61 | 77 | GAACTGGAGCCACCAGC | 552171 | 3-9-5 | 51 | 1291 |
| 61 | 77 | GAACTGGAGCCACCAGC | 552225 | 4-9-4 | 49 | 1291 |
| 253 | 269 | GAAGTCCACCACGAGTC | 552172 | 3-9-5 | 23 | 9 |
| 253 | 269 | GAAGTCCACCACGAGTC | 552226 | 4-9-4 | 36 | 9 |
| 254 | 270 | AGAAGTCCACCACGAGT | 552173 | 3-9-5 | 44 | 10 |
| 254 | 270 | AGAAGTCCACCACGAGT | 552227 | 4-9-4 | 20 | 10 |
| 255 | 271 | GAGAAGTCCACCACGAG | 552174 | 3-9-5 | 28 | 11 |
| 255 | 271 | GAGAAGTCCACCACGAG | 552228 | 4-9-4 | 29 | 11 |
| 256 | 272 | AGAGAAGTCCACCACGA | 552175 | 3-9-5 | 56 | 12 |
| 411 | 427 | GGCATAGCAGCAGGATG | 552176 | 3-9-5 | 66 | 17 |
| 412 | 428 | AGGCATAGCAGCAGGAT | 552177 | 3-9-5 | 53 | 18 |
| 413 | 429 | GAGGCATAGCAGCAGGA | 552178 | 3-9-5 | 57 | 19 |
| 414 | 430 | TGAGGCATAGCAGCAGG | 552179 | 3-9-5 | 56 | 21 |
| 415 | 431 | ATGAGGCATAGCAGCAG | 552180 | 3-9-5 | 51 | 23 |
| 416 | 432 | GATGAGGCATAGCAGCA | 552181 | 3-9-5 | 51 | 25 |
| 417 | 433 | AGATGAGGCATAGCAGC | 552182 | 3-9-5 | 63 | 27 |
| 418 | 434 | AAGATGAGGCATAGCAG | 552183 | 3-9-5 | 60 | 29 |
| 670 | 686 | ACTAGTAAACTGAGCCA | 552185 | 3-9-5 | 67 | 1292 |
| 671 | 687 | CACTAGTAAACTGAGCC | 552186 | 3-9-5 | 37 | 1293 |
| 672 | 688 | GCACTAGTAAACTGAGC | 552187 | 3-9-5 | 68 | 1294 |
| 687 | 703 | ACCACTGAACAAATGGC | 552188 | 3-9-5 | 71 | 40 |
| 688 | 704 | AACCACTGAACAAATGG | 552189 | 3-9-5 | 51 | 41 |
| 689 | 705 | GAACCACTGAACAAATG | 552190 | 3-9-5 | 47 | 42 |
| 690 | 706 | CGAACCACTGAACAAAT | 552191 | 3-9-5 | 50 | 43 |
| 1261 | 1277 | CGCAGTATGGATCGGCA | 552192 | 3-9-5 | 80 | 1295 |
| 1262 | 1278 | CCGCAGTATGGATCGGC | 552193 | 3-9-5 | 73 | 1296 |
| 1263 | 1279 | TCCGCAGTATGGATCGG | 552194 | 3-9-5 | 58 | 1297 |
| 1264 | 1280 | TTCCGCAGTATGGATCG | 552195 | 3-9-5 | 60 | 1298 |

TABLE 44-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1265 | 1281 | GTTCCGCAGTATGGATC | 552196 | 3-9-5 | 54 | 1299 |
| 1266 | 1282 | AGTTCCGCAGTATGGAT | 552197 | 3-9-5 | 64 | 1300 |
| 1267 | 1283 | GAGTTCCGCAGTATGGA | 552198 | 3-9-5 | 62 | 1301 |
| 1268 | 1284 | GGAGTTCCGCAGTATGG | 552199 | 3-9-5 | 57 | 1302 |
| 1269 | 1285 | AGGAGTTCCGCAGTATG | 552200 | 3-9-5 | 52 | 1303 |
| 1577 | 1593 | AAGCGAAGTGCACACGG | 552201 | 3-9-5 | 73 | 1304 |
| 1578 | 1594 | GAAGCGAAGTGCACACG | 552202 | 3-9-5 | 60 | 1305 |
| 1579 | 1595 | TGAAGCGAAGTGCACAC | 552203 | 3-9-5 | 60 | 1306 |
| 1580 | 1596 | GTGAAGCGAAGTGCACA | 552204 | 3-9-5 | 63 | 1307 |
| 1581 | 1597 | GGTGAAGCGAAGTGCAC | 552151 | 2-9-6 | 71 | 1308 |
| 1581 | 1597 | GGTGAAGCGAAGTGCAC | 552205 | 3-9-5 | 64 | 1308 |
| 1582 | 1598 | AGGTGAAGCGAAGTGCA | 552152 | 2-9-6 | 69 | 1309 |
| 1582 | 1598 | AGGTGAAGCGAAGTGCA | 552206 | 3-9-5 | 71 | 1309 |
| 1583 | 1599 | GAGGTGAAGCGAAGTGC | 552153 | 2-9-6 | 63 | 1310 |
| 1583 | 1599 | GAGGTGAAGCGAAGTGC | 552207 | 3-9-5 | 71 | 1310 |
| 1584 | 1600 | AGAGGTGAAGCGAAGTG | 552154 | 2-9-6 | 56 | 1311 |
| 1584 | 1600 | AGAGGTGAAGCGAAGTG | 552208 | 3-9-5 | 52 | 1311 |
| 1585 | 1601 | CAGAGGTGAAGCGAAGT | 552155 | 2-9-6 | 61 | 1312 |
| 1585 | 1601 | CAGAGGTGAAGCGAAGT | 552209 | 3-9-5 | 50 | 1312 |
| 1586 | 1602 | GCAGAGGTGAAGCGAAG | 552156 | 2-9-6 | 40 | 1313 |
| 1586 | 1602 | GCAGAGGTGAAGCGAAG | 552210 | 3-9-5 | 66 | 1313 |
| 1587 | 1603 | TGCAGAGGTGAAGCGAA | 552157 | 2-9-6 | 45 | 1314 |
| 1587 | 1603 | TGCAGAGGTGAAGCGAA | 552211 | 3-9-5 | 63 | 1314 |
| 1588 | 1604 | GTGCAGAGGTGAAGCGA | 552158 | 2-9-6 | 66 | 1315 |
| 1588 | 1604 | GTGCAGAGGTGAAGCGA | 552212 | 3-9-5 | 62 | 1315 |
| 1589 | 1605 | CGTGCAGAGGTGAAGCG | 552159 | 2-9-6 | 68 | 1316 |
| 1589 | 1605 | CGTGCAGAGGTGAAGCG | 552213 | 3-9-5 | 64 | 1316 |
| 1590 | 1606 | ACGTGCAGAGGTGAAGC | 552160 | 2-9-6 | 78 | 1317 |
| 1590 | 1606 | ACGTGCAGAGGTGAAGC | 552214 | 3-9-5 | 72 | 1317 |
| 1778 | 1794 | TTATGCCTACAGCCTCC | 552161 | 2-9-6 | 57 | 47 |
| 1778 | 1794 | TTATGCCTACAGCCTCC | 552215 | 3-9-5 | 54 | 47 |
| 1779 | 1795 | TTTATGCCTACAGCCTC | 552162 | 2-9-6 | 54 | 49 |
| 1779 | 1795 | TTTATGCCTACAGCCTC | 552216 | 3-9-5 | 49 | 49 |
| 1780 | 1796 | ATTTATGCCTACAGCCT | 552163 | 2-9-6 | 65 | 51 |
| 1780 | 1796 | ATTTATGCCTACAGCCT | 552217 | 3-9-5 | 50 | 51 |
| 1781 | 1797 | AATTTATGCCTACAGCC | 552164 | 2-9-6 | 48 | 53 |

TABLE 44-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1781 | 1797 | AATTTATGCCTACAGCC | 552218 | 3-9-5 | 39 | 53 |
| 1782 | 1798 | CAATTTATGCCTACAGC | 552165 | 2-9-6 | 46 | 54 |
| 1782 | 1798 | CAATTTATGCCTACAGC | 552219 | 3-9-5 | 41 | 54 |
| 1783 | 1799 | CCAATTTATGCCTACAG | 552166 | 2-9-6 | 42 | 55 |
| 1783 | 1799 | CCAATTTATGCCTACAG | 552220 | 3-9-5 | 32 | 55 |
| 1784 | 1800 | ACCAATTTATGCCTACA | 552167 | 2-9-6 | 47 | 56 |
| 1784 | 1800 | ACCAATTTATGCCTACA | 552221 | 3-9-5 | 33 | 56 |

TABLE 45

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 87 56 | 224 |
| 1780 | 1799 | CCAATTTATGCCTACAGCCT | 509934 | 5-10-5 | 56 | 50 |
| 411 | 427 | GGCATAGCAGCAGGATG | 510100 | 3-10-4 | 69 | 17 |
| 58 | 77 | GAACTGGAGCCACCAGCAGG | 552071 | 8-10-2 | 73 | 83 |
| 58 | 74 | CTGGAGCCACCAGCAGG | 552114 | 2-9-6 | 64 | 1288 |
| 59 | 75 | ACTGGAGCCACCAGCAG | 552115 | 2-9-6 | 61 | 1289 |
| 60 | 76 | AACTGGAGCCACCAGCA | 552116 | 2-9-6 | 53 | 1290 |
| 61 | 77 | GAACTGGAGCCACCAGC | 552117 | 2-9-6 | 69 | 1291 |
| 253 | 272 | AGAGAAGTCCACCACGAGTC | 552072 | 8-10-2 | 39 | 103 |
| 253 | 269 | GAAGTCCACCACGAGTC | 552118 | 2-9-6 | 49 | 9 |
| 254 | 270 | AGAAGTCCACCACGAGT | 552119 | 2-9-6 | 49 | 10 |
| 255 | 271 | GAGAAGTCCACCACGAG | 552120 | 2-9-6 | 21 | 11 |
| 256 | 272 | AGAGAAGTCCACCACGA | 552121 | 2-9-6 | 27 | 12 |
| 411 | 430 | TGAGGCATAGCAGCAGGATG | 552073 | 8-10-2 | 73 | 136 |
| 411 | 427 | GGCATAGCAGCAGGATG | 552122 | 2-9-6 | 48 | 17 |
| 412 | 431 | ATGAGGCATAGCAGCAGGAT | 552074 | 8-10-2 | 69 | 139 |
| 412 | 428 | AGGCATAGCAGCAGGAT | 552123 | 2-9-6 | 68 | 18 |
| 413 | 432 | GATGAGGCATAGCAGCAGGA | 552075 | 8-10-2 | 78 | 142 |
| 413 | 429 | GAGGCATAGCAGCAGGA | 552124 | 2-9-6 | 47 | 19 |
| 414 | 433 | AGATGAGGCATAGCAGCAGG | 552076 | 8-10-2 | 63 | 20 |
| 414 | 430 | TGAGGCATAGCAGCAGG | 552125 | 2-9-6 | 72 | 21 |
| 415 | 434 | AAGATGAGGCATAGCAGCAG | 552077 | 8-10-2 | 62 | 22 |

TABLE 45-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 415 | 431 | ATGAGGCATAGCAGCAG | 552126 | 2-9-6 | 64 | 23 |
| 416 | 435 | GAAGATGAGGCATAGCAGCA | 552078 | 8-10-2 | 59 | 24 |
| 416 | 432 | GATGAGGCATAGCAGCA | 552127 | 2-9-6 | 65 | 25 |
| 417 | 436 | AGAAGATGAGGCATAGCAGC | 552079 | 8-10-2 | 80 | 26 |
| 417 | 433 | AGATGAGGCATAGCAGC | 552128 | 2-9-6 | 78 | 27 |
| 418 | 437 | AAGAAGATGAGGCATAGCAG | 552080 | 8-10-2 | 74 | 28 |
| 418 | 434 | AAGATGAGGCATAGCAG | 552129 | 2-9-6 | 68 | 29 |
| 457 | 473 | ACGGGCAACATACCTTG | 552130 | 2-9-6 | 46 | 33 |
| 670 | 686 | ACTAGTAAACTGAGCCA | 552131 | 2-9-6 | 61 | 1292 |
| 671 | 687 | CACTAGTAAACTGAGCC | 552132 | 2-9-6 | 66 | 1293 |
| 672 | 688 | GCACTAGTAAACTGAGC | 552133 | 2-9-6 | 78 | 1294 |
| 687 | 706 | CGAACCACTGAACAAATGGC | 552081 | 8-10-2 | 69 | 39 |
| 687 | 703 | ACCACTGAACAAATGGC | 552134 | 2-9-6 | 68 | 40 |
| 688 | 704 | AACCACTGAACAAATGG | 552135 | 2-9-6 | 59 | 41 |
| 689 | 705 | GAACCACTGAACAAATG | 552136 | 2-9-6 | 39 | 42 |
| 690 | 706 | CGAACCACTGAACAAAT | 552137 | 2-9-6 | 36 | 43 |
| 1261 | 1280 | TTCCGCAGTATGGATCGGCA | 552082 | 8-10-2 | 86 | 719 |
| 1261 | 1277 | CGCAGTATGGATCGGCA | 552138 | 2-9-6 | 80 | 1295 |
| 1262 | 1281 | GTTCCGCAGTATGGATCGGC | 552083 | 8-10-2 | 85 | 212 |
| 1262 | 1278 | CCGCAGTATGGATCGGC | 552139 | 2-9-6 | 80 | 1296 |
| 1263 | 1282 | AGTTCCGCAGTATGGATCGG | 552084 | 8-10-2 | 86 | 720 |
| 1263 | 1279 | TCCGCAGTATGGATCGG | 552140 | 2-9-6 | 70 | 1297 |
| 1264 | 1283 | GAGTTCCGCAGTATGGATCG | 552085 | 8-10-2 | 83 | 721 |
| 1264 | 1280 | TTCCGCAGTATGGATCG | 552141 | 2-9-6 | 72 | 1298 |
| 1265 | 1284 | GGAGTTCCGCAGTATGGATC | 552086 | 8-10-2 | 83 | 1349 |
| 1265 | 1281 | GTTCCGCAGTATGGATC | 552142 | 2-9-6 | 58 | 1299 |
| 1266 | 1285 | AGGAGTTCCGCAGTATGGAT | 552087 | 8-10-2 | 77 | 722 |
| 1266 | 1282 | AGTTCCGCAGTATGGAT | 552143 | 2-9-6 | 70 | 1300 |
| 1267 | 1283 | GAGTTCCGCAGTATGGA | 552144 | 2-9-6 | 66 | 1301 |
| 1268 | 1284 | GGAGTTCCGCAGTATGG | 552145 | 2-9-6 | 78 | 1302 |
| 1269 | 1285 | AGGAGTTCCGCAGTATG | 552146 | 2-9-6 | 63 | 1303 |
| 1577 | 1596 | GTGAAGCGAAGTGCACACGG | 552088 | 8-10-2 | 90 | 224 |
| 1577 | 1593 | AAGCGAAGTGCACACGG | 552147 | 2-9-6 | 80 | 1304 |
| 1578 | 1597 | GGTGAAGCGAAGTGCACACG | 552089 | 8-10-2 | 87 | 801 |
| 1578 | 1594 | GAAGCGAAGTGCACACG | 552148 | 2-9-6 | 74 | 1305 |
| 1579 | 1598 | AGGTGAAGCGAAGTGCACAC | 552090 | 8-10-2 | 85 | 802 |

TABLE 45-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1579 | 1595 | TGAAGCGAAGTGCACAC | 552149 | 2-9-6 | 79 | 1306 |
| 1580 | 1599 | GAGGTGAAGCGAAGTGCACA | 552091 | 8-10-2 | 84 | 225 |
| 1581 | 1600 | AGAGGTGAAGCGAAGTGCAC | 552092 | 8-10-2 | 86 | 804 |
| 1582 | 1601 | CAGAGGTGAAGCGAAGTGCA | 552093 | 8-10-2 | 82 | 805 |
| 1583 | 1602 | GCAGAGGTGAAGCGAAGTGC | 552094 | 8-10-2 | 84 | 226 |
| 1584 | 1603 | TGCAGAGGTGAAGCGAAGTG | 552063 | 7-10-3 | 79 | 806 |
| 1584 | 1603 | TGCAGAGGTGAAGCGAAGTG | 552095 | 8-10-2 | 85 | 806 |
| 1585 | 1604 | GTGCAGAGGTGAAGCGAAGT | 552064 | 7-10-3 | 83 | 807 |
| 1585 | 1604 | GTGCAGAGGTGAAGCGAAGT | 552096 | 8-10-2 | 88 | 807 |
| 1586 | 1605 | CGTGCAGAGGTGAAGCGAAG | 552065 | 7-10-3 | 86 | 227 |
| 1586 | 1605 | CGTGCAGAGGTGAAGCGAAG | 552097 | 8-10-2 | 90 | 227 |
| 1587 | 1606 | ACGTGCAGAGGTGAAGCGAA | 552066 | 7-10-3 | 35 | 1350 |
| 1587 | 1606 | ACGTGCAGAGGTGAAGCGAA | 552098 | 8-10-2 | 86 | 1350 |
| 1778 | 1797 | AATTTATGCCTACAGCCTCC | 552067 | 7-10-3 | 53 | 46 |
| 1778 | 1797 | AATTTATGCCTACAGCCTCC | 552099 | 8-10-2 | 66 | 46 |
| 1779 | 1798 | CAATTTATGCCTACAGCCTC | 552068 | 7-10-3 | 70 | 48 |
| 1779 | 1798 | CAATTTATGCCTACAGCCTC | 552100 | 8-10-2 | 67 | 48 |
| 1780 | 1799 | CCAATTTATGCCTACAGCCT | 552069 | 7-10-3 | 68 | 50 |
| 1780 | 1799 | CCAATTTATGCCTACAGCCT | 552101 | 8-10-2 | 65 | 50 |
| 1781 | 1800 | ACCAATTTATGCCTACAGCC | 552070 | 7-10-3 | 64 | 52 |
| 1781 | 1800 | ACCAATTTATGCCTACAGCC | 552102 | 8-10-2 | 54 | 52 |

TABLE 46

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | 5-10-5 | 69 57 | 224 |
| 411 | 427 | GGCATAGCAGCAGGATG | 510100 | 3-10-4 | 59 | 17 |
| 58 | 74 | CTGGAGCCACCAGCAGG | 552330 | 6-9-2 | 50 | 1288 |
| 59 | 75 | ACTGGAGCCACCAGCAG | 552331 | 6-9-2 | 46 | 1289 |
| 60 | 76 | AACTGGAGCCACCAGCA | 552332 | 6-9-2 | 50 | 1290 |
| 61 | 77 | GAACTGGAGCCACCAGC | 552333 | 6-9-2 | 48 | 1291 |
| 253 | 269 | GAAGTCCACCACGAGTC | 552334 | 6-9-2 | 42 | 9 |
| 254 | 270 | AGAAGTCCACCACGAGT | 552335 | 6-9-2 | 30 | 10 |

TABLE 46-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 255 | 271 | GAGAAGTCCACCACGAG | 552336 | 6-9-2 | 23 | 11 |
| 256 | 272 | AGAGAAGTCCACCACGA | 552337 | 6-9-2 | 42 | 12 |
| 411 | 427 | GGCATAGCAGCAGGATG | 552338 | 6-9-2 | 40 | 17 |
| 412 | 428 | AGGCATAGCAGCAGGAT | 552339 | 6-9-2 | 50 | 18 |
| 413 | 429 | GAGGCATAGCAGCAGGA | 552340 | 6-9-2 | 45 | 19 |
| 414 | 430 | TGAGGCATAGCAGCAGG | 552341 | 6-9-2 | 44 | 21 |
| 415 | 431 | ATGAGGCATAGCAGCAG | 552342 | 6-9-2 | 51 | 23 |
| 416 | 432 | GATGAGGCATAGCAGCA | 552343 | 6-9-2 | 44 | 25 |
| 417 | 433 | AGATGAGGCATAGCAGC | 552344 | 6-9-2 | 24 | 27 |
| 418 | 434 | AAGATGAGGCATAGCAG | 552345 | 6-9-2 | 41 | 29 |
| 457 | 473 | ACGGGCAACATACCTTG | 552346 | 6-9-2 | 0 | 33 |
| 670 | 686 | ACTAGTAAACTGAGCCA | 552347 | 6-9-2 | 75 | 1292 |
| 671 | 687 | CACTAGTAAACTGAGCC | 552348 | 6-9-2 | 72 | 1293 |
| 672 | 688 | GCACTAGTAAACTGAGC | 552349 | 6-9-2 | 65 | 1294 |
| 687 | 703 | ACCACTGAACAAATGGC | 552350 | 6-9-2 | 42 | 40 |
| 688 | 704 | AACCACTGAACAAATGG | 552351 | 6-9-2 | 45 | 41 |
| 689 | 705 | GAACCACTGAACAAATG | 552352 | 6-9-2 | 43 | 42 |
| 690 | 706 | CGAACCACTGAACAAAT | 552353 | 6-9-2 | 20 | 43 |
| 1261 | 1277 | CGCAGTATGGATCGGCA | 552354 | 6-9-2 | 70 | 1295 |
| 1262 | 1278 | CCGCAGTATGGATCGGC | 552355 | 6-9-2 | 66 | 1296 |
| 1263 | 1279 | TCCGCAGTATGGATCGG | 552356 | 6-9-2 | 62 | 1297 |
| 1264 | 1280 | TTCCGCAGTATGGATCG | 552357 | 6-9-2 | 53 | 1298 |
| 1265 | 1281 | GTTCCGCAGTATGGATC | 552358 | 6-9-2 | 57 | 1299 |
| 1266 | 1282 | AGTTCCGCAGTATGGAT | 552359 | 6-9-2 | 46 | 1300 |
| 1267 | 1283 | GAGTTCCGCAGTATGGA | 552360 | 6-9-2 | 45 | 1301 |
| 1268 | 1284 | GGAGTTCCGCAGTATGG | 552361 | 6-9-2 | 44 | 1302 |
| 1269 | 1285 | AGGAGTTCCGCAGTATG | 552308 | 5-9-3 | 38 | 1303 |
| 1269 | 1285 | AGGAGTTCCGCAGTATG | 552362 | 6-9-2 | 51 | 1303 |
| 1577 | 1593 | AAGCGAAGTGCACACGG | 552309 | 5-9-3 | 76 | 1304 |
| 1577 | 1593 | AAGCGAAGTGCACACGG | 552363 | 6-9-2 | 73 | 1304 |
| 1578 | 1594 | GAAGCGAAGTGCACACG | 552310 | 5-9-3 | 58 | 1305 |
| 1578 | 1594 | GAAGCGAAGTGCACACG | 552364 | 6-9-2 | 66 | 1305 |
| 1579 | 1595 | TGAAGCGAAGTGCACAC | 552311 | 5-9-3 | 38 | 1306 |
| 1579 | 1595 | TGAAGCGAAGTGCACAC | 552365 | 6-9-2 | 64 | 1306 |
| 1580 | 1596 | GTGAAGCGAAGTGCACA | 552150 | 2-9-6 | 68 | 1307 |
| 1580 | 1596 | GTGAAGCGAAGTGCACA | 552312 | 5-9-3 | 75 | 1307 |

TABLE 46-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1580 | 1596 | GTGAAGCGAAGTGCACA | 552366 | 6-9-2 | 55 | 1307 |
| 1581 | 1597 | GGTGAAGCGAAGTGCAC | 552313 | 5-9-3 | 66 | 1308 |
| 1581 | 1597 | GGTGAAGCGAAGTGCAC | 552367 | 6-9-2 | 67 | 1308 |
| 1582 | 1598 | AGGTGAAGCGAAGTGCA | 552314 | 5-9-3 | 56 | 1309 |
| 1582 | 1598 | AGGTGAAGCGAAGTGCA | 552368 | 6-9-2 | 41 | 1309 |
| 1583 | 1599 | GAGGTGAAGCGAAGTGC | 552315 | 5-9-3 | 46 | 1310 |
| 1583 | 1599 | GAGGTGAAGCGAAGTGC | 552369 | 6-9-2 | 52 | 1310 |
| 1584 | 1600 | AGAGGTGAAGCGAAGTG | 552316 | 5-9-3 | 55 | 1311 |
| 1584 | 1600 | AGAGGTGAAGCGAAGTG | 552370 | 6-9-2 | 35 | 1311 |
| 1585 | 1601 | CAGAGGTGAAGCGAAGT | 552317 | 5-9-3 | 53 | 1312 |
| 1585 | 1601 | CAGAGGTGAAGCGAAGT | 552371 | 6-9-2 | 58 | 1312 |
| 1586 | 1602 | GCAGAGGTGAAGCGAAG | 552318 | 5-9-3 | 59 | 1313 |
| 1586 | 1602 | GCAGAGGTGAAGCGAAG | 552372 | 6-9-2 | 68 | 1313 |
| 1587 | 1603 | TGCAGAGGTGAAGCGAA | 552319 | 5-9-3 | 56 | 1314 |
| 1587 | 1603 | TGCAGAGGTGAAGCGAA | 552373 | 6-9-2 | 63 | 1314 |
| 1588 | 1604 | GTGCAGAGGTGAAGCGA | 552320 | 5-9-3 | 62 | 1315 |
| 1588 | 1604 | GTGCAGAGGTGAAGCGA | 552374 | 6-9-2 | 70 | 1315 |
| 1589 | 1605 | CGTGCAGAGGTGAAGCG | 552321 | 5-9-3 | 63 | 1316 |
| 1589 | 1605 | CGTGCAGAGGTGAAGCG | 552375 | 6-9-2 | 64 | 1316 |
| 1590 | 1606 | ACGTGCAGAGGTGAAGC | 552322 | 5-9-3 | 52 | 1317 |
| 1590 | 1606 | ACGTGCAGAGGTGAAGC | 552376 | 6-9-2 | 58 | 1317 |
| 1778 | 1794 | TTATGCCTACAGCCTCC | 552323 | 5-9-3 | 45 | 47 |
| 1778 | 1794 | TTATGCCTACAGCCTCC | 552377 | 6-9-2 | 42 | 47 |
| 1779 | 1795 | TTTATGCCTACAGCCTC | 552324 | 5-9-3 | 49 | 49 |
| 1779 | 1795 | TTTATGCCTACAGCCTC | 552378 | 6-9-2 | 37 | 49 |
| 1780 | 1796 | ATTTATGCCTACAGCCT | 552325 | 5-9-3 | 48 | 51 |
| 1780 | 1796 | ATTTATGCCTACAGCCT | 552379 | 6-9-2 | 57 | 51 |
| 1781 | 1797 | AATTTATGCCTACAGCC | 552326 | 5-9-3 | 50 | 53 |
| 1781 | 1797 | AATTTATGCCTACAGCC | 552380 | 6-9-2 | 48 | 53 |
| 1782 | 1798 | CAATTTATGCCTACAGC | 552327 | 5-9-3 | 13 | 54 |
| 1782 | 1798 | CAATTTATGCCTACAGC | 552381 | 6-9-2 | 22 | 54 |
| 1783 | 1799 | CCAATTTATGCCTACAG | 552328 | 5-9-3 | 9 | 55 |
| 1783 | 1799 | CCAATTTATGCCTACAG | 552382 | 6-9-2 | 20 | 55 |
| 1784 | 1800 | ACCAATTTATGCCTACA | 552329 | 5-9-3 | 18 | 56 |
| 1784 | 1800 | ACCAATTTATGCCTACA | 552383 | 6-9-2 | 18 | 56 |

Example 15

Antisense Inhibition of HBV Viral mRNA in HepG2 Cells by Deoxy, MOE and (S)-cEt Gapmers Antisense oligonucleotides were designed targeting a HBV viral nucleic acid and were tested for their effects on HBV mRNA in vitro. The antisense oligonucleotides were tested in a series of experiments that had similar culture conditions. The results for each experiment are presented in separate tables shown below. ISIS 146786 and ISIS 509934, which were described in an earlier application (U.S. Provisional Application No. 61/478,040 filed on Apr. 21, 2011), were also included in these studies for comparison. Cultured HepG2 cells at a density of 28,000 cells per well were transfected using LipofectAMINE2000® with 70 nM antisense oligonucleotide. After a treatment period of approximately 24 hours, RNA was isolated from the cells and HBV mRNA levels were measured by quantitative real-time PCR. Viral primer probe set RTS3370 (forward sequence CTTGGTCATGGGCCATCAG, designated herein as SEQ ID NO: 1; reverse sequence CGGCTAGGAGTTCCGCAGTA, designated herein as SEQ ID NO: 2; probe sequence TGCGTGGAACCTTTTCGGCTCC, designated herein as SEQ ID NO: 3) was used to measure mRNA levels. Levels were also measured using primer probe set RTS3371 (forward sequence CCAAACCTTCGGACGGAAA, designated herein as SEQ ID NO: 311; reverse sequence TGAGGCCCACTCCCATAGG, designated herein as SEQ ID NO: 312; probe sequence CCCATCATCCTGGGCTTTCGGAAAAT, designated herein as SEQ ID NO: 313). HBV mRNA levels were adjusted according to total RNA content, as measured by RIBOGREEN®. Results are presented as percent inhibition of HBV, relative to untreated control cells.

The newly designed chimeric antisense oligonucleotides in Tables below were designed as deoxy, MOE and (S)-cEt gapmers. The gapmers are 16 nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; and 'e' indicates a MOE modification. The internucleoside linkages throughout each gapmer are phosphorothioate (P=S) linkages. All cytosine residues throughout each oligonucleotide are 5-methylcytosines.

"Viral Target start site" indicates the 5'-most nucleotide to which the gapmer is targeted in the viral gene sequence. "Viral Target stop site" indicates the 3'-most nucleotide to which the gapmer is targeted viral gene sequence. Each gapmer listed in the Tables is targeted to the viral genomic sequence, designated herein as SEQ ID NO: 1 (GENBANK Accession No. U95551.1). The potency of the newly designed oligonucleotides was compared with ISIS 146786, 509934, ISIS 509959, and ISIS 510100.

TABLE 47

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1780 | 1799 | CCAATTTATGCCTACAGCCT | 509934 | eeeee-10-eeeee | 30 | 50 |
| 58 | 73 | TGGAGCCACCAGCAGG | 552787 | ekk-10-kke | 57 | 1318 |
| 59 | 74 | CTGGAGCCACCAGCAG | 552788 | ekk-10-kke | 60 | 1319 |
| 60 | 75 | ACTGGAGCCACCAGCA | 552789 | ekk-10-kke | 67 | 1320 |
| 61 | 76 | AACTGGAGCCACCAGC | 552790 | ekk-10-kke | 67 | 1321 |
| 62 | 77 | GAACTGGAGCCACCAG | 552791 | ekk-10-kke | 65 | 86 |
| 245 | 260 | CACGAGTCTAGACTCT | 552792 | ekk-10-kke | 44 | 93 |
| 246 | 261 | CCACGAGTCTAGACTC | 552793 | ekk-10-kke | 0 | 95 |
| 250 | 265 | TCCACCACGAGTCTAG | 552794 | ekk-10-kke | 54 | 98 |
| 251 | 266 | GTCCACCACGAGTCTA | 552795 | ekk-10-kke | 55 | 100 |
| 252 | 267 | AGTCCACCACGAGTCT | 552796 | ekk-10-kke | 62 | 102 |
| 253 | 268 | AAGTCCACCACGAGTC | 552797 | ekk-10-kke | 59 | 104 |
| 254 | 269 | GAAGTCCACCACGAGT | 552798 | ekk-10-kke | 59 | 106 |
| 255 | 270 | AGAAGTCCACCACGAG | 552799 | ekk-10-kke | 58 | 109 |
| 256 | 271 | GAGAAGTCCACCACGA | 552800 | ekk-10-kke | 62 | 112 |
| 258 | 273 | GAGAGAAGTCCACCAC | 552801 | ekk-10-kke | 65 | 115 |
| 259 | 274 | TGAGAGAAGTCCACCA | 552802 | ekk-10-kke | 53 | 117 |
| 411 | 426 | GCATAGCAGCAGGATG | 552803 | ekk-10-kke | 67 | 137 |

TABLE 47-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 412 | 427 | GGCATAGCAGCAGGAT | 552804 | ekk-10-kke | 75 | 140 |
| 413 | 428 | AGGCATAGCAGCAGGA | 552805 | ekk-10-kke | 72 | 143 |
| 414 | 429 | GAGGCATAGCAGCAGG | 552806 | ekk-10-kke | 64 | 145 |
| 415 | 430 | TGAGGCATAGCAGCAG | 552807 | ekk-10-kke | 68 | 147 |
| 416 | 431 | ATGAGGCATAGCAGCA | 552808 | ekk-10-kke | 65 | 149 |
| 417 | 432 | GATGAGGCATAGCAGC | 552809 | ekk-10-kke | 60 | 151 |
| 418 | 433 | AGATGAGGCATAGCAG | 552810 | ekk-10-kke | 59 | 153 |
| 419 | 434 | AAGATGAGGCATAGCA | 552811 | ekk-10-kke | 64 | 155 |
| 420 | 435 | GAAGATGAGGCATAGC | 552812 | ekk-10-kke | 69 | 157 |
| 421 | 436 | AGAAGATGAGGCATAG | 552813 | ekk-10-kke | 64 | 159 |
| 422 | 437 | AAGAAGATGAGGCATA | 552814 | ekk-10-kke | 62 | 161 |
| 457 | 472 | CGGGCAACATACCTTG | 552815 | ekk-10-kke | 61 | 167 |
| 458 | 473 | ACGGGCAACATACCTT | 552816 | ekk-10-kke | 63 | 168 |
| 639 | 654 | GGCCCACTCCCATAGG | 552817 | ekk-10-kke | 42 | 176 |
| 641 | 656 | GAGGCCCACTCCCATA | 552818 | ekk-10-kke | 44 | 177 |
| 642 | 657 | TGAGGCCCACTCCCAT | 552819 | ekk-10-kke | 56 | 178 |
| 643 | 658 | CTGAGGCCCACTCCCA | 552820 | ekk-10-kke | 59 | 179 |
| 670 | 685 | CTAGTAAACTGAGCCA | 552821 | ekk-10-kke | 76 | 181 |
| 671 | 686 | ACTAGTAAACTGAGCC | 552822 | ekk-10-kke | 77 | 1322 |
| 672 | 687 | CACTAGTAAACTGAGC | 552823 | ekk-10-kke | 73 | 1323 |
| 673 | 688 | GCACTAGTAAACTGAG | 552824 | ekk-10-kke | 73 | 1324 |
| 678 | 693 | AAATGGCACTAGTAAA | 552825 | ekk-10-kke | 51 | 1364 |
| 679 | 694 | CAAATGGCACTAGTAA | 552826 | ekk-10-kke | 55 | 1365 |
| 680 | 695 | ACAAATGGCACTAGTA | 552827 | ekk-10-kke | 67 | 1366 |
| 681 | 696 | AACAAATGGCACTAGT | 552828 | ekk-10-kke | 78 | 1367 |
| 682 | 697 | GAACAAATGGCACTAG | 552829 | ekk-10-kke | 72 | 1368 |
| 683 | 698 | TGAACAAATGGCACTA | 552830 | ekk-10-kke | 71 | 1369 |
| 684 | 699 | CTGAACAAATGGCACT | 552831 | ekk-10-kke | 69 | 1370 |
| 685 | 700 | ACTGAACAAATGGCAC | 552832 | ekk-10-kke | 67 | 1371 |
| 686 | 701 | CACTGAACAAATGGCA | 552833 | ekk-10-kke | 65 | 1372 |
| 687 | 702 | CCACTGAACAAATGGC | 552834 | ekk-10-kke | 78 | 188 |
| 688 | 703 | ACCACTGAACAAATGG | 552835 | ekk-10-kke | 70 | 190 |
| 689 | 704 | AACCACTGAACAAATG | 552836 | ekk-10-kke | 64 | 191 |
| 690 | 705 | GAACCACTGAACAAAT | 552837 | ekk-10-kke | 65 | 192 |
| 691 | 706 | CGAACCACTGAACAAA | 552838 | ekk-10-kke | 64 | 194 |
| 738 | 753 | CCACATCATCCATATA | 552839 | ekk-10-kke | 60 | 199 |

TABLE 47-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 739 | 754 | ACCACATCATCCATAT | 552840 | ekk-10-kke | 35 | 201 |
| 1176 | 1191 | CAGCAAACACTTGGCA | 552841 | ekk-10-kke | 62 | 208 |
| 1177 | 1192 | TCAGCAAACACTTGGC | 552842 | ekk-10-kke | 67 | 209 |
| 1261 | 1276 | GCAGTATGGATCGGCA | 552843 | ekk-10-kke | 77 | 211 |
| 1262 | 1277 | CGCAGTATGGATCGGC | 552844 | ekk-10-kke | 81 | 1325 |
| 1263 | 1278 | CCGCAGTATGGATCGG | 552845 | ekk-10-kke | 63 | 1326 |
| 1264 | 1279 | TCCGCAGTATGGATCG | 552846 | ekk-10-kke | 79 | 1327 |
| 1265 | 1280 | TTCCGCAGTATGGATC | 552847 | ekk-10-kke | 47 | 1328 |
| 1266 | 1281 | GTTCCGCAGTATGGAT | 552848 | ekk-10-kke | 69 | 1329 |
| 1267 | 1282 | AGTTCCGCAGTATGGA | 552849 | ekk-10-kke | 59 | 1330 |
| 1268 | 1283 | GAGTTCCGCAGTATGG | 552850 | ekk-10-kke | 83 | 1331 |
| 1269 | 1284 | GGAGTTCCGCAGTATG | 552851 | ekk-10-kke | 90 | 1332 |
| 1270 | 1285 | AGGAGTTCCGCAGTAT | 552852 | ekk-10-kke | 89 | 1333 |
| 1577 | 1592 | AGCGAAGTGCACACGG | 552853 | ekk-10-kke | 83 | 1334 |
| 1578 | 1593 | AAGCGAAGTGCACACG | 552854 | ekk-10-kke | 80 | 1335 |
| 1579 | 1594 | GAAGCGAAGTGCACAC | 552855 | ekk-10-kke | 75 | 1336 |
| 1580 | 1595 | TGAAGCGAAGTGCACA | 552856 | ekk-10-kke | 69 | 1337 |
| 1581 | 1596 | GTGAAGCGAAGTGCAC | 552857 | ekk-10-kke | 68 | 1338 |
| 1582 | 1597 | GGTGAAGCGAAGTGCA | 552858 | ekk-10-kke | 79 | 1339 |
| 1583 | 1598 | AGGTGAAGCGAAGTGC | 552859 | ekk-10-kke | 79 | 1340 |
| 1584 | 1599 | GAGGTGAAGCGAAGTG | 552860 | ekk-10-kke | 71 | 1341 |
| 1585 | 1600 | AGAGGTGAAGCGAAGT | 552861 | ekk-10-kke | 68 | 1342 |
| 1586 | 1601 | CAGAGGTGAAGCGAAG | 552862 | ekk-10-kke | 65 | 1343 |
| 1587 | 1602 | GCAGAGGTGAAGCGAA | 552863 | ekk-10-kke | 70 | 1344 |
| 1588 | 1603 | TGCAGAGGTGAAGCGA | 552864 | ekk-10-kke | 71 | 1345 |

TABLE 48

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 58 | 73 | TGGAGCCACCAGCAGG | 552787 | ekk-10-kke | 53 | 1318 |
| 59 | 74 | CTGGAGCCACCAGCAG | 552788 | ekk-10-kke | 45 | 1319 |
| 60 | 75 | ACTGGAGCCACCAGCA | 552789 | ekk-10-kke | 75 | 1320 |
| 61 | 76 | AACTGGAGCCACCAGC | 552790 | ekk-10-kke | 68 | 1321 |
| 62 | 77 | GAACTGGAGCCACCAG | 552791 | ekk-10-kke | 51 | 86 |

TABLE 48-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 245 | 260 | CACGAGTCTAGACTCT | 552792 | ekk-10-kke | 38 | 93 |
| 246 | 261 | CCACGAGTCTAGACTC | 552793 | ekk-10-kke | 0 | 95 |
| 250 | 265 | TCCACCACGAGTCTAG | 552794 | ekk-10-kke | 44 | 98 |
| 251 | 266 | GTCCACCACGAGTCTA | 552795 | ekk-10-kke | 56 | 100 |
| 252 | 267 | AGTCCACCACGAGTCT | 552796 | ekk-10-kke | 45 | 102 |
| 253 | 268 | AAGTCCACCACGAGTC | 552797 | ekk-10-kke | 46 | 104 |
| 254 | 269 | GAAGTCCACCACGAGT | 552798 | ekk-10-kke | 53 | 106 |
| 255 | 270 | AGAAGTCCACCACGAG | 552799 | ekk-10-kke | 48 | 109 |
| 256 | 271 | GAGAAGTCCACCACGA | 552800 | ekk-10-kke | 54 | 112 |
| 258 | 273 | GAGAGAAGTCCACCAC | 552801 | ekk-10-kke | 63 | 115 |
| 259 | 274 | TGAGAGAAGTCCACCA | 552802 | ekk-10-kke | 49 | 117 |
| 411 | 426 | GCATAGCAGCAGGATG | 552803 | ekk-10-kke | 71 | 137 |
| 412 | 427 | GGCATAGCAGCAGGAT | 552804 | ekk-10-kke | 64 | 140 |
| 413 | 428 | AGGCATAGCAGCAGGA | 552805 | ekk-10-kke | 70 | 143 |
| 414 | 429 | GAGGCATAGCAGCAGG | 552806 | ekk-10-kke | 67 | 145 |
| 415 | 430 | TGAGGCATAGCAGCAG | 552807 | ekk-10-kke | 61 | 147 |
| 416 | 431 | ATGAGGCATAGCAGCA | 552808 | ekk-10-kke | 83 | 149 |
| 417 | 432 | GATGAGGCATAGCAGC | 552809 | ekk-10-kke | 59 | 151 |
| 418 | 433 | AGATGAGGCATAGCAG | 552810 | ekk-10-kke | 56 | 153 |
| 419 | 434 | AAGATGAGGCATAGCA | 552811 | ekk-10-kke | 62 | 155 |
| 420 | 435 | GAAGATGAGGCATAGC | 552812 | ekk-10-kke | 66 | 157 |
| 421 | 436 | AGAAGATGAGGCATAG | 552813 | ekk-10-kke | 63 | 159 |
| 422 | 437 | AAGAAGATGAGGCATA | 552814 | ekk-10-kke | 65 | 161 |
| 457 | 472 | CGGGCAACATACCTTG | 552815 | ekk-10-kke | 63 | 167 |
| 458 | 473 | ACGGGCAACATACCTT | 552816 | ekk-10-kke | 88 | 168 |
| 639 | 654 | GGCCCACTCCCATAGG | 552817 | ekk-10-kke | 94 | 176 |
| 641 | 656 | GAGGCCCACTCCCATA | 552818 | ekk-10-kke | 82 | 177 |
| 642 | 657 | TGAGGCCCACTCCCAT | 552819 | ekk-10-kke | 80 | 178 |
| 643 | 658 | CTGAGGCCCACTCCCA | 552820 | ekk-10-kke | 84 | 179 |
| 670 | 685 | CTAGTAAACTGAGCCA | 552821 | ekk-10-kke | 71 | 181 |
| 671 | 686 | ACTAGTAAACTGAGCC | 552822 | ekk-10-kke | 85 | 1322 |
| 672 | 687 | CACTAGTAAACTGAGC | 552823 | ekk-10-kke | 71 | 1323 |
| 673 | 688 | GCACTAGTAAACTGAG | 552824 | ekk-10-kke | 81 | 1324 |
| 678 | 693 | AAATGGCACTAGTAAA | 552825 | ekk-10-kke | 51 | 1364 |
| 679 | 694 | CAAATGGCACTAGTAA | 552826 | ekk-10-kke | 64 | 1365 |
| 680 | 695 | ACAAATGGCACTAGTA | 552827 | ekk-10-kke | 61 | 1366 |

TABLE 48-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 681 | 696 | AACAAATGGCACTAGT | 552828 | ekk-10-kke | 76 | 1367 |
| 682 | 697 | GAACAAATGGCACTAG | 552829 | ekk-10-kke | 61 | 1368 |
| 683 | 698 | TGAACAAATGGCACTA | 552830 | ekk-10-kke | 59 | 1369 |
| 684 | 699 | CTGAACAAATGGCACT | 552831 | ekk-10-kke | 58 | 1370 |
| 685 | 700 | ACTGAACAAATGGCAC | 552832 | ekk-10-kke | 64 | 1371 |
| 686 | 701 | CACTGAACAAATGGCA | 552833 | ekk-10-kke | 75 | 1372 |
| 687 | 702 | CCACTGAACAAATGGC | 552834 | ekk-10-kke | 84 | 188 |
| 688 | 703 | ACCACTGAACAAATGG | 552835 | ekk-10-kke | 57 | 190 |
| 689 | 704 | AACCACTGAACAAATG | 552836 | ekk-10-kke | 51 | 191 |
| 690 | 705 | GAACCACTGAACAAAT | 552837 | ekk-10-kke | 53 | 192 |
| 691 | 706 | CGAACCACTGAACAAA | 552838 | ekk-10-kke | 48 | 194 |
| 738 | 753 | CCACATCATCCATATA | 552839 | ekk-10-kke | 50 | 199 |
| 739 | 754 | ACCACATCATCCATAT | 552840 | ekk-10-kke | 54 | 201 |
| 1176 | 1191 | CAGCAAACACTTGGCA | 552841 | ekk-10-kke | 61 | 208 |
| 1177 | 1192 | TCAGCAAACACTTGGC | 552842 | ekk-10-kke | 71 | 209 |
| 1261 | 1276 | GCAGTATGGATCGGCA | 552843 | ekk-10-kke | 75 | 211 |
| 1262 | 1277 | CGCAGTATGGATCGGC | 552844 | ekk-10-kke | 78 | 1325 |
| 1263 | 1278 | CCGCAGTATGGATCGG | 552845 | ekk-10-kke | 52 | 1326 |
| 1264 | 1279 | TCCGCAGTATGGATCG | 552846 | ekk-10-kke | 76 | 1327 |
| 1265 | 1280 | TTCCGCAGTATGGATC | 552847 | ekk-10-kke | 61 | 1328 |
| 1266 | 1281 | GTTCCGCAGTATGGAT | 552848 | ekk-10-kke | 72 | 1329 |
| 1267 | 1282 | AGTTCCGCAGTATGGA | 552849 | ekk-10-kke | 87 | 1330 |
| 1268 | 1283 | GAGTTCCGCAGTATGG | 552850 | ekk-10-kke | 76 | 1331 |
| 1269 | 1284 | GGAGTTCCGCAGTATG | 552851 | ekk-10-kke | 76 | 1332 |
| 1270 | 1285 | AGGAGTTCCGCAGTAT | 552852 | ekk-10-kke | 79 | 1333 |
| 1577 | 1592 | AGCGAAGTGCACACGG | 552853 | ekk-10-kke | 82 | 1334 |
| 1578 | 1593 | AAGCGAAGTGCACACG | 552854 | ekk-10-kke | 85 | 1335 |
| 1579 | 1594 | GAAGCGAAGTGCACAC | 552855 | ekk-10-kke | 78 | 1336 |
| 1580 | 1595 | TGAAGCGAAGTGCACA | 552856 | ekk-10-kke | 77 | 1337 |
| 1581 | 1596 | GTGAAGCGAAGTGCAC | 552857 | ekk-10-kke | 75 | 1338 |
| 1582 | 1597 | GGTGAAGCGAAGTGCA | 552858 | ekk-10-kke | 75 | 1339 |
| 1583 | 1598 | AGGTGAAGCGAAGTGC | 552859 | ekk-10-kke | 79 | 1340 |
| 1584 | 1599 | GAGGTGAAGCGAAGTG | 552860 | ekk-10-kke | 71 | 1341 |
| 1585 | 1600 | AGAGGTGAAGCGAAGT | 552861 | ekk-10-kke | 74 | 1342 |
| 1586 | 1601 | CAGAGGTGAAGCGAAG | 552862 | ekk-10-kke | 66 | 1343 |

TABLE 48-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1587 | 1602 | GCAGAGGTGAAGCGAA | 552863 | ekk-10-kke | 70 | 1344 |
| 1588 | 1603 | TGCAGAGGTGAAGCGA | 552864 | ekk-10-kke | 73 | 1345 |

TABLE 49

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | eeeee-10-eeeee | 60 | 224 |
| 58 | 73 | TGGAGCCACCAGCAGG | 552889 | ek-10-keke | 59 | 1318 |
| 59 | 74 | CTGGAGCCACCAGCAG | 552890 | ek-10-keke | 56 | 1319 |
| 60 | 75 | ACTGGAGCCACCAGCA | 552891 | ek-10-keke | 67 | 1320 |
| 61 | 76 | AACTGGAGCCACCAGC | 552892 | ek-10-keke | 65 | 1321 |
| 62 | 77 | GAACTGGAGCCACCAG | 552893 | ek-10-keke | 68 | 86 |
| 250 | 265 | TCCACCACGAGTCTAG | 552894 | ek-10-keke | 71 | 98 |
| 251 | 266 | GTCCACCACGAGTCTA | 552895 | ek-10-keke | 51 | 100 |
| 252 | 267 | AGTCCACCACGAGTCT | 552896 | ek-10-keke | 51 | 102 |
| 253 | 268 | AAGTCCACCACGAGTC | 552897 | ek-10-keke | 43 | 104 |
| 254 | 269 | GAAGTCCACCACGAGT | 552898 | ek-10-keke | 43 | 106 |
| 255 | 270 | AGAAGTCCACCACGAG | 552899 | ek-10-keke | 55 | 109 |
| 256 | 271 | GAGAAGTCCACCACGA | 552900 | ek-10-keke | 34 | 112 |
| 258 | 273 | GAGAGAAGTCCACCAC | 552901 | ek-10-keke | 42 | 115 |
| 259 | 274 | TGAGAGAAGTCCACCA | 552902 | ek-10-keke | 60 | 117 |
| 411 | 426 | GCATAGCAGCAGGATG | 552903 | ek-10-keke | 76 | 137 |
| 412 | 427 | GGCATAGCAGCAGGAT | 552904 | ek-10-keke | 74 | 140 |
| 413 | 428 | AGGCATAGCAGCAGGA | 552905 | ek-10-keke | 66 | 143 |
| 415 | 430 | TGAGGCATAGCAGCAG | 552907 | ek-10-keke | 69 | 147 |
| 416 | 431 | ATGAGGCATAGCAGCA | 552908 | ek-10-keke | 63 | 149 |
| 417 | 432 | GATGAGGCATAGCAGC | 552909 | ek-10-keke | 70 | 151 |
| 418 | 433 | AGATGAGGCATAGCAG | 552910 | ek-10-keke | 72 | 153 |
| 457 | 472 | CGGGCAACATACCTTG | 552911 | ek-10-keke | 72 | 167 |
| 458 | 473 | ACGGGCAACATACCTT | 552912 | ek-10-keke | 67 | 168 |
| 670 | 685 | CTAGTAAACTGAGCCA | 552913 | ek-10-keke | 74 | 181 |
| 682 | 697 | GAACAAATGGCACTAG | 552914 | ek-10-keke | 75 | 1368 |
| 684 | 699 | CTGAACAAATGGCACT | 552915 | ek-10-keke | 58 | 1370 |

TABLE 49-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 686 | 701 | CACTGAACAAATGGCA | 552916 | ek-10-keke | 74 | 1372 |
| 687 | 702 | CCACTGAACAAATGGC | 552917 | ek-10-keke | 76 | 188 |
| 688 | 703 | ACCACTGAACAAATGG | 552918 | ek-10-keke | 75 | 190 |
| 689 | 704 | AACCACTGAACAAATG | 552919 | ek-10-keke | 55 | 191 |
| 690 | 705 | GAACCACTGAACAAAT | 552920 | ek-10-keke | 49 | 192 |
| 691 | 706 | CGAACCACTGAACAAA | 552921 | ek-10-keke | 45 | 194 |
| 1261 | 1276 | GCAGTATGGATCGGCA | 552922 | ek-10-keke | 83 | 211 |
| 1262 | 1277 | CGCAGTATGGATCGGC | 552923 | ek-10-keke | 83 | 1325 |
| 1263 | 1278 | CCGCAGTATGGATCGG | 552924 | ek-10-keke | 0 | 1326 |
| 1264 | 1279 | TCCGCAGTATGGATCG | 552925 | ek-10-keke | 85 | 1327 |
| 1265 | 1280 | TTCCGCAGTATGGATC | 552926 | ek-10-keke | 50 | 1328 |
| 1266 | 1281 | GTTCCGCAGTATGGAT | 552927 | ek-10-keke | 76 | 1329 |
| 1267 | 1282 | AGTTCCGCAGTATGGA | 552928 | ek-10-keke | 78 | 1330 |
| 1268 | 1283 | GAGTTCCGCAGTATGG | 552929 | ek-10-keke | 75 | 1331 |
| 1269 | 1284 | GGAGTTCCGCAGTATG | 552930 | ek-10-keke | 78 | 1332 |
| 1270 | 1285 | AGGAGTTCCGCAGTAT | 552931 | ek-10-keke | 74 | 1333 |
| 1577 | 1592 | AGCGAAGTGCACACGG | 552932 | ek-10-keke | 86 | 1334 |
| 1578 | 1593 | AAGCGAAGTGCACACG | 552933 | ek-10-keke | 82 | 1335 |
| 1579 | 1594 | GAAGCGAAGTGCACAC | 552934 | ek-10-keke | 74 | 1336 |
| 1580 | 1595 | TGAAGCGAAGTGCACA | 552935 | ek-10-keke | 76 | 1337 |
| 1581 | 1596 | GTGAAGCGAAGTGCAC | 552936 | ek-10-keke | 81 | 1338 |
| 1582 | 1597 | GGTGAAGCGAAGTGCA | 552937 | ek-10-keke | 80 | 1339 |
| 1583 | 1598 | AGGTGAAGCGAAGTGC | 552938 | ek-10-keke | 78 | 1340 |
| 1584 | 1599 | GAGGTGAAGCGAAGTG | 552939 | ek-10-keke | 75 | 1341 |
| 1585 | 1600 | AGAGGTGAAGCGAAGT | 552940 | ek-10-keke | 63 | 1342 |
| 1586 | 1601 | CAGAGGTGAAGCGAAG | 552941 | ekk-10-kke | 78 | 1343 |
| 1587 | 1602 | GCAGAGGTGAAGCGAA | 552942 | ek-10-keke | 80 | 1344 |
| 1589 | 1604 | GTGCAGAGGTGAAGCG | 552865 | ekk-10-kke | 67 | 1346 |
| 1590 | 1605 | CGTGCAGAGGTGAAGC | 552866 | ekk-10-kke | 68 | 1347 |
| 1778 | 1793 | TATGCCTACAGCCTCC | 552868 | ekk-10-kke | 55 | 230 |
| 1779 | 1794 | TTATGCCTACAGCCTC | 552869 | ekk-10-kke | 48 | 231 |
| 1780 | 1795 | TTTATGCCTACAGCCT | 552870 | ekk-10-kke | 55 | 232 |
| 1781 | 1796 | ATTTATGCCTACAGCC | 552871 | ekk-10-kke | 57 | 233 |
| 1782 | 1797 | AATTTATGCCTACAGC | 552872 | ekk-10-kke | 70 | 234 |
| 1783 | 1798 | CAATTTATGCCTACAG | 552873 | ekk-10-kke | 49 | 235 |
| 1784 | 1799 | CCAATTTATGCCTACA | 552874 | ekk-10-kke | 42 | 236 |

TABLE 49-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1785 | 1800 | ACCAATTTATGCCTAC | 552875 | ekk-10-kke | 41 | 237 |
| 1822 | 1837 | GGCAGAGGTGAAAAG | 552876 | ekk-10-kke | 50 | 244 |
| 1823 | 1838 | AGGCAGAGGTGAAAAA | 552877 | ek-10-keke | 39 | 245 |
| 1824 | 1839 | TAGGCAGAGGTGAAAA | 552878 | ekk-10-kke | 31 | 247 |
| 1865 | 1880 | AGCTTGGAGGCTTGAA | 552879 | ekk-10-kke | 5 | 252 |
| 1866 | 1881 | CAGCTTGGAGGCTTGA | 552880 | ekk-10-kke | 5 | 254 |
| 1867 | 1882 | ACAGCTTGGAGGCTTG | 552881 | ekk-10-kke | 10 | 256 |
| 1868 | 1883 | CACAGCTTGGAGGCTT | 552882 | ekk-10-kke | 11 | 258 |
| 1869 | 1884 | GCACAGCTTGGAGGCT | 552883 | ekk-10-kke | 27 | 260 |
| 1870 | 1885 | GGCACAGCTTGGAGGC | 552884 | ekk-10-kke | 36 | 262 |
| 1871 | 1886 | AGGCACAGCTTGGAGG | 552885 | ekk-10-kke | 12 | 264 |
| 1872 | 1887 | AAGGCACAGCTTGGAG | 552886 | ekk-10-kke | 32 | 266 |
| 1874 | 1889 | CCAAGGCACAGCTTGG | 552888 | ekk-10-kke | 1 | 271 |

TABLE 50

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1577 | 1596 | GTGAAGCGAAGTGCACACGG | 146786 | eeeee-10-eeeee | 59 | 224 |
| 58 | 73 | TGGAGCCACCAGCAGG | 552955 | eee-10-kkk | 60 | 1318 |
| 59 | 74 | CTGGAGCCACCAGCAG | 552956 | eee-10-kkk | 60 | 1319 |
| 60 | 75 | ACTGGAGCCACCAGCA | 552957 | eee-10-kkk | 64 | 1320 |
| 61 | 76 | AACTGGAGCCACCAGC | 552958 | eee-10-kkk | 56 | 1321 |
| 62 | 77 | GAACTGGAGCCACCAG | 552959 | eee-10-kkk | 59 | 86 |
| 250 | 265 | TCCACCACGAGTCTAG | 552960 | eee-10-kkk | 42 | 98 |
| 251 | 266 | GTCCACCACGAGTCTA | 552961 | eee-10-kkk | 41 | 100 |
| 252 | 267 | AGTCCACCACGAGTCT | 552962 | eee-10-kkk | 35 | 102 |
| 253 | 268 | AAGTCCACCACGAGTC | 552963 | eee-10-kkk | 19 | 104 |
| 254 | 269 | GAAGTCCACCACGAGT | 552964 | eee-10-kkk | 34 | 106 |
| 255 | 270 | AGAAGTCCACCACGAG | 552965 | eee-10-kkk | 42 | 109 |
| 256 | 271 | GAGAAGTCCACCACGA | 552966 | eee-10-kkk | 60 | 112 |
| 258 | 273 | GAGAGAAGTCCACCAC | 552967 | eee-10-kkk | 38 | 115 |
| 259 | 274 | TGAGAGAAGTCCACCA | 552968 | eee-10-kkk | 35 | 117 |
| 411 | 426 | GCATAGCAGCAGGATG | 552969 | eee-10-kkk | 67 | 137 |
| 412 | 427 | GGCATAGCAGCAGGAT | 552970 | eee-10-kkk | 56 | 140 |

TABLE 50-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 413 | 428 | AGGCATAGCAGCAGGA | 552971 | eee-10-kkk | 69 | 143 |
| 414 | 429 | GAGGCATAGCAGCAGG | 552972 | eee-10-kkk | 75 | 145 |
| 415 | 430 | TGAGGCATAGCAGCAG | 552973 | eee-10-kkk | 59 | 145 |
| 416 | 431 | ATGAGGCATAGCAGCA | 552974 | eee-10-kkk | 71 | 149 |
| 417 | 432 | GATGAGGCATAGCAGC | 552975 | eee-10-kkk | 56 | 151 |
| 418 | 433 | AGATGAGGCATAGCAG | 552976 | eee-10-kkk | 50 | 153 |
| 457 | 472 | CGGGCAACATACCTTG | 552977 | eee-10-kkk | 56 | 167 |
| 458 | 473 | ACGGGCAACATACCTT | 552978 | eee-10-kkk | 43 | 168 |
| 670 | 685 | CTAGTAAACTGAGCCA | 552979 | eee-10-kkk | 71 | 181 |
| 682 | 697 | GAACAAATGGCACTAG | 552980 | eee-10-kkk | 80 | 1368 |
| 684 | 699 | CTGAACAAATGGCACT | 552981 | eee-10-kkk | 64 | 1370 |
| 686 | 701 | CACTGAACAAATGGCA | 552982 | ek-10-keke | 61 | 1372 |
| 687 | 702 | CCACTGAACAAATGGC | 552983 | eee-10-kkk | 77 | 188 |
| 688 | 703 | ACCACTGAACAAATGG | 552984 | eee-10-kkk | 65 | 190 |
| 689 | 704 | AACCACTGAACAAATG | 552985 | eee-10-kkk | 41 | 191 |
| 690 | 705 | GAACCACTGAACAAAT | 552986 | eee-10-kkk | 30 | 192 |
| 691 | 706 | CGAACCACTGAACAAA | 552987 | eee-10-kkk | 41 | 194 |
| 1261 | 1276 | GCAGTATGGATCGGCA | 552988 | eee-10-kkk | 74 | 211 |
| 1262 | 1277 | CGCAGTATGGATCGGC | 552989 | eee-10-kkk | 85 | 1325 |
| 1263 | 1278 | CCGCAGTATGGATCGG | 552990 | eee-10-kkk | 72 | 1326 |
| 1264 | 1279 | TCCGCAGTATGGATCG | 552991 | eee-10-kkk | 73 | 1327 |
| 1265 | 1280 | TTCCGCAGTATGGATC | 552992 | eee-10-kkk | 60 | 1328 |
| 1266 | 1281 | GTTCCGCAGTATGGAT | 552993 | eee-10-kkk | 52 | 1329 |
| 1267 | 1282 | AGTTCCGCAGTATGGA | 552994 | eee-10-kkk | 58 | 1330 |
| 1268 | 1283 | GAGTTCCGCAGTATGG | 552995 | eee-10-kkk | 70 | 1331 |
| 1269 | 1284 | GGAGTTCCGCAGTATG | 552996 | eee-10-kkk | 74 | 1332 |
| 1270 | 1285 | AGGAGTTCCGCAGTAT | 552997 | eee-10-kkk | 59 | 1333 |
| 1577 | 1592 | AGCGAAGTGCACACGG | 552998 | eee-10-kkk | 82 | 1334 |
| 1578 | 1593 | AAGCGAAGTGCACACG | 552999 | eee-10-kkk | 70 | 1335 |
| 1579 | 1594 | GAAGCGAAGTGCACAC | 553000 | eee-10-kkk | 67 | 1336 |
| 1580 | 1595 | TGAAGCGAAGTGCACA | 553001 | eee-10-kkk | 67 | 1337 |
| 1581 | 1596 | GTGAAGCGAAGTGCAC | 553002 | eee-10-kkk | 74 | 1338 |
| 1582 | 1597 | GGTGAAGCGAAGTGCA | 553003 | eee-10-kkk | 72 | 1339 |
| 1583 | 1598 | AGGTGAAGCGAAGTGC | 553004 | eee-10-kkk | 73 | 1340 |
| 1584 | 1599 | GAGGTGAAGCGAAGTG | 553005 | eee-10-kkk | 67 | 1341 |
| 1585 | 1600 | AGAGGTGAAGCGAAGT | 553006 | eee-10-kkk | 69 | 1342 |

TABLE 50-continued

Inhibition of viral HBV mRNA levels by chimeric antisense oligonucleotides measured with RTS3371

| Viral Target Start Site | Viral Target Stop Site | Sequence | ISIS No | Motif | % inhibition | SEQ ID NO |
|---|---|---|---|---|---|---|
| 1586 | 1601 | CAGAGGTGAAGCGAAG | 553007 | eee-10-kkk | 60 | 1343 |
| 1587 | 1602 | GCAGAGGTGAAGCGAA | 553008 | eee-10-kkk | 71 | 1344 |
| 1588 | 1603 | TGCAGAGGTGAAGCGA | 552943 | ek-10-keke | 77 | 1345 |
| 1588 | 1603 | TGCAGAGGTGAAGCGA | 553009 | eee-10-kkk | 78 | 1345 |
| 1589 | 1604 | GTGCAGAGGTGAAGCG | 552944 | ek-10-keke | 74 | 1346 |
| 1589 | 1604 | GTGCAGAGGTGAAGCG | 553010 | eee-10-kkk | 78 | 1346 |
| 1590 | 1605 | CGTGCAGAGGTGAAGC | 552945 | ek-10-keke | 76 | 1347 |
| 1590 | 1605 | CGTGCAGAGGTGAAGC | 553011 | eee-10-kkk | 72 | 1347 |
| 1591 | 1606 | ACGTGCAGAGGTGAAG | 552946 | ek-10-keke | 71 | 1348 |
| 1591 | 1606 | ACGTGCAGAGGTGAAG | 553012 | eee-10-kkk | 74 | 1348 |
| 1778 | 1793 | TATGCCTACAGCCTCC | 552947 | ek-10-keke | 54 | 230 |
| 1778 | 1793 | TATGCCTACAGCCTCC | 553013 | eee-10-kkk | 39 | 230 |
| 1779 | 1794 | TTATGCCTACAGCCTC | 552948 | ek-10-keke | 50 | 231 |
| 1779 | 1794 | TTATGCCTACAGCCTC | 553014 | eee-10-kkk | 37 | 231 |
| 1780 | 1795 | TTTATGCCTACAGCCT | 552949 | ek-10-keke | 8 | 232 |
| 1780 | 1795 | TTTATGCCTACAGCCT | 553015 | eee-10-kkk | 45 | 232 |
| 1781 | 1796 | ATTTATGCCTACAGCC | 552950 | ek-10-keke | 44 | 233 |
| 1781 | 1796 | ATTTATGCCTACAGCC | 553016 | eee-10-kkk | 47 | 233 |
| 1782 | 1797 | AATTTATGCCTACAGC | 552951 | ek-10-keke | 60 | 234 |
| 1782 | 1797 | AATTTATGCCTACAGC | 553017 | eee-10-kkk | 47 | 234 |
| 1783 | 1798 | CAATTTATGCCTACAG | 552952 | ek-10-keke | 35 | 235 |
| 1783 | 1798 | CAATTTATGCCTACAG | 553018 | eee-10-kkk | 30 | 235 |
| 1784 | 1799 | CCAATTTATGCCTACA | 552953 | ek-10-keke | 37 | 236 |
| 1784 | 1799 | CCAATTTATGCCTACA | 553019 | eee-10-kkk | 37 | 236 |
| 1785 | 1800 | ACCAATTTATGCCTAC | 552954 | ek-10-keke | 40 | 237 |
| 1785 | 1800 | ACCAATTTATGCCTAC | 553020 | eee-10-kkk | 24 | 237 |

TABLE 51

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 58 | 73 | TGGAGCCACCAGCAGG | 552889 | ek-10-keke | 42 | 1318 |
| 59 | 74 | CTGGAGCCACCAGCAG | 552890 | ek-10-keke | 56 | 1319 |
| 60 | 75 | ACTGGAGCCACCAGCA | 552891 | ek-10-keke | 55 | 1320 |

TABLE 51-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 61 | 76 | AACTGGAGCCACCAGC | 552892 | ek-10-keke | 53 | 1321 |
| 62 | 77 | GAACTGGAGCCACCAG | 552893 | ek-10-keke | 56 | 86 |
| 250 | 265 | TCCACCACGAGTCTAG | 552894 | ek-10-keke | 53 | 98 |
| 251 | 266 | GTCCACCACGAGTCTA | 552895 | ek-10-keke | 38 | 100 |
| 252 | 267 | AGTCCACCACGAGTCT | 552896 | ek-10-keke | 43 | 102 |
| 253 | 268 | AAGTCCACCACGAGTC | 552897 | ek-10-keke | 40 | 104 |
| 254 | 269 | GAAGTCCACCACGAGT | 552898 | ek-10-keke | 50 | 106 |
| 255 | 270 | AGAAGTCCACCACGAG | 552899 | ek-10-keke | 37 | 109 |
| 256 | 271 | GAGAAGTCCACCACGA | 552900 | ek-10-keke | 43 | 112 |
| 258 | 273 | GAGAGAAGTCCACCAC | 552901 | ek-10-keke | 56 | 115 |
| 259 | 274 | TGAGAGAAGTCCACCA | 552902 | ek-10-keke | 43 | 117 |
| 411 | 426 | GCATAGCAGCAGGATG | 552903 | ek-10-keke | 78 | 137 |
| 412 | 427 | GGCATAGCAGCAGGAT | 552904 | ek-10-keke | 75 | 140 |
| 413 | 428 | AGGCATAGCAGCAGGA | 552905 | ek-10-keke | 52 | 143 |
| 415 | 430 | TGAGGCATAGCAGCAG | 552907 | ek-10-keke | 75 | 147 |
| 416 | 431 | ATGAGGCATAGCAGCA | 552908 | ek-10-keke | 57 | 149 |
| 417 | 432 | GATGAGGCATAGCAGC | 552909 | ek-10-keke | 66 | 151 |
| 418 | 433 | AGATGAGGCATAGCAG | 552910 | ek-10-keke | 60 | 153 |
| 457 | 472 | CGGGCAACATACCTTG | 552911 | ek-10-keke | 65 | 167 |
| 458 | 473 | ACGGGCAACATACCTT | 552912 | ek-10-keke | 37 | 168 |
| 670 | 685 | CTAGTAAACTGAGCCA | 552913 | ek-10-keke | 76 | 181 |
| 682 | 697 | GAACAAATGGCACTAG | 552914 | ek-10-keke | 79 | 1368 |
| 684 | 699 | CTGAACAAATGGCACT | 552915 | ek-10-keke | 71 | 1370 |
| 686 | 701 | CACTGAACAAATGGCA | 552916 | ek-10-keke | 82 | 1372 |
| 687 | 702 | CCACTGAACAAATGGC | 552917 | ek-10-keke | 78 | 188 |
| 688 | 703 | ACCACTGAACAAATGG | 552918 | ek-10-keke | 64 | 190 |
| 689 | 704 | AACCACTGAACAAATG | 552919 | ek-10-keke | 38 | 191 |
| 690 | 705 | GAACCACTGAACAAAT | 552920 | ek-10-keke | 43 | 192 |
| 691 | 706 | CGAACCACTGAACAAA | 552921 | ek-10-keke | 49 | 194 |
| 1261 | 1276 | GCAGTATGGATCGGCA | 552922 | ek-10-keke | 90 | 211 |
| 1262 | 1277 | CGCAGTATGGATCGGC | 552923 | ek-10-keke | 92 | 1325 |
| 1263 | 1278 | CCGCAGTATGGATCGG | 552924 | ek-10-keke | 30 | 1326 |
| 1264 | 1279 | TCCGCAGTATGGATCG | 552925 | ek-10-keke | 81 | 1327 |
| 1265 | 1280 | TTCCGCAGTATGGATC | 552926 | ek-10-keke | 39 | 1328 |
| 1266 | 1281 | GTTCCGCAGTATGGAT | 552927 | ek-10-keke | 53 | 1329 |
| 1267 | 1282 | AGTTCCGCAGTATGGA | 552928 | ek-10-keke | 48 | 1330 |

TABLE 51-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1268 | 1283 | GAGTTCCGCAGTATGG | 552929 | ek-10-keke | 68 | 1331 |
| 1269 | 1284 | GGAGTTCCGCAGTATG | 552930 | ek-10-keke | 87 | 1332 |
| 1270 | 1285 | AGGAGTTCCGCAGTAT | 552931 | ek-10-keke | 87 | 1333 |
| 1577 | 1592 | AGCGAAGTGCACACGG | 552932 | ek-10-keke | 88 | 1334 |
| 1578 | 1593 | AAGCGAAGTGCACACG | 552933 | ek-10-keke | 75 | 1335 |
| 1579 | 1594 | GAAGCGAAGTGCACAC | 552934 | ek-10-keke | 76 | 1336 |
| 1580 | 1595 | TGAAGCGAAGTGCACA | 552935 | ek-10-keke | 71 | 1337 |
| 1581 | 1596 | GTGAAGCGAAGTGCAC | 552936 | ek-10-keke | 80 | 1338 |
| 1582 | 1597 | GGTGAAGCGAAGTGCA | 552937 | ek-10-keke | 81 | 1339 |
| 1583 | 1598 | AGGTGAAGCGAAGTGC | 552938 | ek-10-keke | 85 | 1340 |
| 1584 | 1599 | GAGGTGAAGCGAAGTG | 552939 | ek-10-keke | 82 | 1341 |
| 1585 | 1600 | AGAGGTGAAGCGAAGT | 552940 | ek-10-keke | 76 | 1342 |
| 1586 | 1601 | CAGAGGTGAAGCGAAG | 552941 | ekk-10-kke | 72 | 1343 |
| 1587 | 1602 | GCAGAGGTGAAGCGAA | 552942 | ek-10-keke | 85 | 1344 |
| 1589 | 1604 | GTGCAGAGGTGAAGCG | 552865 | ekk-10-kke | 70 | 1346 |
| 1590 | 1605 | CGTGCAGAGGTGAAGC | 552866 | ekk-10-kke | 65 | 1347 |
| 1778 | 1793 | TATGCCTACAGCCTCC | 552868 | ekk-10-kke | 36 | 230 |
| 1779 | 1794 | TTATGCCTACAGCCTC | 552869 | ekk-10-kke | 23 | 231 |
| 1780 | 1795 | TTTATGCCTACAGCCT | 552870 | ekk-10-kke | 49 | 232 |
| 1781 | 1796 | ATTTATGCCTACAGCC | 552871 | ekk-10-kke | 46 | 233 |
| 1782 | 1797 | AATTTATGCCTACAGC | 552872 | ekk-10-kke | 73 | 234 |
| 1783 | 1798 | CAATTTATGCCTACAG | 552873 | ekk-10-kke | 41 | 235 |
| 1784 | 1799 | CCAATTTATGCCTACA | 552874 | ekk-10-kke | 18 | 236 |
| 1785 | 1800 | ACCAATTTATGCCTAC | 552875 | ekk-10-kke | 0 | 237 |
| 1822 | 1837 | GGCAGAGGTGAAAAAG | 552876 | ekk-10-kke | 49 | 244 |
| 1823 | 1838 | AGGCAGAGGTGAAAAA | 552877 | ek-10-keke | 37 | 245 |
| 1824 | 1839 | TAGGCAGAGGTGAAAA | 552878 | ekk-10-kke | 28 | 247 |
| 1865 | 1880 | AGCTTGGAGGCTTGAA | 552879 | ekk-10-kke | 0 | 252 |
| 1866 | 1881 | CAGCTTGGAGGCTTGA | 552880 | ekk-10-kke | 12 | 254 |
| 1867 | 1882 | ACAGCTTGGAGGCTTG | 552881 | ekk-10-kke | 0 | 256 |
| 1868 | 1883 | CACAGCTTGGAGGCTT | 552882 | ekk-10-kke | 0 | 258 |
| 1869 | 1884 | GCACAGCTTGGAGGCT | 552883 | ekk-10-kke | 12 | 260 |
| 1870 | 1885 | GGCACAGCTTGGAGGC | 552884 | ekk-10-kke | 39 | 262 |
| 1871 | 1886 | AGGCACAGCTTGGAGG | 552885 | ekk-10-kke | 37 | 264 |
| 1872 | 1887 | AAGGCACAGCTTGGAG | 552886 | ekk-10-kke | 15 | 266 |
| 1874 | 1889 | CCAAGGCACAGCTTGG | 552888 | ekk-10-kke | 0 | 271 |

TABLE 52

Inhibition of viral HBV mRNA levels by chimeric antisense
oligonucleotides measured with RTS3370

| Viral Target Start Site | Viral Target Stop Site | Sequence | ISIS No | Motif | % inhibition | SEQ ID NO |
|---|---|---|---|---|---|---|
| 58 | 73 | TGGAGCCACCAGCAGG | 552955 | eee-10-kkk | 67 | 1318 |
| 59 | 74 | CTGGAGCCACCAGCAG | 552956 | eee-10-kkk | 60 | 1319 |
| 60 | 75 | ACTGGAGCCACCAGCA | 552957 | eee-10-kkk | 73 | 1320 |
| 61 | 76 | AACTGGAGCCACCAGC | 552958 | eee-10-kkk | 63 | 1321 |
| 62 | 77 | GAACTGGAGCCACCAG | 552959 | eee-10-kkk | 58 | 86 |
| 250 | 265 | TCCACCACGAGTCTAG | 552960 | eee-10-kkk | 67 | 98 |
| 251 | 266 | GTCCACCACGAGTCTA | 552961 | eee-10-kkk | 78 | 100 |
| 252 | 267 | AGTCCACCACGAGTCT | 552962 | eee-10-kkk | 29 | 102 |
| 253 | 268 | AAGTCCACCACGAGTC | 552963 | eee-10-kkk | 25 | 104 |
| 254 | 269 | GAAGTCCACCACGAGT | 552964 | eee-10-kkk | 33 | 106 |
| 255 | 270 | AGAAGTCCACCACGAG | 552965 | eee-10-kkk | 55 | 109 |
| 256 | 271 | GAGAAGTCCACCACGA | 552966 | eee-10-kkk | 71 | 112 |
| 258 | 273 | GAGAGAAGTCCACCAC | 552967 | eee-10-kkk | 23 | 115 |
| 259 | 274 | TGAGAGAAGTCCACCA | 552968 | eee-10-kkk | 41 | 117 |
| 411 | 426 | GCATAGCAGCAGGATG | 552969 | eee-10-kkk | 76 | 137 |
| 412 | 427 | GGCATAGCAGCAGGAT | 552970 | eee-10-kkk | 44 | 140 |
| 413 | 428 | AGGCATAGCAGCAGGA | 552971 | eee-10-kkk | 77 | 143 |
| 414 | 429 | GAGGCATAGCAGCAGG | 552972 | eee-10-kkk | 74 | 145 |
| 415 | 430 | TGAGGCATAGCAGCAG | 552973 | eee-10-kkk | 61 | 145 |
| 416 | 431 | ATGAGGCATAGCAGCA | 552974 | eee-10-kkk | 73 | 149 |
| 417 | 432 | GATGAGGCATAGCAGC | 552975 | eee-10-kkk | 66 | 151 |
| 418 | 433 | AGATGAGGCATAGCAG | 552976 | eee-10-kkk | 70 | 153 |
| 457 | 472 | CGGGCAACATACCTTG | 552977 | eee-10-kkk | 65 | 167 |
| 458 | 473 | ACGGGCAACATACCTT | 552978 | eee-10-kkk | 40 | 168 |
| 670 | 685 | CTAGTAAACTGAGCCA | 552979 | eee-10-kkk | 79 | 181 |
| 682 | 697 | GAACAAATGGCACTAG | 552980 | eee-10-kkk | 81 | 64 |
| 684 | 699 | CTGAACAAATGGCACT | 552981 | eee-10-kkk | 74 | 66 |
| 686 | 701 | CACTGAACAAATGGCA | 552982 | ek-10-keke | 52 | 68 |
| 687 | 702 | CCACTGAACAAATGGC | 552983 | eee-10-kkk | 78 | 188 |
| 688 | 703 | ACCACTGAACAAATGG | 552984 | eee-10-kkk | 71 | 190 |
| 689 | 704 | AACCACTGAACAAATG | 552985 | eee-10-kkk | 38 | 191 |
| 690 | 705 | GAACCACTGAACAAAT | 552986 | eee-10-kkk | 48 | 192 |
| 691 | 706 | CGAACCACTGAACAAA | 552987 | eee-10-kkk | 54 | 194 |
| 1261 | 1276 | GCAGTATGGATCGGCA | 552988 | eee-10-kkk | 85 | 211 |
| 1262 | 1277 | CGCAGTATGGATCGGC | 552989 | eee-10-kkk | 84 | 1325 |
| 1263 | 1278 | CCGCAGTATGGATCGG | 552990 | eee-10-kkk | 79 | 1326 |

TABLE 52-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1264 | 1279 | TCCGCAGTATGGATCG | 552991 | eee-10-kkk | 53 | 1327 |
| 1265 | 1280 | TTCCGCAGTATGGATC | 552992 | eee-10-kkk | 68 | 1328 |
| 1266 | 1281 | GTTCCGCAGTATGGAT | 552993 | eee-10-kkk | 67 | 1329 |
| 1267 | 1282 | AGTTCCGCAGTATGGA | 552994 | eee-10-kkk | 69 | 1330 |
| 1268 | 1283 | GAGTTCCGCAGTATGG | 552995 | eee-10-kkk | 62 | 1331 |
| 1269 | 1284 | GGAGTTCCGCAGTATG | 552996 | eee-10-kkk | 82 | 1332 |
| 1270 | 1285 | AGGAGTTCCGCAGTAT | 552997 | eee-10-kkk | 58 | 1333 |
| 1577 | 1592 | AGCGAAGTGCACACGG | 552998 | eee-10-kkk | 86 | 1334 |
| 1578 | 1593 | AAGCGAAGTGCACACG | 552999 | eee-10-kkk | 63 | 1335 |
| 1579 | 1594 | GAAGCGAAGTGCACAC | 553000 | eee-10-kkk | 67 | 1336 |
| 1580 | 1595 | TGAAGCGAAGTGCACA | 553001 | eee-10-kkk | 70 | 1337 |
| 1581 | 1596 | GTGAAGCGAAGTGCAC | 553002 | eee-10-kkk | 84 | 1338 |
| 1582 | 1597 | GGTGAAGCGAAGTGCA | 553003 | eee-10-kkk | 83 | 1339 |
| 1583 | 1598 | AGGTGAAGCGAAGTGC | 553004 | eee-10-kkk | 68 | 1340 |
| 1584 | 1599 | GAGGTGAAGCGAAGTG | 553005 | eee-10-kkk | 57 | 1341 |
| 1585 | 1600 | AGAGGTGAAGCGAAGT | 553006 | eee-10-kkk | 74 | 1342 |
| 1586 | 1601 | CAGAGGTGAAGCGAAG | 553007 | eee-10-kkk | 62 | 1343 |
| 1587 | 1602 | GCAGAGGTGAAGCGAA | 553008 | eee-10-kkk | 50 | 1344 |
| 1588 | 1603 | TGCAGAGGTGAAGCGA | 552943 | ek-10-keke | 86 | 1345 |
| 1588 | 1603 | TGCAGAGGTGAAGCGA | 553009 | eee-10-kkk | 79 | 1345 |
| 1589 | 1604 | GTGCAGAGGTGAAGCG | 552944 | ek-10-keke | 83 | 1346 |
| 1589 | 1604 | GTGCAGAGGTGAAGCG | 553010 | eee-10-kkk | 74 | 1346 |
| 1590 | 1605 | CGTGCAGAGGTGAAGC | 552945 | ek-10-keke | 79 | 1347 |
| 1590 | 1605 | CGTGCAGAGGTGAAGC | 553011 | eee-10-kkk | 60 | 1347 |
| 1591 | 1606 | ACGTGCAGAGGTGAAG | 552946 | ek-10-keke | 68 | 1348 |
| 1591 | 1606 | ACGTGCAGAGGTGAAG | 553012 | eee-10-kkk | 78 | 1348 |
| 1778 | 1793 | TATGCCTACAGCCTCC | 552947 | ek-10-keke | 51 | 230 |
| 1778 | 1793 | TATGCCTACAGCCTCC | 553013 | eee-10-kkk | 45 | 230 |
| 1779 | 1794 | TTATGCCTACAGCCTC | 552948 | ek-10-keke | 56 | 231 |
| 1779 | 1794 | TTATGCCTACAGCCTC | 553014 | eee-10-kkk | 53 | 231 |
| 1780 | 1795 | TTTATGCCTACAGCCT | 552949 | ek-10-keke | 1 | 232 |
| 1780 | 1795 | TTTATGCCTACAGCCT | 553015 | eee-10-kkk | 55 | 232 |
| 1781 | 1796 | ATTTATGCCTACAGCC | 552950 | ek-10-keke | 52 | 233 |
| 1781 | 1796 | ATTTATGCCTACAGCC | 553016 | eee-10-kkk | 65 | 233 |
| 1782 | 1797 | AATTTATGCCTACAGC | 552951 | ek-10-keke | 59 | 234 |
| 1782 | 1797 | AATTTATGCCTACAGC | 553017 | eee-10-kkk | 36 | 234 |

TABLE 52-continued

Inhibition of viral HBV mRNA levels by chimeric antisense oligonucleotides measured with RTS3370

| Viral Target Start Site | Viral Target Stop Site | Sequence | ISIS No | Motif | % inhibition | SEQ ID NO |
|---|---|---|---|---|---|---|
| 1783 | 1798 | CAATTTATGCCTACAG | 552952 | ek-10-keke | 34 | 235 |
| 1783 | 1798 | CAATTTATGCCTACAG | 553018 | eee-10-kkk | 20 | 235 |
| 1784 | 1799 | CCAATTTATGCCTACA | 552953 | ek-10-keke | 55 | 236 |
| 1784 | 1799 | CCAATTTATGCCTACA | 553019 | eee-10-kkk | 34 | 236 |
| 1785 | 1800 | ACCAATTTATGCCTAC | 552954 | ek-10-keke | 51 | 237 |
| 1785 | 1800 | ACCAATTTATGCCTAC | 553020 | eee-10-kkk | 28 | 237 |

Example 16

Dose-Dependent Antisense Inhibition of HBV mRNA in HepG2 Cells by MOE Gapmers Antisense oligonucleotides from the study described in Example 14 exhibiting in vitro inhibition of HBV mRNA were selected and tested at various doses in HepG2 cells. Cells were plated at a density of 28,000 cells per well and transfected using LipofectAMINE2000® with 9.26 nM, 27.78 nM, 83.33 nM, and 250.00 nM concentrations of antisense oligonucleotide, as specified in Table 53. After a treatment period of approximately 16 hours, RNA was isolated from the cells and HBV mRNA levels were measured by quantitative real-time PCR. HBV primer probe set RTS3371 was used to measure mRNA levels. HBV mRNA levels were adjusted according to total RNA content, as measured by RIBOGREEN®. Results are presented as percent inhibition of HBV, relative to untreated control cells.

As illustrated in Table 53, HBV mRNA levels were reduced in a dose-dependent manner in antisense oligonucleotide treated cells. 'n/a' indicates that the data for that dosage is not available.

TABLE 53

Dose-dependent antisense inhibition of human HBV in HepG2 cells

| ISIS No | 9.2593 nM | 27.7778 nM | 83.3333 nM | 250.0 nM |
|---|---|---|---|---|
| 146786 | 10 | 43 | 74 | 89 |
| 509934 | 12 | 31 | 52 | 79 |
| 509959 | 4 | 24 | 49 | 67 |
| 510100 | 11 | 28 | 60 | 77 |
| 510124 | 3 | 11 | 13 | 41 |
| 551926 | 1 | 26 | 51 | 76 |
| 551958 | 15 | 17 | 56 | 82 |
| 551987 | 4 | 40 | 65 | 81 |
| 551990 | 7 | 55 | 78 | 91 |
| 551993 | 15 | 30 | 70 | 80 |
| 551994 | 0 | 30 | 39 | 58 |
| 551995 | 6 | 41 | 73 | 85 |
| 551996 | 13 | 47 | 71 | 85 |
| 551997 | 16 | 38 | 68 | 89 |
| 551998 | 4 | 36 | 69 | 85 |
| 551999 | 10 | 31 | 67 | 86 |
| 552000 | 0 | 17 | 61 | 78 |
| 552006 | 6 | 37 | 74 | 89 |
| 552009 | 1 | 5 | 39 | 60 |
| 552013 | 0 | 28 | 3 | 72 |
| 552014 | 0 | 26 | 32 | 77 |
| 552018 | 6 | 27 | 63 | 81 |
| 552019 | 15 | 34 | 65 | 90 |
| 552020 | 2 | 35 | 65 | 91 |
| 552021 | 4 | 11 | 53 | 82 |
| 552022 | 6 | 35 | 57 | 79 |
| 552023 | 11 | 33 | 59 | 81 |
| 552024 | 15 | 43 | 69 | 91 |
| 552025 | 17 | 35 | 69 | 87 |
| 552026 | 14 | 26 | 66 | 86 |
| 552027 | 3 | 46 | 62 | 88 |
| 552028 | 9 | 43 | 58 | 78 |
| 552029 | 8 | 40 | 72 | 89 |
| 552030 | 18 | 48 | 77 | 92 |
| 552031 | 0 | 38 | 66 | 89 |
| 552032 | 42 | 48 | 80 | 88 |
| 552033 | 2 | 40 | 64 | 84 |
| 552034 | 6 | 40 | 70 | 81 |
| 552039 | 2 | 33 | 56 | 83 |
| 552044 | 19 | 30 | 63 | 84 |
| 552046 | 4 | 21 | 47 | 77 |
| 552050 | 15 | 44 | 70 | 92 |
| 552051 | 8 | 33 | 69 | 90 |
| 552052 | 17 | 38 | 71 | 91 |
| 552053 | 0 | 40 | 59 | 86 |
| 552054 | 7 | 15 | 58 | 75 |
| 552056 | 19 | 62 | 86 | 92 |
| 552057 | 11 | 33 | 69 | 86 |
| 552058 | 30 | 55 | 79 | 90 |
| 552059 | 11 | 25 | 69 | 90 |
| 552060 | 9 | 32 | 61 | 86 |
| 552061 | 6 | 40 | 69 | 88 |
| 552062 | 22 | 48 | 75 | 89 |
| 552064 | 23 | 49 | 69 | 90 |
| 552065 | 10 | 8 | 69 | 86 |
| 552069 | 11 | 4 | 28 | 60 |
| 552073 | 9 | 31 | 62 | 78 |
| 552075 | 21 | 18 | 33 | 65 |
| 552077 | 0 | 17 | 40 | 72 |
| 552079 | 1 | 12 | 44 | 70 |
| 552080 | 3 | 12 | 34 | 69 |
| 552082 | 13 | 29 | 66 | 87 |
| 552083 | 24 | 54 | 69 | 88 |
| 552084 | 10 | 25 | 48 | 82 |
| 552085 | 28 | 35 | 64 | 85 |
| 552086 | 0 | 24 | 65 | 84 |
| 552088 | 33 | 53 | 77 | 93 |
| 552089 | 0 | 41 | 69 | 92 |
| 552090 | 17 | 35 | 70 | 87 |
| 552091 | 13 | 31 | 69 | 89 |
| 552092 | 6 | 23 | 66 | 89 |

TABLE 53-continued

Dose-dependent antisense inhibition of human HBV in HepG2 cells

| ISIS No | 9.2593 nM | 27.7778 nM | 83.3333 nM | 250.0 nM |
|---|---|---|---|---|
| 552093 | 0 | 17 | 61 | 89 |
| 552094 | 12 | 38 | 65 | 88 |
| 552095 | 20 | 42 | 73 | 88 |
| 552096 | n/a | 39 | 66 | 91 |
| 552097 | 24 | 43 | 67 | 88 |
| 552098 | 0 | 24 | 56 | 85 |
| 552101 | 3 | 13 | 28 | 61 |
| 552147 | 11 | 27 | 58 | 80 |
| 552160 | 20 | 25 | 69 | 89 |
| 552163 | 0 | 21 | 22 | 53 |
| 552176 | 16 | 11 | 40 | 66 |
| 552192 | 7 | 38 | 78 | 89 |
| 552222 | 0 | 24 | 65 | 79 |
| 552247 | 0 | 38 | 69 | 86 |
| 552255 | 5 | 27 | 69 | 81 |
| 552301 | 5 | 38 | 65 | 86 |
| 552309 | 8 | 26 | 62 | 85 |
| 552312 | 0 | 4 | 32 | 62 |
| 552347 | 2 | 15 | 38 | 75 |
| 552348 | 12 | 40 | 42 | 65 |
| 552354 | 10 | 35 | 44 | 76 |
| 552361 | 2 | 25 | 55 | 74 |
| 552363 | 20 | 36 | 54 | 76 |
| 552374 | 7 | 4 | 38 | 76 |
| 552379 | 0 | 12 | 24 | 46 |
| 552403 | 8 | 27 | 54 | 76 |
| 552408 | 2 | 25 | 44 | 77 |
| 552409 | 6 | 31 | 56 | 80 |
| 552418 | 0 | 30 | 72 | 84 |
| 552420 | 9 | 34 | 53 | 81 |
| 552442 | 4 | 23 | 46 | 56 |
| 552466 | 0 | 23 | 56 | 79 |
| 552474 | 11 | 34 | 66 | 87 |
| 552477 | 11 | 22 | 44 | 64 |
| 552530 | 25 | 37 | 73 | 87 |
| 552559 | 9 | 13 | 29 | 51 |

Example 17

Dose-Dependent Antisense Inhibition of HBV mRNA in HepG2 Cells by Deoxy, MOE and (S)-cEt Gapmers Antisense oligonucleotides from the study described in Example 15 exhibiting in vitro inhibition of HBV mRNA were selected and tested at various doses in HepG2 cells. Cells were plated at a density of 28,000 cells per well and transfected using LipofectAMINE2000® with 9.26 nM, 27.78 nM, 83.33 nM, and 250.00 nM concentrations of antisense oligonucleotide, as specified in Table 54. After a treatment period of approximately 16 hours, RNA was isolated from the cells and HBV mRNA levels were measured by quantitative real-time PCR. HBV primer probe set RTS3371 was used to measure mRNA levels. HBV mRNA levels were adjusted according to total RNA content, as measured by RIBOGREEN®. Results are presented as percent inhibition of HBV, relative to untreated control cells.

As illustrated in Table 54, HBV mRNA levels were reduced in a dose-dependent manner in antisense oligonucleotide treated cells.

TABLE 54

Dose-dependent antisense inhibition of human HBV in HepG2 cells

| ISIS No | 9.2593 nM | 27.7778 nM | 83.3333 nM | 250.0 nM |
|---|---|---|---|---|
| 146786 | 10 | 43 | 74 | 89 |
| 552808 | 13 | 14 | 55 | 70 |
| 552816 | 38 | 73 | 87 | 92 |
| 552818 | 29 | 63 | 87 | 85 |
| 552820 | 58 | 83 | 90 | 90 |
| 552821 | 33 | 49 | 71 | 88 |
| 552822 | 24 | 55 | 74 | 88 |
| 552824 | 8 | 24 | 65 | 87 |
| 552834 | 11 | 28 | 68 | 89 |
| 552849 | 12 | 25 | 73 | 84 |
| 552851 | 13 | 42 | 74 | 89 |
| 552852 | 4 | 35 | 70 | 87 |
| 552853 | 19 | 52 | 86 | 93 |
| 552854 | 28 | 57 | 80 | 89 |
| 552916 | 5 | 26 | 64 | 82 |
| 552922 | 25 | 44 | 77 | 89 |
| 552923 | 22 | 49 | 82 | 91 |
| 552925 | 33 | 56 | 80 | 92 |
| 552930 | 12 | 49 | 79 | 89 |
| 552931 | 12 | 40 | 62 | 82 |
| 552932 | 24 | 62 | 84 | 91 |
| 552933 | 20 | 40 | 75 | 89 |
| 552936 | 18 | 36 | 75 | 88 |
| 552937 | 22 | 51 | 82 | 88 |
| 552938 | 12 | 36 | 67 | 80 |
| 552939 | 17 | 40 | 65 | 79 |
| 552942 | 21 | 48 | 74 | 88 |
| 552943 | 5 | 39 | 70 | 85 |
| 552944 | 14 | 33 | 70 | 77 |
| 552980 | 15 | 40 | 69 | 86 |
| 552988 | 4 | 36 | 58 | 84 |
| 552989 | 0 | 50 | 74 | 81 |
| 552996 | 0 | 25 | 53 | 72 |
| 552998 | 17 | 49 | 79 | 90 |
| 553002 | 0 | 32 | 68 | 86 |
| 553003 | 15 | 42 | 67 | 88 |

Example 18

Antisense Inhibition of HBV Viral mRNA in HepG2 Cells by Deoxy, MOE and (S)-cEt Gapmers Additional antisense oligonucleotides were designed targeting a HBV viral nucleic acid and were tested for their effects on HBV mRNA in vitro. ISIS 5808 and ISIS 9591, disclosed in U.S. Pat. No. 5,985,662, as well as ISIS 146781, ISIS 146786, 524518, ISIS 552859, and ISIS 552870 were also included in these studies for comparison and are distinguished with an asterisk. Cultured HepG2 cells at a density of 28,000 cells per well were transfected using LipofectAMINE2000® with 100 nM antisense oligonucleotide. After a treatment period of approximately 24 hours, RNA was isolated from the cells and HBV mRNA levels were measured by quantitative real-time PCR. Viral primer probe sets RTS3370 and RTS3371 and were used to separately measure mRNA levels. HBV mRNA levels were adjusted according to total RNA content, as measured by RIBOGREEN®. Results are presented as percent inhibition of HBV, relative to untreated control cells.

The newly designed chimeric antisense oligonucleotides in Table below were designed as MOE gapmers or deoxy, MOE and (S)-cEt gapmers. The 5-10-5 MOE gapmers are 20 nucleosides in length, wherein the central gap segment comprises of ten 2'-deoxynucleosides and is flanked on both sides ides each. The deoxy, MOE and (S)-cEt gapmers are 16

(in the 5' and 3' directions) by wings comprising five nucleos-nucleosides in length wherein the nucleoside have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; otherwise, 'd' indicates a deoxynucleo-side; and 'e' indicates a MOE modification. The internucleoside linkages throughout each gapmer are phosphorothioate (P=S) linkages. All cytosine residues throughout each oligonucleotide are 5-methylcytosines.

"Viral Target start site" indicates the 5'-most nucleotide to which the gapmer is targeted in the viral gene sequence. "Viral Target stop site" indicates the 3'-most nucleotide to which the gapmer is targeted viral gene sequence. Each gapmer listed in Table 55 is targeted to the viral genomic sequence, designated herein as SEQ ID NO: 1 (GENBANK Accession No. U95551.1).

TABLE 55

Inhibition of viral HBV mRNA levels by chimeric antisense oligonucleotides measured with RTS3370 or RTS3371

| Viral Target Start Site | Viral Target Stop Site | ISIS No | Motif | % inhibition (RTS3370) | % inhibition (RTS3371) | Sequence | SEQ ID NO |
|---|---|---|---|---|---|---|---|
| 156 | 176 | 5808* | Uniform deoxy | 57 | 64 | CCTGATGTGATGTTCTCCATG | 1373 |
| 303 | 322 | 524518* | eeeee-10-eeeee | 62 | 72 | GGGACTGCGAATTTTGGCCA | 428 |
| 376 | 395 | 146781* | eeeee-10-eeeee | 72 | 93 | AAACGCCGCAGACACATCCA | 1374 |
| 380 | 399 | 582665 | eeeee-10-eeeee | 57 | 59 | GATAAAACGCCGCAGACACA | 1375 |
| 382 | 401 | 582666 | eeeee-10-eeeee | 49 | 92 | ATGATAAAACGCCGCAGACA | 1376 |
| 411 | 426 | 566831 | kdkdk-9-ee | 96 | 73 | GCATAGCAGCAGGATG | 137 |
| 411 | 427 | 577123 | eekk-9-ekee | 84 | 96 | GGCATAGCAGCAGGATG | 17 |
| 411 | 427 | 577124 | kdkdk-8-eeee | 92 | 96 | GGCATAGCAGCAGGATG | 17 |
| 411 | 426 | 577126 | kkk-8-eeeee | 87 | 90 | GCATAGCAGCAGGATG | 137 |
| 413 | 428 | 566830 | kdkdk-9-ee | 93 | 95 | AGGCATAGCAGCAGGA | 143 |
| 415 | 430 | 577130 | eek-10-kke | 87 | 94 | TGAGGCATAGCAGCAG | 147 |
| 415 | 430 | 577131 | kdkdk-9-ee | 83 | 93 | TGAGGCATAGCAGCAG | 147 |
| 1263 | 1278 | 566828 | kdkdk-9-ee | 97 | 90 | CCGCAGTATGGATCGG | 1236 |
| 1577 | 1596 | 146786* | eeeee-10-eeeee | 93 | 71 | GTGAAGCGAAGTGCACACGG | 224 |
| 1577 | 1592 | 566829 | kdkdk-9-ee | 98 | 84 | AGCGAAGTGCACACGG | 1334 |
| 1577 | 1596 | 577120 | kdkdk-10-eeeee | 94 | 93 | GTGAAGCGAAGTGCACACGG | 224 |
| 1577 | 1592 | 577127 | kkk-8-eeeee | 95 | 70 | AGCGAAGTGCACACGG | 1334 |
| 1577 | 1592 | 577134 | kek-8-eeeee | 94 | 89 | AGCGAAGTGCACACGG | 1334 |
| 1577 | 1592 | 577135 | kek-10-kek | 96 | 94 | AGCGAAGTGCACACGG | 1334 |
| 1583 | 1598 | 552859* | ekk-10-kke | 92 | 91 | AGGTGAAGCGAAGTGC | 1340 |
| 1583 | 1602 | 577121 | kdkdk-10-eeeee | 91 | 74 | GCAGAGGTGAAGCGAAGTGC | 226 |
| 1583 | 1598 | 577128 | kkk-8-eeeee | 92 | 85 | AGGTGAAGCGAAGTGC | 1340 |
| 1583 | 1598 | 577132 | kdkdk-9-ee | 97 | 81 | AGGTGAAGCGAAGTGC | 1340 |
| 1583 | 1598 | 577136 | kek-10-kek | 95 | 95 | AGGTGAAGCGAAGTGC | 1340 |
| 1588 | 1603 | 566832 | kdkdk-9-ee | 95 | 78 | TGCAGAGGTGAAGCGA | 1345 |
| 1780 | 1795 | 552870* | ekk-10-kke | 71 | 93 | TTTATGCCTACAGCCT | 232 |
| 1780 | 1799 | 577122 | kdkdk-10-eeeee | 70 | 96 | CCAATTTATGCCTACAGCCT | 50 |
| 1780 | 1796 | 577125 | kdkdk-8-eeee | 70 | 94 | ATTTATGCCTACAGCCT | 51 |
| 1780 | 1795 | 577129 | kkk-8-eeeee | 76 | 51 | TTTATGCCTACAGCCT | 232 |

TABLE 55-continued

Inhibition of viral HBV mRNA levels by chimeric antisense oligonucleotides measured with RTS3370 or RTS3371

| Viral Target Start Site | Viral Target Stop Site | ISIS No | Motif | % inhibition (RTS3370) | % inhibition (RTS3371) | Sequence | SEQ ID NO |
|---|---|---|---|---|---|---|---|
| 1780 | 1795 | 577133 | kdkdk-9-ee | 80 | 52 | TTTATGCCTACAGCCT | 232 |
| 1873 | 1892 | 9591 | *Uniform deoxy | 30 | 14 | CACCCAAGGCACAGCTTGG | 1377 |

Example 19

Efficacy of Gapmers Targeting HBV in Transgenic Mice

Transgenic mice were treated with ISIS antisense oligonucleotides in a number of studies to evaluate the efficacy of the gapmers. HBV DNA and RNA levels were assessed.

Study 1

Groups of 12 mice each were injected subcutaneously twice a week for 4 weeks with 50 mg/kg of ISIS 510106, ISIS 510116, ISIS 505347, or ISIS 509934. A control group of 12 mice was injected subcutaneously twice a week for 4 weeks with PBS. Mice were euthanized 48 hours after the last dose, and livers were harvested for further analysis.

DNA and RNA Analysis

RNA was extracted from liver tissue for real-time PCR analysis of HBV DNA, using primer probe sets RTS3370, RTS3371, and RTS3372. The DNA levels were normalized to picogreen. HBV RNA samples were also assayed with primer probe sets RTS3370 and RTS3371 after RT-PCR analysis. The mRNA levels were normalized to RIBOGREEN®. The data is presented in Table 56, expressed as percent inhibition compared to the control group. As shown in Table 56, most of the antisense oligonucleotides achieved reduction of HBV DNA and RNA over the PBS control. Results are presented as percent inhibition of HBV mRNA or DNA, relative to control. The Chemistry column indicates the gap-wing motif of each gapmer.

The DNA levels were normalized to picogreen. HBV RNA samples were also assayed with primer probe sets RTS3370 after RT-PCR analysis. The mRNA levels were normalized to RIBOGREEN®. The data is presented in Table 57, expressed as percent inhibition compared to the control group. As shown in Table 57, most of the antisense oligonucleotides achieved reduction of HBV DNA and RNA over the PBS control. Results are presented as percent inhibition of HBV mRNA or DNA, relative to control. The Chemistry column indicates the gap-wing motif of each gapmer.

TABLE 57

Percent inhibition of HBV RNA and DNA in the liver of transgenic mice

| ISIS No | Chemistry | % inhibition DNA | % inhibition RNA |
|---|---|---|---|
| 146779 | 5-10-5 MOE | 39 | 5 |
| 146786 | 5-10-5 MOE | 83 | 73 |
| 505358 | 5-10-5 MOE | 84 | 77 |
| 509958 | 3-10-3 MOE | 82 | 29 |
| 509959 | 3-10-3 MOE | 54 | 30 |
| 509974 | 3-10-3 MOE | 56 | 28 |

Study 3

Groups of 6 mice each were injected subcutaneously twice a week for 4 weeks with 50 mg/kg of ISIS 509960, ISIS 505329, ISIS 146786, ISIS 505339, or ISIS 509927. Another

TABLE 56

Percent inhibition of HBV RNA and DNA in the liver of transgenic mice

| ISIS No | Chemistry | % inhibition DNA (RTS3370) | % inhibition DNA (RTS3371) | % inhibition DNA (RTS3372) | % inhibition RNA (RTS3370) | % inhibition RNA (RTS3371) | % inhibition RNA (RTS3372) |
|---|---|---|---|---|---|---|---|
| 505347 | 5-10-5 MOE | 72 | 79 | 75 | 54 | 28 | 30 |
| 509934 | 5-10-5 MOE | 93 | 95 | 94 | 72 | 75 | 92 |
| 510106 | 3-10-4 MOE | 0 | 0 | 51 | 0 | 0 | 12 |
| 510116 | 3-10-4 MOE | 68 | 79 | 68 | 49 | 54 | 66 |

Study 2

Groups of 6 mice each were injected subcutaneously twice a week for 4 weeks with 50 mg/kg of ISIS 146779, ISIS 505358, ISIS 146786, ISIS 509974, ISIS 509958, or ISIS 509959. A control group of 10 mice was injected subcutaneously twice a week for 4 weeks with PBS. Mice were euthanized 48 hours after the last dose, and livers were harvested for further analysis.

DNA and RNA Analysis

RNA was extracted from liver tissue for real-time PCR analysis of HBV DNA, using primer probe sets RTS3370.

group of 6 mice was administered Entecavir, an oral antiviral drug used to treat Hepatitis B infection, at 1 mg/kg daily for two weeks. A control group of 10 mice was injected subcutaneously twice a week for 4 weeks with PBS. Mice were euthanized 48 hours after the last dose, and livers were harvested for further analysis.

DNA and RNA Analysis

RNA was extracted from liver tissue for real-time PCR analysis of HBV DNA, using primer probe sets RTS3371. The DNA levels were normalized to picogreen. HBV RNA samples were also assayed with primer probe sets RTS3371 after RT-PCR analysis. The mRNA levels were normalized to RIBOGREEN®. The data is presented in Table 58, expressed as percent inhibition compared to the control group. As shown in Table 58, most of the antisense oligonucleotides achieved reduction of HBV DNA and RNA over the PBS control. Results are presented as percent inhibition of HBV mRNA or DNA, relative to control. The Chemistry column indicates the gap-wing motif of each gapmer.

TABLE 58

Percent inhibition of HBV RNA and DNA in the liver of transgenic mice

|  | Oligo Chemistry | % inhibition DNA | % inhibition RNA |
|---|---|---|---|
| entecavir | — | 94 | 0 |
| ISIS 146786 | 5-10-5 MOE | 97 | 92 |
| ISIS 505329 | 5-10-5 MOE | 70 | 63 |
| ISIS 505339 | 5-10-5 MOE | 74 | 63 |
| ISIS 509927 | 5-10-5 MOE | 80 | 57 |
| ISIS 509960 | 3-10-3 MOE | 86 | 60 |

Study 4

Groups of 6 mice each were injected subcutaneously twice a week for 4 weeks with 25 mg/kg of ISIS 146786, ISIS 552176, and ISIS 552073. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of HBV DNA, using primer probe set RTS3371. The DNA levels were normalized to picogreen. HBV RNA samples were also assayed with primer probe set RTS3371 after RT-PCR analysis. The mRNA levels were normalized to RIBOGREEN®. The data is presented in Table 59. As shown in Table 59, the antisense oligonucleotides achieved reduction of HBV DNA and RNA over the PBS control. Results are presented as percent inhibition of HBV mRNA or DNA, relative to control. The Chemistry column indicates the gap-wing motif of each gapmer.

TABLE 59

Percent inhibition of HBV RNA and DNA in transgenic mice

| ISIS No | Chemistry | % inhibition of RNA | % inhibition of DNA |
|---|---|---|---|
| 146786 | 5-10-5 MOE | 81 | 91 |
| 552073 | 8-10-2 MOE | 39 | 22 |
| 552176 | 3-9-5 MOE | 55 | 56 |

Liver Function

To evaluate the effect of ISIS oligonucleotides on hepatic function, plasma concentrations of ALT were measured using an automated clinical chemistry analyzer (Hitachi Olympus AU400e, Melville, N.Y.) (Nyblom, H. et al., Alcohol & Alcoholism 39: 336-339, 2004; Tietz NW (Ed): Clinical Guide to Laboratory Tests, 3rd ed. W.B. Saunders, Philadelphia, Pa., 1995). The results are presented in Table 60 expressed in IU/L. Both the ISIS oligonucleotides were considered tolerable in the mice, as demonstrated by their liver transaminase profile.

TABLE 60

ALT levels (IU/L) of transgenic mice

|  | ALT |
|---|---|
| PBS | 77 |
| ISIS 146786 | 21 |
| ISIS 552073 | 19 |
| ISIS 552176 | 27 |

Study 5

Groups of 6 mice each were injected subcutaneously twice a week for 4 weeks with 25 mg/kg of ISIS 146786, ISIS 552056, ISIS 552088, and ISIS 552309. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of HBV DNA, using primer probe set RTS3371. The DNA levels were normalized to picogreen. HBV RNA samples were also assayed with primer probe set RTS3371 after RT-PCR analysis. The mRNA levels were normalized to RIBOGREEN®. As shown in Table 61, the antisense oligonucleotides achieved reduction of HBV DNA and RNA over the PBS control. Results are presented as percent inhibition of HBV mRNA or DNA, relative to control. The Chemistry column indicates the gap-wing motif of each gapmer.

TABLE 61

Percent inhibition of HBV DNA and RNA in transgenic mice

|  | Chemistry | % inhibition (RNA) | % inhibition (DNA) |
|---|---|---|---|
| ISIS 146786 | 5-10-5 MOE | 60 | 90 |
| ISIS 552056 | 7-10-3 MOE | 25 | 58 |
| ISIS 552088 | 8-10-2 MOE | 8 | 0 |
| ISIS 552309 | 5-9-3 MOE | 35 | 84 |

Study 6

Groups of 6 mice each were injected subcutaneously twice a week for 4 weeks with 25 mg/kg of ISIS 146786, ISIS 505330, ISIS 509932, ISIS 552032, ISIS 552057, ISIS 552075, ISIS 552092, and ISIS 552255. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of HBV DNA, using primer probe set RTS3371. The DNA levels were normalized to picogreen. HBV RNA samples were also assayed with primer probe set RTS3371 after RT-PCR analysis. The mRNA levels were normalized to RIBOGREEN®. As shown in Table 62, the antisense oligonucleotides achieved reduction of HBV DNA and RNA over the PBS control. Results are presented as percent inhibition of HBV mRNA or DNA, relative to control. The Chemistry column indicates the gap-wing motif of each gapmer.

TABLE 62

Percent inhibition of HBV DNA and RNA in transgenic mice

| ISIS No | Chemistry | % inhibition (RNA) | % inhibition (DNA) |
|---------|-----------|--------------------|--------------------|
| 146786 | 5-10-5 MOE | 52 | 95 |
| 505330 | 5-10-5 MOE | 7 | 61 |
| 509932 | 5-10-5 MOE | 83 | 98 |
| 552032 | 6-10-4 MOE | 54 | 97 |
| 552057 | 7-10-3 MOE | 19 | 62 |
| 552075 | 8-10-2 MOE | 12 | 18 |
| 552092 | 8-10-2 MOE | 25 | 74 |
| 552255 | 4-9-4 MOE | 41 | 89 |

Study 7

Groups of 6 mice each were injected subcutaneously twice a week for 4 weeks with 20 mg/kg of ISIS 552859, ISIS 577121, ISIS 577122, ISIS 577123, ISIS 577132, ISIS 577133, and ISIS 577134. These gapmers have deoxy, MOE and (S)-cEt chemistry. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of HBV DNA, using primer probe set RTS3371. The DNA levels were normalized to picogreen. HBV RNA samples were also assayed with primer probe set RTS3371 after RT-PCR analysis. The mRNA levels were normalized to RIBOGREEN®. As shown in Table 63, the antisense oligonucleotides achieved reduction of HBV DNA and RNA over the PBS control. Results are presented as percent inhibition of HBV mRNA or DNA, relative to control. The 'Chemistry' column describes the sugar modifications of each oligonucleotide. 'k' indicates an (S)-cEt sugar modification; the number indicates the number of deoxynucleosides; otherwise, 'd' indicates a deoxynucleoside; and 'e' indicates a MOE modification.

TABLE 63

Percent inhibition of HBV DNA and RNA in transgenic mice

| ISIS No | Chemistry | % inhibition (RNA) | % inhibition (DNA) |
|---------|-----------|--------------------|--------------------|
| 552859 | ekk-10-kke | 60 | 86 |
| 577121 | kdkdk-10-eeeee | 59 | 93 |
| 577122 | kdkdk-10-eeeee | 42 | 68 |
| 577123 | eekk-9-ekee | 0 | 77 |
| 577132 | kdkdk-9-ee | 4 | 24 |
| 577133 | kdkdk-9-ee | 46 | 64 |
| 577134 | kek-8-eeeee | 0 | 17 |

Study 8

A group of 6 mice was injected subcutaneously twice a week for 4 weeks with 25 mg/kg of ISIS 146786, the 5-10-5 MOE gapmer. Groups of 6 mice each were injected subcutaneously twice a week for 4 weeks with 10 mg/kg of ISIS 552803, ISIS 552903, ISIS 552817, ISIS 552822, and ISIS 552907. These gapmers all had deoxy, MOE, and (S)-cEt chemistry. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of HBV DNA, using primer probe set RTS3371. The DNA levels were normalized to picogreen. HBV RNA samples were also assayed with primer probe set RTS3371 after RT-PCR analysis. The mRNA levels were normalized to RIBOGREEN®. The data is presented in Table 64. As shown in Table 64, the antisense oligonucleotides achieved reduction of HBV DNA and RNA over the PBS control. The 'Chemistry' column describes the sugar modifications of each oligonucleotide. 'k' indicates an (S)-cEt sugar modification; the number indicates the number of deoxynucleosides; otherwise, indicates a deoxynucleoside; and 'e' indicates a MOE modification; in case of the MOE gapmers, the Chemistry column defines the gap-wing structure.

TABLE 64

Percent inhibition of HBV RNA and DNA in transgenic mice

| ISIS No | Chemistry | Dose (mg/kg/wk) | % inhibition of RNA | % inhibition of DNA |
|---------|-----------|-----------------|---------------------|---------------------|
| 146786 | 5-10-5 MOE | 50 | 81 | 91 |
| 552803 | ekk-10-kke | 20 | 71 | 95 |
| 552817 | ekk-10-kke | 20 | 86 | 51 |
| 552822 | ekk-10-kke | 20 | 90 | 89 |
| 552903 | ek-10-keke | 20 | 56 | 82 |
| 552907 | ek-10-keke | 20 | 41 | 45 |

Study 9

A group of 6 mice was injected subcutaneously twice a week for 4 weeks with 25 mg/kg of ISIS 146786. Groups of 6 mice each were injected subcutaneously twice a week for 4 weeks with 10 mg/kg of ISIS 552853, ISIS 552854, ISIS 552932, and ISIS 552938. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of HBV DNA, using primer probe set RTS3371. The DNA levels were normalized to picogreen. HBV RNA samples were also assayed with primer probe set RTS3371 after RT-PCR analysis. The mRNA levels were normalized to RIBOGREEN®. As shown in Table 65, the antisense oligonucleotides achieved reduction of HBV DNA and RNA over the PBS control. Results are presented as percent inhibition of HBV mRNA or DNA, relative to control. The 'Chemistry' column describes the sugar modifications of each oligonucleotide. 'k' indicates an (S)-cEt sugar modification; the number indicates the number of deoxynucleosides; otherwise, 'd' indicates a deoxynucleoside; and 'e' indicates a MOE modification; in case of the MOE gapmers, the Chemistry column defines the gap-wing structure.

TABLE 65

Percent inhibition of HBV DNA and RNA in transgenic mice

| | Chemistry | Dose (mg/kg/wk) | % inhibition (DNA) | % inhibition (RNA) |
|---|-----------|-----------------|--------------------|--------------------|
| ISIS 146786 | 5-10-5 MOE | 50 | 90 | 60 |
| ISIS 552853 | ekk-10-kke | 20 | 94 | 60 |
| ISIS 552854 | ekk-10-kke | 20 | 61 | 23 |
| ISIS 552932 | ek-10-keke | 20 | 75 | 70 |
| ISIS 552938 | ek-10-keke | 20 | 67 | 56 |

Study 10

A group of 6 mice was injected subcutaneously twice a week for 4 weeks with 25 mg/kg of ISIS 146786. Groups of 6 mice each were injected subcutaneously twice a week for 4 weeks with 10 mg/kg of ISIS 552922, ISIS 552923, ISIS 552942, ISIS 552872, ISIS 552925, ISIS 552937, and ISIS 552939. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of HBV DNA, using primer probe set RTS3371. The DNA levels were normalized to picogreen. HBV RNA samples were also assayed with primer probe set RTS3371 after RT-PCR analysis. The mRNA levels were normalized to RIBOGREEN®. As shown in Table 66, the antisense oligonucleotides achieved reduction of HBV DNA and RNA over the PBS control. Results are presented as percent inhibition of HBV mRNA or DNA, relative to control. The 'Chemistry' column describes the sugar modifications of each oligonucleotide. 'k' indicates an (S)-cEt sugar modification; the number indicates the number of deoxynucleosides; otherwise, 'd' indicates a deoxynucleoside; and 'e' indicates a MOE modification; in case of the MOE gapmers, the Chemistry column defines the gap-wing structure.

TABLE 66

Percent inhibition of HBV DNA and RNA in transgenic mice

| ISIS No | Chemistry | Dose (mg/kg/wk) | % inhibition (DNA) | % inhibition (RNA) |
|---|---|---|---|---|
| 146786 | 5-10-5 MOE | 50 | 52 | 57 |
| 552922 | ekk-10-kke | 20 | 61 | 50 |
| 552923 | ek-10-keke | 20 | 89 | 76 |
| 552942 | ek-10-keke | 20 | 58 | 52 |
| 552872 | ek-10-keke | 20 | 77 | 46 |
| 552925 | ek-10-keke | 20 | 89 | 65 |
| 552937 | ek-10-keke | 20 | 59 | 35 |
| 552939 | ek-10-keke | 20 | 57 | 19 |

Example 20

Efficacy of Gapmers Targeting HBV in Transgenic Mice

Mice harboring a HBV gene fragment (Guidotti, L. G. et al., *J. Virol.* 1995, 69, 6158-6169) were used. The mice were treated with ISIS antisense oligonucleotides selected from studies described above and evaluated for their efficacy in this model. HBV DNA, RNA, and antigen levels were assessed.

Groups of 10 mice each were injected subcutaneously twice a week for the first with 50 mg/kg and, subsequently, twice a week for the next 3 weeks with 25 mg/kg of ISIS 146786 or ISIS 510100. Control groups of 10 mice each were treated in a similar manner with ISIS 141923 (CCTTCCCT-GAAGGTTCCTCC, SEQ ID NO: 320; 5-10-5 MOE gapmer with no known murine target) or ISIS 459024 (CGGTCCT-TGGAGGATGC, SEQ ID NO: 1351; 3-10-4 MOE gapmer with no known murine target). Mice were euthanized 48 hours after the last dose, and organs and serum were harvested for further analysis.

DNA and RNA Analysis

RNA was extracted from liver tissue for real-time PCR analysis of HBV DNA, using primer probe sets RTS3370, RTS3371, or RTS3372 (forward sequence ATCCTATCAA-CACTTCCGGAAACT, designated SEQ ID NO: 314; reverse sequence CGACGCGGCGATTGAG, designated SEQ ID NO: 315; probe sequence AAGAACTCCCTCGC-CTCGCAGACG, designated SEQ ID NO: 316). The DNA levels were normalized to picogreen. HBV RNA samples were also assayed with primer probe sets RTS3370 and RTS3371 after RT-PCR analysis. The mRNA levels were normalized to RIBOGREEN®. The data is presented in Table 67. Serum DNA samples were analyzed after the study period. The data is presented in Table 68, expressed relative to the levels measured in the control group. As shown in Tables 67 and 68, the antisense oligonucleotides achieved reduction of HBV DNA and RNA over the PBS control. Results are presented as percent inhibition of HBV mRNA or DNA, relative to control. The Chemistry column defines the gap-wing structure of each gapmer.

TABLE 67

Percent inhibition of HBV RNA and DNA in the liver of transgenic mice

| ISIS No | Chemistry | % inhibition DNA (RTS3370) | % inhibition DNA (RTS3371) | % inhibition DNA (RTS3372) | % inhibition RNA (RTS3370) | % inhibition RNA (RTS3371) | % inhibition RNA (RTS3372) |
|---|---|---|---|---|---|---|---|
| 146786 | 5-10-5 MOE | 97 | 97 | 95 | 86 | 85 | 89 |
| 510100 | 3-10-4 MOE | 95 | 94 | 94 | 56 | 64 | 77 |
| 141923 | 5-10-5 MOE | 2 | 0 | 13 | 0 | 7 | 31 |
| 459024 | 3-10-4 MOE | 19 | 0 | 8 | 0 | 0 | 0 |

TABLE 68

Percent inhibition of HBV DNA in the serum of transgenic mice

| ISIS No | % inhibition (RTS3370) | % inhibition (RTS3371) |
|---|---|---|
| 146786 | 98 | 98 |
| 510100 | 99 | 98 |
| 141923 | 0 | 0 |
| 459024 | 0 | 0 |

HBV Antigen Analysis

HBV antigens in the supernatants were detected with the ELISA technique. HBs antigen (HBsAg) levels were detected by ELISA from Abazyme LLC, MA. As presented in Table 57, treatment with ISIS oligonucleotides 146786 or 510100 caused reduction in HBsAg levels. HBe antigen (HBeAg) levels were detected by ELISA from International Immunodiagnostics, CA. As presented in Table 69, treatment with ISIS oligonucleotides 146786 or 510100 also caused reduction in HBeAg levels.

TABLE 69

HBV antigen levels (PEI U/mL) in transgenic mice

|  | HBsAg | HBeAg |
|---|---|---|
| PBS | 40 | 80 |
| 146786 | 3 | 15 |
| 510100 | 15 | 22 |
| 141923 | 32 | 80 |
| 459024 | 44 | 51 |

Example 21

Antisense Inhibition of HBV Viral mRNA in HepG2 Cells by Deoxy, MOE and (S)-cEt Gapmers Additional antisense oligonucleotides were designed targeting a HBV viral nucleic acid and were tested for their effects on HBV mRNA in vitro. ISIS 146786, ISIS 505358, ISIS 509932, and ISIS 510100, disclosed in U.S. Provisional Application No. 61/478,040 filed on Apr. 21, 2011; ISIS 552859 disclosed in U.S. Provisional Application No. 61/596,692 filed on Feb. 8, 2012; ISIS 577121, ISIS 577122, ISIS 577123, ISIS 577132, ISIS 577133, and ISIS 577134, disclosed in the study described above, were also included in the assay. Cultured HepG2 cells at a density of 28,000 cells per well were transfected using Cytofectin with 9.375 nM, 18.75 nM, 37.50 nM, 75.00 nM, 150.00 nM, or 300.00 nM antisense oligonucleotide. After a treatment period of approximately 24 hours, RNA was isolated from the cells and HBV mRNA levels were measured by quantitative real-time PCR. Viral primer probe set RTS3371 was used to measure mRNA levels. HBV mRNA levels were adjusted according to total RNA content, as measured by RIBOGREEN®. Results are presented as percent inhibition of HBV, relative to untreated control cells.

The newly designed chimeric antisense oligonucleotides in Tables below were designed as deoxy, MOE and (S)-cEt gapmers. The deoxy, MOE and (S)-cEt gapmers are 16, 17, or 18 nucleosides in length wherein the nucleosides have either a MOE sugar modification, an (S)-cEt sugar modification, or a deoxy modification. The 'Chemistry' column describes the sugar modifications of each oligonucleotide. 'k' indicates an (S)-cEt sugar modification; the number indicates the number of deoxynucleosides; otherwise, 'd' indicates a deoxynucleoside; and 'e' indicates a MOE modification. The internucleoside linkages throughout each gapmer are phosphorothioate (P=S) linkages. All cytosine residues throughout each oligonucleotide are 5-methylcytosines.

"Viral Target start site" indicates the 5'-most nucleotide to which the gapmer is targeted in the viral gene sequence. "Viral Target stop site" indicates the 3'-most nucleotide to which the gapmer is targeted viral gene sequence. Each gapmer listed in Table 70 is targeted to the viral genomic sequence, designated herein as SEQ ID NO: 1 (GENBANK Accession No. U95551.1).

TABLE 70

Chimeric antisense oligonucleotides targeting SEQ ID NO: 1

| Viral Target Start Site | Viral Target Stop Site | ISIS No | Motif | Sequence | SEQ ID NO |
|---|---|---|---|---|---|
| 411 | 427 | 585163 | eeekk-8-eeee | GGCATAGCAGCAGGATG | 17 |
| 414 | 430 | 585164 | eeekk-7-kkeee | TGAGGCATAGCAGCAGG | 21 |
| 414 | 430 | 585165 | eeek-9-keee | TGAGGCATAGCAGCAGG | 21 |
| 1577 | 1593 | 585170 | eeekk-7-kkeee | AAGCGAAGTGCACACGG | 1304 |
| 1577 | 1593 | 585171 | eeek-9-keee | AAGCGAAGTGCACACGG | 1304 |
| 1577 | 1593 | 585172 | eeeekk-7-eeee | AAGCGAAGTGCACACGG | 1304 |
| 1577 | 1593 | 585173 | ekek-9-eeee | AAGCGAAGTGCACACGG | 1304 |
| 1577 | 1593 | 585174 | ekekdk-7-eeee | AAGCGAAGTGCACACGG | 1304 |
| 1583 | 1599 | 585166 | eeekk-7-kkeee | GAGGTGAAGCGAAGTGC | 1310 |
| 1583 | 1599 | 585167 | eeek-9-keee | GAGGTGAAGCGAAGTGC | 1310 |
| 1780 | 1797 | 577119 | kdkdk-8-eeeee | AATTTATGCCTACAGCCT | 1379 |
| 1780 | 1796 | 585168 | eeekk-7-kkeee | ATTTATGCCTACAGCCT | 51 |
| 1780 | 1796 | 585169 | eeek-9-keee | ATTTATGCCTACAGCCT | 51 |

TABLE 71

Dose dependent inhibition of HBV mRNA levels by chimeric antisense oligonucleotides

| ISIS No | 9.375 nM | 18.75 nM | 37.5 nM | 75.0 nM | 150.0 nM | 300.0 nM |
|---|---|---|---|---|---|---|
| 146786 | 37 | 37 | 58 | 70 | 81 | 93 |
| 505358 | 30 | 26 | 28 | 57 | 74 | 85 |
| 510100 | 42 | 30 | 43 | 61 | 77 | 91 |
| 552859 | 21 | 30 | 39 | 61 | 79 | 91 |
| 577119 | 42 | 43 | 46 | 66 | 74 | 75 |
| 577121 | 10 | 15 | 42 | 64 | 82 | 89 |
| 577122 | 21 | 30 | 53 | 66 | 78 | 84 |
| 577123 | 27 | 29 | 45 | 56 | 78 | 84 |
| 577132 | 14 | 21 | 42 | 61 | 80 | 92 |
| 577133 | 12 | 14 | 32 | 47 | 62 | 77 |
| 577134 | 37 | 39 | 59 | 72 | 86 | 90 |
| 585174 | 31 | 28 | 48 | 61 | 80 | 90 |

TABLE 72

Dose dependent inhibition of HBV mRNA levels by chimeric antisense oligonucleotides

| ISIS No | 9.375 nM | 18.75 nM | 37.5 nM | 75.0 nM | 150.0 nM | 300.0 nM |
|---|---|---|---|---|---|---|
| 146786 | 25 | 34 | 57 | 71 | 85 | 92 |
| 509932 | 9 | 28 | 59 | 62 | 70 | 74 |
| 585163 | 17 | 32 | 52 | 68 | 77 | 81 |
| 585164 | 23 | 4 | 29 | 31 | 36 | 56 |
| 585165 | 6 | 31 | 42 | 58 | 66 | 82 |
| 585166 | 19 | 27 | 35 | 48 | 50 | 63 |
| 585167 | 22 | 25 | 50 | 69 | 76 | 88 |
| 585168 | 4 | 30 | 44 | 52 | 67 | 76 |
| 585169 | 32 | 32 | 42 | 62 | 76 | 80 |
| 585170 | 23 | 19 | 39 | 49 | 66 | 75 |
| 585171 | 28 | 27 | 42 | 59 | 81 | 88 |
| 585172 | 26 | 29 | 30 | 64 | 80 | 91 |
| 585173 | 29 | 30 | 41 | 71 | 86 | 88 |

Example 22

Analysis of the Potency of Uniform Deoxyoligonucleotides in Inhibition of HBV mRNA in HepG2 Cells Additional antisense oligonucleotides were tested for their effects on HBV mRNA in vitro. ISIS 5808 and ISIS 9591, disclosed in U.S. Pat. No. 5,985,662 were also included in the assay. ISIS 146786 was included in the assay as the benchmark. Cultured HepG2 cells at a density of 28,000 cells per well were transfected using LipofectAMINE2000® with 18.75 nM, 37.50 nM, 75.00 nM, 150.00 nM, or 300.00 nM antisense oligonucleotide. After a treatment period of approximately 24 hours, RNA was isolated from the cells and HBV mRNA levels were measured by quantitative real-time PCR. Viral primer probe set RTS3371 was used to measure mRNA and DNA levels. HBV mRNA levels were adjusted according to total RNA content, as measured by RIBOGREEN®. S antigen and E antigen levels were also measured by ELISA. Results are presented as percent inhibition, relative to untreated control cells.

The antisense oligonucleotides tested, ISIS 582699, ISIS 582700, and ISIS 582701, were designed according to the sequences and chemistries disclosed in *Korba and Gerin, Antiviral Research*, 1995, Vol. 28, 225-242; the corresponding names for the oligonucleotides in the reference are S1, C1, and L2c, respectively. The antisense oligonucleotides in Tables below were designed as uniform deoxy oligonucleotides, 16 or 21 nucleosides in length wherein the nucleosides have deoxy modifications. "Viral Target start site" indicates the 5'-most nucleotide to which the oligonucleotide is targeted in the viral gene sequence. "Viral Target stop site" indicates the 3'-most nucleotide to which the oligonucleotide is targeted viral gene sequence. Each oligonucleotide listed in Table 73 is targeted to the viral genomic sequence, designated herein as SEQ ID NO: 1 (GENBANK Accession No. U95551.1). The results indicate that the deoxy oligonucleotides had negligible effect on HBV mRNA expression levels DNA levels and HBV antigen levels.

TABLE 73

Uniform deoxy oligonucleotides targeting SEQ ID NO: 1

| Viral Target Start Site | Viral Target Stop Site | ISIS No | Sequence | SEQ ID NO |
|---|---|---|---|---|
| 160 | 180 | 582699 | GAATCCTGATGTGATGTTCTC | 1378 |
| 1884 | 1899 | 582701 | CCAAAGCCACCCAAGG | 1380 |
| 1910 | 1930 | 582700 | CAAATTCTTTATAAGGGTCGA | 1381 |

TABLE 74

Dose dependent inhibition of HBV mRNA levels after treatment with oligonucleotides

| ISIS No | 18.75 nM | 37.5 nM | 75.0 nM | 150.0 nM | 300.0 nM |
|---|---|---|---|---|---|
| 5808 | 38 | 23 | 29 | 40 | 54 |
| 9591 | 35 | 20 | 32 | 26 | 40 |
| 146786 | 11 | 5 | 45 | 66 | 92 |
| 582699 | 32 | 28 | 27 | 39 | 52 |
| 582700 | 18 | 12 | 20 | 16 | 23 |
| 582701 | 4 | 0 | 0 | 3 | 13 |

TABLE 75

Dose dependent inhibition of HBV DNA levels in HepG2 cells after treatment with oligonucleotides

| ISIS No | 18.75 nM | 37.5 nM | 75.0 nM | 150.0 nM |
|---|---|---|---|---|
| 5808 | 20 | 17 | 0 | 0 |
| 9591 | 0 | 0 | 0 | 0 |
| 146786 | 32 | 50 | 77 | 83 |
| 582699 | 0 | 44 | 0 | 17 |
| 582700 | 0 | 0 | 0 | 0 |
| 582701 | 0 | 0 | 0 | 0 |

TABLE 76

HBV S antigen levels after treatment with oligonucleotides (arbitrary units)

| ISIS No | 18.75 nM | 37.5 nM | 75.0 nM | 150.0 nM |
|---|---|---|---|---|
| 5808 | 9,254 | 8,228 | 4,168 | 2,540 |
| 9591 | 10,924 | 8,683 | 9,334 | 12,142 |
| 146786 | 12,501 | 7,265 | 3,408 | 1,017 |
| 582699 | 9,340 | 9,325 | 7,589 | 4,712 |
| 582700 | 9,697 | 8,350 | 11,168 | 10,703 |
| 582701 | 15,283 | 18,209 | 14,632 | 15,299 |

TABLE 77

HBV E antigen levels after treatment with oligonucleotides (arbitrary units)

| ISIS No | 18.75 nM | 37.5 nM | 75.0 nM | 150.0 nM |
|---|---|---|---|---|
| 5808 | 8,075 | 8,587 | 5,036 | 3,286 |
| 9591 | 9,242 | 8,093 | 8,257 | 6,944 |
| 146786 | 8,532 | 4,034 | 2,301 | 449 |
| 582699 | 7,815 | 7,191 | 7,026 | 5,278 |
| 582700 | 8,690 | 9,304 | 7,941 | 6,315 |
| 582701 | 8,847 | 8,257 | 8,211 | 6,276 |

What is claimed is:

1. A compound, comprising a single-stranded modified oligonucleotide consisting of 20 linked nucleosides and having a nucleobase sequence consisting of the nucleobase sequences of SEQ ID NOs: 224, 226, and 807, wherein the modified oligonucleotide is at least 96% complementary over its entire length with a nucleic acid encoding hepatitis B virus (HBV) and at least one nucleoside of the modified oligonucleotide comprises a modified sugar.

2. The compound of claim 1, wherein said modified oligonucleotide is at least 98% complementary to SEQ ID NO: 1.

3. The compound of claim 1, wherein said modified oligonucleotide is 100% complementary to SEQ ID NO: 1.

4. The compound of claim 1, wherein the modified oligonucleotide comprises at least one modified internucleoside linkage.

5. The compound of claim 4, wherein each internucleoside linkage is a phosphorothioate internucleoside linkage.

6. The compound of claim 1, wherein the at least one modified sugar is a bicyclic sugar.

7. The compound of claim 1, wherein the at least one modified sugar comprises a 2'-O-methoxyethyl group.

8. The compound of claim 1, wherein the at least one modified sugar comprises a 4'-CH(CH$_3$)—O-2' group.

9. The compound of claim 1, wherein at least one nucleoside comprises a modified nucleobase.

10. The compound of claim 9, wherein the modified nucleobase is a 5-methylcytosine.

11. The compound of claim 1, wherein the modified oligonucleotide comprises:
   a gap segment consisting of linked deoxynucleosides;
   a 5' wing segment consisting of linked nucleosides; and
   a 3' wing segment consisting of linked nucleosides;
   wherein the gap segment is positioned between the 5' wing segment and the 3' wing segment and wherein each nucleoside of each wing segment comprises a modified sugar.

12. The compound of claim 11, wherein the gap segment consists of 6, 7, 8, 9, 10, 11, 12, 13, 14, 15 or 16 linked nucleosides.

13. The compound of claim 11, wherein the modified oligonucleotide comprises:
   a gap segment consisting of ten linked deoxynucleosides;
   a 5' wing segment consisting of 1-5 linked nucleosides; and
   a 3' wing segment consisting of 1-5 linked nucleosides;
   wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

14. A method of preventing, treating, ameliorating, or slowing progression of a HBV-related disease, disorder or condition in an animal comprising administering to the animal the compound of claim 1, thereby preventing, treating, ameliorating, or slowing progression of a HBV-related disease, disorder or condition in the animal.

15. The method of claim 14, wherein the animal is a human.

16. The method of claim 14, wherein the disease, disorder or condition is jaundice, liver inflammation, liver fibrosis, inflammation, liver cirrhosis, liver failure, liver cancer, diffuse hepatocellular inflammatory disease, hemophagocytic syndrome, serum hepatitis, HBV viremia, or liver disease-related transplantation.

17. The method of claim 14, wherein administering the compound of claim 1 reduces HBV antigen levels in the animal.

18. The method of claim 17, wherein HBsAG levels are reduced.

19. The method of claim 17, wherein HBeAG levels are reduced.

20. The compound of claim 1, wherein the modified oligonucleotide consists of 20 linked nucleosides having the nucleobase sequence of SEQ ID NO: 224 and comprises:
   a gap segment consisting of ten linked deoxynucleosides;
   a 5' wing segment consisting of 6 linked nucleosides; and a 3' wing segment consisting of 4 linked nucleosides;
wherein the gap segment is positioned between the 5' wing segment and the 3' wing segment, wherein each nucleoside of each wing segment comprises a 2'-O-methoxyethyl sugar, wherein each internucleoside linkage of the modified oligonucleotide is a phosphorothioate linkage, and wherein each cytosine of the modified oligonucleotide is a 5-methylcytosine.

21. The compound of claim 1, wherein the modified oligonucleotide consists of 20 linked nucleosides having the nucleobase sequence of SEQ ID NO: 226 and comprises:
a gap segment consisting of ten linked deoxynucleosides;
a 5' wing segment consisting of 5 linked nucleosides; and
a 3' wing segment consisting of 5 linked nucleosides;
wherein the gap segment is positioned between the 5' wing segment and the 3' wing segment, wherein each nucleoside of each wing segment comprises a 2'-O-methoxyethyl sugar, wherein each internucleoside linkage of the modified oligonucleotide is a phosphorothioate linkage, and wherein each cytosine of the modified oligonucleotide is a 5-methylcytosine.

22. The compound of claim 1, wherein the modified oligonucleotide consists of 20 linked nucleosides having the nucleobase sequence of SEQ ID NO: 807 and comprises:
a gap segment consisting of ten linked deoxynucleosides;
a 5' wing segment consisting of 6 linked nucleosides; and
a 3' wing segment consisting of 4 linked nucleosides;
wherein the gap segment is positioned between the 5' wing segment and the 3' wing segment, wherein each nucleoside of each wing segment comprises a 2'-O-methoxyethyl sugar, wherein each internucleoside linkage of the modified oligonucleotide is a phosphorothioate linkage, and wherein each cytosine of the modified oligonucleotide is a 5-methylcytosine.

23. A method of preventing, treating, ameliorating, or slowing progression of a HBV-related disease, disorder or condition in an animal comprising administering to the animal the compound of claim 20, thereby preventing, treating, ameliorating, or slowing progression of a HBV-related disease, disorder or condition in the animal.

24. The method of claim 23, wherein the disease, disorder or condition is jaundice, liver inflammation, liver fibrosis, inflammation, liver cirrhosis, liver failure, liver cancer, diffuse hepatocellular inflammatory disease, hemophagocytic syndrome, serum hepatitis, HBV viremia, or liver disease-related transplantation.

25. The method of claim 23, wherein administering the compound of claim 20 reduces HBV antigen levels in the animal.

26. The method of claim 25, wherein HBsAG levels are reduced.

27. The method of claim 25, wherein HBeAG levels are reduced.

28. A method of preventing, treating, ameliorating, or slowing progression of a HBV-related disease, disorder or condition in an animal comprising administering to the animal the compound of claim 21, thereby preventing, treating, ameliorating, or slowing progression of a HBV-related disease, disorder or condition in the animal.

29. The method of claim 28, wherein the disease, disorder or condition is jaundice, liver inflammation, liver fibrosis, inflammation, liver cirrhosis, liver failure, liver cancer, diffuse hepatocellular inflammatory disease, hemophagocytic syndrome, serum hepatitis, HBV viremia, or liver disease-related transplantation.

30. The method of claim 28, wherein administering the compound of claim 21 reduces HBV antigen levels in the animal.

31. The method of claim 30, wherein HBsAG levels are reduced.

32. The method of claim 30, wherein HBeAG levels are reduced.

33. A method of preventing, treating, ameliorating, or slowing progression of a HBV-related disease, disorder or condition in an animal comprising administering to the animal the compound of claim 22, thereby preventing, treating, ameliorating, or slowing progression of a HBV-related disease, disorder or condition in the animal.

34. The method of claim 33, wherein the disease, disorder or condition is jaundice, liver inflammation, liver fibrosis, inflammation, liver cirrhosis, liver failure, liver cancer, diffuse hepatocellular inflammatory disease, hemophagocytic syndrome, serum hepatitis, HBV viremia, or liver disease-related transplantation.

35. The method of claim 33, wherein administering the compound of claim 22 reduces HBV antigen levels in the animal.

36. The method of claim 35, wherein HBsAG levels are reduced.

37. The method of claim 35, wherein HBeAG levels are reduced.

* * * * *

UNITED STATES PATENT AND TRADEMARK OFFICE
CERTIFICATE OF CORRECTION

Page 1 of 1

PATENT NO. : 8,642,752 B2
APPLICATION NO. : 13/452703
DATED : February 4, 2014
INVENTOR(S) : Eric E. Swayze et al.

It is certified that error appears in the above-identified patent and that said Letters Patent is hereby corrected as shown below:

In Claim 1, column 753, line 32

"ing a nucleobase sequence consisting of the nucleobase"

should read

--ing a nucleobase sequence consisting of any of the nucleobase--

Signed and Sealed this
Twenty-second Day of December, 2015

Michelle K. Lee
*Director of the United States Patent and Trademark Office*